US009029124B2

(12) United States Patent
Robertson et al.

(10) Patent No.: US 9,029,124 B2
(45) Date of Patent: May 12, 2015

(54) PHOTOALKANOGENS WITH INCREASED PRODUCTIVITY

(75) Inventors: Dan Eric Robertson, Belmont, MA (US); Christian Perry Ridley, Acton, MA (US); Nikos Basil Reppas, Brookline, MA (US); Jacob Carter Harrison, Newtown, MA (US); Michael Connor, Somerville, MA (US); Frank Anthony Skraly, Watertown, MA (US)

(73) Assignee: Joule Unlimited Technologies, Inc., Bedford, MA (US)

( * ) Notice: Subject to any disclaimer, the term of this patent is extended or adjusted under 35 U.S.C. 154(b) by 106 days.

(21) Appl. No.: 13/428,658

(22) Filed: Mar. 23, 2012

(65) Prior Publication Data

US 2012/0244589 A1 Sep. 27, 2012

Related U.S. Application Data

(60) Provisional application No. 61/466,829, filed on Mar. 23, 2011.

(51) Int. Cl.

| | |
|---|---|
| ***C12N 1/12*** | (2006.01) |
| ***C12P 7/04*** | (2006.01) |
| ***C12P 5/02*** | (2006.01) |
| ***C12N 9/02*** | (2006.01) |

(52) U.S. Cl.

CPC ............ *C12N 9/0008* (2013.01); *C12N 9/0071* (2013.01); *C12P 5/02* (2013.01); *C12P 5/026* (2013.01); *C12P 7/04* (2013.01)

(58) Field of Classification Search

None

See application file for complete search history.

(56) References Cited

U.S. PATENT DOCUMENTS

| | | | | |
|---|---|---|---|---|
| 7,794,969 | B1 | 9/2010 | Reppas et al. | |
| 7,919,303 | B2 | 4/2011 | Reppas et al. | |
| 7,955,820 | B1 | 6/2011 | Reppas et al. | |
| 2003/0175903 | A1* | 9/2003 | San et al. | 435/90 |
| 2004/0048343 | A1 | 3/2004 | Hermann et al. | |
| 2005/0196774 | A1 | 9/2005 | Rozzell et al. | |
| 2006/0225145 | A1 | 10/2006 | Ozawa | |
| 2009/0004715 | A1 | 1/2009 | Tribmur et al. | |
| 2009/0011480 | A1 | 1/2009 | Trimbur et al. | |
| 2009/0061493 | A1 | 3/2009 | Trimbur et al. | |
| 2009/0155873 | A1 | 6/2009 | Kashiyama | |
| 2009/0203070 | A1 | 8/2009 | Devroe et al. | |
| 2010/0136595 | A1 | 6/2010 | Tittiger et al. | |
| 2010/0151539 | A1 | 6/2010 | Franklin et al. | |
| 2010/0154293 | A1 | 6/2010 | Hom et al. | |
| 2010/0170826 | A1 | 7/2010 | Friedman et al. | |
| 2010/0249470 | A1 | 9/2010 | Schirmer et al. | |

FOREIGN PATENT DOCUMENTS

| | | |
|---|---|---|
| EP | 0 711 351 | 3/2006 |
| WO | WO 92/14816 | 9/1992 |
| WO | WO 2007/136762 | 11/2007 |
| WO | WO 2008/119082 | 10/2008 |
| WO | WO 2008/147781 | 12/2008 |
| WO | WO 2009/006430 | 1/2009 |
| WO | WO 2009/036095 | 3/2009 |
| WO | WO 2009/062190 | 5/2009 |
| WO | WO 2009/111513 | 9/2009 |
| WO | WO 2009/140695 | 11/2009 |
| WO | WO 2009/140696 | 11/2009 |
| WO | WO 2010/068288 | 6/2010 |

OTHER PUBLICATIONS

Beer, L.L. et al., "Engineering Algae for Biohydrogen and Biofuel Production," *Current Opinion in Biotechnology*, 2009, pp. 264-271, vol. 20, No. 3.

Copeland, A. et al. UniProt Direct Submission ID Q31C01, Jan. 24, 2006, p. 1 [Online] [Retrieved Dec. 7, 2010] Retrieved from the Internet <URL:http://www.uniprot.org/uniprot/Q31C01.txt?version=1.>.

Copeland, A. et al. UniProt Direct Submission ID Q31C02, Jan. 24, 2006, p. 1 [Online] [Retrieved Dec. 7, 2010] Retrieved from the Internet <URL:http://www.uniprot.org/uniprot/Q31CO2.txt?version=1.>.

Fehler, S.W.G. et al., "Biosynthesis of Hydrocarbons in *Anabaena variabilis*. Incorporation of [*methyl*-$^{14}$C]- and [*methyl*-$^{2}H_3$] Methionine into 7- and 8-Methylheptadecanes,"*Biochemistry*, 1970, pp. 418-422, vol. 8, No. 2.

Feyziev, Y.M., et al., "Formate-induced Inhibition of the Water-Oxidizing Complex of Photosystem II Studied by EPR," *Biochemistry*, 2000, pp. 3848-3855, vol. 39.

Heipieper, H.J., "Adaptation of *Escherichia coli* to Ethanol on the Level of membrane Fatty Acid Composition," *Letters to the Editor, Applied and Environment Microbiology*, Jun. 2005, p. 3388, vol. 71.

Jetter, R., et al., "Plant surface lipid biosynthetic pathways and their utility for metabolic engineering of waxes and hydrocarbon biofuels." *The Plant Journal*, 2008, pp. 670-683, vol. 54.

Ladygina, N., et al., "A Review on Microbial Synthesis of Hydrocarbons," *Process Biochemistry*, 2006, pp. 1001-1014, vol. 41, No. 5.

Li, N. et al., "Conversion of Fatty Aldehydes to Alka(e)nes and Formate by a Cyanobacterial Aldehyde Decarbonylase: Cryptic Redox by an Unusual Dimetal Oxygenase," *Journal of the American Chemical Society*, Feb. 12, 2011, pp. A-D (doi:10.1021/ja2013517).

Luque, I. et al. *Synechococcus* sp. nir Gene for Nitrite Reductase. GenBank Direct Submission Accession X67680.1, May 27, 1993, pp. 1-2 [Online] [Retrieved Dec. 7, 2010] Retrieved from the Internet URL:http://www.ncbi.nlm.nih.gov/nuccore/288053.>.

(Continued)

*Primary Examiner* — Iqbal H Chowdhury

(74) *Attorney, Agent, or Firm* — Fenwick & West LLP; Chang B. Hong

(57) ABSTRACT

The present disclosure identifies methods and compositions for modifying photoautotrophic organisms as hosts, such that the organisms efficiently convert inorganic carbon and light into n-alkanes, and in particular the use of such organisms for the commercial production of n-alkanes and related molecules.

15 Claims, 37 Drawing Sheets

(56) References Cited

OTHER PUBLICATIONS

Maeda, S-I. et al., "cis-Acting Sequences Required for NtcB-Dependent, Nitrite-Responsive Positive Regulation of the Nitrate Assimilation Operon in the Cyanobacterium *Synechococcus* sp. Strain PCC 7942," *Journal of Bacteriology*, Aug. 1998, pp. 4080-4088, vol. 180, No. 16.

Mpuru, S. et al., "Mechanism of Hydrocarbon Biosynthesis from Aldehyde in Selected Insect Species: Requirement for $O_2$ and NADPH and Carbonyl Group Released as $CO_2$," *Insect Biochemistry Molecular Biology*, 1996, pp. 203-208, vol. 26, No. 2.

Murata, N. et al., "Acyl-lipid Desaturases and their Importance in the Tolerance and Acclimatization to Cold of Cyanobacteria," *Biochem. J.*, 1995, pp. 1-8, vol. 308.

Murata, N. et al., "Modes of Fatty-Acid Desaturation in Cyanobacteria," *Plant Cell Physiology*, 1992, pp. 933-941, vol. 33, No. 7.

PCT International Search Report and Written Opinion, PCT Application No. PCT/US2012/30445, Jul. 24, 2012, nine pages.

PCT International Search Report and Written Opinion, PCT Application No. PCT/US2010/041619, Jan. 10, 2011, seventeen pages.

PCT Invitation to Pay Additional Fees, etc., PCT Application No. PCT/US2010/041619, Sep. 30, 2010, two pages.

Phung, L.T. UniProt Direct Submission ID Q54764, Nov. 1, 1996, p. 1 [Online] [Retrieved Dec. 7, 2010] Retrieved from the Internet <URL:http:www.uniprotorg/uniprot/Q54764.txt?version=1.>.

Phung, L.T. UniProt Direct Submission ID Q54765, Nov. 1, 1996, p. 1 [Online] [Retrieved Dec. 7, 2010] Retrieved from the Internet <URL:http:www.uniprot.org/uniprot/Q54765.txt?version=1.>.

Phung, L.T., "Genes for Fatty Acid Biosynthesis in the Cyanobacterium *Synechococcus," Abstracts of the 95th General Meeting of the American Society for Microbiology*, Jan. 1, 1995, p. 524.

Posnett, D.N. et al., "A Novel Method for Producing Anti-Peptide Antibodies. Production of Site-Specific Antibodies to the T Cell Antigen Receptor Beta-Chain," *Journal of Biological Chemistry*, 1988, pp. 1719-1725, vol. 263.

Qi, Q. et al., "Application of the *Synechococcus nir*A Promoter to Establish an Inducible Expression System for Engineering the *Synechocystis* Tocopherol Pathway," *Applied and Environmental Microbiology*, Oct. 2005, pp. 5678-5684, vol. 71, No. 10.

Reed, J.R. et al., "Proposed Mechanism for the Cytochrome P450-Catalyzed Conversion of Aldehydes to Hydrocarbons in the House Fly, *Musca domestica," Biochemistry*, 1995, pp. 16221-16227, vol. 34.

Reed, J.R. et al., "Unusual Mechanism of Hydrocarbon Formation in the Housefly: Cytochrome P450 Converts Aldehyde to the Sex Pheromone Component (Z)-9-tricosene and $CO_2$," *Proceedings of the National Academy of Sciences*, USA, Oct. 1994, pp. 10000-10004, vol. 91.

Reiser, S. et al., "Isolation of Mutants of *Acinetobacter calcoaceticus* Deficient in Wax Ester Synthesis and Complementation of One Mutation with a Gene Encoding a Fatty Acyl Coenzyme a Reductase," *Journal of Bacteriology*, May 1997, pp. 2969-2975, vol. 179, No. 9.

Rude, M.A. et al., "New Microbial Fuels: A Biotech Perspective," *Current Opinion in Microbiology*, 2009, pp. 274-281, vol. 12, No. 3.

Stemler, A., "Absence of a Formate-induced Release of Bicarbonate from Photosystem II," *Plant Physiology*, 1989, pp. 287-290, vol. 91.

Tam, J.P., "Synthetic Peptide Vaccine Design: Synthesis and Properties of a High-Density Multiple Antigenic Peptide System," *Proceedings of the National Academy of Sciences USA*, Aug. 1988, pp. 5409-5413, vol. 85, No. 15.

Tishkov, V. et al., "Protein Engineering of Formate Dehydrogenase," *Biomolecular Engineering*, 2006, pp. 89-110, vol. 23.

Warui, D. et al., "Detection of Formate, Rather than Carbon Monoxide, As the Stoichiometric Coproduct in Conversion of Fatty Aldehydes to Alkanes by a Cyanobacterial Aldehyde Decarbonylase," *Journal of the American Chemical Society*, Dec. 24, 2010, four pages.

Welsh, E.A. et al. UniProt Direct Submission B1WR71, May 20, 2008, p. 1 [Online] [Retrieved Dec. 7, 2010] Retrieved from the Internet<URL:http://www.uniprot.org/uniprot/B1WR71.txt?version=1.>.

Welsh, E.A. et al. UniProt Direct Submission B1WWQ6, May 20, 2008, p. 1 [Online] [Retrieved Dec. 7, 2010] Retrieved from the Internet<URL:http://www.uniprot.org/uniprot/B1WWQ6.txt?version=1.>.

Wentzel, A. et al., "Bacterial Metabolism of Long-chain *n*-Alkanes," *Applied Microbiology and Biotechnology*, 2007, pp. 1209-1221, vol. 76.

Winters, K. et al., "Hydrocarbons of Blue-Green Algae: Geochemical Significance," *Science*, Jan. 31, 1969, pp. 467-468, vol. 163, No. 3866.

* cited by examiner

PHOTOALKANOGENS WITH INCREASED PRODUCTIVITY

CROSS-REFERENCE TO RELATED APPLICATIONS

This application claims priority to earlier filed U.S. Provisional Patent Application No. 61/466,829, filed Mar. 23, 2011.

SEQUENCE LISTING CROSS-REFERENCE TO RELATED APPLICATIONS

The instant application contains a Sequence Listing which has been submitted in ASCII format via EFS-Web and is hereby incorporated by reference in its entirety. Said ASCII copy, created on Mar. 23, 2012, is named 20270US_CRF_sequencelisting.txt and is 433,355 bytes in size.

BACKGROUND OF THE INVENTION

Many existing photoautotrophic organisms (i.e., plants, algae, and photosynthetic bacteria) are poorly suited for industrial bioprocessing and have therefore not demonstrated commercial viability. Such organisms typically have slow doubling times (3-72 hrs) compared to industrialized heterotrophic organisms such as *Escherichia coli* (20 minutes), reflective of low total productivities. Photosynthetic organisms suitable for producing alkanes and other carbon-based products of interest have been described in various patent applications, including U.S. Provisional Patent Application No. 61/224,463 filed, Jul. 9, 2009, U.S. Provisional Patent Application No. 61/228,937, filed Jul. 27, 2009, U.S. utility application Ser. No. 12/759,657, filed Apr. 13, 2010, and U.S. utility application Ser. No. 12/833,821, filed Jul. 9, 2010, the disclosures of each which are incorporated herein by reference. Although progress has been made, a need for further improvement in the production rates of alkanes and carbon-based products of interests by these engineered organisms remains.

SUMMARY OF THE INVENTION

The present invention provides, in certain embodiments, isolated polynucleotides comprising or consisting of nucleic acid sequences selected from the group consisting of the coding sequences for AAR and ADM enzymes, nucleic acid sequences that are codon-optimized variants of these sequences, and related nucleic acid sequences and fragments.

An AAR enzyme refers to an enzyme with the amino acid sequence of the SYNPCC7942_1594 protein (SEQ ID NO: 6) or a homolog thereof, wherein a SYNPCC7942_1594 homolog is a protein whose BLAST alignment (i) covers >90% length of SYNPCC7942_1594, (ii) covers >90% of the length of the matching protein, and (iii) has >50% identity with SYNPCC7942_1594 (when optimally aligned using the parameters provided herein), and retains the functional activity of SYNPCC7942_1594, i.e., the conversion of an acyl-ACP (ACP=acyl carrier protein) to an alkanal. An ADM enzyme refers to an enzyme with the amino acid sequence of the SYNPCC7942_1593 protein (SEQ ID NO: 8) or a homolog thereof, wherein a SYNPCC7942_1593 homolog is defined as a protein whose amino acid sequence alignment (i) covers >90% length of SYNPCC7942_1593, (ii) covers >90% of the length of the matching protein, and (iii) has >50% identity with SYNPCC7942_1593 (when aligned using the preferred parameters provided herein), and retains the functional activity of SYNPCC7942_1593, i.e., the conversion of an n-alkanal to an (n−1)-alkane. Exemplary AAR and ADM enzymes are listed in Table 1 and Table 2, respectively. Genes encoding AAR or ADM enzymes are referred to herein as AAR genes (aar) or ADM genes (adm), respectively.

Preferred parameters for BLASTp are: Expectation value: 10 (default); Filter: none; Cost to open a gap: 11 (default); Cost to extend a gap: 1 (default); Maximum alignments: 100 (default); Word size: 11 (default); No. of descriptions: 100 (default); Penalty Matrix: BLOWSUM62.

A formate dehydrogenase enzyme (FDH) refers to an enzyme which catalyzes the conversion of formate and NAD(P)+ into NAD(P)H and $CO_2$. The enzyme classification number for NAD+-specific FDHs is EC 1.2.1.2; the enzyme classification number for NADP+-specific FDHs is EC 1.2.1.43. In certain embodiments, FDH has at least 60%, at least 70%, at least 80%, at least 90%, or at least 95% homology to the NAD+-dependent FDH from *Candida boidinii* (Uniprot O13437) (SEQ ID NO: 32). In other embodiments, FDH has at least 60%, at least 70%, at least 80%, at least 90%, or at least 95% homology to the NADP+-dependent FDH from *Burkholdia multivorans* (SEQ ID NO: 44).

In one embodiment, expression of the formate dehydrogenase gene is under the control of an inducible promoter. In another embodiment expression of the formate dehydrogenase gene is under the control of cpcB promoter from *Synechocystis* sp. PCC 6803 (PcpcB). In still another embodiment, expression of the formate dehydrogenase gene is under the control of a rbcL promoter ($1^{st}$ italic sequence in SEQ ID NO: 34).

The present invention further provides isolated polypeptides comprising or consisting of polypeptide sequences selected from the group consisting of the sequences listed in Table 1 and Table 2, and related polypeptide sequences, fragments and fusions. Antibodies that specifically bind to the isolated polypeptides of the present invention are also contemplated.

The present invention also provides methods for expressing a heterologous nucleic acid sequence encoding AAR and ADM in a host cell lacking catalytic activity for AAR and ADM (thereby conferring n-alkane producing capability in the host cell), or for expressing a nucleic acid encoding AAR and ADM in a host cell which comprises native AAR and/or ADM activity (thereby enhancing n-alkane producing capability in the host cell).

In addition, the present invention provides methods for producing carbon-based products of interest using the AAR and ADM genes, proteins and host cells described herein. For example, in one embodiment the invention provides a method for producing hydrocarbons, comprising: (i) culturing an engineered cyanobacterium in a culture medium, wherein said engineered cyanobacterium comprises a recombinant AAR enzyme and a recombinant ADM enzyme; and (ii) exposing said engineered cyanobacterium to light and inorganic carbon, wherein said exposure results in the conversion of said inorganic carbon by said engineered cynanobacterium into n-alkanes, wherein at least one of said n-alkanes is selected from the group consisting of n-tridecane, n-tetradecane, n-pentadecane, n-hexadecane, and n-heptadecane, and wherein the amount of said n-alkanes produced is between 0.1% and 5% dry cell weight and at least two times the amount produced by an otherwise identical cyanobacterium, cultured under identical conditions, but lacking said recombinant AAR and ADM enzymes.

In a related embodiment, the amount on n-alkanes produced by the engineered cyanobacterium is at least 0.1%, 0.2%, 0.3%, 0.4%, 0.5%, 0.6%, 0.7%, 0.8%, 0.9%, or 1%

DCW, and at least two times the amount producted by an otherwise identical cyanobacterium, cultured under identical conditions, but lacking said recombinant AAR and ADM enzymes.

In a related embodiment, at least one of said recombinant enzymes is heterologous with respect to said engineered cyanobacterium. In another embodiment, said cyanobacterium does not synthesize alkanes in the absence of the expression of one or both of the recombinant enzymes. In another embodiment, at least one of said recombinant AAR or ADM enzymes is not heterologous to said engineered cyanobacterium.

In another related embodiment of the method, said engineered cyanobacterium further produces at least one n-alkene or n-alkanol. In yet another embodiment, the engineered cyanobacterium produces at least one n-alkene or n-alkanol selected from the group consisting of n-pentadecene, n-heptadecene, and 1-octadecanol. In a related embodiment, said n-alkanes comprise predominantly n-heptadecane, n-pentadecane or a combination thereof. In a related embodiment, more n-heptadecane and/or n-pentadecane are produced than all other n-alkane products combined. In yet another related embodiment, more n-heptadecane and/or n-pentadecane are produced by the engineered cyanobacterium than any other n-alkane or n-alkene produced by the engineered cyanobacterium. In yet another related embodiment, at least one n-pentadecene produced by said engineered cyanobacterium is selected from the group consisting of cis-3-heptadecene and cis-4-pentadecene. In yet another related embodiment, at least one n-heptadecene produced by said engineered cyanobacterium is selected from the group consisting of cis-4-pentadecene, cis-6-heptadecene, cis-8-heptadecene, cis-9-heptadecene, and cis, cis-heptadec-di-ene.

In yet another related embodiment, the invention further provides a step of isolating at least one n-alkane, n-alkene or n-alkanol from said engineered cyanobacterium or said culture medium. In yet another related embodiment, the engineered cyanobacterium is cultured in a liquid medium. In yet another related embodiment, the engineered cyanobacterium is cultured in a photobioreactor.

In another related embodiment, the AAR and/or ADM enzymes are encoded by a plasmid. In yet another related embodiment, the AAR and/or ADM enzymes are encoded by recombinant genes incorporated into the genome of the engineered cyanobacterium. In yet another related embodiment, the AAR and/or ADM enzymes are encoded by genes which are present in multiple copies in said engineered cyanobacterium. In yet another related embodiment, the recombinant AAR and/or ADM enzymes are encoded by genes which are part of an operon, wherein the expression of said genes is controlled by a single promoter. In yet another related embodiment, the recombinant AAR and/or ADM enzymes are encoded by genes which are expressed independently under the control of separate promoters. In yet another related embodiment, expression of the recombinant AAR and/or ADM enzymes in an engineered cyanobacterium is controlled by a promoter selected from the group consisting of a cI promoter, a cpcB promoter, a lacI-trc promoter, an EM7 promoter, an aphII promoter, a nirA promoter, and a nir07 promoter (referred to herein as "P(nir07)"). In yet another related embodiment, the enzymes are encoded by genes which are part of an operon, wherein the expression of said genes is controlled by one or more inducible promoters. In yet another related embodiment, at least one promoter is a urea-repressible, nitrate-inducible promoter. In yet another related embodiment, the urea-repressible, nitrate-inducible promoter is a nirA-type promoter. In yet another related embodiment, the nirA-type promoter is P(nir07) (SEQ ID NO: 24).

In yet another related embodiment, the cyanobacterium species that is engineered to express recombinant AAR and/or ADM enzymes produces less than approximately 0.01% DCW n-heptadecane or n-pentadecane in the absence of said recombinant AAR and/or ADM enzymes, 0.01% DCW corresponding approximately to the limit of detection of n-heptadecane and n-pentadecane by the gas chromatographic/flame ionization detection methods described herein. In another related embodiment, the engineered cyanobacterium of the method is a thermophile. In yet another related embodiment, the engineered cyanobacterium of the method is selected from the group consisting of an engineered *Synechococcus* sp. PCC7002 and an engineered *Thermosynechococcus elongatus* BP-1.

In yet another related embodiment, the recombinant AAR and/or ADM enzymes are selected from the group of enzymes listed in Table 1 and Table 2, respectively. In yet another related embodiment, the recombinant AAR enzymes are selected from the group consisting of SYNPCC7942_1594, tll1312, PMT9312_0533, and cce_1430. In yet another related embodiment, the recombinant ADM enzymes are selected from the group consisting of SYNPCC7942_1593, tll1313, PMT9312_0532, and cce_0778.

In yet another related embodiment, the recombinant AAR and ADM enzymes have the amino acid sequences of SEQ ID NO:10 and SEQ ID NO:12, respectively. In certain embodiments, the recombinant AAR and ADM enzymes are encoded by SEQ ID NOs: 9 and 11, respectively. In yet other embodiments, the recombinant AAR and ADM enzymes are encoded by SEQ ID NOs: 26 and 28, respectively, or SEQ ID NOs: 30 and 31 respectively, and have the amino acid sequences of SEQ ID NOs: 27 and 28, respectively. In certain embodiments, the recombinant AAR and ADM enzymes are encoded by SEQ ID NOs: 1 and 3, respectively, and have the amino acid sequences of SEQ NOs: 2 and 4, respectively. In still other embodiments, the recombinant AAR and ADM enzymes are encoded by SEQ ID NOs: 5 and 7, respectively, and have the amino acid sequences of SEQ ID NOs: 6 and 8, respectively.

In yet another related embodiment, the method comprising culturing the engineered cyanobacterium in the presence of an antibiotic, wherein said antibiotic selects for the presence of a recombinant gene encoding an AAR and/or ADM enzyme. In certain embodiments, the antibiotic is spectinomycin or kanamycin. In related embodiments, the amount of spectinomycin in the culture media is between 100 and 700 μg/ml, e.g., 100, 200, 300, 400, 500, 600, or 700 μg/ml of spectinomycin can be added to the culture media. In certain embodiments, the amount of spectinomycin added is about 600 μg/ml, and the amount of n-alkanes produced by the engineered cyanobacterium is at least about 3%, 4% or 5% DCW.

In another embodiment, the method for producing hydrocarbons comprises culturing a cyanobacterium expressing recombinant AAR and/or ADM enzymes in the presence of an exogenous substrate for one or both enzymes. In a related embodiment, the substrate is selected from the group consisting of an acyl-ACP, an acyl-CoA, and a fatty aldehyde. In another related embodiment, exogenous fatty alcohols or fatty esters or other indirect substrates can be added and converted to acyl-ACP or acyl-CoA by the cyanobacterium.

In yet another embodiment, the invention provides a composition comprising an n-alkane produced by any of the recombinant biosynthetic methods described herein. In yet another embodiment, the invention provides a composition comprising an n-alkene or n-alkanol produced by any of the recombinant biosynthetic methods described herein.

In certain embodiments, the invention provides an engineered host cell for producing an n-alkane, wherein said cell comprises one or more recombinant protein activities selected from the group consisting of an acyl-CoA reductase activity, an acyl-ACP reductase activity, an alkanal deformylative monooxygenase activity, and an electron donor activity. In related embodiments, the host cell comprises a recombinant acyl-ACP reductase activity, a recombinant alkanal deformylative monooxygenase activity, and a recombinant electron donor activity. In other embodiments, the host cell comprises a recombinant acyl-ACP reductase activity and a recombinant alkanal deformylative monooxygenase activity. In certain embodiments, the electron donor activity is a ferredoxin. In certain related embodiments, the host cell is capable of photosynthesis. In still other related embodiments, the host cell is a cyanobacterium. In still other embodiments, the host cell is a gram-negative bacterium, a gram-positive bacterium, or a yeast species.

In other embodiments, the invention provides an isolated or recombinant polynucleotide comprising or consisting of a nucleic acid sequence selected from the group consisting of: (a) SEQ ID NOs:1, 3, 5, 7, 9, 11, 13, 14, 30 or 31; (b) a nucleic acid sequence that is a degenerate variant of SEQ ID NOs: 1, 3, 5, 7, 9, 11, 13, 14, 30 or 31; (c) a nucleic acid sequence at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO: 1, 3, 5, 7, 9, 11, 13, 14, 30 or 31; (d) a nucleic acid sequence that encodes a polypeptide having the amino acid sequence of SEQ ID NO:2, 4, 6, 8, 10, 12, 27 or 29; (e) a nucleic acid sequence that encodes a polypeptide at least 50%, at least 60%, at least 70%, at least 80%, at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO:2, 4, 6, 8, 10, 12, 27 or 39; and (f) a nucleic acid sequence that hybridizes under stringent conditions to SEQ ID NOs: 1, 3, 5, 7, 9, 11, 13, 14, 30 or 31. In related embodiments, the nucleic acid sequence encodes a polypeptide having acyl-ACP reductase activity or alkanal deformylative monooxygenase activity.

In yet another embodiment, the invention provides an isolated, soluble polypeptide with alkanal deformylative monooxygenase activity wherein, in certain related embodiments, the polypeptide has an amino acid sequence of one of the proteins listed in Table 2. In related embodiments, the polypeptide has the amino acid sequence identical to, or at least 95% identical to, SEQ ID NO: 4, 8, 12 or 29.

In yet another embodiment, the invention provides a method for synthesizing an n-alkane from an acyl-ACP in vitro, comprising: contacting an acyl-ACP with a recombinant acyl-ACP reductase, wherein said acyl-ACP reductase converts said acyl-ACP to an n-alkanal; then contacting said n-alkanal with a recombinant, soluble alkanal deformylative monooxygenase in the presence of an electron donor, wherein said alkanal deformylative monooxygenase converts said n-alkanal to an (n−1) alkane. In a related embodiment, the invention provides a method for synthesizing an n-alkane from an n-alkanal in vitro, comprising: contacting said n-alkanal with a recombinant, soluble alkanal deformylative monooxygenase in the presence of an electron donor, wherein said alkanal deformylative monooxygenase converts said n-alkanal to an (n−1)-alkane. In certain related embodiments, the electron donor is a ferredoxin protein.

In another embodiment, the invention provides engineered cyanobacterial cells comprising recombinant AAR and ADM enzymes, wherein said cells comprise between 0.1% and 5%, between 1% and 5%, or between 2% and 5% dry cell weight n-alkanes, wherein said n-alkanes are predominantly n-pentadecane, n-heptadecane, or a combination thereof.

In other embodiments, the invention provides one of the expression and/or transformation vectors disclosed herein. In other related embodiments, the invention provides methods of using one of the expression and/or transformation vectors disclosed herein to transform a microorganism, e.g., a cyanobacterium.

In yet another embodiment of the method for producing hydrocarbons, the AAR and ADM enzymes are at least 95%, at least 96%, at least 97%, at least 98%, at least 99%, or 100% identical to SEQ ID NO: 6 and SEQ ID NO: 8, respectively. In a related embodiment, the engineered cyanobacterium produces n-pentadecane and n-heptadecane, wherein the percentage by mass of n-pentadecane relative to n-pentadecane plus n-heptadecane is at least 20%. In yet another related embodiment, the engineered cyanobacterium produces n-pentadecane and n-heptadecane, wherein the percentage by mass of n-pentadecane relative to n-pentadecane plus n-heptadecane is less than 30%. In yet another related embodiment, the engineered cyanobacterium produces n-pentadecane and n-heptadecane, wherein the percentage by mass of n-pentadecane relative to n-pentadecane plus n-heptadecane is between 20% and 30%.

In yet another embodiment of the method for producing hydrocarbons, the AAR and ADM enzymes are at least 95%, at least 96%, at least 97%, at least 98%, at least 99%, or 100% identical to SEQ ID NO:10 and SEQ ID NO: 12, respectively. In a related embodiment, the engineered cyanobacterium produces n-pentadecane and n-heptadecane, wherein the percentage by mass of n-pentadecane relative to n-pentadecane plus n-heptadecane is at least 50%. In yet another related embodiment, the percentage by mass of n-pentadecane relative to n-pentadecane plus n-heptadecane is less than 60%. In yet another related embodiment, the percentage by mass of n-pentadecane relative to n-pentadecane plus n-heptadecane is between 50% and 60%.

In yet another embodiment of the method for producing hydrocarbons, the engineered cyanobacterium comprises at least two distinct recombinant ADM enzymes and at least two distinct recombinant AAR enzymes. In a related embodiment, said engineered cyanobacterium comprises at least one operon encoding AAR and ADM enzymes which are at least 95% identical to SEQ ID NO: 27 and SEQ ID NO: 29, respectively. In yet another related embodiment, said engineered cyanobacterium comprises at least one operon encoding AAR and ADM enzymes which are at least 95% identical to SEQ ID NO:10 and SEQ ID NO: 12, respectively. In yet another related embodiment, expression of said AAR and ADM enzymes is controlled by an inducible promoter, e.g., a P(nir07) promoter. In yet another related embodiment, said recombinant ADM and AAR enzymes are chromosomally integrated. In yet another related embodiment, said engineered cyanobacterium produces n-alkanes in the presence of an inducer, and wherein at least 95% of said n-alkanes are n-pentadecane and n-heptadecane, and wherein the percentage by mass of n-pentadecane relative to n-pentadecane plus n-heptadecane is at least 80%.

In yet another embodiment of the method for producing hydrocarbons, the engineered cyanobacterium comprises recombinant AAR and ADM enzymes which are at least 95% identical to SEQ ID NO:10 and SEQ ID NO: 12, respectively. In a related embodiment, the recombinant AAR and ADM enzymes are under the control of an inducible promoter, e.g., a P(nir07) promoter. In yet another related embodiment, the engineered cyanobacterium produces at least 0.5% DCW n-alkanes in the presence of an inducer, and wherein said n-alkanes comprise n-pentadecane and n-heptadecane, and wherein the percentage by mass of n-pentadecane relative to n-pentadecane plus n-heptadecane is at least 50%.

In yet another embodiment, the invention provides a method for modulating the relative amounts of n-pentadecane and n-heptadecane in an engineered cyanobacterium, comprising controlling the expression of one or more recombinant AAR and/or ADM enzymes in said cyanobacterium, wherein said AAR and/or ADM enzymes are at least 95% identical or identical to the AAR and ADM enzymes of SEQ ID NO:s 10, 12, 27 or 29.

In another embodiment, the invention provides an engineered cyanobacterium, wherein said engineered cyanobacterium comprises one or more recombinant genes encoding an AAR enzyme, an ADM enzyme, or both enzymes, wherein at least one of said recombinant genes is under the control of a nitrate-inducible promoter.

In yet another embodiment, the invention provides a recombinant gene, wherein said gene comprises a promoter for controlling expression of said gene, wherein said promoter comprises a contiguous nucleic acid sequence identical to SEQ ID NO: 24.

In yet another embodiment, the invention provides an isolated DNA molecule comprising a promoter, wherein said promoter comprises a contiguous nucleic acid sequence identical to SEQ ID NO: 24.

In yet another embodiment, the invention provides an engineered bacterial strain selected from the group consisting of JCC1469, JCC1281, JCC1683, JCC1685, JCC1076, JCC1170, JCC1221, JCC879 and JCC1084t.

In one embodiment, the invention provides a method for improving hydrocarbon production by a photosynthetic cell comprising a recombinant ADM enzyme, wherein the method comprises transforming the cell with a nucleic acid functionally encoding a formate dehydrogenase. In one aspect, the photosynthetic cell is a microbial cell. In a further aspect, the microbial cell is a cyanobacterial cell.

In another embodiment, the formate dehydrogenase is an NAD+-dependent formate dehydrogenase (E.C. 1.2.1.2). In a further embodiment, the formate dehydrogenase enzyme is at least 50%, 55%, 60%, 65%, 70%, 75%, 80%, 85%, 90%, or 95% identical to SEQ ID NO: 32. In another embodiment, the formate dehydrogenase enzyme us under the control of a cpcB promoter. In still another embodiment, the formate dehydrogenase enzyme is encoded by a nucleic acid at least 50%, 55%, 60%, 65%, 70%, 75%, 80%, 85%, 90%, or 95% identical to SEQ ID NO: 36.

In yet another embodiment, the invention provides an engineered photosynthetic cell, wherein the engineered cell comprises (1) one or more recombinant genes encoding an acyl-ACP reductase enzyme, an ADM enxyme, or both enzymes, and (2) a recombinant gene encoding a formate dehydrogenase enzyme. In one aspect, the photosynthetic cell is a microbial cell. In a further aspect, the microbial cell is a cyanobacterial cell.

In one aspect, the acyl-ACP reductase enzyme is at least 50%, 55%, 60%, 65%, 70%, 75%, 80%, 85%, 90%, or 95% identical to SEQ ID NO: 27. In another aspect, the ADM enzyme is at least 50%, 55%, 60%, 65%, 70%, 75%, 80%, 85%, 90%, or 95% identical to SEQ ID NO: 29. In another embodiment, the formate dehydrogenase is an NAD+-dependent formate dehydrogenase (E.C. 1.2.1.2). In a further embodiment, the formate dehydrogenase enzyme is at least 50%, 55%, 60%, 65%, 70%, 75%, 80%, 85%, 90%, or 95% identical to SEQ ID NO: 32. In another embodiment, the formate dehydrogenase enzyme us under the control of a cpcB promoter. In still another embodiment, the formate dehydrogenase enzyme is encoded by a nucleic acid at least 50%, 55%, 60%, 65%, 70%, 75%, 80%, 85%, 90%, or 95% identical to SEQ ID NO: 36. In yet another embodiment, the formate dehydrogenase enzyme is encoded by a plasmid.

In another aspect, the invention provides a method for producing hydrocarbons, comprising (1) culturing an engineered photosynthetic cell in a culture medium, and (2) exposing said photosynthetic cell to light and inorganic carbon, wherein said exposure results in the conversion of said inorganic carbon by said engineered photosynthetic cell into n-alkanes, wherein the amount of said n-alkanes produced by said engineered photosynthetic cell is greater than the amount produced by an otherwise identical photosynthetic cell lacking said recombinant gene encoding formate dehydrogenase, cultured under identical conditions. In one aspect, the photosynthetic cell is a microbial cell. In a further aspect, the microbial cell is a cyanobacterial cell.

In another embodiment, the n-alkanes comprise predominantly n-heptadecane, n-pentadecane, or a combination thereof. In still another embodiment, the method further comprises isolating at least one n-alkane, n-alkene, or n-alkanol from the engineered photosynthetic cell or said culture medium.

In another aspect, the method for producing hydrocarbons reduces formate concentration by at least 5% in the culture comprising the photosynthetic cell. In still another aspect, the method for producing hydrocarbons reduces formate concentration by at least 35% in the culture comprising the photosynthetic cell. In another embodiment, the method for producing hydrocarbons reduces formate concentration by at least 10%, 20%, 30%, 40%, 50%, 60%, 70%, 80%, 90%, or by 100% in the culture comprising the photosynthetic cell.

These and other embodiments of the invention are further described in the Figures, Description, Examples and Claims, herein.

DETAILED DESCRIPTION OF THE INVENTION

Figure 1A:
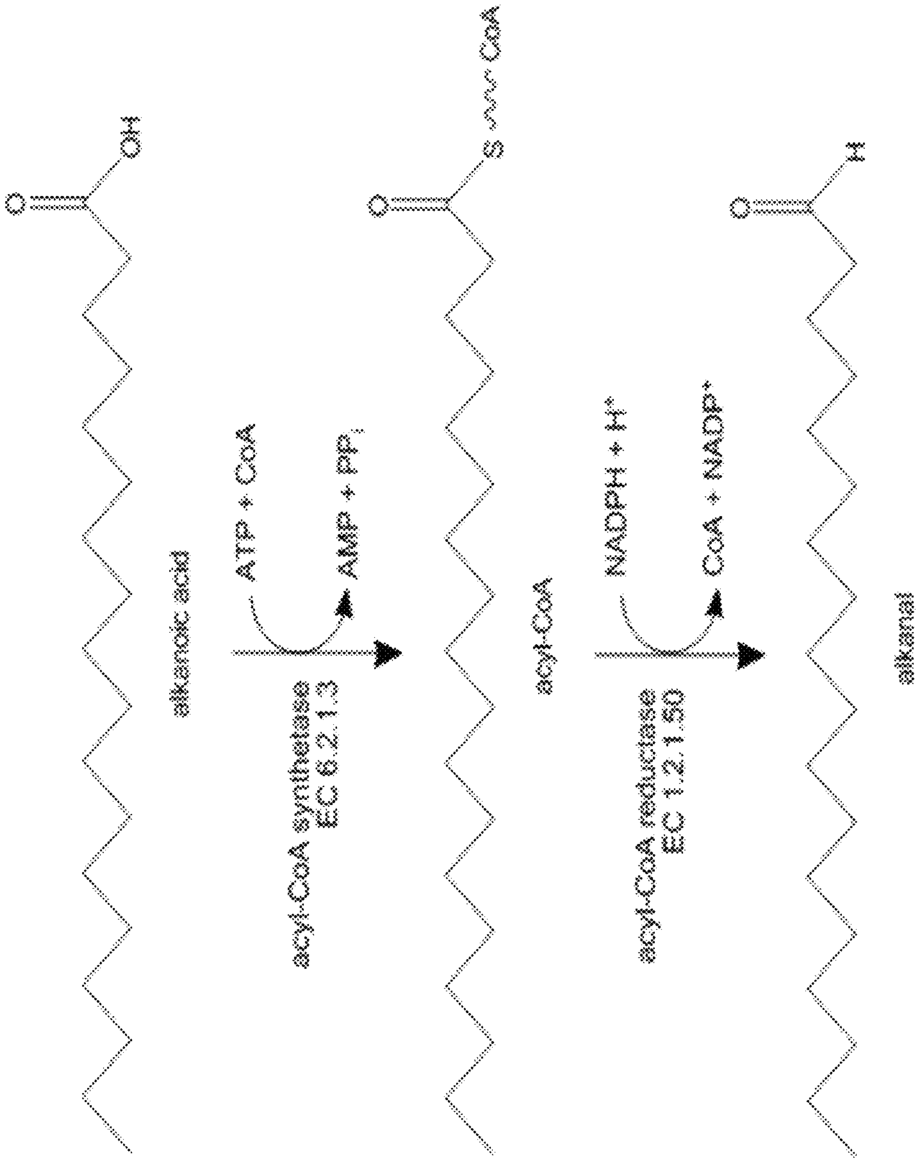
FIG. 1 depicts, in panel A, Biosynthesis of n-alkanal via acyl-CoA. Acyl-CoAs are typically intermediates of fatty acid degradation; B, Biosynthesis of n-alkanal via acyl-ACP. Acyl-ACP's are typically intermediates of fatty acid biosynthesis. Note the three different types of ACP reductase: (i) β-ketoacyl-ACP reductase, (ii) enoyl-ACP reductase, and (iii) acyl-ACP reductase. Acyl-ACP reductase, a new enzyme, generates the substrate for alkanal deformylative monooxygenase. CoA, coenzyme A; ACP, acyl carrier protein; C, an alternative acyl-CoA-mediated alkane biosynthetic pathway. See additional discussion in Example 1, herein.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual,* 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); Handbook of Biochemistry: Section A Proteins, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" organic molecule (e.g., an alkane, alkene, or alkanal) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); and "oligonucleotide-directed mutagenesis" (a process which enables the generation of site-specific mutations in any cloned DNA segment of interest; see, e.g., Reidhaar-Olson and Sauer, Science 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

Deletion:

The removal of one or more nucleotides from a nucleic acid molecule or one or more amino acids from a protein, the regions on either side being joined together.

Knock-Out:

A gene whose level of expression or activity has been reduced to zero. In some examples, a gene is knocked-out via deletion of some or all of its coding sequence. In other examples, a gene is knocked-out via introduction of one or more nucleotides into its open reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab').sub.2, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications*, (Marasco, ed., Springer-Verlag New York, Inc., 1998), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic." See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.,* 8:392-396 (1985); and references sited in each of the above, which are incorporated herein by reference. Such compounds are often developed with the aid of computerized molecular modeling. Peptide mimetics that are structurally similar to useful peptides of the present invention may be used to produce an equivalent effect and are therefore envisioned to be part of the present invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. Even more preferred are muteins having at least 90% overall sequence homology to the wild-type protein.

In an even more preferred embodiment, a mutein exhibits at least 95% sequence identity, even more preferably 98%, even more preferably 99% and even more preferably 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (incorporated by reference herein). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

"Percent dry cell weight" refers to a measurement of hydrocarbon production obtained as follows: a defined volume of culture is centrifuged to pellet the cells. Cells are washed then dewetted by at least one cycle of microcentrifugation and aspiration. Cell pellets are lyophilized overnight, and the tube containing the dry cell mass is weighed again such that the mass of the cell pellet can be calculated within ±0.1 mg. At the same time cells are processed for dry cell weight determination, a second sample of the culture in question is harvested, washed, and dewetted. The resulting cell pellet, corresponding to 1-3 mg of dry cell weight, is then extracted by vortexing in approximately 1 ml acetone plus butylated hydroxytolune (BHT) as antioxidant and an internal standard, e.g., n-heptacosane. Cell debris is then pelleted by centrifugation and the supernatant (extractant) is taken for analysis by GC. For accurate quantitation of n-alkanes, flame ionization detection (FID) was used as opposed to MS total ion count. n-Alkane concentrations in the biological extracts were calculated using calibration relationships between GC-FID peak area and known concentrations of authentic n-alkane standards. Knowing the volume of the extractant, the resulting concentrations of the n-alkane species in the extracant, and the dry cell weight of the cell pellet extracted, the percentage of dry cell weight that comprised n-alkanes can be determined.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

"Carbon-based Products of Interest" include alcohols such as ethanol, propanol, isopropanol, butanol, fatty alcohols, fatty acid esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, ϵ-caprolactone, isoprene, caprolactam, rubber; commodity chemicals such as lactate, Docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

Biofuel: A biofuel refers to any fuel that derives from a biological source. Biofuel can refer to one or more hydrocarbons, one or more alcohols, one or more fatty esters or a mixture thereof.

Hydrocarbon: The term generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

Alkanes, also known as paraffins, are chemical compounds that consist only of the elements carbon (C) and hydrogen (H) (i.e., hydrocarbons), wherein these atoms are linked together exclusively by single bonds (i.e., they are saturated compounds) without any cyclic structure. n-Alkanes are linear, i.e., unbranched, alkanes. Together, AAR and ADM enzymes function to synthesize n-alkanes from acyl-ACP molecules.

Accordingly, the present invention provides isolated nucleic acid molecules for genes encoding AAR and ADM enzymes, and variants thereof. Exemplary full-length nucleic acid sequences for genes encoding AAR are presented as SEQ ID NOs: 1, 5, and 13, and the corresponding amino acid sequences are presented as SEQ ID NOs: 2, 6, and 10, respectively. Exemplary full-length nucleic acid sequences for genes encoding ADM are presented as SEQ ID NOs: 3, 7, 14, and the corresponding amino acid sequences are presented as SEQ ID NOs: 4, 8, and 12, respectively. Additional nucleic acids provided by the invention include any of the genes encoding the AAR and ADM enzymes in Table 1 and Table 2, respectively.

In one embodiment, the present invention provides an isolated nucleic acid molecule having a nucleic acid sequence comprising or consisting of a gene coding for AAR and ADM, and homologs, variants and derivatives thereof expressed in a host cell of interest. The present invention also provides a nucleic acid molecule comprising or consisting of a sequence which is a codon-optimized version of the AAR and ADM genes described herein (e.g., SEQ ID NO: 9 and SEQ ID NO: 11, which are optimized for the expression of the AAR and ADM genes of *Prochlorococcus marinus* MIT 9312 in *Synechoccocus* sp. PCC 7002). In a further embodiment, the present invention provides a nucleic acid molecule and homologs, variants and derivatives of the molecule comprising or consisting of a sequence which is a variant of the AAR or ADM gene having at least 76% identity to the wild-type gene. The nucleic acid sequence can be preferably 80%, 85%, 90%, 95%, 98%, 99%, 99.9% or even higher identity to the wild-type gene.

In another embodiment, the nucleic acid molecule of the present invention encodes a polypeptide having the amino acid sequence of SEQ ID NO:2, 4, 6, 8, 10 or 12. Preferably, the nucleic acid molecule of the present invention encodes a polypeptide sequence of at least 50%, 60, 70%, 80%, 85%, 90% or 95% identity to SEQ ID NO:2, 4, 6, 8, 10 or 12 and the identity can even more preferably be 96%, 97%, 98%, 99%, 99.9% or even higher.

The present invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hydridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip: Tools and Technology*, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach* (Practical Approach Series), Schena (ed.), Oxford University Press (1999) (ISBN: 0199637768); Nature Genet. 21(1)(suppl):1-60 (1999); *Microarray Biochip: Tools and Technology*, Schena (ed.), Eaton Publishing Company/BioTechniques Books Division (2000) (ISBN: 1881299376), the disclosure of each of which is incorporated herein by reference in its entirety.

As is well known in the art, enzyme activities can be measured in various ways. For example, the pyrophosphorolysis of OMP may be followed spectroscopically (Grubmeyer et al., (1993) *J. Biol. Chem.* 268:20299-20304). Alternatively, the activity of the enzyme can be followed using chromatographic techniques, such as by high performance liquid chromatography (Chung and Sloan, (1986) *J. Chromatogr.* 371:71-81). As another alternative the activity can be indirectly measured by determining the levels of product made from the enzyme activity. These levels can be measured with techniques including aqueous chloroform/methanol extraction as known and described in the art (Cf. M. Kates (1986) *Techniques of Lipidology; Isolation, analysis and identification of Lipids*. Elsevier Science Publishers, New York (ISBN: 0444807322)). More modern techniques include using gas chromatography linked to mass spectrometry (Niessen, W. M. A. (2001). *Current practice of gas chromatography—mass spectrometry*. New York, N.Y.: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G (1997) *Am. Chem. Soc. Symp. Series,* 666: 172-208), titration for determining free fatty acids (Komers (1997) *Fett/Lipid,* 99(2): 52-54), enzymatic methods (Bailer (1991) *Fresenius J. Anal. Chem.* 340(3): 186), physical property-based methods, wet chemical methods, etc. can be used to analyze the levels and the identity of the product produced by the organisms of the present invention. Other methods and techniques may also be suitable for the measurement of enzyme activity, as would be known by one of skill in the art.

Vectors

Also provided are vectors, including expression vectors, which comprise the above nucleic acid molecules of the present invention, as described further herein. In a first embodiment, the vectors include the isolated nucleic acid molecules described above. In an alternative embodiment, the vectors of the present invention include the above-described nucleic acid molecules operably linked to one or more expression control sequences. The vectors of the instant invention may thus be used to express an AAR and/or ADM polypeptide contributing to n-alkane producing activity by a host cell.

Vectors useful for expression of nucleic acids in prokaryotes are well known in the art.

Isolated Polypeptides

According to another aspect of the present invention, isolated polypeptides (including muteins, allelic variants, fragments, derivatives, and analogs) encoded by the nucleic acid molecules of the present invention are provided. In one embodiment, the isolated polypeptide comprises the polypeptide sequence corresponding to SEQ ID NO:2, 4, 6, 8 10 or 12. In an alternative embodiment of the present invention, the isolated polypeptide comprises a polypeptide sequence at least 85% identical to SEQ ID NO:2, 4, 6, 8, 10 or 12. Preferably the isolated polypeptide of the present invention has at least 50%, 60, 70%, 80%, 85%, 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to SEQ ID NO:2, 4, 6, 8, 10 or 12.

According to other embodiments of the present invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cell Transformants

In another aspect of the present invention, host cells transformed with the nucleic acid molecules or vectors of the present invention, and descendants thereof, are provided. In some embodiments of the present invention, these cells carry the nucleic acid sequences of the present invention on vectors, which may but need not be freely replicating vectors. In other embodiments of the present invention, the nucleic acids have been integrated into the genome of the host cells.

In a preferred embodiment, the host cell comprises one or more AAR or ADM encoding nucleic acids which express AAR or ADM in the host cell.

In an alternative embodiment, the host cells of the present invention can be mutated by recombination with a disruption, deletion or mutation of the isolated nucleic acid of the present invention so that the activity of the AAR and/or ADM protein(s) in the host cell is reduced or eliminated compared to a host cell lacking the mutation.

Selected or Engineered Microorganisms for the Production of Carbon-Based Products of Interest Microorganism: Includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

A variety of host organisms can be transformed to produce a product of interest. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure-tolerant organisms include piezophiles, which tolerate pressure of 130 MPa. Weight-tolerant organisms include barophiles. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt-tolerant organisms include halophiles (e.g., 2-5 M NaCl) *Halobacteriacea* and *Dunaliella salina*. pH-tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas-tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New YorK: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea.*

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyano-*

*phyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis*, and *Zygonium*. A partial list of cyanobacteria that can be engineered to express recombinant AAR and ADM enzymes is also provided in Table 1 and Table 2, herein. Additional cyanobacteria include members of the genus *Chamaesiphon, Chroococcus, Cyanobacterium, Cyanobium, Cyanothece, Dactylococcopsis, Gloeobacter, Gloeocapsa, Gloeothece, Microcystis, Prochlorococcus, Prochloron, Synechococcus, Synechocystis, Cyanocystis, Dermocarpella, Stanieria, Xenococcus, Chroococcidiopsis, Myxosarcina, Arthrospira, Borzia, Crinalium, Geitlerinemia, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Cyanospira, Cylindrospermopsis, Cylindrospermum, Nodularia, Nostoc, Scylonema, Calothrix, Rivularia, Tolypothrix, Chlorogloeopsis, Fischerella, Geitieria, Iyengariella, Nostochopsis, Stigonema* and *Thermosynechococcus*.

Green non-sulfur bacteria include but are not limited to the following genera: *Chloroflexus, Chloronema, Oscillochloris, Heliothrix, Herpetosiphon, Roseiflexus*, and *Thermomicrobium*.

Green sulfur bacteria include but are not limited to the following genera:

*Chlorobium, Clathrochloris, and Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus, and Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic S-Metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

Preferred organisms for the manufacture of n-alkanes according to the methods disclosed herein include: *Arabidopsis thaliana, Panicum virgatum, Miscanthus giganteus*, and *Zea mays* (plants); *Botryococcus braunii, Chlamydomonas reinhardtii* and *Dunaliela salina* (algae); *Synechococcus* sp PCC 7002, *Synechococcus* sp. PCC 7942, *Synechocystis* sp. PCC 6803, *Thermosynechococcus elongatus* BP-1 (cyanobacteria); *Chlorobium tepidum* (green sulfur bacteria), *Chloroflexus auranticus* (green non-sulfur bacteria); *Chromatium tepidum* and *Chromatium vinosum* (purple sulfur bacteria); *Rhodospirillum rubrum, Rhodobacter capsulatus*, and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix inorganic carbon bacteria such as *Escherichia coli, Acetobacter aceti, Bacillus subtilis*, yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis.*

A suitable organism for selecting or engineering is autotrophic fixation of $CO_2$ to products. This would cover photosynthesis and methanogenesis. Acetogenesis, encompassing the three types of $CO_2$ fixation; Calvin cycle, acetyl-CoA pathway and reductive TCA pathway is also covered. The capability to use inorganic carbon as the sole source of cell carbon (autotrophy) is found in almost all major groups of prokaryotes. The $CO_2$ fixation pathways differ between groups, and there is no clear distribution pattern of the four presently-known autotrophic pathways. See, e.g., Fuchs, G. 1989. *Alternative pathways of autotrophic $CO_2$ fixation*, p. 365-382. In H. G. Schlegel, and B. Bowien (ed.), *Autotrophic bacteria*. Springer-Verlag, Berlin, Germany. The reductive pentose phosphate cycle (Calvin-Bassham-Benson cycle) represents the $CO_2$ fixation pathway in almost all aerobic autotrophic bacteria, for example, the cyanobacteria.

For producing n-alkanes via the recombinant expression of AAR and/or ADM enzymes, an engineered cyanobacteria, e.g., a *Synechococcus* or *Thermosynechococcus* species, is preferred. Other preferred organisms include *Synechocystis, Klebsiella oxytoca, Escherichia coli* or *Saccharomyces cerevisiae*. Other prokaryotic, archaea and eukaryotic host cells are also encompassed within the scope of the present invention.

Carbon-Based Products of Interest: Hydrocarbons & Alcohols

In various embodiments of the invention, desired hydrocarbons and/or alcohols of certain chain length or a mixture thereof can be produced. In certain aspects, the host cell produces at least one of the following carbon-based products of interest: 1-dodecanol, 1-tetradecanol, 1-pentadecanol, n-tridecane, n-tetradecane, 15:1 n-pentadecane, n-pentadecane, 16:1 n-hexadecene, n-hexadecane, 17:1 n-heptadecene, n-heptadecane, 16:1 n-hexadecen-ol, n-hexadecan-1-ol and n-octadecen-1-ol, as shown in the Examples herein. In other aspects, the carbon chain length ranges from $C_{10}$ to $C_{20}$. Accordingly, the invention provides production of various chain lengths of alkanes, alkenes and alkanols suitable for use as fuels & chemicals.

In preferred aspects, the methods provide culturing host cells for direct product secretion for easy recovery without the need to extract biomass. These carbon-based products of interest are secreted directly into the medium. Since the invention enables production of various defined chain length of hydrocarbons and alcohols, the secreted products are easily recovered or separated. The products of the invention, therefore, can be used directly or used with minimal processing.

Fuel Compositions

In various embodiments, compositions produced by the methods of the invention are used as fuels. Such fuels comply with ASTM standards, for instance, standard specifications for diesel fuel oils D 975-09b, and Jet A, Jet A-1 and Jet B as specified in ASTM Specification D. 1655-68. Fuel compositions may require blending of several products to produce a uniform product. The blending process is relatively straightforward, but the determination of the amount of each component to include in a blend is much more difficult. Fuel compositions may, therefore, include aromatic and/or branched hydrocarbons, for instance, 75% saturated and 25% aromatic, wherein some of the saturated hydrocarbons are branched and some are cyclic. Preferably, the methods of the invention produce an array of hydrocarbons, such as $C_{13}$-$C_{17}$ or $C_{10}$-$C_{15}$ to alter cloud point. Furthermore, the compositions may comprise fuel additives, which are used to enhance the performance of a fuel or engine. For example, fuel additives can be used to alter the freezing/gelling point, cloud point, lubricity, viscosity, oxidative stability, ignition quality, octane level, and flash point. Fuels compositions may also comprise, among others, antioxidants, static dissipater, corrosion inhibitor, icing inhibitor, biocide, metal deactivator and thermal stability improver.

In addition to many environmental advantages of the invention such as $CO_2$ conversion and renewable source, other advantages of the fuel compositions disclosed herein include low sulfur content, low emissions, being free or substantially free of alcohol and having high cetane number.

Carbon Fingerprinting

Biologically-produced carbon-based products, e.g., ethanol, fatty acids, alkanes, isoprenoids, represent a new commodity for fuels, such as alcohols, diesel and gasoline. Such biofuels have not been produced using biomass but use CO2 as its carbon source. These new fuels may be distinguishable from fuels derived form petrochemical carbon on the basis of dual carbon-isotopic fingerprinting. Such products, derivatives, and mixtures thereof may be completely distinguished from their petrochemical derived counterparts on the basis of $^{14}C$ (fM) and dual carbon-isotopic fingerprinting, indicating new compositions of matter.

There are three naturally occurring isotopes of carbon: $^{12}C$, $^{13}C$, and $^{14}C$. These isotopes occur in above-ground total carbon at fractions of 0.989, 0.011, and $10^{-12}$, respectively. The isotopes $^{12}C$ and $^{13}C$ are stable, while $^{14}C$ decays naturally to $^{14}N$, a beta particle, and an anti-neutrino in a process with a half-life of 5730 years. The isotope $^{14}C$ originates in the atmosphere, due primarily to neutron bombardment of $^{14}N$ caused ultimately by cosmic radiation. Because of its relatively short half-life (in geologic terms), $^{14}C$ occurs at extremely low levels in fossil carbon. Over the course of 1 million years without exposure to the atmosphere, just 1 part in $10^{50}$ will remain $^{14}C$.

The $^{13}C$:$^{12}C$ ratio varies slightly but measurably among natural carbon sources. Generally these differences are expressed as deviations from the $^{13}C$:$^{12}C$ ratio in a standard material. The international standard for carbon is Pee Dee Belemnite, a form of limestone found in South Carolina, with a $^{13}C$ fraction of 0.0112372. For a carbon source a, the deviation of the $^{13}C$:$^{12}C$ ratio from that of Pee Dee Belemnite is expressed as: $(\delta_a=(R_a/R_s)-1$, where $R_a$=$^{13}C$:$^{12}C$ ratio in the natural source, and $R_s$=$^{13}C$:$^{12}C$ ratio in Pee Dee Belemnite, the standard. For convenience, $\delta_a$ is expressed in parts per thousand, or ‰. A negative value of $\delta_a$ shows a bias toward $^{12}C$ over $^{13}C$ as compared to Pee Dee Belemnite. Table A shows $\delta_a$ and $^{14}C$ fraction for several natural sources of carbon.

TABLE A

13C:12C variations in natural carbon sources

| Source | $-\delta_a$ (‰) | References |
|---|---|---|
| Underground coal | 32.5 | Farquhar et al. (1989) *Plant Mol. Biol.*, 40: 503-37 |
| Fossil fuels | 26 | Farquhar et al. (1989) *Plant Mol. Biol.*, 40: 503-37 |
| Ocean DIC* | 0-1.5 | Goericke et al. (1994) Chapter 9 in *Stable Isotopes in Ecology and Environmental Science*, by K. Lajtha and R. H. Michener, Blackwell Publishing; Ivlev (2010) *Separation Sci. Technol.* 36: 1819-1914 |
| Atmospheric CO2 | 6-8 | Ivlev (2010) *Separation Sci. Technol.* 36: 1819-1914; Farquhar et al. (1989) *Plant Mol. Biol.*, 40: 503-37 |
| Freshwater DIC* | 6-14 | Dettman et al. (1999) *Geochim. Cosmochim. Acta* 63: 1049-1057 |
| Pee Dee Belemnite | 0 | Ivlev (2010) *Separation Sci. Technol.* 36: 1819-1914 |

*DIC = dissolved inorganic carbon

Biological processes often discriminate among carbon isotopes. The natural abundance of $^{14}C$ is very small, and hence discrimination for or against $^{14}C$ is difficult to measure. Biological discrimination between $^{13}C$ and $^{12}C$, however, is well-documented. For a biological product p, we can define similar quantities to those above: $\delta_p=(R_p/R_s)-1$, where $R_p$=$^{13}C$:$^{12}C$ ratio in the biological product, and $R_s$=$^{13}C$:$^{12}C$ ratio in Pee Dee Belemnite, the standard. Table B shows measured deviations in the $^{13}C$:$^{12}C$ ratio for some biological products.

TABLE B $^{13}C$:$^{12}C$ variations in selected biological products

| Product | $-\delta_p$ (‰) | $-D$ (‰)* | References |
|---|---|---|---|
| Plant sugar/starch from atmospheric $CO_2$ | 18-28 | 10-20 | Ivlev (2010) *Separation Sci. Technol.* 36: 1819-1914 |
| Cyanobacterial biomass from marine DIC | 18-31 | 16.5-31 | Goericke et al. (1994) Chapter 9 in *Stable Isotopes in Ecology and Environmental Science*, by K. Lajtha and R. H. Michener, Blackwell Publishing; Sakata et al. (1997) *Geochim. Cosmochim. Acta*, 61: 5379-89 |
| Cyanobacterial lipid from marine DIC | 39-40 | 37.5-40 | Sakata et al. (1997) *Geochim. Cosmochim. Acta*, 61: 5379-89 |
| Algal lipid from marine DIC | 17-28 | 15.5-28 | Goericke et al. (1994) Chapter 9 in *Stable Isotopes in Ecology and Environmental Science*, by K. Lajtha and R. H. Michener, Blackwell Publishing; Abelseon et al. (1961) *Proc. Natl. Acad. Sci.*, 47: 623-32 |
| Algal biomass from freshwater DIC | 17-36 | 3-30 | Marty et al. (2008) *Limnol. Oceanogr.: Methods* 6: 51-63 |
| *E. coli* lipid from plant sugar | 15-27 | near 0 | Monson et al. (1980) *J. Biol. Chem.*, 255: 11435-41 |
| Cyanobacterial lipid from fossil carbon | 63.5-66 | 37.5-40 | — |
| Cyanobacterial biomass from fossil carbon | 42.5-57 | 16.5-31 | — |

*D = discrimination by a biological process in its utilization of $^{12}C$ vs. $^{13}C$ (see text)

Table B introduces a new quantity, D. This is the discrimination by a biological process in its utilization of $^{12}C$ vs. $^{13}C$. We define D as follows: $D=(R_p/R_a)-1$. This quantity is very similar to $\delta_a$ and $\delta_p$, except we now compare the biological product directly to the carbon source rather than to a standard. Using D, we can combine the bias effects of a carbon source and a biological process to obtain the bias of the biological product as compared to the standard. Solving for $\delta_p$, we obtain: $\delta_p=(D)(\delta_a)+D+\delta_a$, and, because $(D)(\delta_a)$ is generally very small compared to the other terms, $\delta_p\approx\delta_a+D$.

For a biological product having a production process with a known D, we may therefore estimate $\delta_p$ by summing $\delta_a$ and D. We assume that D operates irrespective of the carbon source. This has been done in Table B for cyanobacterial lipid and biomass produced from fossil carbon. As shown in the Table A and Table B, above, cyanobacterial products made from fossil carbon (in the form of, for example, flue gas or other emissions) will have a higher $\delta_p$ than those of comparable biological products made from other sources, distinguishing them on the basis of composition of matter from these other biological products. In addition, any product derived solely from fossil carbon will have a negligible fraction of $^{14}C$, while products made from above-ground carbon will have a $^{14}C$ fraction of approximately $10^{-12}$.

Accordingly, in certain aspects, the invention provides various carbon-based products of interest characterized as $-\delta_p$(‰) of about 63.5 to about 66 and −D(‰) of about 37.5 to about 40.

Antibodies

In another aspect, the present invention provides isolated antibodies, including fragments and derivatives thereof that bind specifically to the isolated polypeptides and polypeptide fragments of the present invention or to one or more of the polypeptides encoded by the isolated nucleic acids of the present invention. The antibodies of the present invention may be specific for linear epitopes, discontinuous epitopes or conformational epitopes of such polypeptides or polypeptide fragments, either as present on the polypeptide in its native conformation or, in some cases, as present on the polypeptides as denatured, as, e.g., by solubilization in SDS. Among the useful antibody fragments provided by the instant invention are Fab, Fab', Fv, $F(ab')_2$, and single chain Fv fragments.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies of the present invention will discriminate over adventitious binding to unrelated polypeptides by at least two-fold, more typically by at least 5-fold, typically by more than 10-fold, 25-fold, 50-fold, 75-fold, and often by more than 100-fold, and on occasion by more than 500-fold or 1000-fold.

Typically, the affinity or avidity of an antibody (or antibody multimer, as in the case of an IgM pentamer) of the present invention for a polypeptide or polypeptide fragment of the present invention will be at least about $1\times10^{-6}$ M, typically at least about $5\times10^{-7}$ M, usefully at least about $1\times10^{-7}$ M, with affinities and avidities of $1\times10^{-8}$ M, $5\times10^{-9}$ M, $1\times10^{-10}$ M and even stronger proving especially useful.

The isolated antibodies of the present invention may be naturally-occurring forms, such as IgG, IgM, IgD, IgE, and IgA, from any mammalian species. For example, antibodies are usefully obtained from species including rodents-typically mouse, but also rat, guinea pig, and hamster-lagomorphs, typically rabbits, and also larger mammals, such as sheep, goats, cows, and horses. The animal is typically affirmatively immunized, according to standard immunization protocols, with the polypeptide or polypeptide fragment of the present invention.

Virtually all fragments of 8 or more contiguous amino acids of the polypeptides of the present invention may be used effectively as immunogens when conjugated to a carrier, typically a protein such as bovine thyroglobulin, keyhole limpet hemocyanin, or bovine serum albumin, conveniently using a bifunctional linker. Immunogenicity may also be conferred by fusion of the polypeptide and polypeptide fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. See, e.g., Tam et al., *Proc. Natl. Acad. Sci. USA* 85:5409-5413 (1988); Posnett et al., *J. Biol. Chem.* 263, 1719-1725 (1988).

Protocols for immunization are well-established in the art. Such protocols often include multiple immunizations, either with or without adjuvants such as Freund's complete adjuvant and Freund's incomplete adjuvant. Antibodies of the present invention may be polyclonal or monoclonal, with polyclonal antibodies having certain advantages in immuno-histochemical detection of the proteins of the present invention and monoclonal antibodies having advantages in identifying and distinguishing particular epitopes of the proteins of the present invention. Following immunization, the antibodies of the present invention may be produced using any art-accepted technique. Host cells for recombinant antibody production—either whole antibodies, antibody fragments, or antibody derivatives—can be prokaryotic or eukaryotic. Prokaryotic hosts are particularly useful for producing phage displayed antibodies, as is well known in the art. Eukaryotic cells, including mammalian, insect, plant and fungal cells are also useful for expression of the antibodies, antibody fragments, and antibody derivatives of the present invention. Antibodies of the present invention can also be prepared by cell free translation.

The isolated antibodies of the present invention, including fragments and derivatives thereof, can usefully be labeled. It is, therefore, another aspect of the present invention to provide labeled antibodies that bind specifically to one or more of the polypeptides and polypeptide fragments of the present invention. The choice of label depends, in part, upon the desired use. In some cases, the antibodies of the present invention may usefully be labeled with an enzyme. Alternatively, the antibodies may be labeled with colloidal gold or with a fluorophore. For secondary detection using labeled avidin, streptavidin, captavidin or neutravidin, the antibodies of the present invention may usefully be labeled with biotin. When the antibodies of the present invention are used, e.g., for Western blotting applications, they may usefully be labeled with radioisotopes, such as $^{33}P$, $^{32}P$, $^{35}S$, $^{3}H$ and $^{125}I$. As would be understood, use of the labels described above is not restricted to any particular application.

The following examples are for illustrative purposes and are not intended to limit the scope of the present invention.

Example 1

A Pathway for the Enzymatic Synthesis of n-Alkanes

An enzymatic process for the production of n-alkanes in, e.g., cyanobacteria is based on the sequential activity of (1) an AAR enzyme, e.g., tll1312, an acyl-ACP reductase; and (2) an ADM enzyme, e.g., tll1313, a putative alkanal deformylative monooxygenase, The AAR activity is distinct from the relatively well characterized acyl-CoA reductase activity exhibited by proteins such as Acr1 from *Acinetobacter calcoaceticus* (Reiser S and Somerville C (1997) *J. Bacteriol.* 179:2969-2975). A membranous ADM activity has previously been identified in insect microsomal preparations (Reed J R et al. (1994) *Proc. Natl. Acad. Sci. USA* 91:10000-10004; Reed J R et al. (1995) *Musca domestica. Biochemistry* 34:16221-16227).

Figure 1B:
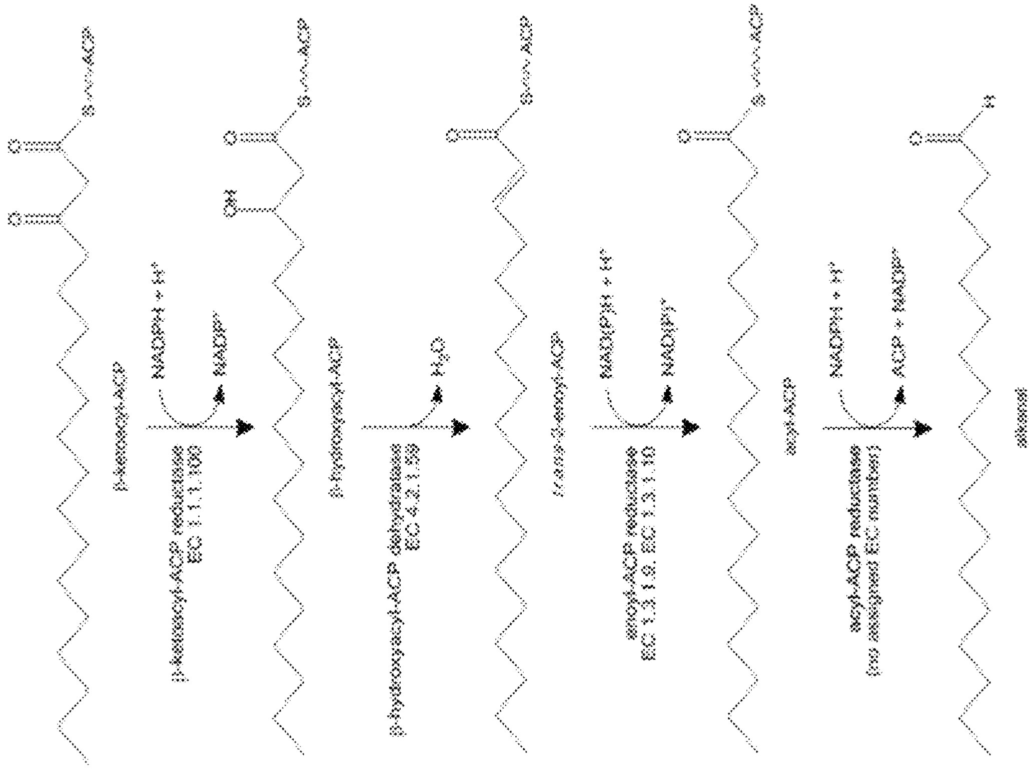

FIGS. 1A and 1B summarize the names and activities of the enzymes involved in the biosynthesis of n-alkanals. FIG. 1A depicts the relatively well characterized acyl-CoA reductase activity (EC 1.2.1.50) exhibited by proteins such as Acr1 from *Acinetobacter calcoaceticus*. In FIG. 1B, the two well-known ACP-related reductases that are involved in fatty acid biosynthesis, β-ketoacyl-ACP reductase (EC 1.1.1.100) and enoyl-ACP reductase (EC 1.3.1.9, 1.3.1.10), are contrasted with the acyl-ACP reductase (AAR) (no EC number yet assigned) believed to be involved in the biosynthetic pathway for n-alkanes in cyanobacteria. The key difference between AAR and acyl-CoA reductase (EC 1.2.1.50) is that ACP is the acyl carrier rather than coenzyme A. Supporting this distinction, it has been shown that acyl-CoA reductase Acr1 from *Acinetobacter calcoaceticus* can only generate alkanals from acyl-CoA and not acyl-ACP (Resier S and Somerville C (1997) *J Bacteriol.* 179: 2969-2975).

ADM also lacks a presently assigned EC number. An alkanal monooxygenase (EC 1.14.14.3), often referred to as luciferase, is known to catalyze the conversion of n-alkanal to n-alkanoic acid. This activity is distinct from the ADM activity (n-alkanal to (n−1)-alkane) proposed herein, although both use n-alkanal and molecular oxygen as substrates.

Cyanobacterial AAR and ADM Homologs for Production of n-Alkanes.

In this example, homologs of cyanobacterial AAR and ADM genes (e.g., homologs of *Synechococcus elongatus* PCC 7942 SYNPCC7942_1594 and/or SYNPCC7942_1593 protein, respectively) are identified using a BLAST search. These proteins can be expressed in a variety of organisms (bacteria, yeast, plant, etc.) for the purpose of generating and isolating n-alkanes and other desired carbon-based products of interest from the organisms. A search of the non-redundant BLAST protein database revealed counterparts for each protein in other cyanobacteria.

To determine the degree of similarity among homologs of the *Synechococcus elongatus* PCC 7942 SYNPCC7942_1594 protein, the 341-amino acid protein sequence was queried using BLAST (http://blast.ncbi.nlm.nih.gov/) against the "nr" non-redundant protein database. Homologs were taken as matching proteins whose alignments (i) covered >90% length of SYNPCC7942_1594, (ii) covered >90% of the length of the matching protein, and (iii) had >50% identity with SYNPCC7942_1594 (Table 1).

TABLE 1

Protein homologs of SYNPCC7942_1594 (AAR)

| Organism | SEQ ID NO: | Homolog accession # | BLAST Score, E-value |
|---|---|---|---|
| *Synechococcus elongatus* PCC 7942 | 6 | (SYNPCC7942_1594) | n/a |
| *Synechococcus elongatus* PCC 7942 [cyanobacteria] taxid 1140 | 45 | YP_400611.1 | 706, 0.0 |
| *Synechococcus elongatus* PCC 6301 [cyanobacteria] taxid 269084 | 46 | YP_170761.1 | 706, 0.0 |
| *Anabaena variabilis* ATCC 29413 [cyanobacteria] taxid 240292 | 47 | YP_323044.1 | 538, 4e−151 |
| *Nostoc* sp. PCC 7120 [cyanobacteria] taxid 103690 | 48 | NP_489324.1 | 535, 3e−150 |
| '*Nostoc azollae*' 0708 [cyanobacteria] taxid 551115 | 49 | ZP_03763674.1 | 533, 1e−149 |
| *Cyanothece* sp. PCC 7425 [cyanobacteria] taxid 395961 | 50 | YP_002481152.1 | 526, 9e−148 |
| *Nodularia spumigena* CCY 9414 [cyanobacteria] taxid 313624 | 51 | ZP_01628095.1 | 521, 3e−146 |
| *Lyngbya* sp. PCC 8106 [cyanobacteria] taxid 313612 | 52 | ZP_01619574.1 | 520, 6e−146 |
| *Nostoc punctiforme* PCC 73102 [cyanobacteria] taxid 63737 | 53 | YP_001865324.1 | 520, 7e−146 |
| *Trichodesmium erythraeum* IMS101 [cyanobacteria] taxid 203124 | 54 | YP_721978.1 | 517, 6e−145 |
| *Thermosynechococcus elongatus* BP-1 [cyanobacteria] taxid 197221 | 2 | NP_682102.1 | 516, 2e−144 |
| *Acaryochloris marina* MBIC11017 [cyanobacteria] taxid 329726 | 55 | YP_001518341.1 | 512, 2e−143 |
| *Cyanothece* sp. PCC 8802 [cyanobacteria] taxid 395962 | 56 | ZP_03142196.1 | 510, 8e−143 |
| *Cyanothece* sp. PCC 8801 [cyanobacteria] taxid 41431 | 57 | YP_002371106.1 | 510, 8e−143 |

TABLE 1-continued

| Protein homologs of SYNPCC7942_1594 (AAR) | | | |
|---|---|---|---|
| Organism | SEQ ID NO: | Homolog accession # | BLAST Score, E-value |
| *Microcoleus chthonoplastes* PCC 7420 [cyanobacteria] taxid 118168 | 58 | YP_002619867.1 | 509, 2e−142 |
| *Arthrospira maxima* CS-328 [cyanobacteria] taxid 513049 | 59 | ZP_03273554.1 | 507, 7e−142 |
| *Synechocystis* sp. PCC 6803 [cyanobacteria] taxid 1148 | 60 | NP_442146.1 | 504, 5e−141 |
| *Cyanothece* sp. CCY 0110 [cyanobacteria] taxid 391612 | 61 | ZP_01728620.1 | 501, 4e−140 |
| *Synechococcus* sp. PCC 7335 [cyanobacteria] taxid 91464 | 62 | YP_002711557.1 | 500, 1e−139 |
| *Cyanothece* sp. ATCC 51142 [cyanobacteria] taxid 43989 | 63 | YP_001802846.1 | 489, 2e−136 |
| *Gloeobacter violaceus* PCC 7421 [cyanobacteria] taxid 251221 | 64 | NP_926091.1 | 487, 7e−136 |
| *Microcystis aeruginosa* NIES-843 [cyanobacteria] taxid 449447 | 65 | YP_001660322.1 | 486, 1e−135 |
| *Crocosphaera watsonii* WH 8501 [cyanobacteria] taxid 165597 | 66 | ZP_00516920.1 | 486, 1e−135 |
| *Microcystis aeruginosa* PCC 7806 [cyanobacteria] taxid 267872 | 67 | emb\|CAO90781.1 | 484, 8e−135 |
| *Synechococcus* sp. WH 5701 [cyanobacteria] taxid 69042 | 68 | ZP_01085337.1 | 471, 4e−131 |
| *Synechococcus* sp. RCC307 [cyanobacteria] taxid 316278 | 69 | YP_001227841.1 | 464, 8e−129 |
| uncultured marine type-A *Synechococcus* GOM 3O6 [cyanobacteria] taxid 364150 | 70 | gb\|ABD96327.1 | 462, 2e−128 |
| *Synechococcus* sp. WH 8102 [cyanobacteria] taxid 84588 | 71 | NP_897828.1 | 462, 2e−128 |
| *Synechococcus* sp. WH 7803 [cyanobacteria] taxid 32051 | 72 | YP_001224378.1 | 459, 2e−127 |
| uncultured marine type-A *Synechococcus* GOM 5D20 [cyanobacteria] taxid 364154 | 73 | gb\|ABD96480.1 | 458, 3e−127 |
| *Synechococcus* sp. WH 7805 [cyanobacteria] taxid 59931 | 74 | ZP_01123215.1 | 457, 5e−127 |
| uncultured marine type-A Synechococcus 5B2 [cyanobacteria] taxid 359140 | 75 | gb\|ABB92249.1 | 457, 8e−127 |
| *Synechococcus* sp. RS9917 [cyanobacteria] taxid 221360 | 76 | ZP_01079773.1 | 456, 2e−126 |
| *Synechococcus* sp. CC9902 [cyanobacteria] taxid 316279 | 77 | YP_377636.1 | 454, 6e−126 |
| *Prochlorococcus marinus* subsp. marinus str. CCMP1375 [cyanobacteria] taxid 167539 | 78 | NP_874926.1 | 453, 9e−126 |
| *Prochlorococcus marinus* str. MIT 9313 [cyanobacteria] taxid 74547 | 79 | NP_895058.1 | 453, 1e−125 |
| uncultured marine type-A *Synechococcus* GOM 3M9 [cyanobacteria] taxid 364149 | 80 | gb\|ABD96274.1 | 452, 2e−125 |

TABLE 1-continued

| Protein homologs of SYNPCC7942_1594 (AAR) | | | |
|---|---|---|---|
| Organism | SEQ ID NO: | Homolog accession # | BLAST Score, E-value |
| uncultured marine type-A *Synechococcus* GOM 4P21 [cyanobacteria] taxid 364153 | 81 | gb\|ABD96442.1 | 452, 2e−125 |
| *Synechococcus* sp. BL107 [cyanobacteria] taxid 313625 | 82 | ZP_01469469.1 | 452, 2e−125 |
| *Cyanobium* sp. PCC 7001 [cyanobacteria] taxid 180281 | 83 | YP_002597253.1 | 451, 4e−125 |
| *Prochlorococcus marinus* str. NATL1A [cyanobacteria] taxid 167555 | 84 | YP_001014416.1 | 449, 2e−124 |
| *Prochlorococcus marinus* str. MIT 9515 [cyanobacteria] taxid 167542 | 85 | YP_001010913.1 | 447, 6e−124 |
| *Synechococcus* sp. CC9605 [cyanobacteria] taxid 110662 | 86 | YP_381056.1 | 447, 8e−124 |
| *Prochlorococcus marinus* str. MIT 9211 [cyanobacteria] taxid 93059 | 87 | YP_001550421.1 | 446, 2e−123 |
| *Prochlorococcus marinus* subsp. *pastoris* str. CCMP1986 [cyanobacteria] taxid 59919 | 88 | NP_892651.1 | 446, 2e−123 |
| *Prochlorococcus marinus* str. MIT 9301 [cyanobacteria] taxid 167546 | 89 | YP_001090783.1 | 445, 3e−123 |
| *Synechococcus* sp. RS9916 [cyanobacteria] taxid 221359 | 90 | ZP_01472595.1 | 445, 3e−123 |
| *Prochlorococcus marinus* str. NATL2A [cyanobacteria] taxid 59920 | 91 | YP_293055.1 | 445, 4e−123 |
| *Prochlorococcus marinus* str. MIT 9202 [cyanobacteria] taxid 93058 | 92 | YP_002673377.1 | 444, 7e−123 |
| *Synechococcus* sp. CC9311 [cyanobacteria] taxid 64471 | 93 | YP_731192.1 | 443, 1e−122 |
| *Prochlorococcus marinus* str. MIT 9215 [cyanobacteria] taxid 93060 | 94 | YP_001483815.1 | 442, 2e−122 |
| *Prochlorococcus marinus* str. AS9601 [cyanobacteria] taxid 146891 | 95 | YP_001008982.1 | 442, 3e−122 |
| *Synechococcus* sp. JA-3-3Ab [cyanobacteria] taxid 321327 | 96 | YP_473896.1 | 441, 5e−122 |
| *Synechococcus* sp. JA-2-3B'a(2-13) [cyanobacteria] taxid 321332 | 97 | YP_478638.1 | 440, 8e−122 |
| *Prochlorococcus marinus* str. MIT 9312 [cyanobacteria] taxid 74546 | 98 | YP_397030.1 | 436, 1e−120 |

To determine the degree of similarity among homologs of the *Synechococcus elongatus* PCC 7942 SYNPCC7942_1593 protein, the 231 amino acid protein sequence was queried using BLAST (http://blast.ncbi.nlm.nih.gov/) against the "nr" non-redundant protein database. Homologs were taken as matching proteins whose alignments (i) covered >90% length of SYNPCC7942_1593, (ii) covered >90% of the length of the matching protein, (iii) and had >50% identity with SYNPCC7942_1593 (Table 2).

TABLE 2

| Protein homologs of SYNPCC7942_1593 (ADM) | | | |
|---|---|---|---|
| Organism | SEQ ID NO: | Homolog accession # | BLAST Score, E-value |
| *Synechococcus elongatus* PCC 7942 [cyanobacteria] | 8 | (SYNPCC7942_1593) | n/a |

TABLE 2-continued

| Protein homologs of SYNPCC7942_1593 (ADM) | | | |
|---|---|---|---|
| Organism | SEQ ID NO: | Homolog accession # | BLAST Score, E-value |
| *Synechococcus elongatus* PCC 7942 [cyanobacteria] taxid 1140 | 99 | YP_400610.1 | 475, 1e−132 |
| *Synechococcus elongatus* PCC 6301 [cyanobacteria] taxid 269084 | 100 | YP_170760.1 | 475, 2e−132 |
| *Arthrospira maxima* CS-328 [cyanobacteria] taxid 513049 | 101 | ZP_03273549.1 | 378, 3e−103 |
| *Microcoleus chthonoplastes* PCC 7420 [cyanobacteria] taxid 118168 | 102 | YP_002619869.1 | 376, 1e−102 |
| *Lyngbya* sp. PCC 8106 [cyanobacteria] taxid 313612 | 103 | ZP_01619575.1 | 374, 5e−102 |
| *Nodularia spumigena* CCY 9414 [cyanobacteria] taxid 313624 | 104 | ZP_01628096.1 | 369, 1e−100 |
| *Microcystis aeruginosa* NIES-843 [cyanobacteria] taxid 449447 | 105 | YP_001660323.1 | 367, 5e−100 |
| *Microcystis aeruginosa* PCC 7806 [cyanobacteria] taxid 267872 | 106 | emb\|CAO90780.1 | 364, 3e−99 |
| *Nostoc* sp. PCC 7120 [cyanobacteria] taxid 103690 | 107 | NP_489323.1 | 363, 1e−98 |
| *Anabaena variabilis* ATCC 29413 [cyanobacteria] taxid 240292 | 108 | YP_323043.1 | 362, 2e−98 |
| *Crocosphaera watsonii* WH 8501 [cyanobacteria] taxid 165597 | 109 | ZP_00514700.1 | 359, 1e−97 |
| *Trichodesmium erythraeum* IMS101 [cyanobacteria] taxid 203124 | 110 | YP_721979.1 | 358, 2e−97 |
| *Synechococcus* sp. PCC 7335 [cyanobacteria] taxid 91464 | 111 | YP_002711558.1 | 357, 6e−97 |
| '*Nostoc azollae*' 0708 [cyanobacteria] taxid 551115 | 112 | ZP_03763673.1 | 355, 3e−96 |
| *Synechocystis* sp. PCC 6803 [cyanobacteria] taxid 1148 | 113 | NP_442147.1 | 353, 5e−96 |
| *Cyanothece* sp. ATCC 51142 [cyanobacteria] taxid 43989 | 114 | YP_001802195.1 | 352, 2e−95 |
| *Cyanothece* sp. CCY 0110 [cyanobacteria] taxid 391612 | 115 | ZP_01728578.1 | 352, 2e−95 |
| *Cyanothece* sp. PCC 7425 [cyanobacteria] taxid 395961 | 116 | YP_002481151.1 | 350, 7e−95 |
| *Nostoc punctiforme* PCC 73102 [cyanobacteria] taxid 63737 | 117 | YP_001865325.1 | 349, 1e−94 |
| *Acaryochloris marina* MBIC11017 [cyanobacteria] taxid 329726 | 118 | YP_001518340.1 | 344, 4e−93 |
| *Cyanothece* sp. PCC 8802 [cyanobacteria] taxid 395962 | 119 | ZP_03142957.1 | 342, 1e−92 |
| *Cyanothece* sp. PCC 8801 [cyanobacteria] taxid 41431 | 120 | YP_002370707.1 | 342, 1e−92 |
| *Thermosynechococcus elongatus* BP-1 [cyanobacteria] taxid 197221 | 4 | NP_682103.1 | 332, 2e−89 |
| *Synechococcus* sp. JA-2-3B'a(2-13) [cyanobacteria] taxid 321332 | 121 | YP_478639.1 | 319, 1e−85 |
| *Synechococcus* sp. RCC307 [cyanobacteria] taxid 316278 | 122 | YP_001227842.1 | 319, 1e−85 |
| *Synechococcus* sp. WH 7803 [cyanobacteria] taxid 32051 | 123 | YP_001224377.1 | 313, 8e−84 |
| *Synechococcus* sp. WH 8102 [cyanobacteria] taxid 84588 | 124 | NP_897829.1 | 311, 3e−83 |

TABLE 2-continued

| Protein homologs of SYNPCC7942_1593 (ADM) | | | |
|---|---|---|---|
| Organism | SEQ ID NO: | Homolog accession # | BLAST Score, E-value |
| *Synechococcus* sp. WH 7805 [cyanobacteria] taxid 59931 | 125 | ZP_01123214.1 | 310, 6e−83 |
| uncultured marine type-A Synechococcus GOM 3O12 [cyanobacteria] taxid 364151 | 126 | gb\|ABD96376.1 | 309, 1e−82 |
| *Synechococcus* sp. JA-3-3Ab [cyanobacteria] taxid 321327 | 127 | YP_473897.1 | 309, 1e−82 |
| uncultured marine type-A *Synechococcus* GOM 3O6 [cyanobacteria] taxid 364150 | 128 | gb\|ABD96328.1 | 309, 1e−82 |
| uncultured marine type-A *Synechococcus* GOM 3M9 [cyanobacteria] taxid 364149 | 129 | gb\|ABD96275.1 | 308, 2e−82 |
| *Synechococcus* sp. CC9311 [cyanobacteria] taxid 64471 | 130 | YP_731193.1 | 306, 7e−82 |
| uncultured marine type-A *Synechococcus* 5B2 [cyanobacteria] taxid 359140 | 131 | gb\|ABB92250.1 | 306, 9e−82 |
| *Synechococcus* sp. WH 5701 [cyanobacteria] taxid 69042 | 132 | ZP_01085338.1 | 305, 3e−81 |
| *Gloeobacter violaceus* PCC 7421 [cyanobacteria] taxid 251221 | 133 | NP_926092.1 | 303, 8e−81 |
| *Synechococcus* sp. RS9916 [cyanobacteria] taxid 221359 | 134 | ZP_01472594.1 | 303, 9e−81 |
| *Synechococcus* sp. RS9917 [cyanobacteria] taxid 221360 | 135 | ZP_01079772.1 | 300, 6e−80 |
| *Synechococcus* sp. CC9605 [cyanobacteria] taxid 110662 | 136 | YP_381055.1 | 300, 7e−80 |
| *Prochlorococcus marinus* str. MIT 9303 [cyanobacteria] taxid 59922 | 137 | YP_001016795.1 | 294, 4e−78 |
| *Cyanobium* sp. PCC 7001 [cyanobacteria] taxid 180281 | 138 | YP_002597252.1 | 294, 6e−78 |
| *Prochlorococcus marinus* str. MIT 9313 [cyanobacteria] taxid 74547 | 139 | NP_895059.1 | 291, 3e−77 |
| *Synechococcus* sp. CC9902 [cyanobacteria] taxid 316279 | 140 | YP_377637.1 | 289, 1e−76 |
| *Prochlorococcus marinus* str. MIT 9301 [cyanobacteria] taxid 167546 | 141 | YP_001090782.1 | 287, 5e−76 |
| *Synechococcus* sp. BL107 [cyanobacteria] taxid 313625 | 142 | ZP_01469468.1 | 287, 6e−76 |
| *Prochlorococcus marinus* str. AS9601 [cyanobacteria] taxid 146891 | 143 | YP_001008981.1 | 286, 2e−75 |
| *Prochlorococcus marinus* str. MIT 9312 [cyanobacteria] taxid 74546 | 12 | YP_397029.1 | 282, 1e−74 |
| *Prochlorococcus marinus* subsp. pastoris str. CCMP1986 [cyanobacteria] taxid 59919 | 144 | NP_892650.1 | 280, 9e−74 |
| *Prochlorococcus marinus* str. MIT 9211 [cyanobacteria] taxid 93059 | 145 | YP_001550420.1 | 279, 2e−73 |
| *Prochlorococcus marinus* str. NATL2A [cyanobacteria] taxid 59920 | 146 | YP_293054.1 | 276, 9e−73 |

TABLE 2-continued

Protein homologs of SYNPCC7942_1593 (ADM)

| Organism | SEQ ID NO: | Homolog accession # | BLAST Score, E-value |
|---|---|---|---|
| *Prochlorococcus marinus* str. NATL1A [cyanobacteria] taxid 167555 | 147 | YP_001014415.1 | 276, 9e−73 |
| *Prochlorococcus marinus* subsp. *marinus* str. CCMP1375 [cyanobacteria] taxid 167539 | 148 | NP_874925.1 | 276, 1e−72 |
| *Prochlorococcus marinus* str. MIT 9515 [cyanobacteria] taxid 167542 | 149 | YP_001010912.1 | 273, 6e−72 |
| *Prochlorococcus marinus* str. MIT 9215 [cyanobacteria] taxid 93060 | 150 | YP_001483814.1 | 273, 9e−72 |

The amino acid sequences referred to in the Table, as those sequences appeared in the NCBI database on Jul. 9, 2009, by accession number are incorporated by reference herein.

An AAR enzyme from Table 1, and/or an ADM enzyme from Table 2, or both can be expressed in a host cell of interest, wherein the host may be a heterologous host or the native host, i.e., the species from which the genes were originally derived. In one embodiment, the invention provides a method of imparting n-alkane synthesis capability in a heterologous organism, lacking native homologs of AAR and/or ADM, by engineering the organism to express a gene encoding one of the enzymes listed in Table 1 or Table 2. Also provided are methods of modulating n-alkane synthesis in an organism which already expresses one or both of the AAR and ADM enzymes by increasing the expression of the native enzymes, or by augmenting native gene expression by the recombinant expression of heterologous AAR and/or ADM enzymes. In addition, the invention provides methods of modulating the degree of alkane synthesis by varying certain parameters, including the identity and/or compatibility of electron donors, culture conditions, promoters for expressing AAR and/or ADM enzymes, and the like.

In addition to the in vivo production of n-alkanes discussed above, AAR and ADM proteins encoded by the genes listed in Tables 1 and 2 can be purified. The proteins will catalyze the enzymatic synthesis of n-alkanes in vitro from appropriate starting materials (e.g., an acyl-ACP or n-alkanal).

Figure 1C:
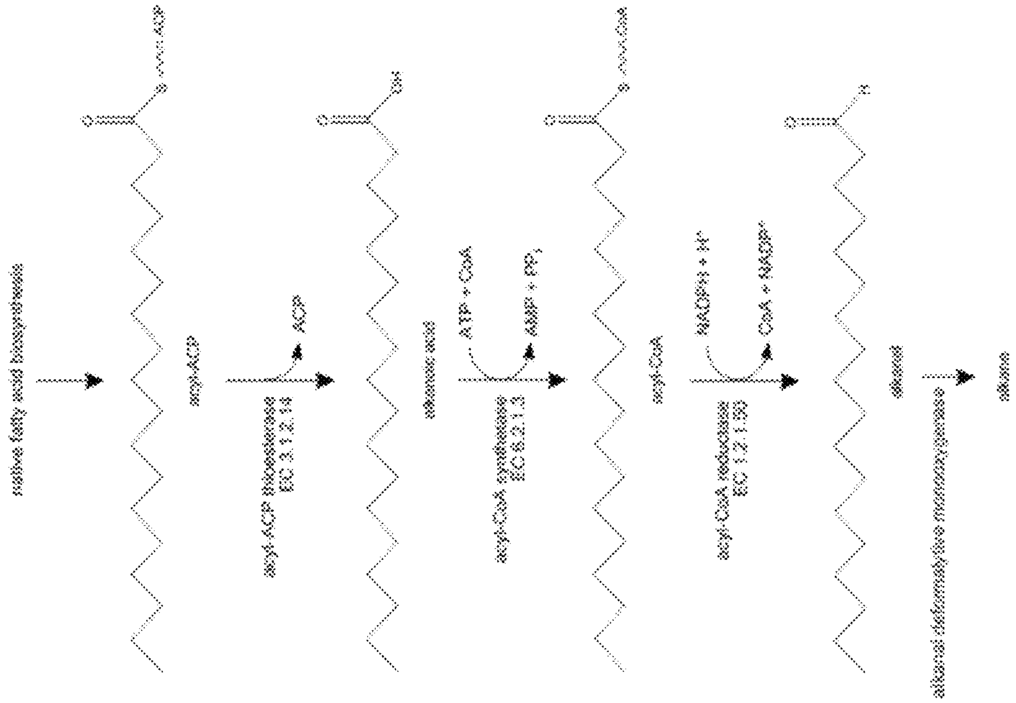

In addition to the pathways for n-alkane synthesis described above, the invention also provides an alternative pathway, namely, acyl-CoA→n-alkanal→(n−1)-alkane, via the successive activities of acyl-CoA reductase (ACR) and ADM. Normally, acyl-CoA is the first intermediate in metabolic pathways of fatty acid oxidation; thus, upon import into the cell, exogenously added free fatty acids are converted to acyl-CoAs by acyl-CoA synthetase (FIG. 1A). Acyl-CoA can also be derived purely biosynthetically as follows: acyl-ACP→free fatty acid→acyl-CoA, via the activities of cytoplasmic acyl-ACP thioesterase (EC 3.1.2.14; an example is leader-signal-less *E. coli* TesA) and the endogenous and/or heterologous acyl-CoA synthetase. Thus, in one embodiment, the invention provides a method for the biosynthesis of n-alkanes via the pathway: acyl-ACP→intracellular free fatty acid→acyl-CoA→n-alkanal→(n−1)-alkane (FIG. 1C), catalzyed by the successive activities of acyl-ACP thioesterase, acyl-CoA synthetase, acyl-CoA reductase, and ADM. For example, the acyl-CoA reductase Acr1 from *Acinetobacter calcoaceticus* and the ADM from *Synechococcus* sp. PCC7942 (SYNPCC7942__1593) can be used to transform *E. coli*, which is cultured in the presence of exogenous free fatty acids. The free fatty acids are taken up by the cells as acyl-CoA, which are then converted to n-alkanal by Acr1, and thence to (n−1)-alkane by ADM.

Example 2

Production of n-Alkanes, n-Alkenes, and Fatty Alcohols in *Escherichia coli* K-12 Through Heterologous Expression of *Synechococcus elongatus* PCC7942 SYNPCC7942__1593 (adm) and SYNPCC7942__1594 (aar)

The natural SYNPCC7942__1593-SYNPCC7942__1594 operonic sequence was PCR-amplified from the genomic DNA of *Synechococcus elongatus* PCC7942 and cloned into the pAQ1 homologous recombination vector pJB5 via NdeI and EcoRI. The resulting plasmid was denoted pJB823. This construct placed the SYNPCC7942__1593-SYNPCC7942__1594 operon under the transcriptional control of the constitutive aphII promoter. The sequence of pJB823 is provided as SEQ ID NO: 15. The intracellular hydrocarbon products of *E. coli* K-12 EPI400™ (Epicentre) harboring pJB823, JCC1076, were compared to those of EPI400™ harboring pJB5, the control strain JCC9a, by gas chromatography-mass spectrometry (GC-MS). Clonal cultures of JCC9a and JCC1076 were grown overnight at 37° C. in Luria Broth (LB) containing 2% glucose, 100 μg/ml carbenicillin, 50 μg/ml spectinomycin, 50 μg/ml streptomycin, and 1× CopyCutter Induction Solution (Epicentre). For each strain, 15 ml of saturated culture was collected by centrifugation. Cell pellets were washed thoroughly by three cycles of resuspension in Milli-Q water and microcentrifugation, and then dewetted as much as possible by three cycles of microcentrifugation and aspiration. Cell pellets were then extracted by vortexing for five minutes in 0.8 ml acetone containing 100 μg/ml butylated hydroxytoluene (BHT; a general antioxidant) and 100 μg/ml ethyl arachidate (EA; an internal reporter of extraction efficiency). Cell debris was pelleted by centrifugation, and 700 μl extractant was pipetted into a GC vial. These JCC9a and JCC1067 acetone samples, along with authentic standards, were then analyzed by GC-MS.

The gas chromatograph was an Agilent 7890A GC equipped with a 5975C electron-impact mass spectrometer. Liquid samples (1.0 μl) were injected into the GC with a 7683 automatic liquid sampler equipped with a 10 μl syringe. The GC inlet temperature was 290° C. and split-less injection was used. The capillary column was an Agilent HP-5MS (30 m×0.25 mm×0.25 μm). The carrier gas was helium at a flow rate of 1.0 ml/min. The GC oven temperature program was 50° C., hold 1 min/10° C. per min to 290° C./hold 9 min. The GC-MS interface temperature was 290° C. The MS source temperature was 230° C., and the quadrapole temperature was 150° C. The mass range was 25-600 amu. MS fragmentation spectra were matched against the NIST MS database, 2008 version.

Peaks present in the total-ion GC-MS chromatograms were chemically assigned in one of two ways. In the first, assignment was done by ensuring that both the retention time and the fragmentation mass spectrum corresponded to the retention time and fragmentation mass spectrum, respectively, of an authentic standard—this is referred to as "Method 1", and is essentially unambiguous. In the absence of authentic standards, only a tentative chemical assignment can be reached; this was done by collectively integrating the following data for the peak in question: (i) the structure of the fragmentation spectrum, especially with regard to the weight of the molecular ion, and to the degree to which it resembled a hydrocarbon-characteristic "envelope" mass spectrum, (ii) the retention time, especially with regard to its qualitative compatibility with the assigned compound, e.g., cis-unsaturated n-alkenes elute slightly before their saturated n-alkane counterparts, and (iii) the likelihood that the assigned compound is chemically compatible with the operation of the AAR-ADM and related pathways in the host organism in question, e.g., fatty aldehydes generated by AAR are expected to be converted to the corresponding fatty alcohols by host dehydrogenases in *E. coli* if they are not acted upon sufficiently quickly by ADM. This second approach to peak assignment is referred to as "Method 2". In the total-ion GC-MS chromatogram in FIG. 2, as well as in all such chromatograms in subsequent figures, peaks chemically assigned by Method 1 are labeled in regular font, whereas those assigned by Method 2 are labeled in italic font.

Figure 2:
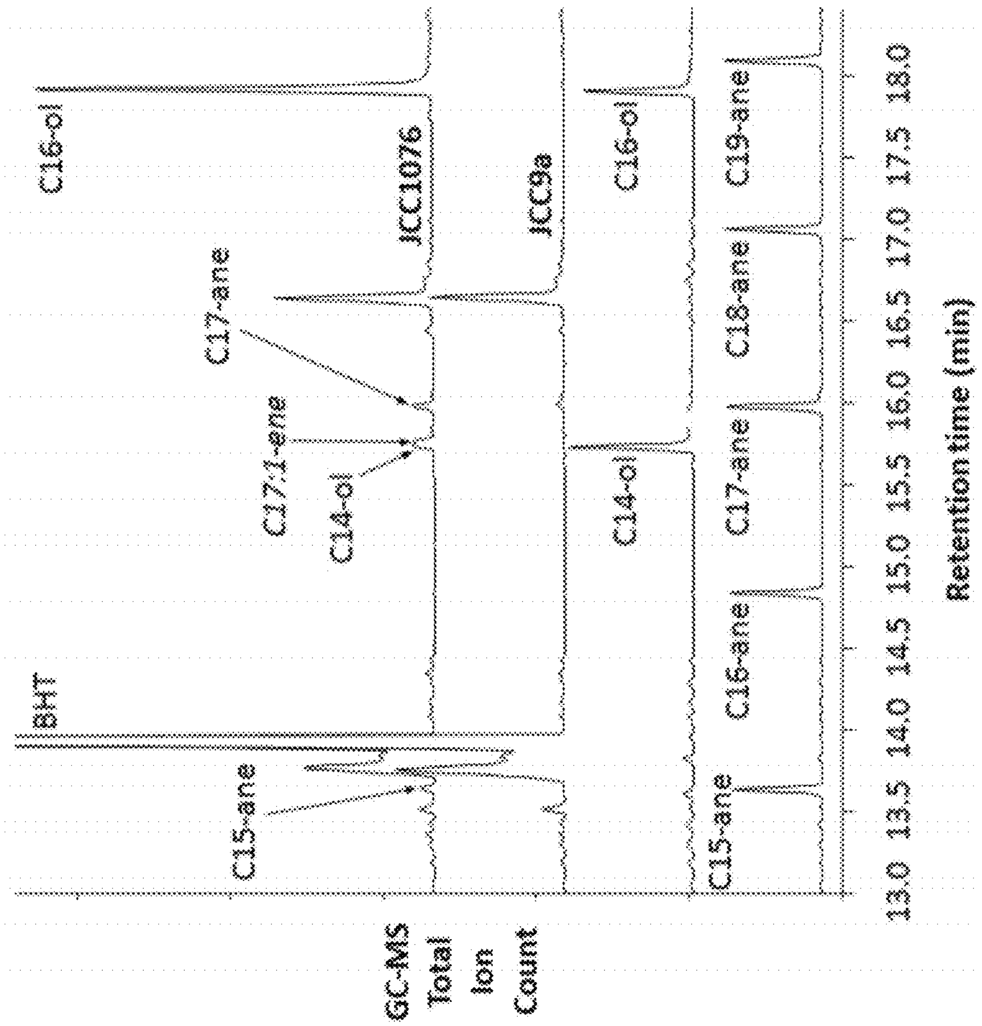
FIG. 2 represents 0-to-2700000-count total ion chromatograms of JCC9a and JCC1076 BHT (butylated hydroxytoluene)-acetone cell pellet extracts, as well as n-alkane and n−1-alkanol authentic standards. Peaks assigned by Method 1 are identified in regular font, those by Method 2 in italic font.
Figure 3A:
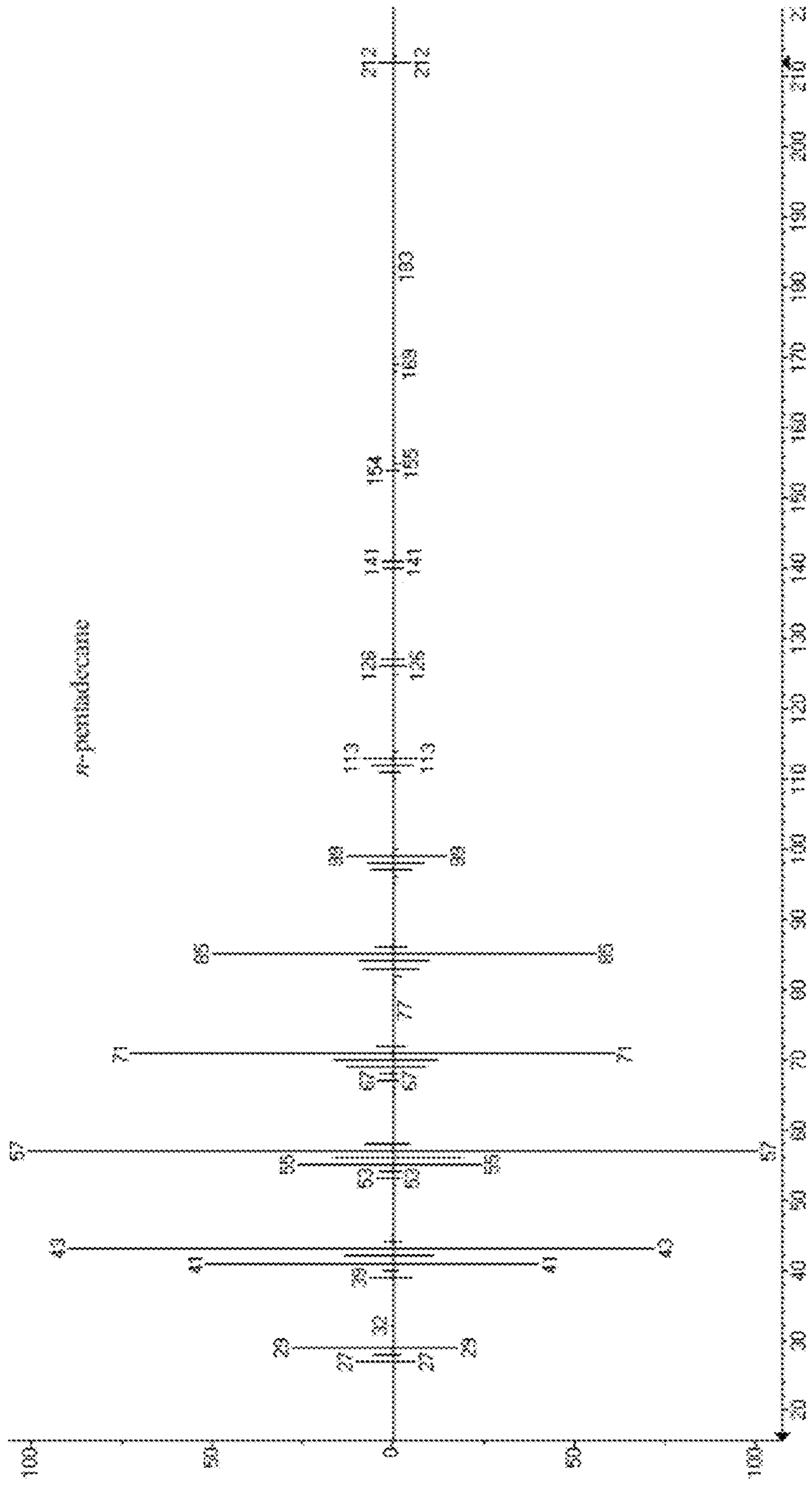
FIG. 3 depicts MS fragmentation spectra of JCC1076 peaks assigned by Method 1 (top mass spectrum of each panel), plotted against their respective NIST library hits (bottom mass spectrum of each panel). A, n-pentadecane; B, 1-tetradecanol; C, n-heptadecane; D, 1-hexadecanol.
Figure 3B:
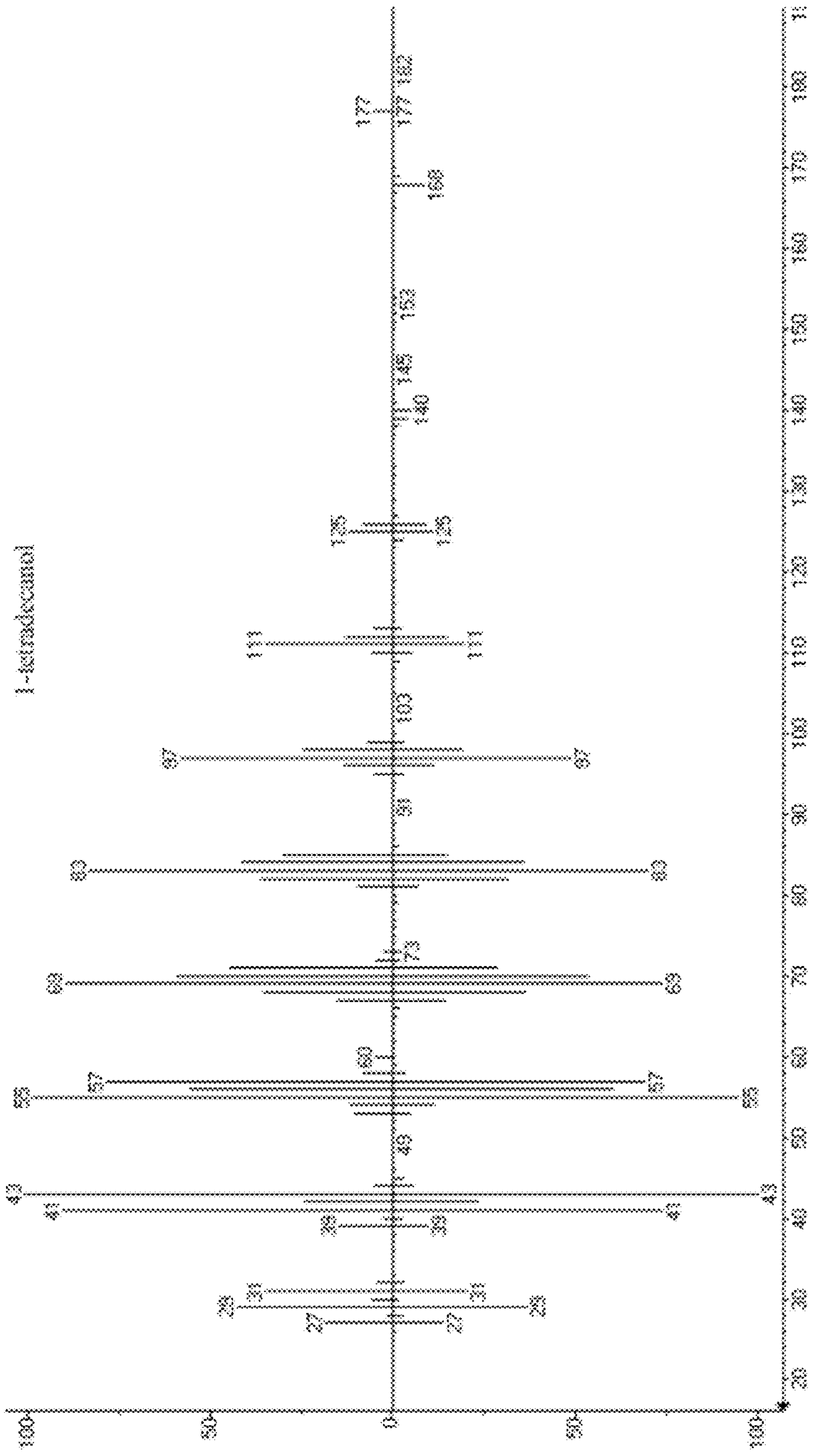
Figure 3C:
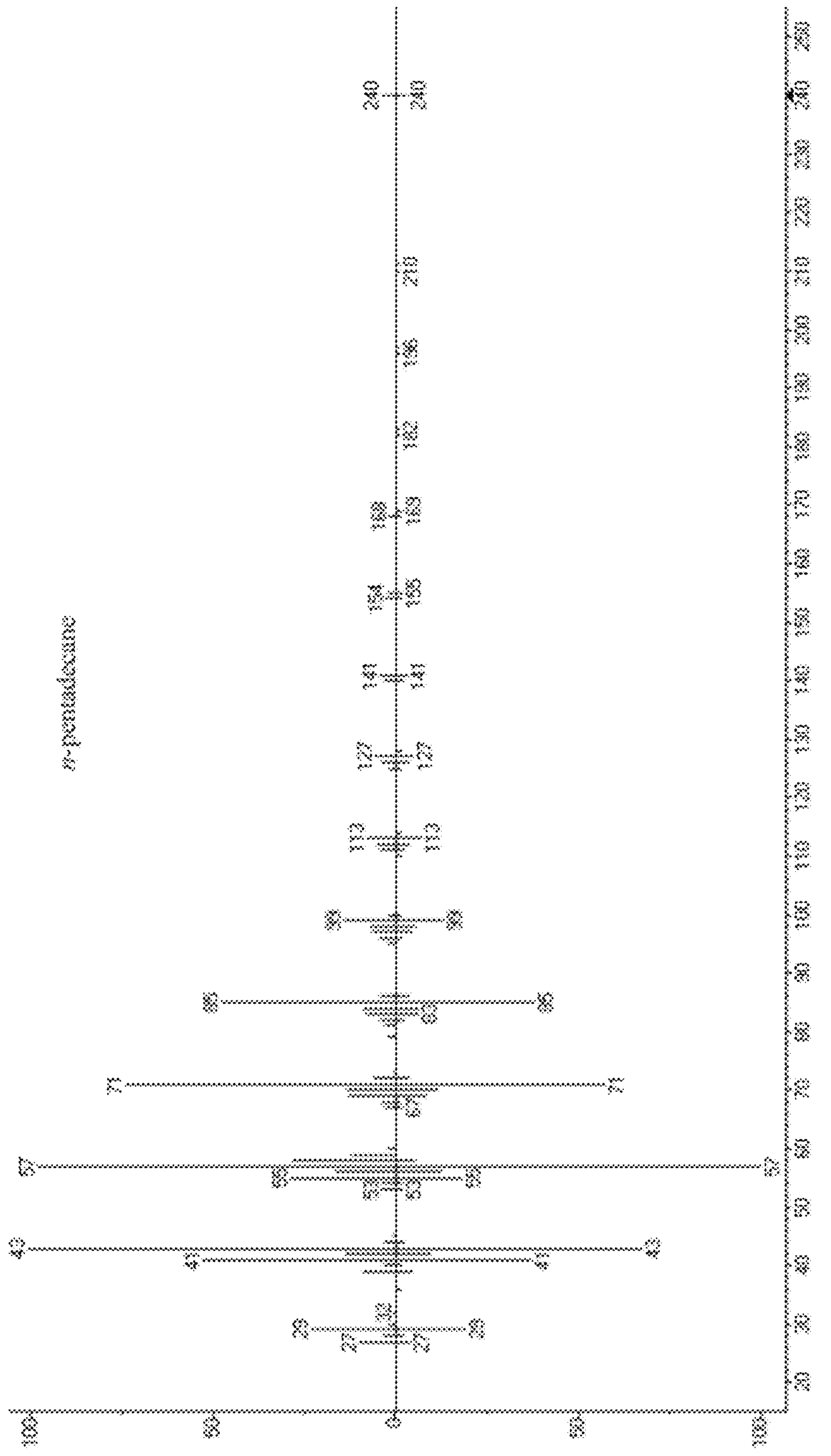
Figure 3D:
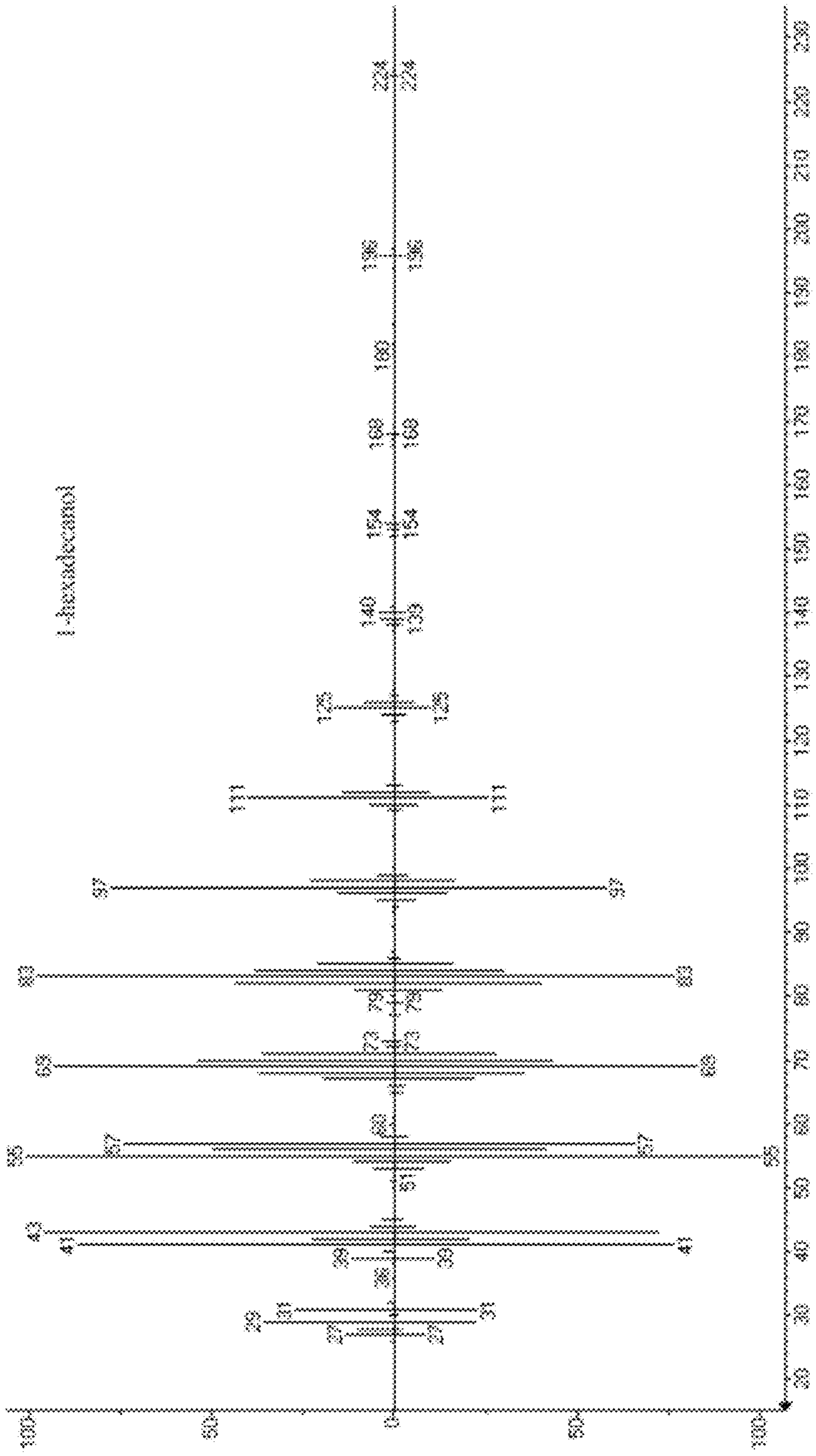

Total ion chromatograms (TICs) of JCC9a and JCC1076 acetone cell pellet extractants are shown in FIG. 2. The TICs of $C_8$-$C_{20}$ n-alkane authentic standards (Sigma 04070), as well as 1-tetradecanol (Sigma 185388) plus 1-hexadecanol (Sigma 258741) plus 1-octadecanol (Sigma 258768), are also shown. Hydrocarbons identified in JCC1076, but not in control strain JCC9a, are detailed in Table 3. These hydrocarbons are n-pentadecane (1), 1-tetradecanol (1), n-heptadecene (2), n-heptadecane (1), and 1-hexadecanol (1), where the number in parentheses indicates the GC-MS peak assignment method. MS fragmentation spectra of the Method 1 peaks are shown in FIG. 3, plotted against their respective library hits.

TABLE 3

Hydrocarbons detected by GC-MS in acetone cell pellet extractants of JCC1076 but not JCC9a, in increasing order of retention time.

| Compound | JCC9a | JCC1076 | GC-MS Peak Assigment | Candidate isomer |
|---|---|---|---|---|
| n-pentadecane | − | + | Method 1 | |
| 1-tetradecanol | − | + | Method 1 | |
| n-heptadecene | − | + | Method 2 (envelope-type MS with molecular ion mass 238) | cis-7-heptadecene |
| n-pentadecane | − | + | Method 1 | |
| 1-hexadecanol | − | + | Method 1 | |

"−" not detected;
"+" detected.

The formation of these five products is consistent with both the expected incomplete operation, i.e., acyl-ACP→fatty aldehyde→fatty alcohol, and expected complete operation, i.e., acyl-ACP→fatty aldehyde→alkane/alkene, of the AAR-ADM pathway in *E. coli*, whose major straight-chain acyl-ACPs include 12:0, 14:0, 16:0, 18:0, 16:1Δ9cis, and 18:1Δ11cis acyl groups (Heipieper H J (2005); *Appl Environ Microbiol* 71:3388). Assuming that n-heptadecene (2) is derived 18:1Δ11cis-ACP, it would correspond to cis-7-heptadecene. Indeed, an n-heptadecene isomer was identified as the highest-confidence MS fragmentation library hit at that retention time, with the expected molecular ion of molecular weight 238; also, as expected, it elutes slightly before n-heptadecane.

Example 3

Production of n-Alkanes, n-Alkenes, and Fatty Alcohols in *Escherichia coli* B Through Heterologous Expression of *Synechococcus elongatus* PCC7942 SYNPCC7942_1593 (adm) and SYNPCC7942_1594 (aar)

The natural SYNPCC7942_1593-SYNPCC7942_1594 operonic sequence was excised from pJB823 using NdeI and EcoRI, and cloned into the commercial expression vector pCDFDuet™-1 (Novagen) cut with via NdeI and MfeI. The resulting plasmid was denoted pJB855 (SEQ ID NO: 16). This construct placed the SYNPCC7942_1593-SYNPCC7942_1594 operon under the transcriptional control of the inducible T7lacO promoter.

Figure 4A:
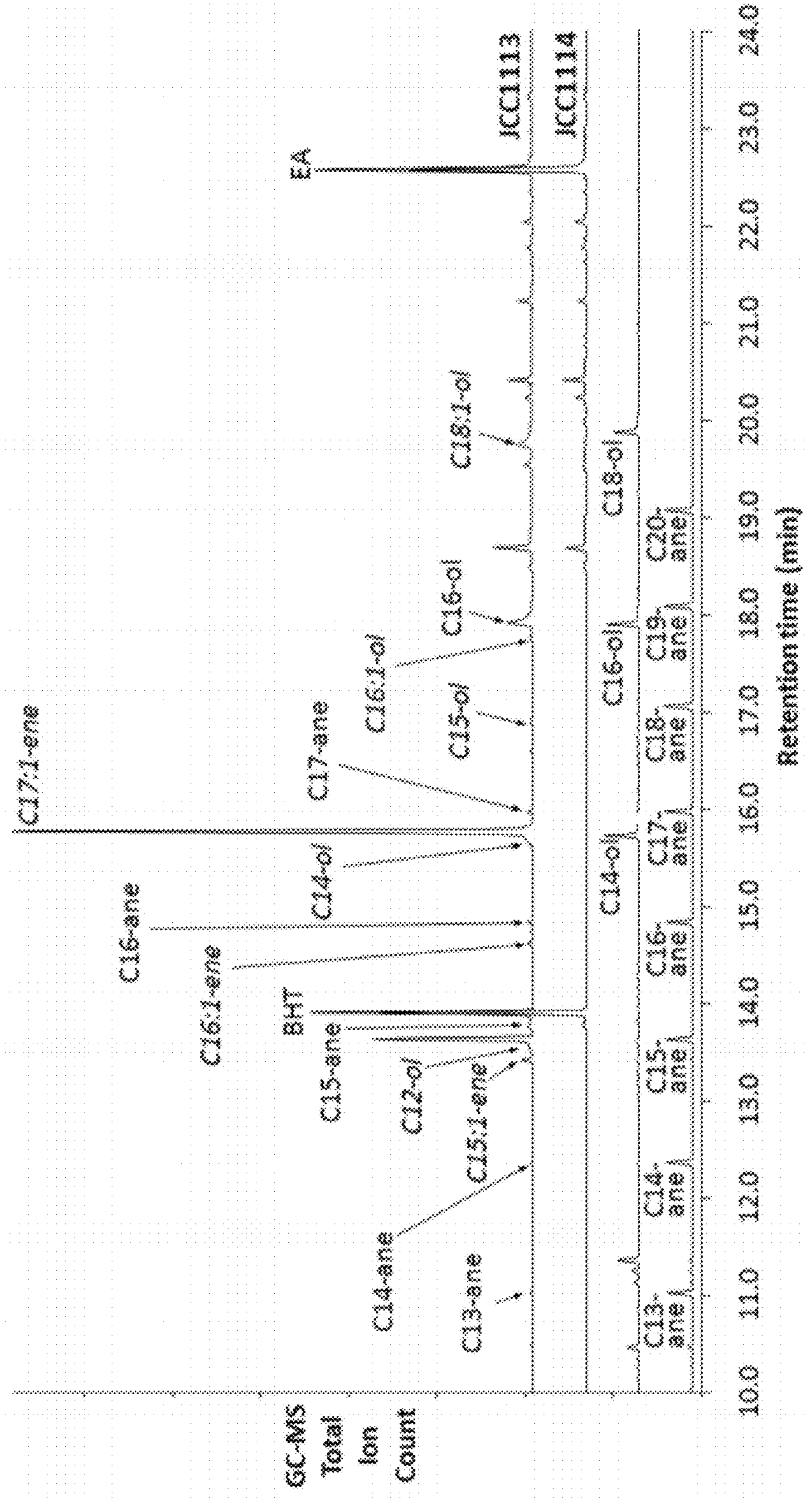
FIG. 4A represents 0-to-7500000-count total ion chromatograms for the BHT-acetone extracts of JCC1113 and JCC1114 cell pellets, as well as $C_{13}$-$C_{20}$ n-alkane and $C_{14}$, $C_{16}$, and $C_{18}$ n−1-alkanol authentic standards; B, represents 0-to-720000-count total ion chromatograms for BHT-acetone extracts of JCC1113 and JCC1114 cell pellets, as well as the n-alkane and n-alkanol authentic standards mentioned in 4A.
Figure 4B:
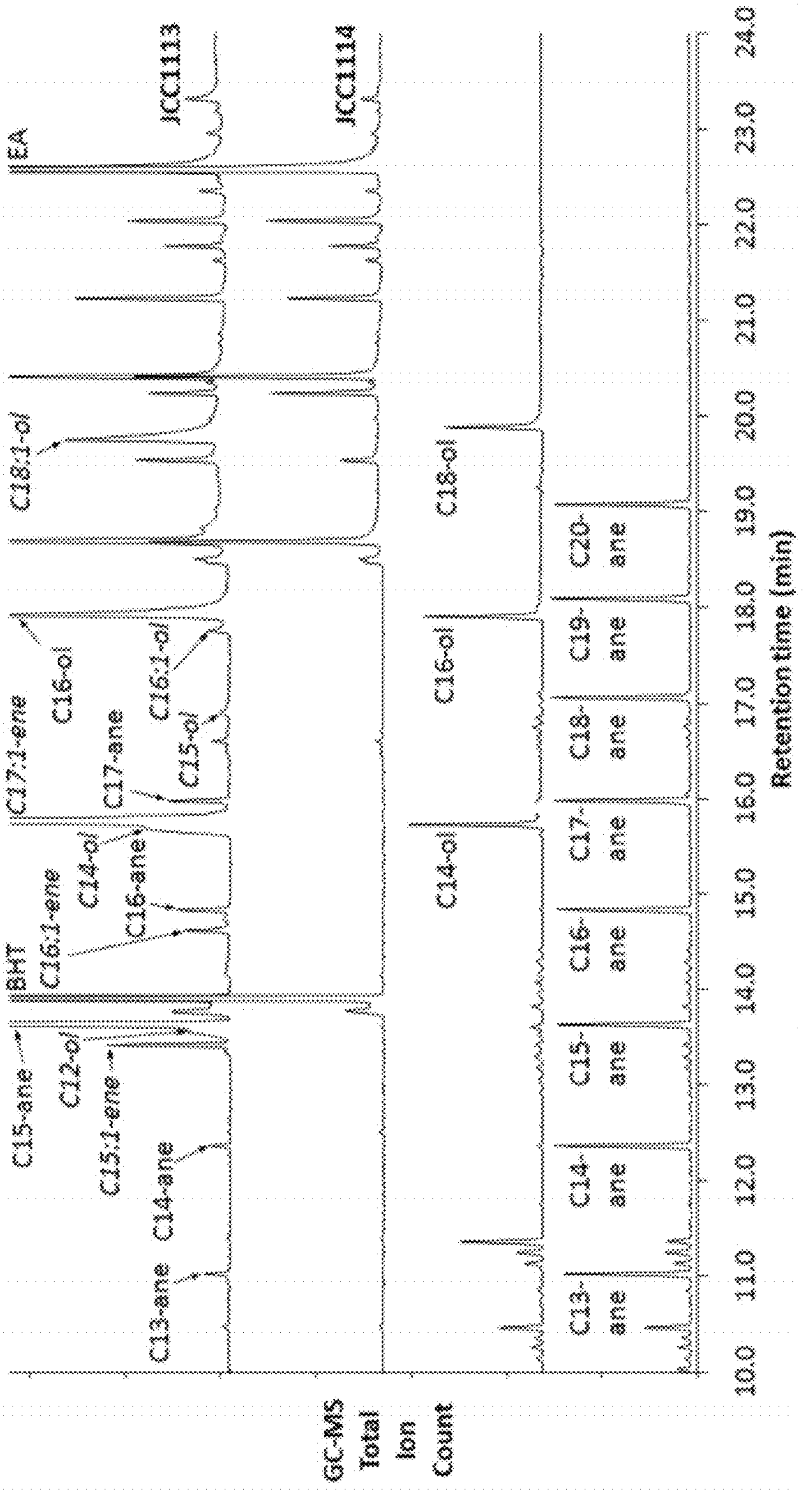
Figure 5A:
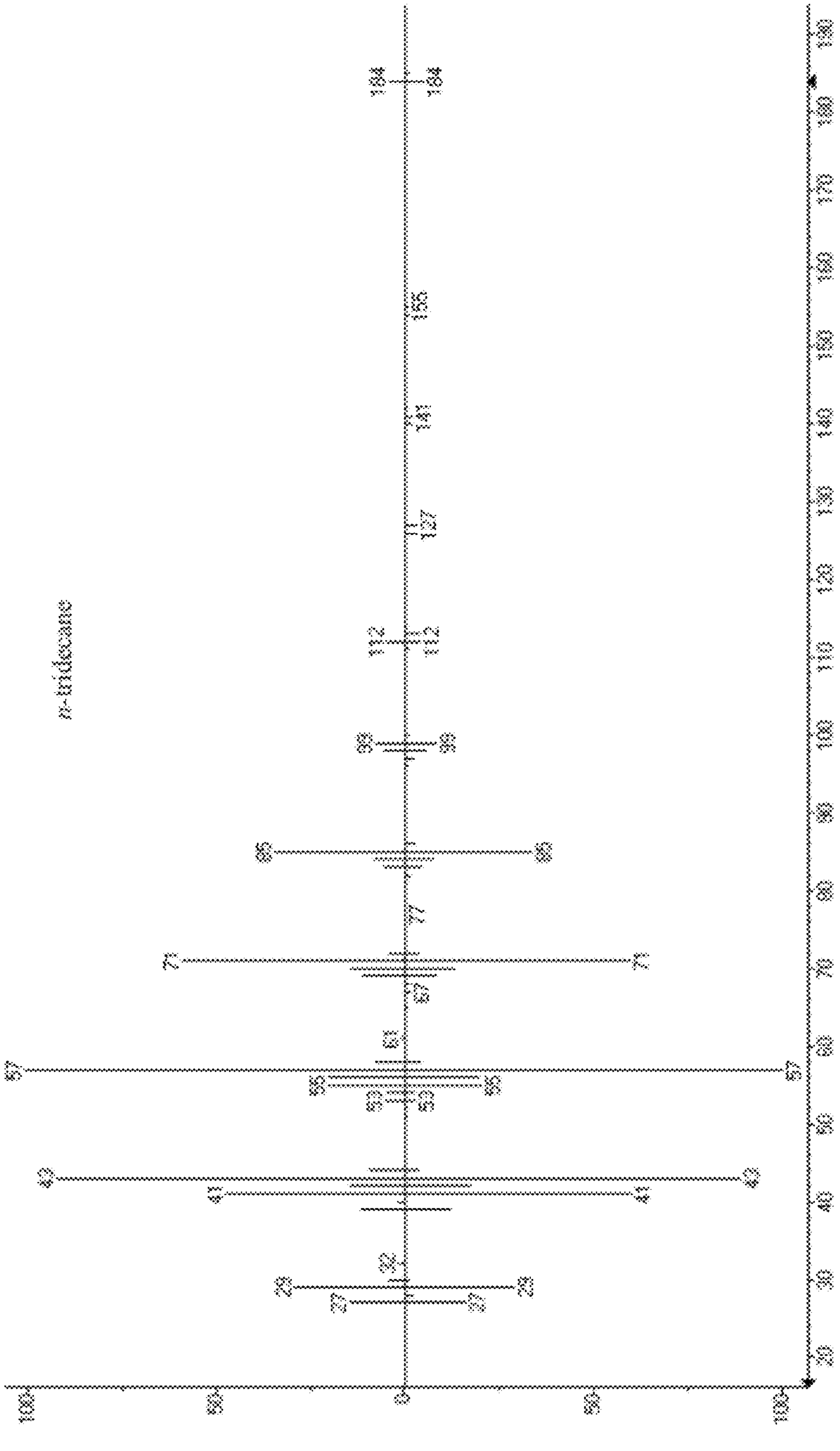
FIG. 5 depicts MS fragmentation spectra of JCC1113 peaks assigned by Method 1 (top mass spectrum of each panel), plotted against their respective NIST library hits (bottom mass spectrum of each panel). A, n-tridecane; B, n-tetradecane; C, n-pentadecane; D, n-hexadecane; E, n-heptadecane; F, 1-hexadecanol.
Figure 5B:
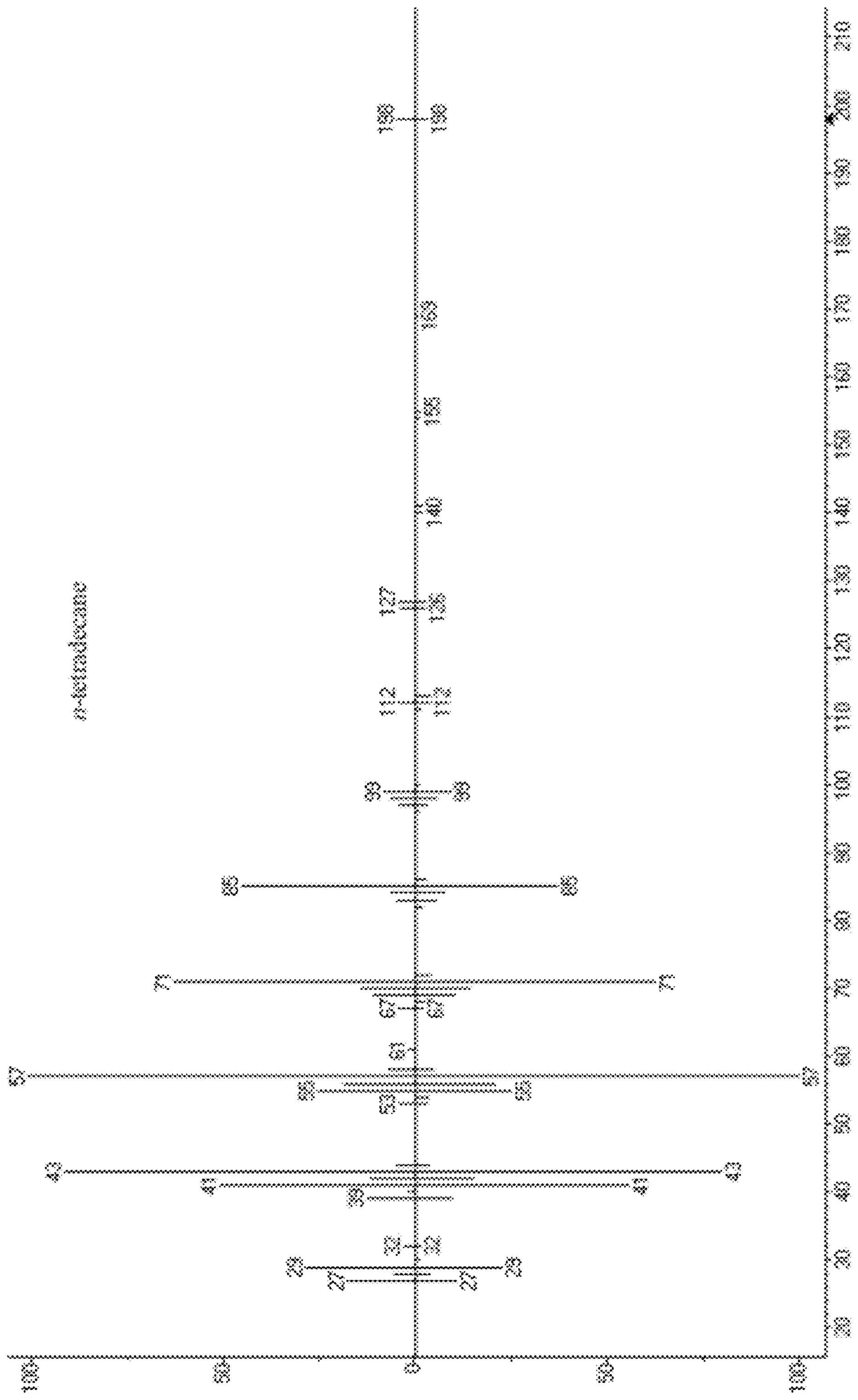
Figure 5C:
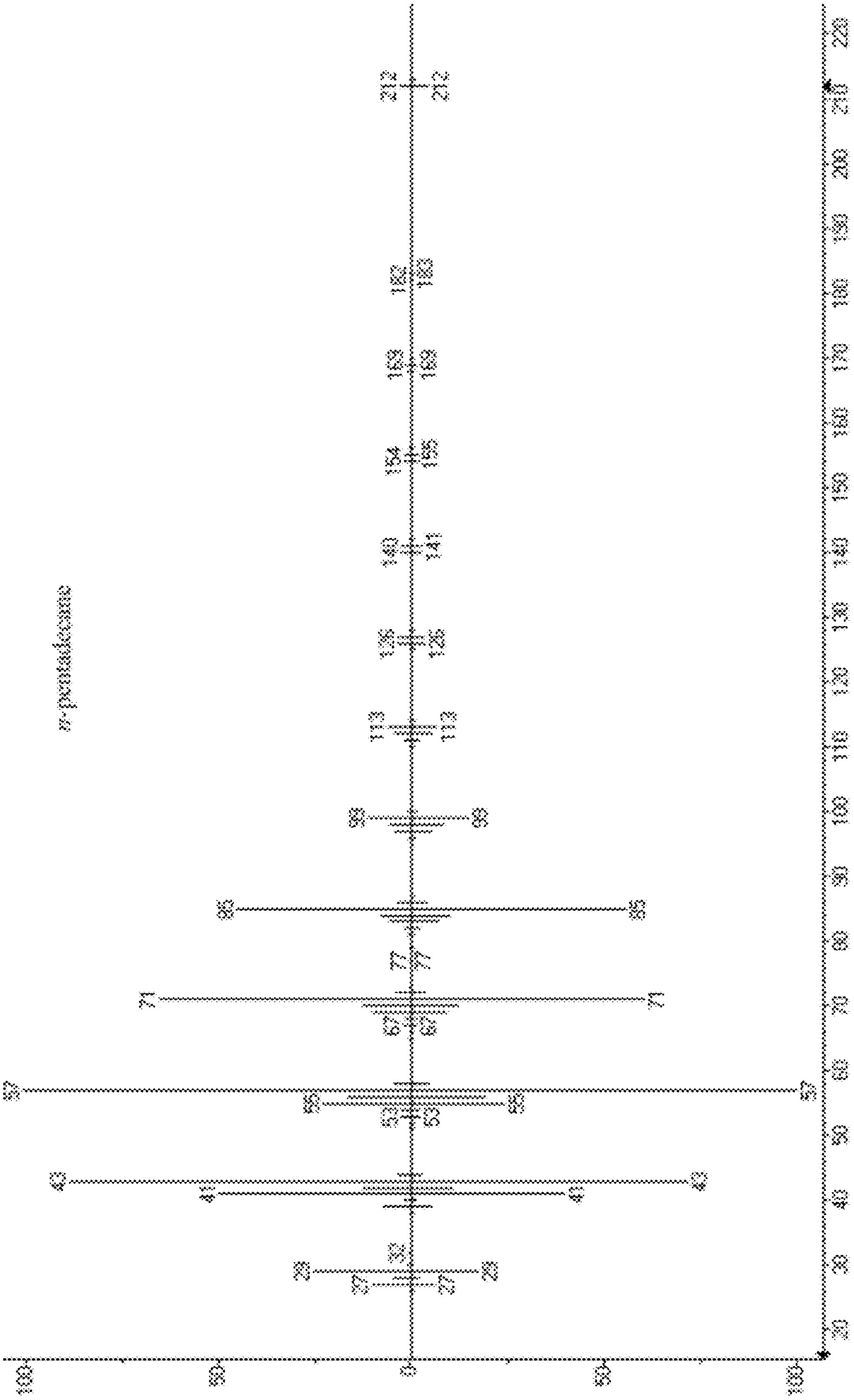
Figure 5D:
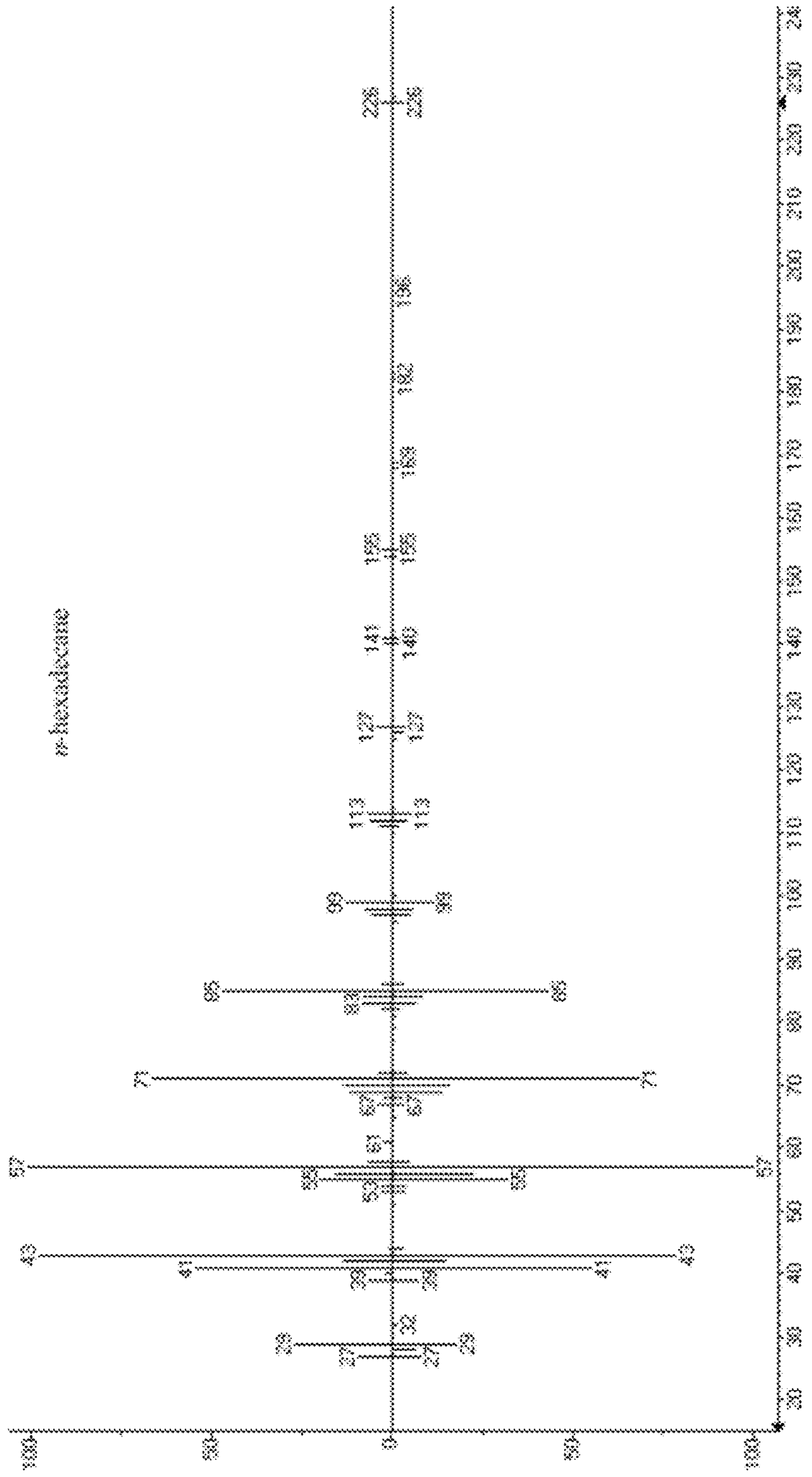
Figure 5E:
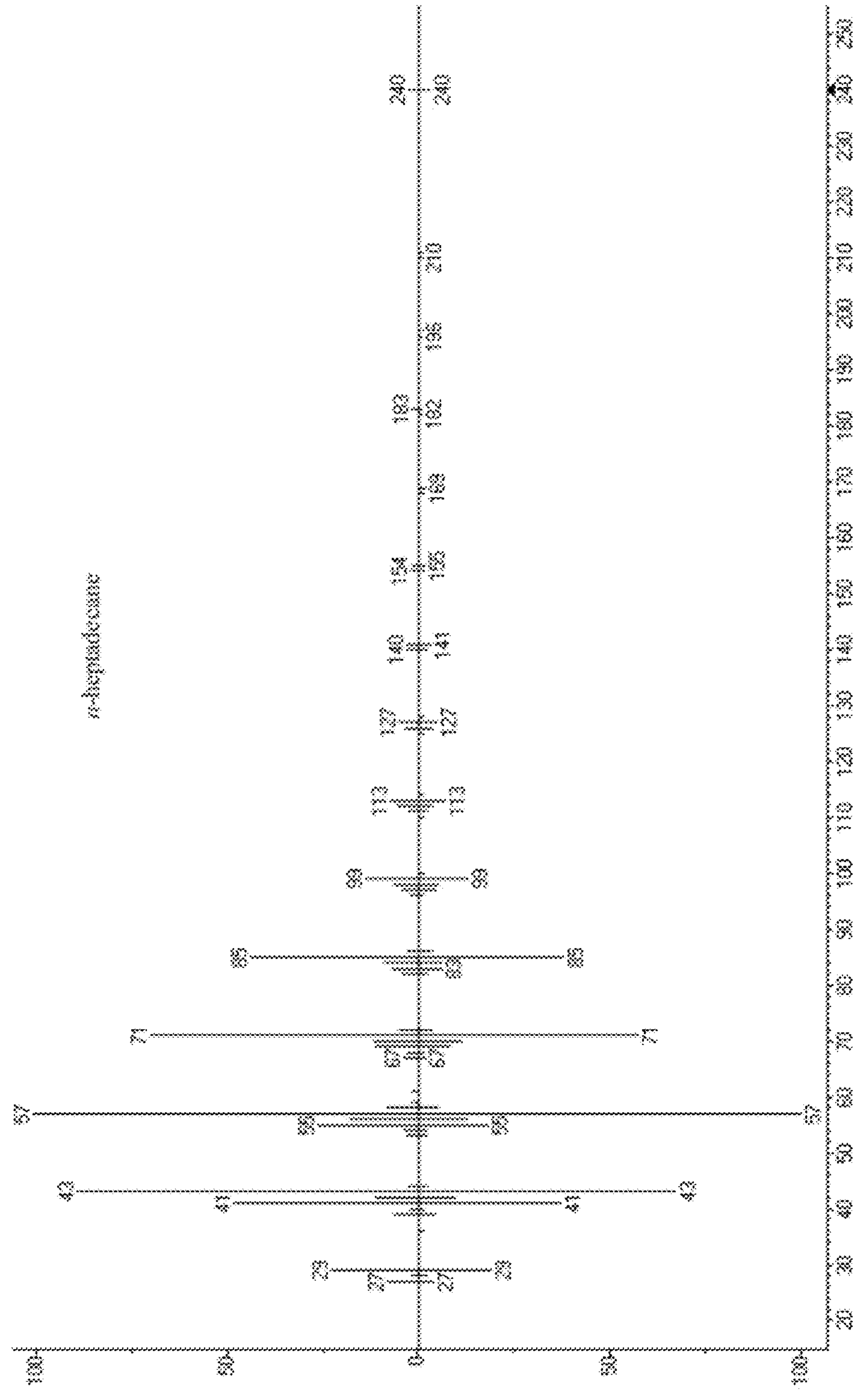
Figure 5F:
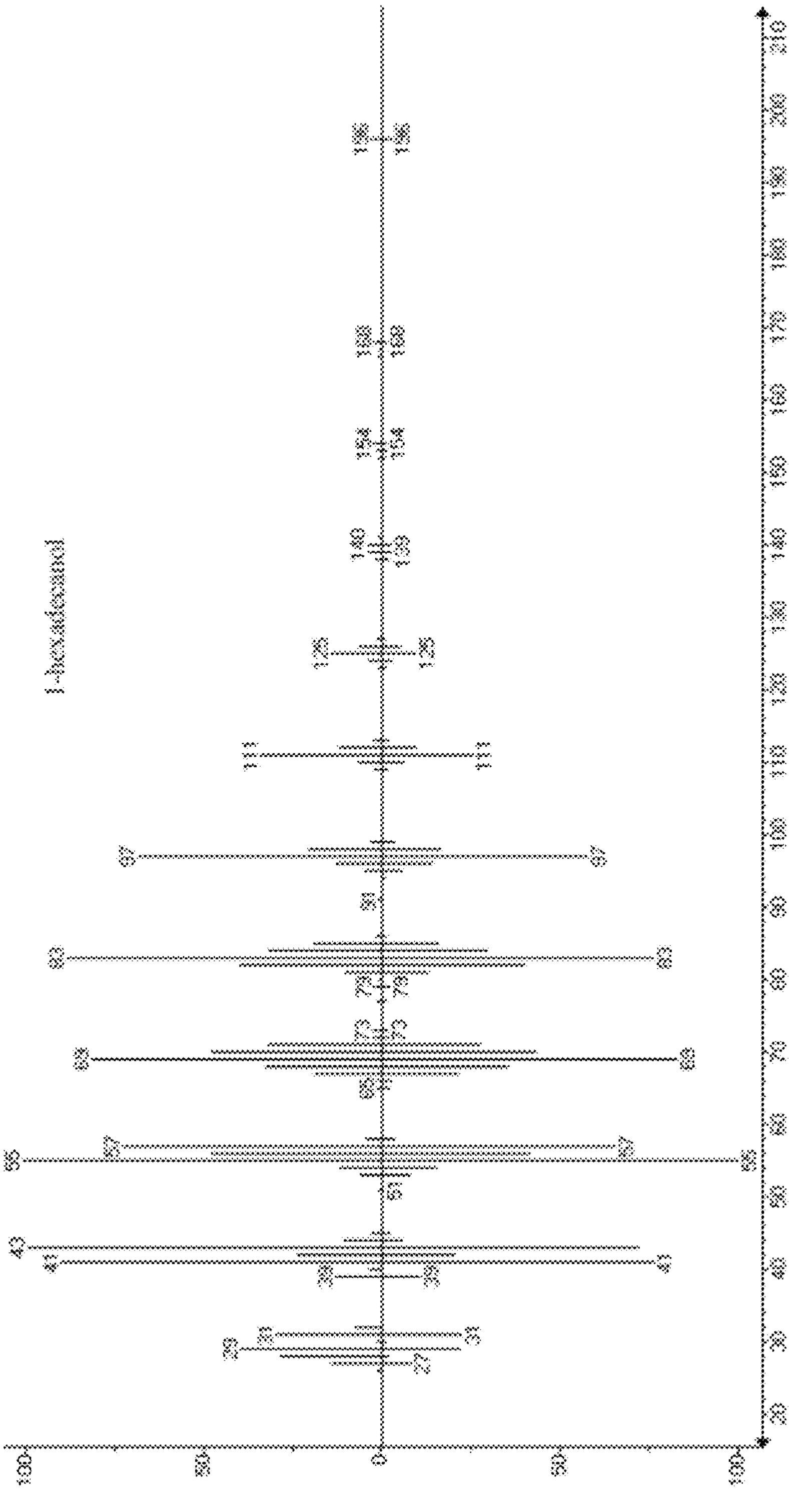

The intracellular hydrocarbon products of *E. coli* BL21 (DE3) (Novagen) harboring pJB855, JCC1113, were compared to those of *E. coli* BL21(DE3) harboring pCDFDuet™-1, the control strain JCC114, by gas chromatography-mass spectrometry (GC-MS). Starter clonal cultures of JCC1114 and JCC1113 were grown overnight at 37° C. in M9 minimal medium supplemented with 6 mg/l $FeSO_4.7H_2O$, 50 μg/ml spectinomycin, and 2% glucose as carbon source; this medium is referred to M9fs. Each starter culture was used to inoculate a 32 ml culture of M9fs at an initial $OD_{600}$ of 0.1. Inoculated cultures were grown at 37° C. at 300 rpm until an $OD_{600}$ of 0.4 has been reached, at which point IPTG was added to a final concentration of 1 mM. After addition of inducer, cultures were grown under the same conditions for an additional 17 hours. For each strain, 12 ml of saturated culture was then collected by centrifugation. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 5 minutes in 0.7 ml acetone containing 20 μg/ml BHT and 20 μg/ml EA. Cell debris was pelleted by centrifugation, and 600 μl supernatant was pipetted into a GC vial. These JCC1114 and JCC1113 samples, along with authentic standards, were then analyzed by GC-MS as described in Example 2. The TICs of JCC1114 and JCC1113 acetone cell pellet extractants are shown in FIG. 4; n-alkane and 1-alkanol standards are as in Example 2. Hydrocarbons identified in JCC1113, but not in control strain JCC1114, are detailed in Table 4.

TABLE 4

Hydrocarbons detected by GC-MS in acetone cell pellet extractants of JCC1113 but not JCC1114 in increasing order of retention time.

| Compound | JCC1114 | JCC1113 | GC-MS Peak Assigment | Candidate isomer |
|---|---|---|---|---|
| n-tridecane | − | + | Method 1 | |
| n-tetradecane | − | + | Method 1 | |
| n-pentadecene | − | + | Method 2 (envelope-type MS with molecular ion mass 210) | cis-7-pentadecene |
| 1-dodecanol | − | + | Method 2 | |
| n-pentadecane | − | + | Method 1 | |
| n-hexadecene | − | + | Method 2 (envelope-type MS with molecular ion mass 224) | cis-8-hexadecene |
| n-hexadecane | − | + | Method 1 | |
| 1-tetradecanol | − | + | Method 1 | |
| n-heptadecene | − | + | Method 2 (envelope-type MS with molecular ion mass 238) | cis-7-heptadecene |
| n-heptadecane | − | + | Method 1 | |
| 1-pentadecanol | − | + | Method 2 | |
| 1-hexadecenol | − | + | Method 2 | cis-9-hexadecen-1-ol |
| 1-hexadecanol | − | + | Method 1 | |
| 1-octadecenol | − | + | Method 2 (envelope-type MS with molecular ion mass 250) | cis-11-octadecen-1-ol |

"−" not detected;
"+" detected.

These hydrocarbons are n-tridecane (1), n-tetradecane (1), n-pentadecene (2), 1-dodecanol (2), n-pentadecane (1), n-hexadecene (2), n-hexadecane (1), 1-tetradecanol (1), n-heptadecene (2), n-heptadecane (1), 1-pentadecanol (2), 1-hexadecenol (2), 1-hexadecanol (1), and 1-octadecenol (2), where the number in parentheses indicates the GC-MS peak assignment method. MS fragmentation spectra of Method 1 peaks are shown in FIG. 5, plotted against their respective library hits. The major products were n-pentadecane and n-heptadecene.

The formation of these fourteen products is consistent with both the expected incomplete operation, i.e., acyl-ACP→fatty aldehyde→fatty alcohol, and expected complete operation, i.e., acyl-ACP→fatty aldehyde→alkane/alkene, of the Aar-Adm pathway in *E. coli*, whose major straight-chain acyl-ACPs include 12:0, 14:0, 16:0, 18:0, 16:1Δ9cis, and 18:1Δ11cis acyl groups (Heipieper H J (2005). Adaptation of *Escherichia coli* to Ethanol on the Level of Membrane Fatty Acid Composition. *Appl Environ Microbiol* 71:3388). Assuming that n-pentadecene (2) is derived 16:1Δ9cis-ACP, it would correspond to cis-7-pentadecene. Indeed, an n-pentadecene isomer was identified as the highest-confidence MS fragmentation library hit at that retention time, with the expected molecular ion of molecular weight 210; also, as expected, it elutes slightly before n-pentadecane. With respect to 1-dodecanol (2), a sufficiently clean fragmentation spectrum could not be obtained for that peak due to the overlapping, much larger n-pentadecane (1) peak. Its presence, however, is consistent with the existence of 12:0-ACP in *E. coli*, and its retention time is exactly that extrapolated from the relationship between 1-alkanol carbon number and observed retention time, for the 1-tetradecanol, 1-hexadecanol, and 1-octadecanol authentic standards that were run. Assuming that n-hexadecene (2) is derived from the trace-level unsaturated 17:1Δ9cis acyl group expected in the *E. coli* acyl-ACP population due to rare acyl chain initiation with propionyl-CoA as opposed to malonyl-CoA, it would correspond to cis-8-hexadecene. Indeed, an n-hexadecene isomer was identified as the highest-confidence MS fragmentation library hit at that retention time, with the expected molecular ion of molecular weight 224; also, as expected, it elutes slightly before n-hexadecane. Assuming that n-heptadecene (2) is derived 18:1Δ11cis-ACP, it would correspond to cis-7-heptadecene. Indeed, an n-heptadecene isomer was identified as the highest-confidence MS fragmentation library hit at that retention time, with the expected molecular ion of molecular weight 238; also, as expected, it elutes slightly before n-heptadecane. With respect to 1-pentadecanol (2), a sufficiently clean fragmentation spectrum could not be obtained for that peak due to its low abundance. Its presence, however, is consistent with the existence of trace-level 15:0 acyl group expected in the *E. coli* acyl-ACP population due to rare acyl chain initiation with propionyl-CoA as opposed to malonyl-CoA, and its retention time is exactly that interpolated from the relationship between 1-alkanol carbon number and observed retention time, for the 1-tetradecanol, 1-hexadecanol, and 1-octadecanol authentic standards that were run. In addition, 1-pentadecanol was identified as the highest-confidence MS fragmentation library hit at that retention time in acetone extracts of JCC1170, a BL21(DE3) derivative that expresses Aar without Adm (see Example 4). With respect to 1-hexadecenol (2), a sufficiently clean fragmentation spectrum could not be obtained for that peak due to its low abundance; however, assuming that it is derived 16:1Δ9cis-ACP, it would correspond to cis-9-hexadecen-1-ol. Also, as expected, it elutes slightly before 1-hexadecanol. Finally, assuming that n-octadecenol (2) is derived 18:11Δ9cis-ACP, it would correspond to cis-11-octadecen-1-ol. Indeed, an n-octadecen-1-ol isomer was identified as the highest-confidence MS fragmentation library hit at that retention time, with the expected molecular ion of molecular weight 250; also, as expected, it elutes slightly before 1-octadecanol.

Example 4

Production of Fatty Alcohols in *Escherichia coli* B Through Heterologous Expression of *Synechococcus elongatus* SYNPCC7942_1594 (Aar) without Co-Expression of SYNPCC7942_1593 (adm)

In order to test the hypothesis that both AAR and ADM are required for alkane biosynthesis, as well as the prediction that expression of AAR alone should result in the production of fatty alcohols only in *E. coli* (due to non-specific dehydrogenation of the fatty aldehydes generated), expression constructs containing just SYNPCC7942_1593 (ADM) and just SYNPCC7942_1594 (AAR), were created. Accordingly, the SYNPCC7942_1593 and SYNPCC7942_1594 coding sequences were individually PCR-amplified and cloned via NdeI and MfeI into the commercial expression vector pCDFDuet™-1 (Novagen). The resulting plasmids were denoted pJB881 (SYNPCC7942_1593 only) and pJB882 (SYN- PCC7942_1594 only); in each construct, the coding sequence was placed under the transcriptional control of the inducible T7lacO promoter.

The intracellular hydrocarbon products of *E. coli* BL21 (DE3) (Novagen) harboring pJB881, JCC1169, and of *E. coli* BL21(DE3) (Novagen) harboring pJB882, JCC1170, were compared to those of *E. coli* BL21(DE3) harboring pCDF-Duet™-1, the negative control strain JCC114, as well as to the positive control SYNPCC7942_1593—SYNPCC7942_1594 strain JCC1113 (Example 3), by gas chromatography-mass spectrometry (GC-MS). Clonal cultures of JCC1169, JCC1170, JCC1114, and JCC1113 were grown, extracted, and analyzed by GC-MS as described in Example 3, with the following exception: the JCC1170 culture was grown overnight in M9fs medium without IPTG, because the culture did not grow if IPTG was added. Presumably, this was due to the toxic over-accumulation of fatty alcohols that occurred even in the absence of inducer.

Figure 6:
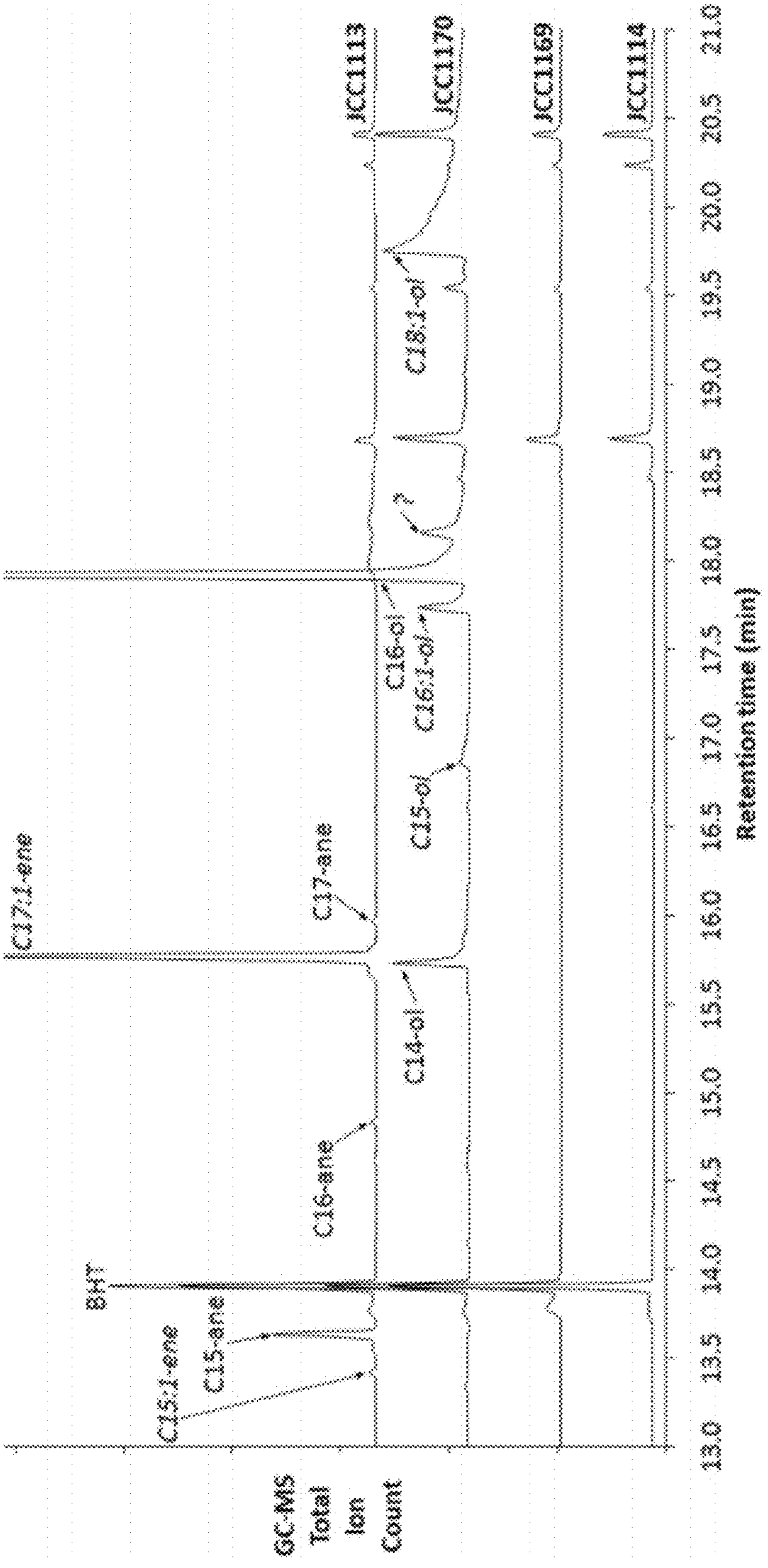
FIG. 6 represents 0-to-6100000-count total ion chromatograms of JCC1170 and JCC1169 BHT-acetone cell pellet extracts versus those of the control strains JCC1113 and JCC1114. No hydrocarbon products were observed in JCC1169. The unidentified peak in JCC1170 is likely cis-11-octadecenal.

The TICs of JCC1169, JCC1170, JCC1114, and JCC1113 acetone cell pellet extractants are shown in FIG. 6; n-alkane and 1-alkanol standard traces have been omitted. Hydrocarbons identified in JCC1170, but not in control strain JCC1114, are detailed in Table 5.

TABLE 5

Hydrocarbons detected by GC-MS in acetone cell pellet extractants of JCC1170 but not JCC1114 in increasing order of retention time.

| Compound | JCC1114 | JCC1170 | GC-MS Peak Assigment | Candidate isomer |
|---|---|---|---|---|
| 1-tetradecanol | − | + | Method 1 | |
| 1-pentadecanol | − | + | Method 2 (envelope-type MS with molecular ion mass 182) | |
| 1-hexadecenol | − | + | Method 2 (envelope-type MS with molecular ion mass 222) | cis-9-hexadecen-1-ol |
| 1-hexadecanol | − | + | Method 1 | |
| 1-octadecenol | − | + | Method 2 (envelope-type MS with molecular ion mass 250) | cis-11-octadecen-1-ol |

"−" not detected;
"+" detected.

Figure 7A:
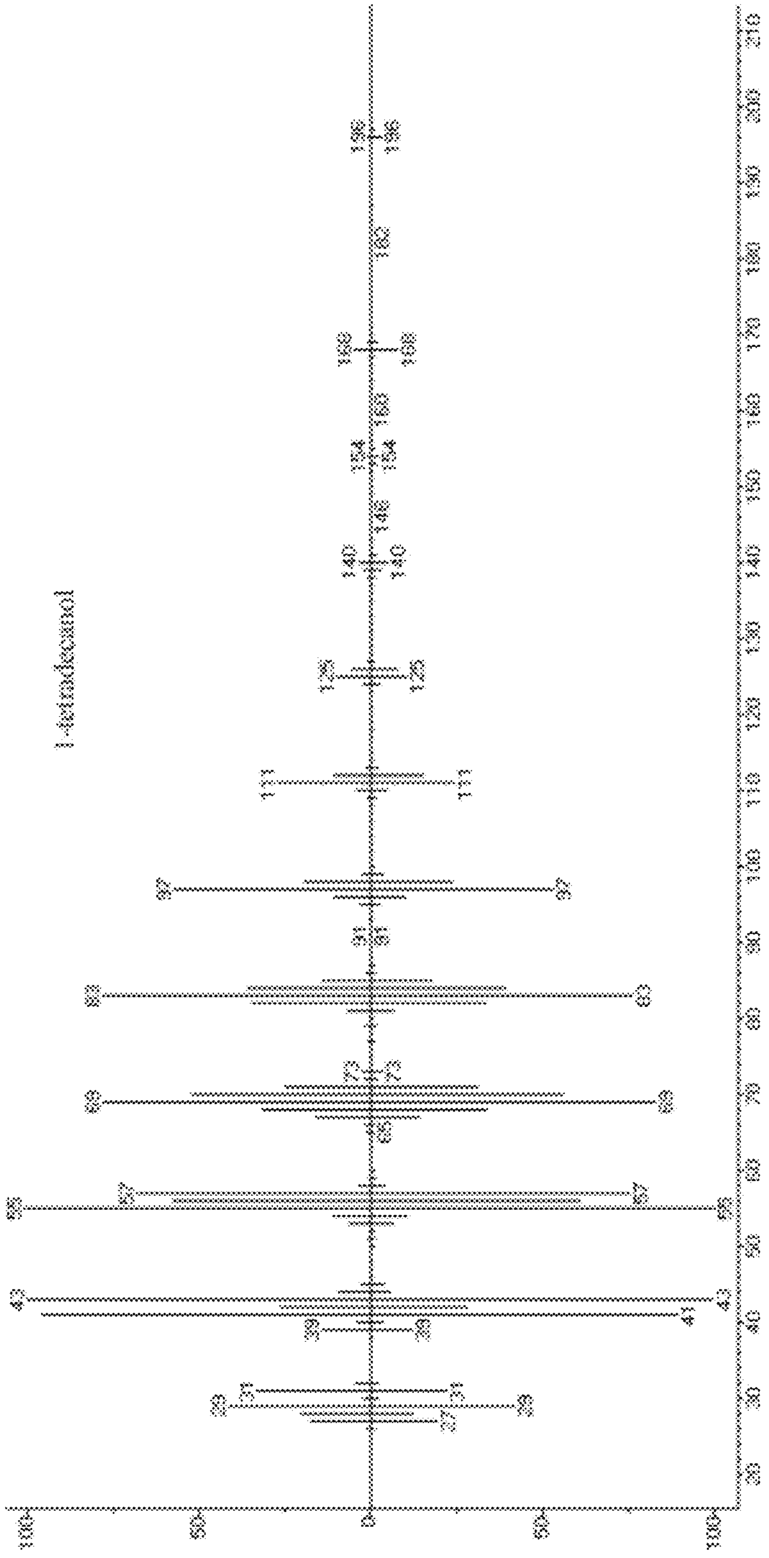
FIG. 7 depicts MS fragmentation spectra of JCC1170 peaks assigned by Method 1 (top mass spectrum of each panel), plotted against their respective NIST library hits (bottom mass spectrum of each panel). A, 1-tetradecanol; B, 1-hexadecanol.
Figure 7B:
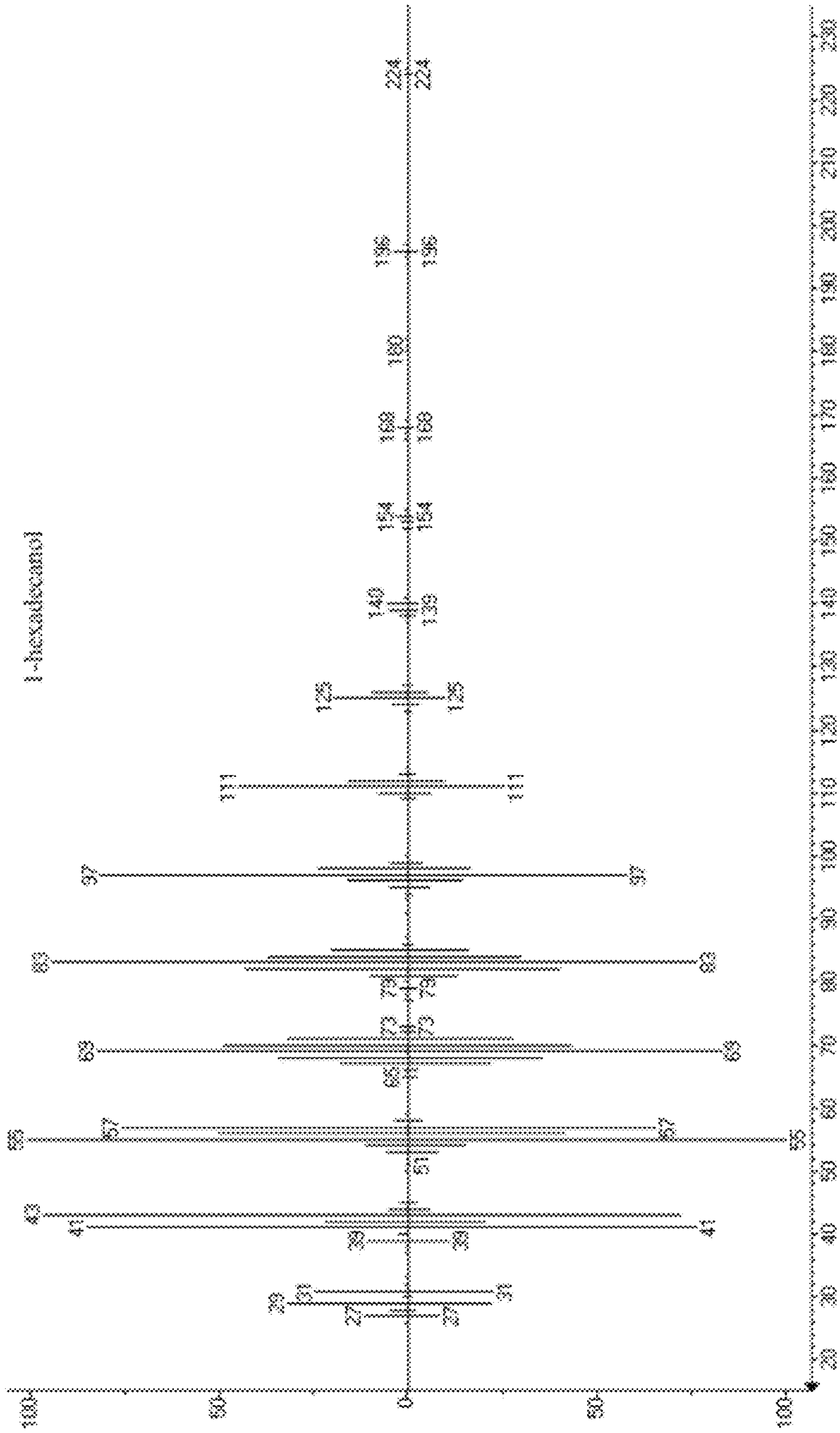

These hydrocarbons are 1-tetradecanol (1), 1-pentadecanol (2), 1-hexadecenol (2), 1-hexadecanol (1), and 1-ocadecenol (2), where the number in parentheses indicates the GC-MS peak assignment method. MS fragmentation spectra of Method 1 peaks are shown in FIG. 7, plotted against their respective library hits. No hydrocarbons were identified in JCC1169, whose trace was indistinguishable from that of JCC1114, as expected owing to absence of fatty aldehyde substrate generation by AAR.

The lack of production of alkanes, alkenes, and fatty alkanols in JCC1169, the production of only fatty alcohols in JCC1170, and the production of alkanes, alkenes, and fatty alkanols in JCC1113 (as discussed in Example 3) are all consistent with the proposed mechanism of alkane biosynthesis by AAR and ADM in *E. coli*. Thus, the formation of the five fatty alcohols in JCC1170 is consistent with only AAR being active, and active on the known straight-chain acyl-ACPs (see Example 3). With respect to 1-pentadecanol (2), its presence is consistent with the existence of trace-level 15:0 acyl group expected in the *E. coli* acyl-ACP population due to rare acyl chain initiation with propionyl-CoA as opposed to malonyl-CoA and its retention time is exactly that interpolated from the relationship between 1-alkanol carbon number and observed retention time, for the 1-tetradecanol, 1-hexadecanol, and 1-octadecanol authentic standards that were run. Most importantly, the 1-pentadecanol (2) peak exhibits an envelope-type fragmentation mass spectrum, with the expected molecular ion of molecular weight 182. Unlike in the case of JCC1113, a clean fragmentation spectrum from the candidate 1-hexadecenol peak could now be obtained due to increased abundance. The top library hit was a 1-hexadecenol with the expected molecular ion of molecular weight 222. Assuming that it is derived from 16:1Δ9cis hexadecenyl-ACP, the isomeric assignment would be cis-9-hexadecen-1-ol; also, as expected, it elutes slightly before 1-hexadecanol. Assuming that n-octadecenol (2) is derived 18:11Δ9cis-ACP, it would correspond to cis-11-octadecen-1-ol. Indeed, an n-octadecen-1-ol isomer was identified as the highest-confidence MS fragmentation library hit at that retention time, with the expected molecular ion of molecular weight 250; also, as expected, it elutes slightly before 1-octadecanol. There is also an unidentified side peak in JCC1170 that elutes in the tail of 1-hexadecenol and whose fragmentation mass spectrum was not sufficiently clean to enable possible identification. It is hypothesized that this could be the primary $C_{18}$ aldehyde product expected of AAR-only activity in *E. coli*, i.e., cis-11-octadecenal.

Example 5

Production of n-Alkanes, n-Alkenes, and Fatty Alcohol in *Synechococcus* sp. PCC 7002 Through Heterologous Expression of *Synechococcus elongatus* PCC7942 SYNPCC7942_1593 (adm) and SYNPCC7942_1594 (aar)

In order to test whether heterologous expression of AAR and ADM would lead to the desired alkane biosynthesis in a cyanobacterial host, the SYNPCC7942_1593-SYNPCC7942_1594 operon was expressed in *Synechococcus* sp. PCC 7002 (JCC138). Accordingly, plasmid pJB823 was transformed into JCC138, generating strain JCC1160. The sequence and annotation of this plasmid is provided as SEQ ID NO: 15, and described in Example 2. In this construct, the SYNPCC7942_1593-SYNPCC7942_1594 operon is placed under the transcriptional control of the constitutive aphII promoter. 500 base pair upstream and downstream homology regions direct homologous recombinational integration into the native high-copy pAQ1 plasmid of JCC138, and an aadA gene permits selection of transformants by virtue of their resistance to spectinomycin.

To test the effect of potentially stronger promoters, constructs directly analogous to pJB823 were also generated that substituted the aphII promoter with the following: the promoter of cro from lambda phage (PcI), the promoter of cpcB from *Synechocystis* sp. PCC 6803 (PcpcB), the trc promoter along with an upstream copy of a promoter-lad cassette (PlacI-trc), the synthetic EM7 promoter (PEM7). Promoters were exchanged via the NotI and NdeI sites flanking the promoter upstream of the SYNPCC7942_1593-SYNPCC7942_1594 operon in the pJB823 vector. The corresponding final plasmids were as follows: pJB886 (PcI), pJB887 (PcpcB), pJB889 (PlacI-trc), pJB888 (PEM7), and pJB823 (PaphII). These sequences of pJB886, pJB887, pJB889, and pJB888 are identical to the sequence of pJB823 except in the region between the NotI and NdeI sites, where they differ according to the promoter used. The sequences of the different promoter regions are provided as SEQ ID NO: 19 (PcI), SEQ ID NO: (PcpcB), SEQ ID NO: 21 (PlacI-trc), and SEQ ID NO: 22 (PEM7). The sequence of the PaphII promoter is presented in SEQ ID NO: 15.

pJB886, pJB887, pJB889, pJB888, pJB823, as well as pJB5 (the empty pAQ1 targeting vector that entirely lacked the SYNPCC7942_1593-SYNPCC7942_1594 operonic sequence) were naturally transformed into JCC138 using a standard cyanobacterial transformation protocol, generating strains JCC1221 (PcI), JCC1220 (PcpcB), JCC1160b (PlacI-trc), JCC1160a (PEM7), JCC1160 (PaphII), and JCC879 (pJB5), respectively. Briefly, 5-10 μg of plasmid DNA was added to 1 ml of neat JCC138 culture that had been grown to an $OD_{730}$ of approximately 1.0. The cell-DNA mixture was incubated at 37° C. for 4 hours in the dark with gentle mixing, plated onto A+ plates, and incubated in a photoincubator (Percival) for 24 hours, at which point spectinomycin was underlaid to a final concentration of 50 μg/ml. Spectinomycin-resistant colonies appeared after 5-8 days of further incubation under 24 hr-light conditions (~100 μmol photons $m^{-2}$ $s^{-1}$). Following one round of colony purification on A+ plates supplemented with 100 μg/ml spectinomycin, single colonies of each of the six transformed strains were grown in test-tubes for 4-8 days at 37° C. at 150 rpm in 3% $CO_2$-enriched air at ~100 μmol photons $m^{-2}$ $s^{-1}$ in a Multitron II (Infors) shaking photoincubator. The growth medium used for liquid culture was A+ with 200 μg/ml spectinomycin.

In order to compare the intracellular hydrocarbon products of strains JCC1221, JCC1220, JCC1160b, JCC1160a, JCC1160, and JCC879, 24 $OD_{730}$-ml worth of cells (~2.4×$10^9$ cells) of each strain was collected from the aforementioned test-tube cultures by centrifugation. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 5 minutes in 0.7 ml acetone containing 20 μg/ml BHT and 20 μg/ml EA. Cell debris was pelleted by centrifugation, and 600 μl supernatant was pipetted into a GC vial. The six extractants, along with authentic standards, were then analyzed by GC-MS as described in Example 2.

Figure 8A:
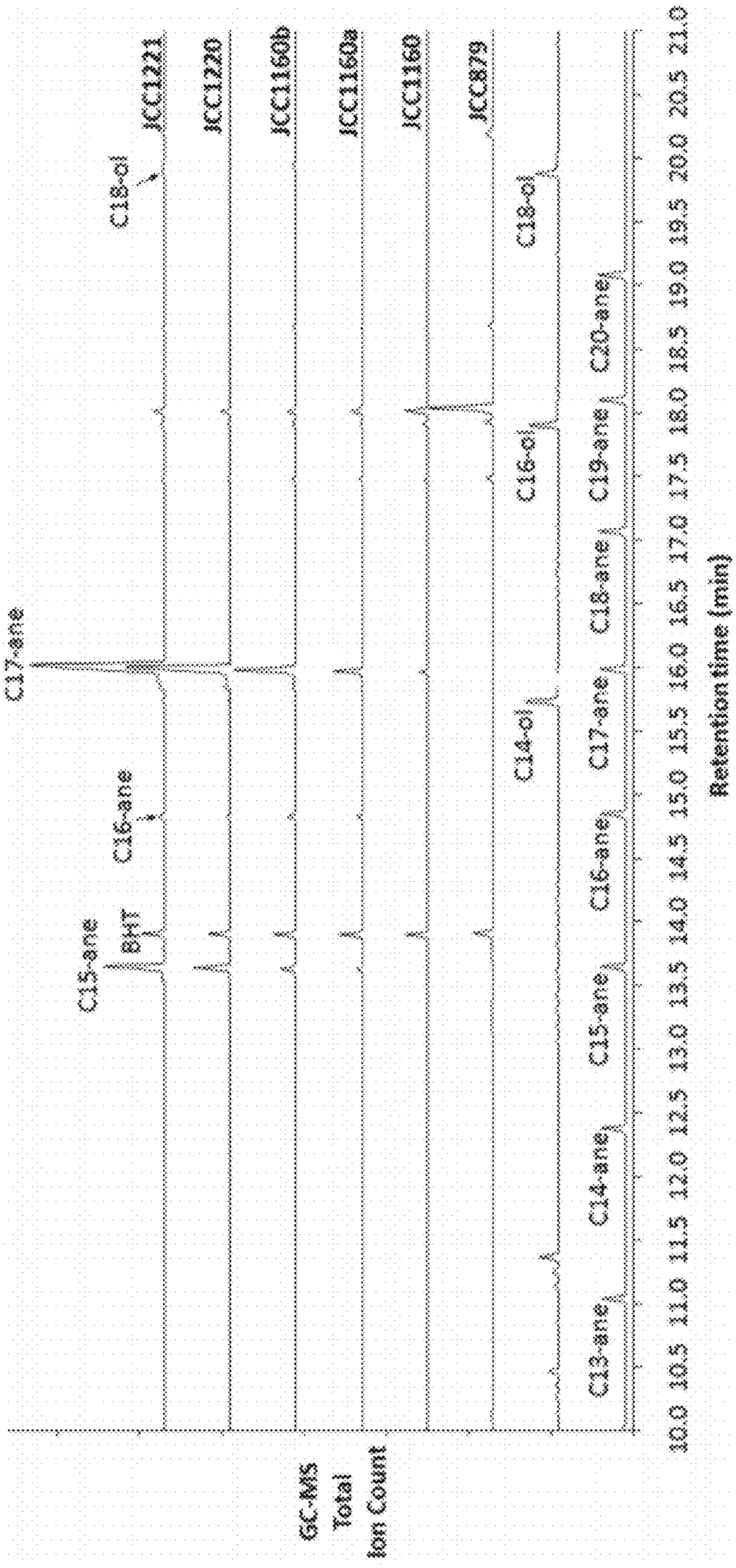
FIG. 8A represents 0-to-75000000-count total ion chromatograms for BHT-acetone extracts of JCC1221, JCC1220, JCC1160b, JCC1160a, JCC1160 and JCC879 cell pellets, as well as $C_{13}$-$C_{20}$ n-alkane and $C_{14}$, $C_{16}$, and $C_{18}$ n-alkanol authentic standards. The doublet around 18.0 minutes corresponds to nonadec-di-ene and 1-nonadecene, respectively (data not shown), n-alkenes that are naturally produced by JCC138; 8B represents 0-to-2250000-count total ion chromatograms for BHT-acetone extracts of JCC1221 and JCC879 cell pellets, as well as the n-alkane and n-alkanol authentic standards mentioned in 8A.
Figure 8B:
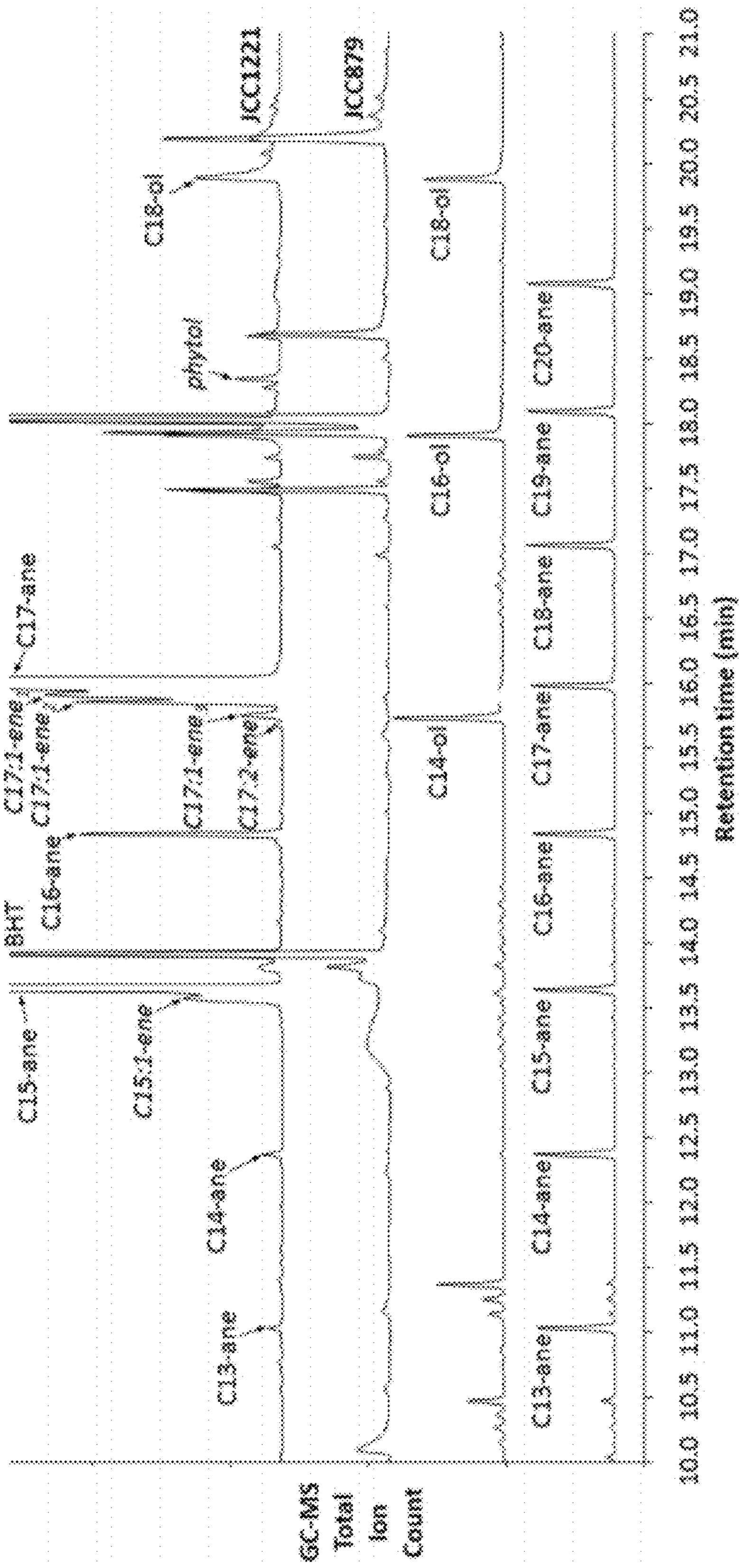
Figure 9A:
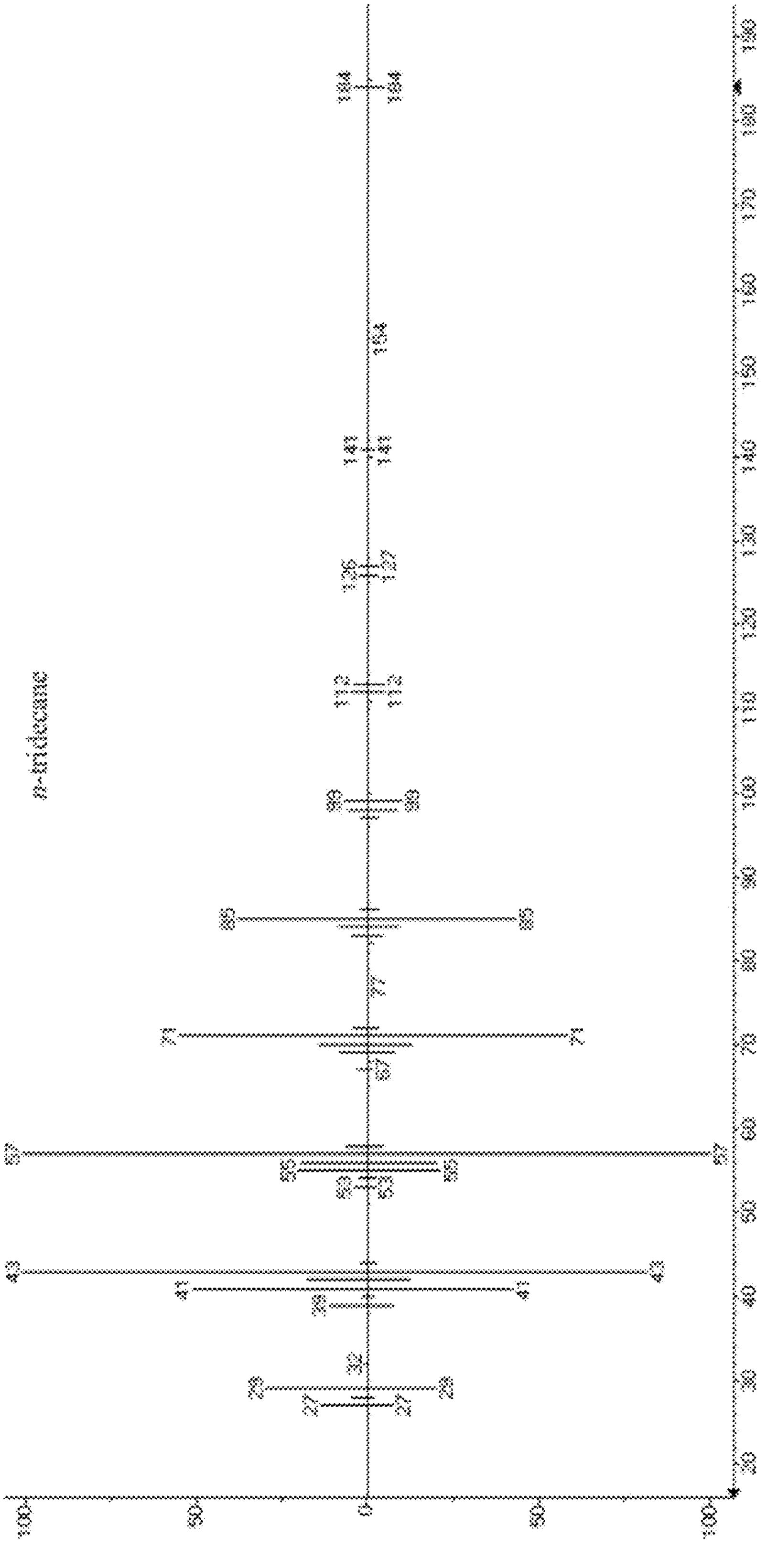
FIG. 9 depicts MS fragmentation spectra of JCC1221 peaks assigned by Method 1 (top mass spectrum of each panel), plotted against their respective NIST library hits (bottom mass spectrum of each panel). A, n-tridecane; B, n-tetradecane; C, n-pentadecane; D, n-hexadecane; E, n-heptadecane; F, 1-octadecanol.
Figure 9B:
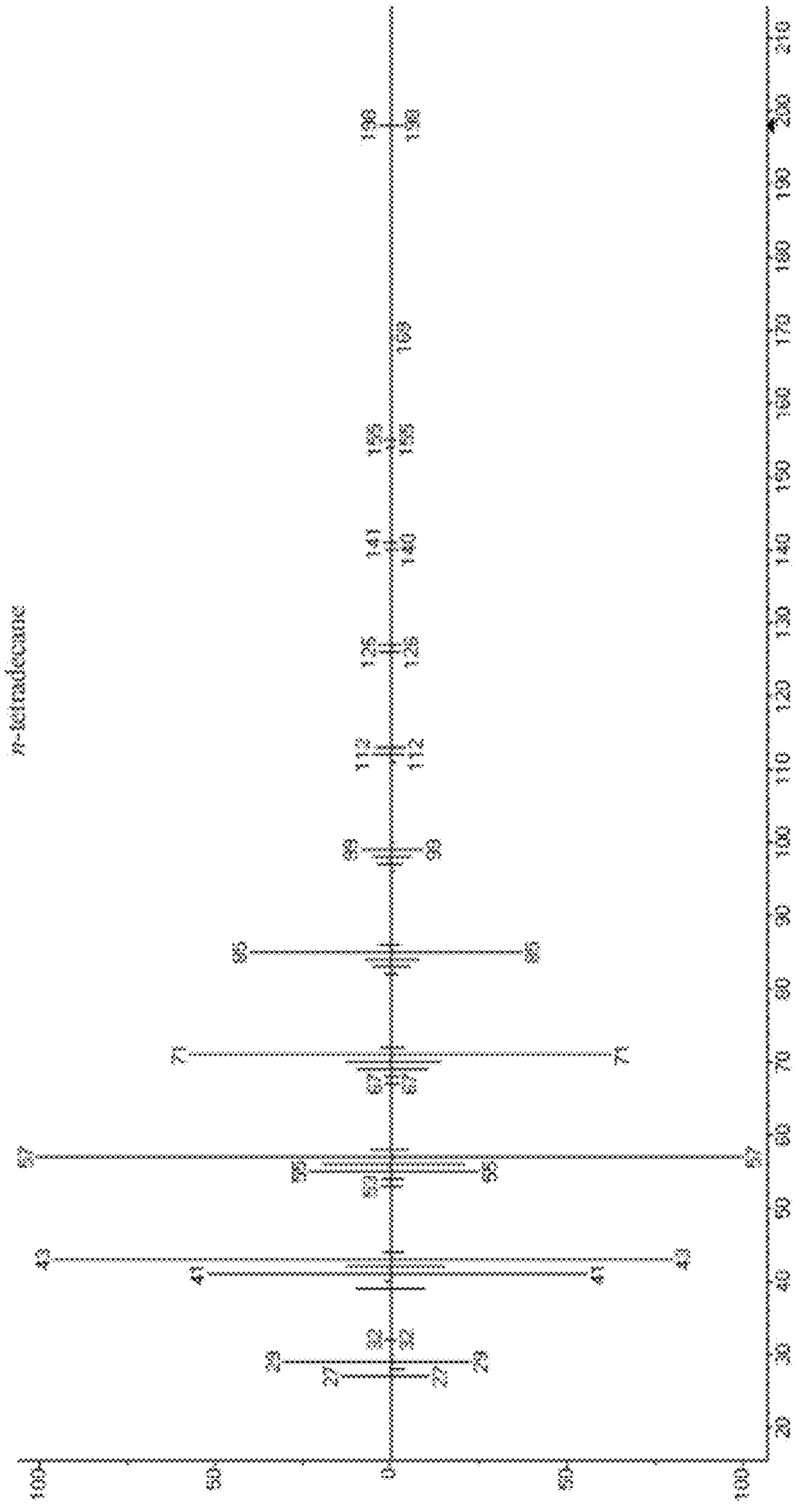
Figure 9C:
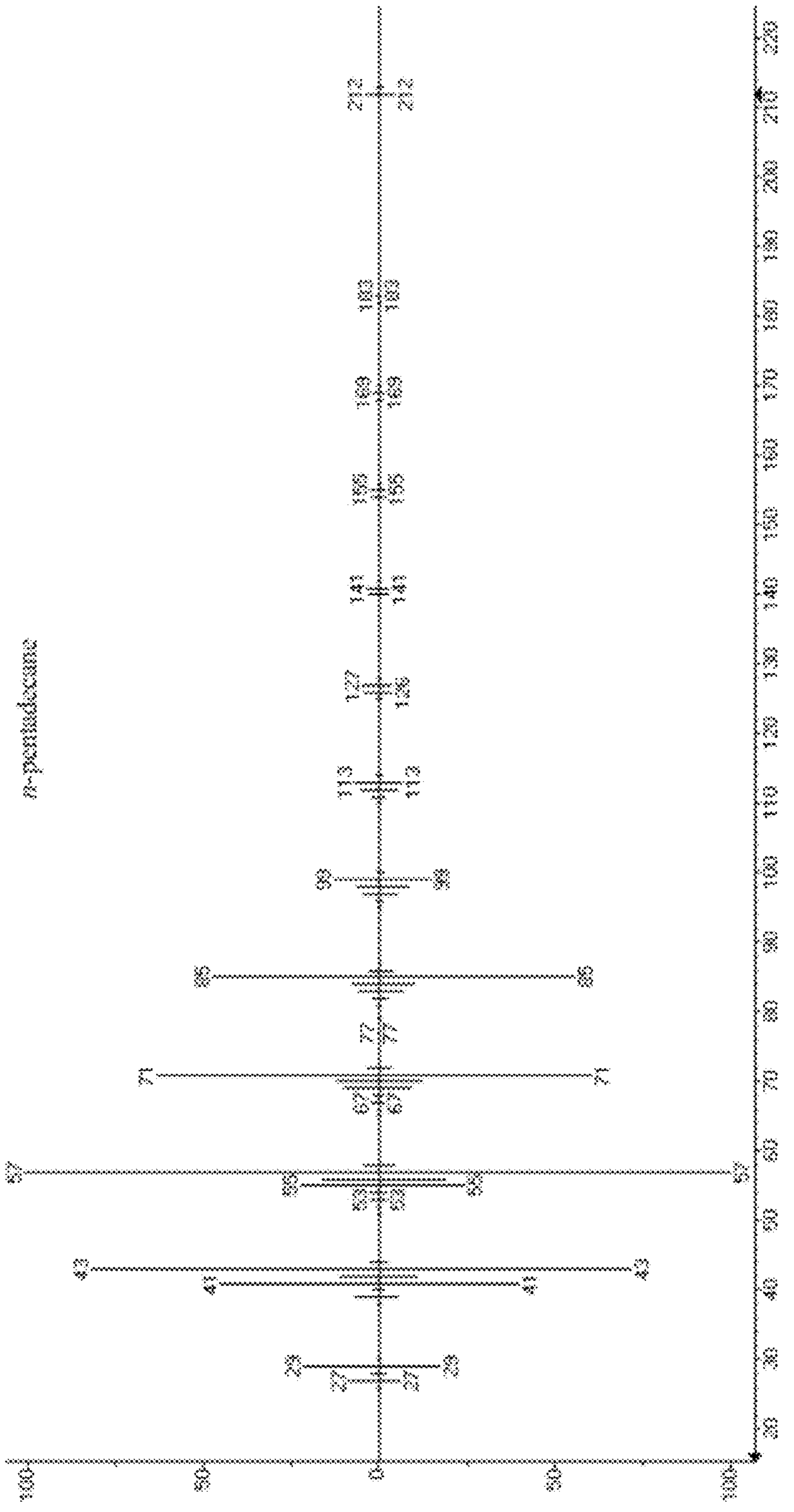
Figure 9D:
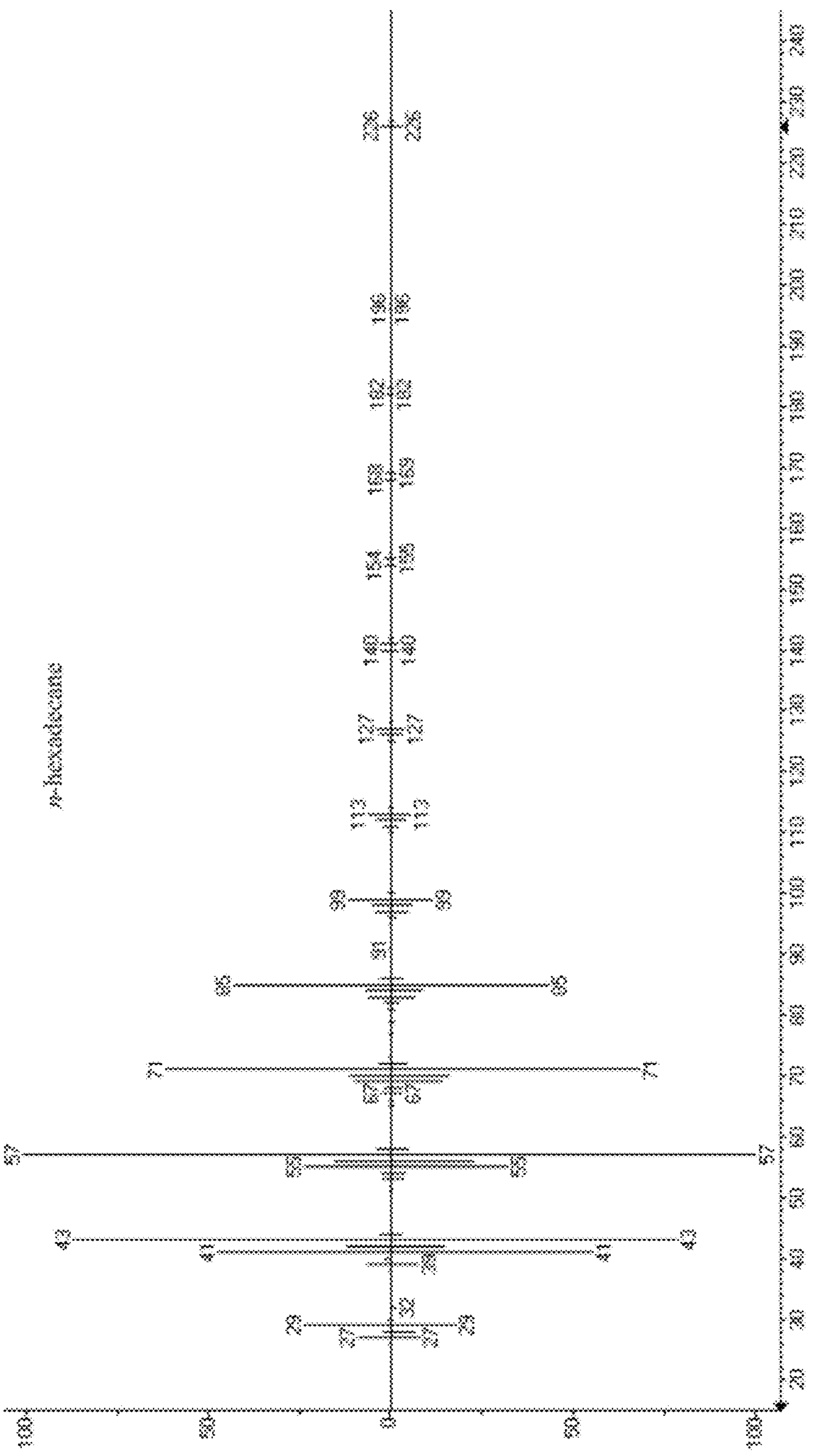
Figure 9E:
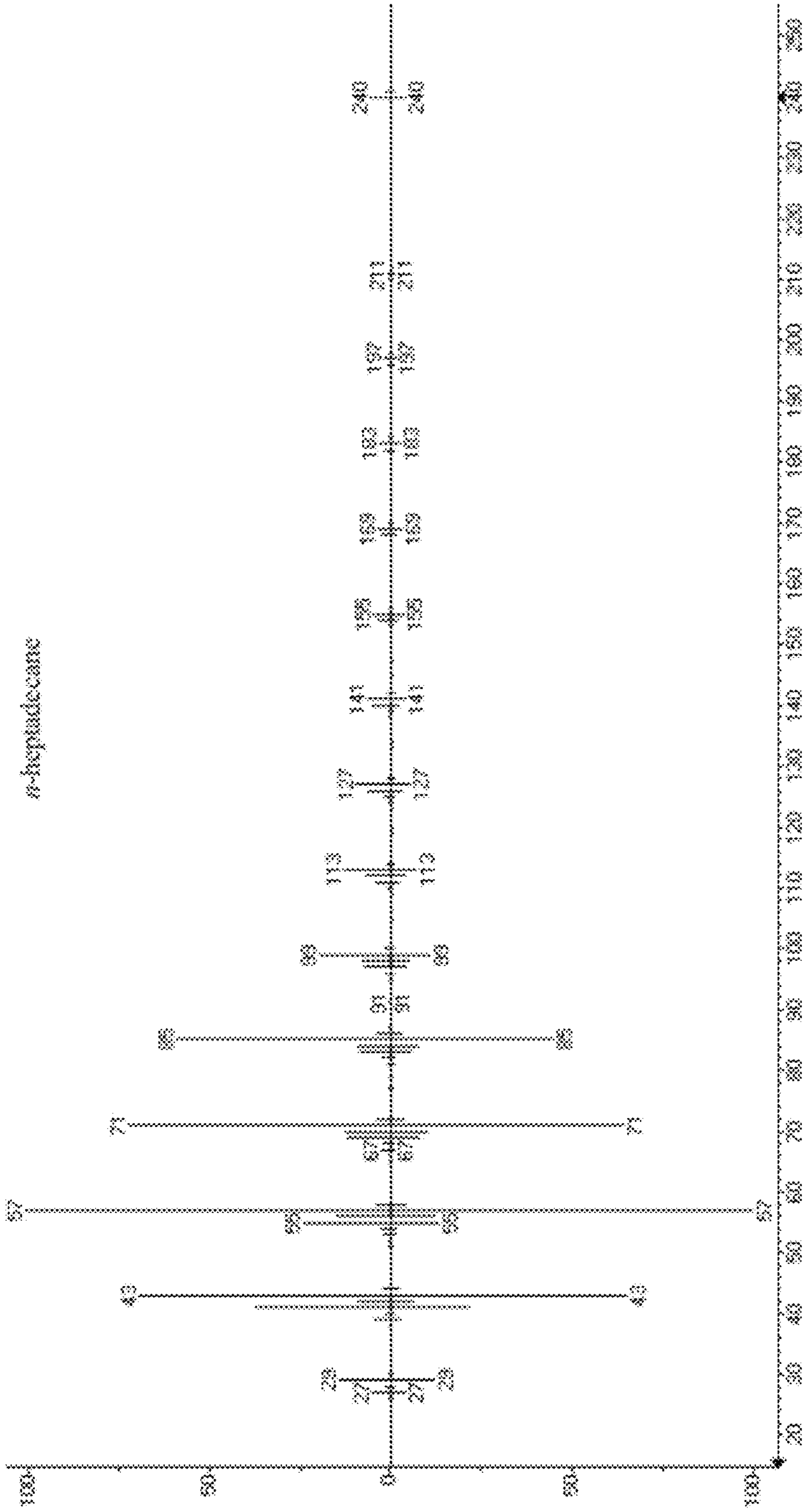
Figure 9F:
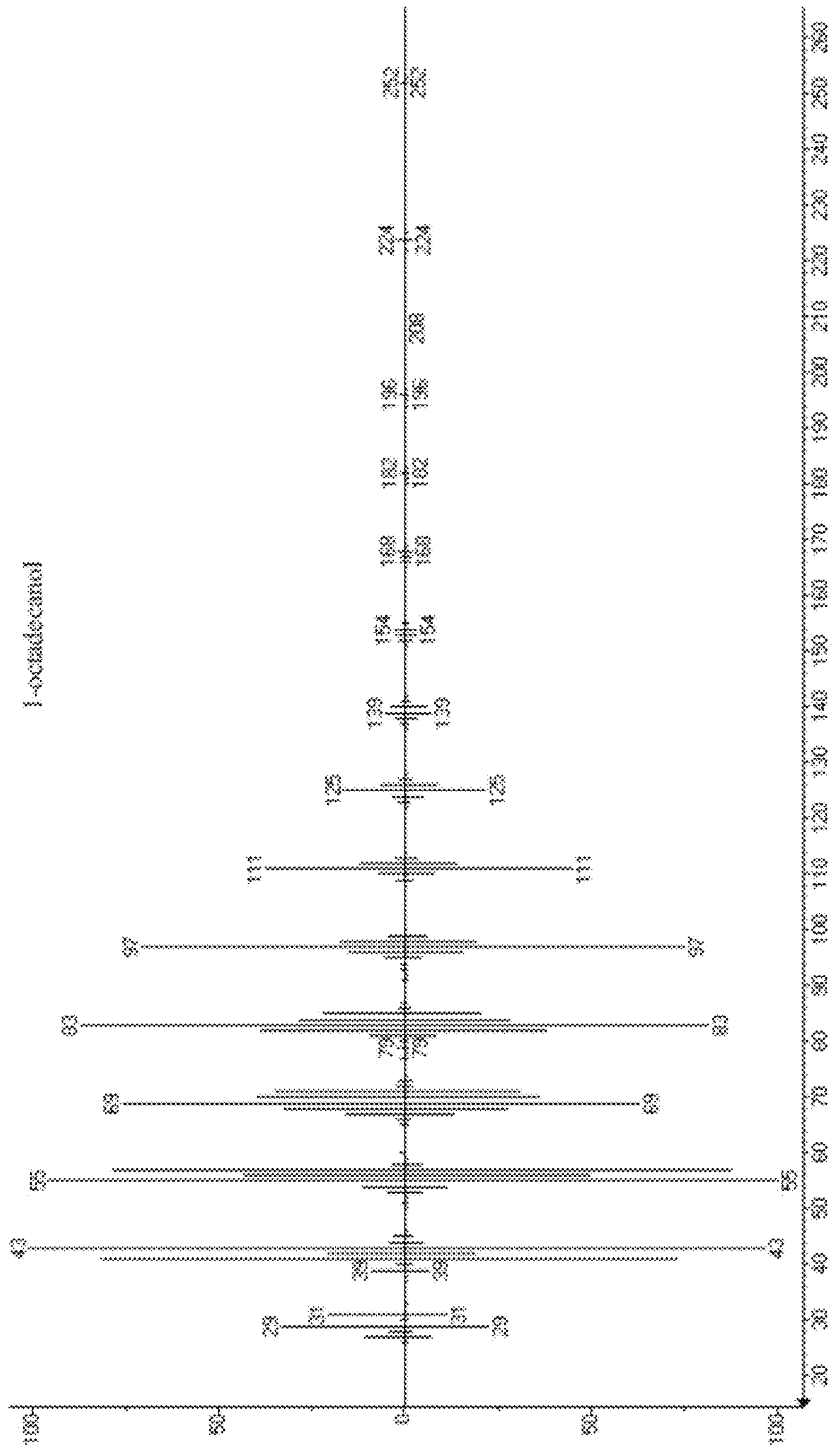

The TICs of JCC1221, JCC1220, JCC1160b, JCC1160a, JCC1160, and JCC879 acetone cell pellet extractants are shown in FIG. 8; n-alkane and 1-alkanol standards are as in Example 2. Consistent with a range of promoter strengths, and with function of the AAR-ADM pathway, there was a range of hydrocarbon accumulation, the order of accumulation being PcI>PcpcB>PlacI-trc>PEM7>PaphII (FIG. 8A).

In JCC1160, approximately 0.2% of dry cell weight was found as n-alkanes and n-alkan-1-ol (excluding n-nonadec-1-ene). Of this 0.2%, approximately three-quarters corresponded to n-alkanes, primary products being n-heptadecane and n-pentadecane. These hydrocarbons were not detected in JCC879. The data are summarized in Table 6A.

TABLE 6A

Hydrocarbons detected in acetone extracts of JCC1160 and JCC879.

| | Approximate % of dry cell weight | |
|---|---|---|
| Compound | JCC879 | JCC1160 |
| n-pentadecane | not detected | 0.024% |
| n-hexadecane | nd | 0.004% |
| n-heptadecane | nd | 0.110% |
| n-octadecan-1-ol | nd | 0.043% |
| Total | | 0.181% |
| % of products that are n-alkanes | | 76% |

The highest accumulator was JCC1221 (PcI). Hydrocarbons identified in JCC1221, but not in control strain JCC879, are detailed in Table 6B, Table 6C and FIG. 8B. These hydrocarbons are n-tridecane (1), n-tetradecane (1), n-pentadecene (2), n-pentadecane (1), n-hexadecane (1), n-heptadec-di-ene (2), three isomers of n-heptadecene (2), n-heptadecane (1), and 1-ocadecanol (1), where the number in parentheses indicates the GC-MS peak assignment method.

TABLE 6B n-Alkanes quantitated in acetone extract of JCC1221

| Compound | % of JCC1221 dry cell weight |
|---|---|
| n-tridecane | <0.001% |
| n-tetradecane | 0.0064% |
| n-pentadecane | 0.40% |
| n-hexadecane | 0.040% |
| n-heptadecane | 1.2% |
| Total | 1.67% |

MS fragmentation spectra of Method 1 peaks are shown in FIG. 9, plotted against their respective library hits. The only alkanes/alkenes observed in JCC879 were 1-nonadecene and a smaller amount of nonadec-di-ene, alkenes that are known to be naturally synthesized by JCC138 (Winters K et al. (1969) *Science* 163:467-468). The major products observed in JCC1221 were n-pentadecane (~25%) and n-heptadecane (~75%); all others were in relatively trace levels.

The formation of n-pentadecane and n-heptadecane in JCC1221, as well as the nine other trace hydrocarbon products, is consistent with the virtually complete operation of the ADM-AAR pathway in JCC138, i.e., 16:0 hexadecyl-ACP→n-hexadecanal→n-pentadecane and 18:0 octadecyl-ACP→n-octadecanal→n-heptadecane. Indeed it is known that the major acyl-ACP species in this organism are $C_{16:0}$ and $C_{18:0}$ (Murata N et al. (1992) *Plant Cell Physiol* 33:933-941). Relatively much less fatty alcohol is produced relative to AAR-ADM expression in *E. coli* (Example 3), thereby preventing the accumulation of hexadecanal and octadecanal that could in turn be non-specifically dehydrogenated to the corresponding 1-alkanols. Thus, in JCC1221, only a very small 1-octadecanol (1) peak is observed (FIG. 8).

The other trace hydrocarbons seen in JCC1221 are believed to be unsaturated isomers of n-pentadecane and n-heptadecane (Table 6C). It is hypothesized that all these alkenes are generated by desaturation events following the production of the corresponding alkanes by the SYNPCC7942_1593 Adm. This contrasts with the situation in *E. coli*, where double bonds are introduced into the growing acyl chain while it is linked to the acyl carrier protein (Example 3). JCC138 is known to have a variety of position-specific acyl-lipid desaturases that, while nominally active only on fatty acids esterified to glycerolipids, could potentially act on otherwise unreactive alkanes produced nonphysiologically by the action of AAR and ADM. JCC138 desaturases, i.e., DesA, DesB, and DesC, introduce cis double bonds at the Δ9, Δ12, and Δ15 positions of $C_{18}$ acyl chains, and at the Δ9 and Δ12 positions of $C_{16}$ acyl chains (Murata N and Wada H (1995) *Biochem J.* 308:1-8). The candidate n-pentadecene peak is believed to be cis-4-pentadecene (Table 6C).

Assuming also that heptadecane could also serve as a substrate for JCC138 desaturases, and that it would be desaturated at positions analogous to the Δ9, Δ12, and Δ15 of the $C_{18}$ acyl moiety, there are four theoretically possible mono-unsaturated isomers: cis-3-heptadecene, cis-6-heptadecene, cis-8-heptadecene, and cis-9-heptadecene. These isomers do not include the single n-heptadecene species nominally observed in *E. coli*, cis-7-heptadecene (Example 2). It is believed that the three peaks closest to the n-heptadecane peak—denoted by subscripts 1, 2, and 3 in Table 6C and FIG. 8B—encompass at least three of these four mono-unsaturated heptadecane isomers. Consistent with this, n-heptadecene$_2$ and n-heptadecene$_3$ peaks have the expected molecular ions of mass 238 in their envelope-type fragmentation spectra. There are many isomeric possibilities, accordingly, for the putative cis,cis-heptadec-di-ene peak, which has an envelope-type fragmentation spectrum with the expected molecular ions of mass 236. As expected, all putative heptadecene species elute slightly before n-heptadecane.

TABLE 6C

Alkane and alkenes detected by GC-MS in acetone cell pellet extractants of JCC1221 but not JCC879 in increasing order of retention time.

| Compound | JCC879 | JCC1221 | GC-MS Peak Assigment | Candidate isomer |
|---|---|---|---|---|
| n-tridecane | − | + | Method 1 | |
| n-tetradecane | − | + | Method 1 | |
| n-pentadecene | − | + | Method 2 | cis-4-pentadecene |
| n-pentadecane | − | + | Method 1 | |
| n-hexadecane | − | + | Method 1 | |
| n-heptadec-di-ene | − | + | Method 2 (envelope-type MS with molecular ion mass 236) | cis,cis-heptadec-di-ene |
| n-heptadecene$_3$ | − | + | Method 2 (envelope-type MS with molecular ion mass 238) | cis-[3/6/8/9]-heptadecene |
| n-heptadecene$_2$ | − | + | Method 2 (envelope-type MS with molecular ion mass 238) | cis-[3/6/8/9]-heptadecene |
| n-heptadecene$_1$ | − | + | Method 2 | cis-[3/6/8/9]-heptadecene |
| n-heptadecane | − | + | Method 1 | |
| 1-octadecanol | − | + | Method 1 | |

"−", not detected;

"+", detected.

Example 6

Intracellular Accumulation of n-Alkanes to up to 5% of Dry Cell Weight in *Synechococcus* sp. PCC 7002 Through Heterologous Expression of *Synechococcus elongatus* PCC7942 SYNPCC7942_1593 (adm) and SYNPCC7942_1594 (aar)

In order to quantitate more accurately the level of intracellular accumulation of n-alkane products in the alkanogen JCC1221 (Example 5), the levels of n-pentadecane and n-heptadecane, as well as the relatively trace products n-tetradecane and n-hexadecane, were quantified with respect to dry cell weight (DCW). Based on the hypothesis that the extent of n-alkane production could correlate positively with the level of SYNPCC7942_1593-SYNPCC7942_1594 operon expression, the DCW-normalized n-alkane levels of JCC1221 were determined as a function of the spectinomycin concentration of the growth medium. The rationale was that the higher the spectinomycin selective pressure, the higher the relative copy number of pAQ1, and the more copies of the aadA-linked SYNPCC7942_1593-SYNPCC7942_1594 operon.

A clonal starter culture of JCC1221 was grown up in A+ medium supplemented with 100 μg/ml spectinomycin in for 7 days at 37° C. at 150 rpm in 3% $CO_2$-enriched air at ~100 μmol photons $m^{-2}$ $s^{-1}$ in a Multitron II (Infors) shaking photoincubator. At this point, this culture was used to inoculate triplicate 30 ml JB2.1 medium (PCT/US2009/006516) flask cultures supplemented with 100, 200, 300, 400, or 600 μg/ml spectinomycin. JB2.1 medium consists of 18.0 g/l sodium chloride, 5.0 g/l magnesium sulfate heptahydrate, 4.0 g/l sodium nitrate, 1.0 g/l Tris, 0.6 g/l potassium chloride, 0.3 g/l calcium chloride (anhydrous), 0.2 g/l potassium phosphate monobasic, 34.3 mg/l boric acid, 29.4 mg/l EDTA (disodium salt dihydrate), 14.1 mg/l iron (III) citrate hydrate, 4.3 mg/l manganese chloride tetrahydrate, 315.0 μg/l zinc chloride, 30.0 μg/l molybdenum (VI) oxide, 12.2 μg/l cobalt (II) chloride hexahydrate, 10.0 μg/l vitamin $B_{12}$, and 3.0 μg/l copper (II) sulfate pentahydrate. The 15 cultures were grown for 10 days at 37° C. at 150 rpm in 3% $CO_2$-enriched air at ~100 μmol photons $m^{-2}$ $s^{-1}$ in a Multitron II (Infors) shaking photoincubator.

For each culture, 5-10 ml was used for dry cell weight determination. To do so, a defined volume of culture—corresponding to approximately 20 mg DCW—was centrifuged to pellet the cells. Cells were transferred to a pre-weighed eppendorf tube, and then washed by 2 cycles of resuspension in Milli-Q water and microcentrifugation, and dewetted by 3 cycles of microcentrifugation and aspiration. Wet cell pellets were frozen at −80° C. for two hours and then lyophilized overnight, at which point the tube containing the dry cell mass was weighed again such that the mass of the cell pellet could be calculated within ±0.1 mg. In addition, for each culture, 0.3-0.8 ml was used for acetone extraction of the cell pellet for GC analysis. To do so, a defined volume of culture—corresponding to approximately 1.4 mg DCW—was microcentrifuged to pellet the cells. Cells were then washed by 2 cycles of resuspension in Milli-Q water and microcentrifugation, and then dewetted by 4 cycles of microcentrifugation and aspiration. Dewetted cell pellets were then extracted by vortexing for 1 minute in 1.0 ml acetone containing 50 μg/ml BHT and 160 μg/ml n-heptacosane internal standard (Sigma 51559). Cell debris was pelleted by centrifugation, and 700 μl supernatant was pipetted into a GC vial.

Concentrations of n-tetradecane, n-pentadecane, n-hexadecane, and n-heptadecane in the fifteen extractants were quantitated by gas chromatography/flame ionization detection (GC/FID). Unknown n-alkane peak areas in biological samples were converted to concentrations via linear calibration relationships determined between known n-tetradecane, n-pentadecane, n-hexadecane, and n-heptadecane authentic standard concentrations and their corresponding GC-FID peak areas. Standards were obtained from Sigma. GC-FID conditions were as follows. An Agilent 7890A GC/FID equipped with a 7683 series autosampler was used. 1 μl of each sample was injected into the GC inlet (split 5:1, pressure: 20 psi, pulse time: 0.3 min, purge time: 0.2 min, purge flow: 15 ml/min) and an inlet temperature of 280° C. The column was a HP-5MS (Agilent, 30 m×0.25 mm×0.25 μm) and the carrier gas was helium at a flow of 1.0 ml/min. The GC oven temperature program was 50° C., hold one minute; 10° C./min increase to 280° C.; hold ten minutes. n-Alkane production was calculated as a percentage of the DCW extracted in acetone.

Figure 10:
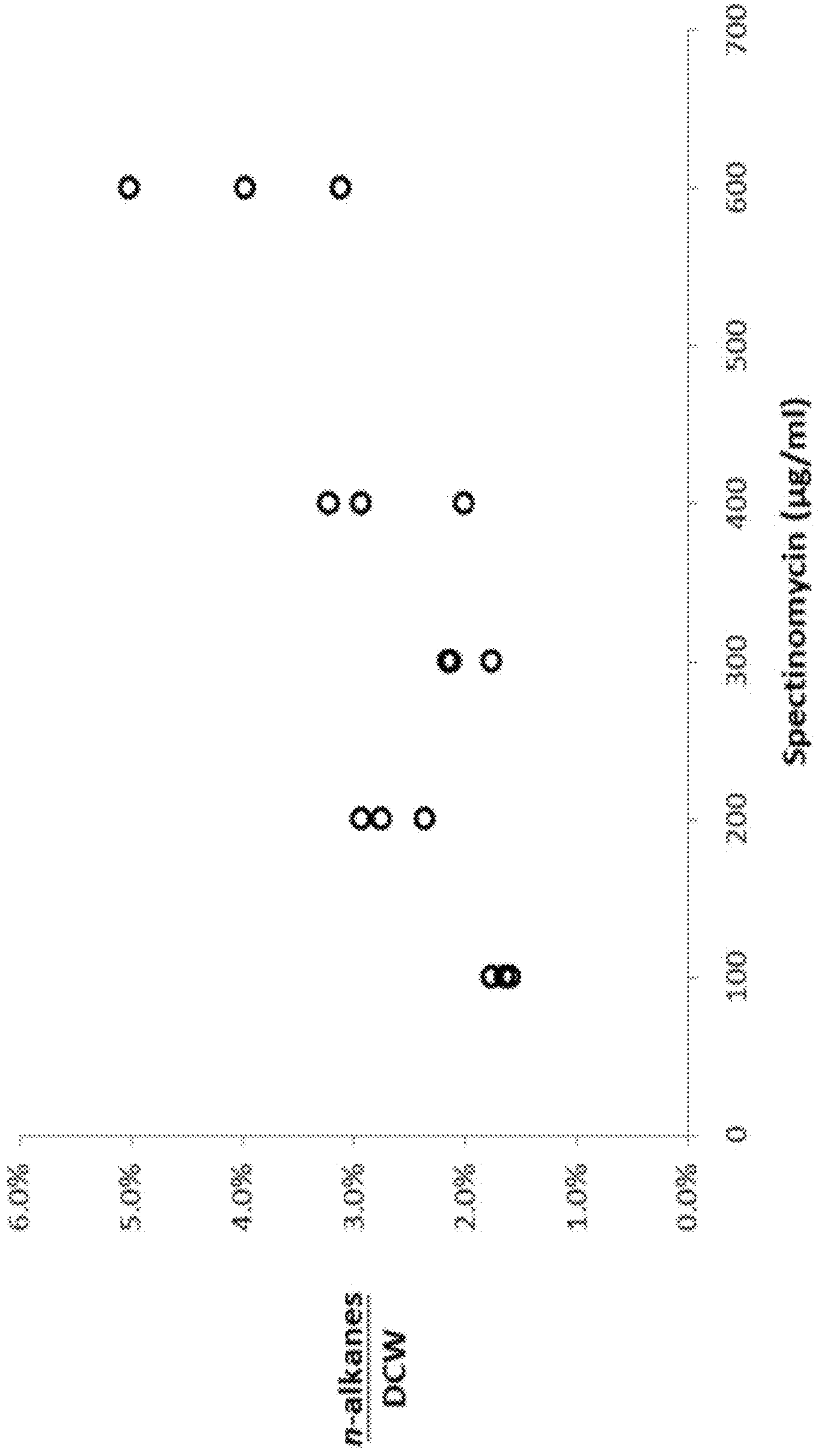
FIG. 10 depicts intracellular n-alkane production as a function of spectinomycin concentration in JCC1221.

Consistent with scaling between pAQ1 selective pressure and the extent of intracellular n-alkane production in JCC1221, there was a roughly positive relationship between the % n-alkanes with respect to DCW and spectinomycin concentration (FIG. 10). For all JCC1221 cultures, n-alkanes were ~25% n-pentadecane and ~75% n-heptadecane. The minimum n-alkane production was ~1.8% of DCW at 100 μg/ml spectinomycin and 5.0% in one of the 600 μg/ml spectinomycin cultures.

Example 7

Production of n-Alkanes in *Synechococcus* sp. PCC 7002 Through Heterologous Expression of *Prochlorococcus marinus* MIT 9312 PMT9312_0532 (adm) and PMT9312_0533 (aar)

This candidate Adm/Aar pair from *Prochlorococcus marinus* MIT9312 was selected for functional testing by heterologous expression in JCC138 because of the relatively low amino acid homology (≤62%) of these proteins to their *Synechococcus elongatus* PCC7942 counterparts, SYNPCC7942_1593 and SYNPCC7942_1594. Specifically, the 252-amino acid protein PMT9312_0532 exhibits only 62% amino acid identity with the 232 amino acid protein SYNPCC7942_1593, wherein amino acids 33-246 of the former are aligned with amino acids 11-224 of the latter. The 347 amino acid protein PMT9312_0533 exhibits only 61% amino acid identity with the 342 amino acid protein SYNPCC7942_1594, wherein amino acids 1-337 of the former are aligned with amino acids 1-339 of the latter.

A codon- and restriction-site-optimized version of the PMT9312_0532-PMT9312_0533 operon was synthesized by DNA2.0 (Menlo Park, Calif.), flanked by NdeI and EcoRI sites. The operon was cloned into the pAQ1 homologous recombination vector pJB5 via NdeI and EcoRI, such that the PMT9312_0532-PMT9312_0533 operon was placed under transcriptional control of the aphII promoter. The sequence of the pJB947 vector is provided as SEQ ID NO: 17.

pJB947 was transformed into JCC138 as described in Example 5, generating strain JCC1281. The hydrocarbon products of this strain were compared to those of the negative control strain JCC879, corresponding to JCC138 transformed with empty pJB5 (see Example 5). Eight $OD_{730}$-ml worth of cells (~$8\times10^8$ cells) of each strain was collected by centrifugation, having been grown in A+ medium supplemented with 200 μg/ml spectinomycin as described in Example 5. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 5 minutes in 0.7 ml acetone containing 20 μg/ml BHT and 20 μg/ml EA. Cell debris was pelleted by centrifugation, and 600 μl supernatant was pipetted into a GC vial. Samples were analyzed by GC-MS as described in Example 5.

Figure 11:
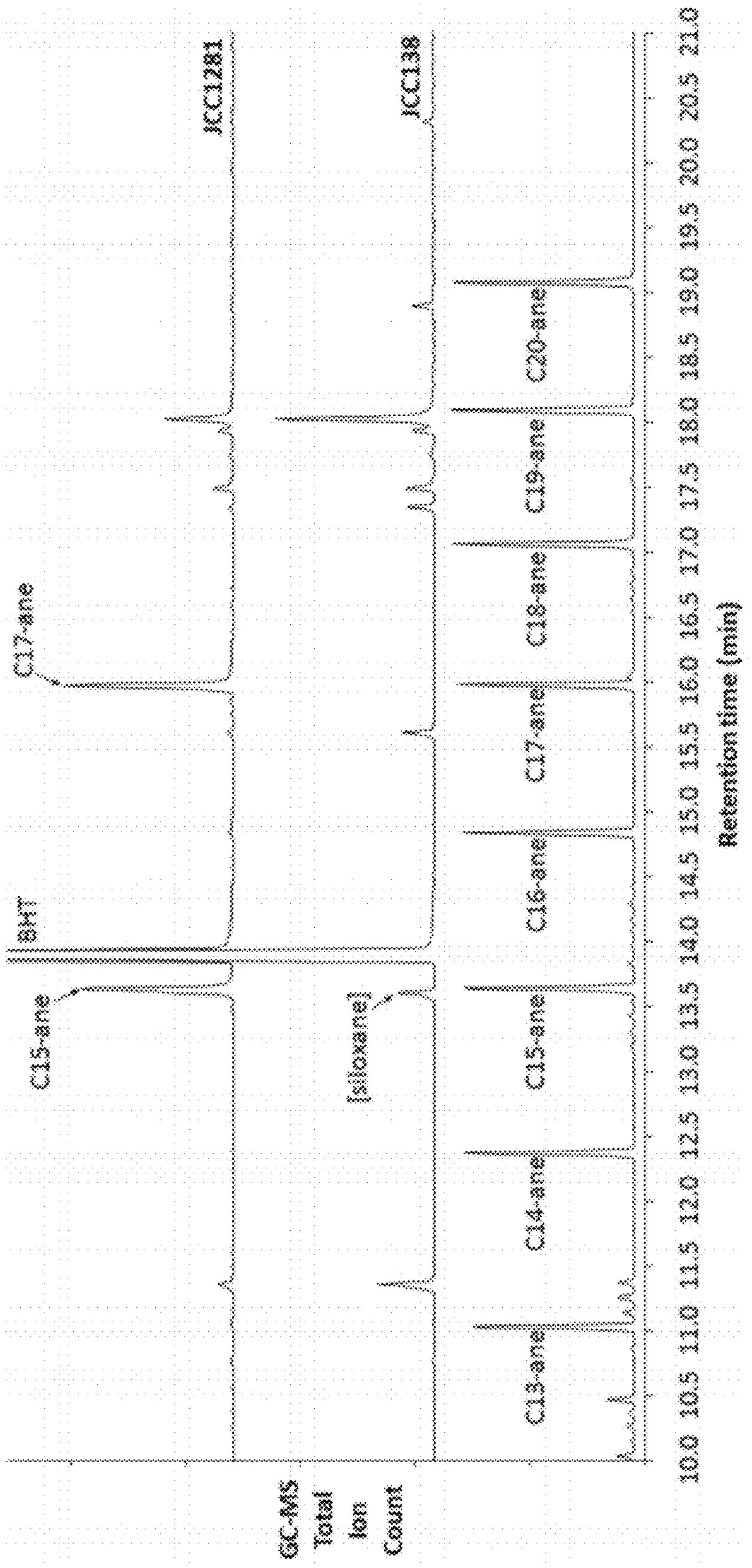
FIG. 11 represents 0-to-1080000-count total ion chromatograms of the JCC1281 BHT-acetone cell pellet extractant versus that of the control strain JCC138, as well as of authentic standard n-alkanes.
Figure 12A:
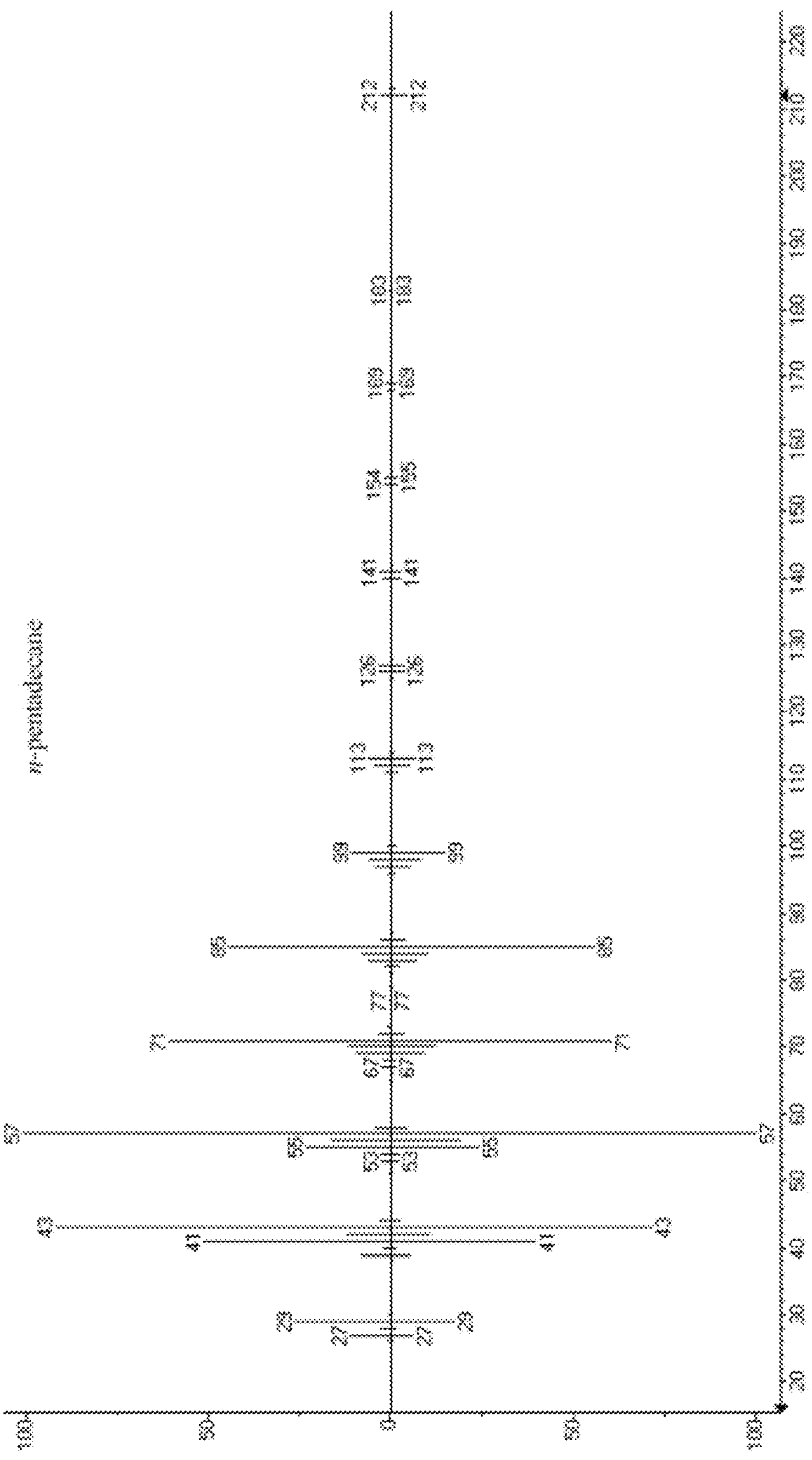
FIG. 12 depicts MS fragmentation spectra of JCC1281 peaks assigned by Method 1 (top mass spectrum of each panel), plotted against their respective NIST library hits (bottom mass spectrum of each panel). A, n-pentadecane; B, n-heptadecane.
Figure 12B:
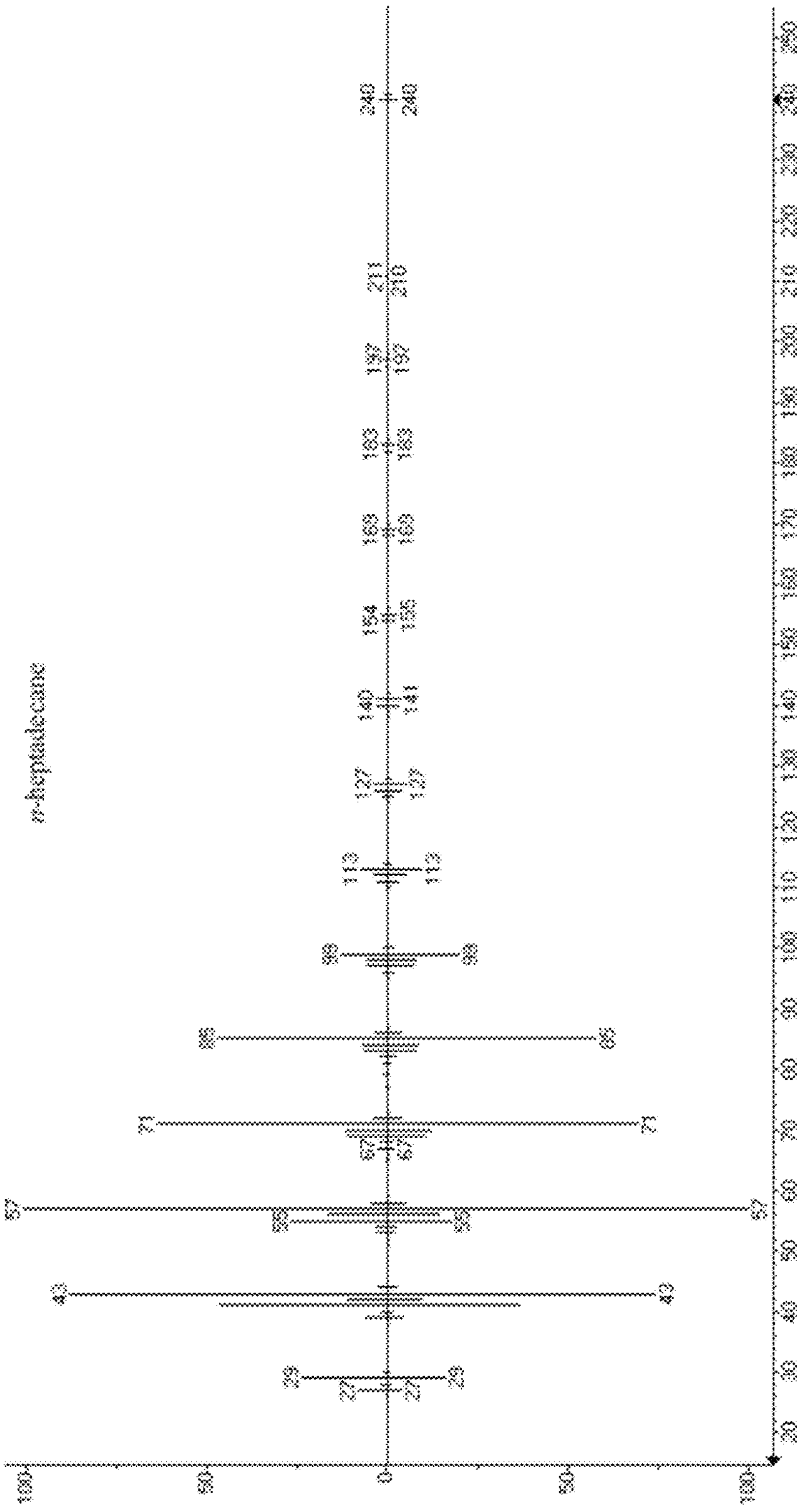

The TICs of JCC1281 and JCC879 acetone cell pellet extractants are shown in FIG. 11; n-alkane standards are as in Example 6. Hydrocarbons identified in JCC1281, but not in control strain JCC879, were n-pentadecane (1) and n-heptadecane (1), where the number in parentheses indicates the GC-MS peak assignment method. MS fragmentation spectra of Method 1 peaks are shown in FIG. 12, plotted against their respective library hits (as noted in Example 5, the only alkanes/alkenes observed in JCC879 were 1-nonadecene and a smaller amount of nonadec-di-ene, alkenes that are known to be naturally synthesized by JCC138). The amount of n-alkanes produced in JCC1281 is at least 0.1% dry cell weight, and at least 2-two times higher than the amount produced by JCC879. The ratio of n-pentadecane:n-heptadecane (~40%: ~60%) in JCC1281 was higher than that observed in JCC1221 (~25%:~75%), suggesting that the PMT9312_0532 (ADM) and/or the PMT9312_0533 (AAR) exhibit higher activity towards the $C_{16}$ substrates relative to $C_{18}$ substrates, compared to SYNPCC7942_1593 (ADM) and/or SYNPCC7942_1594 (AAR).

Example 8

Augmentation of Native n-Alkane Production in *Thermosynechococcus elongatus* BP-1 by Overexpression of the Native tll1313 (adm)-tll1312 (aar) Operon Genes encoding *Thermosynechococcus elongatus* BP-1 tll1312 (AAR) and tll1313 (ADM) are incorporated into one or more plasmids (e.g., pJB5 derivatives), comprising promoters of differing strength. The plasmids are used to transform *Thermosynechococcus elongatus* BP-1. Overexpression of the genes in the transformed cells are measured as will the amount of n-alkanes, particularly heptadecane, produced by the transformed cells, in a manner similar to that described in Example 3. The n-alkanes and other carbon-based products of interest can also be isolated from the cell or cell culture, as needed.

Figure 13A:
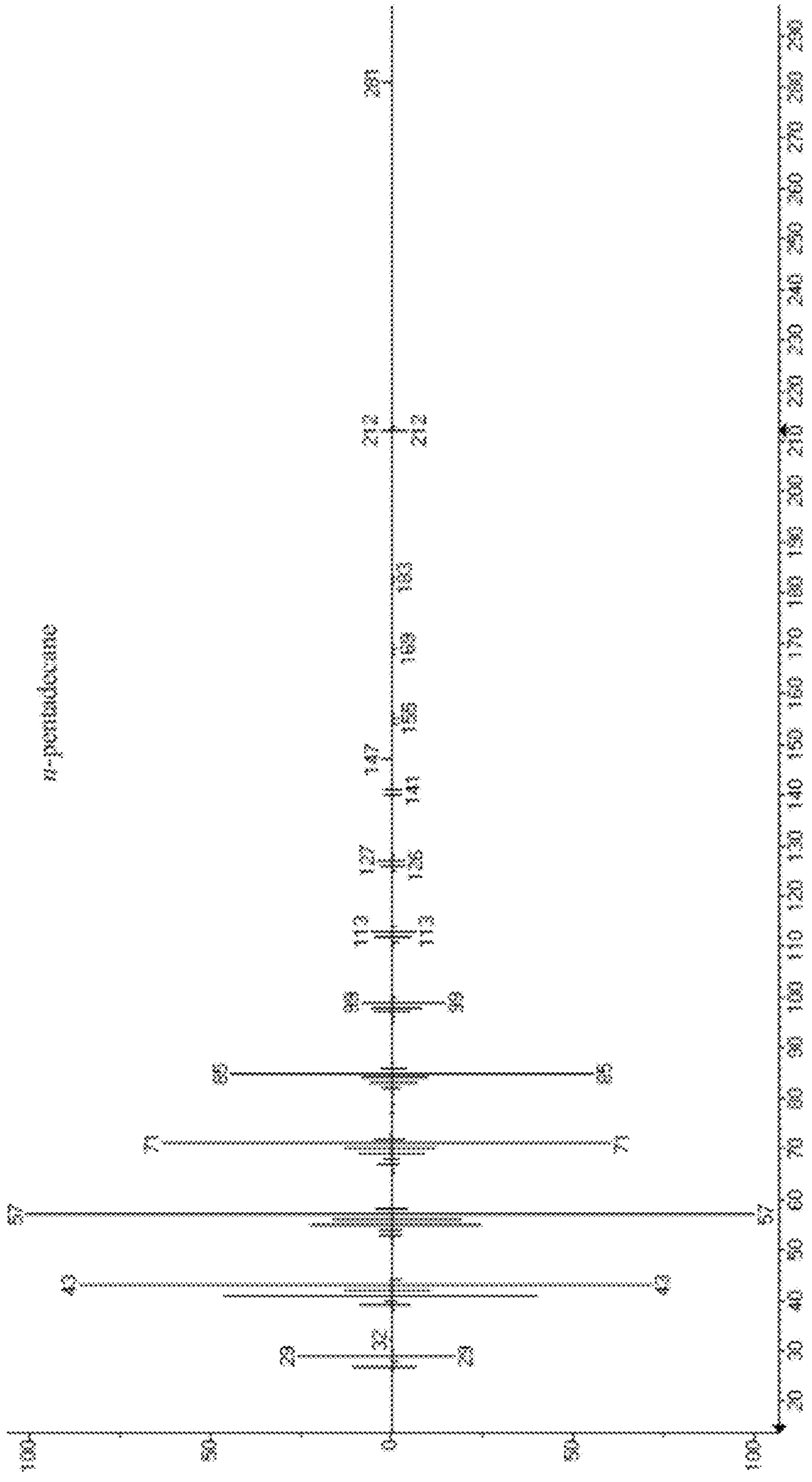
FIG. 13 depicts MS fragmentation spectra of JCC3 peaks assigned by Method 1 (top mass spectrum of each panel), plotted against their respective NIST library hits (bottom mass spectrum of each panel). A, n-pentadecane; B, n-hexadecane; C, n-heptadecane.
Figure 13B:
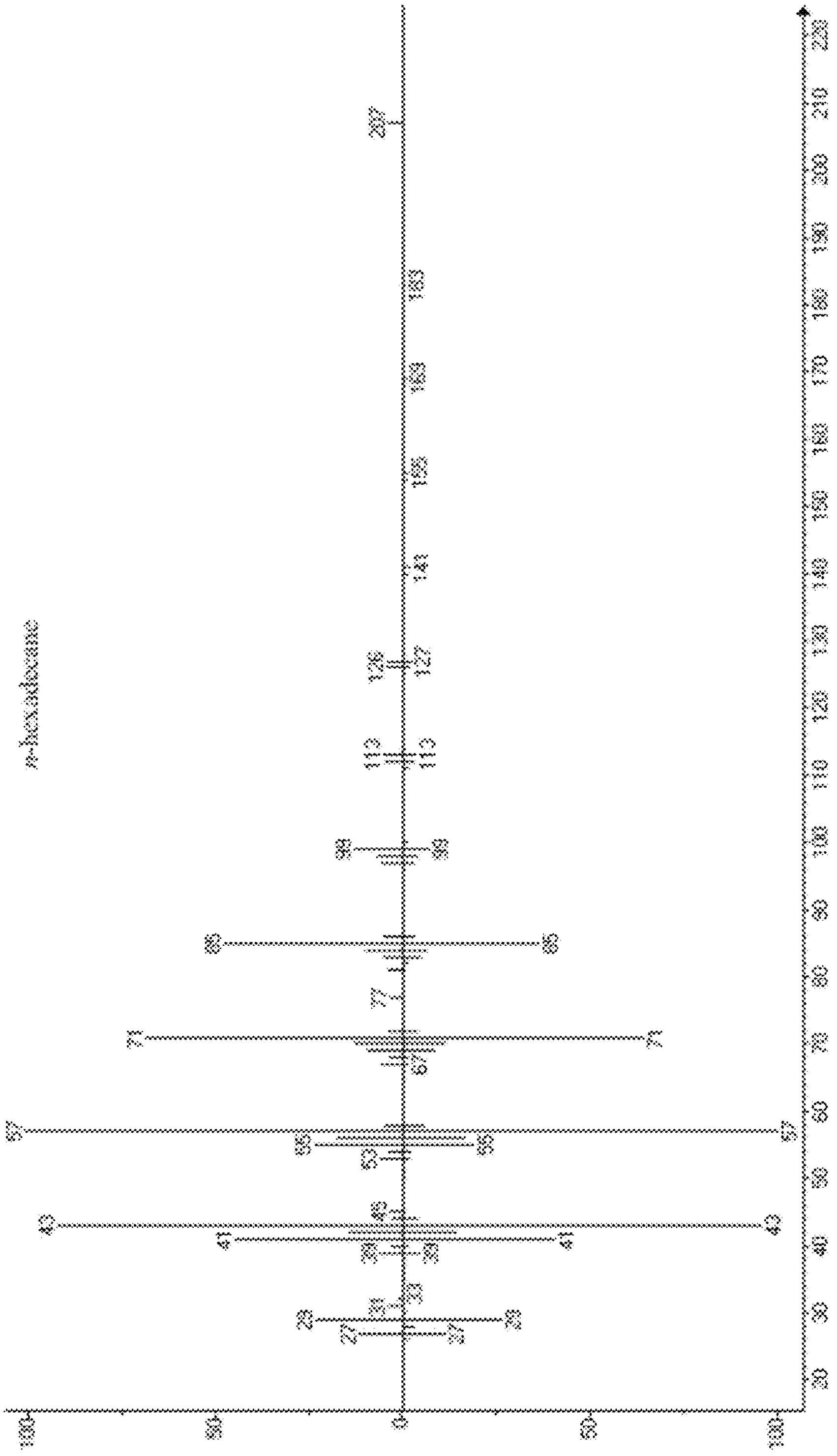
Figure 13C:
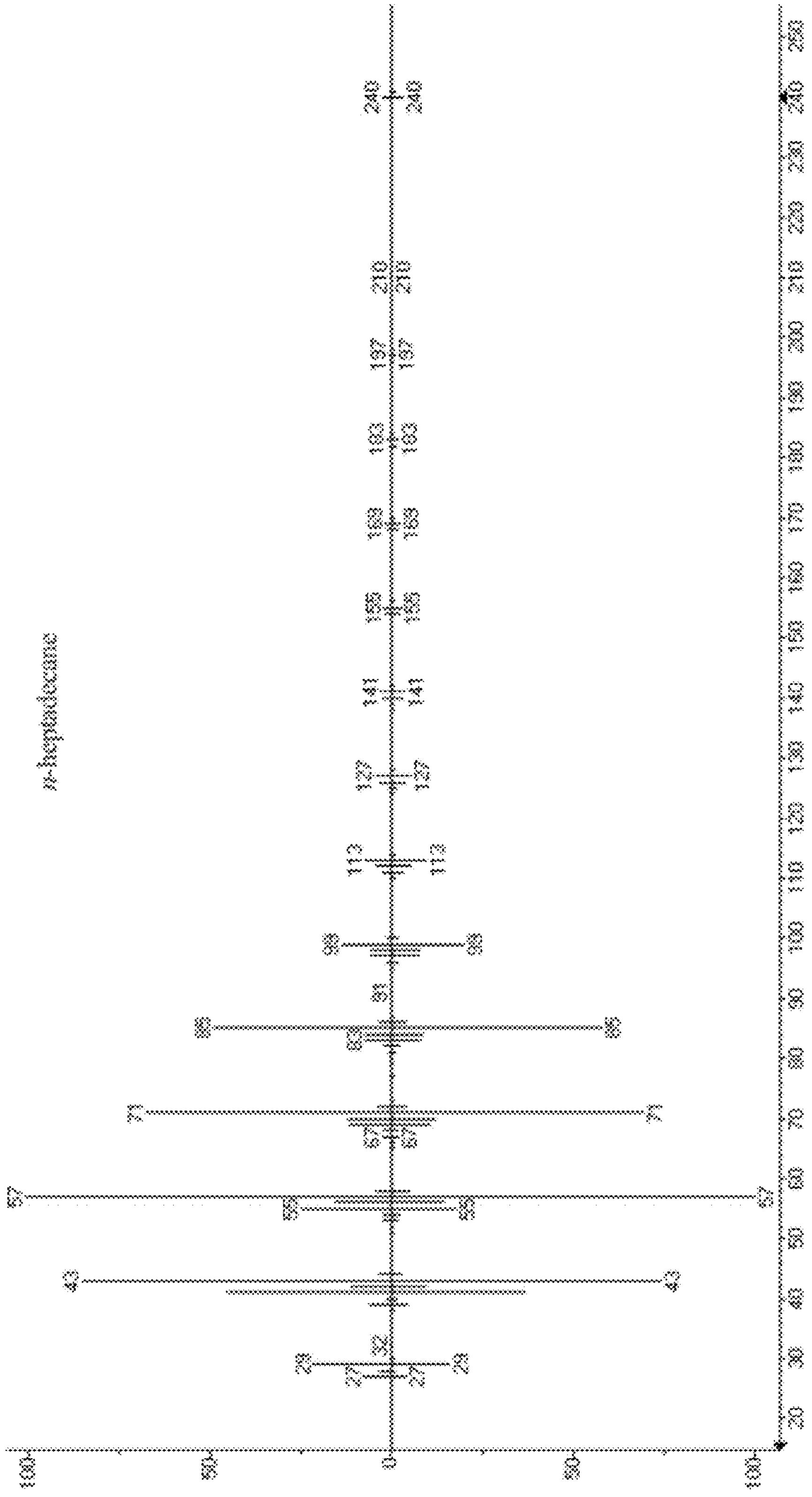

Wild-type *Thermosynechococcus elongatus* BP-1, referred to as JCC3, naturally produces n-heptadecane as the major intracellular hydrocarbon product, with traces of n-hexadecane and n-pentadecane. These n-alkanes were identified by GC-MS using Method 1; fragmentation spectra are shown in FIG. 13. Briefly, a colony of JCC3 was grown in B-HEPES medium to a final $OD_{730}$ of ~4, at which point 5 $OD_{730}$-ml worth of cells was harvested, extracted in acetone, and analyzed by GC-MS as detailed in Example 5.

In an effort to augment this n-alkane production, the native tll1313-tll1312 operonic sequence from this organism was PCR-amplified and cloned into the *Thermosynechococcus elongatus* BP-1 chromosomal integration vector pJB825. This construct places the tll1313-tll1312 operon under the transcriptional control of the constitutive cI promoter. The sequence of the resulting plasmid, pJB825t, is shown in SEQ ID NO:18.

pJB825 and pJB825t were naturally transformed into JCC3 using a standard cyanobacterial transformation protocol, generating strains JCC1084 and JCC1084t, respectively. Briefly, 25 μg of plasmid DNA was added to 0.5 ml of concentrated JCC3 culture ($OD_{730}$~100) that had originally been grown to an $OD_{730}$ of approximately 1.0 in B-HEPES at 45° C. in 3% $CO_2$-enriched air at ~100 μmol photons $m^{-2}$ $s^{-1}$ in a Multitron II (Infors) shaking photoincubator. The cell-DNA mixture was incubated at 37° C. for 4 hours in the dark with gentle mixing, made up to 7 ml with fresh B-HEPES medium, and then incubated under continuous light conditions (~100 μmol photons $m^{-2}$ $s^{-1}$) for 20 hours at 45° C. at 150 rpm in 3% $CO_2$-enriched air at ~100 μmol photons $m^{-2}$ $s^{-1}$ in a Multitron II (Infors) shaking photoincubator. At this point, cells were collected by centrifugation and serial dilutions were mixed with molten top agar and plated on the surface of B-HEPES plates supplemented with 60 μg/ml kanamycin. Transformant colonies appeared in the top agar layer within around 7 days upon incubation in a photoincubator (Percival) in 1% $CO_2$-enriched air at continuous ~100 μmol photons $m^{-2}$ $s^{-1}$ irradiance. Single colonies of JCC1084 and JCC1084t were then grown up in triplicate to an $OD_{730}$ of ~6 in B-HEPES/60 μg/ml kanamycin liquid culture, and their intracellular hydrocarbon products quantitated by GC-FID.

3.5 $OD_{730}$-ml worth of cells (~3.5×$10^8$ cells) of each replicate culture of each strain was collected by centrifugation. Cell pellets were washed thoroughly by 3 cycles of resuspension in Milli-Q water and microcentrifugation, and then dewetted as much as possible by 3 cycles of microcentrifugation and aspiration. Cell pellets were then extracted by vortexing for 1 minutes in 0.7 ml acetone containing 20 μg/ml BHT and 20 μg/ml n-heptacosane. Cell debris was pelleted by centrifugation, and 600 μl supernatant was pipetted into a GC vial. The two extractants, along with authentic $C_8$-$C_{20}$ n-alkane authentic standards (Sigma 04070), were then analyzed by GC coupled with flame ionization detection (FID) as described in Example 6. Quantitation of n-pentadecane, n-hexadecane, and n-heptadecane by GC-FID, and dry cell weights were taken as described in Example 6.

Figure 14:
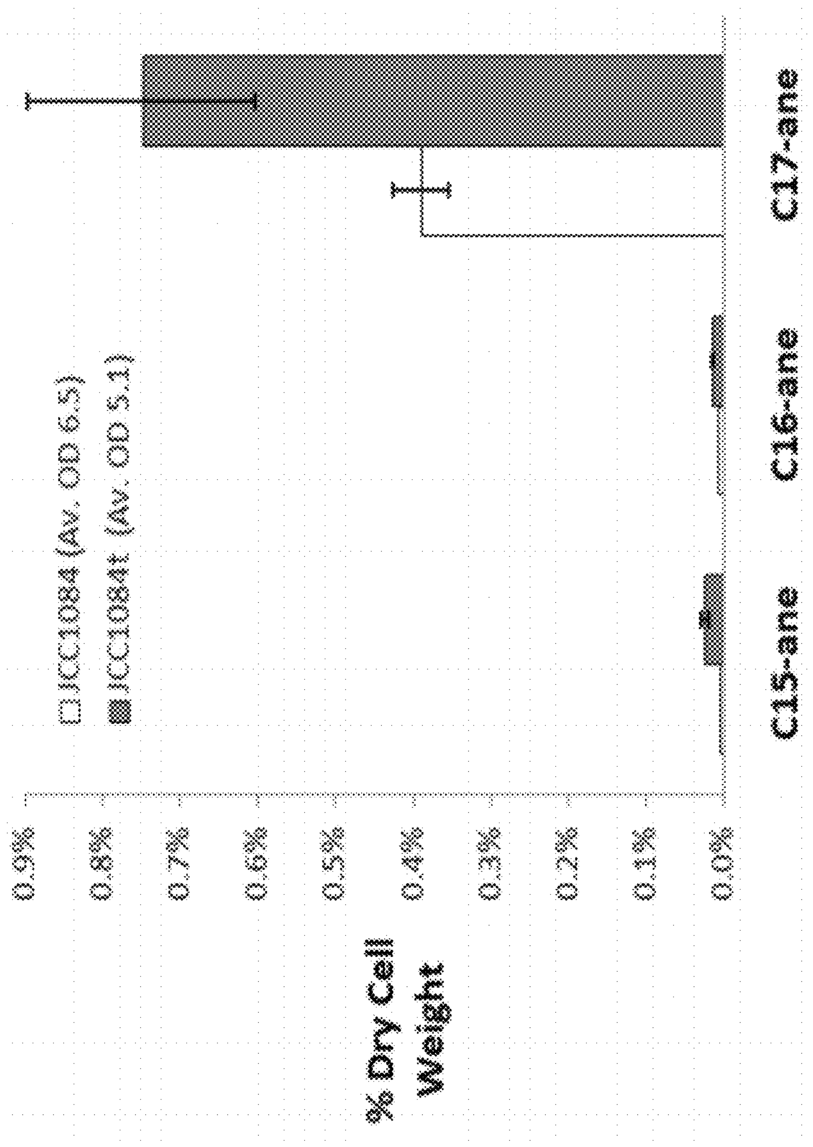
FIG. 14 depicts enhanced intracellular production of n-alkanes in JCC1084t compared to the control strain JCC1084. Error bars represent standard deviation of three independent observations.

Consistent with increased expression of tll1313-tll1312 in JCC1084t relative to the control strain JCC1084, n-pentadecane, n-hexadecane, and n-heptadecane were ~500%, ~100%, and ~100% higher, respectively, in JCC1084t relative to their % DCW levels in JCC1084 (FIG. 14). The total n-alkane concentration in both strains was less than 1%. The n-alkane concentration in JCC1084t was at least 0.62% and at least twice as much n-alkane was produced relative to JCC1084.

Example 9

Comparison of Intracellular Hydrocarbon Products of JCC1113 (a Derivative of *E. coli*) and JCC1221 (a Derivative of *Synechococcus* sp. PCC 7002), Both Strains Heterologously Expressing *Synechococcus elongatus* SYNPCC7942_1593 (adm) and SYNPCC7942_1594 (aar)

Figure 15:
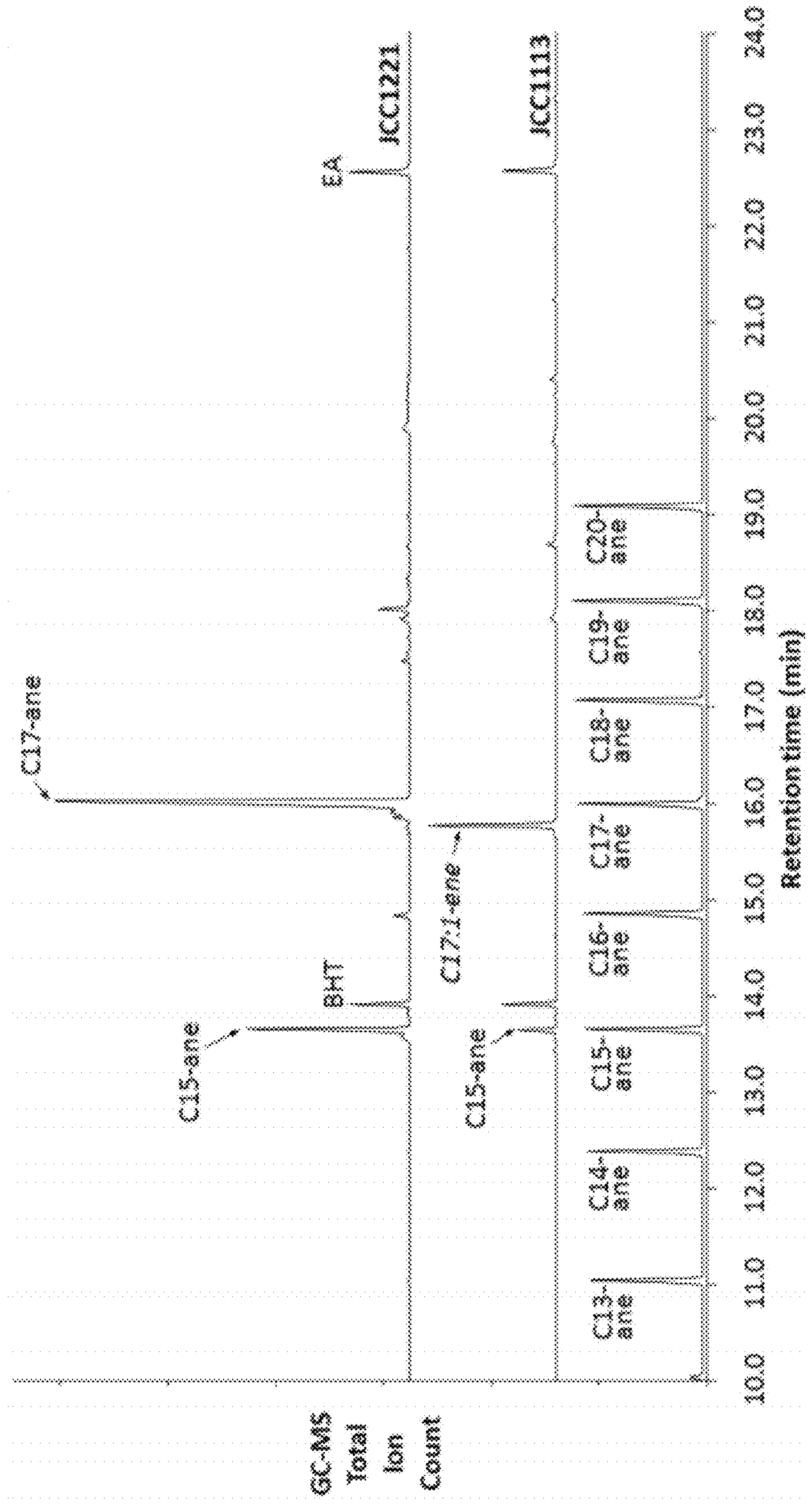
FIG. 15 represents 0-to-31500000-count total ion chromatograms of JCC1113 and JCC1221 BHT-acetone cell pellet extracts, as well as authentic n-alkane standards.

GC-MS TICs of JCC1113 and JCC1221 acetone cell pellet extractants are shown in FIG. 15, along with the TIC of $C_8$-$C_{20}$ n-alkane authentic standards (Sigma 04070). These two strains are derived from *E. coli* BL21(DE3) and *Synechococcus* sp. PCC7002, respectively, and are described in detail in Examples 3 and 5, respectively. JCC1113 synthesizes predominantly n-heptadecene and n-pentadecane, whereas JCC1221 synthesizes predominantly n-heptadecane and n-pentadecane. This figure visually emphasizes the different retention times of the n-heptadecene isomer produced in JCC1113 and n-heptadecane produced in JCC1221.

Example 10

Production of Hydrocarbons in Yeast

The methods of the invention can be performed in a number of lower eukaryotes such as *Saccharomyces cerevisiae, Trichoderma reesei, Aspergillus nidulans* and *Pichia pastoris*. Engineering such organisms may include optimization of genes for efficient transcription and/or translation of the encoded protein. For instance, because the ADM and AAR genes introduced into a fungal host are of cyanobacterial origin, it may be necessary to optimize the base pair composition. This includes codon optimization to ensure that the cellular pools of tRNA are sufficient. The foreign genes (ORFs) may contain motifs detrimental to complete transcription/translation in the fungal host and, thus, may require substitution to more amenable sequences. The expression of each introduced protein can be followed both at the transcriptional and translational stages by well known Northern and Western blotting techniques, respectively.

Use of various yeast expression vectors including genes encoding activities which promote the ADM or AAR pathways, a promoter, a terminator, a selectable marker and targeting flanking regions. Such promoters, terminators, selectable markers and flanking regions are readily available in the art. In a preferred embodiment, the promoter in each case is selected to provide optimal expression of the protein encoded by that particular ORF to allow sufficient catalysis of the desired enzymatic reaction. This step requires choosing a promoter that is either constitutive or inducible, and provides regulated levels of transcription. In another embodiment, the terminator selected enables sufficient termination of transcription. In yet another embodiment, the selectable/counterselectable markers used are unique to each ORF to enable the subsequent selection of a fungal strain that contains a specific combination of the ORFs to be introduced. In a further embodiment, the locus to which relevant plasmid construct (encoding promoter, ORF and terminator) is localized, is determined by the choice of flanking region.

The engineered strains can be transformed with a range of different genes for production of carbon-based products of interest, and these genes are stably integrated to ensure that the desired activity is maintained throughout the fermentation process. Various combinations of enzyme activities can be engineered into the fungal host such as the ADM, ADR pathways while undesired pathways are attenuated or knocked out.

Example 11

Quantitation of Intracellular n-pentadecane:n-heptadecane Ratio of *Synechococcus* sp. PCC 7002 Strains Constitutively Expressing Heterologous *Synechococcus elongatus* SYNPCC7942_1593 (adm) Plus SYNPCC7942_1594 (aar) or Heterologous *Prochlorococcus marinus* MIT 9312 PMT9312_0532 (adm) Plus PMT9312_0533 (aar) on pAQ1

In Example 5 ("Production of n-Alkanes, n-Alkenes, and Fatty Alcohol in *Synechococcus* sp. PCC 7002 through Heterologous Expression of *Synechococcus elongatus* PCC7942 SYNPCC7942_1593 (adm) and SYNPCC7942_1594 (aar)") and Example 7 ("Production of n-Alkanes in *Synechococcus* sp. PCC 7002 through Heterologous Expression of *Prochlorococcus marinus* MIT 9312 PMT9312_0532 (adm) and PMT9312_0533 (aar)"), the intracellular hydrocarbon products of JCC138 (*Synechococcus* sp. PCC 7002) strains expressing the *Synechococcus elongatus* sp. PCC7942 and *Prochlorococcus marinus* MIT 9312 adm-aar operons were analyzed by GC-MS. In this Example, GC-FID (Gas Chromatography-Flame Ionization Detection) was applied to more accurately measure these products with respect to dry cell weight. Of special interest was the ratio between n-pentadecane and n-heptadecane. In this regard, it is noted that *Synechococcus elongatus* sp. PCC7942 naturally synthesizes n-heptadecane as the major intracellular n-alkane, whereas *Prochlorococcus marinus* MIT 9312 naturally synthesizes n-pentadecane as the major intracellular n-alkane.

The following four strains were compared: (1) JCC138, corresponding to wild-type *Synechococcus* sp. PCC 7002, (2) JCC879, corresponding to negative control strain JCC138 transformed with pAQ1-targeting plasmid pJB5 described in Example 5, (3) JCC1469, corresponding to JCC138 ΔSYNPCC7002_A1173::gent (JCC1218) transformed with pAQ1-targeting plasmid pJB886 encoding constitutively expressed *Synechococcus elongatus* sp. PCC7942 adm-aar described in Example 5, and (4) JCC1281, corresponding to JCC138 transformed with pAQ1-targeting plasmid pJB947 encoding constitutively expressed *Prochlorococcus marinus* MIT 9312 adm-aar, described in Example 7. A clonal starter culture of each strain was grown up for 5 days at 37° C. at 150 rpm in 2% $CO_2$-enriched air at ~100 μmol photons $m^{-2}$ $s^{-1}$ in a Multitron II (Infors) shaking photoincubator in A+ (JCC138), A+ supplemented with 100 μg/ml spectinomycin (JCC879 and JCC1281), or A+ supplemented with 100 μg/ml spectinomycin and 50 μg/ml gentamycin (JCC1469). At this point, each starter culture was used to inoculate duplicate 30 ml JB2.1 medium flask cultures supplemented with no antibiotics (JCC138) or 400 μg/ml spectinomycin (JCC879, JCC1469, and JCC1281). The eight cultures were then grown for 14 days at 37° C. at 150 rpm in 2% CO2-enriched air at ~100 μmol photons $m^{-2}$ $s^{-1}$ in a Multitron II (Infors) shaking photoincubator.

For each culture, 25 $OD_{730}$-ml worth of cells was collected by centrifugation in a pre-weighed eppendorf tube. Cells were washed by two cycles of resuspension in Milli-Q water and microcentrifugation, and dewetted by two cycles of microcentrifugation and aspiration. Wet cell pellets were frozen at −80° C. for two hours and then lyophilized overnight, at which point the tube containing the dry cell mass was weighed again such that the mass of the cell pellet (~6 mg) could be calculated within ±0.1 mg. In parallel, 4 $OD_{730}$-ml worth of cells from each culture was collected by centrifugation in an eppendorf tube, washed thoroughly by three cycles of resuspension in Milli-Q water and microcentrifugation, and then dewetted as much as possible by threes cycles of microcentrifugation and aspiration. Dewetted cell pellets were then extracted by vortexing for 15 seconds in 1 ml acetone containing 23.6 mg/l BHT and 24.4 mg/l n-heptacosane ($C_{27}$) internal standard (ABH); cell debris was pelleted by centrifugation, and 450 μl supernatant was submitted for GC-FID. Acetone-extracted DCW was calculated as 4/25, or 16%, of the DCW measured for 25 OD730-ml worth of cells. In parallel with the eight biological sample extractions, six empty eppendorf tubes were extracted with ABH in the same fashion. The extraction/injection efficiency of all ABH extractants was assessed by calculating the ratio between the n-heptacosane GC-FID peak area of the sample and the average n-heptacosane GC-FID peak area of the six empty-tube controls—only ratios of 100%±3% were accepted (Table 7).

Concentrations of n-tridecane ($C_{13}$), n-tetradecane ($C_{14}$), n-pentadecane ($C_{15}$), n-hexadecane ($C_{16}$), n-heptadecane ($C_{17}$), and n-octadecane ($C_{18}$), in the eight extractants were quantitated by (GC/FID). Unknown n-alkane peak areas in biological samples were converted to concentrations via linear calibration relationships determined between known n-tridecane, n-tetradecane, n-pentadecane, n-hexadecane, n-heptadecane, and n-octadecane authentic standard concentrations and their corresponding GC-FID peak areas. Based on these linear-regression calibration relationships, 95% confidence intervals (95% CI) were calculated for interpolated n-alkane concentrations in the biological samples; interpolation was used in all cases, never extrapolation. 95% confidence intervals were reported as percentages—95% CI % in Table 1—of the interpolated concentration in question. GC-FID conditions were as follows. An Agilent 7890A GC/FID equipped with a 7683 series autosampler was used. 1 μl of each sample was injected into the GC inlet (split 8:1, pressure) and an inlet temperature of 290° C. The column was a HP-5MS (Agilent, 20 m×0.18 mm×0.18 μm) and the carrier gas was helium at a flow of 1.0 ml/min. The GC oven temperature program was 80° C., hold 0.3 minutes; 17.6° C./min increase to 290° C.; hold 6 minutes. n-Alkane production was expressed as a percentage of the acetone-extracted DCW. The coefficient of variation of the n-heptacosane GC-FID peak area of the six empty-tube controls was 1.0%.

GC-FID data are summarized in Table 7. As expected, control strains JCC138 and JCC879 made no n-alkanes, whereas JCC1469 and JCC1281 made n-alkanes, ~98% of which comprised n-pentadecane and n-heptadecane. JCC1469 made significantly more n-alkanes as a percentage of DCW (~1.9%) compared to JCC1281 (~0.7%), likely explaining the relatively low final $OD_{730}$ of the JCC1469 cultures. For the duplicate JCC121 cultures expressing *Synechococcus elongatus* sp. PCC7942 adm-aar, the percentage by mass of n-pentadecane relative to n-pentadecane plus n-heptadecane was 26.2% and 25.3%, whereas it was 57.4% and 57.2% for the duplicate JCC1221 cultures expressing *Prochlorococcus marinus* MIT 9312 adm-aar (Table 7). This result quantitatively confirms that these two different adm-aar operons generate different n-alkane product length distributions when expressed in vivo in a cyanobacterial host.

TABLE 7

Table 7 n-Pentadecane and n-heptadecane quantitated by GC-FID in acetone cell pellet extractants of JCC138, JCC879, JCC1469, and JCC1281.

| Strain | $OD_{730}$ | $C_{27}$-normalized extraction/injection efficiency | $C_{15}$ as % of DCW (95% CI %) | $C_{17}$ as % of DCW (95% CI %) | $(C_{15} + C_{17})/(C_{13} + C_{14} + C_{15} + C_{16} + C_{17})$ Mass % | $C_{15}/(C_{15} + C_{17})$ Mass % |
|---|---|---|---|---|---|---|
| JCC138 #1 | 12.5 | 98% | nd | nd | na | na |
| JCC138 #2 | 13.5 | 99% | nd | nd | na | na |
| JCC879 #1 | 9.8 | 100% | nd | nd | na | na |
| JCC879 #2 | 8.5 | 101% | nd | nd | na | na |
| JCC1469 #1 | 3.1 | 101% | 0.60% (1.1%) | 1.69% (0.7%) | 97.8% | 26.2% |
| JCC1469 #2 | 3.2 | 102% | 0.36% (1.0%) | 1.05% (1.1%) | 98.0% | 25.3% |
| JCC1281 #1 | 9.7 | 101% | 0.26% (1.2%) | 0.19% (0.9%) | 97.2% | 57.4% |
| JCC1281 #2 | 4.8 | 101% | 0.51% (1.9%) | 0.38% (1.1%) | 97.2% | 57.2% |

n-Octadecane was not detected in any of the samples; nd: not detected, na: not applicable.

Example 12

Quantitation of Intracellular n-Pentadecane:n-Heptadecane Ratio of *Synechococcus* sp. PCC 7002 Strains Inducibly Expressing Chromosomally-Integrated Heterologous *Prochlorococcus marinus* MIT 9312 PMT9312_0532 (adm) Plus PMT9312_0533 (aar) with or without Heterologous *Cyanothece* sp. ATCC 51142 Cce_0778 (adm) Plus Cce_1430 (aar)

In order to confirm that heterologous expression of Aar and Adm from the chromosome would lead to intracellular n-alkane accumulation, the *Prochlorococcus marinus* MIT9312 adm-aar operon (encoding PMT9312_0532 plus PMT9312_0533) described in Example 7 was chromosomally integrated at the SYNPCC7002_A0358 locus. To do so, a SYNPCC7002_A0358-targeting vector (pJB1279; SEQ ID NO: 23) was constructed containing 750 bp regions of upstream and downstream homology designed to recombinationally replace the SYNPCC7002_A0358 gene with a spectinomycin-resistance cassette downstream of a multiple cloning site (MCS) situated between said regions of homology. Instead of using a constitutive promoter to express the adm-aar operon, an inducible promoter was employed. Specifically, a urea-repressible, nitrate-inducible nirA-type promoter, P(nir07) (SEQ ID NO:24), was inserted into the MCS via NotI and NdeI, generating the base homologous recombination vector pJB1279.

Two operons were cloned downstream of P(nir07) of pJB1279 to generate two experimental constructs, wherein said operons were placed under transcriptional control of P(nir07). The first operon comprised only the aforementioned *Prochlorococcus* PMT9312_0532-PMT9312_0533 operon, inserted via NdeI and EcoRI, resulting in the final plasmid pJB286alk_p; the sequence of this adm-aar operon was exactly as described in Example 7. The second operon comprised (1) the same *Prochlorococcus* PMT9312_0532-PMT9312_0533 adm-aar operon, followed by (2) an adm-aar operon derived from *Cyanothece* sp. ATCC51142 genes cce_0778 (SEQ ID NO: 31) and cce_1430 (SEQ ID NO: 30), respectively, inserted via EcoRI (selecting the correct orientation by screening), resulting in the final plasmid pJB1256. It is to be noted that *Cyanothece* sp. ATCC51142 naturally synthesizes n-pentadecane as the major intracellular n-alkane. This *Cyanothece* adm-aar operon (SEQ ID NO: 25) was codon- and restriction-site-optimized prior to synthesis by DNA2.0 (Menlo Park, Calif.). The operon expresses proteins with amino acid sequences identical to those of the AAR and ADM enzymes from *Cyanothece* sp. ATCC51142 (SEQ ID NOs: 27 and 29, respectively). The complete operon in plasmid pJB1256, therefore, comprises 4 genes—ADM and AAR from *Prochlorococcus* PMT9312 and ADM and AAR from *Cyanothece* sp. ATCC51142—under the control of a single P(nir07) promoter.

pJB1279, pJB286alk_p, and pJB1256 were naturally transformed into JCC138 exactly as described in Example 5, generating spectinomycin-resistant strains JCC1683c, JCC1683, and JCC1685, respectively. As a first test, a clonal starter culture of each of these three strains, as well as of JCC138, was grown up for 5 days at 37° C. at 150 rpm in 2% $CO_2$-enriched air at ~100 μmol photons $m^{-2}$ $s^{-1}$ in a Multitron II (Infors) shaking photoincubator in A+ (JCC138) or A+ supplemented with 100 μg/ml spectinomycin (JCC1683c, JCC1683, and JCC1685). At this point, each starter culture was used to inoculate a 30 ml JB2.1 medium plus 3 mM urea flask culture supplemented with no antibiotics (JCC138) or 100 μg/ml spectinomycin (JCC1683c, JCC1683, and JCC1685). The four cultures were then grown for 14 days at 37° C. at 150 rpm in 2% $CO_2$-enriched air at ~100 μmol photons $m^{-2}$ $s^{-1}$ in a Multitron II (Infors) shaking photoincubator.

20 $OD_{730}$-ml worth of cells was collected by centrifugation in a pre-weighed eppendorf tube. Cells were washed by two cycles of resuspension in Milli-Q water and microcentrifugation, and dewetted by two cycles of microcentrifugation and aspiration. Wet cell pellets were frozen at −80° C. for two hours and then lyophilized overnight, at which point the tube containing the dry cell mass was weighed again such that the mass of the cell pellet (~6 mg) could be calculated within ±0.1 mg. In parallel, 3.5 $OD_{730}$-ml worth of cells from each culture was collected by centrifugation in an eppendorf tube, washed thoroughly by three cycles of resuspension in Milli-Q water and microcentrifugation, and then dewetted as much as possible by three cycles of microcentrifugation and aspiration. Dewetted cell pellets were then extracted by vortexing for 15 seconds in 1.0 ml acetone containing 18.2 mg/l BHT and 16.3 mg/l n-heptacosane ($C_{27}$) internal standard (ABH); cell debris was pelleted by centrifugation, and 500 µl supernatant was submitted for GC-FID. Acetone-extracted DCW was calculated as 3.5/20, or 17.5%, of the DCW measured for 20 $OD_{730}$-ml worth of cells. In parallel with the four biological sample extractions, eight empty eppendorf tubes were extracted with ABH in the same fashion. The extraction/injection efficiency of all ABH extractants was assessed by calculating the ratio between the n-heptacosane GC-FID peak area of the sample and the average n-heptacosane GC-FID peak area of the six empty-tube controls—only ratios of 100%±11% were accepted (Table 8).

Concentrations of n-tridecane ($C_{13}$), n-tetradecane ($C_{14}$), n-pentadecane ($C_{15}$), n-hexadecane ($C_{16}$), n-heptadecane ($C_{17}$), and n-octadecane ($C_{18}$), in the four extractants were quantitated by (GC/FID) as described in Example 11. GC-FID conditions were as follows. An Agilent 7890A GC/FID equipped with a 7683 series autosampler was used. 1 µl of each sample was injected into the GC inlet (split 5:1, pressure) and an inlet temperature of 290° C. The column was a HP-5 (Agilent, 30 m×0.32 mm×0.25 µm) and the carrier gas was helium at a flow of 1.0 ml/min. The GC oven temperature program was 50° C., hold 1.0 minute; 10° C./min increase to 290° C.; hold 9 minutes. n-Alkane production was calculated as a percentage of the acetone-extracted DCW. The coefficient of variation of the n-heptacosane GC-FID peak area of the eight empty-tube controls was 3.6%.

GC-FID data are summarized in Table 8. As expected, controls strains JCC138 and JCC1683c made no n-alkanes, whereas JCC683 and JCC1685 made n-alkanes, ~97% of which comprised n-pentadecane and n-heptadecane. JCC1685 made significantly more n-alkanes as a percentage of DCW (~0.42%) compared to JCC1683 (~0.16%), likely explaining the relatively low final $OD_{730}$ of the JCC1685 culture. For JCC1683 expressing *Prochlorococcus marinus* MIT 9312 adm-aar, the percentage by mass of n-pentadecane relative to n-pentadecane plus n-heptadecane was 53.2%, in quantitative agreement with that of JCC1281 expressing the same operon on pAQ1 (57.3%; Table 7). In contrast, for JCC1685 which additionally expresses *Cyanothece* sp. ATCC51142 adm-aar, the percentage by mass of n-pentadecane relative to n-pentadecane plus n-heptadecane was 83.7%. This result demonstrates that the in vivo expression of cce_0778 and cce_1430 in a cyanobacterial host biases the n-alkane product length distribution towards n-pentadecane—even more so than does expression of PMT9312_0532 and PMT9312_0533. The total amount of intracellular n-alkane produced by chromosomal integrants JCC1683 and JCC1685 is apparently lower than that of pAQ1-based transformants such as JCC1469, presumably owing to a combination of lower-copy expression (i.e., chromosome versus high-copy pAQ1), and partially repressed transcription—due to the initial presence of urea in the growth medium—of P(nir07) compared to the constitutive promoters P(aphII) (JCC1281) and P(cI) (JCC1469).

TABLE 8

Table 8 n-Pentadecane and n-heptadecane quantitated by GC-FID in acetone cell pellet extractants of JCC138, JCC1683c, JCC1683, and JCC1685.

| Strain | $OD_{730}$ | $C_{27}$-normalized extraction/injection efficiency | $C_{15}$ as % of DCW (95% CI%) | $C_{17}$ as % of DCW (95% CI%) | $(C_{15} + C_{17})/(C_{13} + C_{14} + C_{15} + C_{16} + C_{17})$ Mass % | $C_{15}/(C_{15} + C_{17})$ Mass % |
|---|---|---|---|---|---|---|
| JCC138 | 17.0 | 110% | nd | nd | na | na |
| JCC1683c | 13.4 | 108% | nd | nd | na | na |
| JCC1683 | 12.2 | 111% | 0.083% (7.6%) | 0.073% (12.5%) | 97.3% | 53.2% |
| JCC1685 | 10.0 | 110% | 0.341% (13.0%) | 0.066% (8.8%) | 96.7% | 83.7% |

n-Octadecane was not detected in any of the samples; nd: not detected, na: not applicable.

In order to confirm the urea-repressibility/nitrate-inducibility of P(nir07), the intracellular n-alkane product distribution of JCC1685 was determined from cultures grown in either JB2.1 medium, containing only nitrate as the nitrogen source, and JB2.1 supplemented with 6 mM urea, urea being preferentially utilized as nitrogen source relative to nitrate and provided at a concentration such that it became depleted when the culture reached an $OD_{730}$ of ~4. JCC1683c in JB2.1 was run in parallel as a negative control. Accordingly, a clonal starter culture of JCC1683c and JCC1685 was grown up for 5 days at 37° C. at 150 rpm in 2% $CO_2$-enriched air at ~100 µmol photons $m^{-2}$ $s^{-1}$ in a Multitron II (Infors) shaking photoincubator in A+ supplemented with 100 µg/ml spectinomycin. At this point, each starter culture was used to inoculate duplicate 30 ml JB2.1 medium flask cultures supplemented with 400 µg/ml spectinomycin; in addition, the JCC1685 starter culture was used to inoculate duplicate 30 ml JB2.1 medium plus 6 mM urea flask cultures supplemented with 400 µg/ml spectinomycin. The six cultures were then grown for 14 days at 37° C. at 150 rpm in 2% $CO_2$-enriched air at ~100 µmol photons $m^{-2}$ $s^{-1}$ in a Multitron II (Infors) shaking photoincubator. Intracellular n-alkanes as a percentage of DCW were determined exactly as described in Example 11; data are summarized in Table 9. Consistent with the urea repressibility of P(nir07), n-alkanes as a percentage of JCC185 DCW were significantly higher in the absence of urea (~0.59%) compared to in the presence of urea (~0.15%). This likely explained the relatively low final $OD_{730}$ of the no-urea cultures.

TABLE 9

Table 9 n-Pentadecane and n-heptadecane quantitated by GC-FID in acetone cell pellet extractants of JCC1683c and JCC1685 as a function of urea in the growth medium.

| Strain | Medium | $OD_{730}$ | $C_{27}$-normalized extraction/injection efficiency | $C_{15}$ as % of DCW (95% CI %) | $C_{17}$ as % of DCW (95% CI %) | n-alkanes as % of DCW | $(C_{15} + C_{17})/(C_{13} + C_{14} + C_{15} + C_{16} + C_{17})$ Mass % | $C_{15}/(C_{15} + C_{17})$ Mass % |
|---|---|---|---|---|---|---|---|---|
| JCC1683c #1 | JB2.1 | 9.5 | 101% | nd | nd | na | na | na |
| JCC1683c #2 | JB2.1 | 9.5 | 101% | nd | nd | na | na | na |
| JCC1685 #1 | JB2.1 + 6 mM | 7.4 | 102% | 0.076% (7.1%) | 0.067% (1.5%) | 0.14% | 100% | 53.2% |
| JCC1685 #2 | JB2.1 + 6 mM | 6.4 | 102% | 0.090% (3.3%) | 0.051% (2.3%) | 0.15% | 94.6% | 63.9% |
| JCC1685 #1 | JB2.1 | 1.2 | 101% | 0.42% (1.4%) | 0.14% (1.1%) | 0.57% | 97.9% | 74.9% |
| JCC1685 #2 | JB2.1 | 3.3 | 102% | 0.49% (1.6%) | 0.11% (1.6%) | 0.60% | 100% | 81.4% |

n-Octadecane was not detected in any of the samples; nd: not detected, na: not applicable.

Example 13

Recombinant Expression of Formate Dehydrogenase in a Photoalkanogenic Cell

Engineered photosynthetic organisms such as those described herein utilize light and inorganic carbon during synthesis of carbon-based products of interest, including alkanes. Increased alkane production in engineered cells expressing ADM may be achieved by recombinantly expressing formate dehydrogenase (FDH), an enzyme which catalyzes the conversion of formate and NAD(P)+ into NAD(P)H and $CO_2$. The enzyme classification number for NAD+-specific FDH is EC 1.2.1.2; the enzyme classification number for NADP+-specific FDH is EC 1.2.1.43.

In one embodiment, the invention provides an engineered photosynthetic cell (e.g., a cyanobacterial cell) described herein, wherein said engineered cell comprises a recombinant ADM enzyme, and wherein said engineered cell further comprises a recombinant FDH. In related embodiments, the engineered cell comprises a recombinant ADM and a recombinant AAR enzyme, in addition to a recombinant FDH enzyme. In yet another related embodiment, the engineered cell is a cyanobacterium, e.g., an engineered *Synechoccus* described herein, that has been further transformed to recombinantly express FDH. In yet another related embodiment, the engineered cell is JCC2055 (JCC138 pAQ3::P(nir07)-adm_Cy-aar_Cy-spec), further comprising a recombinantly expressed FDH gene.

In yet another a related embodiment, the FDH is selected from an FDH described by Tishkov et al. (2006) *Biomolecular Engineering* 23:89-110 (incorporated herein by reference). In another related embodiment, the FDH is selected from the group consisting of

- Wild-type *Candida boidinii* FDH (NAD+-specific enzyme; Uniprot O13437) (SEQ ID NO: 32); and
- Engineered *Candida boidinii* FDH (D195S/Y196H/K356T, engineered for enhanced NADP+ utilization) (SEQ ID NO: 33).

In yet another related embodiment, the FDH is selected from the group consisting of

- Mutant *Pseudomonas* sp. 101 PseFDH GAV (NAD+-specific; Uniprot P33160); and
- Mutant *Pseudomonas* sp. 101 PseFDH T5M9-10 (NADP+-specific).

In related embodiments, the FDH is at least 95% identical to the FDH of SEQ ID NO:32 or SEQ ID NO:33.

Engineered photosynthetic cells, including photoalkanogens such as the engineered cyanobacteria described herein which comprise recombinant ADM, can be transformed to further express recombinant FDH using methods well known to those skilled in the art and described in detail herein and elsewhere. After transformation, the production of alkanes (and/or other carbon-based products of interest) by the FDH-expressing cells can be compared to the parent cells (e.g., engineered cyanobacteria expressing recombinant ADM but lacking a recombinant FDH activity) to demonstrate the improved rates of production of alkanes and/or other carbon-based products of interest in FDH-expres sing cells relative to the parent cells.

One skilled in the art will recognize that the expression of recombinant FDH can be modulated or increased by utilizing promoters of different strength or by utilizing inducible promoters, including any of the various promoters described herein.

Example 14

Recombinant Expression of *Candida boidinii* and *Burkholderia multivorans* Formate Dehydrogenase in a Photoalkanogenic Cell Engineered photosynthetic organisms such as those described herein utilize light and inorganic carbon during synthesis of carbon-based products of interest, including alkanes. Increased alkane production in engineered cells expressing ADM may be sustained by recombinantly expressing formate dehydrogenase (FDH), an enzyme which catalyzes the conversion of formate and NAD(P)+ into NAD(P)H and $CO_2$.

*Synechococcus* sp. PCC7002 (JCC138) was engineered to express recombinant NAD+ (EC 1.2.1.2) or NADP+ (EC 1.2.1.43) formate dehydrogenase. Specifically, JCC138-derived strains expressing a codon-optimized NAD+-dependent FDH from *Candida boidinii* or an NAD(P)+-dependent FDH from *Burkholderia multivorans* were generated according to the following method.

JCC2927:

Formate dehydrogenase from *Candida boidinii* (CBFDH) (SEQ ID NO: 36) was codon optimized for expression in *Escherichia coli* and synthesized de novo by DNA2.0 (Menlo Park, Calif.). The 5.7 kb NdeI-XhoI pJB1228 fragment (SEQ ID NO: 34) was ligated with the 1.1 kb CBFDH fragment (SEQ ID NO: 36) cut with the same enzymes to create plasmid pJB1882 (SEQ ID NO: 38). Approximately one μg of pJB1882 DNA was transformed into JCC138 (*Synechococcus* sp PCC 7002) and selected on 20 mg $L^{-1}$ erythromycin. JCC2927 was created after propagation on 100 mg $L^{-1}$ erythromycin until segregation was complete.

JCC2928:

The 6 kb NdeI-XhoI pJB1732 fragment (SEQ ID NO: 35) was ligated with the 1.1 kb CBFDH fragment (SEQ ID NO: 36) cut with the same enzymes to create plasmid pJB1883 (SEQ ID NO: 39). Approximately one μg of pJB1883 was transformed into JCC138 and selected on 20 mg $L^{-1}$ erythromycin. JCC2928 was created after propagation on 100 mg $L^{-1}$ erythromycin until segregation was complete.

JCC2929:

The formate dehydrogenase gene from *Burkholderia multivorans* ATCC 17616 (BMFDH) (SEQ ID NO: 37) was amplified by PCR using KOD Polymerase (Merck KGaA, Darmstadt, Germany) from genomic DNA obtained from ATCC (Manassas, Va.) using primers MC31 (SEQ ID NO: 42) and MC32 (SEQ ID NO: 43). The BMFDH 1.2 kb PCR product (SEQ ID NO: 37) was digested with NdeI and XhoI and ligated with the 5.7 kb NdeI-XhoI pJB1228 fragment (SEQ ID NO: 34) to create plasmid pJB1914 (SEQ ID NO: 40). Approximately one μg of pJB1914 was transformed into JCC138 and selected on 20 mg $L^{-1}$ erythromycin. JCC2929 was created after propagation on 100 mg $L^{-1}$ erythromycin until segregation was complete.

JCC2930:

The 6 kb NdeI-XhoI pJB1732 fragment (SEQ ID NO: 35) was ligated with the BMFDH 1.2 kb PCR product (SEQ ID NO: 37) digested with the same enzymes to create plasmid pJB1915 (SEQ ID NO: 41). Approximately one μg of pJB1915 was transformed into JCC138 and selected on 20 mg $L^{-1}$ erythromycin. JCC2930 was created after propagation on 100 mg $L^{-1}$ erythromycin until segregation was complete.

The genetic feature of all the plasmids are detailed in Table 10. A summary of the strain features are shown in Table 11.

TABLE 10

<table>
<tr><th>Plasmid</th><th>Features</th></tr>
<tr><td>pJB1228<br>(SEQ ID NO: 34)</td><td>|<kan$^R$|T(rrnB)|Aqul UHR|P(rbcL)>|Ery$^R$>|Aqul DHR|<br>T(b/a)|T(rpoC)|pUC ori|</td></tr>
<tr><td>pJB1732<br>(SEQ ID NO: 35)</td><td>|<kan$^R$|T(rrnB)|Aqul UHR|P(cpcB)>|Ery$^R$>|Aqul DHR|<br>T(b/a)|T(rpoC)|pUC ori|</td></tr>
<tr><td>pJB1882<br>(SEQ ID NO: 38)</td><td>|<kan$^R$|T(rrnB)|Aqul UHR|P(rbcL)>|CBFDH>|Ery$^R$>|<br>Aqul DHR|T(b/a)|T(rpoC)|pUC ori|</td></tr>
<tr><td>pJB1883<br>(SEQ ID NO: 39)</td><td>|<kan$^R$|T(rrnB)|Aqul UHR|P(cpcB)>|CBFDH>|Ery$^R$>|<br>Aqul DHR|T(b/a)|T(rpoC)|pUC ori|</td></tr>
<tr><td>pJB1914<br>(SEQ ID NO: 40)</td><td>|<kan$^R$|T(rrnB)|Aqul UHR|P(rbcL)>|BMFDH>|Ery$^R$>|<br>Aqul DHR|T(b/a)|T(rpoC)|pUC ori|</td></tr>
<tr><td>pJB1915<br>(SEQ ID NO: 41)</td><td>|<kan$^R$|T(rrnB)|Aqul UHR|P(cpcB)>|BMFDH>|Ery$^R$>|<br>Aqul DHR|T(b/a)|T(rpoC)|pUC ori|</td></tr>
</table>

TABLE 11

| Strain | Relevant Genotype | Recombinant Formate Dehydrogenase Source | Strain-specific plasmid expressing recombinant FDH |
|---|---|---|---|
| JCC138 | WT | N/A | N/A |
| JCC2927 | Aqul::P(rbcL)-CBFDH | *Candida boidinii* | pJB1882 (SEQ ID NO: 38) |
| JCC2928 | Aqul::P(cpcB)-CBFDH | *Candida boidinii* | pJB1883 (SEQ ID NO: 39) |
| JCC2929 | Aqul::P(rbcL)-BMFDH | *Burkholderia multivorans* | pJB1914 (SEQ ID NO: 40) |
| JCC2930 | Aqul::P(cpcB)-BMFDH | *Burkholderia multivorans* | pJB1915 (SEQ ID NO: 41) |

We tested the effect of the recombinant expression of formate dehydrogenase from *Candida boidinii* (SEQ ID NO: 32) and *Burkholderia multivorans* (SEQ ID NO: 44) in *Synechococcus* sp. PCC7002 (JCC138). To determine the ability of the recombinant photoalkanogenic cell expressing formate dehydrogenase to metabolize formate, JCC138 (control) and JCC138-derived strains expressing a codon-optimized NAD+-dependent FDH from *Candida boidinii* (JCC2927, JCC2928) or an NADP+-dependent FDH from *Burkholderia multivorans* (JCC2929 and JCC2930) were incubated in the presence of 10 mM formate. The concentration of formate in the medium was followed over time according to the following procedure.

15 mL of A+ media in shake flasks was inoculated to $OD_{730}$=0.1 for all five strains (Table 11) from 5 mL tube seed cultures ($A^+$, Ery(erythromycin)$^{20}$, $OD_{730}$~1-2) grown under standard conditions (~100 μE $m^{-2}$ $s^{-1}$, 37° C., 2% $CO_2$, Infors). Formate was added to a final concentration of 10 mM and the cultures were grown under standard conditions. Cultures were monitored for growth by measuring $OD_{730}$, and supernatant samples were saved for formate quantification by HPLC.

Figure 16:
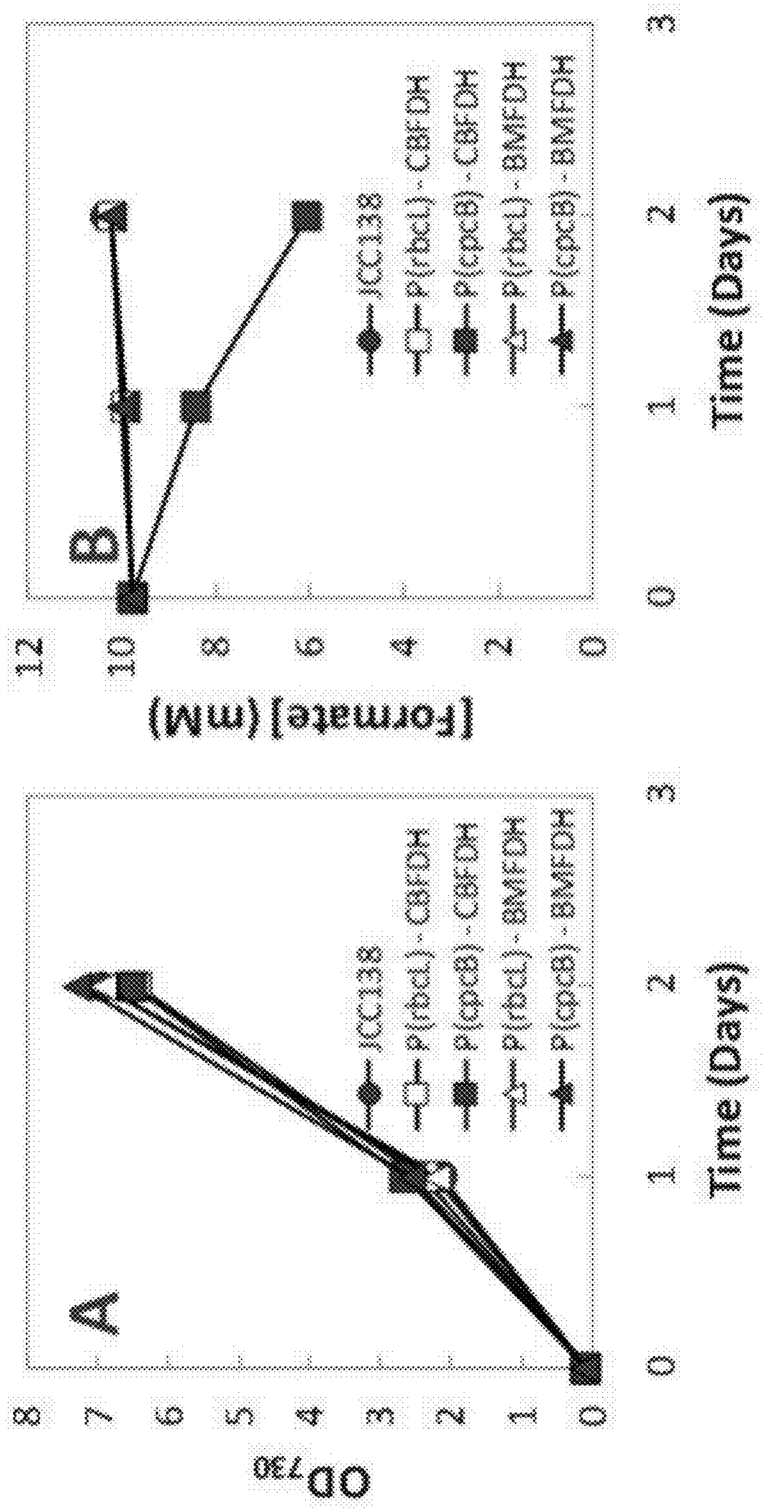
FIG. 16 shows (A) the growth of, and (B) formate consumption by wild-type JCC138 and recombinant *Synechococcus* strains expressing recombinant formate dehydrogenase.

The growth and formate consumption by WT and recombinant Synechococcus strains overexpressing FDH are shown in FIG. 16. JCC138 was found not to metabolize formate, but expression of the FDH from *Candida boidinii* from a P(cpcB) promoter on the chromosome (JCC2928) did allow breakdown of formate (FIG. 16). Over the course of 2 days, formate concentration in the JCC2928 culture decreased by at least 40% (from 10 mM to 6 mM) under the experimental conditions described above.

A number of embodiments of the invention have been described. Nevertheless, it will be understood that various modifications may be made without departing from the spirit and scope of the invention. All publications, patents and other references mentioned herein are hereby incorporated by reference in their entirety.

INFORMAL SEQUENCE LISTING

SEQ ID NO: 1
*ThermoSynechococcus elongatus* BP-1; tll1312 (AAR)
nucleic acid sequence (SEQ ID NO: 1)

ATGTTTGGATTAATTGGTCATCTGACGAGTCTGGAGCACGCCCAAGCCGTTGCCCATCAGTTGGG
TTACCCCGAATATGCCGATCAAGGCTTGGAATTTTGGTGTATGGCACCGCCGCAGATCGTCGATG
AGATTACGGTGACGAGCGTAACGGGCAAAACTATCTATGGCAAATACGTTGAGTCCTGCTTTTTA
CCAGAGATGCTGGCCAACCAGCGGGTGAAGGCAGCGACTCGCAAAGTTATTAACGCCATGGCCCA
TGCCCAAAAGCACAACATTGACATTACGGCCTTGGGGGGCTTCTCCTCGATCATCTTTGAGAACT
TTGATCTGGAGAAAATGTCCCACATTCGCAACATTGAACTGGACTTTCGCCGCTTTACAACGGGG

-continued

AATACCCATACCGCCTATATCATCTGCCAACAAATTGAGCAGGCGGCGCCCCAAGTGGGGATTGA
TTTGCGGCAGGCAACCGTGGCTGTTTGTGGGGCTACGGGGGATATTGGTAGTGCCGTCTGCCGTT
GGTTGAATACCTGTTTAGATGTGCAAGATCTCTTACTCGTAGCACGGAATCGCGATCGCCTGCTG
GAGCTACAGGCGGAATTGGGACGGGGGAAAATCCTCGACTTGATGGAGGCGCTGCCCCTTGCCGA
TATTGTGGTTTGGGTGGCCAGTATGCCCAAGGGAGTTGAGCTGAGCATTGAGCAGTTAAAACGCC
CCTCCCTGATGATTGATGGTGGTTATCCCAAAAATATGGCCACCAAAATTCAGCACCCCCAGATT
CATGTTCTCAATGGTGGCATTGTCGAGCATGCCCTCGACATTGACTGGAAAATTATGGAAATTGT
GAATATGGATGTGCCCTCGCGGCAGATGTTTGCCTGTTTTGCAGAGGCTATGCTTTTAGAGTTCG
AGGGCTGGCACACCAATTTCTCTTGGGGACGCAATCAAATCACTGTGGAAAAGATGCAGCAAATT
GGTGAGGTCTCCCGTAAACATGGATTTCAGCCACTACTGTTGAATCCTCAGTAA

SEQ ID NO: 2
*ThermoSynechococcus elongatus* BP-1 tll1312 (AAR)
amino acid sequence (SEQ ID NO: 2)

MFGLIGHLTSLEHAQAVAHQLGYPEYADQGLEFWCMAPPQIVDEITVTSVTGKTIYGKYVESCFL
PEMLANQRVKAATRKVINAMAHAQKHNIDITALGGFSSIIFENFDLEKMSHIRNIELDFRRFTTG
NTHTAYIICQQIEQAAPQVGIDLRQATVAVCGATGDIGSAVCRWLNTCLDVQDLLLVARNRDRLL
ELQAELGRGKILDLMEALPLADIVVWVASMPKGVELSIEQLKRPSLMIDGGYPKNMATKIQHPQI
HVLNGGIVEHALDIDWKIMEIVNMDVPSRQMFACFAEAMLLEFEGWHTNFSWGRNQITVEKMQQI
GEVSRKHGFQPLLLNPQ

SEQ ID NO: 3
*ThermoSynechococcus elongatus* BP-1 tll1313 (ADM)
nucleic acid sequence (SEQ ID NO: 3)

ATGACAACGGCTACCGCTACACCTGTTTTGGACTACCATAGCGATCGCTACAAGGATGCCTACAG
CCGCATTAACGCCATTGTCATTGAAGGTGAACAGGAAGCTCACGATAACTATATCGATTTAGCCA
AGCTGCTGCCACAACACCAAGAGGAACTCACCCGCCTTGCCAAGATGGAAGCTCGCCACAAAAAG
GGGTTTGAGGCCTGTGGTCGCAACCTGAGCGTAACGCCAGATATGGAATTTGCCAAAGCCTTCTT
TGAAAAACTGCGCGCTAACTTTCAGAGGGCTCTGGCGGAGGGAAAAACTGCGACTTGTCTTCTGA
TTCAAGCTTTGATCATCGAATCCTTTGCGATCGCGGCCTACAACATCTACATCCCAATGGCGGAT
CCTTTCGCCCGTAAAATTACTGAGAGTGTTGTTAAGGACGAATACAGCCACCTCAACTTTGGCGA
AATCTGGCTCAAGGAACACTTTGAAAGCGTCAAAGGAGAGCTCGAAGAAGCCAATCGCGCCAATT
TACCCTTGGTCTGGAAAATGCTCAACCAAGTGGAAGCAGATGCCAAAGTGCTCGGCATGGAAAAA
GATGCCCTTGTGGAAGACTTCATGATTCAGTACAGTGGTGCCCTAGAAAATATCGGCTTTACCAC
CCGCGAAATTATGAAGATGTCAGTTTATGGCCTCACTGGGGCATAA

SEQ ID NO: 4
*ThermoSynechococcus elongatus* BP-1 tll1313 (ADM)
amino acid sequence (SEQ ID NO: 4)

MTTATATPVLDYHSDRYKDAYSRINAIVIEGEQEAHDNYIDLAKLLPQHQEELTRLAKMEARHKK
GFEACGRNLSVTPDMEFAKAFFEKLRANFQRALAEGKTATCLLIQALIIESFAIAAYNIYIPMAD
PFARKITESVVKDEYSHLNFGEIWLKEHFESVKGELEEANRANLPLVWKMLNQVEADAKVLGMEK
DALVEDFMIQYSGALENIGFTTREIMKMSVYGLTGA

SEQ ID NO: 5
*Synechococcus elongatus* PCC 7942; SYNPCC7942_1594 (AAR)
nucleic acid sequence (SEQ ID NO: 5)

ATGTTCGGTCTTATCGGTCATCTCACCAGTTTGGAGCAGGCCCGCGACGTTTCTCGCAGGATGG
GCTACGACGAATACGCCGATCAAGGATTGGAGTTTTGGAGTAGCGCTCCTCCTCAAATCGTTGA
TGAAATCACAGTCACCAGTGCCACAGGCAAGGTGATTCACGGTCGCTACATCGAATCGTGTTTC
TTGCCGGAAATGCTGGCGGCGCGCCGCTTCAAAACAGCCACGCGCAAAGTTCTCAATGCCATGT
CCCATGCCCAAAAACACGGCATCGACATCTCGGCCTTGGGGGGCTTTACCTCGATTATTTTCGA
GAATTTCGATTTGGCCAGTTTGCGGCAAGTGCGCGACACTACCTTGGAGTTTGAACGGTTCACC
ACCGGCAATACTCACACGGCCTACGTAATCTGTAGACAGGTGGAAGCCGCTGCTAAAACGCTGG
GCATCGACATTACCCAAGCGACAGTAGCGGTTGTCGGCGCGACTGGCGATATCGGTAGCGCTGT
CTGCCGCTGGCTCGACCTCAAACTGGGTGTCGGTGATTTGATCCTGACGGCGCGCAATCAGGAG
CGTTTGGATAACCTGCAGGCTGAACTCGGCCGGGGCAAGATTCTGCCCTTGGAAGCCGCTCTGC
CGGAAGCTGACTTTATCGTGTGGGTCGCCAGTATGCCTCAGGGCGTAGTGATCGACCCAGCAAC
CCTGAAGCAACCCTGCGTCCTAATCGACGGGGGCTACCCCAAAAACTTGGGCAGCAAAGTCCAA
GGTGAGGGCATCTATGTCCTCAATGGCGGGGTAGTTGAACATTGCTTCGACATCGACTGGCAGA
TCATGTCCGCTGCAGAGATGGCGCGGCCCGAGCGCCAGATGTTTGCCTGCTTTGCCGAGGCGAT
GCTCTTGGAATTTGAAGGCTGGCATACTAACTTCTCCTGGGGCCGCAACCAAATCACGATCGAG
AAGATGGAAGCGATCGGTGAGGCATCGGTGCGCCACGGCTTCCAACCCTTGGCATTGGCAATTT
GA

SEQ ID NO: 6
*Synechococcus elongatus* PCC 7942; SYNPCC7942_1594 (AAR)
amino acid sequence (SEQ ID NO: 6)

MFGLIGHLTSLEQARDVSRRMGYDEYADQGLEFWSSAPPQIVDEITVTSATGKVIHGRYIESCFL
PEMLAARRFKTATRKVLNAMSHAQKHGIDISALGGFTSIIFENFDLASLRQVRDTTLEFERFTTG
NTHTAYVICRQVEAAAKTLGIDITQATVAVVGATGDIGSAVCRWLDLKLGVGDLILTARNQERLD
NLQAELGRGKILPLEAALPEADFIVWVASMPQGVVIDPATLKQPCVLIDGGYPKNLGSKVQGEGI
YVLNGGVVEHCFDIDWQIMSAAEMARPERQMFACFAEAMLLEFEGWHTNFSWGRNQITIEKMEAI
GEASVRHGFQPLALAI

-continued

SEQ ID NO: 7
*Synechococcus elongatus* PCC 7942; SYNPCC7942_1593 (ADM)
nucleic acid sequence (SEQ ID NO: 7)
ATGCCGCAGCTTGAAGCCAGCCTTGAACTGGACTTTCAAAGCGAGTCCTACAAAGACGCTTACAG
CCGCATCAACGCGATCGTGATTGAAGGCGAACAAGAGGCGTTCGACAACTACAATCGCCTTGCTG
AGATGCTGCCCGACCAGCGGGATGAGCTTCACAAGCTAGCCAAGATGGAACAGCGCCACATGAAA
GGCTTTATGGCCTGTGGCAAAAATCTCTCCGTCACTCCTGACATGGGTTTTGCCCAGAAATTTTT
CGAGCGCTTGCACGAGAACTTCAAAGCGGCGGCTGCGGAAGGCAAGGTCGTCACCTGCCTACTGA
TTCAATCGCTAATCATCGAGTGCTTTGCGATCGCGGCTTACAACATCTACATCCCAGTGGCGGAT
GCTTTTGCCCGCAAAATCACGGAGGGGGTCGTGCGCGACGAATACCTGCACCGCAACTTCGGTGA
AGAGTGGCTGAAGGCGAATTTTGATGCTTCCAAAGCCGAACTGGAAGAAGCCAATCGTCAGAACC
TGCCCTTGGTTTGGCTAATGCTCAACGAAGTGGCCGATGATGCTCGCGAACTCGGGATGGAGCGT
GAGTCGCTCGTCGAGGACTTTATGATTGCCTACGGTGAAGCTCTGGAAAACATCGGCTTCACAAC
GCGCGAAATCATGCGTATGTCCGCCTATGGCCTTGCGGCCGTTTGA SEQ ID NO: 8
*Synechococcus elongatus* PCC 7942; SYNPCC7942_1593 (ADM)
amino acid sequence (SEQ ID NO: 8)
MPQLEASLELDFQSESYKDAYSRINAIVIEGEQEAFDNYNRLAEMLPDQRDELHKLAKMEQRHMK
GFMACGKNLSVTPDMGFAQKFFERLHENFKAAAAEGKVVTCLLIQSLIIECFAIAAYNIYIPVAD
AFARKITEGVVRDEYLHRNFGEEWLKANFDASKAELEEANRQNLPLVWLMLNEVADDARELGMER
ESLVEDFMIAYGEALENIGFTTREIMRMSAYGLAAV SEQ ID NO: 9
*Prochlorococcus marinus* MIT9312 PMT9312_0533 (AAR)
optimized nucleic acid sequence (SEQ ID NO: 9)
ATGTTTGGTCTGATTGGTCATAGCACCAGCTTTGAGGACGCAAAGCGCAAGGCGAGCCTGCTGGG
TTTCGACCACATCGCGGATGGCGATCTGGATGTGTGGTGTACCGCACCGCCGCAACTGGTTGAAA
ACGTGGAAGTCAAAAGCGCGACGGGTATCAGCATTGAAGGTAGCTATATCGATAGCTGCTTCGTG
CCGGAGATGCTGAGCCGCTTCAAGACCGCGCGTCGTAAAGTTCTGAATGCAATGGAGCTGGCGCA
GAAAAAGGGTATCAATATCACTGCCCTGGGTGGCTTTACCTCCATTATCTTTGAGAACTTCAACC
TGTTGCAGCACAAGCAAATCCGTAATACCAGCCTGGAGTGGGAGCGTTTCACCACGGGTAACACG
CACACGGCATGGGTGATTTGTCGTCAGCTGGAGATCAACGCACCGCGCATTGGCATCGACCTGAA
AACTGCAACGGTCGCTGTTATCGGCGCGACCGGCGATATTGGTAGCGCGGTGTGTCGCTGGCTGG
TCAATAAGACCGGCATTAGCGAACTGCTGATGGTCGCTCGCCAACAACAGCCACTGACCCTGCTG
CAAAAAGAACTGGACGGTGGCACCATCAAGAGCCTGGATGAAGCCCTGCCGCAGGCGGATATTGT
CGTGTGGGTTGCTTCGATGCCTAAGACGATCGAAATTGAGATTGAAAACCTGAAAAAGCCGTGCC
TGATGATCGACGGTGGCTACCCGAAGAATCTGGACGAGAAATTCAAAGGCAAAAACATTCACGTG
TTGAAGGGTGGTATCGTCGAGTTTTTCAACGACATTGGCTGGAACATGATGGAGTTGGCGGAGAT
GCAAAACCCGCAGCGTGAGATGTTTGCGTGCTTCGCCGAAGCTATGATTCTGGAGTTTGAGAAAT
GCCATACCAACTTTAGCTGGGGCCGTAACAATATCAGCTTGGAGAAGATGGAGTTCATCGGTGCT
GCATCTCTGAAGCACGGTTTCAGCGCGATCGGTCTGGATAAACAGCCGAAAGTCTTGACCGTTTG
A SEQ ID NO: 10
*Prochlorococcus marinus* MIT9312 PMT9312_0533 (AAR)
protein sequence (SEQ ID NO: 10)
MFGLIGHSTSFEDAKRKASLLGFDHIADGDLDVWCTAPPQLVENVEVKSATGISIEGSYIDSCFV
PEMLSRFKTARRKVLNAMELAQKKGINITALGGFTSIIFENFNLLQHKQIRNTSLEWERFTTGNT
HTAWVICRQLEINAPRIGIDLKTATVAVIGATGDIGSAVCRWLVNKTGISELLMVARQQQPLTLL
QKELDGGTIKSLDEALPQADIVVWVASMPKTIEIEIENLKKPCLMIDGGYPKNLDEKFKGKNIHV
LKGGIVEFFNDIGWNMMELAEMQNPQREMFACFAEAMILEEKCHTNFSWGRNNISLEKMEFIGAA
SLKHGFSAIGLDKQPKVLTV SEQ ID NO: 11
*Prochlorococcus marinus* MIT9312 PMT9312_0532 (ADM)
optimized nucleic acid sequence (SEQ ID NO: 11)
ATGCACAATGAATTGAAAATCACGGATATGCAAACGCTGGAAACCAACACCAAGACGACCGAAGA
GTCTATTGACACCAATAGCCTGAACCTGCCGGACTTTACTACCGACAGCTACAAGGATGCCTATT
CTCGCATTAACGCCATCGTTATTGAGGGCGAACAGGAAGCTCATGACAATTACATCTCCATCGCA
ACGCTGATCCCGAATGAGCTGGAAGAGCTGACGAAGCTGGCACGTATGGAGCTGAAACACAAGAA
AGGTTTTACTGCGTGCGGTCGTAATCTGGGTGTGGACGCAGACATGGTTTTCGCGAAAAAGTTCT
TCAGCAAACTGCACGGCAATTTCCAAATCGCGCTGGAAAAAGGTAACCTGACCACCTGCTTGCTG
ATCCAAGCGATTCTGATCGAAGCATTTGCGATTTCCGCGTACAATGTTTACATCCGTGTGGCCGA
CCCATTTGCCAAAAAGATTACCGAGGGTGTTGTCAAAGACGAGTATCTGCATCTGAACTATGGTC
AGGAGTGGCTGAAAAAGAATCTGTCCACGTGTAAAGAAGAGCTGATGGAGGCCAACAAGGTCAAT
CTGCCGCTGATTAAGAAAATGCTGGACGAAGTGGCAGAAGATGCGAGCGTTTTGGCGATGGATCG
TGAAGAGTTGATGGAAGAGTTCATGATTGCGTACCAGGATACCCTGTTGGAGATTGGCCTGGATA
ATCGCGAAATTGCCCGTATGGCGATGGCGGCCATTGTTTAG -continued SEQ ID NO: 12
*Prochlorococcus marinus* MIT9312 PMT9312_0532 (ADM)
protein sequence (SEQ ID NO: 12)

MHNELKITDMQTLETNTKTTEESIDTNSLNLPDFTTDSYKDAYSRINAIVIEGEQEAHDNYISIA
TLIPNELEELTKLARMELKHKKGFTACGRNLGVDADMVFAKKFFSKLHGNFQIALEKGNLTTCLL
IQAILIEAFAISAYNVYIRVADPFAKKITEGVVKDEYLHLNYGQEWLKKNLSTCKEELMEANKVN
LPLIKKMLDEVAEDASVLAMDREELMEEFMIAYQDTLLEIGLDNREIARMAMAAIV

SEQ ID NO: 13
*Prochlorococcus marinus* MIT9312 PMT9312_0533 (AAR)
nucleic acid sequence (SEQ ID NO: 13)

ATGTTTGGGTTAATAGGCCACTCAACTAGTTTTGAAGATGCAAAAAGAAAAGCTTCATTACTAGG
CTTTGATCATATTGCTGATGGTGATCTAGATGTTTGGTGTACAGCCCCTCCTCAATTGGTTGAAA
ATGTAGAAGTTAAGAGTGCTACTGGAATATCTATTGAAGGTTCTTATATAGATTCTTGCTTTGTT
CCTGAAATGCTTTCTAGGTTTAAAACCGCAAGAAGAAAAGTATTAAATGCTATGGAATTAGCTCA
GAAAAAAGGGATTAACATTACGGCTTTAGGAGGATTTACTTCTATTATTTTCGAAAATTTTAATC
TTCTTCAACATAAACAAATTAGAAATACTTCATTAGAGTGGGAAAGGTTTACTACAGGTAATACA
CACACTGCCTGGGTTATTTGTAGGCAACTAGAAATAAATGCTCCTCGCATAGGGATAGATCTTAA
AACTGCAACTGTTGCTGTTATTGGTGCTACAGGTGATATAGGAAGTGCTGTTTGTAGGTGGCTTG
TCAATAAAACTGGTATTTCAGAACTTCTTATGGTGGCTAGACAACAACAACCATTAACTCTATTA
CAGAAAGAATTAGATGGTGGCACTATAAAAAGTTTAGATGAAGCATTGCCTCAAGCGGATATTGT
TGTATGGGTTGCAAGTATGCCTAAAACGATTGAAATTGAAATTGAAAACTTAAAAAAACCATGTT
TAATGATTGATGGTGGATACCCTAAAAATCTTGATGAGAAATTTAAAGGTAAAAATATTCATGTT
TTAAAAGGAGGTATAGTAGAGTTTTTCAATGATATTGGCTGGAATATGATGGAACTTGCAGAAAT
GCAGAACCCTCAGAGAGAGATGTTTGCTTGCTTTGCAGAAGCTATGATTTTAGAATTTGAAAAGT
GTCATACCAACTTTAGTTGGGGAAGGAATAACATTTCTCTTGAAAAAATGGAATTTATTGGAGCA
GCTTCTTTGAAACATGGTTTTTCTGCGATTGGACTTGATAAACAGCCTAAAGTATTGACTGTTTG
A

SEQ ID NO: 14
*Prochlorococcus marinus* MIT9312 PMT9312_0532 (ADM)
nucleic acid sequence (SEQ ID NO: 14)

ATGCATAATGAGCTAAAGATTACTGACATGCAAACTCTAGAAACAAATACAAAAACTACTGAAGA
ATCCATAGACACGAATTCTTTGAATCTTCCCGACTTTACAACAGATTCCTATAAGGATGCATATA
GCAGAATAAATGCAATTGTTATAGAGGGAGAGCAAGAGGCTCATGATAATTACATTTCAATAGCA
ACGTTAATACCAAATGAGTTAGAAGAATTAACTAAGTTGGCGAGAATGGAACTCAAGCATAAAAA
AGGATTTACTGCTTGTGGAAGAAATTTAGGAGTAGATGCTGATATGGTATTCGCAAAAAAATTCT
TTTCTAAATTGCATGGTAATTTTCAAATTGCTTTAGAAAAAGGAAATTTAACAACTTGTCTTCTG
ATACAAGCTATTTTAATTGAAGCTTTTGCTATATCTGCTTATAACGTTTACATAAGAGTTGCTGA
TCCTTTTGCAAAAAAAATAACAGAGGGAGTGGTTAAAGATGAATATCTCCATCTAAATTACGGCC
AAGAGTGGCTTAAAAAGAATTTATCTACTTGTAAAGAAGAATTAATGGAAGCCAATAAGGTTAAC
CTTCCCTTAATTAAAAAGATGTTAGATGAAGTAGCAGAAGATGCATCAGTTTTGGCTATGGATAG
AGAAGAGTTAATGGAAGAATTTATGATTGCTTACCAAGACACTCTTCTAGAAATAGGTCTTGATA
ATAGAGAAATTGCAAGAATGGCTATGGCAGCGATTGTTTAA

SEQ ID NO: 15
plasmid JB823

| | |
|---|---|
| $1^{st}$ underlined sequence | Upstream homology region for pAQ1 |
| $1^{st}$ double-underlined lowercase sequence | NotI site for promoter swapping |
| $1^{st}$ italic sequence | aphII promoter |
| $2^{nd}$ double-underlined lowercase sequence | NdeI site for promoter swapping |
| $1^{st}$ bold sequence | SYNPCC7942_1593 (adm) coding sequence |
| $1^{st}$ lower case sequence | Intergenic sequence |
| 2nd bold sequence | SYNPCC7942_1594 (aar) coding sequence |
| $2^{nd}$ italic sequence | aadA coding sequence; $spec^R$ selection marker |
| $2^{nd}$ underlined sequence | Downstream homology region for pAQ1 |
| $2^{nd}$ lowercase sequence | Vector backbone |

(SEQ ID NO: 15)

GTCAGCAAGCTCTGGAATTTCCCGATTCTCTGATGGGAGATCCAAAAATTCTCGCAGTCCCTCA
ATCACGATATCGGTCTTGGATCGCCCTGTAGCTTCCGACAACTGCTCAATTTTTTCGAGCATCT
CTACCGGGCATCGGAATGAAATTAACGGTGTTTTAGCCATGTGTTATACAGTGTTTACAACTTG
ACTAACAAATACCTGCTAGTGTATACATATTGTATTGCAATGTATACGCTATTTTCACTGCTGT
CTTTAATGGGGATTATCGCAAGCAAGTAAAAAAGCCTGAAAACCCCAATAGGTAAGGGATTCCG
AGCTTACTCGATAATTATCACCTTTGAGCGCCCCTAGGAGGAGGCGAAAAGCTATGTCTGACAA
GGGGTTTGACCCCTGAAGTCGTTGCGCGAGCATTAAGGTCTGCGGATAGCCCATAACATACTTT
TGTTGAACTTGTGCGCTTTTATCAACCCCTTAAGGGCTTGGGAGCGTTTTATgcggccgc*GGGG*
*GGGGGGGGGAAAGCCACGTTGTGTCTCAAAATCTCTGATGTTACATTGCACAAGATAAAAATAT*
*ATCATCATGAACAATAAAACTGTCTGCTTACATAAACAGTAATACAAGGGGT*catatgCCGCAG
CTTGAAGCCAGCCTTGAACTGGACTTTCAAAGCGAGTCCTACAAAGACGCTTACAGCCGCATCA
ACGCGATCGTGATTGAAGGCGAACAAGAGGCGTTCGACAACTACAATCGCCTTGCTGAGATGCT
GCCCGACCAGCGGGATGAGCTTCACAAGCTAGCCAAGATGGAACAGCGCCACATGAAAGGCTTT
ATGGCCTGTGGCAAAAATCTCTCCGTCACTCCTGACATGGGTTTTGCCCAGAAATTTTTCGAGC
GCTTGCACGAGAACTTCAAAGCGGCGGCTGCGGAAGGCAAGGTCGTCACCTGCCTACTGATTCA
ATCGCTAATCATCGAGTGCTTTGCGATCGCGGCTTACAACATCTACATCCCAGTGGCGGATGCT

-continued

TTTGCCCGCAAAATCACGGAGGGGGTCGTGCGCGACGAATACCTGCACCGCAACTTCGGTGAAG
AGTGGCTGAAGGCGAATTTTGATGCTTCCAAAGCCGAACTGGAAGAAGCCAATCGTCAGAACCT
GCCCTTGGTTTGGCTAATGCTCAACGAAGTGGCCGATGATGCTCGCGAACTCGGGATGGAGCGT
GAGTCGCTCGTCGAGGACTTTATGATTGCCTACGGTGAAGCTCTGGAAAACATCGGCTTCACAA
CGCGCGAAATCATGCGTATGTCCGCCTATGGCCTTGCGGCCGTTTGAtccaggaaatctgaATG
TTCGGTCTTATCGGTCATCTCACCAGTTTGGAGCAGGCCCGCGACGTTTCTCGCAGGATGGGCT
ACGACGAATACGCCGATCAAGGATTGGAGTTTTGGAGTAGCGCTCCTCCTCAAATCGTTGATGA
AATCACAGTCACCAGTGCCACAGGCAAGGTGATTCACGGTCGCTACATCGAATCGTGTTTCTTG
CCGGAAATGCTGGCGGCGCGCCGCTTCAAAACAGCCACGCGCAAAGTTCTCAATGCCATGTCCC
ATGCCCAAAAACACGGCATCGACATCTCGGCCTTGGGGGGCTTTACCTCGATTATTTTCGAGAA
TTTCGATTTGGCCAGTTTGCGGCAAGTGCGCGACACTACCTTGGAGTTTGAACGGTTCACCACC
GGCAATACTCACACGGCCTACGTAATCTGTAGACAGGTGGAAGCCGCTGCTAAAACGCTGGGCA
TCGACATTACCCAAGCGACAGTAGCGGTTGTCGGCGCGACTGGCGATATCGGTAGCGCTGTCTG
CCGCTGGCTCGACCTCAAACTGGGTGTCGGTGATTTGATCCTGACGGCGCGCAATCAGGAGCGT
TTGGATAACCTGCAGGCTGAACTCGGCCGGGGCAAGATTCTGCCCTTGGAAGCCGCTCTGCCGG
AAGCTGACTTTATCGTGTGGGTCGCCAGTATGCCTCAGGGCGTAGTGATCGACCCAGCAACCCT
GAAGCAACCCTGCGTCCTAATCGACGGGGGCTACCCCAAAAACTTGGGCAGCAAAGTCCAAGGT
GAGGGCATCTATGTCCTCAATGGCGGGGTAGTTGAACATTGCTTCGACATCGACTGGCAGATCA
TGTCCGCTGCAGAGATGGCGCGGCCCGAGCGCCAGATGTTTGCCTGCTTTGCCGAGGCGATGCT
CTTGGAATTTGAAGGCTGGCATACTAACTTCTCCTGGGGCCGCAACCAAATCACGATCGAGAAG
ATGGAAGCGATCGGTGAGGCATCGGTGCGCCACGGCTTCCAACCCTTGGCATTGGCAATTTGAG
GTCTGTGAATTCGGTTTTCCGTCCTGTCTTGATTTTCAAGCAAACAATGCCTCCGATTTCTAAT
CGGAGGCATTTGTTTTTGTTTATTGCAAAAACAAAAAATATTGTTACAAATTTTTACAGGCTAT
TAAGCCTACCGTCATAAATAATTTGCCATTTACTAGTTTTTAATTAACCAGAACCTTGACCGAA
CGCAGCGGTGGTAACGGCGCAGTGGCGGTTTTCATGGCTTGTTATGACTGTTTTTTTGGGGTAC
AGTCTATGCCTCGGGCATCCAAGCAGCAAGCGCGTTACGCCGTGGGTCGATGTTTGATGTTATG
GAGCAGCAACGATGTTACGCAGCAGGGCAGTCGCCCTAAAACAAAGTTAAACATCATGAGGGAA
GCGGTGATCGCCGAAGTATCGACTCAACTATCAGAGGTAGTTGGCGTCATCGAGCGCCATCTCG
AACCGACGTTGCTGGCCGTACATTTGTACGGCTCCGCAGTGGATGGCGGCCTGAAGCCACACAG
TGATATTGATTTGCTGGTTACGGTGACCGTAAGGCTTGATGAAACAACGCGGCGAGCTTTGATC
AACGACCTTTTGGAAACTTCGGCTTCCCCTGGAGAGAGCGAGATTCTCCGCGCTGTAGAAGTCA
CCATTGTTGTGCACGACGACATCATTCCGTGGCGTTATCCAGCTAAGCGCGAACTGCAATTTGG
AGAATGGCAGCGCAATGACATTCTTGCAGGTATCTTCGAGCCAGCCACGATCGACATTGATCTG
GCTATCTTGCTGACAAAAGCAAGAGAACATAGCGTTGCCTTGGTAGGTCCAGCGGCGGAGGAAC
TCTTTGATCCGGTTCCTGAACAGGATCTATTTGAGGCGCTAAATGAAACCTTAACGCTATGGAA
CTCGCCGCCCGACTGGGCTGGCGATGAGCGAAATGTAGTGCTTACGTTGTCCCGCATTTGGTAC
AGCGCAGTAACCGGCAAAATCGCGCCGAAGGATGTCGCTGCCGACTGGGCAATGGAGCGCCTGC
CGGCCCAGTATCAGCCCGTCATACTTGAAGCTAGACAGGCTTATCTTGGACAAGAAGAAGATCG
CTTGGCCTCGCGCGCAGATCAGTTGGAAGAATTTGTCCACTACGTGAAAGGCGAGATCACCAAG
GTAGTCGGCAAATAATGTCTAACAATTCGTTCAAGCCGACGCCGCTTCGCGGCGCGGCTTAACT
CAAGCGTTAGATGCACTAAGCACATAATTGCTCACAGCCAAACTATCAGGTCAAGTCTGCTTTT
ATTATTTTTAAGCGTGCATAATAAGCCCTACACAAATTGGGAGATATATCATGAGGCGCGCCAC
GAGTGCGGGGAAATTTCGGGGGCGATCGCCCCTATATCGCAAAAAGGAGTTACCCCATCAGAGC
TATAGTCGAGAAGAAAACCATCATTCACTCAACAAGGCTATGTCAGAAGAGAAACTAGACCGGA
TCGAAGCAGCCCTAGAGCAATTGGATAAGGATGTGCAAACGCTCCAAACAGAGCTTCAGCAATC
CCAAAAATGGCAGGACAGGACATGGGATGTTGTGAAGTGGGTAGGCGGAATCTCAGCGGGCCTA
GCGGTGAGCGCTTCCATTGCCCTGTTCGGGTTGGTCTTTAGATTTTCTGTTTCCCTGCCATAAA
AGCACATTCTTATAAGTCATACTTGTTTACATCAAGGAACAAAAACGGCATTGTGCCTTGCAAG
GCACAATGTCTTTCTCTTATGCACAGATGGGGACTGGAAACCACACGCACAATTCCCTTAAAAA
GCAACCGCAAAAAATAACCATCAAAATAAAACTGGACAAATTCTCATGTGggccggccaaaatg
aagtgaagttcctatactttctagagaataggaacttctatagtgagtcgaataagggcgacac
aaaatttattctaaatgcataataaatactgataacatcttatagtttgtattatattttgtat
tatcgttgacatgtataattttgatatcaaaaactgattttccctttattattttcgagattta
ttttcttaattctctttaacaaactagaaatattgtatatacaaaaaatcataaataatagatg
aatagtttaattataggtgttcatcaatcgaaaaagcaacgtatcttatttaaagtgcgttgct
tttttctcatttataaggttaaataattctcatatatcaagcaaagtgacaggcgcccttaaat
attctgacaaatgctctttccctaaactccccccataaaaaaacccgccgaagcgggtttttac
gttatttgcggattaacgattactcgttatcagaaccgcccagggggcccgagcttaagactgg
ccgtcgttttacaacacagaaagagtttgtagaaacgcaaaaaggccatccgtcaggggccttc
tgcttagtttgatgcctggcagttccctactctcgccttccgcttcctcgctcactgactcgct
gcgctcggtcgttcggctgcggcgagcggtatcagctcactcaaaggcggtaatacggttatcc
acagaatcaggggataacgcaggaaagaacatgtgagcaaaaggccagcaaaaggccaggaacc
gtaaaaaggccgcgttgctggcgtttttccataggctccgcccccctgacgagcatcacaaaaa
tcgacgctcaagtcagaggtggcgaaacccgacaggactataaagataccaggcgtttccccct
ggaagctccctcgtgcgctctcctgttccgaccctgccgcttaccggatacctgtccgcctttc
tcccttcgggaagcgtggcgctttctcatagctcacgctgtaggtatctcagttcggtgtaggt
cgttcgctccaagctgggctgtgtgcacgaaccccccgttcagcccgaccgctgcgccttatcc
ggtaactatcgtcttgagtccaacccggtaagacacgacttatcgccactggcagcagccactg
gtaacaggattagcagagcgaggtatgtaggcggtgctacagagttcttgaagtggtggctaa
ctacggctacactagaagaacagtatttggtatctgcgctctgctgaagccagttaccttcgga
aaaagagttggtagctcttgatccggcaaacaaaccaccgctggtagcggtggtttttttgttt
gcaagcagcagattacgcgcagaaaaaaaggatctcaagaagatcctttgatcttttctacggg
gtctgacgctcagtggaacgacgcgcgcgtaactcacgttaagggattttggtcatgagcttgc
gccgtcccgtcaagtcagcgtaatgctctgcttttaccaatgcttaatcagtgaggcacctatc
tcagcgatctgtctatttcgttcatccatagttgcctgactccccgtcgtgtagataactacga
tacgggagggcttaccatctggccccagcgctgcgatgataccgcgagaaccacgctcaccggc
tccggatttatcagcaataaaccagccagccggaagggccgagcgcagaagtggtcctgcaact
ttatccgcctccatccagtctattaattgttgccgggaagctagagtaagtagttcgccagtta
atagtttgcgcaacgttgttgccatcgctacaggcatcgtggtgtcacgctcgtcgtttggtat
ggcttcattcagctccggttcccaacgatcaaggcgagttacatgatcccccatgttgtgcaaa
aaagcggttagctccttcggtcctccgatcgttgtcagaagtaagttggccgcagtgttatcac -continued tcatggttatggcagcactgcataattctcttactgtcatgccatccgtaagatgcttttctgt
gactggtgagtactcaaccaagtcattctgagaatagtgtatgcggcgaccgagttgctcttgc
ccggcgtcaatacgggataataccgcgccacatagcagaactttaaaagtgctcatcattggaa
aacgttcttcggggcgaaaactctcaaggatcttaccgctgttgagatccagttcgatgtaacc
cactcgtgcacccaactgatcttcagcatcttttactttcaccagcgtttctgggtgagcaaaa
acaggaaggcaaaatgccgcaaaaaagggaataagggcgacacggaaatgttgaatactcatat
tcttcctttttcaatattattgaagcatttatcagggttattgtctcatgagcggatacatatt
tgaatgtatttagaaaaataaacaaataggggtcagtgttacaaccaattaaccaattctgaac
attatcgcgagcccatttatacctgaatatggctcataacaccccttgtttgcctggcggcagt
agcgcggtggtcccacctgaccccatgccgaactcagaagtgaaacgccgtagcgccgatggta
gtgtggggactccccatgcgagagtagggaactgccaggcatcaaataaaacgaaaggctcagt
cgaaagactgggcctttcgcccgggctaattatggggtgtcgcccttattcgactctatagtga
agttcctattctctagaaagtataggaacttctgaagtggggcctgcagg SEQ ID NO: 16
plasmid pJB855
1st bold sequence SYNPCC7942_1593 coding sequence
2nd bold sequence SYNPCC7942_1594 coding sequence
Italic sequence aadA spectinomycin selection marker (reverse complement)

(SEQ ID NO: 16)

GGGGAATTGTGAGCGGATAACAATTCCCCTGTAGAAATAATTTTGTTTAACTTTAATAAGGAGAT
ATACCATGGGCAGCAGCCATCACCATCATCACCACAGCCAGGATCCGAATTCGAGCTCGGCGCGC
CTGCAGGTCGACAAGCTTGCGGCCGCATAATGCTTAAGTCGAACAGAAAGTAATCGTATTGTACA
CGGCCGCATAATCGAAATTAATACGACTCACTATAGGGGAATTGTGAGCGGATAACAATTCCCCA
TCTTAGTATATTAGTTAAGTATAAGAAGGAGATATACATATGCCGCAGCTTGAAGCCAGCCTTGA
ACTGGACTTTCAAAGCGAGTCCTACAAAGACGCTTACAGCCGCATCAACGCGATCGTGATTGAAG
GCGAACAAGAGGCGTTCGACAACTACAATCGCCTTGCTGAGATGCTGCCCGACCAGCGGGATGAG
CTTCACAAGCTAGCCAAGATGGAACAGCGCCACATGAAAGGCTTTATGGCCTGTGGCAAAAATCT
CTCCGTCACTCCTGACATGGGTTTTGCCCAGAAATTTTTCGAGCGCTTGCACGAGAACTTCAAAG
CGGCGGCTGCGGAAGGCAAGGTCGTCACCTGCCTACTGATTCAATCGCTAATCATCGAGTGCTTT
GCGATCGCGGCTTACAACATCTACATCCCAGTGGCGGATGCTTTTGCCCGCAAAATCACGGAGGG
GGTCGTGCGCGACGAATACCTGCACCGCAACTTCGGTGAAGAGTGGCTGAAGGCGAATTTTGATG
CTTCCAAAGCCGAACTGGAAGAAGCCAATCGTCAGAACCTGCCCTTGGTTTGGCTAATGCTCAAC
GAAGTGGCCGATGATGCTCGCGAACTCGGGATGGAGCGTGAGTCGCTCGTCGAGGACTTTATGAT
TGCCTACGGTGAAGCTCTGGAAAACATCGGCTTCACAACGCGCGAAATCATGCGTATGTCCGCCT
ATGGCCTTGCGGCCGTTTGATCCAGGAAATCTGAATGTTCGGTCTTATCGGTCATCTCACCAGTT
TGGAGCAGGCCCGCGACGTTTCTCGCAGGATGGGCTACGACGAATACGCCGATCAAGGATTGGAG
TTTTGGAGTAGCGCTCCTCCTCAAATCGTTGATGAAATCACAGTCACCAGTGCCACAGGCAAGGT
GATTCACGGTCGCTACATCGAATCGTGTTTCTTGCCGGAAATGCTGGCGGCGCGCCGCTTCAAAA
CAGCCACGCGCAAAGTTCTCAATGCCATGTCCCATGCCCAAAAACACGGCATCGACATCTCGGCC
TTGGGGGGCTTTACCTCGATTATTTTCGAGAATTTCGATTTGGCCAGTTTGCGGCAAGTGCGCGA
CACTACCTTGGAGTTTGAACGGTTCACCACCGGCAATACTCACACGGCCTACGTAATCTGTAGAC
AGGTGGAAGCCGCTGCTAAAACGCTGGGCATCGACATTACCCAAGCGACAGTAGCGGTTGTCGGC
GCGACTGGCGATATCGGTAGCGCTGTCTGCCGCTGGCTCGACCTCAAACTGGGTGTCGGTGATTT
GATCCTGACGGCGCGCAATCAGGAGCGTTTGGATAACCTGCAGGCTGAACTCGGCCGGGGCAAGA
TTCTGCCCTTGGAAGCCGCTCTGCCGGAAGCTGACTTTATCGTGTGGGTCGCCAGTATGCCTCAG
GGCGTAGTGATCGACCCAGCAACCCTGAAGCAACCCTGCGTCCTAATCGACGGGGGCTACCCCAA
AAACTTGGGCAGCAAAGTCCAAGGTGAGGGCATCTATGTCCTCAATGGCGGGGTAGTTGAACATT
GCTTCGACATCGACTGGCAGATCATGTCCGCTGCAGAGATGGCGCGGCCCGAGCGCCAGATGTTT
GCCTGCTTTGCCGAGGCGATGCTCTTGGAATTTGAAGGCTGGCATACTAACTTCTCCTGGGGCCG
CAACCAAATCACGATCGAGAAGATGGAAGCGATCGGTGAGGCATCGGTGCGCCACGGCTTCCAAC
CCTTGGCATTGGCAATTTGAGGTCTGTGAATTGGATATCGGCCGGCCACGCGATCGCTGACGTCG
GTACCCTCGAGTCTGGTAAAGAAACCGCTGCTGCGAAATTTGAACGCCAGCACATGGACTCGTCT
ACTAGCGCAGCTTAATTAACCTAGGCTGCTGCCACCGCTGAGCAATAACTAGCATAACCCCTTGG
GGCCTCTAAACGGGTCTTGAGGGGTTTTTTGCTGAAACCTCAGGCATTTGAGAAGCACACGGTCA
CACTGCTTCCGGTAGTCAATAAACCGGTAAACCAGCAATAGACATAAGCGGCTATTTAACGACCC
TGCCCTGAACCGACGACCGGGTCATCGTGGCCGGATCTTGCGGCCCCTCGGCTTGAACGAATTGT
TAGAC*ATTATTTGCCGACTACCTTGGTGATCTCGCCTTTCACGTAGTGGACAAATTCTTCCAACT*
*GATCTGCGCGCGAGGCCAAGCGATCTTCTTCTTGTCCAAGATAAGCCTGTCTAGCTTCAAGTATG*
*ACGGGCTGATACTGGGCCGGCAGGCGCTCCATTGCCCAGTCGGCAGCGACATCCTTCGGCGCGAT*
*TTTGCCGGTTACTGCGCTGTACCAAATGCGGGACAACGTAAGCACTACATTTCGCTCATCGCCAG*
*CCCAGTCGGGCGGCGAGTTCCATAGCGTTAAGGTTTCATTTAGCGCCTCAAATAGATCCTGTTCA*
*GGAACCGGATCAAAGAGTTCCTCCGCCGCTGGACCTACCAAGGCAACGCTATGTTCTCTTGCTTT*
*TGTCAGCAAGATAGCCAGATCAATGTCGATCGTGGCTGGCTCGAAGATACCTGCAAGAATGTCAT*
*TGCGCTGCCATTCTCCAAATTGCAGTTCGCGCTTAGCTGGATAACGCCACGGAATGATGTCGTCG*
*TGCACAACAATGGTGACTTCTACAGCGCGGAGAATCTCGCTCTCTCCAGGGGAAGCCGAAGTTTC*
*CAAAAGGTCGTTGATCAAAGCTCGCCGCGTTGTTTCATCAAGCCTTACGGTCACCGTAACCAGCA*
*AATCAATATCACTGTGTGGCTTCAGGCCGCCATCCACTGCGGAGCCGTACAAATGTACGGCCAGC*
*AACGTCGGTTCGAGATGGCGCTCGATGACGCCAACTACCTCTGATAGTTGAGTCGATACTTCGGC*
*GATCACCGCTTCCCTCATA*CTCTTCCTTTTTCAATATTATTGAAGCATTTATCAGGGTTATTGTC
TCATGAGCGGATACATATTTGAATGTATTTAGAAAAATAAACAAATAGCTAGCTCACTCGGTCGC
TACGCTCCGGGCGTGAGACTGCGGCGGGCGCTGCGGACACATACAAAGTTACCCACAGATTCCGT
GGATAAGCAGGGGACTAACATGTGAGGCAAAACAGCAGGGCCGCGCCGGTGGCGTTTTTCCATAG
GCTCCGCCCTCCTGCCAGAGTTCACATAAACAGACGCTTTTCCGGTGCATCTGTGGGAGCCGTGA
GGCTCAACCATGAATCTGACAGTACGGGCGAAACCCGACAGGACTTAAAGATCCCCACCGTTTCC
GGCGGGTCGCTCCCTCTTGCGCTCTCCTGTTCCGACCCTGCCGTTTACCGGATACCTGTTCCGCC
TTTCTCCCTTACGGGAAGTGTGGCGCTTTCTCATAGCTCACACACTGGTATCTCGGCTCGGTGTA
GGTCGTTCGCTCCAAGCTGGGCTGTAAGCAAGAACTCCCCGTTCAGCCCGACTGCTGCGCCTTAT

-continued

CCGGTAACTGTTCACTTGAGTCCAACCCGGAAAAGCACGGTAAAACGCCACTGGCAGCAGCCATT
GGTAACTGGGAGTTCGCAGAGGATTTGTTTAGCTAAACACGCGGTTGCTCTTGAAGTGTGCGCCA
AAGTCCGGCTACACTGGAAGGACAGATTTGGTTGCTGTGCTCTGCGAAAGCCAGTTACCACGGTT
AAGCAGTTCCCCAACTGACTTAACCTTCGATCAAACCACCTCCCCAGGTGGTTTTTTCGTTTACA
GGGCAAAAGATTACGCGCAGAAAAAAAGGATCTCAAGAAGATCCTTTGATCTTTTCTACTGAACC
GCTCTAGATTTCAGTGCAATTTATCTCTTCAAATGTAGCACCTGAAGTCAGCCCCATACGATATA
AGTTGTAATTCTCATGTTAGTCATGCCCCGCGCCCACCGGAAGGAGCTGACTGGGTTGAAGGCTC
TCAAGGGCATCGGTCGAGATCCCGGTGCCTAATGAGTGAGCTAACTTACATTAATTGCGTTGCGC
TCACTGCCCGCTTTCCAGTCGGGAAACCTGTCGTGCCAGCTGCATTAATGAATCGGCCAACGCGC
GGGGAGAGGCGGTTTGCGTATTGGGCGCCAGGGTGGTTTTTCTTTTCACCAGTGAGACGGGCAAC
AGCTGATTGCCCTTCACCGCCTGGCCCTGAGAGAGTTGCAGCAAGCGGTCCACGCTGGTTTGCCC
CAGCAGGCGAAAATCCTGTTTGATGGTGGTTAACGGCGGGATATAACATGAGCTGTCTTCGGTAT
CGTCGTATCCCACTACCGAGATGTCCGCACCAACGCGCAGCCCGGACTCGGTAATGGCGCGCATT
GCGCCCAGCGCCATCTGATCGTTGGCAACCAGCATCGCAGTGGGAACGATGCCCTCATTCAGCAT
TTGCATGGTTTGTTGAAAACCGGACATGGCACTCCAGTCGCCTTCCCGTTCCGCTATCGGCTGAA
TTTGATTGCGAGTGAGATATTTATGCCAGCCAGCCAGACGCAGACGCGCCGAGACAGAACTTAAT
GGGCCCGCTAACAGCGCGATTTGCTGGTGACCCAATGCGACCAGATGCTCCACGCCCAGTCGCGT
ACCGTCTTCATGGGAGAAAATAATACTGTTGATGGGTGTCTGGTCAGAGACATCAAGAAATAACG
CCGGAACATTAGTGCAGGCAGCTTCCACAGCAATGGCATCCTGGTCATCCAGCGGATAGTTAATG
ATCAGCCCACTGACGCGTTGCGCGAGAAGATTGTGCACCGCCGCTTTACAGGCTTCGACGCCGCT
TCGTTCTACCATCGACACCACCACGCTGGCACCCAGTTGATCGGCGCGAGATTTAATCGCCGCGA
CAATTTGCGACGGCGCGTGCAGGGCCAGACTGGAGGTGGCAACGCCAATCAGCAACGACTGTTTG
CCCGCCAGTTGTTGTGCCACGCGGTTGGGAATGTAATTCAGCTCCGCCATCGCCGCTTCCACTTT
TTCCCGCGTTTTCGCAGAAACGTGGCTGGCCTGGTTCACCACGCGGGAAACGGTCTGATAAGAGA
CACCGGCATACTCTGCGACATCGTATAACGTTACTGGTTTCACATTCACCACCCTGAATTGACTC
TCTTCCGGGCGCTATCATGCCATACCGCGAAAGGTTTTGCGCCATTCGATGGTGTCCGGGATCTC
GACGCTCTCCCTTATGCGACTCCTGCATTAGGAAATTAATACGACTCACTATA

SEQ ID NO: 17
plasmid pJB947

| | |
|---|---|
| $1^{st}$ underlined sequence | Upstream homology region for pAQ1 |
| $1^{st}$ italic sequence | aphII promoter |
| $1^{st}$ bold sequence | PMT9312_0532 (adm) coding sequence |
| $1^{st}$ lower case sequence | Intergenic sequence |
| $2^{nd}$ bold sequence | PMT9312_0533 (aar) |
| $2^{nd}$ italic sequence | aadA coding sequence; spectinomycin selection marker |
| $2^{nd}$ underlined sequence | Downstream homology region for pAQ1 |
| $2^{nd}$ lower case sequence | Vector backbone |

(SEQ ID NO: 17)

GTCAGCAAGCTCTGGAATTTCCCGATTCTCTGATGGGAGATCCAAAAATTCTCGCAGTCCCTCAAT
CACGATATCGGTCTTGGATCGCCCTGTAGCTTCCGACAACTGCTCAATTTTTTCGAGCATCTCTAC
CGGGCATCGGAATGAAATTAACGGTGTTTTAGCCATGTGTTATACAGTGTTTACAACTTGACTAAC
AAATACCTGCTAGTGTATACATATTGTATTGCAATGTATACGCTATTTTCACTGCTGTCTTTAATG
GGGATTATCGCAAGCAAGTAAAAAAGCCTGAAAACCCCAATAGGTAAGGGATTCCGAGCTTACTCG
ATAATTATCACCTTTGAGCGCCCCTAGGAGGAGGCGAAAAGCTATGTCTGACAAGGGGTTTGACCC
CTGAAGTCGTTGCGCGAGCATTAAGGTCTGCGGATAGCCCATAACATACTTTTGTTGAACTTGTGC
GCTTTTATCAACCCCTTAAGGGCTTGGGAGCGTTTTATGCGGCCGC*GGGGGGGGGGGGGAAAGCCA*
*CGTTGTGTCTCAAAATCTCTGATGTTACATTGCACAAGATAAAAATATATCATCATGAACAATAAA*
*ACTGTCTGCTTACATAAACAGTAATACAAGGGGTCAT*ATGCACAATGAATTGAAAATCACGGATAT
GCAAACGCTGGAAACCAACACCAAGACGACCGAAGAGTCTATTGACACCAATAGCCTGAACCTGCC
GGACTTTACTACCGACAGCTACAAGGATGCCTATTCTCGCATTAACGCCATCGTTATTGAGGGCGA
ACAGGAAGCTCATGACAATTACATCTCCATCGCAACGCTGATCCCGAATGAGCTGGAAGAGCTGAC
GAAGCTGGCACGTATGGAGCTGAAACACAAGAAAGGTTTTACTGCGTGCGGTCGTAATCTGGGTGT
GGACGCAGACATGGTTTTCGCGAAAAAGTTCTTCAGCAAACTGCACGGCAATTTCCAAATCGCGCT
GGAAAAAGGTAACCTGACCACCTGCTTGCTGATCCAAGCGATTCTGATCGAAGCATTTGCGATTTC
CGCGTACAATGTTTACATCCGTGTGGCCGACCCATTTGCCAAAAAGATTACCGAGGGTGTTGTCAA
AGACGAGTATCTGCATCTGAACTATGGTCAGGAGTGGCTGAAAAAGAATCTGTCCACGTGTAAAGA
AGAGCTGATGGAGGCCAACAAGGTCAATCTGCCGCTGATTAAGAAAATGCTGGACGAAGTGGCAGA
AGATGCGAGCGTTTTGGCGATGGATCGTGAAGAGTTGATGGAAGAGTTCATGATTGCGTACCAGGA
TACCCTGTTGGAGATTGGCCTGGATAATCGCGAAATTGCCCGTATGGCGATGGCGGCCATTGTTTA
GtaatatttctaattaactaataaaggaagtctgaATGTTTGGTCTGATTGGTCATAGCACCAGCT
TTGAGGACGCAAAGCGCAAGGCGAGCCTGCTGGGTTTCGACCACATCGCGGATGGCGATCTGGATG
TGTGGTGTACCGCACCGCCGCAACTGGTTGAAAACGTGGAAGTCAAAAGCGCGACGGGTATCAGCA
TTGAAGGTAGCTATATCGATAGCTGCTTCGTGCCGGAGATGCTGAGCCGCTTCAAGACCGCGCGTC
GTAAAGTTCTGAATGCAATGGAGCTGGCGCAGAAAAAGGGTATCAATATCACTGCCCTGGGTGGCT
TTACCTCCATTATCTTTGAGAACTTCAACCTGTTGCAGCACAAGCAAATCCGTAATACCAGCCTGG
AGTGGGAGCGTTTCACCACGGGTAACACGCACACGGCATGGGTGATTTGTCGTCAGCTGGAGATCA
ACGCACCGCGCATTGGCATCGACCTGAAAACTGCAACGGTCGCTGTTATCGGCGCGACCGGCGATA
TTGGTAGCGCGGTGTGTCGCTGGCTGGTCAATAAGACCGGCATTAGCGAACTGCTGATGGTCGCTC
GCCAACAACAGCCACTGACCCTGCTGCAAAAAGAACTGGACGGTGGCACCATCAAGAGCCTGGATG
AAGCCCTGCCGCAGGCGGATATTGTCGTGTGGGTTGCTTCGATGCCTAAGACGATCGAAATTGAGA
TTGAAAACCTGAAAAAGCCGTGCCTGATGATCGACGGTGGCTACCCGAAGAATCTGGACGAGAAAT
TCAAAGGCAAAAACATTCACGTGTTGAAGGGTGGTATCGTCGAGTTTTTCAACGACATTGGCTGGA
ACATGATGGAGTTGGCGGAGATGCAAAACCCGCAGCGTGAGATGTTTGCGTGCTTCGCCGAAGCTA
TGATTCTGGAGTTTGAGAAATGCCATACCAACTTTAGCTGGGGCCGTAACAATATCAGCTTGGAGA
AGATGGAGTTCATCGGTGCTGCATCTCTGAAGCACGGTTTCAGCGCGATCGGTCTGGATAAACAGC
CGAAAGTCTTGACCGTTTGAaattGAATTCGGTTTTCCGTCCTGTCTTGATTTTCAAGCAAACAAT
GCCTCCGATTTCTAATCGGAGGCATTTGTTTTTGTTTATTGCAAAAACAAAAAATATTGTTACAAA
TTTTTACAGGCTATTAAGCCTACCGTCATAAATAATTTGCCATTTACTAGTTTTTAATTAACCAGA
ACCTTGACCGAACGCAGCGGTGGTAACGGCGCAGTGGCGGTTTTCATGGCTTGTTATGACTGTTTT -continued TTTGGGGTACAGTCTATGCCTCGGGCATCCAAGCAGCAAGCGCGTTACGCCGTGGGTCGATGTTTG
ATGTTATGGAGCAGCAACGATGTTACGCAGCAGGGCAGTCGCCCTAAAACAAAGTTAAACATC*ATG*
*AGGGAAGCGGTGATCGCCGAAGTATCGACTCAACTATCAGAGGTAGTTGGCGTCATCGAGCGCCAT*
*CTCGAACCGACGTTGCTGGCCGTACATTTGTACGGCTCCGCAGTGGATGGCGGCCTGAAGCCACAC*
*AGTGATATTGATTTGCTGGTTACGGTGACCGTAAGGCTTGATGAAACAACGCGGCGAGCTTTGATC*
*AACGACCTTTTGGAAACTTCGGCTTCCCCTGGAGAGAGCGAGATTCTCCGCGCTGTAGAAGTCACC*
*ATTGTTGTGCACGACGACATCATTCCGTGGCGTTATCCAGCTAAGCGCGAACTGCAATTTGGAGAA*
*TGGCAGCGCAATGACATTCTTGCAGGTATCTTCGAGCCAGCCACGATCGACATTGATCTGGCTATC*
*TTGCTGACAAAAGCAAGAGAACATAGCGTTGCCTTGGTAGGTCCAGCGGCGGAGGAACTCTTTGAT*
*CCGGTTCCTGAACAGGATCTATTTGAGGCGCTAAATGAAACCTTAACGCTATGGAACTCGCCGCCC*
*GACTGGGCTGGCGATGAGCGAAATGTAGTGCTTACGTTGTCCCGCATTTGGTACAGCGCAGTAACC*
*GGCAAAATCGCGCCGAAGGATGTCGCTGCCGACTGGGCAATGGAGCGCCTGCCGGCCCAGTATCAG*
*CCCGTCATACTTGAAGCTAGACAGGCTTATCTTGGACAAGAAGAAGATCGCTTGGCCTCGCGCGCA*
*GATCAGTTGGAAGAATTTGTCCACTACGTGAAAGGCGAGATCACCAAGGTAGTCGGCAAATAA*TGT
CTAACAATTCGTTCAAGCCGACGCCGCTTCGCGGCGCGGCTTAACTCAAGCGTTAGATGCACTAAG
CACATAATTGCTCACAGCCAAACTATCAGGTCAAGTCTGCTTTTATTATTTTTAAGCGTGCATAAT
AAGCCCTACACAAATTGGGAGATATATCATGAGGCGCGCCACGAGTGCGGGGAAATTTCGGGGGCG
ATCGCCCCTATATCGCAAAAAGGAGTTACCCCATCAGAGCTATAGTCGAGAAGAAAACCATCATTC
ACTCAACAAGGCTATGTCAGAAGAGAAACTAGACCGGATCGAAGCAGCCCTAGAGCAATTGGATAA
GGATGTGCAAACGCTCCAAACAGAGCTTCAGCAATCCCAAAAATGGCAGGACAGGACATGGGATGT
TGTGAAGTGGGTAGGCGGAATCTCAGCGGGCCTAGCGGTGAGCGCTTCCATTGCCCTGTTCGGGTT
GGTCTTTAGATTTTCTGTTTCCCTGCCATAAAAGCACATTCTTATAAGTCATACTTGTTTACATCA
AGGAACAAAAACGGCATTGTGCCTTGCAAGGCACAATGTCTTTCTCTTATGCACAGATGGGGACTG
GAAACCACACGCACAATTCCCTTAAAAAGCAACCGCAAAAAATAACCATCAAAATAAAACTGGACA
AATTCTCATGTGggccggccaaaatgaagtgaagttcctatactttctagagaataggaacttcta
tagtgagtcgaataagggcgacacaaaatttattctaaatgcataataaatactgataacatctta
tagtttgtattatattttgtattatcgttgacatgtataattttgatatcaaaaactgattttccc
tttattattttcgagatttattttcttaattctctttaacaaactagaaatattgtatatacaaaa
aatcataaataatagatgaatagtttaattataggtgttcatcaatcgaaaaagcaacgtatctta
tttaaagtgcgttgctttttctcatttataaggttaaataattctcatatatcaagcaaagtgac
aggcgcccttaaatattctgacaaatgctctttccctaaactccccccataaaaaaacccgccgaa
gcgggtttttacgttatttgcggattaacgattactcgttatcagaaccgcccagggggcccgagc
ttaagactggccgtcgttttacaacacagaaagagtttgtagaaacgcaaaaaggccatccgtcag
gggccttctgcttagtttgatgcctggcagttccctactctcgccttccgcttcctcgctcactga
ctcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaa
ccgtaaaaaggccgcgttgctggcgtttttccataggctccgcccccctgacgagcatcacaaaaa
tcgacgctcaagtcagaggtggcgaaacccgacaggactataaagataccaggcgtttccccctgg
aagctccctcgtgcgctctcctgttccgaccctgccgcttaccggatacctgtccgcctttctccc
ttcgggaagcgtggcgctttctcatagctcacgctgtaggtatctcagttcggtgtaggtcgttcg
ctccaagctgggctgtgtgcacgaaccccccgttcagcccgaccgctgcgccttatccggtaacta
tcgtcttgagtccaacccggtaagacacgacttatcgccactggcagcagccactggtaacaggat
tagcagagcgaggtatgtaggcggtgctacagagttcttgaagtggtggcctaactacggctacac
tagaagaacagtatttggtatctgcgctctgctgaagccagttaccttcggaaaaagagttggtag
ctcttgatccggcaaacaaaccaccgctggtagcggtggtttttttgtttgcaagcagcagattac
gcgcagaaaaaaaggatctcaagaagatcctttgatcttttctacggggtctgacgctcagtggaa
cgacgcgcgcgtaactcacgttaagggattttggtcatgagcttgcgccgtcccgtcaagtcagcg
taatgctctgcttttaccaatgcttaatcagtgaggcacctatctcagcgatctgtctatttcgtt
catccatagttgcctgactccccgtcgtgtagataactacgatacgggagggcttaccatctggcc
ccagcgctgcgatgataccgcgagaaccacgctcaccggctccggatttatcagcaataaaccagc
cagccggaagggccgagcgcagaagtggtcctgcaactttatccgcctccatccagtctattaatt
gttgccgggaagctagagtaagtagttcgccagttaatagtttgcgcaacgttgttgccatcgcta
caggcatcgtggtgtcacgctcgtcgtttggtatggcttcattcagctccggttcccaacgatcaa
ggcgagttacatgatcccccatgttgtgcaaaaaagcggttagctccttcggtcctccgatcgttg
tcagaagtaagttggccgcagtgttatcactcatggttatggcagcactgcataattctcttactg
tcatgccatccgtaagatgcttttctgtgactggtgagtactcaaccaagtcattctgagaatagt
gtatgcggcgaccgagttgctcttgcccggcgtcaatacgggataataccgcgccacatagcagaa
ctttaaaagtgctcatcattggaaaacgttcttcggggcgaaaactctcaaggatcttaccgctgt
tgagatccagttcgatgtaacccactcgtgcacccaactgatcttcagcatcttttactttcacca
gcgtttctgggtgagcaaaaacaggaaggcaaaatgccgcaaaaaagggaataagggcgacacgga
aatgttgaatactcatattcttcctttttcaatattattgaagcatttatcagggttattgtctca
tgagcggatacatatttgaatgtatttagaaaaataaacaaataggggtcagtgttacaaccaatt
aaccaattctgaacattatcgcgagcccatttatacctgaatatggctcataacaccccttgtttg
cctggcggcagtagcgcggtggtcccacctgaccccatgccgaactcagaagtgaaacgccgtagc
gccgatggtagtgtggggactccccatgcgagagtagggaactgccaggcatcaaataaaacgaaa
ggctcagtcgaaagactgggcctttcgcccgggctaattatggggtgtcgcccttattcgactcta
tagtgaagttcctattctctagaaagtataggaacttctgaagtggggcctgcagg SEQ ID NO: 18
plasmid pJB825t

| | |
|---|---|
| 1st underlined sequence | Upstream homology region for TS1 chromosomal integration site |
| 1st italic sequence | cI promoter with JCC138 rbcL ribosome-binding sequence |
| 1st bold sequence | tll1313 (adm) coding sequence |
| 1st lower case sequence | Native intergenic sequence |
| 2nd bold sequence | tll1312 (aar) coding sequence |
| 2nd italic sequence | $kan^{HTK}$ coding sequence; thermostable kanamycin selection marker |

-continued

2nd underlined sequence   Downstream homology region for TS1
                          chromosomal integration site
2nd lower case sequence   Vector backbone (SEQ ID NO: 18)

TGGGAGTCAATAAACCCGATGTGCGTTGGATTTGCCACTACCAGCCGCCCCTGCAACTCAGTGAA
TATCTCCAAGAGGTGGGACGCGCTGGGCGAGATGGCGAAGCGGCACAGGCCCTGGTTTTGGTGAG
CGATCGCTGGGGCTTGGATCGCGAAGATCAACAGCGTTGGTCTTTTTTTCAGCACCAAAGTCAAG
ACACCTACAATCGCGCCATGGCACTTCAGACGCAGCTGCCCCTCCAGGGTAATCTGCAGCAACTG
CGGCAACACTTTCCTGAAGTGGAATTGACCCTGGCATTACTGCATCAACAGGGGGCCCTCCGCTG
GCAAGATCCCTTTCACTATTGCCGTCAACCCTTGGCACAGGTGCCACCCCCACCCAAAGACCCTC
AAGAACAGTTGATGCAAAAGTTCCTCTATCACCGGGGCTGCCGCTGGCAGTTTCTCCTCCAAGCC
TTTGGTTTTGCCACTGAGGCAAGGGGATTCCACTGTGGCCATTGCGATCGCTGTCGGCCGCCGCA
CCGCTCCCGCAAAATACCGTAAATTGCCAGCGCTGTATCACTGGAATATTGGGTACACTGGCACA
TAGAACGGTCGCTTTACCATTGGTAGGCAAAAGTTTCTCAGCAGTCATTCTGTTGCCGCAAGGTA
GGGGTTGCAGGCATGGGGCTACTACAAGTTGAGGAAATTCGCGAAGCACTTCAAGATGTGCTTTC
AGAACACGCCCTTGTTGTGCAAGTTAATCAGTTTCGCAACCAATTAAACATTATTTTGAACAAGC
CCCCCGGCACCGTTGCCCATTATTCTGCCCTAGCGGATTTTCTCAAGTCGCGCTTGGGACAGTTT
CATCTCAATGATATTGACCGCATTAAAATAATTGGCCGCATACAGGGTTCGCCTAAACCCGATTG
GGAAGAGGTCATTGATCTACGTCCCCCAACCCAGCCCTAGCTGCCCCTGTGTATGCTTCTTCTG
CCCCGTGGGTGGTGGCGATCGCTGCTGGCTTTGTCAGTTTACTGGTGATCTTTAGCTATCACCTT
GGTCAGTAGCAGCAACAGCAACGGCTGTAGCCGTTGATCGAAGGTTCCTTTGGTCAAAGGGCGT
CGTGATGACGGACTTTAAGTGGCACATTGAGGGTGGTACAGGGTTTATTGTCGGGGTTCTTAAAA
ACTACAGTAAAGGGTATTTTCGCTTAGTTCAGGCGGACTTTGAACTCTTTGACCAAGGCGGTCAG
CAAGTTGGGACAGTGGCGGTACAGGTTTATGGTCTTGGCCCTGAGGAAACATGGCAATTCCGTGA
ACTGATAGCCAATCATCAGGCAGTGCGAGCACGGCTGGTAAAATTACAGTCATTCAATTAAGGTT
TTTCTAATGTTTAGGTTTCCCCAGCAGGGAGCGACACCGCTTGCTATGGCACACCTTAAAGCCCT
GATCTTTGATGTCGATGGCACCTTAGCAGATACGGAGCGGGATGGCCATCGTATCGCCTTCAACA
AGGCCTTTGCCGCCGCTGGTCTAGATTGGGAATGGGACATTCCCCTCTATGGTCAACTCCTGGCG
GTGGCTGGGGGCAAGGAGCGGATCCGGTATTACCTTGAGTGCTTTCGTCCCGATTGGCCACGTCC
CCAAAATTTGGATGCTCTGATTGCCGATTTACACAAGGCCAAGACCCGCTATTATACCGAGCTAT
TGGCGGCAGGGGCTATTCCCCTGCGGCCGGGGGTGAAACGGCTCCTCACTGAAGCCCGGGAAGCA
GGATTACGTTTGGCGATCGCCACCACGACCACCCCTGCCAATGTCACCGCACTCCTTGAAAATGC
CCTCGCTCCTGATGGCGTCAGTTGGTTTGAGATAATTGCTGCCGGGGATGTAGTTCCAGCCAAGA
AACCCGCGCCCGACATTTACTTCTACACGCTTGAAAAGATGCGCCTCTCACCCCAAGAGTGCCTT
GCCTTTGAGGATTCCGCCAATGGGATTCAGGCGGCCACTGCCAGTCACCTAGCGACCATTATCAC
GATTACCGACTACACCAAGGATCATGATTTTCGTGATGCAGCGCTGGTCTTGGATTGCTTAGGGG
AACCGGACTACCCCTTTCAGGTTCTGCGCGGTGAGGTGGGTTGGACAACCTATGTGGATGTCCCC
CTATTGCGATCGCTGCACCAGCAGTGGACAAGCACGTTGAGTCAGGGATAATTTTCTGGCCGCAG
CGTTTTACATTGAATATGACCCCCTTAGTCTGAGGATCAAGGAACATAATGTACACGATTGATTT
AATTCTGCGTCATGTCCCCATGCCCGTCAGCATTGAACGCAAGGAAAGTGCAGCAGCGATGGCAG
TCTATCAGCAAATTCAGCAGGCCATGGCCAGTGGTACTCCAACTTTCCTCGAACTGACGTGCGAT
CGCCAAGTGGGCAAGAAGTTAACGGTGCTCACCTCAGAAATTGTCGCCGTGCAAATGGCGGATAA
GGATGCCCCCTCCAGTACTATCAGTCGTGGGGGATTCTTTGCTCAATTAGTGCAGCAAACCAGCA
ACTGAGGGAAAATGCCTCAATAAAGTTGAGTTTTTCTTGGCAATGCTGATTCTTTGCCGTTAGGA
TACTAAGCAGACCGATCCGTAGGGGAACGTGAAGCAAATCCTCCCCGTCTGAAAGTCAGGTATCT
CTGGTGTGTCGTAATAGGGTTGTCTATGGTGCAGCGTTTCCTGCCGGTTCTGATTTTGTTGGGGT
GTAGTTTTGGTCTTGCGACCCCTGCCCTTGTGCGTGCCCAAGCCAATCAGGGCTTTACGTTTACT
TGGGGTGAGGGGCCGAGTGGCCGACAGCAGTTGCAATACCACTTAGATAACGGCACCCCCGGTTT
TATGGGCGATCGCTATTGGCTGCGGCTGGGTCAGCAGAAAGTGGCCATCAATCGCATTAACATTA
CCTATCCCGACTACTACAACGGTATTATTGATCCCAAAGGCATTGAGGTGCGCATCGGTGGCGAT
CGCGGCAATCGCTTCTTCCAATTTCGCCGTGACCCCGGCACCAAAATTCAATTGGCGGAAGTCTC
CGTTGATCGCGATAACCGCGTGATTGATATTGTGCCGGCTGAGGTGATTCCCGCCGGACACCGG
TGCAAGTTATTCTCAATAATGTGCGCAACCCTAACAATGGCGGCATGTACTATTTCAATGCCCGC
ATTGGCTCCCCTGGAGATATTCCCCTCATGCGCTACGTTGGCACCTGGATTCTCAGCATTGCCAA
TAACTAAAACCCGTCAAACTCGAGCATTGGTGAGCGGGTTAGCCATTTCTAACTATTGCGGGGCG
ATCGCCCTAGACTAGTTTTTTGTCTATTATTGCCGGTTCACTCTTTACACCAGATGCCAGATTCC
GTTAGGTCTTCATTCCCCTCCATTTCTCCTCTGCTCACGCCTCTGATGTACCGCCTCGTGGGGGA
CGTTGTCCTGCGGCGCTATTTTCGTACCCTTGAGGTGCAAGGGCAGGAGCGGGTGCCCCAAAGGG
GTCCAGTGATCTTGGCCCCCACCCACCGTTCCCGCTGGGATGCGCTGATTATTCCCTATGTCACT
GGGCGGCGGGTGAGTGGGCGCGACCTCTACTACATGGTGTCCCACGATGAGATGTTGGGACTACA
GGGCTGGGTGATTGCTCAGTGTGGCGGTTTTCCCGTCAATACCCAAGCGCCTTCGGTGAGTGCGT
TGCGTACGGGTGTGGAACTGCTCCGGCAGGGGCAAGCCTTGGTGGTGTTCCCTGAGGGGAATATC
TTTCGCGATCGCCAGATTCATCCCCTCAAGCCGGGGTTGGCTCGCTTAGCCCTTCAGGCGGCCCA
GCGCTGTGAACAAGCAATCCAGATTCTGCCAATTTTACTCGATTATGCCCAGCCCTACCCACAGT
GGGGAAGTGCGGTCAAGGTAATCATTGGGGCTCCCTTGAGTACCGACAATTACGATGCCAGCCGG
CCAAAAAGTGCTGCCCAACAACTGACCAGTGATCTCTTTAGAAGACTTCAGCAGCTCCAAGGGGG
GCGATCGCCCCTGTGTTTGCTTAGACCTCAAACTTCCATCCCCGCGGCCGCTCTTGATAACCCA
AGAGGGCATTTTTTAGGCGCGCCTCGAG*TAACACCGTGCGTGTTGACTATTTTACCTCTGGCGGT*
*GATAATGGTTGCAGGATCCTTTTGCTGGAGGAAGAATTC*ATGACAACGGCTACCGCTACACCTGT
TTTGGACTACCATAGCGATCGCTACAAGGATGCCTACAGCCGCATTAACGCCATTGTCATTGAAG
GTGAACAGGAAGCTCACGATAACTATATCGATTTAGCCAAGCTGCTGCCACAACACCAAGAGGAA
CTCACCCGCCTTGCCAAGATGGAAGCTCGCCACAAAAAGGGGTTTGAGGCCTGTGGTCGCAACCT
GAGCGTAACGCCAGATATGGAATTTGCCAAAGCCTTCTTTGAAAAACTGCGCGCTAACTTTCAGA
GGGCTCTGGCGGAGGGAAAAACTGCGACTTGTCTTCTGATTCAAGCTTTGATCATCGAATCCTTT
GCGATCGCGGCCTACAACATCTACATCCCAATGGCGGATCCTTTCGCCCGTAAAATTACTGAGAG
TGTTGTTAAGGACGAATACAGCCACCTCAACTTTGGCGAAATCTGGCTCAAGGAACACTTTGAAA
GCGTCAAAGGAGAGCTCGAAGAAGCCAATCGCGCCAATTTACCCTTGGTCTGGAAAATGCTCAAC
CAAGTGGAAGCAGATGCCAAAGTGCTCGGCATGGAAAAAGATGCCCTTGTGGAAGACTTCATGAT
TCAGTACAGTGGTGCCCTAGAAAATATCGGCTTTACCACCCGCGAAATTATGAAGATGTCAGTTT
ATGGCCTCACTGGGGCATAAtggtggcttaacgtatcgttacatttcagtcacacacgcttgtA
TGTTTGGATTAATTGGTCATCTGACGAGTCTGGAGCACGCCCAAGCCGTTGCCCATCAGTTGGGT

-continued

TACCCCGAATATGCCGATCAAGGCTTGGAATTTTGGTGTATGGCACCGCCGCAGATCGTCGATGA
GATTACGGTGACGAGCGTAACGGGCAAAACTATCTATGGCAAATACGTTGAGTCCTGCTTTTTAC
CAGAGATGCTGGCCAACCAGCGGGTGAAGGCAGCGACTCGCAAAGTTATTAACGCCATGGCCCAT
GCCCAAAAGCACAACATTGACATTACGGCCTTGGGGGGCTTCTCCTCGATCATCTTTGAGAACTT
TGATCTGGAGAAAATGTCCCACATTCGCAACATTGAACTGGACTTTCGCCGCTTTACAACGGGGA
ATACCCATACCGCCTATATCATCTGCCAACAAATTGAGCAGGCGGCGCCCCAAGTGGGGATTGAT
TTGCGGCAGGCAACCGTGGCTGTTTGTGGGGCTACGGGGGATATTGGTAGTGCCGTCTGCCGTTG
GTTGAATACCTGTTTAGATGTGCAAGATCTCTTACTCGTAGCACGGAATCGCGATCGCCTGCTGG
AGCTACAGGCGGAATTGGGACGGGGGAAAATCCTCGACTTGATGGAGGCGCTGCCCCTTGCCGAT
ATTGTGGTTTGGGTGGCCAGTATGCCCAAGGGAGTTGAGCTGAGCATTGAGCAGTTAAAACGCCC
CTCCCTGATGATTGATGGTGGTTATCCCAAAAATATGGCCACCAAAATTCAGCACCCCCAGATTC
ATGTTCTCAATGGTGGCATTGTCGAGCATGCCCTCGACATTGACTGGAAAATTATGGAAATTGTG
AATATGGATGTGCCCTCGCGGCAGATGTTTGCCTGTTTTGCAGAGGCTATGCTTTTAGAGTTCGA
GGGCTGGCACACCAATTTCTCTTGGGGACGCAATCAAATCACTGTGGAAAAGATGCAGCAAATTG
GTGAGGTCTCCCGTAAACATGGATTTCAGCCACTACTGTTGAATCCTCAGTAAGCGGCCGCAAAA
AAAACGGGCCGGCGTATTATCGCCGGCCCGAGTAACACCGTGCGTGTTGACTATTTTACCTCTGG
CGGTGATAATGGTTGCAGGATCCTTTTGCTGGAGGAAAACCAT*ATGAAAGGACCAATAATAATGA*
*CTAGAGAAGAAAGAATGAAGATTGTTCATGAAATTAAGGAACGAATATTGGATAAATATGGGGAT*
*GATGTTAAGGCAATTGGTGTTTATGGCTCTCTTGGTCGTCAGACTGATGGGCCCTATTCGGATAT*
*TGAGATGATGTGTGTTCTGTCAACAGAGGGAGTAGAGTTCAGCTATGAATGGACAACCGGTGAGT*
*GGAAGGCGGAAGTGAATTTTTATAGCGAAGAGATTCTACTAGATTATGCATCTCGGGTGGAACCG*
*GATTGGCCGCTTACACATGGTCGATTTTTCTCTATTTTGCCGATTTATGATCCAGGTGGATACTT*
*TGAGAAAGTGTACCAAACTGCTAAATCGGTAGAAGCCCAAAAGTTCCACGATGCGATCTGTGCCC*
*TTATCGTAGAAGAGCTGTTTGAATATGCAGGCAAATGGCGTAATATTCGTGTGCAAGGACCGACA*
*ACATTTCTACCATCCTTGACTGTACAGGTGGCAATGGCAGGTGCCATGTTGATTGGTCTGCATCA*
*TCGCATCTGTTATACGACGAGCGCTTCGGTCTTAACTGAAGCAGTTAAGCAACCAGATCTTCCTC*
*CAGGTTATGTCCAACTGTGCCAGCTCGTAATGTCTGGTCAACTTTCCGACCCTGAGAAACTTCTG*
*GAATCGCTAGAGAATTTCTGGAATGGGGTTCAGGAGTGGGCGGAACGACACGGATATATAGTGGA*
*TGTGTCAAAACGCATACCATTTTG*ATGTCTAACCCCCTTCCTTGCCCACAGCTTCGTCGATGGCG
CGAAATTTCGGGTAAATATAATGACCCTCTTGATAACCCAAGAGGGCATTTTTTAGGCGCGCCCT
AAGCGTCCGTAGGCACAATTAAGGCTTCAAATTGTTGGCGAAGCTGCTCAGTCACTTCCTTGACG
GCTTGCCGTGCCCCTTGGCGATCGCGCCGGTACAGAGGCCAATAGCTCTCTAAATTGAGAGGGTC
GCCGACACTGAGGCGCACCTGCCGCAAACCCACCAAACGATTGAGATTCGAGCTTTTTCCCTCTA
GCCAATCAAATGTGCGCCAGAGAATCAGCGCGACATCTGCAAAGCGATGAATCGTGAATTTCTCA
CGGATATAGCTACCCGTAATTGAGGTAAATCGCTCCGCAAGACGCATATGACGCAATCGCACATT
GGCTTCCTCGGCCAACCAATCGGCTAGGCAGCGCTCTACGGCCGAAAGTTGTGCCAAATCACTGC
GAAACATCCGTTCCCAAGCAGCCTGTTCAATGCGTCGGCAGCGACTCACAAAATCGGCACTGGGC
TTCAGACCAAAGTAGGACTCTGCCACCACAAGGGCGCTGTTGAGGAGGCGCTGAATTCGCGCTGC
CAATTTAGCATTGGCAGAGTCAAAGGGGGGCAGTTCGGGAAAATCTTGACCATAGGAGGTGGCAT
AAAAAGCCTCCAGGCGATCCAAGAGGTGGATCGCTAAATTCAGCAGGCGGCGGTAGAGGTCGTCT
GGCTGGGTACTGTGAGAATCTGTAGGGCACCCAAGGCGGTTCTCCAGTTGTGCCATCAGCCTTGC
CATGCGCTCCCAAGAGGGCTGACTGAGGCTGTACTGAATGCCAATGGGAAGAATGACCACGGGGA
GCGATCGCCCCGCCTTGGCTAAATCTTCTAGACACCAAAATCCCAGTTGGGCCACCCCCGGCTCC
AAAGGTGCGACCAGTTCGTTGTGCTCATTCGTTGCTCCCTCCGGCGCTGCCGCTAGGGGAAATCG
TCCTCCGAGAAGTAGCTCCCGCGCTGAGCGCAGGGCTTGGCTATCGAGCTTACCGCGCATGATGG
AAATCCCCCCCAACCGTGAAAAGAGCCAACCAATCTGCGCCCCTGCCCAGAGGGGAATCCCGCGA
TCGTAGAGAAAATAGCCATTTGTCGGCGGACGCAAGGGAATGCCCAGCCGCCGTGCTGTTTGCGG
CAGTAAATGCCACATCAAATAGCCCATCACCAACGGATCATCCGTACAGGGATGGCGAAAGGCAA
TGAGGAGCCGGACCTGTCCCTGCTGAAACTGCTGGTAATAACGGGCAAGGGTCTCCACATTCACC
CCTTCAACCCGCTGTAGCCCAAGACCATAGCGAATGTAGAGGGGCAGGAGTCTTGCTACTGTCCA
CCAGACGGGGTAGCTAAACCGCTGGGGGAGAAAATGCAACGGCGGTTGGGCAGTTGTCACTACAC
TGGACATTAGGCAAGCTCCTCAGGGCAATGGCTAAACTGAGGCAGTGGCCAACTCCGCAATTAAC
TGCTCTAACATCGGTTGATCGGCCCAATAGACAGCATTACAAAACTGACAGGTGGCTTCTGCCTT
TGCCTCTGTGGCTAGGATATCTCTTAATTCTGCCTCCCCTAGGAGCTTGAGTGCCGCTAACATCC
GTTCATGGGAACAGCCACAGTGGAAGCGCACCATTTGCCGTTGGGGCAAGATTTGTAAATCCATA
TCCCCTAAGAGTTCCTGAAAGATATCTGGCAGTGTCCGCCCTGCCTGTAGCAGTGGTGTAAAGCC
CTTAAGATTGGCCACCCGTTGTTCAAGGGTCGCGATCAGGTGTTCATCATTGGCCGCTTTGGGTA
GCACCTGTAACATCAACCCACCGGCGGCAGTCACCCCGGACTCTTCGACAAAAACACCCAACATC
AGGGCGGAGGGGGTTTGCTCTGAGGTGGCGAGGTAGTAGGTGATGTCTTCTGCAATTTCGCCGGA
GACTAGCTCCACCGTGCTGGAATAGGGGTAGCCGTAGCCAAGATCGTGGATGACGTAGAGATATC
CCTGATGGCCCACCGCTGCCCCCACATCGAGTTTGCCCTTGGCATTGGGGGGCAGTTCAACACTG
GGGTACTGCACATAGCCGCGAACTGTGCCATCGGCACCAGCATCGGCAAAAATGGTTCCTAGGGG
ACCGTTGCCCTGAATGCGCACATTCACCCGTGCTTGGGGCTGTTTGAAACTGGAGGCAAGGATTA
AGCCTGCGGCCATGGTTCGTCCCAAGGCCGCTGTGGCCACGTAGGACAGTTGGTGACGTTTGCGG
GCTTCATCAGTGAGTTGAGTGGTAATCACACCTACGGCCCGGATGCCTTCGGCAGCGGCAGTTGC
TCGCAACAGAAAATCGGCCATGTTCAACCTACGAAATGTTTTGTTACATTTAGTGTGACATACTC
CCACCGCTGACCAGGGCACAATGGGGCAAAAAACCATCAATCCTGCCTTTGGTGACCGATCCAGT
ACAGCCAGCCAGGGCTTAAGACTGGGAAGACCCCTAGCACTGGGGCTAGAAAATTGGCGATGATA
GGCAAGCAATAGTCATTCAGCGTCCAGTCATTCCGCCTATGGCCATGCCCCTCACTGTCTTGCCT
GCCACAACTGTTTTGACAGAAGCGACTCAATTGCCCCAGGGCGGCTTGATTACGGAGATTCCGAC
GCTGGCGATCGCCCACCGTTTGGCCCAGCAGTTGCGCCGCCATTGGCCCCTAGAGACCCCCTTAA
CGCTGATTGATGCGCAATACCAGAGTATCCCCCTGACCCTTGGGGAATTGGCCGAGCTCACCGAT
GCCAACTGTCCTTTACAGCTCTATGTGCCGCCCCCCTTGCCAGAGGCCTTGACGCAATTTCAACG
CCTGATGGATGTGGTTCGAGAGCTGCGCCATCCGGAGCGTGGCTGTCCTTGGGATTTGCAGCAAA
CCCCAACCAGTCTCATTCCCTATGTCCTTGAGGAAGCCTATGAAGTGGTACATGCCCTGCAGGAG
GGAGATGCGGGGGCGATCGCCGAAGAATTGGGAGACCTGTTGCTTCAAGTTGTTCTCCAGAGCCA
ACTTGCCCAAGAAGCCGGCCAATTTACCCTTGCTCAAGTCATTCAAAGGATTACCGATAAACTCA
TCCGCCGCCATCCCCACGTCTTTGGTGAAGTGGCACTCACCACTGCTCAAGAGGTGCGCGACCAA
TGGGAGCAAATCAAAGCGGCTGAAAAAGGCACCGAACTCCCCCTGAGTCAAACGCTGCAACGTTA
CGCACGCACCCTCCCACCCCTGATGGCCGGCATGAAAATTGGTGAGCGAGCCAGTCGCGCTGGCC
TCGATTGGCCGACGATTAGTGGTGCATGGGAGAAATTTTACGAGGAACTGGCGGAGTTTCAGGAG

-continued

GCCCTTCTGCAAGGGAATGCTGAGCAACAGGCAGCGGAATTAGGAGACCTGCTCTTCAGTGTGAT
TAACCTTGCCCGCTGGTGCCAACTGGATCCTGTTAATGCCCTGCAACAAACCTACCAACGCTTTA
TTCAACGCTTGGCCTGTATTGAGGCAGTCATCGATCGCCCCCTTGAGACGTACACCCTAGAAGAA
CTAGAAGCCCTCTGGCAACAGGCCAAAGTACAGTTAGCCACCGACAGCGAGGCAACCCCTATGGA
GACTGAGGAAGAGGCCTAGTCCGCTGCGGCCCTTGCCACCTTCAGTTCATCGAGATTCCACAGGG
GGCCCCCCAGCGCCGTGGGCTTGGCGCCAATGACATGATTGCGAAAAGCTGTAAGGGAGAGGGGA
TTCACGAGGTAAATAAAGGGGAGATATTCCTGAGCTAGTCGTTGGGCTTCCGCATAAATTTGCTG
CCGTCGTTCCAGATTGAGCTCCTGGGCACCTTGGACATACAGGTCACTGATGCGCTGCTCCCAGT
CAGCGACGACTCGACCCGTAATGGGTGGTTGATTCGGTGACGGTTGCTGATTGAATGTATGCAAA
AGGCCATCCACACGCCAGATATTGGCACCGCTATTGGGTTCATTGCCCCCCCCAGTAAAGCCGAG
GATATGGGCTTCCCACTCTAGGGAATTGGAGAGACGATCCACGAGGGTACCAAAGGCCAAAAATT
GCAGATCCACCTGCATGCCGATCGCCCCTAGGTCCTGCTGAACTTGCGTCGggccggccaaaatg
aagtgaagttcctatactttctagagaataggaacttctatagtgagtcgaataagggcgacaca
aaatttattctaaatgcataataaatactgataacatcttatagtttgtattatattttgtatta
tcgttgacatgtataattttgatatcaaaaactgattttccctttattattttcgagatttattt
tcttaattctctttaacaaactagaaatattgtatatacaaaaaatcataaataatagatgaata
gtttaattataggtgttcatcaatcgaaaaagcaacgtatcttatttaaagtgcgttgcttttt
ctcatttataaggttaaataattctcatatatcaagcaaagtgacaggcgcccttaaatattctg
acaaatgctctttccctaaactccccccataaaaaaacccgccgaagcgggtttttacgttattt
gcggattaacgattactcgttatcagaaccgcccagggggcccgagcttaagactggccgtcgtt
ttacaacacagaaagagtttgtagaaacgcaaaaaggccatccgtcaggggccttctgcttagtt
tgatgcctggcagttccctactctcgccttccgcttcctcgctcactgactcgctgcgctcggtc
gttcggctgcggcgagcggtatcagctcactcaaaggcggtaatacggttatccacagaatcagg
ggataacgcaggaaagaacatgtgagcaaaaggccagcaaaaggccaggaaccgtaaaaaggccg
cgttgctggcgtttttccataggctccgcccccctgacgagcatcacaaaaatcgacgctcaagt
cagaggtggcgaaacccgacaggactataaagataccaggcgtttccccctggaagctccctcgt
gcgctctcctgttccgaccctgccgcttaccggatacctgtccgcctttctcccttcgggaagcg
tggcgctttctcatagctcacgctgtaggtatctcagttcggtgtaggtcgttcgctccaagctg
ggctgtgtgcacgaaccccccgttcagcccgaccgctgcgccttatccggtaactatcgtcttga
gtccaacccggtaagacacgacttatcgccactggcagcagccactggtaacaggattagcagag
cgaggtatgtaggcggtgctacagagttcttgaagtggtggcctaactacggctacactagaaga
acagtatttggtatctgcgctctgctgaagccagttaccttcggaaaaagagttggtagctcttg
atccggcaaacaaaccaccgctggtagcggtggtttttttgtttgcaagcagcagattacgcgca
gaaaaaaaggatctcaagaagatcctttgatcttttctacggggtctgacgctcagtggaacgac
gcgcgcgtaactcacgttaagggattttggtcatgagcttgcgccgtcccgtcaagtcagcgtaa
tgctctgcttttaccaatgcttaatcagtgaggcacctatctcagcgatctgtctatttcgttca
tccatagttgcctgactccccgtcgtgtagataactacgatacgggagggcttaccatctggccc
cagcgctgcgatgataccgcgagaaccacgctcaccggctccggatttatcagcaataaaccagc
cagccggaagggccgagcgcagaagtggtcctgcaactttatccgcctccatccagtctattaat
tgttgccgggaagctagagtaagtagttcgccagttaatagtttgcgcaacgttgttgccatcgc
tacaggcatcgtggtgtcacgctcgtcgtttggtatggcttcattcagctccggttcccaacgat
caaggcgagttacatgatcccccatgttgtgcaaaaaagcggttagctccttcggtcctccgatc
gttgtcagaagtaagttggccgcagtgttatcactcatggttatggcagcactgcataattctct
tactgtcatgccatccgtaagatgcttttctgtgactggtgagtactcaaccaagtcattctgag
aatagtgtatgcggcgaccgagttgctcttgcccggcgtcaatacgggataataccgcgccacat
agcagaactttaaaagtgctcatcattggaaaacgttcttcggggcgaaaactctcaaggatctt
accgctgttgagatccagttcgatgtaacccactcgtgcacccaactgatcttcagcatcttta
ctttcaccagcgtttctgggtgagcaaaaacaggaaggcaaaatgccgcaaaaaagggaataagg
gcgacacggaaatgttgaatactcatattcttcctttttcaatattattgaagcatttatcaggg
ttattgtctcatgagcggatacatatttgaatgtatttagaaaaataaacaaataggggtcagtg
ttacaaccaattaaccaattctgaacattatcgcgagcccatttatacctgaatatggctcataa
caccccttgtttgcctggcggcagtagcgcggtggtcccacctgaccccatgccgaactcagaag
tgaaacgccgtagcgccgatggtagtgtggggactccccatgcgagagtagggaactgccaggca
tcaaataaaacgaaaggctcagtcgaaagactgggcctttcgcccgggctaattatggggtgtcg
cccttattcgactctatagtgaagttcctattctctagaaagtataggaacttctgaagtggggc
ctgcagg SEQ ID NO: 19
cI promoter used for transcription in pJB886. Terminal NotI and
NdeI sites used for promoter exchanges are capitalized.

(SEQ ID NO: 19)

GCGGCCGCtcgagtaacaccgtgcgtgttgactattttacctctggcggtgataatggt
tgcaggatccttttgctggaggaaaacCATATG SEQ ID NO: 20
cpcB promoter used for transcription in pJB887.

(SEQ ID NO: 20)

GCGGCCGCttcgttataaaataaacttaacaaatctatacccacctgtagagaagagtc
cctgaatatcaaaatggtgggataaaaagctcaaaaaggaaagtaggctgtggttccct
aggcaacagtcttccctaccccactggaaactaaaaaaacgagaaaagttcgcaccgaa
catcaattgcataattttagccctaaaacataagctgaacgaaactggttgtcttccct
tcccaatccaggacaatctgagaatcccctgcaacattacttaacaaaaaagcaggaat
aaaattaacaagatgtaacagacataagtcccatcaccgttgtataaagttaactgtgg
gattgcaaaagcattcaagcctaggcgctgagctgtttgagcatcccggtggcccttgt
cgctgcctccgtgtttctccctggatttatttaggtaatatctctcataaatccccggg
tagttaacgaaagttaatggagatcagtaacaataactctagggtcattactttggact
ccctcagtttatccgggggaattgtgtttaagaaaatcccaactcataaagtcaagtag
gagattaatCATATG -continued SEQ ID NO: 21
lacI-trc promoter used for transcription in pJB889. Terminal NotI and NdeI sites used for promoter exchanges are capitalized.

(SEQ ID NO: 21)

GCGGCCGCgaaggcgaagcggcatgcatttacgttgacaccatcgaatggtgcaaaacc
tttcgcggtatggcatgatagcgcccggaagagagtcaattcagggtggtgaatatgaa
accagtaacgttatacgatgtcgcagagtatgccggtgtctcttatcagaccgtttccc
gcgtggtgaaccaggccagccacgtttctgcgaaaacgcgggaaaaagtggaagcggcg
atggcggagctgaattacattcccaaccgcgtggcacaacaactggcgggcaaacagtc
gttgctgattggcgttgccacctccagtctggccctgcacgcgccgtcgcaaattgtcg
cggcgattaaatctcgcgccgatcaactgggtgccagcgtggtggtgtcgatggtagaa
cgaagcggcgtcgaagcctgtaaagcggcggtgcacaatcttctcgcgcaacgcgtcag
tgggctgatcattaactatccgctggatgaccaggatgccattgctgtggaagctgcct
gcactaatgttccggcgttatttcttgatgtctctgaccagacacccatcaacagtatt
attttctcccatgaagacggtacgcgactgggcgtggagcatctggtcgcattgggtca
ccagcaaatcgcgctgttagcgggcccattaagttctgtctcggcgcgtctgcgtctgg
ctggctggcataaatatctcactcgcaatcaaattcagccgatagcggaacgggaaggc
gactggagtgccatgtccggttttcaacaaaccatgcaaatgctgaatgagggcatcgt
tcccactgcgatgctggttgccaacgatcagatggcgctgggcgcaatgcgcgccatta
ccgagtccgggctgcgcgttggtgcggatatctcggtagtgggatacgacgataccgaa
gacagctcatgttatatcccgccgtcaaccaccatcaaacaggattttcgcctgctggg
gcaaaccagcgtggaccgcttgctgcaactctctcagggccaggcggtgaagggcaatc
agctgttgcccgtctcactggtgaaaagaaaaaccaccctggcgcccaatacgcaaacc
gcctctccccgcgcgttggccgattcattaatgcagctggcacgacaggtttcccgact
ggaaagcgggcagtgagcgcaacgcaattaatgtgagttagcgcgaattgatctggttt
gacagcttatcatcgagctcgactgcacggtgcaccaatgcttctggcgtcaggcagcc
atcggaagctgtggtatggctgtgcaggtcgtaaatcactgcataattcgtgtcgctca
aggcgcactcccgttctggataatgttttttgcgccgacatcataacggttctggcaaa
tattctgaaatgagctgttgacaattaatcatccggctcgtataatgtgtggaattgtg
agcggataacaatttcacacaggaaacagCATATG SEQ ID NO: 22
EM7 promoter used for transcription in pJB888. Terminal NotI and NdeI sites used for promoter exchanges are capitalized.

(SEQ ID NO: 22)

GCGGCCGCtgttgacaattaatcatcggcatagtatatcggcatagtataatacgacaa
ggtgaggaactaaCATATG

SEQ ID NO: 23
DNA sequence of pJB1279.

| | |
|---|---|
| 1st underlined sequence | Upstream homology region for SYNPCC7002_A0358 |
| 1st italic sequence | P(nir07) promoter; this promoter is a synthetic construct based on the nirA promoter from *Synechococcus* sp. PCC 7942. (Shin-Ichi Maeda et al. (1998) *J. Bacteriol.*, 180: 4080-4088. |
| 2nd italic sequence | aadA coding sequence; spectinomycin selection marker |
| 2nd underlined sequence | Downstream homology region for SYNPCC7002_A0358 |
| Lower case sequence | *E. coli* vector backbone (pUC ori, kan) |

(SEQ ID NO: 23)

ACAACTCGGCTTCCGAGCTTGGCTCCACCATGGTTATATCTGGAGTAACCAGAATTTCG
ACAACTTCGACGACTATCTCGGTGCTTTTACCTCCAACCAACGCAAAAACATTAAGCGC
GAACGCAAAGCCGTTGACAAAGCAGGTTTATCCCTCAAGATGATGACCGGGGACGAAAT
TCCCGCCCATTACTTCCCACTCATTTATCGTTTCTATAGCAGCACCTGCGACAAATTTT
TTTGGGGGAGTAAATATCTCCGGAAACCCTTTTTTGAAACCCTAGAATCTACCTATCGC
CATCGCGTTGTTCTGGCCGCCGCTTACACGCCAGAAGATGACAAACATCCCGTCGGTTT
ATCTTTTTGTATCCGTAAAGATGATTATCTTTATGGTCGTTATTGGGGGGCCTTTGATG
AATATGACTGTCTCCATTTTGAAGCCTGCTATTACAAACCGATCCAATGGGCAATCGAG
CAGGGAATTACGATGTACGATCCGGGCGCTGGCGGAAAACATAAGCGACGACGTGGTTT
CCCGGCAACCCCAAACTATAGCCTCCACCGTTTTTATCAACCCCGCATGGGCCAAGTTT
TAGACGCTTATATTGATGAAATTAATGCCATGGAGCAACAGGAAATTGAAGCGATCAAT
GCGGATATTCCCTTTAAACGGCAGGAAGTTCAATTGAAAATTTCCTAGCTTCACTAGCC
AAAAGCGCGATCGCCCACCGACCATCCTCCCTTGGGGGAGATGCGGCC*GCTT*GTAGCAA
TTGCTACTAAAAACTGCGATCGC*TGCTGAAATGAGCTGGAATTTTGTCCCTCTCAGCTC*
*AAAAAGTATCAATGATTACTTAATGTTTGTTCTGCGCAAACTTCTTGCAGAACATGCAT*
*GATTTACAAAAAGTTGTAGTTTCTGTTACCAATTGCGAATCGAGAACTGCCTAATCTGC*
*CGAGTATGCGATCCTTTAGCAGGAGGAAAACCAT*ATGAGATCTGTAGTAGGATCCCTCG
AGAGTGAGAGCCGGCGAGCTCATAGTATGTACATGATGACTGTACCCATGGTTGAATTC
GGTTTTCCGTCCTGTCTTGATTTTCAAGCAAACAATGCCTCCGATTTCTAATCGGAGGC
ATTTGTTTTTGTTTATTGCAAAAACAAAAAATATTGTTACAAATTTTTACAGGCTATTA
AGCCTACCGTCATAAATAATTTGCCATTTACTAGTTTTTAATTAACCAGAACCTTGACC
GAACGCAGCGGTGGTAACGGCGCAGTGGCGGTTTTCATGGCTTGTTATGACTGTTTTTT
TGGGGTACAGTCTATGCCTCGGGCATCCAAGCAGCAAGCGCGTTACGCCGTGGGTCGAT
GTTTGATGTTATGGAGCAGCAACGATGTTACGCAGCAGGGCAGTCGCCCTAAAACAAAG
TTAAACATC*ATGAGGGAAGCGGTGATCGCCGAAGTATCGACTCAACTATCAGAGGTAGT*
*TGGCGTCATCGAGCGCCATCTCGAACCGACGTTGCTGGCCGTACATTTGTACGGCTCCG*
*CAGTGGATGGCGGCCTGAAGCCACACAGTGATATTGATTTGCTGGTTACGGTGACCGTA*

-continued

*AGGCTTGATGAAACAACGCGGCGAGCTTTGATCAACGACCTTTTGGAAACTTCGGCTTC*
*CCCTGGAGAGAGCGAGATTCTCCGCGCTGTAGAAGTCACCATTGTTGTGCACGACGACA*
*TCATTCCGTGGCGTTATCCAGCTAAGCGCGAACTGCAATTTGGAGAATGGCAGCGCAAT*
*GACATTCTTGCAGGTATCTTCGAGCCAGCCACGATCGACATTGATCTGGCTATCTTGCT*
*GACAAAAGCAAGAGAACATAGCGTTGCCTTGGTAGGTCCAGCGGCGGAGGAACTCTTTG*
*ATCCGGTTCCTGAACAGGATCTATTTGAGGCGCTAAATGAAACCTTAACGCTATGGAAC*
*TCGCCGCCCGACTGGGCTGGCGATGAGCGAAATGTAGTGCTTACGTTGTCCCGCATTTG*
*GTACAGCGCAGTAACCGGCAAAATCGCGCCGAAGGATGTCGCTGCCGACTGGGCAATGG*
*AGCGCCTGCCGGCCCAGTATCAGCCCGTCATACTTGAAGCTAGACAGGCTTATCTTGGA*
*CAAGAAGAAGATCGCTTGGCCTCGCGCGCAGATCAGTTGGAAGAATTTGTCCACTACGT*
*GAAAGGCGAGATCACCAAGGTAGTCGGCAAATAA*TGTCTAACAATTCGTTCAAGCCGAC
GCCGCTTCGCGGCGCGGCTTAACTCAAGCGTTAGATGCACTAAGCACATAATTGCTCAC
AGCCAAACTATCAGGTCAAGTCTGCTTTTATTATTTTTAAGCGTGCATAATAAGCCCTA
CACAAATTGGGAGATATATCATGAGGCGCGCCTGATCAGTTGGTGCTGCATTAGCTAAG
AAGGTCAGGAGATATTATTCGACATCTAGCTGACGGCCATTGCGATCATAAACGAGGAT
ATCCCACTGGCCATTTTCAGCGGCTTCAAAGGCAATTTTAGACCCATCAGCACTAATGG
TTGGATTACGCACTTCTTGGTTTAAGTTATCGGTTAAATTCCGCTTTTGTTCAAACTCG
CGATCATAGAGATAAATATCAGATTCGCCGCGACGATTGACCGCAAAGACAATGTAGCG
ACCATCTTCAGAAACGGCAGGATGGGAGGCAATTTCATTTAGGGTATTGAGGCCCGGTA
ACAGAATCGTTTGCCTGGTGCTGGTATCAAATAGATAGATATCCTGGGAACCATTGCGG
TCTGAGGCAAAAACGAGGTAGGGTTCGGCGATCGCCGGGTCAAATTCGAGGGCCCGACT
ATTTAAACTGCGGCCACCGGGATCAACGGGAAAATTGACAATGCGCGGATAACCAACGC
AGCTCTGGAGCAGCAAACCGAGGCTACCGAGGAAAAAACTGCGTAGAAAAGAAACATAG
CGCATAGGTCAAAGGGAAATCAAAGGGCGGGCGATCGCCAATTTTTCTATAATATTGTC
CTAACAGCACACTAAAACAGAGCCATGCTAGCAAAAATTTGGAGTGCCACCATTGTCGG
GGTCGATGCCCTCAGGGTCGGGGTGGAAGTGGATATTTCCGGCGGCTTACCGAAAATGA
TGGTGGTCGGACTGCggccggccaaaatgaagtgaagttcctatactttctagagaata
ggaacttctatagtgagtcgaataagggcgacacaaaatttattctaaatgcataataa
atactgataacatcttatagtttgtattatattttgtattatcgttgacatgtataatt
ttgatatcaaaaactgattttccctttattattttcgagatttattttcttaattctct
ttaacaaactagaaatattgtatatacaaaaaatcataaataatagatgaatagtttaa
ttataggtgttcatcaatcgaaaaagcaacgtatcttatttaaagtgcgttgcttttttt
ctcatttataaggttaaataattctcatatatcaagcaaagtgacaggcgcccttaaat
attctgacaaatgctctttccctaaactccccccataaaaaaacccgccgaagcgggtt
tttacgttatttgcggattaacgattactcgttatcagaaccgcccagggggcccgagc
ttaagactggccgtcgttttacaacacagaaagagtttgtagaaacgcaaaaaggccat
ccgtcaggggccttctgcttagtttgatgcctggcagttccctactctcgccttccgct
tcctcgctcactgactcgctgcgctcggtcgttcggctgcggcgagcggtatcagctca
ctcaaaggcggtaatacggttatccacagaatcaggggataacgcaggaaagaacatgt
gagcaaaaggccagcaaaaggccaggaaccgtaaaaaggccgcgttgctggcgtttttc
cataggctccgcccccctgacgagcatcacaaaaatcgacgctcaagtcagaggtggcg
aaacccgacaggactataaagataccaggcgtttccccctggaagctccctcgtgcgct
ctcctgttccgaccctgccgcttaccggatacctgtccgcctttctcccttcgggaagc
gtggcgctttctcatagctcacgctgtaggtatctcagttcggtgtaggtcgttcgctc
caagctgggctgtgtgcacgaaccccccgttcagcccgaccgctgcgccttatccggta
actatcgtcttgagtccaacccggtaagacacgacttatcgccactggcagcagccact
ggtaacaggattagcagagcgaggtatgtaggcggtgctacagagttcttgaagtggtg
ggctaactacggctacactagaagaacagtatttggtatctgcgctctgctgaagccag
ttaccttcggaaaaagagttggtagctcttgatccggcaaacaaaccaccgctggtagc
ggtggtttttttgtttgcaagcagcagattacgcgcagaaaaaaaggatctcaagaaga
tcctttgatcttttctacggggtctgacgctcagtggaacgacgcgcgcgtaactcacg
ttaagggattttggtcatgagcttgcgccgtcccgtcaagtcagcgtaatgctctgctt
ttagaaaaactcatcgagcatcaaatgaaactgcaatttattcatatcaggattatcaa
taccatatttttgaaaaagccgtttctgtaatgaaggagaaaactcaccgaggcagttc
cataggatggcaagatcctggtatcggtctgcgattccgactcgtccaacatcaataca
acctattaatttcccctcgtcaaaaataaggttatcaagtgagaaatcaccatgagtga
cgactgaatccggtgagaatggcaaaagtttatgcatttctttccagacttgttcaaca
ggccagccattacgctcgtcatcaaaatcactcgcatcaaccaaaccgttattcattcg
tgattgcgcctgagcgaggcgaaatacgcgatcgctgttaaaaggacaattacaaacag
gaatcgagtgcaaccggcgcaggaacactgccagcgcatcaacaatattttcacctgaa
tcaggatattcttctaatacctggaacgctgtttttccggggatcgcagtggtgagtaa
ccatgcatcatcaggagtacggataaaatgcttgatggtcggaagtggcataaattccg
tcagccagtttagtctgaccatctcatctgtaacatcattggcaacgctacctttgcca
tgtttcagaaacaactctggcgcatcgggcttcccatacaagcgatagattgtcgcacc
tgattgcccgacattatcgcgagcccatttatacccatataaatcagcatccatgttgg
aatttaatcgcggcctcgacgtttcccgttgaatatggctcatattcttcctttttcaa
tattattgaagcatttatcagggttattgtctcatgagcggatacatatttgaatgtat
ttagaaaaataaacaaataggggtcagtgttacaaccaattaaccaattctgaacatta
tcgcgagcccatttatacctgaatatggctcataacaccccttgtttgcctggcggcag
tagcgcggtggtcccacctgaccccatgccgaactcagaagtgaaacgccgtagcgccg
atggtagtgtggggactccccatgcgagagtagggaactgccaggcatcaaataaaacg
aaaggctcagtcgaaagactgggcctttcgcccgggctaattagggggtgtcgccctta
ttcgactctatagtgaagttcctattctctagaaagtataggaacttctgaagtggggc
ctgcagg SEQ ID NO: 24
P(nir07) promoter; this promoter is a synthetic construct based on the nirA promoter from *Synechococcus* sp. PCC 7942. (Shin-Ichi Maeda et al. (1998). cis-Acting Sequences Required for -continued NtcB-Dependent, Nitrite-Responsive Positive Regulation of the Nitrate Assimilation Operon in the Cyanobacterium *Synechococcus* sp. Strain PCC 7942. *J. Bacteriol.* 180: 4080-4088

(SEQ ID NO: 24)

GCTTGTAGCAATTGCTACTAAAAACTGCGATCGCTGCTGAAATGAGCTGGAATTTTGTC
CCTCTCAGCTCAAAAAGTATCAATGATTACTTAATGTTTGTTCTGCGCAAACTTCTTGC
AGAACATGCATGATTTACAAAAAGTTGTAGTTTCTGTTACCAATTGCGAATCGAGAACT
GCCTAATCTGCCGAGTATGCGATCCTTTAGCAGGAGGAAAACCAT

SEQ ID NO: 25

DNA sequence of synthetic operon encoding the *Cyanothece* sp. ATCC 51142 adm and aar genes

| | |
|---|---|
| $1^{st}$ underlined sequence | EcoRI site used to subclone operon into pJB286alk_p |
| Italic sequence | 3' UTR sequence containing ribosome-binding sequence |
| $1^{st}$ bold sequence | cce_0778 (adm) coding sequence |
| Lower case sequence | Intergenic sequence |
| $2^{nd}$ bold sequence | cce_1430 (aar) coding sequence |
| $2^{nd}$ underlined sequence | EcoRI site used to subclone operon into pJB286alk_p |

(SEQ ID NO: 25)

GAATTC*TATAAGTAGGAGGTAAAAAC*ATGCAAGAACTGGCCCTGAGAAGCGAGCTGGAC
TTCAATAGCGAAACCTATAAAGATGCGTATAGCCGTATTAACGCCATTGTGATCGAAGG
CGAGCAAGAAGCATACCAAAACTACCTGGACATGGCGCAACTGCTGCCGGAGGACGAGG
CTGAGCTGATTCGTTTGAGCAAGATGGAGAACCGTCACAAAAAGGGTTTTCAAGCGTGC
GGCAAGAACCTCAATGTGACTCCGGATATGGATTATGCACAGCAGTTCTTTGCGGAGCT
GCACGGCAATTTTCAGAAGGCTAAAGCCGAGGGTAAGATTGTTACCTGCCTGCTCATCC
AAAGCCTGATCATCGAGGCGTTTGCGATTGCAGCCTACAACATTTACATTCCAGTGGCT
GATCCGTTTGCACGTAAAATCACCGAGGGTGTCGTCAAGGATGAGTATACCCACCTGAA
TTTCGGCGAAGTTTGGTTGAAGGAACATTTTGAAGCAAGCAAGGCGGAGTTGGAGGACG
CCAACAAAGAGAACTTACCGCTGGTCTGGCAGATGTTGAACCAGGTCGAAAAGGATGCC
GAAGTGCTGGGTATGGAGAAAGAGGCTCTGGTGGAGGACTTTATGATTAGCTATGGTGA
GGCACTGAGCAACATCGGCTTTTCTACGAGAGAAATCATGAAGATGAGCGCGTACGGTC
TGCGTGCAGCATAActcgagtataagtaggagataaaaacATGTTCGGCTTGATTGGCC
ACCTGACTAGCCTGGAGCACGCGCACAGCGTGGCGGATGCGTTTGGCTACGGCCCGTAC
GCAACCCAGGGTTTAGACCTGTGGTGTAGCGCACCGCCACAGTTTGTTGAGCACTTTCA
TGTCACGAGCATTACGGGCCAAACGATTGAGGGTAAATACATTGAGAGCGCGTTTTTGC
CGGAGATGTTGATTAAACGTCGTATCAAAGCAGCGATCCGTAAGATTCTGAACGCGATG
GCATTTGCGCAGAAGAACAATTTGAACATTACCGCGCTGGGTGGCTTCAGCAGCATTAT
CTTTGAGGAGTTTAATCTGAAGGAGAATCGTCAGGTTCGCAATGTGAGCTTGGAGTTTG
ACCGCTTCACCACCGGTAACACCCATACTGCTTACATTATCTGCCGTCAAGTCGAACAG
GCGAGCGCGAAACTGGGTATCGACCTGTCCCAAGCGACCGTGGCGATTTGCGGTGCCAC
GGGTGATATTGGCAGCGCAGTTTGTCGCTGGCTGGATCGCAAAACCGACACCCAAGAGC
TGTTCCTGATTGCGCGCAATAAGGAACGCTTGCAACGTCTGCAAGATGAACTGGGTCGC
GGCAAGATCATGGGCCTGGAAGAGGCACTGCCGGAAGCAGACATTATTGTGTGGGTTGC
CTCCATGCCGAAGGGCGTGGAGATTAATGCGGAAACCCTGAAGAAGCCGTGTCTGATCA
TTGACGGTGGCTACCCGAAGAATCTGGACACGAAAATCAAGCATCCGGACGTGCACATT
TTGAAGGGTGGTATTGTAGAGCATTCGTTGGACATTGATTGGAAAATCATGGAAACCGT
GAACATGGACGTTCCGAGCCGTCAAATGTTTGCGTGCTTCGCAGAGGCGATCTTGCTGG
AGTTCGAGCAATGGCACACGAACTTCTCGTGGGGTCGCAATCAAATCACGGTGACGAAG
ATGGAACAGATTGGTGAGGCGAGCGTGAAGCATGGTCTGCAACCGCTGCTGTCCTGGTA
AGAATTC

SEQ ID NO: 26

*Cyanothece* sp. ATCC 51142 aar optimized nucleotide coding sequence (SEQ ID NO: 26)

ATGTTCGGCTTGATTGGCCACCTGACTAGCCTGGAGCACGCGCACAGCGTGGCGGATGC
GTTTGGCTACGGCCCGTACGCAACCCAGGGTTTAGACCTGTGGTGTAGCGCACCGCCAC
AGTTTGTTGAGCACTTTCATGTCACGAGCATTACGGGCCAAACGATTGAGGGTAAATAC
ATTGAGAGCGCGTTTTTGCCGGAGATGTTGATTAAACGTCGTATCAAAGCAGCGATCCG
TAAGATTCTGAACGCGATGGCATTTGCGCAGAAGAACAATTTGAACATTACCGCGCTGG
GTGGCTTCAGCAGCATTATCTTTGAGGAGTTTAATCTGAAGGAGAATCGTCAGGTTCGC
AATGTGAGCTTGGAGTTTGACCGCTTCACCACCGGTAACACCCATACTGCTTACATTAT
CTGCCGTCAAGTCGAACAGGCGAGCGCGAAACTGGGTATCGACCTGTCCCAAGCGACCG
TGGCGATTTGCGGTGCCACGGGTGATATTGGCAGCGCAGTTTGTCGCTGGCTGGATCGC
AAAACCGACACCCAAGAGCTGTTCCTGATTGCGCGCAATAAGGAACGCTTGCAACGTCT
GCAAGATGAACTGGGTCGCGGCAAGATCATGGGCCTGGAAGAGGCACTGCCGGAAGCAG
ACATTATTGTGTGGGTTGCCTCCATGCCGAAGGGCGTGGAGATTAATGCGGAAACCCTG
AAGAAGCCGTGTCTGATCATTGACGGTGGCTACCCGAAGAATCTGGACACGAAAATCAA
GCATCCGGACGTGCACATTTTGAAGGGTGGTATTGTAGAGCATTCGTTGGACATTGATT
GGAAAATCATGGAAACCGTGAACATGGACGTTCCGAGCCGTCAAATGTTTGGGTGCTTC
GCAGAGGCGATCTTGCTGGAGTTCGAGCAATGGCACACGAACTTCTCGTGGGGTCGCAA
TCAAATCACGGTGACGAAGATGGAACAGATTGGTGAGGCGAGCGTGAAGCATGGTCTGC
AACCGCTGCTGTCCTGGTAA

SEQ ID NO: 27

*Cyanothece* sp. ATCC 51142 AAR amino acid sequence (SEQ ID NO: 27)

MFGLIGHLTSLEHAHSVADAFGYGPYATQGLDLWCSAPPQFVEHFHVTSITGQTIEGKYIESAF
LPEMLIKRRIKAAIRKILNAMAFAQKNNLNITALGGFSSIIFEEFNLKENRQVRNVSLEFDRFT

-continued

TGNTHTAYIICRQVEQASAKLGIDLSQATVAICGATGDIGSAVCRWLDRKTDTQELFLIARNKE
RLQRLQDELGRGKIMGLEEALPEADIIVWVASMPKGVEINAETLKKPCLIIDGGYPKNLDTKIK
HPDVHILKGGIVEHSLDIDWKIMETVNMDVPSRQMFACFAEAILLEFEQWHTNFSWGRNQITVT
KMEQIGEASVKHGLQPLLSW

SEQ ID NO: 28
*Cyanothece* sp. ATCC 51142 adm optimized nucleotide coding sequence
(SEQ ID NO: 28)
ATGCAAGAACTGGCCCTGAGAAGCGAGCTGGACTTCAATAGCGAAACCTATAAAGATGC
GTATAGCCGTATTAACGCCATTGTGATCGAAGGCGAGCAAGAAGCATACCAAAACTACC
TGGACATGGCGCAACTGCTGCCGGAGGACGAGGCTGAGCTGATTCGTTTGAGCAAGATG
GAGAACCGTCACAAAAAGGGTTTCAAGCGTGCGGCAAGAACCTCAATGTGACTCCGGA
TATGGATTATGCACAGCAGTTCTTTGCGGAGCTGCACGGCAATTTTCAGAAGGCTAAAG
CCGAGGGTAAGATTGTTACCTGCCTGCTCATCCAAAGCCTGATCATCGAGGCGTTTGCG
ATTGCAGCCTACAACATTTACATTCCAGTGGCTGATCCGTTTGCACGTAAAATCACCGA
GGGTGTCGTCAAGGATGAGTATACCCACCTGAATTTCGGCGAAGTTTGGTTGAAGGAAC
ATTTTGAAGCAAGCAAGGCGGAGTTGGAGGACGCCAACAAAGAGAACTTACCGCTGGTC
TGGCAGATGTTGAACCAGGTCGAAAAGGATGCCGAAGTGCTGGGTATGGAGAAAGAGGC
TCTGGTGGAGGACTTTATGATTAGCTATGGTGAGGCACTGAGCAACATCGGCTTTTCTA
CGAGAGAAATCATGAAGATGAGCGCGTACGGTCTGCGTGCAGCATAA SEQ ID NO: 29
*Cyanothece* sp. ATCC 51142 ADM amino acid sequence
(SEQ ID NO: 29)
MQELALRSELDFNSETYKDAYSRINAIVIEGEQEAYQNYLDMAQLLPEDEAELIRLSKMENRHK
KGFQACGKNLNVTPDMDYAQQFFAELHGNFQKAKAEGKIVTCLLIQSLIIEAFAIAAYNIYIPV
ADPFARKITEGVVKDEYTHLNFGEVWLKEHFEASKAELEDANKENLPLVWQMLNQVEKDAEVLG
MEKEALVEDFMISYGEALSNIGFSTREIMKMSAYGLRAA SEQ ID NO: 30
cce_1430 *Cyanothece* sp. ATCC 51142 coding sequence (aar)
(SEQ ID NO: 30)
ATGTTTGGTTTAATTGGTCATCTTACAAGTTTAGAACACGCCCACTCCGTTGCTGATGCC
TTTGGCTATGGCCCATACGCCACTCAGGGACTTGATTTGTGGTGTTCTGCTCCACCCCAA
TTCGTCGAGCATTTTCATGTTACTAGCATCACAGGACAAACCATCGAAGGAAAGTATATA
GAATCCGCTTTCTTACCAGAAATGCTGATAAAGCGACGGATTAAAGCAGCAATTCGCAAA
ATACTGAATGCGATGGCCTTTGCTCAGAAAAATAACCTTAACATCACAGCATTAGGGGGC
TTTTCTTCGATTATTTTTGAAGAATTTAATCTCAAAGAGAATAGACAAGTTCGTAATGTC
TCTTTAGAGTTTGATCGCTTCACCACCGGAAACACCCATACTGCTTATATCATTTGTCGT
CAAGTTGAACAGGCATCCGCTAAACTAGGGATTGACTTATCCCAAGCAACGGTTGCTATT
TGCGGGGCAACCGGAGATATTGGCAGTGCAGTGTGTCGTTGGTTAGATAGAAAAACCGAT
ACCCAGGAACTATTCTTAATTGCTCGCAATAAAGAACGATTACAACGACTGCAAGATGAG
TTGGGACGGGGTAAAATTATGGGATTGGAGGAGGCTTTACCCGAAGCAGATATTATCGTT
TGGGTGGCGAGTATGCCCAAAGGAGTGGAAATTAATGCCGAAACTCTCAAAAAACCCTGT
TTAATTATCGATGGTGGTTATCCTAAGAATTTAGACACAAAAATTAAACATCCTGATGTC
CATATCCTGAAAGGGGGAATTGTAGAACATTCTCTAGATATTGACTGGAAGATTATGGAA
ACTGTCAATATGGATGTTCCTTCTCGTCAAATGTTTGCTTGTTTTGCCGAAGCCATTTTA
TTAGAGTTTGAACAATGGCACACTAATTTTTCTTGGGGACGCAATCAAATTACAGTGACT
AAAATGGAACAAATAGGAGAAGCTTCTGTCAAACATGGGTTACAACCGTTGTTGAGTTGG
TAA SEQ ID NO: 31
cce_0778 *Cyanthece* sp. ATCC 51142 coding sequence (adm)
(SEQ ID NO: 31)
ATGCAAGAGCTTGCTTTACGCTCAGAGCTTGATTTTAACAGCGAAACCTATAAAGATGCT
TACAGTCGCATCAATGCTATTGTCATTGAAGGGGAACAAGAAGCCTATCAAAATTATCTT
GATATGGCGCAACTTCTCCCAGAAGACGAGGCTGAGTTAATTCGTCTCTCCAAGATGGAA
AACCGTCACAAAAAAGGCTTTCAAGCCTGTGGCAAGAATTTGAATGTGACCCCAGATATG
GACTACGCTCAACAATTTTTTGCTGAACTTCATGGCAACTTCCAAAAGGCAAAAGCCGAA
GGCAAAATTGTCACTTGCTTATTAATTCAATCTTTGATCATCGAAGCCTTTGCGATCGCC
GCTTATAATATTTATATTCCTGTGGCAGATCCCTTTGCTCGTAAAATCACCGAAGGGGTA
GTTAAGGATGAATATACCCACCTCAATTTTGGGGAAGTCTGGTTAAAAGAGCATTTTGAA
GCCTCTAAAGCAGAATTAGAAGACGCAAATAAAGAAAATTTACCCCTTGTTTGGCAAATG
CTCAACCAAGTTGAAAAAGATGCCGAAGTGTTAGGGATGGAGAAAGAAGCCTTAGTGGAA
GATTTCATGATTAGTTATGGAGAAGCTTTAAGTAATATTGGTTTCTCTACCCGTGAGATC
ATGAAAATGTCTGCTTACGGGCTACGGGCTGCTTAA SEQ ID NO: 32
Wild-type *Candida boidinii* FDH (NAD+-specific enzyme;
Uniprot O13437)
(SEQ ID NO: 32)
MKIVLVLYDAGKHAADEEKLYGCTENKLGIANWLKDQGHELITTSDKEGETSELDKHIPDADII
ITTPFHPAYITKERLDKAKNLKLVVVAGVGSDHIDLDYINQTGKKISVLEVTGSNVVSVAEHVV
MTMLVLVRNFVPAHEQIINHDWEVAAIAKDAYDIEGKTIATIGAGRIGYRVLERLLPFNPKELL
YYDYQALPKEAEEKVGARRVENIEELVAQADIVTVNAPLHAGTKGLINKELLSKFKKGAWLVNT
ARGAICVAEDVAAALESGQLRGYGGDVWFPQPAPKDHPWRDMRNKYGAGNAMTPHYSGTTLDAQ
TRYAEGTKNILESFFTGKFDYRPQDIILLNGEYVTKAYGKHDKK -continued SEQ ID NO: 33
Engineered *Candida boidinii* FDH (D195S/Y196H/K356T, enhanced NADP+ utilization)

(SEQ ID NO: 33)

MKIVLVLYDAGKHAADEEKLYGCTENKLGIANWLKDQGHELITTSDKEGETSELDKHIPDADII
ITTPFHPAYITKERLDKAKNLKLVVVAGVGSDHIDLDYINQTGKKISVLEVTGSNV
VSVAEHVVMTMLVLVRNFVPAHEQIINHDWEVAAIAKDAYDIEGKTIATIGAGRIGYRVLERLL
PFNPKELLYYSHQALPKEAEEKVGARRVENIEELVAQADIVTVNAPLHAGTKGLINKELLSKFK
KGAWLVNTARGAICVAEDVAAALESGQLRGYGGDVWFPQPAPKDHPWRDMRNKYGAGNAMTPHY
SGTTLDAQTRYAEGTKNILESFFTGKFDYRPQDIILLNGEYVTTAYGKHDKK

SEQ ID NO: 34
DNA sequence of pJB1228

| | |
|---|---|
| $1^{st}$ underlined sequence | Upstream homology region for aquI (SYNPCC7002_A1194) |
| $1^{st}$ double-underlined lowercase sequence | NotI site for promoter swapping |
| $1^{st}$ italic sequence | rbcL promoter |
| $2^{nd}$ double-underlined lowercase sequence | NdeI site for cloning |
| $1^{st}$ bold sequence | Multiple Cloning Site (MCS) |
| $1^{st}$ bold and capitalized sequence in MCS | XhoI site used for cloning of fdh genes |
| $2^{nd}$ italic sequence | ermC coding sequence; erythromycin$^R$ selection marker |
| $2^{nd}$ underlined sequence | Downstream homology region for aquI (SYNPCC7002_A1190) |
| $2^{nd}$ lowercase sequence | Vector backbone |

GAAAGGCTCTTGAGGCTATCATGACAGAAGCATCGCAGCCTATAAAATACGCTGGAAAAGAATA
TAAATATGCTGTTTCGTATCATGTCCTAAATGCTGCTGATTTTGGTGTTCCGCAATTTAGAGAA
AGAGTATTCATCGTAGGTAATCGTTTGGGCAAAACATTCCAATTTCCTGAACCAACTCATGGGC
CTAGCAACCAAGCGAGACAGATAGATCTTTTTGGCAAGCAGCTAAAACCTTACAAAACTGTTCA
AGATGCAATTAGCACTCTCCCCCCTGCAACCCCTCCTTCAGCGATGGCACTAAGAGTTTCGCAG
ACCATAAAAGATAGGATAAAGAATCATGGATATTAAAAACGTTCATATCAAAAATCACGAACAA
ACAGCTCATGCACCTTCCACTCTAGAAAAAATTCGTAAAGTCAAACAAGGGGGTAAACTCTCAG
AACAGACAAAGACATTTGGTTCAACCTACCGCAGGTTAGATCCGAACCAGCCATCTCCTACAGT
GACCCGTAGTGGTTATCGAGATTTTATTCATCCTTTTGAAGATCGAATGCTCACAGTTCGTGAA
CTGGCTTGTTTGCAAACCTTTCCCCTTGATTGGGAGTTTACCGGAACTCGACTTGATTCTTATA
GTAGTAAACGTAAAGTGACGATGACTCAGTTTGGACAAGTGGGTAATGCAGTACCGCCGTTACT
TGCTGAAGCTGTTGCTAAAGCGGTTAGCGAACAGCTTCTGGATGTCgcggccgc*AGATTGATAA*
*CCCAAACCTATAGAATAATTAAGAATCTCCAAAGCAACAGTTATTGCATTGGGTATCAACTAAG*
*CTGATCCTAAGCATAAGACCTACGACAATATCACAGGCTTGCGGATGGTTGCATCATCTCGCTG*
*AGTTTTGCACTGCTCAATTTTGCCCCATTTGCGGGGAATCGTAGCGTTCACACTACCCATTGCA*
*AAGGTTGCCCGTAGAGATTGCTCTATTCGGCACAGTCACTGTTAAAGAGGAACAACG*catatgc
agtcgacataacccgggtaatgacagatctgcggatccattagCTCGAGgcgagctcagactgt
tgtacagcatgctagctacacagacgcgtccatggtaggtacctgttaacgttagaccggtcag
gatctgcagatgacaccgcggtgcagctgaaggccacgtgggccgtagggaattcactagtttt
taattaa*CGTGCTATAATTATACTAATTTTATAAGGAGGAAAAAATATGGGCATTTTTAGTATT*
*TTTGTAATCAGCACAGTTCATTATCAACCAAACAAAAAATAAGTGGTTATAATGAATCGTTAAT*
*AAGCAAAATTCATATAACCAAATTAAAGAGGGTTATAATGAACGAGAAAAATATAAAACACAGT*
*CAAAACTTTATTACTTCAAAACATAATATAGATAAAATAATGACAAATATAAGATTAAATGAAC*
*ATGATAATATCTTTGAAATCGGCTCAGGAAAAGGCCATTTTACCCTTGAATTAGTAAAGAGGTG*
*TAATTTCGTAACTGCCATTGAAATAGACCATAAATTATGCAAAACTACAGAAAATAAACTTGTT*
*GATCACGATAATTTCCAAGTTTTAAACAAGGATATATTGCAGTTTAAATTTCCTAAAAACCAAT*
*CCTATAAAATATATGGTAATATACCTTATAACATAAGTACGGATATAATACGCAAAATTGTTTT*
*TGATAGTATAGCTAATGAGATTTATTTAATCGTGGAATACGGGTTTGCTAAAAGATTATTAAAT*
*ACAAAACGCTCATTGGCATTACTTTTAATGGCAGAAGTTGATATTTCTATATTAAGTATGGTTC*
*CAAGAGAATATTTTCATCCTAAACCTAAAGTGAATAGCTCACTTATCAGATTAAGTAGAAAAAA*
*ATCAAGAATATCACACAAAGATAAACAAAAGTATAATTATTTCGTTATGAAATGGGTTAACAAA*
*GAATACAAGAAAATATTTACAAAAAATCAATTTAACAATTCCTTAAAACATGCAGGAATTGACG*
*ATTTAAACAATATTAGCTTTGAACAATTCTTATCTCTTTTCAATAGCTATAAATTATTTAATAA*
*GTAAGTTAAGGGATGCATAAACTGCATCCCTTAACTTGTTTTTCGTGTGCCTATTTTTTGT*GGC
GCGCCCTTTACAAAATCAAACCCGATCGCCTCTCTATTTTGATAAATCTATGTCTACTCCCTCT
GTTACCCCTGTAGAATCTAGCACCCTAATCAAAACCCCTGAACTGCTGGCTCCGGCGGGAAATT
GGGACTGTGCGATCACCGCCGTGGAGAATGGGGCTGATGCGATTTATTTTGGGCTGGATAAATT
TAATGCCCGGATGCGATCACAAAACTTTGTCGAGTCAGATTTGCCGGAGTTGATGGCATACTTA
CATCGGCGCGGCGTGAAGGGCTATGTGACGTTAAATACGCTGATTTTCACCTCGGAATTGGCGG
CAGTCGAACAATATTTGCGGTCGATTATTGCGGCGGGAGTCGATGCGGCGATCGTCCAGGATGT
GGGGCTGTGCCAATTAATTTGGCAATTGTCGCCCGATTTTCCGATCCATGGTTCGACGCAAATG
ACCGTCACCAGCGCCGCAGGGGTCGAGTTCGCGCAAAACTTGGGTTGTGATTTGGTGGTATTGG
CGCGGGAATGTTCGATCAAGGAAATCAATAAAATCCAGCAGGAATTGGGTCAACAAAAGATCTC
AATGCCGCTAGAAGTGTTTGTCCACGGGGCGTTGTGCGTCGCCTATTCTGGGCAATGTTTAACC
AGTGAATCCCTCGGCGGACGGTCGGCCAATCGCGGAGAATGCGCCCAAGCCTGCCGGATGCCCT
ACGAAATGATTGTCGATGGTAGGCCATTTGATCTGAGCGACAGACGTTACCggccggccaaaat
gaagtgaagttcctatacttaagcttaaaatgaagtgaagttcctatactttctagagaatagg
aacttctatagtgagtcgaataagggcgacacaaaatttattctaaatgcataataaatactga
taacatcttatagtttgtattatattttgtattatcgttgacatgtataattttgatatcaaaa
actgattttccctttattattttcgagatttattttcttaattctctttaacaaactagaaata
ttgtatatacaaaaaatcataaataatagatgaatagtttaattataggtgttcatcaatcgaa
aaagcaacgtatcttatttaaagtgcgttgctttttctcatttataaggttaaataattctca -continued tatatcaagcaaagtgacaggcgcccttaaatattctgacaaatgctctttccctaaactcccc
ccataaaaaaacccgccgaagcgggtttttacgttatttgcggattaacgattactcgttatca
gaaccgcccagggggcccgagcttaagactggccgtcgttttacaacacagaaagagtttgtag
aaacgcaaaaaggccatccgtcaggggccttctgcttagtttgatgcctggcagttccctactc
tcgccttccgcttcctcgctcactgactcgctgcgctcggtcgttcggctgcggcgagcggtat
cagctcactcaaaggcggtaatacggttatccacagaatcaggggataacgcaggaaagaacat
gtgagcaaaaggccagcaaaaggccaggaaccgtaaaaaggccgcgttgctggcgtttttccat
aggctccgcccccctgacgagcatcacaaaaatcgacgctcaagtcagaggtggcgaaacccga
caggactataaagataccaggcgtttccccctggaagctccctcgtgcgctctcctgttccgac
cctgccgcttaccggatacctgtccgcctttctcccttcgggaagcgtggcgctttctcatagc
tcacgctgtaggtatctcagttcggtgtaggtcgttcgctccaagctgggctgtgtgcacgaac
cccccgttcagcccgaccgctgcgccttatccggtaactatcgtcttgagtccaacccggtaag
acacgacttatcgccactggcagcagccactggtaacaggattagcagagcgaggtatgtaggc
ggtgctacagagttcttgaagtggtggcctaactacggctacactagaagaacagtatttggta
tctgcgctctgctgaagccagttaccttcggaaaaagagttggtagctcttgatccggcaaaca
aaccaccgctggtagcggtggtttttttgtttgcaagcagcagattacgcgcagaaaaaaagga
tctcaagaagatcctttgatcttttctacggggtctgacgctcagtggaacgacgcgcgcgtaa
ctcacgttaagggattttggtcatgagcttgcgccgtcccgtcaagtcagcgtaatgctctgct
tttagaaaaactcatcgagcatcaaatgaaactgcaatttattcatatcaggattatcaatacc
atatttttgaaaaagccgtttctgtaatgaaggagaaaactcaccgaggcagttccataggatg
gcaagatcctggtatcggtctgcgattccgactcgtccaacatcaatacaacctattaatttcc
cctcgtcaaaaataaggttatcaagtgagaaatcaccatgagtgacgactgaatccggtgagaa
tggcaaaagtttatgcatttctttccagacttgttcaacaggccagccattacgctcgtcatca
aaatcactcgcatcaaccaaaccgttattcattcgtgattgcgcctgagcgaggcgaaatacgc
gatcgctgttaaaaggacaattacaaacaggaatcgagtgcaaccggcgcaggaacactgccag
cgcatcaacaatattttcacctgaatcaggatattcttctaatacctggaacgctgtttttccg
gggatcgcagtggtgagtaaccatgcatcatcaggagtacggataaaatgcttgatggtcggaa
gtggcataaattccgtcagccagtttagtctgaccatctcatctgtaacatcattggcaacgct
acctttgccatgtttcagaaacaactctggcgcatcgggcttcccatacaagcgatagattgtc
gcacctgattgcccgacattatcgcgagcccatttatacccatataaatcagcatccatgttgg
aatttaatcgcggcctcgacgtttcccgttgaatatggctcatattcttcctttttcaatatta
ttgaagcatttatcagggttattgtctcatgagcggatacatatttgaatgtatttagaaaaat
aaacaaataggggtcagtgttacaaccaattaaccaattctgaacattatcgcgagcccattta
tacctgaatatggctcataacaccccttgtttgcctggcggcagtagcgcggtggtcccacctg
accccatgccgaactcagaagtgaaacgccgtagcgccgatggtagtgtggggactccccatgc
gagagtagggaactgccaggcatcaaataaaacgaaaggctcagtcgaaagactgggcctttcg
cccgggctaattagggggtgtcgcccttattcgactctatagtgaagttcctattctctagaaa
gtataggaacttctgaagtggggaagcttaagtataggaacttctgaagtggggcctgcagg SEQ ID NO: 35
DNA sequence of pJB1732

| | |
|---|---|
| 1st underlined sequence | Upstream homology region for aquI (SYNPCC7002_A1194) |
| 1st double-underlined lowercase sequence | NotI site for promoter swapping |
| 1st italic sequence | cbcB promoter |
| 2nd double-underlined lowercase sequence | NdeI site for cloning |
| 1st bold sequence | Multiple Cloning Site (MCS) |
| 1st bold and capitalized sequence in MCS | XhoI site used for cloning of fdh genes |
| 2nd italic sequence | ermC coding sequence; erythromycin$^R$ selection marker |
| 2nd underlined sequence | Downstream homology region for aquI (SYNPCC7002_A1190) |
| 2nd lowercase sequence | Vector backbone |

GAAAGGCTCTTGAGGCTATCATGACAGAAGCATCGCAGCCTATAAAATACGCTGGAAAAGAATA
TAAATATGCTGTTTCGTATCATGTCCTAAATGCTGCTGATTTTGGTGTTCCGCAATTTAGAGAA
AGAGTATTCATCGTAGGTAATCGTTTGGGCAAAACATTCCAATTTCCTGAACCAACTCATGGGC
CTAGCAACCAAGCGAGACAGATAGATCTTTTTGGCAAGCAGCTAAAACCTTACAAAACTGTTCA
AGATGCAATTAGCACTCTCCCCCCTGCAACCCCTCCTTCAGCGATGGCACTAAGAGTTTCGCAG
ACCATAAAAGATAGGATAAAGAATCATGGATATTAAAAACGTTCATATCAAAAATCACGAACAA
ACAGCTCATGCACCTTCCACTCTAGAAAAAATTCGTAAAGTCAAACAAGGGGGTAAACTCTCAG
AACAGACAAAGACATTTGGTTCAACCTACCGCAGGTTAGATCCGAACCAGCCATCTCCTACAGT
GACCCGTAGTGGTTATCGAGATTTTATTCATCCTTTTGAAGATCGAATGCTCACAGTTCGTGAA
CTGGCTTGTTTGCAAACCTTTCCCCTTGATTGGGAGTTTACCGGAACTCGACTTGATTCTTATA
GTAGTAAACGTAAAGTGACGATGACTCAGTTTGGACAAGTGGGTAATGCAGTACCGCCGTTACT
TGCTGAAGCTGTTGCTAAAGCGGTTAGCGAACAGCTTCTGGATGTCgcggccgc*GTCGACTTCG*
*TTATAAAATAAACTTAACAAATCTATACCCACCTGTAGAGAAGAGTCCCTGAATATCAAAATGG*
*TGGGATAAAAAGCTCAAAAAGGAAAGTAGGCTGTGGTTCCCTAGGCAACAGTCTTCCCTACCCC*
*ACTGGAAACTAAAAAAACGAGAAAAGTTCGCACCGAACATCAATTGCATAATTTTAGCCCTAAA*
*ACATAAGCTGAACGAAACTGGTTGTCTTCCCTTCCCAATCCAGGACAATCTGAGAATCCCCTGC*
*AACATTACTTAACAAAAAAGCAGGAATAAAATTAACAAGATGTAACAGACATAAGTCCCATCAC*
*CGTTGTATAAAGTTAACTGTGGGATTGCAAAAGCATTCAAGCCTAGGCGCTGAGCTGTTTGAGC*
*ATCCCGGTGGCCCTTGTCGCTGCCTCCGTGTTTCTCCCTGGATTTATTTAGGTAATATCTCTCA*
*TAAATCCCCGGGTAGTTAACGAAAGTTAATGGAGATCAGTAACAATAACTCTAGGGTCATTACT*
*TTGGACTCCCTCAGTTTATCCGGGGGAATTGTGTTTAAGAAAATCCCAACTCATAAAGTCAAGT*
*AGGAGATTAATcat* atgcagtcgacataacccgggtaatgacagatctgcggatccattagCTC

-continued

GAGgcgagctcagactgttgtacagcatgctagctacacagacgcgtccatggtaggtacctgt
taacgttagaccggtcaggatctgcagatgacaccgcggtgcagctgaaggccacgtgggccgt
agggaattcactagtttttaattaa*CGTGCTATAATTATACTAATTTTATAAGGAGGAAAAAAT*
*ATGGGCATTTTTAGTATTTTTGTAATCAGCACAGTTCATTATCAACCAAACAAAAAATAAGTGG*
*TTATAATGAATCGTTAATAAGCAAAATTCATATAACCAAATTAAAGAGGGTTATAATGAACGAG*
*AAAAATATAAAACACAGTCAAAACTTTATTACTTCAAAACATAATATAGATAAAATAATGACAA*
*ATATAAGATTAAATGAACATGATAATATCTTTGAAATCGGCTCAGGAAAAGGCCATTTTACCCT*
*TGAATTAGTAAAGAGGTGTAATTTCGTAACTGCCATTGAAATAGACCATAAATTATGCAAAACT*
*ACAGAAAATAAACTTGTTGATCACGATAATTTCCAAGTTTTAAACAAGGATATATTGCAGTTTA*
*AATTTCCTAAAAACCAATCCTATAAAATATATGGTAATATACCTTATAACATAAGTACGGATAT*
*AATACGCAAAATTGTTTTTGATAGTATAGCTAATGAGATTTATTTAATCGTGGAATACGGGTTT*
*GCTAAAAGATTATTAAATACAAAACGCTCATTGGCATTACTTTTAATGGCAGAAGTTGATATTT*
*CTATATTAAGTATGGTTCCAAGAGAATATTTTCATCCTAAACCTAAAGTGAATAGCTCACTTAT*
*CAGATTAAGTAGAAAAAAATCAAGAATATCACACAAAGATAAACAAAAGTATAATTATTTCGTT*
*ATGAAATGGGTTAACAAAGAATACAAGAAAATATTTACAAAAAATCAATTTAACAATTCCTTAA*
*AACATGCAGGAATTGACGATTTAAACAATATTAGCTTTGAACAATTCTTATCTCTTTTCAATAG*
*CTATAAATTATTTAATAAGTAAGTTAAGGGATGCATAAACTGCATCCCTTAACTTGTTTTTCGT*
*GTGCCTATTTTTTGT*GGCGCGCCCTTTACAAAATCAAACCCGATCGCCTCTCTATTTTGATAAA
TCTATGTCTACTCCCTCTGTTACCCCTGTAGAATCTAGCACCCTAATCAAAACCCCTGAACTGC
TGGCTCCGGCGGGAAATTGGGACTGTGCGATCACCGCCGTGGAGAATGGGGCTGATGCGATTTA
TTTTGGGCTGGATAAATTTAATGCCCGGATGCGATCACAAAACTTTGTCGAGTCAGATTTGCCG
GAGTTGATGGCATACTTACATCGGCGCGGCGTGAAGGGCTATGTGACGTTAAATACGCTGATTT
TCACCTCGGAATTGGCGGCAGTCGAACAATATTTGCGGTCGATTATTGCGGCGGGAGTCGATGC
GGCGATCGTCCAGGATGTGGGGCTGTGCCAATTAATTTGGCAATTGTCGCCCGATTTTCCGATC
CATGGTTCGACGCAAATGACCGTCACCAGCGCCGCAGGGGTCGAGTTCGCGCAAAACTTGGGTT
GTGATTTGGTGGTATTGGCGCGGGAATGTTCGATCAAGGAAATCAATAAAATCCAGCAGGAATT
GGGTCAACAAAAGATCTCAATGCCGCTAGAAGTGTTTGTCCACGGGGCGTTGTGCGTCGCCTAT
TCTGGGCAATGTTTAACCAGTGAATCCCTCGGCGGACGGTCGGCCAATCGCGGAGAATGCGCCC
AAGCCTGCCGGATGCCCTACGAAATGATTGTCGATGGTAGGCCATTTGATCTGAGCGACAGACG
TTACCggccggccaaaatgaagtgaagttcctatacttaagcttaaaatgaagtgaagttccta
tactttctagagaataggaacttctatagtgagtcgaataagggcgacacaaaatttattctaa
atgcataataaatactgataacatcttatagtttgtattatattttgtattatcgttgacatgt
ataattttgatatcaaaaactgattttccctttattattttcgagatttatttcttaattctc
tttaacaaactagaaatattgtatatacaaaaaatcataaataatagatgaatagtttaattat
aggtgttcatcaatcgaaaaagcaacgtatcttatttaaagtgcgttgcttttttctcatttat
aaggttaaataattctcatatatcaagcaaagtgacaggcgcccttaaatattctgacaaatgc
tctttccctaaactccccccataaaaaaacccgccgaagcgggtttttacgttatttgcggatt
aacgattactcgttatcagaaccgcccagggggcccgagcttaagactggccgtcgttttacaa
cacagaaagagtttgtagaaacgcaaaaaggccatccgtcaggggccttctgcttagtttgatg
cctggcagttccctactctcgccttccgcttcctcgctcactgactcgctgcgctcggtcgttc
ggctgcggcgagcggtatcagctcactcaaaggcggtaatacggttatccacagaatcagggga
taacgcaggaaagaacatgtgagcaaaaggccagcaaaaggccaggaaccgtaaaaaggccgcg
ttgctggcgtttttccataggctccgcccccctgacgagcatcacaaaaatcgacgctcaagtc
agaggtggcgaaacccgacaggactataaagataccaggcgtttccccctggaagctccctcgt
gcgctctcctgttccgaccctgccgcttaccggatacctgtccgcctttctcccttcgggaagc
gtggcgctttctcatagctcacgctgtaggtatctcagttcggtgtaggtcgttcgctccaagc
tgggctgtgtgcacgaaccccccgttcagcccgaccgctgcgccttatccggtaactatcgtct
tgagtccaacccggtaagacacgacttatcgccactggcagcagccactggtaacaggattagc
agagcgaggtatgtaggcggtgctacagagttcttgaagtggtggcctaactacggctacacta
gaagaacagtatttggtatctgcgctctgctgaagccagttaccttcggaaaaagagttggtag
ctcttgatccggcaaacaaaccaccgctggtagcggtggtttttttgtttgcaagcagcagatt
acgcgcagaaaaaaaggatctcaagaagatcctttgatcttttctacggggtctgacgctcagt
ggaacgacgcgcgcgtaactcacgttaagggattttggtcatgagcttgcgccgtcccgtcaag
tcagcgtaatgctctgcttttagaaaaactcatcgagcatcaaatgaaactgcaatttattcat
atcaggattatcaataccatatttttgaaaaagccgtttctgtaatgaaggagaaaactcaccg
aggcagttccataggatggcaagatcctggtatcggtctgcgattccgactcgtccaacatcaa
tacaacctattaatttcccctcgtcaaaaataaggttatcaagtgagaaatcaccatgagtgac
gactgaatccggtgagaatggcaaaagtttatgcatttctttccagacttgttcaacaggccag
ccattacgctcgtcatcaaaatcactcgcatcaaccaaaccgttattcattcgtgattgcgcct
gagcgaggcgaaatacgcgatcgctgttaaaaggacaattacaaacaggaatcgagtgcaaccg
gcgcaggaacactgccagcgcatcaacaatattttcacctgaatcaggatattcttctaatacc
tggaacgctgtttttccggggatcgcagtggtgagtaaccatgcatcatcaggagtacggataa
aatgcttgatggtcggaagtggcataaattccgtcagccagtttagtctgaccatctcatctgt
aacatcattggcaacgctacctttgccatgtttcagaaacaactctggcgcatcgggcttccca
tacaagcgatagattgtcgcacctgattgcccgacattatcgcgagcccatttatacccatata
aatcagcatccatgttggaatttaatcgcggcctcgacgtttcccgttgaatatggctcatatt
cttcctttttcaatattattgaagcatttatcagggttattgtctcatgagcggatacatattt
gaatgtatttagaaaaataaacaaataggggtcagtgttacaaccaattaaccaattctgaaca
ttatcgcgagcccatttatacctgaatatggctcataacaccccttgtttgcctggcggcagta
gcgcggtggtcccacctgaccccatgccgaactcagaagtgaaacgccgtagcgccgatggtag
tgtggggactccccatgcgagagtagggaactgccaggcatcaaataaaacgaaaggctcagtc
gaaagactgggcctttcgcccgggctaattagggggtgtcgcccttattcgactctatagtgaa
gttcctattctctagaaagtataggaacttctgaagtggggaagcttaagtataggaacttctg
aagtggggcctgcagg

SEQ ID NO: 36

*Candida boidinii* FDH (cbfdh) gene is underlined. Terminal NdeI and XhoI sites used for the cloning are capitalized.

CATATGaagatcgtgctggtcctgtacgacgcaggcaagcatgcggcggacgaagagaagctgt
atggctgtaccgaaaacaagctgggtatcgcgaattggctgaaggatcagggtcacgagctgat
tactacctctgacaaagagggtgaaacgagcgagctggacaaacacattcctgatgcggatatc -continued atcattaccaccccgttccacccggcctacatcacgaaggaacgtctggataaggctaaaaact
tgaagctggtcgtggtagctggtgttggcagcgaccacatcgacctggactacattaaccagac
cggcaaaaagatttccgttctggaagtcacgggtagcaatgttgtctcggtggccgagcacgtt
gtgatgaccatgctggtgctggttcgcaattttgttccggcgcacgaacagatcatcaatcacg
actgggaagtggcagcgattgcgaaggatgcgtacgacatcgaaggtaagaccattgcgaccat
tggtgcaggccgcatcggttaccgtgtgctggagcgtctgctgccatttaacccgaaagagctg
ctgtattatgactatcaggcgctgccgaaagaagcggaagagaaagttggcgctcgtcgcgtcg
agaacatcgaggaactggtcgcgcaagcagatattgttaccgtgaatgccccgctgcatgcggg
tacgaaaggtctgattaacaaagagttgctgagcaaattcaagaaaggcgcgtggttggtgaat
acggcccgtggtgccatttgcgtcgcagaggacgtcgctgccgcactggagagcggccagttgc
gtggttatggcggtgacgtttggttcccacaaccggcaccgaaagaccatccgtggcgcgatat
gcgtaacaaatacggtgcgggcaatgccatgacgccgcattacagcggtaccaccctggatgcg
caaactcgctatgcagaaggcaccaaaaacatcctggagagctttttcacgggtaagtttgatt
accgtccgcaagatatcattttgttgaacggtgagtatgtgaccaaggcttacggtaaacatga
taagaaataaCTCGAG SEQ ID NO: 37
*Burkholdia multivorans* FDH (bmfdh) gene is underlined. Terminal N-
deI
and XhoI sites used for the cloning are capitalized.
CATATGgcgaccgtcctctgcgtgctgtaccccgaccccgtcgacggctatccgccgcgctacg
tgcgcgacacgattcccgtcatcacgcactacgcggacggccagctcgcgccgacgccgtccgg
gccgcccggttttcggccgggcgaactcgtcggctcggtatcgggcgcgctcgggttgcgcgac
tatctggcggcgcacggtcatacgctgatcgtgacgagcgacaaggacggccccgactccgaat
tcgagcgccggctgccggaagcggacgtcgtgatttcgcagccgttctggcccgcgtatctgac
cgccgaggggatcgcgcgcgcgccgaagctgcggctcgcgctgactgcgggcatcggctccgat
cacgtcgatctcgcggcggccgcgcgcgcgggcatcaccgtcgcggaagtcaccggatcgaaca
gcgtcagcgtcgccgagcatgtcgtgatgacgacgcttgcgctcgtgcgcaactatctgccgtc
gcacgcgatcgcgcagcaaggcggctggaacatcgccgactgcgtatcgcgcagctacgacatc
gagggcatgcatttcggcacggtcggcgccggccgcatcgggctcgcggtgctgcggcggctga
agccgttcgggctggcgctgcactatacgcagcggcatcggctcgatccggcgatcgaacacga
actcgcgctgacctatcacgcggacgtcgcgtcgctcgcgagcgcggtcgacatcgtgaatctg
cagattccgctctatccgtcgaccgagcatctgttcgatgccgcaatgatcgcgcgcatgaagc
gcggcgcgtatctgatcaacaccgcgcgcgcgaaactcgtcgatcgcgacgcggtcgtgcgtgc
ggtcgcctcgggccatctggccggctacggcggcgacgtgtggtttcccgagcccgcaccggcc
gatcatccgtggcgcgcgatgccgttcaacgggatgacgccgcatatctcgggcacgtcgctgt
ccgcgcaggcgcgctacgcggccggtacgctcgaaattctgcagtgctggttcgagcgccggcc
gattcgcgaggcctacctgatcgtcgacggcggcacgctcgcgggcaccggcgagcagtcgtac
cggctcacgtgaCTCGAG SEQ ID NO: 38
DNA sequence of pJB1882

| | |
|---|---|
| 1st underlined capitalized sequence | Upstream homology region for aquI (SYNPCC7002_A1194) |
| 1st double-underlined lowercase sequence | NotI site for promoter swapping |
| 1st italic sequence | rbcL promoter |
| 2nd double-underlined lowercase sequence | NdeI site for cloning |
| 1st bold sequence | cbfdh gene (*Candida boidinii* formate dehydrogenase) |
| 3rd double-underlined lowercase sequence | XhoI site used for cloning |
| 2nd italic sequence | ermC coding sequence; erythromycin$^R$ selection marker |
| 2nd underlined capitalized sequence | Downstream homology region for aquI (SYNPCC7002_A1190) |
| 2nd lowercase sequence | Vector backbone |

GAAAGGCTCTTGAGGCTATCATGACAGAAGCATCGCAGCCTATAAAATACGCTGGAAAAGAATA
TAAATATGCTGTTTCGTATCATGTCCTAAATGCTGCTGATTTTGGTGTTCCGCAATTTAGAGAA
AGAGTATTCATCGTAGGTAATCGTTTGGGCAAAACATTCCAATTTCCTGAACCAACTCATGGGC
CTAGCAACCAAGCGAGACAGATAGATCTTTTTGGCAAGCAGCTAAAACCTTACAAAACTGTTCA
AGATGCAATTAGCACTCTCCCCCCTGCAACCCCTCCTTCAGCGATGGCACTAAGAGTTTCGCAG
ACCATAAAAGATAGGATAAAGAATCATGGATATTAAAAACGTTCATATCAAAAATCACGAACAA
ACAGCTCATGCACCTTCCACTCTAGAAAAAATTCGTAAAGTCAAACAAGGGGGTAAACTCTCAG
AACAGACAAAGACATTTGGTTCAACCTACCGCAGGTTAGATCCGAACCAGCCATCTCCTACAGT
GACCCGTAGTGGTTATCGAGATTTTATTCATCCTTTTGAAGATCGAATGCTCACAGTTCGTGAA
CTGGCTTGTTTGCAAACCTTTCCCCTTGATTGGGAGTTTACCGGAACTCGACTTGATTCTTATA
GTAGTAAACGTAAAGTGACGATGACTCAGTTTGGACAAGTGGGTAATGCAGTACCGCCGTTACT
TGCTGAAGCTGTTGCTAAAGCGGTTAGCGAACAGCTTCTGGATGTCgcggccgc*AGATTGATAA*
*CCCAAACCTATAGAATAATTAAGAATCTCCAAAGCAACAGTTATTGCATTGGGTATCAACTAAG*
*CTGATCCTAAGCATAAGACCTACGACAATATCACAGGCTTGCGGATGGTTGCATCATCTCGCTG*
*AGTTTTGCACTGCTCAATTTTGCCCCATTTGCGGGGAATCGTAGCGTTCACACTACCCATTGCA*
*AAGGTTGCCCGTAGAGATTGCTCTATTCGGCACAGTCACTGTTAAAGAGGAACAACG*catatga
agatcgtgctggtcctgtacgacgcaggcaagcatgcggcggacgaagagaagctgtatggctg
taccgaaaacaagctgggtatcgcgaattggctgaaggatcagggtcacgagctgattactacc
tctgacaaagagggtgaaacgagcgagctggacaaacacattcctgatgcggatatcatcatta
ccaccccgttccacccggcctacatcacgaaggaacgtctggataaggctaaaaacttgaagct
ggtcgtggtagctggtgttggcagcgaccacatcgacctggactacattaaccagaccggcaaa
aagatttccgttctggaagtcacgggtagcaatgttgtctcggtggccgagcacgttgtgatga
ccatgctggtgctggttcgcaattttgttccggcgcacgaacagatcatcaatcacgactggga

-continued agtggcagcgattgcgaaggatgcgtacgacatcgaaggtaagaccattgcgaccattggtgca
ggccgcatcggttaccgtgtgctggagcgtctgctgccatttaacccgaaagagctgctgtatt
atgactatcaggcgctgccgaaagaagcggaagagaaagttggcgctcgtcgcgtcgagaacat
cgaggaactggtcgcgcaagcagatattgttaccgtgaatgccccgctgcatgcgggtacgaaa
ggtctgattaacaaagagttgctgagcaaattcaagaaaggcgcgtggttggtgaatacggccc
gtggtgccatttgcgtcgcagaggacgtcgctgccgcactggagagcggccagttgcgtggtta
tggcggtgacgtttggttcccacaaccggcaccgaaagaccatccgtggcgcgatatgcgtaac
aaatacggtgcgggcaatgccatgacgccgcattacagcggtaccaccctggatgcgcaaactc
gctatgcagaaggcaccaaaaacatcctggagagcttttcacgggtaagtttgattaccgtcc
gcaagatatcatttgttgaacggtgagtatgtgaccaaggcttacggtaaacatgataagaaa
taactcgaggcgagctcagactgttgtacagcatgctagctacacagacgcgtccatggtaggt
acctgttaacgttagaccggtcaggatctgcagatgacaccgcggtgcagctgaaggccacgtg
ggccgtagggaattcactagtttttaattaaCGTGCTATAATTATACTAATTTTATAAGGAGGA
AAAAATATGGGCATTTTTAGTATTTTTGTAATCAGCACAGTTCATTATCAACCAAACAAAAAAT
AAGTGGTTATAATGAATCGTTAATAAGCAAAATTCATATAACCAAATTAAAGAGGGTTATAATG
AACGAGAAAAATATAAAACACAGTCAAAACTTTATTACTTCAAAACATAATATAGATAAAATAA
TGACAAATATAAGATTAAATGAACATGATAATATCTTTGAAATCGGCTCAGGAAAAGGCCATTT
TACCCTTGAATTAGTAAAGAGGTGTAATTTCGTAACTGCCATTGAAATAGACCATAAATTATGC
AAAACTACAGAAAATAAACTTGTTGATCACGATAATTTCCAAGTTTTAAACAAGGATATATTGC
AGTTTAAATTTCCTAAAAACCAATCCTATAAAATATATGGTAATATACCTTATAACATAAGTAC
GGATATAATACGCAAAATTGTTTTTGATAGTATAGCTAATGAGATTTATTTAATCGTGGAATAC
GGGTTTGCTAAAAGATTATTAAATACAAAACGCTCATTGGCATTACTTTTAATGGCAGAAGTTG
ATATTTCTATATTAAGTATGGTTCCAAGAGAATATTTTCATCCTAAACCTAAAGTGAATAGCTC
ACTTATCAGATTAAGTAGAAAAAAATCAAGAATATCACACAAAGATAAACAAAAGTATAATTAT
TTCGTTATGAAATGGGTTAACAAAGAATACAAGAAAATATTTACAAAAAATCAATTTAACAATT
CCTTAAAACATGCAGGAATTGACGATTTAAACAATATTAGCTTTGAACAATTCTTATCTCTTTT
CAATAGCTATAAATTATTTAATAAGTAAGTTAAGGGATGCATAAACTGCATCCCTTAACTTGTT
TTTCGTGTGCCTATTTTTTGTGGCGCGCCCTTTACAAAATCAAACCCGATCGCCTCTCTATTTT
GATAAATCTATGTCTACTCCCTCTGTTACCCCTGTAGAATCTAGCACCCTAATCAAAACCCCTG
AACTGCTGGCTCCGGCGGGAAATTGGGACTGTGCGATCACCGCCGTGGAGAATGGGGCTGATGC
GATTTATTTTGGGCTGGATAAATTTAATGCCCGGATGCGATCACAAAACTTTGTCGAGTCAGAT
TTGCCGGAGTTGATGGCATACTTACATCGGCGCGGCGTGAAGGGCTATGTGACGTTAAATACGC
TGATTTTCACCTCGGAATTGGCGGCAGTCGAACAATATTTGCGGTCGATTATTGCGGCGGGAGT
CGATGCGGCGATCGTCCAGGATGTGGGGCTGTGCCAATTAATTTGGCAATTGTCGCCCGATTTT
CCGATCCATGGTTCGACGCAAATGACCGTCACCAGCGCCGCAGGGGTCGAGTTCGCGCAAAACT
TGGGTTGTGATTTGGTGGTATTGGCGCGGGAATGTTCGATCAAGGAAATCAATAAAATCCAGCA
GGAATTGGGTCAACAAAAGATCTCAATGCCGCTAGAAGTGTTTGTCCACGGGGCGTTGTGCGTC
GCCTATTCTGGGCAATGTTTAACCAGTGAATCCCTCGGCGGACGGTCGGCCAATCGCGGAGAAT
GCGCCCAAGCCTGCCGGATGCCCTACGAAATGATTGTCGATGGTAGGCCATTTGATCTGAGCGA
CAGACGTTACCggccggccaaaatgaagtgaagttcctatacttaagcttaaaatgaagtgaag
ttcctatactttctagagaataggaacttctatagtgagtcgaataagggcgacacaaaattta
ttctaaatgcataataaatactgataacatcttatagtttgtattatattttgtattatcgttg
acatgtataattttgatatcaaaaactgattttccctttattattttcgagatttattttctta
attctctttaacaaactagaaatattgtatatacaaaaaatcataaataatagatgaatagttt
aattataggtgttcatcaatcgaaaaagcaacgtatcttatttaaagtgcgttgcttttttctc
atttataaggttaaataattctcatatatcaagcaaagtgacaggcgcccttaaatattctgac
aaatgctctttccctaaactccccccataaaaaaacccgccgaagcgggtttttacgttatttg
cggattaacgattactcgttatcagaaccgcccagggggcccgagcttaagactggccgtcgtt
ttacaacacagaaagagtttgtagaaacgcaaaaaggccatccgtcaggggccttctgcttagt
ttgatgcctggcagttccctactctcgccttccgcttcctcgctcactgactcgctgcgctcgg
tcgttcggctgcggcgagcggtatcagctcactcaaaggcggtaatacggttatccacagaatc
aggggataacgcaggaaagaacatgtgagcaaaaggccagcaaaaggccaggaaccgtaaaaag
gccgcgttgctggcgtttttccataggctccgcccccctgacgagcatcacaaaaatcgacgct
caagtcagaggtggcgaaacccgacaggactataaagataccaggcgtttccccctggaagctc
cctcgtgcgctctcctgttccgaccctgccgcttaccggatacctgtccgcctttctcccttcg
ggaagcgtggcgctttctcatagctcacgctgtaggtatctcagttcggtgtaggtcgttcgct
ccaagctgggctgtgtgcacgaaccccccgttcagcccgaccgctgcgccttatccggtaacta
tcgtcttgagtccaacccggtaagacacgacttatcgccactggcagcagccactggtaacagg
attagcagagcgaggtatgtaggcggtgctacagagttcttgaagtggtggcctaactacggct
acactagaagaacagtatttggtatctgcgctctgctgaagccagttaccttcggaaaaagagt
tggtagctcttgatccggcaaacaaaccaccgctggtagcggtggtttttttgtttgcaagcag
cagattacgcgcagaaaaaaaggatctcaagaagatcctttgatcttttctacggggtctgacg
ctcagtggaacgacgcgcgcgtaactcacgttaagggattttggtcatgagcttgcgccgtccc
gtcaagtcagcgtaatgctctgcttttagaaaaactcatcgagcatcaaatgaaactgcaattt
attcatatcaggattatcaataccatatttttgaaaaagccgtttctgtaatgaaggagaaaac
tcaccgaggcagttccataggatggcaagatcctggtatcggtctgcgattccgactcgtccaa
catcaatacaacctattaatttcccctcgtcaaaaataaggttatcaagtgagaaatcaccatg
agtgacgactgaatccggtgagaatggcaaaagtttatgcatttctttccagacttgttcaaca
ggccagccattacgctcgtcatcaaaatcactcgcatcaaccaaaccgttattcattcgtgatt
gcgcctgagcgaggcgaaatacgcgatcgctgttaaaaggacaattacaaacaggaatcgagtg
caaccggcgcaggaacactgccagcgcatcaacaatattttcacctgaatcaggatattcttct
aatacctggaacgctgtttttccggggatcgcagtggtgagtaaccatgcatcatcaggagtac
ggataaaatgcttgatggtcggaagtggcataaattccgtcagccagtttagtctgaccatctc
atctgtaacatcattggcaacgctacctttgccatgtttcagaaacaactctggcgcatcgggc
ttcccatacaagcgatagattgtcgcacctgattgcccgacattatcgcgagcccatttatacc
catataaatcagcatccatgttggaatttaatcgcggcctcgacgtttcccgttgaatatggct
catattcttcctttttcaatattattgaagcatttatcagggttattgtctcatgagcggatac
atatttgaatgtatttagaaaaataaacaaataggggtcagtgttacaaccaattaaccaattc
tgaacattatcgcgagcccatttatacctgaatatggctcataacaccccttgtttgcctggcg
gcagtagcgcggtggtcccacctgaccccatgccgaactcagaagtgaaacgccgtagcgccga
tggtagtgtggggactccccatgcgagagtagggaactgccaggcatcaaataaaacgaaaggc -continued tcagtcgaaagactgggcctttcgcccgggctaattagggggtgtcgcccttattcgactctat
agtgaagttcctattctctagaaagtataggaacttctgaagtggggaagcttaagtataggaa
cttctgaagtggggcctgcagg SEQ ID NO: 39
DNA sequence of pJB1883

| | |
|---|---|
| 1st underlined capitalized sequence | Upstream homology region for aquI (SYNPCC7002_A1194) |
| 1st double-underlined lowercase sequence | NotI site for promoter swapping |
| 1st italic sequence | cbcB promoter |
| 2nd double-underlined lowercase sequence | NdeI site for cloning |
| 1st bold sequence | cbfdh gene (*Candida boidinii* formate dehydrogenase) |
| 3rd double-underlined lowercase sequence | XhoI site used for cloning |
| 2nd italic sequence | ermC coding sequence; erythromycin$^R$ selection marker |
| 2nd underlined capitalized sequence | Downstream homology region for aquI (SYNPCC7002_A1190) |
| 2nd lowercase sequence | Vector backbone |

GAAAGGCTCTTGAGGCTATCATGACAGAAGCATCGCAGCCTATAAAATACGCTGGAAAAGAATA
TAAATATGCTGTTTCGTATCATGTCCTAAATGCTGCTGATTTTGGTGTTCCGCAATTTAGAGAA
AGAGTATTCATCGTAGGTAATCGTTTGGGCAAAACATTCCAATTTCCTGAACCAACTCATGGGC
CTAGCAACCAAGCGAGACAGATAGATCTTTTTGGCAAGCAGCTAAAACCTTACAAAACTGTTCA
AGATGCAATTAGCACTCTCCCCCCTGCAACCCCTCCTTCAGCGATGGCACTAAGAGTTTCGCAG
ACCATAAAAGATAGGATAAAGAATCATGGATATTAAAAACGTTCATATCAAAAATCACGAACAA
ACAGCTCATGCACCTTCCACTCTAGAAAAAATTCGTAAAGTCAAACAAGGGGGTAAACTCTCAG
AACAGACAAAGACATTTGGTTCAACCTACCGCAGGTTAGATCCGAACCAGCCATCTCCTACAGT
GACCCGTAGTGGTTATCGAGATTTTATTCATCCTTTTGAAGATCGAATGCTCACAGTTCGTGAA
CTGGCTTGTTTGCAAACCTTTCCCCTTGATTGGGAGTTTACCGGAACTCGACTTGATTCTTATA
GTAGTAAACGTAAAGTGACGATGACTCAGTTTGGACAAGTGGGTAATGCAGTACCGCCGTTACT
TGCTGAAGCTGTTGCTAAAGCGGTTAGCGAACAGCTTCTGGATGTCgcggccgc*GTCGACTTCG*
*TTATAAAATAAACTTAACAAATCTATACCCACCTGTAGAGAAGAGTCCCTGAATATCAAAATGG*
*TGGGATAAAAAGCTCAAAAAGGAAAGTAGGCTGTGGTTCCCTAGGCAACAGTCTTCCCTACCCC*
*ACTGGAAACTAAAAAAACGAGAAAAGTTCGCACCGAACATCAATTGCATAATTTTAGCCCTAAA*
*ACATAAGCTGAACGAAACTGGTTGTCTTCCCTTCCCAATCCAGGACAATCTGAGAATCCCCTGC*
*AACATTACTTAACAAAAAAGCAGGAATAAAATTAACAAGATGTAACAGACATAAGTCCCATCAC*
*CGTTGTATAAAGTTAACTGTGGGATTGCAAAAGCATTCAAGCCTAGGCGCTGAGCTGTTTGAGC*
*ATCCCGGTGGCCCTTGTCGCTGCCTCCGTGTTTCTCCCTGGATTTATTTAGGTAATATCTCTCA*
*TAAATCCCCGGGTAGTTAACGAAAGTTAATGGAGATCAGTAACAATAACTCTAGGGTCATTACT*
*TTGGACTCCCTCAGTTTATCCGGGGGAATTGTGTTTAAGAAAATCCCAACTCATAAAGTCAAGT*
*AGGAGATTAATcat*atgaagatcgtgctggtcctgtacgacgcaggcaagcatgcggcggacga
agagaagctgtatggctgtaccgaaaacaagctgggtatcgcgaattggctgaaggatcagggt
cacgagctgattactacctctgacaaagagggtgaaacgagcgagctggacaaacacattcctg
atgcggatatcatcattaccaccccgttccacccggcctacatcacgaaggaacgtctggataa
ggctaaaaacttgaagctggtcgtggtagctggtgttggcagcgaccacatcgacctggactac
attaaccagaccggcaaaaagatttccgttctggaagtcacgggtagcaatgttgtctcggtgg
ccgagcacgttgtgatgaccatgctggtgctggttcgcaattttgttccggcgcacgaacagat
catcaatcacgactgggaagtggcagcgattgcgaaggatgcgtacgacatcgaaggtaagacc
attgcgaccattggtgcaggccgcatcggttaccgtgtgctggagcgtctgctgccatttaacc
cgaaagagctgctgtattatgactatcaggcgctgccgaaagaagcggaagagaaagttggcgc
tcgtcgcgtcgagaacatcgaggaactggtcgcgcaagcagatattgttaccgtgaatgccccg
ctgcatgcgggtacgaaaggtctgattaacaaagagttgctgagcaaattcaagaaaggcgcgt
ggttggtgaatacggcccgtggtgccatttgcgtcgcagaggacgtcgctgccgcactggagag
cggccagttgcgtggttatggcggtgacgtttggttcccacaaccggcaccgaaagaccatccg
tggcgcgatatgcgtaacaaatacggtgcgggcaatgccatgacgccgcattacagcggtacca
ccctggatgcgcaaactcgctatgcagaaggcaccaaaaacatcctggagagctttttcacggg
taagtttgattaccgtccgcaagatatcattttgttgaacggtgagtatgtgaccaaggcttac
ggtaaacatgataagaaataactcgaggcgagctcagactgttgtacagcatgctagctacaca
gacgcgtccatggtaggtacctgttaacgttagaccggtcaggatctgcagatgacaccgcggt
gcagctgaaggccacgtgggccgtagggaattcactagtttttaattaa*CGTGCTATAATTATA*
*CTAATTTTATAAGGAGGAAAAAATATGGGCATTTTTAGTATTTTTGTAATCAGCACAGTTCATT*
*ATCAACCAAACAAAAAATAAGTGGTTATAATGAATCGTTAATAAGCAAAATTCATATAACCAAA*
*TTAAAGAGGGTTATAATGAACGAGAAAAATATAAAACACAGTCAAAACTTTATTACTTCAAAAC*
*ATAATATAGATAAAATAATGACAAATATAAGATTAAATGAACATGATAATATCTTTGAAATCGG*
*CTCAGGAAAAGGCCATTTTACCCTTGAATTAGTAAAGAGGTGTAATTTCGTAACTGCCATTGAA*
*ATAGACCATAAATTATGCAAAACTACAGAAAATAAACTTGTTGATCACGATAATTTCCAAGTTT*
*TAAACAAGGATATATTGCAGTTTAAATTTCCTAAAAACCAATCCTATAAAATATATGGTAATAT*
*ACCTTATAACATAAGTACGGATATAATACGCAAAATTGTTTTTGATAGTATAGCTAATGAGATT*
*TATTTAATCGTGGAATACGGGTTTGCTAAAAGATTATTAAATACAAAACGCTCATTGGCATTAC*
*TTTTAATGGCAGAAGTTGATATTTCTATATTAAGTATGGTTCCAAGAGAATATTTTCATCCTAA*
*ACCTAAAGTGAATAGCTCACTTATCAGATTAAGTAGAAAAAAATCAAGAATATCACACAAAGAT*
*AAACAAAAGTATAATTATTTCGTTATGAAATGGGTTAACAAAGAATACAAGAAAATATTTACAA*
*AAAATCAATTTAACAATTCCTTAAAACATGCAGGAATTGACGATTTAAACAATATTAGCTTTGA*
*ACAATTCTTATCTCTTTTCAATAGCTATAAATTATTTAATAAGTAAGTTAAGGGATGCATAAAC*
*TGCATCCCTTAACTTGTTTTTCGTGTGCCTATTTTTTGT*GGCGCGCCCTTTACAAAATCAAACC
CGATCGCCTCTCTATTTTGATAAATCTATGTCTACTCCCTCTGTTACCCCTGTAGAATCTAGCA
CCCTAATCAAAACCCCTGAACTGCTGGCTCCGGCGGGAAATTGGGACTGTGCGATCACCGCCGT
GGAGAATGGGGCTGATGCGATTTATTTTGGGCTGGATAAATTTAATGCCCGGATGCGATCACAA -continued AACTTTGTCGAGTCAGATTTGCCGGAGTTGATGGCATACTTACATCGGCGCGGCGTGAAGGGCT
ATGTGACGTTAAATACGCTGATTTTCACCTCGGAATTGGCGGCAGTCGAACAATATTTGCGGTC
GATTATTGCGGCGGGAGTCGATGCGGCGATCGTCCAGGATGTGGGGCTGTGCCAATTAATTTGG
CAATTGTCGCCCGATTTTCCGATCCATGGTTCGACGCAAATGACCGTCACCAGCGCCGCAGGGG
TCGAGTTCGCGCAAAACTTGGGTTGTGATTTGGTGGTATTGGCGCGGGAATGTTCGATCAAGGA
AATCAATAAAATCCAGCAGGAATTGGGTCAACAAAAGATCTCAATGCCGCTAGAAGTGTTTGTC
CACGGGGCGTTGTGCGTCGCCTATTCTGGGCAATGTTTAACCAGTGAATCCCTCGGCGGACGGT
CGGCCAATCGCGGAGAATGCGCCCAAGCCTGCCGGATGCCCTACGAAATGATTGTCGATGGTAG
GCCATTTGATCTGAGCGACAGACGTTACCggccggccaaaatgaagtgaagttcctatacttaa
gcttaaaatgaagtgaagttcctatactttctagagaataggaacttctatagtgagtcgaata
agggcgacacaaaatttattctaaatgcataataaatactgataacatcttatagtttgtatta
tattttgtattatcgttgacatgtataattttgatatcaaaaactgattttccctttattattt
tcgagatttattttcttaattctctttaacaaactagaaatattgtatatacaaaaaatcataa
ataatagatgaatagtttaattataggtgttcatcaatcgaaaaagcaacgtatcttatttaaa
gtgcgttgctttttctcatttataaggttaaataattctcatatatcaagcaaagtgacaggc
gcccttaaatattctgacaaatgctctttccctaaactccccccataaaaaaacccgccgaagc
gggtttttacgttatttgcggattaacgattactcgttatcagaaccgcccagggggcccgagc
ttaagactggccgtcgttttacaacacagaaagagtttgtagaaacgcaaaaaggccatccgtc
aggggccttctgcttagtttgatgcctggcagttccctactctcgccttccgcttcctcgctca
ctgactcgctgcgctcggtcgttcggctgcggcgagcggtatcagctcactcaaaggcggtaat
acggttatccacagaatcaggggataacgcaggaaagaacatgtgagcaaaaggccagcaaaag
gccaggaaccgtaaaaaggccgcgttgctggcgtttttccataggctccgcccccctgacgagc
atcacaaaaatcgacgctcaagtcagaggtggcgaaacccgacaggactataaagataccaggc
gtttccccctggaagctccctcgtgcgctctcctgttccgaccctgccgcttaccggatacctg
tccgcctttctcccttcgggaagcgtggcgctttctcatagctcacgctgtaggtatctcagtt
cggtgtaggtcgttcgctccaagctgggctgtgtgcacgaaccccccgttcagcccgaccgctg
cgccttatccggtaactatcgtcttgagtccaacccggtaagacacgacttatcgccactggca
gcagccactggtaacaggattagcagagcgaggtatgtaggcggtgctacagagttcttgaagt
ggtgggctaactacggctacactagaagaacagtatttggtatctgcgctctgctgaagccagt
taccttcggaaaaagagttggtagctcttgatccggcaaacaaaccaccgctggtagcggtggt
ttttttgtttgcaagcagcagattacgcgcagaaaaaaaggatctcaagaagatcctttgatct
tttctacggggtctgacgctcagtggaacgacgcgcgcgtaactcacgttaagggattttggtc
atgagcttgcgccgtcccgtcaagtcagcgtaatgctctgcttttagaaaaactcatcgagcat
caaatgaaactgcaatttattcatatcaggattatcaataccatatttttgaaaaagccgtttc
tgtaatgaaggagaaaactcaccgaggcagttccataggatggcaagatcctggtatcggtctg
cgattccgactcgtccaacatcaatacaacctattaatttcccctcgtcaaaaataaggttatc
aagtgagaaatcaccatgagtgacgactgaatccggtgagaatggcaaaagtttatgcatttct
ttccagacttgttcaacaggccagccattacgctcgtcatcaaaatcactcgcatcaaccaaac
cgttattcattcgtgattgcgcctgagcgaggcgaaatacgcgatcgctgttaaaaggacaatt
acaaacaggaatcgagtgcaaccggcgcaggaacactgccagcgcatcaacaatattttcacct
gaatcaggatattcttctaatacctggaacgctgtttttccggggatcgcagtggtgagtaacc
atgcatcatcaggagtacggataaaatgcttgatggtcggaagtggcataaattccgtcagcca
gtttagtctgaccatctcatctgtaacatcattggcaacgctacctttgccatgtttcagaaac
aactctggcgcatcgggcttcccatacaagcgatagattgtcgcacctgattgcccgacattat
cgcgagcccatttatacccatataaatcagcatccatgttggaatttaatcgcggcctcgacgt
ttcccgttgaatatggctcatattcttcctttttcaatattattgaagcatttatcagggttat
tgtctcatgagcggatacatatttgaatgtatttagaaaaataaacaaataggggtcagtgtta
caaccaattaaccaattctgaacattatcgcgagcccatttatacctgaatatggctcataaca
ccccttgtttgcctggcggcagtagcgcggtggtcccacctgaccccatgccgaactcagaagt
gaaacgccgtagcgccgatggtagtgtggggactccccatgcgagagtagggaactgccaggca
tcaaataaaacgaaaggctcagtcgaaagactgggcctttcgcccgggctaattagggggtgtc
gcccttattcgactctatagtgaagttcctattctctagaaagtataggaacttctgaagtggg
gaagcttaagtataggaacttctgaagtggggcctgcagg SEQ ID NO: 40
DNA sequence of pJB1914

| | |
|---|---|
| $1^{st}$ underlined capitalized sequence | Upstream homology region for aquI (SYNPCC7002_A1194) |
| $1^{st}$ double-underlined lowercase sequence | NotI site for promoter swapping |
| $1^{st}$ italic sequence | rbcL promoter |
| $2^{nd}$ double-underlined lowercase sequence | NdeI site for cloning |
| $1^{st}$ bold sequence | bmfdh gene (*Burkholderia multivorans* formate dehydrogenase) |
| $3^{rd}$ double-underlined lowercase sequence | XhoI site used for cloning |
| $2^{nd}$ italic sequence | ermC coding sequence; erythromycin$^R$ selection marker |
| $2^{nd}$ underlined capitalized sequence | Downstream homology region for aquI (SYNPCC7002_A1190) |
| $2^{nd}$ lowercase sequence | Vector backbone |

GAAAGGCTCTTGAGGCTATCATGACAGAAGCATCGCAGCCTATAAAATACGCTGGAAAAGAATA
TAAATATGCTGTTTCGTATCATGTCCTAAATGCTGCTGATTTTGGTGTTCCGCAATTTAGAGAA
AGAGTATTCATCGTAGGTAATCGTTTGGGCAAAACATTCCAATTTCCTGAACCAACTCATGGGC
CTAGCAACCAAGCGAGACAGATAGATCTTTTTGGCAAGCAGCTAAAACCTTACAAAACTGTTCA
AGATGCAATTAGCACTCTCCCCCCTGCAACCCCTCCTTCAGCGATGGCACTAAGAGTTTCGCAG
ACCATAAAAGATAGGATAAAGAATCATGGATATTAAAAACGTTCATATCAAAAATCACGAACAA
ACAGCTCATGCACCTTCCACTCTAGAAAAAATTCGTAAAGTCAAACAAGGGGGTAAACTCTCAG

-continued

AACAGACAAAGACATTTGGTTCAACCTACCGCAGGTTAGATCCGAACCAGCCATCTCCTACAGT
GACCCGTAGTGGTTATCGAGATTTTATTCATCCTTTTGAAGATCGAATGCTCACAGTTCGTGAA
CTGGCTTGTTTGCAAACCTTTCCCCTTGATTGGGAGTTTACCGGAACTCGACTTGATTCTTATA
GTAGTAAACGTAAAGTGACGATGACTCAGTTTGGACAAGTGGGTAATGCAGTACCGCCGTTACT
TGCTGAAGCTGTTGCTAAAGCGGTTAGCGAACAGCTTCTGGATGTCgcggccgcAGATTGATAA
CCCAAACCTATAGAATAATTAAGAATCTCCAAAGCAACAGTTATTGCATTGGGTATCAACTAAG
CTGATCCTAAGCATAAGACCTACGACAATATCACAGGCTTGCGGATGGTTGCATCATCTCGCTG
AGTTTTGCACTGCTCAATTTTGCCCCATTTGCGGGGAATCGTAGCGTTCACACTACCCATTGCA
AAGGTTGCCCGTAGAGATTGCTCTATTCGGCACAGTCACTGTTAAAGAGGAACAACGcatatgg
cgaccgtcctctgcgtgctgtaccccgaccccgtcgacggctatccgccgcgctacgtgcgcga
cacgattcccgtcatcacgcactacgcggacggccagctcgcgccgacgccgtccgggccgccc
ggttttcggccgggcgaactcgtcggctcggtatcgggcgcgctcgggttgcgcgactatctgg
cggcgcacggtcatacgctgatcgtgacgagcgacaaggacggccccgactccgaattcgagcg
ccggctgccggaagcggacgtcgtgatttcgcagccgttctggcccgcgtatctgaccgccgag
gggatcgcgcgcgcgccgaagctgcggctcgcgctgactgcgggcatcggctccgatcacgtcg
atctcgcggcggccgcgcgcgcgggcatcaccgtcgcggaagtcaccggatcgaacagcgtcag
cgtcgccgagcatgtcgtgatgacgacgcttgcgctcgtgcgcaactatctgccgtcgcacgcg
atcgcgcagcaaggcggctggaacatcgccgactgcgtatcgcgcagctacgacatcgagggca
tgcatttcggcacggtcggcgccggccgcatcgggctcgcggtgctgcggcggctgaagccgtt
cgggctggcgctgcactatacgcagcggcatcggctcgatccggcgatcgaacacgaactcgcg
ctgacctatcacgcggacgtcgcgtcgctcgcgagcgcggtcgacatcgtgaatctgcagattc
cgctctatccgtcgaccgagcatctgttcgatgccgcaatgatcgcgcgcatgaagcgcggcgc
gtatctgatcaacaccgcgcgcgcgaaactcgtcgatcgcgacgcggtcgtgcgtgcggtcgcc
tcgggccatctggccggctacggcggcgacgtgtggtttcccgagcccgcaccggccgatcatc
cgtggcgcgcgatgccgttcaacgggatgacgccgcatatctcgggcacgtcgctgtccgcgca
ggcgcgctacgcggccggtacgctcgaaattctgcagtgctggttcgagcgccggccgattcgc
gaggcctacctgatcgtcgacggcggcacgctcgcgggcaccggcgagcagtcgtaccggctca
cgtgactcgaggcgagctcagactgttgtacagcatgctagctacacagacgcgtccatggtag
gtacctgttaacgttagaccggtcaggatctgcagatgacaccgcggtgcagctgaaggccacg
tgggccgtagggaattcactagtttttaattaaCGTGCTATAATTATACTAATTTTATAAGGAG
GAAAAAATATGGGCATTTTTAGTATTTTTGTAATCAGCACAGTTCATTATCAACCAAACAAAAA
ATAAGTGGTTATAATGAATCGTTAATAAGCAAAATTCATATAACCAAATTAAAGAGGGTTATAA
TGAACGAGAAAAATATAAAACACAGTCAAAACTTTATTACTTCAAAACATAATATAGATAAAAT
AATGACAAATATAAGATTAAATGAACATGATAATATCTTTGAAATCGGCTCAGGAAAAGGCCAT
TTTACCCTTGAATTAGTAAAGAGGTGTAATTTCGTAACTGCCATTGAAATAGACCATAAATTAT
GCAAAACTACAGAAAATAAACTTGTTGATCACGATAATTTCCAAGTTTTAAACAAGGATATATT
GCAGTTTAAATTTCCTAAAAACCAATCCTATAAAATATATGGTAATATACCTTATAACATAAGT
ACGGATATAATACGCAAAATTGTTTTTGATAGTATAGCTAATGAGATTTATTTAATCGTGGAAT
ACGGGTTTGCTAAAAGATTATTAAATACAAAACGCTCATTGGCATTACTTTTAATGGCAGAAGT
TGATATTTCTATATTAAGTATGGTTCCAAGAGAATATTTTCATCCTAAACCTAAAGTGAATAGC
TCACTTATCAGATTAAGTAGAAAAAAATCAAGAATATCACACAAAGATAAACAAAAGTATAATT
ATTTCGTTATGAAATGGGTTAACAAAGAATACAAGAAAATATTTACAAAAAATCAATTTAACAA
TTCCTTAAAACATGCAGGAATTGACGATTTAAACAATATTAGCTTTGAACAATTCTTATCTCTT
TTCAATAGCTATAAATTATTTAATAAGTAAGTTAAGGGATGCATAAACTGCATCCCTTAACTTG
TTTTTCGTGTGCCTATTTTTTGTGGCGCGCCCTTTACAAAATCAAACCCGATCGCCTCTCTATT
TTGATAAATCTATGTCTACTCCCTCTGTTACCCCTGTAGAATCTAGCACCCTAATCAAAACCCC
TGAACTGCTGGCTCCGGCGGAAATTGGGACTGTGCGATCACCGCCGTGGAGAATGGGGCTGAT
GCGATTTATTTTGGGCTGGATAAATTTAATGCCCGGATGCGATCACAAAACTTTGTCGAGTCAG
ATTTGCCGGAGTTGATGGCATACTTACATCGGCGCGGCGTGAAGGGCTATGTGACGTTAAATAC
GCTGATTTTCACCTCGGAATTGGCGGCAGTCGAACAATATTTGCGGTCGATTATTGCGGCGGGA
GTCGATGCGGCGATCGTCCAGGATGTGGGGCTGTGCCAATTAATTTGGCAATTGTCGCCCGATT
TTCCGATCCATGGTTCGACGCAAATGACCGTCACCAGCGCCGCAGGGGTCGAGTTCGCGCAAAA
CTTGGGTTGTGATTTGGTGGTATTGGCGCGGGAATGTTCGATCAAGGAAATCAATAAAATCCAG
CAGGAATTGGGTCAACAAAAGATCTCAATGCCGCTAGAAGTGTTTGTCCACGGGGCGTTGTGCG
TCGCCTATTCTGGGCAATGTTTAACCAGTGAATCCCTCGGCGGACGGTCGGCCAATCGCGGAGA
ATGCGCCCAAGCCTGCCGGATGCCCTACGAAATGATTGTCGATGGTAGGCCATTTGATCTGAGC
GACAGACGTTACCggccggccaaaatgaagtgaagttcctatacttaagcttaaaatgaagtga
agttcctatactttctagagaataggaacttctatagtgagtcgaataagggcgacacaaaatt
tattctaaatgcataataaatactgataacatcttatagtttgtattatattttgtattatcgt
tgacatgtataattttgatatcaaaaactgattttccctttattattttcgagatttattttct
taattctctttaacaaactagaaatattgtatatacaaaaaatcataaataatagatgaatagt
ttaattataggtgttcatcaatcgaaaaagcaacgtatcttatttaaagtgcgttgcttttttc
tcatttataaggttaaataattctcatatatcaagcaaagtgacaggcgcccttaaatattctg
acaaatgctctttccctaaactccccccataaaaaaacccgccgaagcgggtttttacgttatt
tgcggattaacgattactcgttatcagaaccgcccagggggcccgagcttaagactggccgtcg
ttttacaacacagaaagagtttgtagaaacgcaaaaaggccatccgtcaggggccttctgctta
gtttgatgcctggcagttccctactctcgccttccgcttcctcgctcactgactcgctgcgctc
ggtcgttcggctgcggcgagcggtatcagctcactcaaaggcggtaatacggttatccacagaa
tcaggggataacgcaggaaagaacatgtgagcaaaaggccagcaaaaggccaggaaccgtaaaa
aggccgcgttgctggcgtttttccataggctccgcccccctgacgagcatcacaaaaatcgacg
ctcaagtcagaggtggcgaaacccgacaggactataaagataccaggcgtttccccctggaagc
tccctcgtgcgctctcctgttccgaccctgccgcttaccggatacctgtccgcctttctccctt
cgggaagcgtggcgctttctcatagctcacgctgtaggtatctcagttcggtgtaggtcgttcg
ctccaagctgggctgtgtgcacgaaccccccgttcagcccgaccgctgcgccttatccggtaac
tatcgtcttgagtccaacccggtaagacacgacttatcgccactggcagcagccactggtaaca
ggattagcagagcgaggtatgtaggcggtgctacagagttcttgaagtggtggcctaactacgg
ctacactagaagaacagtatttggtatctgcgctctgctgaagccagttaccttcggaaaaaga
gttggtagctcttgatccggcaaacaaaccaccgctggtagcggtggtttttttgtttgcaagc
agcagattacgcgcagaaaaaaaggatctcaagaagatcctttgatcttttctacggggtctga
cgctcagtggaacgacgcgcgcgtaactcacgttaagggattttggtcatgagcttgcgccgtc
ccgtcaagtcagcgtaatgctctgcttttagaaaaactcatcgagcatcaaatgaaactgcaat -continued ttattcatatcaggattatcaataccatatttttgaaaaagccgtttctgtaatgaaggagaaa
actcaccgaggcagttccataggatggcaagatcctggtatcggtctgcgattccgactcgtcc
aacatcaatacaacctattaatttcccctcgtcaaaaataaggttatcaagtgagaaatcacca
tgagtgacgactgaatccggtgagaatggcaaaagtttatgcatttctttccagacttgttcaa
caggccagccattacgctcgtcatcaaaatcactcgcatcaaccaaaccgttattcattcgtga
ttgcgcctgagcgaggcgaaatacgcgatcgctgttaaaaggacaattacaaacaggaatcgag
tgcaaccggcgcaggaacactgccagcgcatcaacaatattttcacctgaatcaggatattctt
ctaatacctggaacgctgtttttccggggatcgcagtggtgagtaaccatgcatcatcaggagt
acggataaaatgcttgatggtcggaagtggcataaattccgtcagccagtttagtctgaccatc
tcatctgtaacatcattggcaacgctacctttgccatgtttcagaaacaactctggcgcatcgg
gcttcccatacaagcgatagattgtcgcacctgattgcccgacattatcgcgagcccatttata
cccatataaatcagcatccatgttggaatttaatcgcggcctcgacgtttcccgttgaatatgg
ctcatattcttcctttttcaatattattgaagcatttatcagggttattgtctcatgagcggat
acatatttgaatgtatttagaaaaataaacaaataggggtcagtgttacaaccaattaaccaat
tctgaacattatcgcgagcccatttatacctgaatatggctcataacaccccttgtttgcctgg
cggcagtagcgcggtggtcccacctgaccccatgccgaactcagaagtgaaacgccgtagcgcc
gatggtagtgtggggactccccatgcgagagtagggaactgccaggcatcaaataaaacgaaag
gctcagtcgaaagactgggcctttcgcccgggctaattagggggtgtcgcccttattcgactct
atagtgaagttcctattctctagaaagtataggaacttctgaagtggggaagcttaagtatagg
aacttctgaagtggggcctgcagg SEQ ID NO: 41
DNA sequence of pJB1915

| | |
|---|---|
| 1st underlined capitalized sequence | Upstream homology region for aquI (SYNPCC7002_A1194) |
| 1st double-underlined lowercase sequence | NotI site for promoter swapping |
| 1st italic sequence | cbcB promoter |
| 2nd double-underlined lowercase sequence | NdeI site for cloning |
| 1st bold sequence | bmfdh gene (*Burkholderia multivorans* formate dehydrogenase) |
| 3rd double-underlined lowercase sequence | XhoI site used for cloning |
| 2nd italic sequence | ermC coding sequence; erythromycin$^R$ selection marker |
| 2nd underlined capitalized sequence | Downstream homology region for aquI (SYNPCC7002_A1190) |
| 2nd lowercase sequence | Vector backbone |

GAAAGGCTCTTGAGGCTATCATGACAGAAGCATCGCAGCCTATAAAATACGCTGGAAAAGAATA
TAAATATGCTGTTTCGTATCATGTCCTAAATGCTGCTGATTTTGGTGTTCCGCAATTTAGAGAA
AGAGTATTCATCGTAGGTAATCGTTTGGGCAAAACATTCCAATTTCCTGAACCAACTCATGGGC
CTAGCAACCAAGCGAGACAGATAGATCTTTTTGGCAAGCAGCTAAAACCTTACAAAACTGTTCA
AGATGCAATTAGCACTCTCCCCCCTGCAACCCCTCCTTCAGCGATGGCACTAAGAGTTTCGCAG
ACCATAAAAGATAGGATAAAGAATCATGGATATTAAAAACGTTCATATCAAAAATCACGAACAA
ACAGCTCATGCACCTTCCACTCTAGAAAAAATTCGTAAAGTCAAACAAGGGGGTAAACTCTCAG
AACAGACAAAGACATTTGGTTCAACCTACCGCAGGTTAGATCCGAACCAGCCATCTCCTACAGT
GACCCGTAGTGGTTATCGAGATTTTATTCATCCTTTTGAAGATCGAATGCTCACAGTTCGTGAA
CTGGCTTGTTTGCAAACCTTTCCCCTTGATTGGGAGTTTACCGGAACTCGACTTGATTCTTATA
GTAGTAAACGTAAAGTGACGATGACTCAGTTTGGACAAGTGGGTAATGCAGTACCGCCGTTACT
TGCTGAAGCTGTTGCTAAAGCGGTTAGCGAACAGCTTCTGGATGTCgcggccgc*GTCGACTTCG*
*TTATAAAATAAACTTAACAAATCTATACCCACCTGTAGAGAAGAGTCCCTGAATATCAAAATGG*
*TGGGATAAAAAGCTCAAAAAGGAAAGTAGGCTGTGGTTCCCTAGGCAACAGTCTTCCCTACCCC*
*ACTGGAAACTAAAAAAACGAGAAAAGTTCGCACCGAACATCAATTGCATAATTTTAGCCCTAAA*
*ACATAAGCTGAACGAAACTGGTTGTCTTCCCTTCCCAATCCAGGACAATCTGAGAATCCCCTGC*
*AACATTACTTAACAAAAAAGCAGGAATAAAATTAACAAGATGTAACAGACATAAGTCCCATCAC*
*CGTTGTATAAAGTTAACTGTGGGATTGCAAAAGCATTCAAGCCTAGGCGCTGAGCTGTTTGAGC*
*ATCCCGGTGGCCCTTGTCGCTGCCTCCGTGTTTCTCCCTGGATTTATTTAGGTAATATCTCTCA*
*TAAATCCCCGGGTAGTTAACGAAAGTTAATGGAGATCAGTAACAATAACTCTAGGGTCATTACT*
*TTGGACTCCCTCAGTTTATCCGGGGGAATTGTGTTTAAGAAAATCCCAACTCATAAAGTCAAGT*
*AGGAGATTAAT*catatggcgaccgtcctctgcgtgctgtaccccgaccccgtcgacggctatcc
gccgcgctacgtgcgcgacacgattcccgtcatcacgcactacgcggacggccagctcgcgccg
acgccgtccgggccgcccggttttcggccgggcgaactcgtcggctcggtatcgggcgcgctcg
ggttgcgcgactatctggcggcgcacggtcatacgctgatcgtgacgagcgacaaggacggccc
cgactccgaattcgagcgccggctgccggaagcggacgtcgtgatttcgcagccgttctggccc
gcgtatctgaccgccgagggggatcgcgcgcgcgccgaagctgcggctcgcgctgactgcgggca
tcggctccgatcacgtcgatctcgcggcggccgcgcgcgcgggcatcaccgtcgcggaagtcac
cggatcgaacagcgtcagcgtcgccgagcatgtcgtgatgacgacgcttgcgctcgtgcgcaac
tatctgccgtcgcacgcgatcgcgcagcaaggcggctggaacatcgccgactgcgtatcgcgca
gctacgacatcgagggcatgcatttcggcacggtcggcgccggccgcatcgggctcgcggtgct
gcggcggctgaagccgttcgggctggcgctgcactatacgcagcggcatcggctcgatccggcg
atcgaacacgaactcgcgctgacctatcacgcggacgtcgcgtcgctcgcgagcgcggtcgaca
tcgtgaatctgcagattccgctctatccgtcgaccgagcatctgttcgatgccgcaatgatcgc
gcgcatgaagcgcggcgcgtatctgatcaacaccgcgcgcgcgaaactcgtcgatcgcgacgcg
gtcgtgcgtgcggtcgcctcgggccatctggccggctacggcggcgacgtgtggtttcccgagc
ccgcaccggccgatcatccgtggcgcgcgatgccgttcaacgggatgacgccgcatatctcggg
cacgtcgctgtccgcgcaggcgcgctacgcggccggtacgctcgaaattctgcagtgctggttc
gagcgccggccgattcgcgaggcctacctgatcgtcgacggcggcacgctcgcgggcaccggcg
agcagtcgtaccggctcacgtgactcgaggcgagctcagactgttgtacagcatgctagctaca
cagacgcgtccatggtaggtacctgttaacgttagaccggtcaggatctgcagatgacaccgcg
gtgcagctgaaggccacgtgggccgtagggaattcactagtttttaattaa*CGTGCTATAATTA*

-continued

TACTAATTTTATAAGGAGGAAAAAATATGGGCATTTTTAGTATTTTTGTAATCAGCACAGTTCA
TTATCAACCAAACAAAAAATAAGTGGTTATAATGAATCGTTAATAAGCAAAATTCATATAACCA
AATTAAAGAGGGTTATAATGAACGAGAAAAATATAAAACACAGTCAAAACTTTATTACTTCAAA
ACATAATATAGATAAAATAATGACAAATATAAGATTAAATGAACATGATAATATCTTTGAAATC
GGCTCAGGAAAAGGCCATTTTACCCTTGAATTAGTAAAGAGGTGTAATTTCGTAACTGCCATTG
AAATAGACCATAAATTATGCAAAACTACAGAAAATAAACTTGTTGATCACGATAATTTCCAAGT
TTTAAACAAGGATATATTGCAGTTTAAATTTCCTAAAAACCAATCCTATAAAATATATGGTAAT
ATACCTTATAACATAAGTACGGATATAATACGCAAAATTGTTTTTGATAGTATAGCTAATGAGA
TTTATTTAATCGTGGAATACGGGTTTGCTAAAAGATTATTAAATACAAAACGCTCATTGGCATT
ACTTTTAATGGCAGAAGTTGATATTTCTATATTAAGTATGGTTCCAAGAGAATATTTTCATCCT
AAACCTAAAGTGAATAGCTCACTTATCAGATTAAGTAGAAAAAAATCAAGAATATCACACAAAG
ATAAACAAAAGTATAATTATTTCGTTATGAAATGGGTTAACAAAGAATACAAGAAAATATTTAC
AAAAAATCAATTTAACAATTCCTTAAAACATGCAGGAATTGACGATTTAAACAATATTAGCTTT
GAACAATTCTTATCTCTTTTCAATAGCTATAAATTATTTAATAAGTAAGTTAAGGGATGCATAA
ACTGCATCCCTTAACTTGTTTTTCGTGTGCCTATTTTTTGTGGCGCGCCCTTTACAAAATCAAA
CCCGATCGCCTCTCTATTTTGATAAATCTATGTCTACTCCCTCTGTTACCCCTGTAGAATCTAG
CACCCTAATCAAAACCCCTGAACTGCTGGCTCCGGCGGGAAATTGGGACTGTGCGATCACCGCC
GTGGAGAATGGGGCTGATGCGATTTATTTTGGGCTGGATAAATTTAATGCCCGGATGCGATCAC
AAAACTTTGTCGAGTCAGATTTGCCGGAGTTGATGGCATACTTACATCGGCGCGGCGTGAAGGG
CTATGTGACGTTAAATACGCTGATTTTCACCTCGGAATTGGCGGCAGTCGAACAATATTTGCGG
TCGATTATTGCGGCGGGAGTCGATGCGGCGATCGTCCAGGATGTGGGGCTGTGCCAATTAATTT
GGCAATTGTCGCCCGATTTTCCGATCCATGGTTCGACGCAAATGACCGTCACCAGCGCCGCAGG
GGTCGAGTTCGCGCAAAACTTGGGTTGTGATTTGGTGGTATTGGCGCGGGAATGTTCGATCAAG
GAAATCAATAAAATCCAGCAGGAATTGGGTCAACAAAAGATCTCAATGCCGCTAGAAGTGTTTG
TCCACGGGGCGTTGTGCGTCGCCTATTCTGGGCAATGTTTAACCAGTGAATCCCTCGGCGGACG
GTCGGCCAATCGCGGAGAATGCGCCCAAGCCTGCCGGATGCCCTACGAAATGATTGTCGATGGT
AGGCCATTTGATCTGAGCGACAGACGTTACCggccggccaaaatgaagtgaagttcctatactt
aagcttaaaatgaagtgaagttcctatactttctagagaataggaacttctatagtgagtcgaa
taagggcgacacaaaatttattctaaatgcataataaatactgataacatcttatagtttgtat
tatattttgtattatcgttgacatgtataattttgatatcaaaaactgattttccctttattat
tttcgagatttattttcttaattctctttaacaaactagaaatattgtatatacaaaaaatcat
aaataatagatgaatagtttaattataggtgttcatcaatcgaaaaagcaacgtatcttattta
aagtgcgttgctttttttctcatttataaggttaaataattctcatatatcaagcaaagtgacag
gcgcccttaaatattctgacaaatgctctttccctaaactccccccataaaaaaacccgccgaa
gcgggtttttacgttatttgcggattaacgattactcgttatcagaaccgcccagggggcccga
gcttaagactggccgtcgttttacaacacagaaagagtttgtagaaacgcaaaaaggccatccg
tcaggggccttctgcttagtttgatgcctggcagttccctactctcgccttccgcttcctcgct
cactgactcgctgcgctcggtcgttcggctgcggcgagcggtatcagctcactcaaaggcggta
atacggttatccacagaatcaggggataacgcaggaaagaacatgtgagcaaaaggccagcaaa
aggccaggaaccgtaaaaaggccgcgttgctggcgtttttccataggctccgcccccctgacga
gcatcacaaaaatcgacgctcaagtcagaggtggcgaaacccgacaggactataaagataccag
gcgtttccccctggaagctccctcgtgcgctctcctgttccgaccctgccgcttaccggatacc
tgtccgcctttctcccttcgggaagcgtggcgctttctcatagctcacgctgtaggtatctcag
ttcggtgtaggtcgttcgctccaagctgggctgtgtgcacgaaccccccgttcagcccgaccgc
tgcgccttatccggtaactatcgtcttgagtccaacccggtaagacacgacttatcgccactgg
cagcagccactggtaacaggattagcagagcgaggtatgtaggcggtgctacagagttcttgaa
gtggtgggctaactacggctacactagaagaacagtatttggtatctgcgctctgctgaagcca
gttaccttcggaaaaagagttggtagctcttgatccggcaaacaaaccaccgctggtagcggtg
gtttttttgtttgcaagcagcagattacgcgcagaaaaaaaggatctcaagaagatcctttgat
cttttctacggggtctgacgctcagtggaacgacgcgcgcgtaactcacgttaagggattttgg
tcatgagcttgcgccgtcccgtcaagtcagcgtaatgctctgcttttagaaaaactcatcgagc
atcaaatgaaactgcaatttattcatatcaggattatcaataccatatttttgaaaaagccgtt
tctgtaatgaaggagaaaactcaccgaggcagttccataggatggcaagatcctggtatcggtc
tgcgattccgactcgtccaacatcaatacaacctattaatttcccctcgtcaaaaataaggtta
tcaagtgagaaatcaccatgagtgacgactgaatccggtgagaatggcaaaagtttatgcattt
ctttccagacttgttcaacaggccagccattacgctcgtcatcaaaatcactcgcatcaaccaa
accgttattcattcgtgattgcgcctgagcgaggcgaaatacgcgatcgctgttaaaaggacaa
ttacaaacaggaatcgagtgcaaccggcgcaggaacactgccagcgcatcaacaatattttcac
ctgaatcaggatattcttctaatacctggaacgctgtttttccggggatcgcagtggtgagtaa
ccatgcatcatcaggagtacggataaaatgcttgatggtcggaagtggcataaattccgtcagc
cagtttagtctgaccatctcatctgtaacatcattggcaacgctacctttgccatgtttcagaa
acaactctggcgcatcgggcttcccatacaagcgatagattgtcgcacctgattgcccgacatt
atcgcgagcccatttatacccatataaatcagcatccatgttggaatttaatcgcggcctcgac
gtttcccgttgaatatggctcatattcttcctttttcaatattattgaagcatttatcagggtt
attgtctcatgagcggatacatatttgaatgtatttagaaaaataaacaaataggggtcagtgt
tacaaccaattaaccaattctgaacattatcgcgagcccatttatacctgaatatggctcataa
caccccttgtttgcctggcggcagtagcgcggtggtcccacctgaccccatgccgaactcagaa
gtgaaacgccgtagcgccgatggtagtgtggggactccccatgcgagagtagggaactgccagg
catcaaataaaacgaaaggctcagtcgaaagactgggcctttcgcccgggctaattagggggtg
tcgcccttattcgactctatagtgaagttcctattctctagaaagtataggaacttctgaagtg
gggaagcttaagtataggaacttctgaagtggggcctgcagg SEQ ID NO: 42
DNA sequence of MC31 primer
5' CTATCATATGGCGACCGTCCTCTGCGTG 3'

SEQ ID NO: 43
DNA sequence of MC32 primer
5' CTATCTCGAGTCACGTGAGCCGGTACGACTGCT 3'

-continued

SEQ ID NO: 44
Wild-type *Burkholdia multivorans* FDH (NAD+-specific enzyme)
(SEQ ID NO: 44)
MATVLCVLYPDPVDGYPPRYVRDTIPVITHYADGQLAPTPSGPPGFRPGELVGSVSGALGLRDY
LAAHGHTLIVTSDKDGPDSEFERRLPEADVVISQPFWPAYLTAEGIARAPKLRLALTAGIGSDH
VDLAAAARAGITVAEVTGSNSVSVAEHVVMTTLALVRNYLPSHAIAQQGGWNIADCVSRSYDIE
GMHFGTVGAGRIGLAVLRRLKPFGLALHYTQRHRLDPAIEHELALTYHADVASLASAVDIVNLQ
IPLYPSTEHLFDAAMIARMKRGAYLINTARAKLVDRDAVVRAVASGHLAGYGGDVWFPEPAPAD
HPWRAMPFNGMTPHISGTSLSAQARYAAGTLEILQCWFERRPIREAYLIVDGGTLAGTGEQSYR
LT

What is claimed is:

1. An engineered photosynthetic cell for producing one or more hydrocarbons, wherein said engineered cell comprises (1) one or more recombinant nucleic acid sequences encoding an alkanal deformylative monooxygenase (ADM) enzyme, and (2) a recombinant nucleic acid sequence encoding a formate dehydrogenase enzyme, and wherein upon culture of the engineered photosynthetic cell for at least 2 days the amount of formate accumulation is reduced by at least 5% relative to a control cell that does not comprise a recombinant nucleic acid sequence encoding a formate dehydrogenase enzyme.

2. The engineered cell of claim 1, wherein said photosynthetic cell is a microbial cell.

3. The engineered cell of claim 2, wherein said photosynthetic cell is a cyanobacterial cell.

4. The engineered cell of claim 1, wherein said formate dehydrogenase enzyme is an NAD+-dependent formate dehydrogenase (E.C. 1.2.1.2).

5. The engineered cell of claim 4, wherein said formate dehydrogenase enzyme is at least 95% identical to SEQ ID NO: 32.

6. The engineered cell of claim 5, wherein said formate dehydrogenase enzyme is encoded by a nucleotide sequence at least 95% identical to SEQ ID NO: 36.

7. The engineered cell of any of claims 4-6, wherein the expression of said formate dehydrogenase is under the control of a cpcB promoter.

8. The engineered cell of claim 7, wherein said formate dehydrogenase enzyme is encoded by a plasmid.

9. A method for producing hydrocarbons, comprising:

(i) culturing an engineered photosynthetic cell of claim 1 in a culture medium; and (ii) exposing said engineered photosynthetic cell to light and inorganic carbon, wherein said exposure results in the conversion of said inorganic carbon by said engineered photosynthetic cell into the hydrocarbons.

10. The method of claim 9, wherein said photosynthetic cell is a microbial cell.

11. The method of claim 10, wherein said photosynthetic cell is a cyanobacterial cell.

12. The method of claim 9, wherein said hydrocarbons comprise n-alkanes which comprise predominantly n-heptadecane, n-pentadecane or a combination thereof.

13. The method of claim 9, further comprising isolating at least one n-alkane, n-alkene or n-alkanol from said engineered photosynthetic cell or said culture medium.

14. The method of claim 9, wherein said method reduces formate concentration by at least 5% in said culture comprising said photosynthetic cell.

15. The method of claim 9, wherein said method reduces formate concentration by at least 35% in said culture comprising said photosynthetic cell.

* * * * *

SEQUENCE LISTING

<160> NUMBER OF SEQ ID NOS: 150

<210> SEQ ID NO 1
<211> LENGTH: 1029
<212> TYPE: DNA
<213> ORGANISM: Thermosynechococcus elongates

<400> SEQUENCE: 1
atgtttggat taattggtca tctgacgagt ctggagcacg cccaagccgt tgcccatcag 60
ttgggttacc ccgaatatgc cgatcaaggc ttggaatttt ggtgtatggc accgccgcag 120
atcgtcgatg agattacggt gacgagcgta acgggcaaaa ctatctatgg caaatacgtt 180
gagtcctgct ttttaccaga gatgctggcc aaccagcggg tgaaggcagc gactcgcaaa 240
gttattaacg ccatggccca tgcccaaaag cacaacattg acattacggc cttggggggc 300
ttctcctcga tcatctttga gaactttgat ctggagaaaa tgtcccacat tcgcaacatt 360
gaactggact ttcgccgctt tacaacgggg aatacccata ccgcctatat catctgccaa 420
caaattgagc aggcggcgcc ccaagtgggg attgatttgc ggcaggcaac cgtggctgtt 480
tgtggggcta cgggggatat tggtagtgcc gtctgccgtt ggttgaatac ctgtttagat 540
gtgcaagatc tcttactcgt agcacggaat cgcgatcgcc tgctggagct acaggcggaa 600
ttgggacggg ggaaaatcct cgacttgatg gaggcgctgc cccttgccga tattgtggtt 660
tgggtggcca gtatgcccaa gggagttgag ctgagcattg agcagttaaa acgcccctcc 720
ctgatgattg atggtggtta tcccaaaaat atggccacca aaattcagca cccccagatt 780
catgttctca atggtggcat tgtcgagcat gccctcgaca ttgactggaa aattatggaa 840
attgtgaata tggatgtgcc ctcgcggcag atgtttgcct gttttgcaga ggctatgctt 900
ttagagttcg agggctggca caccaatttc tcttggggac gcaatcaaat cactgtggaa 960
aagatgcagc aaattggtga ggtctcccgt aaacatggat ttcagccact actgttgaat 1020
cctcagtaa 1029

<210> SEQ ID NO 2
<211> LENGTH: 342
<212> TYPE: PRT
<213> ORGANISM: Thermosynechococcus elongates

<400> SEQUENCE: 2

Met Phe Gly Leu Ile Gly His Leu Thr Ser Leu Glu His Ala Gln Ala
1 5 10 15

Val Ala His Gln Leu Gly Tyr Pro Glu Tyr Ala Asp Gln Gly Leu Glu
20 25 30

Phe Trp Cys Met Ala Pro Pro Gln Ile Val Asp Glu Ile Thr Val Thr
35 40 45

Ser Val Thr Gly Lys Thr Ile Tyr Gly Lys Tyr Val Glu Ser Cys Phe

-continued

```
    50                  55                  60

Leu Pro Glu Met Leu Ala Asn Gln Arg Val Lys Ala Ala Thr Arg Lys
65                  70                  75                  80

Val Ile Asn Ala Met Ala His Ala Gln Lys His Asn Ile Asp Ile Thr
                85                  90                  95

Ala Leu Gly Gly Phe Ser Ser Ile Ile Phe Glu Asn Phe Asp Leu Glu
            100                 105                 110

Lys Met Ser His Ile Arg Asn Ile Glu Leu Asp Phe Arg Arg Phe Thr
        115                 120                 125

Thr Gly Asn Thr His Thr Ala Tyr Ile Ile Cys Gln Gln Ile Glu Gln
    130                 135                 140

Ala Ala Pro Gln Val Gly Ile Asp Leu Arg Gln Ala Thr Val Ala Val
145                 150                 155                 160

Cys Gly Ala Thr Gly Asp Ile Gly Ser Ala Val Cys Arg Trp Leu Asn
                165                 170                 175

Thr Cys Leu Asp Val Gln Asp Leu Leu Leu Val Ala Arg Asn Arg Asp
            180                 185                 190

Arg Leu Leu Glu Leu Gln Ala Glu Leu Gly Arg Gly Lys Ile Leu Asp
        195                 200                 205

Leu Met Glu Ala Leu Pro Leu Ala Asp Ile Val Val Trp Val Ala Ser
    210                 215                 220

Met Pro Lys Gly Val Glu Leu Ser Ile Glu Gln Leu Lys Arg Pro Ser
225                 230                 235                 240

Leu Met Ile Asp Gly Gly Tyr Pro Lys Asn Met Ala Thr Lys Ile Gln
                245                 250                 255

His Pro Gln Ile His Val Leu Asn Gly Gly Ile Val Glu His Ala Leu
            260                 265                 270

Asp Ile Asp Trp Lys Ile Met Glu Ile Val Asn Met Asp Val Pro Ser
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Val Glu
305                 310                 315                 320

Lys Met Gln Gln Ile Gly Glu Val Ser Arg Lys His Gly Phe Gln Pro
                325                 330                 335

Leu Leu Leu Asn Pro Gln
            340


<210> SEQ ID NO 3
<211> LENGTH: 696
<212> TYPE: DNA
<213> ORGANISM: Thermosynechococcus elongates

<400> SEQUENCE: 3

atgacaacgg ctaccgctac acctgttttg gactaccata gcgatcgcta caaggatgcc      60

tacagccgca ttaacgccat tgtcattgaa ggtgaacagg aagctcacga taactatatc     120

gatttagcca agctgctgcc acaacaccaa gaggaactca cccgccttgc caagatggaa     180

gctcgccaca aaaaggggtt tgaggcctgt ggtcgcaacc tgagcgtaac gccagatatg     240

gaatttgcca aagccttctt tgaaaaactg cgcgctaact ttcagagggc tctggcggag     300

ggaaaaactg cgacttgtct tctgattcaa gctttgatca tcgaatcctt tgcgatcgcg     360

gcctacaaca tctacatccc aatggcggat cctttcgccc gtaaaattac tgagagtgtt     420

gttaaggacg aatacagcca cctcaacttt ggcgaaatct ggctcaagga acactttgaa     480
```

agcgtcaaag gagagctcga agaagccaat cgcgccaatt tacccttggt ctggaaaatg 540
ctcaaccaag tggaagcaga tgccaaagtg ctcggcatgg aaaaagatgc ccttgtggaa 600
gacttcatga ttcagtacag tggtgcccta gaaaatatcg gctttaccac ccgcgaaatt 660
atgaagatgt cagtttatgg cctcactggg gcataa 696

<210> SEQ ID NO 4
<211> LENGTH: 231
<212> TYPE: PRT
<213> ORGANISM: Thermosynechococcus elongates

<400> SEQUENCE: 4

```
Met Thr Thr Ala Thr Ala Thr Pro Val Leu Asp Tyr His Ser Asp Arg
1               5                   10                  15

Tyr Lys Asp Ala Tyr Ser Arg Ile Asn Ala Ile Val Ile Glu Gly Glu
            20                  25                  30

Gln Glu Ala His Asp Asn Tyr Ile Asp Leu Ala Lys Leu Leu Pro Gln
        35                  40                  45

His Gln Glu Glu Leu Thr Arg Leu Ala Lys Met Glu Ala Arg His Lys
    50                  55                  60

Lys Gly Phe Glu Ala Cys Gly Arg Asn Leu Ser Val Thr Pro Asp Met
65                  70                  75                  80

Glu Phe Ala Lys Ala Phe Phe Glu Lys Leu Arg Ala Asn Phe Gln Arg
                85                  90                  95

Ala Leu Ala Glu Gly Lys Thr Ala Thr Cys Leu Leu Ile Gln Ala Leu
            100                 105                 110

Ile Ile Glu Ser Phe Ala Ile Ala Ala Tyr Asn Ile Tyr Ile Pro Met
        115                 120                 125

Ala Asp Pro Phe Ala Arg Lys Ile Thr Glu Ser Val Val Lys Asp Glu
    130                 135                 140

Tyr Ser His Leu Asn Phe Gly Glu Ile Trp Leu Lys Glu His Phe Glu
145                 150                 155                 160

Ser Val Lys Gly Glu Leu Glu Glu Ala Asn Arg Ala Asn Leu Pro Leu
                165                 170                 175

Val Trp Lys Met Leu Asn Gln Val Glu Ala Asp Ala Lys Val Leu Gly
            180                 185                 190

Met Glu Lys Asp Ala Leu Val Glu Asp Phe Met Ile Gln Tyr Ser Gly
        195                 200                 205

Ala Leu Glu Asn Ile Gly Phe Thr Thr Arg Glu Ile Met Lys Met Ser
    210                 215                 220

Val Tyr Gly Leu Thr Gly Ala
225                 230
```

<210> SEQ ID NO 5
<211> LENGTH: 1026
<212> TYPE: DNA
<213> ORGANISM: Synechococcus elongatus

<400> SEQUENCE: 5
atgttcggtc ttatcggtca tctcaccagt ttggagcagg cccgcgacgt ttctcgcagg 60
atgggctacg acgaatacgc cgatcaagga ttggagtttt ggagtagcgc tcctcctcaa 120
atcgttgatg aaatcacagt caccagtgcc acaggcaagg tgattcacgg tcgctacatc 180
gaatcgtgtt tcttgccgga aatgctggcg gcgcgccgct tcaaaacagc cacgcgcaaa 240
gttctcaatg ccatgtccca tgcccaaaaa cacggcatcg acatctcggc cttgggggc 300

```
tttacctcga ttattttcga gaatttcgat ttggccagtt tgcggcaagt gcgcgacact    360

accttggagt ttgaacggtt caccaccggc aatactcaca cggcctacgt aatctgtaga    420

caggtggaag ccgctgctaa aacgctgggc atcgacatta cccaagcgac agtagcggtt    480

gtcggcgcga ctggcgatat cggtagcgct gtctgccgct ggctcgacct caaactgggt    540

gtcggtgatt tgatcctgac ggcgcgcaat caggagcgtt tggataacct gcaggctgaa    600

ctcggccggg gcaagattct gcccttggaa gccgctctgc cggaagctga ctttatcgtg    660

tgggtcgcca gtatgcctca gggcgtagtg atcgacccag caaccctgaa gcaaccctgc    720

gtcctaatcg acgggggcta ccccaaaaac ttgggcagca aagtccaagg tgagggcatc    780

tatgtcctca atggcggggt agttgaacat tgcttcgaca tcgactggca gatcatgtcc    840

gctgcagaga tggcgcggcc cgagcgccag atgtttgcct gctttgccga ggcgatgctc    900

ttggaatttg aaggctggca tactaacttc tcctggggcc gcaaccaaat cacgatcgag    960

aagatggaag cgatcggtga ggcatcggtg cgccacggct tccaaccctt ggcattggca   1020

atttga                                                              1026
```

```
<210> SEQ ID NO 6
<211> LENGTH: 341
<212> TYPE: PRT
<213> ORGANISM: Synechococcus elongatus

<400> SEQUENCE: 6

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240
```

```
Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340


<210> SEQ ID NO 7
<211> LENGTH: 696
<212> TYPE: DNA
<213> ORGANISM: Synechococcus elongatus

<400> SEQUENCE: 7

atgccgcagc ttgaagccag ccttgaactg gactttcaaa gcgagtccta caaagacgct      60

tacagccgca tcaacgcgat cgtgattgaa ggcgaacaag aggcgttcga caactacaat     120

cgccttgctg agatgctgcc cgaccagcgg gatgagcttc acaagctagc caagatggaa     180

cagcgccaca tgaaaggctt tatggcctgt ggcaaaaatc tctccgtcac tcctgacatg     240

ggttttgccc agaaattttt cgagcgcttg cacgagaact tcaaagcggc ggctgcggaa     300

ggcaaggtcg tcacctgcct actgattcaa tcgctaatca tcgagtgctt tgcgatcgcg     360

gcttacaaca tctacatccc agtggcggat gcttttgccc gcaaaatcac ggagggggtc     420

gtgcgcgacg aatacctgca ccgcaacttc ggtgaagagt ggctgaaggc gaattttgat     480

gcttccaaag ccgaactgga agaagccaat cgtcagaacc tgcccttggt ttggctaatg     540

ctcaacgaag tggccgatga tgctcgcgaa ctcgggatgg agcgtgagtc gctcgtcgag     600

gactttatga ttgcctacgg tgaagctctg gaaaacatcg gcttcacaac gcgcgaaatc     660

atgcgtatgt ccgcctatgg ccttgcggcc gtttga                               696


<210> SEQ ID NO 8
<211> LENGTH: 231
<212> TYPE: PRT
<213> ORGANISM: Synechococcus elongatus

<400> SEQUENCE: 8

Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30

Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80

Gly Phe Ala Gln Lys Phe Phe Glu Arg Leu His Glu Asn Phe Lys Ala
                85                  90                  95
```

```
Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190

Met Glu Arg Glu Ser Leu Val Glu Asp Phe Met Ile Ala Tyr Gly Glu
        195                 200                 205

Ala Leu Glu Asn Ile Gly Phe Thr Thr Arg Glu Ile Met Arg Met Ser
    210                 215                 220

Ala Tyr Gly Leu Ala Ala Val
225                 230
```

<210> SEQ ID NO 9
<211> LENGTH: 1041
<212> TYPE: DNA
<213> ORGANISM: Prochlorococcus marinus

<400> SEQUENCE: 9

```
atgtttggtc tgattggtca tagcaccagc tttgaggacg caaagcgcaa ggcgagcctg      60

ctgggtttcg accacatcgc ggatggcgat ctggatgtgt ggtgtaccgc accgccgcaa     120

ctggttgaaa acgtggaagt caaaagcgcg acgggtatca gcattgaagg tagctatatc     180

gatagctgct tcgtgccgga gatgctgagc cgcttcaaga ccgcgcgtcg taaagttctg     240

aatgcaatgg agctggcgca gaaaaagggt atcaatatca ctgccctggg tggctttacc     300

tccattatct ttgagaactt caacctgttg cagcacaagc aaatccgtaa taccagcctg     360

gagtgggagc gtttcaccac gggtaacacg cacacggcat gggtgatttg tcgtcagctg     420

gagatcaacg caccgcgcat tggcatcgac ctgaaaactg caacggtcgc tgttatcggc     480

gcgaccggcg atattggtag cgcggtgtgt cgctggctgg tcaataagac cggcattagc     540

gaactgctga tggtcgctcg ccaacaacag ccactgaccc tgctgcaaaa agaactggac     600

ggtggcacca tcaagagcct ggatgaagcc ctgccgcagg cggatattgt cgtgtgggtt     660

gcttcgatgc ctaagacgat cgaaattgag attgaaaacc tgaaaaagcc gtgcctgatg     720

atcgacggtg gctacccgaa gaatctggac gagaaattca aaggcaaaaa cattcacgtg     780

ttgaagggtg gtatcgtcga gtttttcaac gacattggct ggaacatgat ggagttggcg     840

gagatgcaaa acccgcagcg tgagatgttt gcgtgcttcg ccgaagctat gattctggag     900

tttgagaaat gccataccaa ctttagctgg ggccgtaaca atatcagctt ggagaagatg     960

gagttcatcg gtgctgcatc tctgaagcac ggtttcagcg cgatcggtct ggataaacag    1020

ccgaaagtct tgaccgtttg a                                              1041
```

<210> SEQ ID NO 10
<211> LENGTH: 345
<212> TYPE: PRT
<213> ORGANISM: Prochlorococcus marinus

<400> SEQUENCE: 10

```
Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Arg Ile Gly Ile Asp Leu Lys Thr Ala Thr Val Ala Val Ile Gly
145                 150                 155                 160

Ala Thr Gly Asp Ile Gly Ser Ala Val Cys Arg Trp Leu Val Asn Lys
                165                 170                 175

Thr Gly Ile Ser Glu Leu Leu Met Val Ala Arg Gln Gln Gln Pro Leu
            180                 185                 190

Thr Leu Leu Gln Lys Glu Leu Asp Gly Gly Thr Ile Lys Ser Leu Asp
        195                 200                 205

Glu Ala Leu Pro Gln Ala Asp Ile Val Val Trp Val Ala Ser Met Pro
    210                 215                 220

Lys Thr Ile Glu Ile Glu Ile Glu Asn Leu Lys Lys Pro Cys Leu Met
225                 230                 235                 240

Ile Asp Gly Gly Tyr Pro Lys Asn Leu Asp Glu Lys Phe Lys Gly Lys
                245                 250                 255

Asn Ile His Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Glu Lys Cys His
    290                 295                 300

Thr Asn Phe Ser Trp Gly Arg Asn Asn Ile Ser Leu Glu Lys Met Glu
305                 310                 315                 320

Phe Ile Gly Ala Ala Ser Leu Lys His Gly Phe Ser Ala Ile Gly Leu
                325                 330                 335

Asp Lys Gln Pro Lys Val Leu Thr Val
            340                 345


<210> SEQ ID NO 11
<211> LENGTH: 756
<212> TYPE: DNA
<213> ORGANISM: Prochlorococcus marinus

<400> SEQUENCE: 11

atgcacaatg aattgaaaat cacggatatg caaacgctgg aaaccaacac caagacgacc      60

gaagagtcta ttgacaccaa tagcctgaac ctgccggact ttactaccga cagctacaag     120
```

-continued

```
gatgcctatt ctcgcattaa cgccatcgtt attgagggcg aacaggaagc tcatgacaat    180

tacatctcca tcgcaacgct gatcccgaat gagctggaag agctgacgaa gctggcacgt    240

atggagctga aacacaagaa aggttttact gcgtgcggtc gtaatctggg tgtggacgca    300

gacatggttt tcgcgaaaaa gttcttcagc aaactgcacg gcaatttcca aatcgcgctg    360

gaaaaaggta acctgaccac ctgcttgctg atccaagcga ttctgatcga agcatttgcg    420

atttccgcgt acaatgttta catccgtgtg gccgacccat ttgccaaaaa gattaccgag    480

ggtgttgtca aagacgagta tctgcatctg aactatggtc aggagtggct gaaaaagaat    540

ctgtccacgt gtaaagaaga gctgatggag gccaacaagg tcaatctgcc gctgattaag    600

aaaatgctgg acgaagtggc agaagatgcg agcgttttgg cgatggatcg tgaagagttg    660

atggaagagt tcatgattgc gtaccaggat accctgttgg agattggcct ggataatcgc    720

gaaattgccc gtatggcgat ggcggccatt gtttag                              756
```

<210> SEQ ID NO 12
<211> LENGTH: 251
<212> TYPE: PRT
<213> ORGANISM: Prochlorococcus marinus

<400> SEQUENCE: 12

```
Met His Asn Glu Leu Lys Ile Thr Asp Met Gln Thr Leu Glu Thr Asn
1               5                   10                  15

Thr Lys Thr Thr Glu Glu Ser Ile Asp Thr Asn Ser Leu Asn Leu Pro
            20                  25                  30

Asp Phe Thr Thr Asp Ser Tyr Lys Asp Ala Tyr Ser Arg Ile Asn Ala
        35                  40                  45

Ile Val Ile Glu Gly Glu Gln Glu Ala His Asp Asn Tyr Ile Ser Ile
    50                  55                  60

Ala Thr Leu Ile Pro Asn Glu Leu Glu Glu Leu Thr Lys Leu Ala Arg
65                  70                  75                  80

Met Glu Leu Lys His Lys Lys Gly Phe Thr Ala Cys Gly Arg Asn Leu
                85                  90                  95

Gly Val Asp Ala Asp Met Val Phe Ala Lys Lys Phe Phe Ser Lys Leu
            100                 105                 110

His Gly Asn Phe Gln Ile Ala Leu Glu Lys Gly Asn Leu Thr Thr Cys
        115                 120                 125

Leu Leu Ile Gln Ala Ile Leu Ile Glu Ala Phe Ala Ile Ser Ala Tyr
    130                 135                 140

Asn Val Tyr Ile Arg Val Ala Asp Pro Phe Ala Lys Lys Ile Thr Glu
145                 150                 155                 160

Gly Val Val Lys Asp Glu Tyr Leu His Leu Asn Tyr Gly Gln Glu Trp
                165                 170                 175

Leu Lys Lys Asn Leu Ser Thr Cys Lys Glu Glu Leu Met Glu Ala Asn
            180                 185                 190

Lys Val Asn Leu Pro Leu Ile Lys Lys Met Leu Asp Glu Val Ala Glu
        195                 200                 205

Asp Ala Ser Val Leu Ala Met Asp Arg Glu Glu Leu Met Glu Glu Phe
    210                 215                 220

Met Ile Ala Tyr Gln Asp Thr Leu Leu Glu Ile Gly Leu Asp Asn Arg
225                 230                 235                 240

Glu Ile Ala Arg Met Ala Met Ala Ala Ile Val
                245                 250
```

<210> SEQ ID NO 13
<211> LENGTH: 1041
<212> TYPE: DNA
<213> ORGANISM: Prochlorococcus marinus

<400> SEQUENCE: 13

```
atgtttgggt taataggcca ctcaactagt tttgaagatg caaaaagaaa agcttcatta     60
ctaggctttg atcatattgc tgatggtgat ctagatgttt ggtgtacagc ccctcctcaa    120
ttggttgaaa atgtagaagt taagagtgct actggaatat ctattgaagg ttcttatata    180
gattcttgct ttgttcctga aatgctttct aggtttaaaa ccgcaagaag aaaagtatta    240
aatgctatgg aattagctca gaaaaaaggg attaacatta cggctttagg aggatttact    300
tctattattt tcgaaaattt taatcttctt caacataaac aaattagaaa tacttcatta    360
gagtgggaaa ggtttactac aggtaataca cacactgcct gggttatttg taggcaacta    420
gaaataaatg ctcctcgcat agggatagat cttaaaactg caactgttgc tgttattggt    480
gctacaggtg atataggaag tgctgtttgt aggtggcttg tcaataaaac tggtatttca    540
gaacttctta tggtggctag acaacaacaa ccattaactc tattacagaa agaattagat    600
ggtggcacta taaaaagttt agatgaagca ttgcctcaag cggatattgt tgtatgggtt    660
gcaagtatgc ctaaaacgat tgaaattgaa attgaaaact taaaaaaacc atgtttaatg    720
attgatggtg gataccctaa aaatcttgat gagaaattta aaggtaaaaa tattcatgtt    780
ttaaaaggag gtatagtaga gtttttcaat gatattggct ggaatatgat ggaacttgca    840
gaaatgcaga accctcagag agagatgttt gcttgctttg cagaagctat gattttagaa    900
tttgaaaagt gtcataccaa ctttagttgg ggaaggaata acatttctct tgaaaaaatg    960
gaatttattg gagcagcttc tttgaaacat ggtttttctg cgattggact tgataaacag   1020
cctaaagtat tgactgtttg a                                              1041
```

<210> SEQ ID NO 14
<211> LENGTH: 756
<212> TYPE: DNA
<213> ORGANISM: Prochlorococcus marinus

<400> SEQUENCE: 14

```
atgcataatg agctaaagat tactgacatg caaactctag aaacaaatac aaaaactact     60
gaagaatcca tagacacgaa ttctttgaat cttcccgact ttacaacaga ttcctataag    120
gatgcatata gcagaataaa tgcaattgtt atagagggag agcaagaggc tcatgataat    180
tacatttcaa tagcaacgtt aataccaaat gagttagaag aattaactaa gttggcgaga    240
atggaactca agcataaaaa aggatttact gcttgtggaa gaaatttagg agtagatgct    300
gatatggtat tcgcaaaaaa attcttttct aaattgcatg gtaattttca aattgcttta    360
gaaaaaggaa atttaacaac ttgtcttctg atacaagcta ttttaattga agcttttgct    420
atatctgctt ataacgttta cataagagtt gctgatcctt ttgcaaaaaa aataacagag    480
ggagtggtta aagatgaata tctccatcta aattacggcc aagagtggct taaaaagaat    540
ttatctactt gtaaagaaga attaatggaa gccaataagg ttaaccttcc cttaattaaa    600
aagatgttag atgaagtagc agaagatgca tcagttttgg ctatggatag agaagagtta    660
atggaagaat ttatgattgc ttaccaagac actcttctag aaataggtct tgataataga    720
gaaattgcaa gaatggctat ggcagcgatt gtttaa                              756
```

<210> SEQ ID NO 15

-continued

<211> LENGTH: 7026
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
gtcagcaagc tctggaattt cccgattctc tgatgggaga tccaaaaatt ctcgcagtcc 60
ctcaatcacg atatcggtct tggatcgccc tgtagcttcc gacaactgct caattttttc 120
gagcatctct accgggcatc ggaatgaaat taacggtgtt ttagccatgt gttatacagt 180
gtttacaact tgactaacaa atacctgcta gtgtatacat attgtattgc aatgtatacg 240
ctattttcac tgctgtcttt aatggggatt atcgcaagca agtaaaaaag cctgaaaacc 300
ccaataggta agggattccg agcttactcg ataattatca cctttgagcg cccctaggag 360
gaggcgaaaa gctatgtctg acaaggggtt tgacccctga agtcgttgcg cgagcattaa 420
ggtctgcgga tagcccataa catacttttg ttgaacttgt gcgcttttat caacccctta 480
agggcttggg agcgttttat gcggccgcgg gggggggggg gaaagccacg ttgtgtctca 540
aaatctctga tgttacattg cacaagataa aaatatatca tcatgaacaa taaaactgtc 600
tgcttacata aacagtaata caaggggtca tatgccgcag cttgaagcca gccttgaact 660
ggactttcaa agcgagtcct acaaagacgc ttacagccgc atcaacgcga tcgtgattga 720
aggcgaacaa gaggcgttcg acaactacaa tcgccttgct gagatgctgc ccgaccagcg 780
ggatgagctt cacaagctag ccaagatgga acagcgccac atgaaaggct ttatggcctg 840
tggcaaaaat ctctccgtca ctcctgacat gggttttgcc cagaaatttt tcgagcgctt 900
gcacgagaac ttcaaagcgg cggctgcgga aggcaaggtc gtcacctgcc tactgattca 960
atcgctaatc atcgagtgct ttgcgatcgc ggcttacaac atctacatcc cagtggcgga 1020
tgcttttgcc cgcaaaatca cggagggggt cgtgcgcgac gaatacctgc accgcaactt 1080
cggtgaagag tggctgaagg cgaattttga tgcttccaaa gccgaactgg aagaagccaa 1140
tcgtcagaac ctgcccttgg tttggctaat gctcaacgaa gtggccgatg atgctcgcga 1200
actcgggatg gagcgtgagt cgctcgtcga ggactttatg attgcctacg gtgaagctct 1260
ggaaaacatc ggcttcacaa cgcgcgaaat catgcgtatg tccgcctatg gccttgcggc 1320
cgtttgatcc aggaaatctg aatgttcggt cttatcggtc atctcaccag tttggagcag 1380
gcccgcgacg tttctcgcag gatgggctac gacgaatacg ccgatcaagg attggagttt 1440
tggagtagcg ctcctcctca aatcgttgat gaaatcacag tcaccagtgc cacaggcaag 1500
gtgattcacg gtcgctacat cgaatcgtgt ttcttgccgg aaatgctggc ggcgcgccgc 1560
ttcaaaacag ccacgcgcaa agttctcaat gccatgtccc atgcccaaaa acacggcatc 1620
gacatctcgg ccttgggggg ctttacctcg attattttcg agaatttcga tttggccagt 1680
ttgcggcaag tgcgcgacac taccttggag tttgaacggt tcaccaccgg caatactcac 1740
acggcctacg taatctgtag acaggtggaa gccgctgcta aaacgctggg catcgacatt 1800
acccaagcga cagtagcggt tgtcggcgcg actggcgata tcggtagcgc tgtctgccgc 1860
tggctcgacc tcaaactggg tgtcggtgat ttgatcctga cggcgcgcaa tcaggagcgt 1920
ttggataacc tgcaggctga actcggccgg ggcaagattc tgcccttgga agccgctctg 1980
ccggaagctg actttatcgt gtgggtcgcc agtatgcctc agggcgtagt gatcgaccca 2040
gcaaccctga agcaaccctg cgtcctaatc gacgggggct accccaaaaa cttgggcagc 2100

-continued

```
aaagtccaag gtgagggcat ctatgtcctc aatggcgggg tagttgaaca ttgcttcgac   2160
atcgactggc agatcatgtc cgctgcagag atggcgcggc ccgagcgcca gatgtttgcc   2220
tgctttgccg aggcgatgct cttggaattt gaaggctggc atactaactt ctcctggggc   2280
cgcaaccaaa tcacgatcga gaagatggaa gcgatcggtg aggcatcggt gcgccacggc   2340
ttccaaccct tggcattggc aatttgaggt ctgtgaattc ggttttccgt cctgtcttga   2400
ttttcaagca aacaatgcct ccgatttcta atcggaggca tttgtttttg tttattgcaa   2460
aaacaaaaaa tattgttaca aatttttaca ggctattaag cctaccgtca taaataattt   2520
gccatttact agtttttaat taaccagaac cttgaccgaa cgcagcggtg gtaacggcgc   2580
agtggcggtt ttcatggctt gttatgactg tttttttggg gtacagtcta tgcctcgggc   2640
atccaagcag caagcgcgtt acgccgtggg tcgatgtttg atgttatgga gcagcaacga   2700
tgttacgcag cagggcagtc gccctaaaac aaagttaaac atcatgaggg aagcggtgat   2760
cgccgaagta tcgactcaac tatcagaggt agttggcgtc atcgagcgcc atctcgaacc   2820
gacgttgctg gccgtacatt tgtacggctc cgcagtggat ggcggcctga agccacacag   2880
tgatattgat ttgctggtta cggtgaccgt aaggcttgat gaaacaacgc ggcgagcttt   2940
gatcaacgac cttttggaaa cttcggcttc ccctggagag agcgagattc tccgcgctgt   3000
agaagtcacc attgttgtgc acgacgacat cattccgtgg cgttatccag ctaagcgcga   3060
actgcaattt ggagaatggc agcgcaatga cattcttgca ggtatcttcg agccagccac   3120
gatcgacatt gatctggcta tcttgctgac aaaagcaaga gaacatagcg ttgccttggt   3180
aggtccagcg gcggaggaac tctttgatcc ggttcctgaa caggatctat ttgaggcgct   3240
aaatgaaacc ttaacgctat ggaactcgcc gcccgactgg gctggcgatg agcgaaatgt   3300
agtgcttacg ttgtcccgca tttggtacag cgcagtaacc ggcaaaatcg cgccgaagga   3360
tgtcgctgcc gactgggcaa tggagcgcct gccggcccag tatcagcccg tcatacttga   3420
agctagacag gcttatcttg gacaagaaga agatcgcttg gcctcgcgcg cagatcagtt   3480
ggaagaattt gtccactacg tgaaaggcga gatcaccaag gtagtcggca aataatgtct   3540
aacaattcgt tcaagccgac gccgcttcgc ggcgcggctt aactcaagcg ttagatgcac   3600
taagcacata attgctcaca gccaaactat caggtcaagt ctgcttttat tatttttaag   3660
cgtgcataat aagccctaca caaattggga gatatatcat gaggcgcgcc acgagtgcgg   3720
ggaaatttcg gggcgatcg  cccctatatc gcaaaaagga gttaccccat cagagctata   3780
gtcgagaaga aaaccatcat tcactcaaca aggctatgtc agaagagaaa ctagaccgga   3840
tcgaagcagc cctagagcaa ttggataagg atgtgcaaac gctccaaaca gagcttcagc   3900
aatcccaaaa atggcaggac aggacatggg atgttgtgaa gtgggtaggc ggaatctcag   3960
cgggcctagc ggtgagcgct tccattgccc tgttcgggtt ggtctttaga ttttctgttt   4020
ccctgccata aaagcacatt cttataagtc atacttgttt acatcaagga acaaaaacgg   4080
cattgtgcct tgcaaggcac aatgtctttc tcttatgcac agatggggac tggaaaccac   4140
acgcacaatt cccttaaaaa gcaaccgcaa aaaataacca tcaaaataaa actggacaaa   4200
ttctcatgtg ggccggccaa aatgaagtga agttcctata ctttctagag aataggaact   4260
tctatagtga gtcgaataag ggcgacacaa aatttattct aaatgcataa taaatactga   4320
taacatctta tagtttgtat tatattttgt attatcgttg acatgtataa ttttgatatc   4380
aaaaactgat tttcccttta ttattttcga gatttatttt cttaattctc tttaacaaac   4440
tagaaatatt gtatatacaa aaaatcataa ataatagatg aatagtttaa ttataggtgt   4500
```

-continued tcatcaatcg aaaaagcaac gtatcttatt taaagtgcgt tgcttttttc tcatttataa 4560
ggttaaataa ttctcatata tcaagcaaag tgacaggcgc ccttaaatat tctgacaaat 4620
gctctttccc taaactcccc ccataaaaaa acccgccgaa gcgggttttt acgttatttg 4680
cggattaacg attactcgtt atcagaaccg cccagggggc ccgagcttaa gactggccgt 4740
cgttttacaa cacagaaaga gtttgtagaa acgcaaaaag gccatccgtc aggggccttc 4800
tgcttagttt gatgcctggc agttccctac tctcgccttc cgcttcctcg ctcactgact 4860
cgctgcgctc ggtcgttcgg ctgcggcgag cggtatcagc tcactcaaag gcggtaatac 4920
ggttatccac agaatcaggg gataacgcag gaaagaacat gtgagcaaaa ggccagcaaa 4980
aggccaggaa ccgtaaaaag gccgcgttgc tggcgttttt ccataggctc cgcccccctg 5040
acgagcatca caaaaatcga cgctcaagtc agaggtggcg aaacccgaca ggactataaa 5100
gataccaggc gtttccccct ggaagctccc tcgtgcgctc tcctgttccg accctgccgc 5160
ttaccggata cctgtccgcc tttctccctt cgggaagcgt ggcgctttct catagctcac 5220
gctgtaggta tctcagttcg gtgtaggtcg ttcgctccaa gctgggctgt gtgcacgaac 5280
cccccgttca gcccgaccgc tgcgccttat ccggtaacta tcgtcttgag tccaacccgg 5340
taagacacga cttatcgcca ctggcagcag ccactggtaa caggattagc agagcgaggt 5400
atgtaggcgg tgctacagag ttcttgaagt ggtgggctaa ctacggctac actagaagaa 5460
cagtatttgg tatctgcgct ctgctgaagc cagttacctt cggaaaaaga gttggtagct 5520
cttgatccgg caaacaaacc accgctggta gcggtggttt ttttgtttgc aagcagcaga 5580
ttacgcgcag aaaaaaagga tctcaagaag atcctttgat cttttctacg gggtctgacg 5640
ctcagtggaa cgacgcgcgc gtaactcacg ttaagggatt ttggtcatga gcttgcgccg 5700
tcccgtcaag tcagcgtaat gctctgcttt taccaatgct taatcagtga ggcacctatc 5760
tcagcgatct gtctatttcg ttcatccata gttgcctgac tccccgtcgt gtagataact 5820
acgatacggg agggcttacc atctggcccc agcgctgcga tgataccgcg agaaccacgc 5880
tcaccggctc cggatttatc agcaataaac cagccagccg gaagggccga gcgcagaagt 5940
ggtcctgcaa ctttatccgc ctccatccag tctattaatt gttgccggga agctagagta 6000
agtagttcgc cagttaatag tttgcgcaac gttgttgcca tcgctacagg catcgtggtg 6060
tcacgctcgt cgtttggtat ggcttcattc agctccggtt cccaacgatc aaggcgagtt 6120
acatgatccc ccatgttgtg caaaaaagcg gttagctcct tcggtcctcc gatcgttgtc 6180
agaagtaagt tggccgcagt gttatcactc atggttatgg cagcactgca taattctctt 6240
actgtcatgc catccgtaag atgcttttct gtgactggtg agtactcaac caagtcattc 6300
tgagaatagt gtatgcggcg accgagttgc tcttgcccgg cgtcaatacg ggataatacc 6360
gcgccacata gcagaacttt aaaagtgctc atcattggaa aacgttcttc ggggcgaaaa 6420
ctctcaagga tcttaccgct gttgagatcc agttcgatgt aacccactcg tgcacccaac 6480
tgatcttcag catcttttac tttcaccagc gtttctgggt gagcaaaaac aggaaggcaa 6540
aatgccgcaa aaaagggaat aagggcgaca cggaaatgtt gaatactcat attcttcctt 6600
tttcaatatt attgaagcat ttatcagggt tattgtctca tgagcggata catatttgaa 6660
tgtatttaga aaaataaaca aataggggtc agtgttacaa ccaattaacc aattctgaac 6720
attatcgcga gcccatttat acctgaatat ggctcataac accccttgtt tgcctggcgg 6780
cagtagcgcg gtggtcccac ctgaccccat gccgaactca gaagtgaaac gccgtagcgc 6840

-continued cgatggtagt gtggggactc cccatgcgag agtagggaac tgccaggcat caaataaaac 6900
gaaaggctca gtcgaaagac tgggcctttc gcccgggcta attatggggt gtcgccctta 6960
ttcgactcta tagtgaagtt cctattctct agaaagtata ggaacttctg aagtggggcc 7020
tgcagg 7026

<210> SEQ ID NO 16
<211> LENGTH: 5513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
ggggaattgt gagcggataa caattcccct gtagaaataa ttttgtttaa ctttaataag 60
gagatatacc atgggcagca gccatcacca tcatcaccac agccaggatc cgaattcgag 120
ctcggcgcgc ctgcaggtcg acaagcttgc ggccgcataa tgcttaagtc gaacagaaag 180
taatcgtatt gtacacggcc gcataatcga aattaatacg actcactata ggggaattgt 240
gagcggataa caattcccca tcttagtata ttagttaagt ataagaagga gatatacata 300
tgccgcagct tgaagccagc cttgaactgg actttcaaag cgagtcctac aaagacgctt 360
acagccgcat caacgcgatc gtgattgaag gcgaacaaga ggcgttcgac aactacaatc 420
gccttgctga gatgctgccc gaccagcggg atgagcttca caagctagcc aagatggaac 480
agcgccacat gaaaggcttt atggcctgtg gcaaaaatct ctccgtcact cctgacatgg 540
gttttgccca gaaatttttc gagcgcttgc acgagaactt caaagcggcg gctgcggaag 600
gcaaggtcgt cacctgccta ctgattcaat cgctaatcat cgagtgcttt gcgatcgcgg 660
cttacaacat ctacatccca gtggcggatg cttttgcccg caaaatcacg gagggggtcg 720
tgcgcgacga atacctgcac cgcaacttcg gtgaagagtg gctgaaggcg aattttgatg 780
cttccaaagc cgaactggaa gaagccaatc gtcagaacct gcccttggtt tggctaatgc 840
tcaacgaagt ggccgatgat gctcgcgaac tcgggatgga gcgtgagtcg ctcgtcgagg 900
actttatgat tgcctacggt gaagctctgg aaaacatcgg cttcacaacg cgcgaaatca 960
tgcgtatgtc cgcctatggc cttgcggccg tttgatccag gaaatctgaa tgttcggtct 1020
tatcggtcat ctcaccagtt tggagcaggc ccgcgacgtt tctcgcagga tgggctacga 1080
cgaatacgcc gatcaaggat tggagttttg gagtagcgct cctcctcaaa tcgttgatga 1140
aatcacagtc accagtgcca caggcaaggt gattcacggt cgctacatcg aatcgtgttt 1200
cttgccggaa atgctggcgg cgcgccgctt caaaacagcc acgcgcaaag ttctcaatgc 1260
catgtcccat gcccaaaaac acggcatcga catctcggcc ttggggggct ttacctcgat 1320
tattttcgag aatttcgatt tggccagttt gcggcaagtg cgcgacacta ccttggagtt 1380
tgaacggttc accaccggca atactcacac ggcctacgta atctgtagac aggtggaagc 1440
cgctgctaaa acgctgggca tcgacattac ccaagcgaca gtagcggttg tcggcgcgac 1500
tggcgatatc ggtagcgctg tctgccgctg gctcgacctc aaactgggtg tcggtgattt 1560
gatcctgacg gcgcgcaatc aggagcgttt ggataacctg caggctgaac tcggccgggg 1620
caagattctg cccttggaag ccgctctgcc ggaagctgac tttatcgtgt gggtcgccag 1680
tatgcctcag ggcgtagtga tcgacccagc aaccctgaag caaccctgcg tcctaatcga 1740 cggggggctac cccaaaaact tgggcagcaa agtccaaggt gagggcatct atgtcctcaa 1800

-continued

```
tggcggggta gttgaacatt gcttcgacat cgactggcag atcatgtccg ctgcagagat   1860
ggcgcggccc gagcgccaga tgtttgcctg ctttgccgag gcgatgctct tggaatttga   1920
aggctggcat actaacttct cctggggccg caaccaaatc acgatcgaga agatggaagc   1980
gatcggtgag gcatcggtgc gccacggctt ccaacccttg gcattggcaa tttgaggtct   2040
gtgaattgga tatcggccgg ccacgcgatc gctgacgtcg gtaccctcga gtctggtaaa   2100
gaaaccgctg ctgcgaaatt tgaacgccag cacatggact cgtctactag cgcagcttaa   2160
ttaacctagg ctgctgccac cgctgagcaa taactagcat aaccccttgg ggcctctaaa   2220
cgggtcttga ggggtttttt gctgaaacct caggcatttg agaagcacac ggtcacactg   2280
cttccggtag tcaataaacc ggtaaaccag caatagacat aagcggctat ttaacgaccc   2340
tgccctgaac cgacgaccgg gtcatcgtgg ccggatcttg cggcccctcg gcttgaacga   2400
attgttagac attatttgcc gactaccttg gtgatctcgc ctttcacgta gtggacaaat   2460
tcttccaact gatctgcgcg cgaggccaag cgatcttctt cttgtccaag ataagcctgt   2520
ctagcttcaa gtatgacggg ctgatactgg gccggcaggc gctccattgc ccagtcggca   2580
gcgacatcct tcggcgcgat tttgccggtt actgcgctgt accaaatgcg ggacaacgta   2640
agcactacat ttcgctcatc gccagcccag tcgggcggcg agttccatag cgttaaggtt   2700
tcatttagcg cctcaaatag atcctgttca ggaaccggat caaagagttc ctccgccgct   2760
ggacctacca aggcaacgct atgttctctt gcttttgtca gcaagatagc cagatcaatg   2820
tcgatcgtgg ctggctcgaa gatacctgca agaatgtcat tgcgctgcca ttctccaaat   2880
tgcagttcgc gcttagctgg ataacgccac ggaatgatgt cgtcgtgcac aacaatggtg   2940
acttctacag cgcggagaat ctcgctctct ccaggggaag ccgaagtttc caaaaggtcg   3000
ttgatcaaag ctcgccgcgt tgtttcatca agccttacgg tcaccgtaac cagcaaatca   3060
atatcactgt gtggcttcag gccgccatcc actgcggagc cgtacaaatg tacggccagc   3120
aacgtcggtt cgagatggcg ctcgatgacg ccaactacct ctgatagttg agtcgatact   3180
tcggcgatca ccgcttccct catactcttc ctttttcaat attattgaag catttatcag   3240
ggttattgtc tcatgagcgg atacatattt gaatgtattt agaaaaataa acaaatagct   3300
agctcactcg gtcgctacgc tccgggcgtg agactgcggc gggcgctgcg gacacataca   3360
aagttaccca cagattccgt ggataagcag gggactaaca tgtgaggcaa aacagcaggg   3420
ccgcgccggt ggcgtttttc cataggctcc gccctcctgc cagagttcac ataaacagac   3480
gcttttccgg tgcatctgtg ggagccgtga ggctcaacca tgaatctgac agtacgggcg   3540
aaacccgaca ggacttaaag atccccaccg tttccggcgg gtcgctccct cttgcgctct   3600
cctgttccga ccctgccgtt taccggatac ctgttccgcc tttctccctt acgggaagtg   3660
tggcgctttc tcatagctca cacactggta tctcggctcg gtgtaggtcg ttcgctccaa   3720
gctgggctgt aagcaagaac tccccgttca gcccgactgc tgcgccttat ccggtaactg   3780
ttcacttgag tccaacccgg aaaagcacgg taaaacgcca ctggcagcag ccattggtaa   3840
ctgggagttc gcagaggatt tgtttagcta aacacgcggt tgctcttgaa gtgtgcgcca   3900
aagtccggct acactggaag gacagatttg gttgctgtgc tctgcgaaag ccagttacca   3960
cggttaagca gttccccaac tgacttaacc ttcgatcaaa ccacctcccc aggtggtttt   4020
ttcgtttaca gggcaaaaga ttacgcgcag aaaaaaagga tctcaagaag atcctttgat   4080
cttttctact gaaccgctct agatttcagt gcaatttatc tcttcaaatg tagcacctga   4140
agtcagcccc atacgatata agttgtaatt ctcatgttag tcatgccccg cgcccaccgg   4200
```

aaggagctga ctgggttgaa ggctctcaag ggcatcggtc gagatcccgg tgcctaatga 4260
gtgagctaac ttacattaat tgcgttgcgc tcactgcccg ctttccagtc gggaaacctg 4320
tcgtgccagc tgcattaatg aatcggccaa cgcgcgggga gaggcggttt gcgtattggg 4380
cgccagggtg gtttttcttt tcaccagtga gacgggcaac agctgattgc ccttcaccgc 4440
ctggccctga gagagttgca gcaagcggtc cacgctggtt tgccccagca ggcgaaaatc 4500
ctgtttgatg gtggttaacg gcgggatata acatgagctg tcttcggtat cgtcgtatcc 4560
cactaccgag atgtccgcac caacgcgcag cccggactcg gtaatggcgc gcattgcgcc 4620
cagcgccatc tgatcgttgg caaccagcat cgcagtggga acgatgccct cattcagcat 4680
ttgcatggtt tgttgaaaac cggacatggc actccagtcg ccttcccgtt ccgctatcgg 4740
ctgaatttga ttgcgagtga gatatttatg ccagccagcc agacgcagac gcgccgagac 4800
agaacttaat gggcccgcta acagcgcgat ttgctggtga cccaatgcga ccagatgctc 4860
cacgcccagt cgcgtaccgt cttcatggga gaaaataata ctgttgatgg gtgtctggtc 4920
agagacatca agaaataacg ccggaacatt agtgcaggca gcttccacag caatggcatc 4980
ctggtcatcc agcggatagt taatgatcag cccactgacg cgttgcgcga gaagattgtg 5040
caccgccgct ttacaggctt cgacgccgct tcgttctacc atcgacacca ccacgctggc 5100
acccagttga tcggcgcgag atttaatcgc cgcgacaatt tgcgacggcg cgtgcagggc 5160
cagactggag gtggcaacgc caatcagcaa cgactgtttg cccgccagtt gttgtgccac 5220
gcggttggga atgtaattca gctccgccat cgccgcttcc actttttccc gcgttttcgc 5280
agaaacgtgg ctggcctggt tcaccacgcg ggaaacggtc tgataagaga caccggcata 5340
ctctgcgaca tcgtataacg ttactggttt cacattcacc accctgaatt gactctcttc 5400
cgggcgctat catgccatac cgcgaaaggt tttgcgccat tcgatggtgt ccgggatctc 5460
gacgctctcc cttatgcgac tcctgcatta ggaaattaat acgactcact ata 5513

<210> SEQ ID NO 17
<211> LENGTH: 7118
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
gtcagcaagc tctggaattt cccgattctc tgatgggaga tccaaaaatt ctcgcagtcc 60
ctcaatcacg atatcggtct tggatcgccc tgtagcttcc gacaactgct caattttttc 120
gagcatctct accgggcatc ggaatgaaat taacggtgtt ttagccatgt gttatacagt 180
gtttacaact tgactaacaa atacctgcta gtgtatacat attgtattgc aatgtatacg 240
ctattttcac tgctgtcttt aatggggatt atcgcaagca agtaaaaaag cctgaaaacc 300
ccaataggta agggattccg agcttactcg ataattatca cctttgagcg cccctaggag 360
gaggcgaaaa gctatgtctg acaaggggtt tgacccctga agtcgttgcg cgagcattaa 420
ggtctgcgga tagcccataa catacttttg ttgaacttgt gcgcttttat caacccctta 480
agggcttggg agcgttttat gcggccgcgg gggggggggg gaaagccacg ttgtgtctca 540
aaatctctga tgttacattg cacaagataa aaatatatca tcatgaacaa taaaactgtc 600
tgcttacata aacagtaata caaggggtca tatgcacaat gaattgaaaa tcacggatat 660
gcaaacgctg gaaaccaaca ccaagacgac cgaagagtct attgacacca atagcctgaa 720

```
cctgccggac tttactaccg acagctacaa ggatgcctat tctcgcatta acgccatcgt    780
tattgagggc gaacaggaag ctcatgacaa ttacatctcc atcgcaacgc tgatcccgaa    840
tgagctggaa gagctgacga agctggcacg tatggagctg aaacacaaga aaggttttac    900
tgcgtgcggt cgtaatctgg gtgtggacgc agacatggtt ttcgcgaaaa agttcttcag    960
caaactgcac ggcaatttcc aaatcgcgct ggaaaaaggt aacctgacca cctgcttgct   1020
gatccaagcg attctgatcg aagcatttgc gatttccgcg tacaatgttt acatccgtgt   1080
ggccgaccca tttgccaaaa agattaccga gggtgttgtc aaagacgagt atctgcatct   1140
gaactatggt caggagtggc tgaaaaagaa tctgtccacg tgtaaagaag agctgatgga   1200
ggccaacaag gtcaatctgc cgctgattaa gaaaatgctg gacgaagtgg cagaagatgc   1260
gagcgttttg gcgatggatc gtgaagagtt gatggaagag ttcatgattg cgtaccagga   1320
taccctgttg gagattggcc tggataatcg cgaaattgcc cgtatggcga tggcggccat   1380
tgtttagtaa tatttctaat taactaataa aggaagtctg aatgtttggt ctgattggtc   1440
atagcaccag ctttgaggac gcaaagcgca aggcgagcct gctgggtttc gaccacatcg   1500
cggatggcga tctggatgtg tggtgtaccg caccgccgca actggttgaa aacgtggaag   1560
tcaaaagcgc gacgggtatc agcattgaag gtagctatat cgatagctgc ttcgtgccgg   1620
agatgctgag ccgcttcaag accgcgcgtc gtaaagttct gaatgcaatg gagctggcgc   1680
agaaaaaggg tatcaatatc actgccctgg gtggctttac ctccattatc tttgagaact   1740
tcaacctgtt gcagcacaag caaatccgta ataccagcct ggagtgggag cgtttcacca   1800
cgggtaacac gcacacggca tgggtgattt gtcgtcagct ggagatcaac gcaccgcgca   1860
ttggcatcga cctgaaaact gcaacggtcg ctgttatcgg cgcgaccggc gatattggta   1920
gcgcggtgtg tcgctggctg gtcaataaga ccggcattag cgaactgctg atggtcgctc   1980
gccaacaaca gccactgacc ctgctgcaaa aagaactgga cggtggcacc atcaagagcc   2040
tggatgaagc cctgccgcag gcggatattg tcgtgtgggt tgcttcgatg cctaagacga   2100
tcgaaattga gattgaaaac ctgaaaaagc cgtgcctgat gatcgacggt ggctacccga   2160
agaatctgga cgagaaattc aaaggcaaaa acattcacgt gttgaagggt ggtatcgtcg   2220
agtttttcaa cgacattggc tggaacatga tggagttggc ggagatgcaa aacccgcagc   2280
gtgagatgtt tgcgtgcttc gccgaagcta tgattctgga gtttgagaaa tgccatacca   2340
actttagctg ggccgtaac aatatcagct tggagaagat ggagttcatc ggtgctgcat   2400
ctctgaagca cggtttcagc gcgatcggtc tggataaaca gccgaaagtc ttgaccgttt   2460
gaaattgaat tcggttttcc gtcctgtctt gattttcaag caaacaatgc ctccgatttc   2520
taatcggagg catttgtttt tgtttattgc aaaaacaaaa aatattgtta caaattttta   2580
caggctatta agcctaccgt cataaataat ttgccattta ctagttttta attaaccaga   2640
accttgaccg aacgcagcgg tggtaacggc gcagtggcgg ttttcatggc ttgttatgac   2700
tgttttttg gggtacagtc tatgcctcgg gcatccaagc agcaagcgcg ttacgccgtg   2760
ggtcgatgtt tgatgttatg gagcagcaac gatgttacgc agcagggcag tcgccctaaa   2820
acaaagttaa acatcatgag ggaagcggtg atcgccgaag tatcgactca actatcagag   2880
gtagttggcg tcatcgagcg ccatctcgaa ccgacgttgc tggccgtaca tttgtacggc   2940
tccgcagtgg atggcggcct gaagccacac agtgatattg atttgctggt tacggtgacc   3000
gtaaggcttg atgaaacaac gcggcgagct ttgatcaacg accttttgga aacttcggct   3060
```

-continued

```
tcccctggag agagcgagat tctccgcgct gtagaagtca ccattgttgt gcacgacgac   3120
atcattccgt ggcgttatcc agctaagcgc gaactgcaat ttggagaatg gcagcgcaat   3180
gacattcttg caggtatctt cgagccagcc acgatcgaca ttgatctggc tatcttgctg   3240
acaaaagcaa gagaacatag cgttgccttg gtaggtccag cggcggagga actctttgat   3300
ccggttcctg aacaggatct atttgaggcg ctaaatgaaa ccttaacgct atggaactcg   3360
ccgcccgact gggctggcga tgagcgaaat gtagtgctta cgttgtcccg catttggtac   3420
agcgcagtaa ccggcaaaat cgcgccgaag gatgtcgctg ccgactgggc aatggagcgc   3480
ctgccggccc agtatcagcc cgtcatactt gaagctagac aggcttatct tggacaagaa   3540
gaagatcgct tggcctcgcg cgcagatcag ttggaagaat ttgtccacta cgtgaaaggc   3600
gagatcacca aggtagtcgg caaataatgt ctaacaattc gttcaagccg acgccgcttc   3660
gcggcgcggc ttaactcaag cgttagatgc actaagcaca taattgctca cagccaaact   3720
atcaggtcaa gtctgctttt attattttta agcgtgcata ataagcccta cacaaattgg   3780
gagatatatc atgaggcgcg ccacgagtgc ggggaaattt cgggggcgat cgcccctata   3840
tcgcaaaaag gagttacccc atcagagcta tagtcgagaa gaaaaccatc attcactcaa   3900
caaggctatg tcagaagaga aactagaccg gatcgaagca gccctagagc aattggataa   3960
ggatgtgcaa acgctccaaa cagagcttca gcaatcccaa aaatggcagg acaggacatg   4020
ggatgttgtg aagtgggtag gcggaatctc agcgggccta gcggtgagcg cttccattgc   4080
cctgttcggg ttggtcttta gattttctgt ttccctgcca taaaagcaca ttcttataag   4140
tcatacttgt ttacatcaag gaacaaaaac ggcattgtgc cttgcaaggc acaatgtctt   4200
tctcttatgc acagatgggg actggaaacc acacgcacaa ttcccttaaa aagcaaccgc   4260
aaaaaataac catcaaaata aaactggaca aattctcatg tgggccggcc aaaatgaagt   4320
gaagttccta tactttctag agaataggaa cttctatagt gagtcgaata agggcgacac   4380
aaaatttatt ctaaatgcat aataaatact gataacatct tatagtttgt attatatttt   4440
gtattatcgt tgacatgtat aattttgata tcaaaaactg attttccctt tattattttc   4500
gagatttatt ttcttaattc tctttaacaa actagaaata ttgtatatac aaaaaatcat   4560
aaataataga tgaatagttt aattataggt gttcatcaat cgaaaaagca acgtatctta   4620
tttaaagtgc gttgcttttt tctcatttat aaggttaaat aattctcata tatcaagcaa   4680
agtgacaggc gcccttaaat attctgacaa atgctctttc cctaaactcc ccccataaaa   4740
aaacccgccg aagcgggttt ttacgttatt tgcggattaa cgattactcg ttatcagaac   4800
cgcccagggg gcccgagctt aagactggcc gtcgttttac aacacagaaa gagtttgtag   4860
aaacgcaaaa aggccatccg tcaggggcct tctgcttagt ttgatgcctg gcagttccct   4920
actctcgcct tccgcttcct cgctcactga ctcgctgcgc tcggtcgttc ggctgcggcg   4980
agcggtatca gctcactcaa aggcggtaat acggttatcc acagaatcag gggataacgc   5040
aggaaagaac atgtgagcaa aaggccagca aaaggccagg aaccgtaaaa aggccgcgtt   5100
gctggcgttt ttccataggc tccgcccccc tgacgagcat cacaaaaatc gacgctcaag   5160
tcagaggtgg cgaaacccga caggactata aagataccag gcgtttcccc ctggaagctc   5220
cctcgtgcgc tctcctgttc cgaccctgcc gcttaccgga tacctgtccg cctttctccc   5280
ttcgggaagc gtggcgcttt ctcatagctc acgctgtagg tatctcagtt cggtgtaggt   5340
cgttcgctcc aagctgggct gtgtgcacga accccccgtt cagcccgacc gctgcgcctt   5400
atccggtaac tatcgtcttg agtccaaccc ggtaagacac gacttatcgc cactggcagc   5460
```

agccactggt aacaggatta gcagagcgag gtatgtaggc ggtgctacag agttcttgaa 5520
gtggtgggct aactacggct acactagaag aacagtattt ggtatctgcg ctctgctgaa 5580
gccagttacc ttcggaaaaa gagttggtag ctcttgatcc ggcaaacaaa ccaccgctgg 5640
tagcggtggt ttttttgttt gcaagcagca gattacgcgc agaaaaaaag gatctcaaga 5700
agatcctttg atcttttcta cggggtctga cgctcagtgg aacgacgcgc gcgtaactca 5760
cgttaaggga ttttggtcat gagcttgcgc cgtcccgtca agtcagcgta atgctctgct 5820
tttaccaatg cttaatcagt gaggcaccta tctcagcgat ctgtctattt cgttcatcca 5880
tagttgcctg actccccgtc gtgtagataa ctacgatacg ggagggctta ccatctggcc 5940
ccagcgctgc gatgataccg cgagaaccac gctcaccggc tccggattta tcagcaataa 6000
accagccagc cggaagggcc gagcgcagaa gtggtcctgc aactttatcc gcctccatcc 6060
agtctattaa ttgttgccgg gaagctagag taagtagttc gccagttaat agtttgcgca 6120
acgttgttgc catcgctaca ggcatcgtgg tgtcacgctc gtcgtttggt atggcttcat 6180
tcagctccgg ttcccaacga tcaaggcgag ttacatgatc ccccatgttg tgcaaaaaag 6240
cggttagctc cttcggtcct ccgatcgttg tcagaagtaa gttggccgca gtgttatcac 6300
tcatggttat ggcagcactg cataattctc ttactgtcat gccatccgta agatgctttt 6360
ctgtgactgg tgagtactca accaagtcat tctgagaata gtgtatgcgg cgaccgagtt 6420
gctcttgccc ggcgtcaata cgggataata ccgcgccaca tagcagaact ttaaaagtgc 6480
tcatcattgg aaaacgttct tcggggcgaa aactctcaag gatcttaccg ctgttgagat 6540
ccagttcgat gtaacccact cgtgcaccca actgatcttc agcatctttt actttcacca 6600
gcgtttctgg gtgagcaaaa acaggaaggc aaaatgccgc aaaaaaggga ataagggcga 6660
cacggaaatg ttgaatactc atattcttcc tttttcaata ttattgaagc atttatcagg 6720
gttattgtct catgagcgga tacatatttg aatgtattta gaaaaataaa caaatagggg 6780
tcagtgttac aaccaattaa ccaattctga acattatcgc gagcccattt atacctgaat 6840
atggctcata acaccccttg tttgcctggc ggcagtagcg cggtggtccc acctgacccc 6900
atgccgaact cagaagtgaa acgccgtagc gccgatggta gtgtggggac tccccatgcg 6960
agagtaggga actgccaggc atcaaataaa acgaaaggct cagtcgaaag actgggcctt 7020
tcgcccgggc taattatggg gtgtcgccct tattcgactc tatagtgaag ttcctattct 7080
ctagaaagta taggaacttc tgaagtgggg cctgcagg 7118

<210> SEQ ID NO 18
<211> LENGTH: 13852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
tgggagtcaa taaacccgat gtgcgttgga tttgccacta ccagccgccc ctgcaactca 60
gtgaatatct ccaagaggtg ggacgcgctg ggcgagatgg cgaagcggca caggccctgg 120
ttttggtgag cgatcgctgg ggcttggatc gcgaagatca acagcgttgg tcttttttc 180 agcaccaaag tcaagacacc tacaatcgcg ccatggcact tcagacgcag ctgcccctcc 240
agggtaatct gcagcaactg cggcaacact ttcctgaagt ggaattgacc ctggcattac 300
tgcatcaaca gggggccctc cgctggcaag atccctttca ctattgccgt caacccttgg 360

-continued

```
cacaggtgcc acccccaccc aaagaccctc aagaacagtt gatgcaaaag ttcctctatc    420
accggggctg ccgctggcag tttctcctcc aagcctttgg ttttgccact gaggcaaggg    480
gattccactg tggccattgc gatcgctgtc ggccgccgca ccgctcccgc aaaataccgt    540
aaattgccag cgctgtatca ctggaatatt gggtacactg gcacatagaa cggtcgcttt    600
accattggta ggcaaaagtt tctcagcagt cattctgttg ccgcaaggta ggggttgcag    660
gcatggggct actacaagtt gaggaaattc gcgaagcact tcaagatgtg ctttcagaac    720
acgcccttgt tgtgcaagtt aatcagtttc gcaaccaatt aaacattatt ttgaacaagc    780
cccccggcac cgttgcccat tattctgccc tagcggattt tctcaagtcg cgcttgggac    840
agtttcatct caatgatatt gaccgcatta aaataattgg ccgcatacag ggttcgccta    900
aacccgattg ggaagaggtc attgatctac gtccccccaa cccagcccta gctgcccctg    960
tgtatgcttc ttctgccccg tgggtggtgg cgatcgctgc tggctttgtc agtttactgg   1020
tgatctttag ctatcacctt ggtcagtagc agcaacagca acggctgtag ccgttgatcg   1080
aaggttcctt tggtcaaaag ggcgtcgtga tgacggactt taagtggcac attgagggtg   1140
gtacagggtt tattgtcggg gttcttaaaa actacagtaa agggtatttt cgcttagttc   1200
aggcggactt tgaactcttt gaccaaggcg gtcagcaagt tgggacagtg gcggtacagg   1260
tttatggtct tggccctgag gaaacatggc aattccgtga actgatagcc aatcatcagg   1320
cagtgcgagc acggctggta aaattacagt cattcaatta aggtttttct aatgtttagg   1380
tttccccagc agggagcgac accgcttgct atggcacacc ttaaagccct gatctttgat   1440
gtcgatggca ccttagcaga tacggagcgg gatggccatc gtatcgcctt caacaaggcc   1500
tttgccgccg ctggtctaga ttgggaatgg gacattcccc tctatggtca actcctggcg   1560
gtggctgggg gcaaggagcg gatccggtat taccttgagt gctttcgtcc cgattggcca   1620
cgtccccaaa atttggatgc tctgattgcc gatttacaca aggccaagac ccgctattat   1680
accgagctat tggcggcagg ggctattccc ctgcggccgg gggtgaaacg gctcctcact   1740
gaagcccggg aagcaggatt acgtttggcg atcgccacca cgaccacccc tgccaatgtc   1800
accgcactcc ttgaaaatgc cctcgctcct gatggcgtca gttggtttga gataattgct   1860
gccggggatg tagttccagc caagaaaccc gcgcccgaca tttacttcta cacgcttgaa   1920
aagatgcgcc tctcacccca agagtgcctt gcctttgagg attccgccaa tgggattcag   1980
gcggccactg ccagtcacct agcgaccatt atcacgatta ccgactacac caaggatcat   2040
gattttcgtg atgcagcgct ggtcttggat tgcttagggg aaccggacta cccctttcag   2100
gttctgcgcg gtgaggtggg ttggacaacc tatgtggatg tcccccctatt gcgatcgctg   2160
caccagcagt ggacaagcac gttgagtcag ggataatttt ctggccgcag cgttttacat   2220
tgaatatgac cccctttagtc tgaggatcaa ggaacataat gtacacgatt gatttaattc   2280
tgcgtcatgt ccccatgccc gtcagcattg aacgcaagga aagtgcagca gcgatggcag   2340
tctatcagca aattcagcag gccatggcca gtggtactcc aactttcctc gaactgacgt   2400
gcgatcgcca agtgggcaag aagttaacgg tgctcacctc agaaattgtc gccgtgcaaa   2460
tggcggataa ggatgccccc tccagtacta tcagtcgtgg gggattcttt gctcaattag   2520
tgcagcaaac cagcaactga gggaaaatgc ctcaataaag ttgagttttt cttggcaatg   2580
ctgattcttt gccgttagga tactaagcag accgatccgt aggggaacgt gaagcaaatc   2640
ctccccgtct gaaagtcagg tatctctggt gtgtcgtaat agggttgtct atggtgcagc   2700
```

-continued

```
gtttcctgcc ggttctgatt ttgttggggt gtagttttgg tcttgcgacc cctgcccttg   2760
tgcgtgccca agccaatcag ggctttacgt ttacttgggg tgaggggccg agtggccgac   2820
agcagttgca ataccactta gataacggca cccccggttt tatgggcgat cgctattggc   2880
tgcggctggg tcagcagaaa gtggccatca atcgcattaa cattacctat cccgactact   2940
acaacggtat tattgatccc aaaggcattg aggtgcgcat cggtggcgat cgcggcaatc   3000
gcttcttcca atttcgccgt gaccccggca ccaaaattca attggcggaa gtctccgttg   3060
atcgcgataa ccgcgtgatt gatattgtgc cggctgaggt gattcccgcc ggaacaccgg   3120
tgcaagttat tctcaataat gtgcgcaacc ctaacaatgg cggcatgtac tatttcaatg   3180
cccgcattgg ctcccctgga gatattcccc tcatgcgcta cgttggcacc tggattctca   3240
gcattgccaa taactaaaac ccgtcaaact cgagcattgg tgagcgggtt agccatttct   3300
aactattgcg gggcgatcgc cctagactag ttttttgtct attattgccg gttcactctt   3360
tacaccagat gccagattcc gttaggtctt cattcccctc catttctcct ctgctcacgc   3420
ctctgatgta ccgcctcgtg ggggacgttg tcctgcggcg ctattttcgt acccttgagg   3480
tgcaagggca ggagcgggtg ccccaaaggg gtccagtgat cttggccccc acccaccgtt   3540
cccgctggga tgcgctgatt attccctatg tcactgggcg gcgggtgagt gggcgcgacc   3600
tctactacat ggtgtcccac gatgagatgt tgggactaca gggctgggtg attgctcagt   3660
gtggcggttt tcccgtcaat acccaagcgc cttcggtgag tgcgttgcgt acgggtgtgg   3720
aactgctccg gcaggggcaa gccttggtgg tgttccctga ggggaatatc tttcgcgatc   3780
gccagattca tcccctcaag ccggggttgg ctcgcttagc ccttcaggcg gcccagcgct   3840
gtgaacaagc aatccagatt ctgccaattt tactcgatta tgcccagccc tacccacagt   3900
ggggaagtgc ggtcaaggta atcattgggg ctcccttgag taccgacaat tacgatgcca   3960
gccggccaaa aagtgctgcc caacaactga ccagtgatct ctttagaaga cttcagcagc   4020
tccaaggggg gcgatcgccc ctgtgttttg cttagacctc aaacttccat ccccgcggcc   4080
gctcttgata acccaagagg gcattttta ggcgcgcctc gagtaacacc gtgcgtgttg    4140
actattttac ctctggcggt gataatggtt gcaggatcct tttgctggag gaagaattca   4200
tgacaacggc taccgctaca cctgttttgg actaccatag cgatcgctac aaggatgcct   4260
acagccgcat taacgccatt gtcattgaag gtgaacagga agctcacgat aactatatcg   4320
atttagccaa gctgctgcca caacaccaag aggaactcac ccgccttgcc aagatggaag   4380
ctcgccacaa aaaggggttt gaggcctgtg gtcgcaacct gagcgtaacg ccagatatgg   4440
aatttgccaa agccttcttt gaaaaactgc gcgctaactt tcagagggct ctggcggagg   4500
gaaaaactgc gacttgtctt ctgattcaag ctttgatcat cgaatccttt gcgatcgcgg   4560
cctacaacat ctacatccca atggcggatc ctttcgcccg taaaattact gagagtgttg   4620
ttaaggacga atacagccac ctcaactttg gcgaaatctg gctcaaggaa cactttgaaa   4680
gcgtcaaagg agagctcgaa gaagccaatc gcgccaattt acccttggtc tggaaaatgc   4740
tcaaccaagt ggaagcagat gccaaagtgc tcggcatgga aaaagatgcc cttgtggaag   4800
acttcatgat tcagtacagt ggtgccctag aaaatatcgg ctttaccacc cgcgaaatta   4860
tgaagatgtc agtttatggc ctcactgggg cataatggtg gcttaacgta tcgttacatt   4920
tcagtcacca cacgcttgta tgtttggatt aattggtcat ctgacgagtc tggagcacgc   4980
ccaagccgtt gcccatcagt tgggttaccc cgaatatgcc gatcaaggct tggaattttg   5040
gtgtatggca ccgccgcaga tcgtcgatga gattacggtg acgagcgtaa cgggcaaaac   5100
```

tatctatggc aaatacgttg agtcctgctt tttaccagag atgctggcca accagcgggt 5160
gaaggcagcg actcgcaaag ttattaacgc catggcccat gcccaaaagc acaacattga 5220
cattacggcc ttggggggct tctcctcgat catctttgag aactttgatc tggagaaaat 5280
gtcccacatt cgcaacattg aactggactt tcgccgcttt acaacgggga atacccatac 5340
cgcctatatc atctgccaac aaattgagca ggcggcgccc caagtgggga ttgatttgcg 5400
gcaggcaacc gtggctgttt gtggggctac gggggatatt ggtagtgccg tctgccgttg 5460
gttgaatacc tgtttagatg tgcaagatct cttactcgta gcacggaatc gcgatcgcct 5520
gctggagcta caggcggaat tgggacgggg gaaaatcctc gacttgatgg aggcgctgcc 5580
ccttgccgat attgtggttt gggtggccag tatgcccaag ggagttgagc tgagcattga 5640
gcagttaaaa cgcccctccc tgatgattga tggtggttat cccaaaaata tggccaccaa 5700
aattcagcac ccccagattc atgttctcaa tggtggcatt gtcgagcatg ccctcgacat 5760
tgactggaaa attatggaaa ttgtgaatat ggatgtgccc tcgcggcaga tgtttgcctg 5820
ttttgcagag gctatgcttt tagagttcga gggctggcac accaatttct cttggggacg 5880
caatcaaatc actgtggaaa agatgcagca aattggtgag gtctcccgta aacatggatt 5940
tcagccacta ctgttgaatc ctcagtaagc ggccgcaaaa aaaacgggcc ggcgtattat 6000
cgccggcccg agtaacaccg tgcgtgttga ctattttacc tctggcggtg ataatggttg 6060
caggatcctt ttgctggagg aaaaccatat gaaaggacca ataataatga ctagagaaga 6120
aagaatgaag attgttcatg aaattaagga acgaatattg gataaatatg gggatgatgt 6180
taaggcaatt ggtgtttatg gctctcttgg tcgtcagact gatgggccct attcggatat 6240
tgagatgatg tgtgttctgt caacagaggg agtagagttc agctatgaat ggacaaccgg 6300
tgagtggaag gcggaagtga atttttatag cgaagagatt ctactagatt atgcatctcg 6360
ggtggaaccg gattggccgc ttacacatgg tcgatttttc tctattttgc cgatttatga 6420
tccaggtgga tactttgaga aagtgtacca aactgctaaa tcggtagaag cccaaaagtt 6480
ccacgatgcg atctgtgccc ttatcgtaga agagctgttt gaatatgcag gcaaatggcg 6540
taatattcgt gtgcaaggac cgacaacatt tctaccatcc ttgactgtac aggtggcaat 6600
ggcaggtgcc atgttgattg gtctgcatca tcgcatctgt tatacgacga gcgcttcggt 6660
cttaactgaa gcagttaagc aaccagatct tcctccaggt tatgtccaac tgtgccagct 6720
cgtaatgtct ggtcaacttt ccgaccctga gaaacttctg gaatcgctag agaatttctg 6780
gaatggggtt caggagtggg cggaacgaca cggatatata gtggatgtgt caaaacgcat 6840
accattttga tgtctaaccc ccttccttgc ccacagcttc gtcgatggcg cgaaatttcg 6900
ggtaaatata atgaccctct tgataaccca agagggcatt ttttaggcgc gccctaagcg 6960
tccgtaggca caattaaggc ttcaaattgt tggcgaagct gctcagtcac ttccttgacg 7020
gcttgccgtg ccccttggcg atcgcgccgg tacagaggcc aatagctctc taaattgaga 7080
gggtcgccga cactgaggcg cacctgccgc aaacccacca aacgattgag attcgagctt 7140
tttccctcta gccaatcaaa tgtgcgccag agaatcagcg cgacatctgc aaagcgatga 7200
atcgtgaatt tctcacggat atagctaccc gtaattgagg taaatcgctc cgcaagacgc 7260
atatgacgca atcgcacatt ggcttcctcg gccaaccaat cggctaggca gcgctctacg 7320
gccgaaagtt gtgccaaatc actgcgaaac atccgttccc aagcagcctg ttcaatgcgt 7380
cggcagcgac tcacaaaatc ggcactgggc ttcagaccaa agtaggactc tgccaccaca 7440

-continued agggcgctgt tgaggaggcg ctgaattcgc gctgccaatt tagcattggc agagtcaaag 7500
gggggcagtt cgggaaaatc ttgaccatag gaggtggcat aaaaagcctc caggcgatcc 7560
aagaggtgga tcgctaaatt cagcaggcgg cggtagaggt cgtctggctg ggtactgtga 7620
gaatctgtag ggcacccaag gcggttctcc agttgtgcca tcagccttgc catgcgctcc 7680
caagagggct gactgaggct gtactgaatg ccaatgggaa gaatgaccac ggggagcgat 7740
cgccccgcct tggctaaatc ttctagacac caaaatccca gttgggccac ccccggctcc 7800
aaaggtgcga ccagttcgtt gtgctcattc gttgctccct ccggcgctgc cgctagggga 7860
aatcgtcctc cgagaagtag ctcccgcgct gagcgcaggg cttggctatc gagcttaccg 7920
cgcatgatgg aaatcccccc caaccgtgaa aagagccaac caatctgcgc ccctgcccag 7980
aggggaatcc cgcgatcgta gagaaaatag ccatttgtcg gcggacgcaa gggaatgccc 8040
agccgccgtg ctgtttgcgg cagtaaatgc cacatcaaat agcccatcac caacggatca 8100
tccgtacagg gatggcgaaa ggcaatgagg agccggacct gtccctgctg aaactgctgg 8160
taataacggg caagggtctc cacattcacc ccttcaaccc gctgtagccc aagaccatag 8220
cgaatgtaga ggggcaggag tcttgctact gtccaccaga cggggtagct aaaccgctgg 8280
gggagaaaat gcaacggcgg ttgggcagtt gtcactacac tggacattag gcaagctcct 8340
cagggcaatg gctaaactga ggcagtggcc aactccgcaa ttaactgctc taacatcggt 8400
tgatcggccc aatagacagc attacaaaac tgacaggtgg cttctgcctt tgcctctgtg 8460
gctaggatat ctcttaattc tgcctcccct aggagcttga gtgccgctaa catccgttca 8520
tgggaacagc cacagtggaa gcgcaccatt tgccgttggg gcaagatttg taaatccata 8580
tcccctaaga gttcctgaaa gatatctggc agtgtccgcc ctgcctgtag cagtggtgta 8640
aagcccttaa gattggccac ccgttgttca agggtcgcga tcaggtgttc atcattggcc 8700
gctttgggta gcacctgtaa catcaaccca ccggcggcag tcaccccgga ctcttcgaca 8760
aaaacaccca acatcagggc ggagggggtt tgctctgagg tggcgaggta gtaggtgatg 8820
tcttctgcaa tttcgccgga gactagctcc accgtgctgg aataggggta gccgtagcca 8880
agatcgtgga tgacgtagag atatccctga tggcccaccg ctgcccccac atcgagtttg 8940
cccttggcat tggggggcag ttcaacactg gggtactgca catagccgcg aactgtgcca 9000
tcggcaccag catcggcaaa aatggttcct aggggaccgt tgccctgaat gcgcacattc 9060
acccgtgctt ggggctgttt gaaactggag gcaaggatta agcctgcggc catggttcgt 9120
cccaaggccg ctgtggccac gtaggacagt tggtgacgtt tgcgggcttc atcagtgagt 9180
tgagtggtaa tcacacctac ggcccggatg ccttcggcag cggcagttgc tcgcaacaga 9240
aaatcggcca tgttcaacct acgaaatgtt ttgttacatt tagtgtgaca tactcccacc 9300
gctgaccagg gcacaatggg gcaaaaaacc atcaatcctg cctttggtga ccgatccagt 9360
acagccagcc agggcttaag actgggaaga cccctagcac tggggctaga aaattggcga 9420
tgataggcaa gcaatagtca ttcagcgtcc agtcattccg cctatggcca tgcccctcac 9480
tgtcttgcct gccacaactg ttttgacaga agcgactcaa ttgccccagg gcggcttgat 9540
tacggagatt ccgacgctgg cgatcgccca ccgtttggcc cagcagttgc gccgccattg 9600
gcccctagag accccttaa cgctgattga tgcgcaatac cagagtatcc ccctgaccct 9660
tggggaattg gccgagctca ccgatgccaa ctgtccttta cagctctatg tgccgccccc 9720
cttgccagag gccttgacgc aatttcaacg cctgatggat gtggttcgag agctgcgcca 9780
tccggagcgt ggctgtcctt gggatttgca gcaaacccca accagtctca ttccctatgt 9840

-continued

```
ccttgaggaa gcctatgaag tggtacatgc cctgcaggag ggagatgcgg gggcgatcgc   9900
cgaagaattg ggagacctgt tgcttcaagt tgttctccag agccaacttg cccaagaagc   9960
cggccaattt acccttgctc aagtcattca aaggattacc gataaactca tccgccgcca  10020
tccccacgtc tttggtgaag tggcactcac cactgctcaa gaggtgcgcg accaatggga  10080
gcaaatcaaa gcggctgaaa aaggcaccga actccccctg agtcaaacgc tgcaacgtta  10140
cgcacgcacc ctcccacccc tgatggccgg catgaaaatt ggtgagcgag ccagtcgcgc  10200
tggcctcgat tggccgacga ttagtggtgc atgggagaaa ttttacgagg aactggcgga  10260
gtttcaggag gcccttctgc aagggaatgc tgagcaacag gcagcggaat taggagacct  10320
gctcttcagt gtgattaacc ttgcccgctg gtgccaactg gatcctgtta atgccctgca  10380
acaaacctac caacgcttta ttcaacgctt ggcctgtatt gaggcagtca tcgatcgccc  10440
ccttgagacg tacaccctag aagaactaga agccctctgg caacaggcca aagtacagtt  10500
agccaccgac agcgaggcaa cccctatgga gactgaggaa gaggcctagt ccgctgcggc  10560
ccttgccacc ttcagttcat cgagattcca caggggggccc cccagcgccg tgggcttggc  10620
gccaatgaca tgattgcgaa aagctgtaag ggagagggga ttcacgaggt aaataaaggg  10680
gagatattcc tgagctagtc gttgggcttc cgcataaatt tgctgccgtc gttccagatt  10740
gagctcctgg gcaccttgga catacaggtc actgatgcgc tgctcccagt cagcgacgac  10800
tcgacccgta atgggtggtt gattcggtga cggttgctga ttgaatgtat gcaaaaggcc  10860
atccacacgc cagatattgg caccgctatt gggttcattg ccccccccag taaagccgag  10920
gatatgggct tcccactcta gggaattgga gagacgatcc acgagggtac caaaggccaa  10980
aaattgcaga tccacctgca tgccgatcgc ccctaggtcc tgctgaactt gcgtcgggcc  11040
ggccaaaatg aagtgaagtt cctatacttt ctagagaata ggaacttcta tagtgagtcg  11100
aataagggcg acacaaaatt tattctaaat gcataataaa tactgataac atcttatagt  11160
ttgtattata ttttgtatta tcgttgacat gtataatttt gatatcaaaa actgattttc  11220
cctttattat tttcgagatt tattttctta attctcttta acaaactaga aatattgtat  11280
atacaaaaaa tcataaataa tagatgaata gtttaattat aggtgttcat caatcgaaaa  11340
agcaacgtat cttatttaaa gtgcgttgct tttttctcat ttataaggtt aaataattct  11400
catatatcaa gcaaagtgac aggcgccctt aaatattctg acaaatgctc tttccctaaa  11460
ctccccccat aaaaaaaccc gccgaagcgg gtttttacgt tatttgcgga ttaacgatta  11520
ctcgttatca gaaccgccca gggggcccga gcttaagact ggccgtcgtt ttacaacaca  11580
gaaagagttt gtagaaacgc aaaaaggcca tccgtcaggg gccttctgct tagtttgatg  11640
cctggcagtt ccctactctc gccttccgct tcctcgctca ctgactcgct gcgctcggtc  11700
gttcggctgc ggcgagcggt atcagctcac tcaaaggcgg taatacggtt atccacagaa  11760
tcaggggata acgcaggaaa gaacatgtga gcaaaaggcc agcaaaaggc caggaaccgt  11820
aaaaaggccg cgttgctggc gtttttccat aggctccgcc cccctgacga gcatcacaaa  11880
aatcgacgct caagtcagag gtggcgaaac ccgacaggac tataaagata ccaggcgttt  11940
ccccctggaa gctccctcgt gcgctctcct gttccgaccc tgccgcttac cggatacctg  12000
tccgcctttc tcccttcggg aagcgtggcg ctttctcata gctcacgctg taggtatctc  12060
agttcggtgt aggtcgttcg ctccaagctg ggctgtgtgc acgaaccccc cgttcagccc  12120
gaccgctgcg ccttatccgg taactatcgt cttgagtcca acccggtaag acacgactta  12180
```

-continued

```
tcgccactgg cagcagccac tggtaacagg attagcagag cgaggtatgt aggcggtgct  12240

acagagttct tgaagtggtg ggctaactac ggctacacta gaagaacagt atttggtatc  12300

tgcgctctgc tgaagccagt taccttcgga aaaagagttg gtagctcttg atccggcaaa  12360

caaaccaccg ctggtagcgg tggttttttt gtttgcaagc agcagattac gcgcagaaaa  12420

aaaggatctc aagaagatcc tttgatcttt tctacggggt ctgacgctca gtggaacgac  12480

gcgcgcgtaa ctcacgttaa gggattttgg tcatgagctt gcgccgtccc gtcaagtcag  12540

cgtaatgctc tgcttttacc aatgcttaat cagtgaggca cctatctcag cgatctgtct  12600

atttcgttca tccatagttg cctgactccc cgtcgtgtag ataactacga tacgggaggg  12660

cttaccatct ggccccagcg ctgcgatgat accgcgagaa ccacgctcac cggctccgga  12720

tttatcagca ataaaccagc cagccggaag ggccgagcgc agaagtggtc ctgcaacttt  12780

atccgcctcc atccagtcta ttaattgttg ccgggaagct agagtaagta gttcgccagt  12840

taatagtttg cgcaacgttg ttgccatcgc tacaggcatc gtggtgtcac gctcgtcgtt  12900

tggtatggct tcattcagct ccggttccca acgatcaagg cgagttacat gatcccccat  12960

gttgtgcaaa aaagcggtta gctccttcgg tcctccgatc gttgtcagaa gtaagttggc  13020

cgcagtgtta tcactcatgg ttatggcagc actgcataat tctcttactg tcatgccatc  13080

cgtaagatgc ttttctgtga ctggtgagta ctcaaccaag tcattctgag aatagtgtat  13140

gcggcgaccg agttgctctt gcccggcgtc aatacgggat aataccgcgc cacatagcag  13200

aactttaaaa gtgctcatca ttggaaaacg ttcttcgggg cgaaaactct caaggatctt  13260

accgctgttg agatccagtt cgatgtaacc cactcgtgca cccaactgat cttcagcatc  13320

ttttactttc accagcgttt ctgggtgagc aaaaacagga aggcaaaatg ccgcaaaaaa  13380

gggaataagg gcgacacgga aatgttgaat actcatattc ttcctttttc aatattattg  13440

aagcatttat cagggttatt gtctcatgag cggatacata tttgaatgta tttagaaaaa  13500

taaacaaata ggggtcagtg ttacaaccaa ttaaccaatt ctgaacatta tcgcgagccc  13560

atttatacct gaatatggct cataacaccc cttgtttgcc tggcggcagt agcgcggtgg  13620

tcccacctga ccccatgccg aactcagaag tgaaacgccg tagcgccgat ggtagtgtgg  13680

ggactcccca tgcgagagta gggaactgcc aggcatcaaa taaaacgaaa ggctcagtcg  13740

aaagactggg cctttcgccc gggctaatta tggggtgtcg cccttattcg actctatagt  13800

gaagttccta ttctctagaa agtataggaa cttctgaagt ggggcctgca gg          13852
```

```
<210> SEQ ID NO 19
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

gcggccgctc gagtaacacc gtgcgtgttg actattttac ctctggcggt gataatggtt     60

gcaggatcct tttgctggag gaaaaccata tg                                   92


<210> SEQ ID NO 20
<211> LENGTH: 605
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 20
gcggccgctt cgttataaaa taaacttaac aaatctatac ccacctgtag agaagagtcc 60
ctgaatatca aaatggtggg ataaaaagct caaaaaggaa agtaggctgt ggttccctag 120
gcaacagtct tccctacccc actggaaact aaaaaaacga gaaaagttcg caccgaacat 180
caattgcata attttagccc taaaacataa gctgaacgaa actggttgtc ttcccttccc 240
aatccaggac aatctgagaa tcccctgcaa cattacttaa caaaaaagca ggaataaaat 300
taacaagatg taacagacat aagtcccatc accgttgtat aaagttaact gtgggattgc 360
aaaagcattc aagcctaggc gctgagctgt ttgagcatcc cggtggccct tgtcgctgcc 420
tccgtgtttc tccctggatt tatttaggta atatctctca taaatccccg ggtagttaac 480
gaaagttaat ggagatcagt aacaataact ctagggtcat tactttggac tccctcagtt 540
tatccggggg aattgtgttt aagaaaatcc caactcataa agtcaagtag gagattaatc 600
atatg 605

<210> SEQ ID NO 21
<211> LENGTH: 1510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gcggccgcga aggcgaagcg gcatgcattt acgttgacac catcgaatgg tgcaaaacct 60
ttcgcggtat ggcatgatag cgcccggaag agagtcaatt cagggtggtg aatatgaaac 120
cagtaacgtt atacgatgtc gcagagtatg ccggtgtctc ttatcagacc gtttcccgcg 180
tggtgaacca ggccagccac gtttctgcga aaacgcggga aaaagtggaa gcggcgatgg 240
cggagctgaa ttacattccc aaccgcgtgg cacaacaact ggcgggcaaa cagtcgttgc 300
tgattggcgt tgccacctcc agtctggccc tgcacgcgcc gtcgcaaatt gtcgcggcga 360
ttaaatctcg cgccgatcaa ctgggtgcca gcgtggtggt gtcgatggta gaacgaagcg 420
gcgtcgaagc ctgtaaagcg gcggtgcaca atcttctcgc gcaacgcgtc agtgggctga 480
tcattaacta tccgctggat gaccaggatg ccattgctgt ggaagctgcc tgcactaatg 540
ttccggcgtt atttcttgat gtctctgacc agacacccat caacagtatt attttctccc 600
atgaagacgg tacgcgactg ggcgtggagc atctggtcgc attgggtcac cagcaaatcg 660
cgctgttagc gggcccatta agttctgtct cggcgcgtct gcgtctggct ggctggcata 720
aatatctcac tcgcaatcaa attcagccga tagcggaacg ggaaggcgac tggagtgcca 780
tgtccggttt tcaacaaacc atgcaaatgc tgaatgaggg catcgttccc actgcgatgc 840
tggttgccaa cgatcagatg gcgctgggcg caatgcgcgc cattaccgag tccgggctgc 900
gcgttggtgc ggatatctcg gtagtgggat acgacgatac cgaagacagc tcatgttata 960
tcccgccgtc aaccaccatc aaacaggatt ttcgcctgct ggggcaaacc agcgtggacc 1020
gcttgctgca actctctcag ggccaggcgg tgaagggcaa tcagctgttg cccgtctcac 1080
tggtgaaaag aaaaaccacc ctggcgccca atacgcaaac cgcctctccc cgcgcgttgg 1140
ccgattcatt aatgcagctg gcacgacagg tttcccgact ggaaagcggg cagtgagcgc 1200
aacgcaatta atgtgagtta gcgcgaattg atctggtttg acagcttatc atcgagctcg 1260
actgcacggt gcaccaatgc ttctggcgtc aggcagccat cggaagctgt ggtatggctg 1320

-continued tgcaggtcgt aaatcactgc ataattcgtg tcgctcaagg cgcactcccg ttctggataa 1380 tgtttttgc gccgacatca taacggttct ggcaaatatt ctgaaatgag ctgttgacaa 1440
ttaatcatcc ggctcgtata atgtgtggaa ttgtgagcgg ataacaattt cacacaggaa 1500
acagcatatg 1510

<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
gcggccgctg ttgacaatta atcatcggca tagtatatcg gcatagtata atacgacaag 60
gtgaggaact aacatatg 78

<210> SEQ ID NO 23
<211> LENGTH: 5907
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23
acaactcggc ttccgagctt ggctccacca tggttatatc tggagtaacc agaatttcga 60
caacttcgac gactatctcg gtgcttttac ctccaaccaa cgcaaaaaca ttaagcgcga 120
acgcaaagcc gttgacaaag caggtttatc cctcaagatg atgaccgggg acgaaattcc 180
cgcccattac ttcccactca tttatcgttt ctatagcagc acctgcgaca aattttttg 240 ggggagtaaa tatctccgga aaccctttt tgaaacccta gaatctacct atcgccatcg 300
cgttgttctg gccgccgctt acacgccaga agatgacaaa catcccgtcg gtttatcttt 360
ttgtatccgt aaagatgatt atctttatgg tcgttattgg ggggcctttg atgaatatga 420
ctgtctccat tttgaagcct gctattacaa accgatccaa tgggcaatcg agcagggaat 480
tacgatgtac gatccgggcg ctggcggaaa acataagcga cgacgtggtt tcccggcaac 540
cccaaactat agcctccacc gtttttatca accccgcatg ggccaagttt tagacgctta 600
tattgatgaa attaatgcca tggagcaaca ggaaattgaa gcgatcaatg cggatattcc 660
ctttaaacgg caggaagttc aattgaaaat ttcctagctt cactagccaa aagcgcgatc 720
gcccaccgac catcctccct tgggggagat gcggccgctt gtagcaattg ctactaaaaa 780
ctgcgatcgc tgctgaaatg agctggaatt ttgtccctct cagctcaaaa agtatcaatg 840
attacttaat gtttgttctg cgcaaacttc ttgcagaaca tgcatgattt acaaaaagtt 900
gtagtttctg ttaccaattg cgaatcgaga actgcctaat ctgccgagta tgcgatcctt 960
tagcaggagg aaaaccatat gagatctgta gtaggatccc tcgagagtga gagccggcga 1020
gctcatagta tgtacatgat gactgtaccc atggttgaat tcggttttcc gtcctgtctt 1080
gattttcaag caaacaatgc ctccgatttc taatcggagg catttgtttt tgtttattgc 1140
aaaaacaaaa aatattgtta caaattttta caggctatta agcctaccgt cataaataat 1200
ttgccattta ctagttttta attaaccaga accttgaccg aacgcagcgg tggtaacggc 1260
gcagtggcgg ttttcatggc ttgttatgac tgtttttttg gggtacagtc tatgcctcgg 1320

-continued

```
gcatccaagc agcaagcgcg ttacgccgtg ggtcgatgtt tgatgttatg gagcagcaac   1380
gatgttacgc agcagggcag tcgccctaaa acaaagttaa acatcatgag ggaagcggtg   1440
atcgccgaag tatcgactca actatcagag gtagttggcg tcatcgagcg ccatctcgaa   1500
ccgacgttgc tggccgtaca tttgtacggc tccgcagtgg atggcggcct gaagccacac   1560
agtgatattg atttgctggt tacggtgacc gtaaggcttg atgaaacaac gcggcgagct   1620
ttgatcaacg accttttgga aacttcggct tcccctggag agagcgagat tctccgcgct   1680
gtagaagtca ccattgttgt gcacgacgac atcattccgt ggcgttatcc agctaagcgc   1740
gaactgcaat ttggagaatg gcagcgcaat gacattcttg caggtatctt cgagccagcc   1800
acgatcgaca ttgatctggc tatcttgctg acaaaagcaa gagaacatag cgttgccttg   1860
gtaggtccag cggcggagga actctttgat ccggttcctg aacaggatct atttgaggcg   1920
ctaaatgaaa ccttaacgct atggaactcg ccgcccgact gggctggcga tgagcgaaat   1980
gtagtgctta cgttgtcccg catttggtac agcgcagtaa ccggcaaaat cgcgccgaag   2040
gatgtcgctg ccgactgggc aatggagcgc ctgccggccc agtatcagcc cgtcatactt   2100
gaagctagac aggcttatct tggacaagaa gaagatcgct tggcctcgcg cgcagatcag   2160
ttggaagaat ttgtccacta cgtgaaaggc gagatcacca aggtagtcgg caaataatgt   2220
ctaacaattc gttcaagccg acgccgcttc gcggcgcggc ttaactcaag cgttagatgc   2280
actaagcaca taattgctca cagccaaact atcaggtcaa gtctgctttt attattttta   2340
agcgtgcata ataagcccta cacaaattgg gagatatatc atgaggcgcg cctgatcagt   2400
tggtgctgca ttagctaaga aggtcaggag atattattcg acatctagct gacggccatt   2460
gcgatcataa acgaggatat cccactggcc attttcagcg gcttcaaagg caattttaga   2520
cccatcagca ctaatggttg gattacgcac ttcttggttt aagttatcgg ttaaattccg   2580
cttttgttca aactcgcgat catagagata aatatcagat tcgccgcgac gattgaccgc   2640
aaagacaatg tagcgaccat cttcagaaac ggcaggatgg gaggcaattt catttagggt   2700
attgaggccc ggtaacagaa tcgtttgcct ggtgctggta tcaaatagat agatatcctg   2760
ggaaccattg cggtctgagg caaaaacgag gtagggttcg gcgatcgccg ggtcaaattc   2820
gagggcccga ctatttaaac tgcggccacc gggatcaacg ggaaaattga caatgcgcgg   2880
ataaccaacg cagctctgga gcagcaaacc gaggctaccg aggaaaaaac tgcgtagaaa   2940
agaaacatag cgcataggtc aaagggaaat caaagggcgg gcgatcgcca atttttctat   3000
aatattgtcc taacagcaca ctaaaacaga gccatgctag caaaaatttg gagtgccacc   3060
attgtcgggg tcgatgccct cagggtcggg gtggaagtgg atatttccgg cggcttaccg   3120
aaaatgatgg tggtcggact gcggccggcc aaaatgaagt gaagttccta tactttctag   3180
agaataggaa cttctatagt gagtcgaata agggcgacac aaaatttatt ctaaatgcat   3240
aataaatact gataacatct tatagtttgt attatatttt gtattatcgt tgacatgtat   3300
aattttgata tcaaaaactg attttccctt tattattttc gagatttatt ttcttaattc   3360
tctttaacaa actagaaata ttgtatatac aaaaaatcat aaataataga tgaatagttt   3420
aattataggt gttcatcaat cgaaaaagca acgtatctta tttaaagtgc gttgcttttt   3480
tctcatttat aaggttaaat aattctcata tatcaagcaa agtgacaggc gcccttaaat   3540
attctgacaa atgctctttc cctaaactcc ccccataaaa aaacccgccg aagcgggttt   3600
ttacgttatt tgcggattaa cgattactcg ttatcagaac cgcccagggg gcccgagctt   3660
aagactggcc gtcgttttac aacacagaaa gagtttgtag aaacgcaaaa aggccatccg   3720
```

```
tcaggggcct tctgcttagt ttgatgcctg gcagttccct actctcgcct tccgcttcct   3780
cgctcactga ctcgctgcgc tcggtcgttc ggctgcggcg agcggtatca gctcactcaa   3840
aggcggtaat acggttatcc acagaatcag gggataacgc aggaaagaac atgtgagcaa   3900
aaggccagca aaaggccagg aaccgtaaaa aggccgcgtt gctggcgttt ttccataggc   3960
tccgcccccc tgacgagcat cacaaaaatc gacgctcaag tcagaggtgg cgaaacccga   4020
caggactata aagataccag gcgtttcccc ctggaagctc cctcgtgcgc tctcctgttc   4080
cgaccctgcc gcttaccgga tacctgtccg cctttctccc ttcgggaagc gtggcgcttt   4140
ctcatagctc acgctgtagg tatctcagtt cggtgtaggt cgttcgctcc aagctgggct   4200
gtgtgcacga accccccgtt cagcccgacc gctgcgcctt atccggtaac tatcgtcttg   4260
agtccaaccc ggtaagacac gacttatcgc cactggcagc agccactggt aacaggatta   4320
gcagagcgag gtatgtaggc ggtgctacag agttcttgaa gtggtgggct aactacggct   4380
acactagaag aacagtattt ggtatctgcg ctctgctgaa gccagttacc ttcggaaaaa   4440
gagttggtag ctcttgatcc ggcaaacaaa ccaccgctgg tagcggtggt ttttttgttt   4500
gcaagcagca gattacgcgc agaaaaaaag gatctcaaga agatcctttg atcttttcta   4560
cggggtctga cgctcagtgg aacgacgcgc gcgtaactca cgttaaggga ttttggtcat   4620
gagcttgcgc cgtcccgtca agtcagcgta atgctctgct tttagaaaaa ctcatcgagc   4680
atcaaatgaa actgcaattt attcatatca ggattatcaa taccatattt ttgaaaaagc   4740
cgtttctgta atgaaggaga aaactcaccg aggcagttcc ataggatggc aagatcctgg   4800
tatcggtctg cgattccgac tcgtccaaca tcaatacaac ctattaattt cccctcgtca   4860
aaaataaggt tatcaagtga gaaatcacca tgagtgacga ctgaatccgg tgagaatggc   4920
aaaagtttat gcatttcttt ccagacttgt tcaacaggcc agccattacg ctcgtcatca   4980
aaatcactcg catcaaccaa accgttattc attcgtgatt gcgcctgagc gaggcgaaat   5040
acgcgatcgc tgttaaaagg acaattacaa acaggaatcg agtgcaaccg gcgcaggaac   5100
actgccagcg catcaacaat attttcacct gaatcaggat attcttctaa tacctggaac   5160
gctgtttttc cggggatcgc agtggtgagt aaccatgcat catcaggagt acggataaaa   5220
tgcttgatgg tcggaagtgg cataaattcc gtcagccagt ttagtctgac catctcatct   5280
gtaacatcat tggcaacgct acctttgcca tgtttcagaa acaactctgg cgcatcgggc   5340
ttcccataca agcgatagat tgtcgcacct gattgcccga cattatcgcg agcccattta   5400
tacccatata aatcagcatc catgttggaa tttaatcgcg gcctcgacgt ttcccgttga   5460
atatggctca tattcttcct ttttcaatat tattgaagca tttatcaggg ttattgtctc   5520
atgagcggat acatatttga atgtatttag aaaaataaac aaataggggt cagtgttaca   5580
accaattaac caattctgaa cattatcgcg agcccattta tacctgaata tggctcataa   5640
cacccccttgt ttgcctggcg gcagtagcgc ggtggtccca cctgacccca tgccgaactc   5700
agaagtgaaa cgccgtagcg ccgatggtag tgtggggact ccccatgcga gagtagggaa   5760
ctgccaggca tcaaataaaa cgaaaggctc agtcgaaaga ctgggccttt cgcccgggct   5820
aattaggggg tgtcgccctt attcgactct atagtgaagt tcctattctc tagaaagtat   5880
aggaacttct gaagtggggc ctgcagg                                       5907
```

<210> SEQ ID NO 24
<211> LENGTH: 222
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 24

```
gcttgtagca attgctacta aaaactgcga tcgctgctga aatgagctgg aattttgtcc     60

ctctcagctc aaaaagtatc aatgattact taatgtttgt tctgcgcaaa cttcttgcag    120

aacatgcatg atttacaaaa agttgtagtt tctgttacca attgcgaatc gagaactgcc    180

taatctgccg agtatgcgat cctttagcag gaggaaaacc at                      222
```

<210> SEQ ID NO 25
<211> LENGTH: 1777
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25

```
gaattctata agtaggaggt aaaaacatgc aagaactggc cctgagaagc gagctggact     60

tcaatagcga aacctataaa gatgcgtata gccgtattaa cgccattgtg atcgaaggcg    120

agcaagaagc ataccaaaac tacctggaca tggcgcaact gctgccggag gacgaggctg    180

agctgattcg tttgagcaag atggagaacc gtcacaaaaa gggttttcaa gcgtgcggca    240

agaacctcaa tgtgactccg gatatggatt atgcacagca gttctttgcg gagctgcacg    300

gcaattttca gaaggctaaa gccgagggta agattgttac ctgcctgctc atccaaagcc    360

tgatcatcga ggcgtttgcg attgcagcct acaacattta cattccagtg gctgatccgt    420

ttgcacgtaa aatcaccgag ggtgtcgtca aggatgagta tacccacctg aatttcggcg    480

aagtttggtt gaaggaacat tttgaagcaa gcaaggcgga gttggaggac gccaacaaag    540

agaacttacc gctggtctgg cagatgttga accaggtcga aaaggatgcc gaagtgctgg    600

gtatggagaa agaggctctg gtggaggact ttatgattag ctatggtgag gcactgagca    660

acatcggctt ttctacgaga gaaatcatga agatgagcgc gtacggtctg cgtgcagcat    720

aactcgagta taagtaggag ataaaaacat gttcggcttg attggccacc tgactagcct    780

ggagcacgcg cacagcgtgg cggatgcgtt tggctacggc ccgtacgcaa cccagggttt    840

agacctgtgg tgtagcgcac cgccacagtt tgttgagcac tttcatgtca cgagcattac    900

gggccaaacg attgagggta aatacattga gagcgcgttt ttgccggaga tgttgattaa    960

acgtcgtatc aaagcagcga tccgtaagat tctgaacgcg atggcatttg cgcagaagaa   1020

caatttgaac attaccgcgc tgggtggctt cagcagcatt atctttgagg agtttaatct   1080

gaaggagaat cgtcaggttc gcaatgtgag cttggagttt gaccgcttca ccaccggtaa   1140

cacccatact gcttacatta tctgccgtca agtcgaacag gcgagcgcga aactgggtat   1200

cgacctgtcc caagcgaccg tggcgatttg cggtgccacg ggtgatattg gcagcgcagt   1260

ttgtcgctgg ctggatcgca aaaccgacac ccaagagctg ttcctgattg cgcgcaataa   1320

ggaacgcttg caacgtctgc aagatgaact gggtcgcggc aagatcatgg gcctggaaga   1380

ggcactgccg gaagcagaca ttattgtgtg ggttgcctcc atgccgaagg gcgtggagat   1440

taatgcggaa accctgaaga agccgtgtct gatcattgac ggtggctacc cgaagaatct   1500

ggacacgaaa atcaagcatc cggacgtgca cattttgaag ggtggtattg tagagcattc   1560

gttggacatt gattggaaaa tcatggaaac cgtgaacatg gacgttccga gccgtcaaat   1620
```

```
gtttgcgtgc ttcgcagagg cgatcttgct ggagttcgag caatggcaca cgaacttctc   1680

gtggggtcgc aatcaaatca cggtgacgaa gatggaacag attggtgagg cgagcgtgaa   1740

gcatggtctg caaccgctgc tgtcctggta agaattc                            1777


<210> SEQ ID NO 26
<211> LENGTH: 1023
<212> TYPE: DNA
<213> ORGANISM: Cyanothece sp.

<400> SEQUENCE: 26

atgttcggct tgattggcca cctgactagc ctggagcacg cgcacagcgt ggcggatgcg     60

tttggctacg gcccgtacgc aacccagggt ttagacctgt ggtgtagcgc accgccacag    120

tttgttgagc actttcatgt cacgagcatt acgggccaaa cgattgaggg taaatacatt    180

gagagcgcgt tttgccggga gatgttgatt aaacgtcgta tcaaagcagc gatccgtaag    240

attctgaacg cgatggcatt tgcgcagaag aacaatttga acattaccgc gctgggtggc    300

ttcagcagca ttatctttga ggagtttaat ctgaaggaga atcgtcaggt tcgcaatgtg    360

agcttggagt ttgaccgctt caccaccggt aacacccata ctgcttacat tatctgccgt    420

caagtcgaac aggcgagcgc gaaactgggt atcgacctgt cccaagcgac cgtggcgatt    480

tgcggtgcca cgggtgatat tggcagcgca gtttgtcgct ggctggatcg caaaaccgac    540

acccaagagc tgttcctgat tgcgcgcaat aaggaacgct tgcaacgtct gcaagatgaa    600

ctgggtcgcg gcaagatcat gggcctggaa gaggcactgc cggaagcaga cattattgtg    660

tgggttgcct ccatgccgaa gggcgtggag attaatgcgg aaaccctgaa gaagccgtgt    720

ctgatcattg acggtggcta cccgaagaat ctggacacga aaatcaagca tccggacgtg    780

cacattttga agggtggtat tgtagagcat tcgttggaca ttgattggaa aatcatggaa    840

accgtgaaca tggacgttcc gagccgtcaa atgtttgcgt gcttcgcaga ggcgatcttg    900

ctggagttcg agcaatggca cacgaacttc tcgtggggtc gcaatcaaat cacggtgacg    960

aagatggaac agattggtga ggcgagcgtg aagcatggtc tgcaaccgct gctgtcctgg   1020

taa                                                                 1023


<210> SEQ ID NO 27
<211> LENGTH: 340
<212> TYPE: PRT
<213> ORGANISM: Cyanothece sp.

<400> SEQUENCE: 27

Met Phe Gly Leu Ile Gly His Leu Thr Ser Leu Glu His Ala His Ser
1               5                   10                  15

Val Ala Asp Ala Phe Gly Tyr Gly Pro Tyr Ala Thr Gln Gly Leu Asp
            20                  25                  30

Leu Trp Cys Ser Ala Pro Pro Gln Phe Val Glu His Phe His Val Thr
        35                  40                  45

Ser Ile Thr Gly Gln Thr Ile Glu Gly Lys Tyr Ile Glu Ser Ala Phe
    50                  55                  60

Leu Pro Glu Met Leu Ile Lys Arg Arg Ile Lys Ala Ala Ile Arg Lys
65                  70                  75                  80

Ile Leu Asn Ala Met Ala Phe Ala Gln Lys Asn Asn Leu Asn Ile Thr
                85                  90                  95

Ala Leu Gly Gly Phe Ser Ser Ile Ile Phe Glu Glu Phe Asn Leu Lys
            100                 105                 110
```

Glu Asn Arg Gln Val Arg Asn Val Ser Leu Glu Phe Asp Arg Phe Thr
115 120 125

Thr Gly Asn Thr His Thr Ala Tyr Ile Ile Cys Arg Gln Val Glu Gln
130 135 140

Ala Ser Ala Lys Leu Gly Ile Asp Leu Ser Gln Ala Thr Val Ala Ile
145 150 155 160

Cys Gly Ala Thr Gly Asp Ile Gly Ser Ala Val Cys Arg Trp Leu Asp
165 170 175

Arg Lys Thr Asp Thr Gln Glu Leu Phe Leu Ile Ala Arg Asn Lys Glu
180 185 190

Arg Leu Gln Arg Leu Gln Asp Glu Leu Gly Arg Gly Lys Ile Met Gly
195 200 205

Leu Glu Glu Ala Leu Pro Glu Ala Asp Ile Ile Val Trp Val Ala Ser
210 215 220

Met Pro Lys Gly Val Glu Ile Asn Ala Glu Thr Leu Lys Lys Pro Cys
225 230 235 240

Leu Ile Ile Asp Gly Gly Tyr Pro Lys Asn Leu Asp Thr Lys Ile Lys
245 250 255

His Pro Asp Val His Ile Leu Lys Gly Gly Ile Val Glu His Ser Leu
260 265 270

Asp Ile Asp Trp Lys Ile Met Glu Thr Val Asn Met Asp Val Pro Ser
275 280 285

Arg Gln Met Phe Ala Cys Phe Ala Glu Ala Ile Leu Leu Glu Phe Glu
290 295 300

Gln Trp His Thr Asn Phe Ser Trp Gly Arg Asn Gln Ile Thr Val Thr
305 310 315 320

Lys Met Glu Gln Ile Gly Glu Ala Ser Val Lys His Gly Leu Gln Pro
325 330 335

Leu Leu Ser Trp
340

<210> SEQ ID NO 28
<211> LENGTH: 696
<212> TYPE: DNA
<213> ORGANISM: Cyanothece sp.

<400> SEQUENCE: 28
atgcaagaac tggccctgag aagcgagctg gacttcaata gcgaaaccta taaagatgcg 60
tatagccgta ttaacgccat tgtgatcgaa ggcgagcaag aagcatacca aaactacctg 120
gacatggcgc aactgctgcc ggaggacgag gctgagctga ttcgtttgag caagatggag 180
aaccgtcaca aaaagggttt tcaagcgtgc ggcaagaacc tcaatgtgac tccggatatg 240
gattatgcac agcagttctt tgcggagctg cacggcaatt ttcagaaggc taaagccgag 300
ggtaagattg ttacctgcct gctcatccaa agcctgatca tcgaggcgtt tgcgattgca 360
gcctacaaca tttacattcc agtggctgat ccgtttgcac gtaaaatcac cgagggtgtc 420
gtcaaggatg agtataccca cctgaatttc ggcgaagttt ggttgaagga acattttgaa 480
gcaagcaagg cggagttgga ggacgccaac aaagagaact taccgctggt ctggcagatg 540
ttgaaccagg tcgaaaagga tgccgaagtg ctgggtatgg agaaagaggc tctggtggag 600
gactttatga ttagctatgg tgaggcactg agcaacatcg gcttttctac gagagaaatc 660
atgaagatga gcgcgtacgg tctgcgtgca gcataa 696

-continued

<210> SEQ ID NO 29
<211> LENGTH: 231
<212> TYPE: PRT
<213> ORGANISM: Cyanothece sp.

<400> SEQUENCE: 29

```
Met Gln Glu Leu Ala Leu Arg Ser Glu Leu Asp Phe Asn Ser Glu Thr
1               5                   10                  15

Tyr Lys Asp Ala Tyr Ser Arg Ile Asn Ala Ile Val Ile Glu Gly Glu
            20                  25                  30

Gln Glu Ala Tyr Gln Asn Tyr Leu Asp Met Ala Gln Leu Leu Pro Glu
        35                  40                  45

Asp Glu Ala Glu Leu Ile Arg Leu Ser Lys Met Glu Asn Arg His Lys
    50                  55                  60

Lys Gly Phe Gln Ala Cys Gly Lys Asn Leu Asn Val Thr Pro Asp Met
65                  70                  75                  80

Asp Tyr Ala Gln Gln Phe Phe Ala Glu Leu His Gly Asn Phe Gln Lys
                85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Thr His Leu Asn Phe Gly Glu Val Trp Leu Lys Glu His Phe Glu
145                 150                 155                 160

Ala Ser Lys Ala Glu Leu Glu Asp Ala Asn Lys Glu Asn Leu Pro Leu
                165                 170                 175

Val Trp Gln Met Leu Asn Gln Val Glu Lys Asp Ala Glu Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Lys Met Ser
    210                 215                 220

Ala Tyr Gly Leu Arg Ala Ala
225                 230
```

<210> SEQ ID NO 30
<211> LENGTH: 1023
<212> TYPE: DNA
<213> ORGANISM: Cyanothece sp.

<400> SEQUENCE: 30

```
atgtttggtt taattggtca tcttacaagt ttagaacacg cccactccgt tgctgatgcc      60

tttggctatg gcccatacgc cactcaggga cttgatttgt ggtgttctgc tccaccccaa     120

ttcgtcgagc attttcatgt tactagcatc acaggacaaa ccatcgaagg aaagtatata     180

gaatccgctt tcttaccaga aatgctgata aagcgacgga ttaaagcagc aattcgcaaa     240

atactgaatg cgatggcctt tgctcagaaa aataacctta acatcacagc attagggggc     300

ttttcttcga ttatttttga agaatttaat ctcaaagaga atagacaagt tcgtaatgtc     360

tctttagagt ttgatcgctt caccaccgga aacacccata ctgcttatat catttgtcgt     420

caagttgaac aggcatccgc taaactaggg attgacttat cccaagcaac ggttgctatt     480

tgcggggcaa ccggagatat tggcagtgca gtgtgtcgtt ggttagatag aaaaaccgat     540

acccaggaac tattcttaat tgctcgcaat aaagaacgat tacaacgact gcaagatgag     600
```

-continued

```
ttgggacggg gtaaaattat gggattggag gaggctttac ccgaagcaga tattatcgtt    660

tgggtggcga gtatgcccaa aggagtggaa attaatgccg aaactctcaa aaaaccctgt    720

ttaattatcg atggtggtta tcctaagaat ttagacacaa aaattaaaca tcctgatgtc    780

catatcctga aagggggaat tgtagaacat tctctagata ttgactggaa gattatggaa    840

actgtcaata tggatgttcc ttctcgtcaa atgtttgctt gttttgccga agccatttta    900

ttagagtttg aacaatggca cactaatttt tcttggggac gcaatcaaat tacagtgact    960

aaaatggaac aaataggaga agcttctgtc aaacatgggt tacaaccgtt gttgagttgg   1020

taa                                                                 1023


<210> SEQ ID NO 31
<211> LENGTH: 696
<212> TYPE: DNA
<213> ORGANISM: Cyanthece sp.

<400> SEQUENCE: 31

atgcaagagc ttgctttacg ctcagagctt gattttaaca gcgaaaccta taaagatgct     60

tacagtcgca tcaatgctat tgtcattgaa ggggaacaag aagcctatca aaattatctt    120

gatatggcgc aacttctccc agaagacgag gctgagttaa ttcgtctctc caagatggaa    180

aaccgtcaca aaaaaggctt tcaagcctgt ggcaagaatt tgaatgtgac cccagatatg    240

gactacgctc aacaattttt tgctgaactt catggcaact tccaaaaggc aaaagccgaa    300

ggcaaaattg tcacttgctt attaattcaa tctttgatca tcgaagcctt tgcgatcgcc    360

gcttataata tttatattcc tgtggcagat ccctttgctc gtaaaatcac cgaagggggta    420

gttaaggatg aatataccca cctcaatttt ggggaagtct ggttaaaaga gcattttgaa    480

gcctctaaag cagaattaga agacgcaaat aaagaaaatt taccccttgt ttggcaaatg    540

ctcaaccaag ttgaaaaaga tgccgaagtg ttagggatgg agaaagaagc cttagtggaa    600

gatttcatga ttagttatgg agaagcttta agtaatattg gtttctctac ccgtgagatc    660

atgaaaatgt ctgcttacgg gctacgggct gcttaa                              696


<210> SEQ ID NO 32
<211> LENGTH: 364
<212> TYPE: PRT
<213> ORGANISM: Candida boidinii

<400> SEQUENCE: 32

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
```

```
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360


<210> SEQ ID NO 33
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95

His Ile Asp Leu Asp Tyr Ile Asn Gln Thr Gly Lys Lys Ile Ser Val
            100                 105                 110
```

```
Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Ser His Gln Ala Leu Pro Lys Glu Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Thr Ala Tyr Gly Lys His Asp Lys Lys
        355                 360


<210> SEQ ID NO 34
<211> LENGTH: 5758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

gaaaggctct tgaggctatc atgacagaag catcgcagcc tataaaatac gctggaaaag      60

aatataaata tgctgtttcg tatcatgtcc taaatgctgc tgattttggt gttccgcaat     120

ttagagaaag agtattcatc gtaggtaatc gtttgggcaa aacattccaa tttcctgaac     180

caactcatgg gcctagcaac caagcgagac agatagatct ttttggcaag cagctaaaac     240

cttacaaaac tgttcaagat gcaattagca ctctcccccc tgcaacccct ccttcagcga     300

tggcactaag agtttcgcag accataaaag ataggataaa gaatcatgga tattaaaaac     360

gttcatatca aaaatcacga acaaacagct catgcacctt ccactctaga aaaaattcgt     420

aaagtcaaac aagggggtaa actctcagaa cagacaaaga catttggttc aacctaccgc     480

aggttagatc cgaaccagcc atctcctaca gtgacccgta gtggttatcg agattttatt     540

catccttttg aagatcgaat gctcacagtt cgtgaactgg cttgtttgca aacctttccc     600
```

-continued

```
cttgattggg agtttaccgg aactcgactt gattcttata gtagtaaacg taaagtgacg    660
atgactcagt ttggacaagt gggtaatgca gtaccgccgt tacttgctga agctgttgct    720
aaagcggtta gcgaacagct tctggatgtc gcggccgcag attgataacc caaacctata    780
gaataattaa gaatctccaa agcaacagtt attgcattgg gtatcaacta agctgatcct    840
aagcataaga cctacgacaa tatcacaggc ttgcggatgg ttgcatcatc tcgctgagtt    900
ttgcactgct caattttgcc ccatttgcgg ggaatcgtag cgttcacact acccattgca    960
aaggttgccc gtagagattg ctctattcgg cacagtcact gttaaagagg aacaacgcat   1020
atgcagtcga cataacccgg gtaatgacag atctgcggat ccattagctc gaggcgagct   1080
cagactgttg tacagcatgc tagctacaca gacgcgtcca tggtaggtac ctgttaacgt   1140
tagaccggtc aggatctgca gatgacaccg cggtgcagct gaaggccacg tgggccgtag   1200
ggaattcact agtttttaat taacgtgcta taattatact aattttataa ggaggaaaaa   1260
atatgggcat ttttagtatt tttgtaatca gcacagttca ttatcaacca aacaaaaaat   1320
aagtggttat aatgaatcgt taataagcaa aattcatata accaaattaa agagggttat   1380
aatgaacgag aaaaatataa aacacagtca aaactttatt acttcaaaac ataatataga   1440
taaaataatg acaaatataa gattaaatga acatgataat atctttgaaa tcggctcagg   1500
aaaaggccat tttacccttg aattagtaaa gaggtgtaat ttcgtaactg ccattgaaat   1560
agaccataaa ttatgcaaaa ctacagaaaa taaacttgtt gatcacgata atttccaagt   1620
tttaaacaag gatatattgc agtttaaatt tcctaaaaac caatcctata aaatatatgg   1680
taatatacct tataacataa gtacggatat aatacgcaaa attgtttttg atagtatagc   1740
taatgagatt tatttaatcg tggaatacgg gtttgctaaa agattattaa atacaaaacg   1800
ctcattggca ttacttttaa tggcagaagt tgatatttct atattaagta tggttccaag   1860
agaatatttt catcctaaac ctaaagtgaa tagctcactt atcagattaa gtagaaaaaa   1920
atcaagaata tcacacaaag ataaacaaaa gtataattat ttcgttatga aatgggttaa   1980
caaagaatac aagaaaatat ttacaaaaaa tcaatttaac aattccttaa aacatgcagg   2040
aattgacgat ttaaacaata ttagctttga acaattctta tctcttttca atagctataa   2100
attatttaat aagtaagtta agggatgcat aaactgcatc ccttaacttg tttttcgtgt   2160
gcctattttt tgtggcgcgc cctttacaaa atcaaacccg atcgcctctc tattttgata   2220
aatctatgtc tactccctct gttacccctg tagaatctag caccctaatc aaaacccctg   2280
aactgctggc tccggcggga aattgggact gtgcgatcac cgccgtggag aatggggctg   2340
atgcgattta ttttgggctg gataaattta atgcccggat gcgatcacaa aactttgtcg   2400
agtcagattt gccggagttg atggcatact tacatcggcg cggcgtgaag ggctatgtga   2460
cgttaaatac gctgattttc acctcggaat tggcggcagt cgaacaatat ttgcggtcga   2520
ttattgcggc gggagtcgat gcggcgatcg tccaggatgt ggggctgtgc caattaattt   2580
ggcaattgtc gcccgatttt ccgatccatg gttcgacgca aatgaccgtc accagcgccg   2640
caggggtcga gttcgcgcaa aacttgggtt gtgatttggt ggtattggcg cgggaatgtt   2700
cgatcaagga aatcaataaa atccagcagg aattgggtca acaaaagatc tcaatgccgc   2760
tagaagtgtt tgtccacggg gcgttgtgcg tcgcctattc tgggcaatgt ttaaccagtg   2820
aatccctcgg cggacggtcg gccaatcgcg gagaatgcgc ccaagcctgc cggatgccct   2880
acgaaatgat tgtcgatggt aggccatttg atctgagcga cagacgttac cggccggcca   2940
aaatgaagtg aagttcctat acttaagctt aaaatgaagt gaagttccta tactttctag   3000
```

-continued agaataggaa cttctatagt gagtcgaata agggcgacac aaaatttatt ctaaatgcat 3060
aataaatact gataacatct tatagtttgt attatatttt gtattatcgt tgacatgtat 3120
aattttgata tcaaaaactg attttccctt tattattttc gagatttatt ttcttaattc 3180
tctttaacaa actagaaata ttgtatatac aaaaaatcat aaataataga tgaatagttt 3240
aattataggt gttcatcaat cgaaaaagca acgtatctta tttaaagtgc gttgcttttt 3300
tctcatttat aaggttaaat aattctcata tatcaagcaa agtgacaggc gcccttaaat 3360
attctgacaa atgctctttc cctaaactcc ccccataaaa aaacccgccg aagcgggttt 3420
ttacgttatt tgcggattaa cgattactcg ttatcagaac cgcccagggg gcccgagctt 3480
aagactggcc gtcgttttac aacacagaaa gagtttgtag aaacgcaaaa aggccatccg 3540
tcaggggcct tctgcttagt ttgatgcctg gcagttccct actctcgcct tccgcttcct 3600
cgctcactga ctcgctgcgc tcggtcgttc ggctgcggcg agcggtatca gctcactcaa 3660
aggcggtaat acggttatcc acagaatcag gggataacgc aggaaagaac atgtgagcaa 3720
aaggccagca aaaggccagg aaccgtaaaa aggccgcgtt gctggcgttt ttccataggc 3780
tccgcccccc tgacgagcat cacaaaaatc gacgctcaag tcagaggtgg cgaaacccga 3840
caggactata aagataccag gcgtttcccc ctggaagctc cctcgtgcgc tctcctgttc 3900
cgaccctgcc gcttaccgga tacctgtccg cctttctccc ttcgggaagc gtggcgcttt 3960
ctcatagctc acgctgtagg tatctcagtt cggtgtaggt cgttcgctcc aagctgggct 4020
gtgtgcacga accccccgtt cagcccgacc gctgcgcctt atccggtaac tatcgtcttg 4080
agtccaaccc ggtaagacac gacttatcgc cactggcagc agccactggt aacaggatta 4140
gcagagcgag gtatgtaggc ggtgctacag agttcttgaa gtggtggcct aactacggct 4200
acactagaag aacagtattt ggtatctgcg ctctgctgaa gccagttacc ttcggaaaaa 4260
gagttggtag ctcttgatcc ggcaaacaaa ccaccgctgg tagcggtggt ttttttgttt 4320
gcaagcagca gattacgcgc agaaaaaaag gatctcaaga agatcctttg atcttttcta 4380
cggggtctga cgctcagtgg aacgacgcgc gcgtaactca cgttaaggga ttttggtcat 4440
gagcttgcgc cgtcccgtca agtcagcgta atgctctgct tttagaaaaa ctcatcgagc 4500
atcaaatgaa actgcaattt attcatatca ggattatcaa taccatattt ttgaaaaagc 4560
cgtttctgta atgaaggaga aaactcaccg aggcagttcc ataggatggc aagatcctgg 4620
tatcggtctg cgattccgac tcgtccaaca tcaatacaac ctattaattt cccctcgtca 4680
aaaataaggt tatcaagtga gaaatcacca tgagtgacga ctgaatccgg tgagaatggc 4740
aaaagtttat gcatttcttt ccagacttgt tcaacaggcc agccattacg ctcgtcatca 4800
aaatcactcg catcaaccaa accgttattc attcgtgatt gcgcctgagc gaggcgaaat 4860
acgcgatcgc tgttaaaagg acaattacaa acaggaatcg agtgcaaccg gcgcaggaac 4920
actgccagcg catcaacaat attttcacct gaatcaggat attcttctaa tacctggaac 4980
gctgtttttc cggggatcgc agtggtgagt aaccatgcat catcaggagt acggataaaa 5040
tgcttgatgg tcggaagtgg cataaattcc gtcagccagt ttagtctgac catctcatct 5100
gtaacatcat tggcaacgct acctttgcca tgtttcagaa acaactctgg cgcatcgggc 5160
ttcccataca agcgatagat tgtcgcacct gattgcccga cattatcgcg agcccattta 5220
tacccatata aatcagcatc catgttggaa tttaatcgcg gcctcgacgt ttcccgttga 5280
atatggctca tattcttcct ttttcaatat tattgaagca tttatcaggg ttattgtctc 5340

```
atgagcggat acatatttga atgtatttag aaaaataaac aaataggggt cagtgttaca   5400
accaattaac caattctgaa cattatcgcg agcccattta tacctgaata tggctcataa   5460
caccccttgt ttgcctggcg gcagtagcgc ggtggtccca cctgacccca tgccgaactc   5520
agaagtgaaa cgccgtagcg ccgatggtag tgtggggact ccccatgcga gagtagggaa   5580
ctgccaggca tcaaataaaa cgaaaggctc agtcgaaaga ctgggccttt cgcccgggct   5640
aattaggggg tgtcgccctt attcgactct atagtgaagt tcctattctc tagaaagtat   5700
aggaacttct gaagtgggga agcttaagta taggaacttc tgaagtgggg cctgcagg     5758
```

<210> SEQ ID NO 35
<211> LENGTH: 6096
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
gaaaggctct tgaggctatc atgacagaag catcgcagcc tataaaatac gctggaaaag     60
aatataaata tgctgtttcg tatcatgtcc taaatgctgc tgattttggt gttccgcaat    120
ttagagaaag agtattcatc gtaggtaatc gtttgggcaa aacattccaa tttcctgaac    180
caactcatgg gcctagcaac caagcgagac agatagatct ttttggcaag cagctaaaac    240
cttacaaaac tgttcaagat gcaattagca ctctcccccc tgcaacccct ccttcagcga    300
tggcactaag agtttcgcag accataaaag ataggataaa gaatcatgga tattaaaaac    360
gttcatatca aaaatcacga acaaacagct catgcacctt ccactctaga aaaaattcgt    420
aaagtcaaac aagggggtaa actctcagaa cagacaaaga catttggttc aacctaccgc    480
aggttagatc cgaaccagcc atctcctaca gtgacccgta gtggttatcg agattttatt    540
catccttttg aagatcgaat gctcacagtt cgtgaactgg cttgtttgca aacctttccc    600
cttgattggg agtttaccgg aactcgactt gattcttata gtagtaaacg taaagtgacg    660
atgactcagt ttggacaagt gggtaatgca gtaccgccgt tacttgctga agctgttgct    720
aaagcggtta gcgaacagct tctggatgtc gcggccgcgt cgacttcgtt ataaaataaa    780
cttaacaaat ctatacccac ctgtagagaa gagtccctga atatcaaaat ggtgggataa    840
aaagctcaaa aaggaaagta ggctgtggtt ccctaggcaa cagtcttccc taccccactg    900
gaaactaaaa aaacgagaaa agttcgcacc gaacatcaat tgcataattt tagccctaaa    960
acataagctg aacgaaactg gttgtcttcc cttcccaatc caggacaatc tgagaatccc   1020
ctgcaacatt acttaacaaa aaagcaggaa taaaattaac aagatgtaac agacataagt   1080
cccatcaccg ttgtataaag ttaactgtgg gattgcaaaa gcattcaagc ctaggcgctg   1140
agctgtttga gcatcccggt ggcccttgtc gctgcctccg tgtttctccc tggatttatt   1200
taggtaatat ctctcataaa tccccgggta gttaacgaaa gttaatggag atcagtaaca   1260
ataactctag ggtcattact ttggactccc tcagtttatc cgggggaatt gtgtttaaga   1320
aaatcccaac tcataaagtc aagtaggaga ttaatcatat gcagtcgaca taacccgggt   1380
aatgacagat ctgcggatcc attagctcga ggcgagctca gactgttgta cagcatgcta   1440
gctacacaga cgcgtccatg gtaggtacct gttaacgtta gaccggtcag gatctgcaga   1500
tgacaccgcg gtgcagctga aggccacgtg ggccgtaggg aattcactag tttttaatta   1560
acgtgctata attatactaa ttttataagg aggaaaaaat atgggcattt ttagtatttt   1620
```

-continued

```
tgtaatcagc acagttcatt atcaaccaaa caaaaaataa gtggttataa tgaatcgtta    1680
ataagcaaaa ttcatataac caaattaaag agggttataa tgaacgagaa aaatataaaa    1740
cacagtcaaa actttattac ttcaaaacat aatatagata aaataatgac aaatataaga    1800
ttaaatgaac atgataatat ctttgaaatc ggctcaggaa aaggccattt taccccttgaa   1860
ttagtaaaga ggtgtaattt cgtaactgcc attgaaatag accataaatt atgcaaaact    1920
acagaaaata aacttgttga tcacgataat ttccaagttt taaacaagga tatattgcag    1980
tttaaatttc ctaaaaacca atcctataaa atatatggta ataaccctta taacataagt    2040
acggatataa tacgcaaaat tgtttttgat agtatagcta atgagattta tttaatcgtg    2100
gaatacgggt ttgctaaaag attattaaat acaaaacgct cattggcatt acttttaatg    2160
gcagaagttg atatttctat attaagtatg gttccaagag aatattttca tcctaaacct    2220
aaagtgaata gctcacttat cagattaagt agaaaaaaat caagaatatc acacaaagat    2280
aaacaaaagt ataattattt cgttatgaaa tgggttaaca aagaatacaa gaaaatattt    2340
acaaaaaatc aatttaacaa ttccttaaaa catgcaggaa ttgacgattt aaacaatatt    2400
agctttgaac aattcttatc tcttttcaat agctataaat tatttaataa gtaagttaag    2460
ggatgcataa actgcatccc ttaacttgtt tttcgtgtgc ctattttttg tggcgcgccc    2520
tttacaaaat caaacccgat cgcctctcta ttttgataaa tctatgtcta ctccctctgt    2580
taccccctgta gaatctagca ccctaatcaa aacccctgaa ctgctggctc cggcgggaaa    2640
ttgggactgt gcgatcaccg ccgtggagaa tggggctgat gcgatttatt ttgggctgga    2700
taaatttaat gcccggatgc gatcacaaaa ctttgtcgag tcagatttgc cggagttgat    2760
ggcatactta catcggcgcg gcgtgaaggg ctatgtgacg ttaaatacgc tgattttcac    2820
ctcggaattg gcggcagtcg aacaatattt gcggtcgatt attgcggcgg gagtcgatgc    2880
ggcgatcgtc caggatgtgg ggctgtgcca attaatttgg caattgtcgc ccgattttcc    2940
gatccatggt tcgacgcaaa tgaccgtcac cagcgccgca ggggtcgagt tcgcgcaaaa    3000
cttgggttgt gatttggtgg tattggcgcg ggaatgttcg atcaaggaaa tcaataaaat    3060
ccagcaggaa ttgggtcaac aaaagatctc aatgccgcta gaagtgtttg tccacggggc    3120
gttgtgcgtc gcctattctg ggcaatgttt aaccagtgaa tccctcggcg gacggtcggc    3180
caatcgcgga gaatgcgccc aagcctgccg gatgccctac gaaatgattg tcgatggtag    3240
gccatttgat ctgagcgaca gacgttaccg gccggccaaa atgaagtgaa gttcctatac    3300
ttaagcttaa aatgaagtga agttcctata ctttctagag aataggaact tctatagtga    3360
gtcgaataag ggcgacacaa aatttattct aaatgcataa taaatactga taacatctta    3420
tagtttgtat tatattttgt attatcgttg acatgtataa ttttgatatc aaaaactgat    3480
tttcccttta ttattttcga gatttatttt cttaattctc tttaacaaac tagaaatatt    3540
gtatatacaa aaaatcataa ataatagatg aatagtttaa ttataggtgt tcatcaatcg    3600
aaaaagcaac gtatcttatt taaagtgcgt tgcttttttc tcatttataa ggttaaataa    3660
ttctcatata tcaagcaaag tgacaggcgc ccttaaatat tctgacaaat gctctttccc    3720
taaactcccc ccataaaaaa acccgccgaa gcgggttttt acgttatttg cggattaacg    3780
attactcgtt atcagaaccg cccagggggc ccgagcttaa gactggccgt cgttttacaa    3840
cacagaaaga gtttgtagaa acgcaaaaag gccatccgtc aggggccttc tgcttagttt    3900
gatgcctggc agttccctac tctcgccttc cgcttcctcg ctcactgact cgctgcgctc    3960
ggtcgttcgg ctgcggcgag cggtatcagc tcactcaaag gcggtaatac ggttatccac    4020
```

agaatcaggg gataacgcag gaaagaacat gtgagcaaaa ggccagcaaa aggccaggaa 4080
ccgtaaaaag gccgcgttgc tggcgttttt ccataggctc cgcccccctg acgagcatca 4140
caaaaatcga cgctcaagtc agaggtggcg aaacccgaca ggactataaa gataccaggc 4200
gtttccccct ggaagctccc tcgtgcgctc tcctgttccg accctgccgc ttaccggata 4260
cctgtccgcc tttctccctt cgggaagcgt ggcgctttct catagctcac gctgtaggta 4320
tctcagttcg gtgtaggtcg ttcgctccaa gctgggctgt gtgcacgaac cccccgttca 4380
gcccgaccgc tgcgccttat ccggtaacta tcgtcttgag tccaacccgg taagacacga 4440
cttatcgcca ctggcagcag ccactggtaa caggattagc agagcgaggt atgtaggcgg 4500
tgctacagag ttcttgaagt ggtggcctaa ctacggctac actagaagaa cagtatttgg 4560
tatctgcgct ctgctgaagc cagttacctt cggaaaaaga gttggtagct cttgatccgg 4620
caaacaaacc accgctggta gcggtggttt ttttgtttgc aagcagcaga ttacgcgcag 4680
aaaaaaagga tctcaagaag atcctttgat cttttctacg gggtctgacg ctcagtggaa 4740
cgacgcgcgc gtaactcacg ttaagggatt ttggtcatga gcttgcgccg tcccgtcaag 4800
tcagcgtaat gctctgcttt tagaaaaact catcgagcat caaatgaaac tgcaatttat 4860
tcatatcagg attatcaata ccatattttt gaaaaagccg tttctgtaat gaaggagaaa 4920
actcaccgag gcagttccat aggatggcaa gatcctggta tcggtctgcg attccgactc 4980
gtccaacatc aatacaacct attaatttcc cctcgtcaaa aataaggtta tcaagtgaga 5040
aatcaccatg agtgacgact gaatccggtg agaatggcaa aagtttatgc atttctttcc 5100
agacttgttc aacaggccag ccattacgct cgtcatcaaa atcactcgca tcaaccaaac 5160
cgttattcat tcgtgattgc gcctgagcga ggcgaaatac gcgatcgctg ttaaaaggac 5220
aattacaaac aggaatcgag tgcaaccggc gcaggaacac tgccagcgca tcaacaatat 5280
tttcacctga atcaggatat tcttctaata cctggaacgc tgtttttccg gggatcgcag 5340
tggtgagtaa ccatgcatca tcaggagtac ggataaaatg cttgatggtc ggaagtggca 5400
taaattccgt cagccagttt agtctgacca tctcatctgt aacatcattg gcaacgctac 5460
ctttgccatg tttcagaaac aactctggcg catcgggctt cccatacaag cgatagattg 5520
tcgcacctga ttgcccgaca ttatcgcgag cccatttata cccatataaa tcagcatcca 5580
tgttggaatt taatcgcggc ctcgacgttt cccgttgaat atggctcata ttcttccttt 5640
ttcaatatta ttgaagcatt tatcagggtt attgtctcat gagcggatac atatttgaat 5700
gtatttagaa aaataaacaa ataggggtca gtgttacaac caattaacca attctgaaca 5760
ttatcgcgag cccatttata cctgaatatg gctcataaca ccccttgttt gcctggcggc 5820
agtagcgcgg tggtcccacc tgaccccatg ccgaactcag aagtgaaacg ccgtagcgcc 5880
gatggtagtg tggggactcc ccatgcgaga gtagggaact gccaggcatc aaataaaacg 5940
aaaggctcag tcgaaagact gggcctttcg cccgggctaa ttagggggtg tcgcccttat 6000
tcgactctat agtgaagttc ctattctcta gaaagtatag gaacttctga agtggggaag 6060
cttaagtata ggaacttctg aagtggggcc tgcagg 6096

<210> SEQ ID NO 36
<211> LENGTH: 1104
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36

```
catatgaaga tcgtgctggt cctgtacgac gcaggcaagc atgcggcgga cgaagagaag      60
ctgtatggct gtaccgaaaa caagctgggt atcgcgaatt ggctgaagga tcagggtcac     120
gagctgatta ctacctctga caaagagggt gaaacgagcg agctggacaa acacattcct     180
gatgcggata tcatcattac caccccgttc cacccggcct acatcacgaa ggaacgtctg     240
gataaggcta aaaacttgaa gctggtcgtg gtagctggtg ttggcagcga ccacatcgac     300
ctggactaca ttaaccagac cggcaaaaag atttccgttc tggaagtcac gggtagcaat     360
gttgtctcgg tggccgagca cgttgtgatg accatgctgg tgctggttcg caattttgtt     420
ccggcgcacg aacagatcat caatcacgac tgggaagtgg cagcgattgc gaaggatgcg     480
tacgacatcg aaggtaagac cattgcgacc attggtgcag gccgcatcgg ttaccgtgtg     540
ctggagcgtc tgctgccatt taacccgaaa gagctgctgt attatgacta tcaggcgctg     600
ccgaaagaag cggaagagaa agttggcgct cgtcgcgtcg agaacatcga ggaactggtc     660
gcgcaagcag atattgttac cgtgaatgcc ccgctgcatg cgggtacgaa aggtctgatt     720
aacaaagagt tgctgagcaa attcaagaaa ggcgcgtggt tggtgaatac ggcccgtggt     780
gccatttgcg tcgcagagga cgtcgctgcc gcactggaga gcggccagtt gcgtggttat     840
ggcggtgacg tttggttccc acaaccggca ccgaaagacc atccgtggcg cgatatgcgt     900
aacaaatacg gtgcgggcaa tgccatgacg ccgcattaca gcggtaccac cctggatgcg     960
caaactcgct atgcagaagg caccaaaaac atcctggaga gcttttcac gggtaagttt    1020
gattaccgtc cgcaagatat cattttgttg aacggtgagt atgtgaccaa ggcttacggt    1080
aaacatgata agaaataact cgag                                          1104
```

<210> SEQ ID NO 37
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
catatggcga ccgtcctctg cgtgctgtac cccgaccccg tcgacggcta tccgccgcgc      60
tacgtgcgcg acacgattcc cgtcatcacg cactacgcgg acggccagct cgcgccgacg     120
ccgtccgggc cgcccggttt tcggccgggc gaactcgtcg gctcggtatc gggcgcgctc     180
gggttgcgcg actatctggc ggcgcacggt catacgctga tcgtgacgag cgacaaggac     240
ggccccgact ccgaattcga gcgccggctg ccggaagcgg acgtcgtgat ttcgcagccg     300
ttctggcccg cgtatctgac cgccgagggg atcgcgcgcg cgccgaagct gcggctcgcg     360
ctgactgcgg gcatcggctc cgatcacgtc gatctcgcgg cggccgcgcg cgcgggcatc     420
accgtcgcgg aagtcaccgg atcgaacagc gtcagcgtcg ccgagcatgt cgtgatgacg     480
acgcttgcgc tcgtgcgcaa ctatctgccg tcgcacgcga tcgcgcagca aggcggctgg     540
aacatcgccg actgcgtatc gcgcagctac gacatcgagg gcatgcattt cggcacggtc     600
ggcgccggcc gcatcgggct cgcggtgctg cggcggctga agccgttcgg gctggcgctg     660
cactatacgc agcggcatcg gctcgatccg gcgatcgaac acgaactcgc gctgacctat     720
cacgcggacg tcgcgtcgct cgcgagcgcg gtcgacatcg tgaatctgca gattccgctc     780
tatccgtcga ccgagcatct gttcgatgcc gcaatgatcg cgcgcatgaa gcgcggcgcg     840
```

tatctgatca acaccgcgcg cgcgaaactc gtcgatcgcg acgcggtcgt gcgtgcggtc 900
gcctcgggcc atctggccgg ctacggcggc gacgtgtggt ttcccgagcc cgcaccggcc 960
gatcatccgt ggcgcgcgat gccgttcaac gggatgacgc cgcatatctc gggcacgtcg 1020
ctgtccgcgc aggcgcgcta cgcggccggt acgctcgaaa ttctgcagtg ctggttcgag 1080
cgccggccga ttcgcgaggc ctacctgatc gtcgacggcg gcacgctcgc gggcaccggc 1140
gagcagtcgt accggctcac gtgactcgag 1170

<210> SEQ ID NO 38
<211> LENGTH: 6806
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
gaaaggctct tgaggctatc atgacagaag catcgcagcc tataaaatac gctggaaaag 60
aatataaata tgctgtttcg tatcatgtcc taaatgctgc tgattttggt gttccgcaat 120
ttagagaaag agtattcatc gtaggtaatc gtttgggcaa aacattccaa tttcctgaac 180
caactcatgg gcctagcaac caagcgagac agatagatct ttttggcaag cagctaaaac 240
cttacaaaac tgttcaagat gcaattagca ctctcccccc tgcaacccct ccttcagcga 300
tggcactaag agtttcgcag accataaaag ataggataaa gaatcatgga tattaaaaac 360
gttcatatca aaaatcacga acaaacagct catgcacctt ccactctaga aaaaattcgt 420
aaagtcaaac aagggggtaa actctcagaa cagacaaaga catttggttc aacctaccgc 480
aggttagatc cgaaccagcc atctcctaca gtgacccgta gtggttatcg agattttatt 540
catccttttg aagatcgaat gctcacagtt cgtgaactgg cttgtttgca aacctttccc 600
cttgattggg agtttaccgg aactcgactt gattcttata gtagtaaacg taaagtgacg 660
atgactcagt ttggacaagt gggtaatgca gtaccgccgt tacttgctga agctgttgct 720
aaagcggtta gcgaacagct tctggatgtc gcggccgcag attgataacc caaacctata 780
gaataattaa gaatctccaa agcaacagtt attgcattgg gtatcaacta agctgatcct 840
aagcataaga cctacgacaa tatcacaggc ttgcggatgg ttgcatcatc tcgctgagtt 900
ttgcactgct caattttgcc ccatttgcgg ggaatcgtag cgttcacact acccattgca 960
aaggttgccc gtagagattg ctctattcgg cacagtcact gttaaagagg aacaacgcat 1020
atgaagatcg tgctggtcct gtacgacgca ggcaagcatg cggcggacga agagaagctg 1080
tatggctgta ccgaaaacaa gctgggtatc gcgaattggc tgaaggatca gggtcacgag 1140
ctgattacta cctctgacaa agagggtgaa acgagcgagc tggacaaaca cattcctgat 1200
gcggatatca tcattaccac cccgttccac ccggcctaca tcacgaagga acgtctggat 1260
aaggctaaaa acttgaagct ggtcgtggta gctggtgttg gcagcgacca catcgacctg 1320
gactacatta accagaccgg caaaaagatt tccgttctgg aagtcacggg tagcaatgtt 1380
gtctcggtgg ccgagcacgt tgtgatgacc atgctggtgc tggttcgcaa ttttgttccg 1440
gcgcacgaac agatcatcaa tcacgactgg gaagtggcag cgattgcgaa ggatgcgtac 1500
gacatcgaag gtaagaccat tgcgaccatt ggtgcaggcc gcatcggtta ccgtgtgctg 1560
gagcgtctgc tgccatttaa cccgaaagag ctgctgtatt atgactatca ggcgctgccg 1620
aaagaagcgg aagagaaagt tggcgctcgt cgcgtcgaga acatcgagga actggtcgcg 1680

-continued caagcagata ttgttaccgt gaatgccccg ctgcatgcgg gtacgaaagg tctgattaac 1740
aaagagttgc tgagcaaatt caagaaaggc gcgtggttgg tgaatacggc ccgtggtgcc 1800
atttgcgtcg cagaggacgt cgctgccgca ctggagagcg gccagttgcg tggttatggc 1860
ggtgacgttt ggttcccaca accggcaccg aaagaccatc cgtggcgcga tatgcgtaac 1920
aaatacggtg cgggcaatgc catgacgccg cattacagcg gtaccaccct ggatgcgcaa 1980
actcgctatg cagaaggcac caaaaacatc ctggagagct tttcacggg taagtttgat 2040
taccgtccgc aagatatcat tttgttgaac ggtgagtatg tgaccaaggc ttacggtaaa 2100
catgataaga aataactcga ggcgagctca gactgttgta cagcatgcta gctacacaga 2160
cgcgtccatg gtaggtacct gttaacgtta gaccggtcag gatctgcaga tgacaccgcg 2220
gtgcagctga aggccacgtg ggccgtaggg aattcactag tttttaatta acgtgctata 2280
attatactaa ttttataagg aggaaaaaat atgggcattt ttagtatttt tgtaatcagc 2340
acagttcatt atcaaccaaa caaaaaataa gtggttataa tgaatcgtta ataagcaaaa 2400
ttcatataac caaattaaag agggttataa tgaacgagaa aaatataaaa cacagtcaaa 2460
actttattac ttcaaaacat aatatagata aaataatgac aaatataaga ttaaatgaac 2520
atgataatat ctttgaaatc ggctcaggaa aaggccattt taccttgaa ttagtaaaga 2580
ggtgtaattt cgtaactgcc attgaaatag accataaatt atgcaaaact acagaaaata 2640
aacttgttga tcacgataat ttccaagttt taaacaagga tatattgcag tttaaatttc 2700
ctaaaaacca atcctataaa atatatggta atataccta taacataagt acggatataa 2760
tacgcaaaat tgtttttgat agtatagcta atgagattta tttaatcgtg gaatacgggt 2820
ttgctaaaag attattaaat acaaaacgct cattggcatt acttttaatg gcagaagttg 2880
atatttctat attaagtatg gttccaagag aatattttca tcctaaacct aaagtgaata 2940
gctcacttat cagattaagt agaaaaaaat caagaatatc acacaaagat aaacaaaagt 3000
ataattattt cgttatgaaa tgggttaaca aagaatacaa gaaaatattt acaaaaaatc 3060
aatttaacaa ttccttaaaa catgcaggaa ttgacgattt aaacaatatt agctttgaac 3120
aattcttatc tcttttcaat agctataaat tatttaataa gtaagttaag ggatgcataa 3180
actgcatccc ttaacttgtt tttcgtgtgc ctattttttg tggcgcgccc tttacaaaat 3240
caaacccgat cgcctctcta ttttgataaa tctatgtcta ctccctctgt taccctgta 3300
gaatctagca ccctaatcaa aacccctgaa ctgctggctc cggcgggaaa ttgggactgt 3360
gcgatcaccg ccgtggagaa tggggctgat gcgatttatt ttgggctgga taaatttaat 3420
gcccggatgc gatcacaaaa ctttgtcgag tcagatttgc cggagttgat ggcatactta 3480
catcggcgcg gcgtgaaggg ctatgtgacg ttaaatacgc tgattttcac ctcggaattg 3540
gcggcagtcg aacaatattt gcggtcgatt attgcggcgg gagtcgatgc ggcgatcgtc 3600
caggatgtgg ggctgtgcca attaatttgg caattgtcgc ccgattttcc gatccatggt 3660
tcgacgcaaa tgaccgtcac cagcgccgca ggggtcgagt tcgcgcaaaa cttgggttgt 3720
gatttggtgg tattggcgcg ggaatgttcg atcaaggaaa tcaataaaat ccagcaggaa 3780
ttgggtcaac aaaagatctc aatgccgcta gaagtgtttg tccacggggc gttgtgcgtc 3840
gcctattctg ggcaatgttt aaccagtgaa tccctcggcg gacggtcggc caatcgcgga 3900
gaatgcgccc aagcctgccg gatgccctac gaaatgattg tcgatggtag gccatttgat 3960
ctgagcgaca gacgttaccg gccggccaaa atgaagtgaa gttcctatac ttaagcttaa 4020

-continued

```
aatgaagtga agttcctata ctttctagag aataggaact tctatagtga gtcgaataag   4080
ggcgacacaa aatttattct aaatgcataa taaatactga taacatctta tagtttgtat   4140
tatattttgt attatcgttg acatgtataa ttttgatatc aaaaactgat tttcccttta   4200
ttattttcga gatttatttt cttaattctc tttaacaaac tagaaatatt gtatatacaa   4260
aaaatcataa ataatagatg aatagtttaa ttataggtgt tcatcaatcg aaaaagcaac   4320
gtatcttatt taaagtgcgt tgcttttttc tcatttataa ggttaaataa ttctcatata   4380
tcaagcaaag tgacaggcgc ccttaaatat tctgacaaat gctctttccc taaactcccc   4440
ccataaaaaa acccgccgaa gcgggttttt acgttatttg cggattaacg attactcgtt   4500
atcagaaccg cccagggggc ccgagcttaa gactggccgt cgttttacaa cacagaaaga   4560
gtttgtagaa acgcaaaaag gccatccgtc aggggccttc tgcttagttt gatgcctggc   4620
agttccctac tctcgccttc cgcttcctcg ctcactgact cgctgcgctc ggtcgttcgg   4680
ctgcggcgag cggtatcagc tcactcaaag gcggtaatac ggttatccac agaatcaggg   4740
gataacgcag gaaagaacat gtgagcaaaa ggccagcaaa aggccaggaa ccgtaaaaag   4800
gccgcgttgc tggcgttttt ccataggctc cgcccccctg acgagcatca caaaaatcga   4860
cgctcaagtc agaggtggcg aaacccgaca ggactataaa gataccaggc gtttccccct   4920
ggaagctccc tcgtgcgctc tcctgttccg accctgccgc ttaccggata cctgtccgcc   4980
tttctccctt cgggaagcgt ggcgctttct catagctcac gctgtaggta tctcagttcg   5040
gtgtaggtcg ttcgctccaa gctgggctgt gtgcacgaac cccccgttca gcccgaccgc   5100
tgcgccttat ccggtaacta tcgtcttgag tccaacccgg taagacacga cttatcgcca   5160
ctggcagcag ccactggtaa caggattagc agagcgaggt atgtaggcgg tgctacagag   5220
ttcttgaagt ggtgggctaa ctacggctac actagaagaa cagtatttgg tatctgcgct   5280
ctgctgaagc cagttacctt cggaaaaaga gttggtagct cttgatccgg caaacaaacc   5340
accgctggta gcggtggttt ttttgtttgc aagcagcaga ttacgcgcag aaaaaaagga   5400
tctcaagaag atcctttgat cttttctacg gggtctgacg ctcagtggaa cgacgcgcgc   5460
gtaactcacg ttaagggatt ttggtcatga gcttgcgccg tcccgtcaag tcagcgtaat   5520
gctctgcttt tagaaaaact catcgagcat caaatgaaac tgcaatttat tcatatcagg   5580
attatcaata ccatattttt gaaaaagccg tttctgtaat gaaggagaaa actcaccgag   5640
gcagttccat aggatggcaa gatcctggta tcggtctgcg attccgactc gtccaacatc   5700
aatacaacct attaatttcc cctcgtcaaa aataaggtta tcaagtgaga aatcaccatg   5760
agtgacgact gaatccggtg agaatggcaa aagtttatgc atttctttcc agacttgttc   5820
aacaggccag ccattacgct cgtcatcaaa atcactcgca tcaaccaaac cgttattcat   5880
tcgtgattgc gcctgagcga ggcgaaatac gcgatcgctg ttaaaaggac aattacaaac   5940
aggaatcgag tgcaaccggc gcaggaacac tgccagcgca tcaacaatat tttcacctga   6000
atcaggatat tcttctaata cctggaacgc tgtttttccg gggatcgcag tggtgagtaa   6060
ccatgcatca tcaggagtac ggataaaatg cttgatggtc ggaagtggca taaattccgt   6120
cagccagttt agtctgacca tctcatctgt aacatcattg gcaacgctac ctttgccatg   6180
tttcagaaac aactctggcg catcgggctt cccatacaag cgatagattg tcgcacctga   6240
ttgcccgaca ttatcgcgag cccatttata cccatataaa tcagcatcca tgttggaatt   6300
taatcgcggc ctcgacgttt cccgttgaat atggctcata ttcttccttt ttcaatatta   6360
ttgaagcatt tatcagggtt attgtctcat gagcggatac atatttgaat gtatttagaa   6420
```

aaataaacaa ataggggtca gtgttacaac caattaacca attctgaaca ttatcgcgag 6480
cccatttata cctgaatatg gctcataaca ccccttgttt gcctggcggc agtagcgcgg 6540
tggtcccacc tgaccccatg ccgaactcag aagtgaaacg ccgtagcgcc gatggtagtg 6600
tggggactcc ccatgcgaga gtagggaact gccaggcatc aaataaaacg aaaggctcag 6660
tcgaaagact gggcctttcg cccgggctaa ttagggggtg tcgcccttat tcgactctat 6720
agtgaagttc ctattctcta gaaagtatag gaacttctga agtggggaag cttaagtata 6780
ggaacttctg aagtggggcc tgcagg 6806

<210> SEQ ID NO 39
<211> LENGTH: 7144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
gaaaggctct tgaggctatc atgacagaag catcgcagcc tataaaatac gctggaaaag 60
aatataaata tgctgtttcg tatcatgtcc taaatgctgc tgattttggt gttccgcaat 120
ttagagaaag agtattcatc gtaggtaatc gtttgggcaa aacattccaa tttcctgaac 180
caactcatgg gcctagcaac caagcgagac agatagatct tttggcaag cagctaaaac 240 cttacaaaac tgttcaagat gcaattagca ctctcccccc tgcaacccct ccttcagcga 300
tggcactaag agtttcgcag accataaaag ataggataaa gaatcatgga tattaaaaac 360
gttcatatca aaaatcacga acaaacagct catgcacctt ccactctaga aaaaattcgt 420
aaagtcaaac aagggggtaa actctcagaa cagacaaaga catttggttc aacctaccgc 480
aggttagatc cgaaccagcc atctcctaca gtgacccgta gtggttatcg agattttatt 540
catccttttg aagatcgaat gctcacagtt cgtgaactgg cttgtttgca aacctttccc 600
cttgattggg agtttaccgg aactcgactt gattcttata gtagtaaacg taaagtgacg 660
atgactcagt ttggacaagt gggtaatgca gtaccgccgt tacttgctga agctgttgct 720
aaagcggtta gcgaacagct tctggatgtc gcggccgcgt cgacttcgtt ataaaataaa 780
cttaacaaat ctatacccac ctgtagagaa gagtccctga atatcaaaat ggtgggataa 840
aaagctcaaa aaggaaagta ggctgtggtt ccctaggcaa cagtcttccc taccccactg 900
gaaactaaaa aaacgagaaa agttcgcacc gaacatcaat tgcataattt tagccctaaa 960
acataagctg aacgaaactg gttgtcttcc cttcccaatc caggacaatc tgagaatccc 1020
ctgcaacatt acttaacaaa aaagcaggaa taaaattaac aagatgtaac agacataagt 1080
cccatcaccg ttgtataaag ttaactgtgg gattgcaaaa gcattcaagc ctaggcgctg 1140
agctgtttga gcatcccggt ggcccttgtc gctgcctccg tgtttctccc tggatttatt 1200
taggtaatat ctctcataaa tccccgggta gttaacgaaa gttaatggag atcagtaaca 1260
ataactctag ggtcattact ttggactccc tcagtttatc cgggggaatt gtgtttaaga 1320
aaatcccaac tcataaagtc aagtaggaga ttaatcatat gaagatcgtg ctggtcctgt 1380
acgacgcagg caagcatgcg gcggacgaag agaagctgta tggctgtacc gaaaacaagc 1440
tgggtatcgc gaattggctg aaggatcagg gtcacgagct gattactacc tctgacaaag 1500
agggtgaaac gagcgagctg gacaaacaca ttcctgatgc ggatatcatc attaccaccc 1560
cgttccaccc ggcctacatc acgaaggaac gtctggataa ggctaaaaac ttgaagctgg 1620

-continued

```
tcgtggtagc tggtgttggc agcgaccaca tcgacctgga ctacattaac cagaccggca   1680
aaaagatttc cgttctggaa gtcacgggta gcaatgttgt ctcggtggcc gagcacgttg   1740
tgatgaccat gctggtgctg gttcgcaatt ttgttccggc gcacgaacag atcatcaatc   1800
acgactggga agtggcagcg attgcgaagg atgcgtacga catcgaaggt aagaccattg   1860
cgaccattgg tgcaggccgc atcggttacc gtgtgctgga gcgtctgctg ccatttaacc   1920
cgaaagagct gctgtattat gactatcagg cgctgccgaa agaagcggaa gagaaagttg   1980
gcgctcgtcg cgtcgagaac atcgaggaac tggtcgcgca agcagatatt gttaccgtga   2040
atgccccgct gcatgcgggt acgaaaggtc tgattaacaa agagttgctg agcaaattca   2100
agaaaggcgc gtggttggtg aatacggccc gtggtgccat ttgcgtcgca gaggacgtcg   2160
ctgccgcact ggagagcggc cagttgcgtg gttatggcgg tgacgtttgg ttcccacaac   2220
cggcaccgaa agaccatccg tggcgcgata tgcgtaacaa atacggtgcg ggcaatgcca   2280
tgacgccgca ttacagcggt accaccctgg atgcgcaaac tcgctatgca gaaggcacca   2340
aaaacatcct ggagagcttt ttcacgggta agtttgatta ccgtccgcaa gatatcattt   2400
tgttgaacgg tgagtatgtg accaaggctt acggtaaaca tgataagaaa taactcgagg   2460
cgagctcaga ctgttgtaca gcatgctagc tacacagacg cgtccatggt aggtacctgt   2520
taacgttaga ccggtcagga tctgcagatg acaccgcggt gcagctgaag gccacgtggg   2580
ccgtagggaa ttcactagtt tttaattaac gtgctataat tatactaatt ttataaggag   2640
gaaaaaatat gggcattttt agtatttttg taatcagcac agttcattat caaccaaaca   2700
aaaaataagt ggttataatg aatcgttaat aagcaaaatt catataacca aattaaagag   2760
ggttataatg aacgagaaaa atataaaaca cagtcaaaac tttattactt caaaacataa   2820
tatagataaa ataatgacaa atataagatt aaatgaacat gataatatct ttgaaatcgg   2880
ctcaggaaaa ggccatttta cccttgaatt agtaaagagg tgtaatttcg taactgccat   2940
tgaaatagac cataaattat gcaaaactac agaaaataaa cttgttgatc acgataattt   3000
ccaagtttta aacaaggata tattgcagtt taaatttcct aaaaaccaat cctataaaat   3060
atatggtaat ataccttata acataagtac ggatataata cgcaaaattg tttttgatag   3120
tatagctaat gagatttatt taatcgtgga atacgggttt gctaaaagat tattaaatac   3180
aaaacgctca ttggcattac ttttaatggc agaagttgat atttctatat taagtatggt   3240
tccaagagaa tattttcatc ctaaacctaa agtgaatagc tcacttatca gattaagtag   3300
aaaaaaatca agaatatcac acaaagataa acaaaagtat aattatttcg ttatgaaatg   3360
ggttaacaaa gaatacaaga aaatatttac aaaaaatcaa tttaacaatt ccttaaaaca   3420
tgcaggaatt gacgatttaa acaatattag ctttgaacaa ttcttatctc ttttcaatag   3480
ctataaatta tttaataagt aagttaaggg atgcataaac tgcatccctt aacttgtttt   3540
tcgtgtgcct atttttttgtg gcgcgccctt tacaaaatca aacccgatcg cctctctatt   3600
ttgataaatc tatgtctact ccctctgtta cccctgtaga atctagcacc ctaatcaaaa   3660
cccctgaact gctggctccg gcgggaaatt gggactgtgc gatcaccgcc gtggagaatg   3720
gggctgatgc gatttatttt gggctggata aatttaatgc ccggatgcga tcacaaaact   3780
ttgtcgagtc agatttgccg gagttgatgg catacttaca tcggcgcggc gtgaagggct   3840
atgtgacgtt aaatacgctg attttcacct cggaattggc ggcagtcgaa caatatttgc   3900
ggtcgattat tgcggcggga gtcgatgcgg cgatcgtcca ggatgtgggg ctgtgccaat   3960
```

taatttggca attgtcgccc gattttccga tccatggttc gacgcaaatg accgtcacca 4020
gcgccgcagg ggtcgagttc gcgcaaaact tgggttgtga tttggtggta ttggcgcggg 4080
aatgttcgat caaggaaatc aataaaatcc agcaggaatt gggtcaacaa aagatctcaa 4140
tgccgctaga agtgtttgtc cacggggcgt tgtgcgtcgc ctattctggg caatgtttaa 4200
ccagtgaatc cctcggcgga cggtcggcca atcgcggaga atgcgcccaa gcctgccgga 4260
tgccctacga aatgattgtc gatggtaggc catttgatct gagcgacaga cgttaccggc 4320
cggccaaaat gaagtgaagt tcctatactt aagcttaaaa tgaagtgaag ttcctatact 4380
ttctagagaa taggaacttc tatagtgagt cgaataaggg cgacacaaaa tttattctaa 4440
atgcataata aatactgata acatcttata gtttgtatta tattttgtat tatcgttgac 4500
atgtataatt ttgatatcaa aaactgattt tccctttatt attttcgaga tttatttttct 4560 taattctctt taacaaacta gaaatattgt atatacaaaa aatcataaat aatagatgaa 4620
tagtttaatt ataggtgttc atcaatcgaa aaagcaacgt atcttattta aagtgcgttg 4680 ctttttctc atttataagg ttaaataatt ctcatatatc aagcaaagtg acaggcgccc 4740
ttaaatattc tgacaaatgc tctttcccta aactcccccc ataaaaaaac ccgccgaagc 4800
gggtttttac gttatttgcg gattaacgat tactcgttat cagaaccgcc caggggggccc 4860 gagcttaaga ctggccgtcg ttttacaaca cagaaagagt ttgtagaaac gcaaaaaggc 4920
catccgtcag gggccttctg cttagtttga tgcctggcag ttccctactc tcgccttccg 4980
cttcctcgct cactgactcg ctgcgctcgg tcgttcggct gcggcgagcg gtatcagctc 5040
actcaaaggc ggtaatacgg ttatccacag aatcagggga taacgcagga aagaacatgt 5100
gagcaaaagg ccagcaaaag gccaggaacc gtaaaaaggc cgcgttgctg gcgtttttcc 5160
ataggctccg cccccctgac gagcatcaca aaaatcgacg ctcaagtcag aggtggcgaa 5220
acccgacagg actataaaga taccaggcgt ttccccctgg aagctccctc gtgcgctctc 5280
ctgttccgac cctgccgctt accggatacc tgtccgcctt tctcccttcg ggaagcgtgg 5340
cgctttctca tagctcacgc tgtaggtatc tcagttcggt gtaggtcgtt cgctccaagc 5400
tgggctgtgt gcacgaaccc cccgttcagc ccgaccgctg cgccttatcc ggtaactatc 5460
gtcttgagtc caacccggta agacacgact tatcgccact ggcagcagcc actggtaaca 5520
ggattagcag agcgaggtat gtaggcggtg ctacagagtt cttgaagtgg tgggctaact 5580
acggctacac tagaagaaca gtatttggta tctgcgctct gctgaagcca gttaccttcg 5640
gaaaaagagt tggtagctct tgatccggca aacaaaccac cgctggtagc ggtggttttt 5700
ttgtttgcaa gcagcagatt acgcgcagaa aaaaaggatc tcaagaagat cctttgatct 5760
tttctacggg gtctgacgct cagtggaacg acgcgcgcgt aactcacgtt aagggatttt 5820
ggtcatgagc ttgcgccgtc ccgtcaagtc agcgtaatgc tctgctttta gaaaaactca 5880
tcgagcatca aatgaaactg caatttattc atatcaggat tatcaatacc atatttttga 5940
aaaagccgtt tctgtaatga aggagaaaac tcaccgaggc agttccatag gatggcaaga 6000
tcctggtatc ggtctgcgat tccgactcgt ccaacatcaa tacaacctat taatttcccc 6060
tcgtcaaaaa taaggttatc aagtgagaaa tcaccatgag tgacgactga atccggtgag 6120
aatggcaaaa gtttatgcat ttctttccag acttgttcaa caggccagcc attacgctcg 6180
tcatcaaaat cactcgcatc aaccaaaccg ttattcattc gtgattgcgc ctgagcgagg 6240
cgaaatacgc gatcgctgtt aaaaggacaa ttacaaacag gaatcgagtg caaccggcgc 6300
aggaacactg ccagcgcatc aacaatattt tcacctgaat caggatattc ttctaatacc 6360

-continued

```
tggaacgctg tttttccggg gatcgcagtg gtgagtaacc atgcatcatc aggagtacgg   6420

ataaaatgct tgatggtcgg aagtggcata aattccgtca gccagtttag tctgaccatc   6480

tcatctgtaa catcattggc aacgctacct ttgccatgtt tcagaaacaa ctctggcgca   6540

tcgggcttcc catacaagcg atagattgtc gcacctgatt gcccgacatt atcgcgagcc   6600

catttatacc catataaatc agcatccatg ttggaattta atcgcggcct cgacgtttcc   6660

cgttgaatat ggctcatatt cttccttttt caatattatt gaagcattta tcagggttat   6720

tgtctcatga gcggatacat atttgaatgt atttagaaaa ataaacaaat aggggtcagt   6780

gttacaacca attaaccaat tctgaacatt atcgcgagcc catttatacc tgaatatggc   6840

tcataacacc ccttgtttgc ctggcggcag tagcgcggtg gtcccacctg accccatgcc   6900

gaactcagaa gtgaaacgcc gtagcgccga tggtagtgtg gggactcccc atgcgagagt   6960

agggaactgc caggcatcaa ataaaacgaa aggctcagtc gaaagactgg gcctttcgcc   7020

cgggctaatt agggggtgtc gcccttattc gactctatag tgaagttcct attctctaga   7080

aagtatagga acttctgaag tggggaagct taagtatagg aacttctgaa gtggggcctg   7140

cagg                                                                7144
```

<210> SEQ ID NO 40
<211> LENGTH: 6872
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40

```
gaaaggctct tgaggctatc atgacagaag catcgcagcc tataaaatac gctggaaaag     60

aatataaata tgctgtttcg tatcatgtcc taaatgctgc tgattttggt gttccgcaat    120

ttagagaaag agtattcatc gtaggtaatc gtttgggcaa aacattccaa tttcctgaac    180

caactcatgg gcctagcaac caagcgagac agatagatct tttggcaagg cagctaaaac    240

cttacaaaac tgttcaagat gcaattagca ctctcccccc tgcaacccct ccttcagcga    300

tggcactaag agtttcgcag accataaaag ataggataaa gaatcatgga tattaaaaac    360

gttcatatca aaaatcacga acaaacagct catgcacctt ccactctaga aaaaattcgt    420

aaagtcaaac aagggggtaa actctcagaa cagacaaaga catttggttc aacctaccgc    480

aggttagatc cgaaccagcc atctcctaca gtgacccgta gtggttatcg agattttatt    540

catccttttg aagatcgaat gctcacagtt cgtgaactgg cttgtttgca aacctttccc    600

cttgattggg agtttaccgg aactcgactt gattcttata gtagtaaacg taaagtgacg    660

atgactcagt ttggacaagt gggtaatgca gtaccgccgt tacttgctga agctgttgct    720

aaagcggtta gcgaacagct tctggatgtc gcggccgcag attgataacc caaacctata    780

gaataattaa gaatctccaa agcaacagtt attgcattgg gtatcaacta agctgatcct    840

aagcataaga cctacgacaa tatcacaggc ttgcggatgg ttgcatcatc tcgctgagtt    900

ttgcactgct caattttgcc ccatttgcgg ggaatcgtag cgttcacact acccattgca    960

aaggttgccc gtagagattg ctctattcgg cacagtcact gttaaagagg aacaacgcat   1020

atggcgaccg tcctctgcgt gctgtacccc gaccccgtcg acggctatcc gccgcgctac   1080

gtgcgcgaca cgattcccgt catcacgcac tacgcggacg gccagctcgc gccgacgccg   1140

tccgggccgc ccggttttcg gccgggcgaa ctcgtcggct cggtatcggg cgcgctcggg   1200
```

-continued

```
ttgcgcgact atctggcggc gcacggtcat acgctgatcg tgacgagcga caaggacggc   1260
cccgactccg aattcgagcg ccggctgccg gaagcggacg tcgtgatttc gcagccgttc   1320
tggcccgcgt atctgaccgc cgaggggatc gcgcgcgcgc cgaagctgcg gctcgcgctg   1380
actgcgggca tcggctccga tcacgtcgat ctcgcggcgg ccgcgcgcgc gggcatcacc   1440
gtcgcggaag tcaccggatc gaacagcgtc agcgtcgccg agcatgtcgt gatgacgacg   1500
cttgcgctcg tgcgcaacta tctgccgtcg cacgcgatcg cgcagcaagg cggctggaac   1560
atcgccgact gcgtatcgcg cagctacgac atcgagggca tgcatttcgg cacggtcggc   1620
gccggccgca tcgggctcgc ggtgctgcgg cggctgaagc cgttcgggct ggcgctgcac   1680
tatacgcagc ggcatcggct cgatccggcg atcgaacacg aactcgcgct gacctatcac   1740
gcggacgtcg cgtcgctcgc gagcgcggtc gacatcgtga atctgcagat tccgctctat   1800
ccgtcgaccg agcatctgtt cgatgccgca atgatcgcgc gcatgaagcg cggcgcgtat   1860
ctgatcaaca ccgcgcgcgc gaaactcgtc gatcgcgacg cggtcgtgcg tgcggtcgcc   1920
tcgggccatc tggccggcta cggcggcgac gtgtggtttc ccgagcccgc accggccgat   1980
catccgtggc gcgcgatgcc gttcaacggg atgacgccgc atatctcggg cacgtcgctg   2040
tccgcgcagg cgcgctacgc ggccggtacg ctcgaaattc tgcagtgctg gttcgagcgc   2100
cggccgattc gcgaggccta cctgatcgtc gacggcggca cgctcgcggg caccggcgag   2160
cagtcgtacc ggctcacgtg actcgaggcg agctcagact gttgtacagc atgctagcta   2220
cacagacgcg tccatggtag gtacctgtta acgttagacc ggtcaggatc tgcagatgac   2280
accgcggtgc agctgaaggc cacgtgggcc gtagggaatt cactagtttt taattaacgt   2340
gctataatta tactaatttt ataaggagga aaaaatatgg gcatttttag tatttttgta   2400
atcagcacag ttcattatca accaaacaaa aaataagtgg ttataatgaa tcgttaataa   2460
gcaaaattca tataaccaaa ttaaagaggg ttataatgaa cgagaaaaat ataaaacaca   2520
gtcaaaactt tattacttca aaacataata tagataaaat aatgacaaat ataagattaa   2580
atgaacatga taatatcttt gaaatcggct caggaaaagg ccattttacc cttgaattag   2640
taaagaggtg taatttcgta actgccattg aaatagacca taaattatgc aaaactacag   2700
aaaataaact tgttgatcac gataatttcc aagttttaaa caaggatata ttgcagttta   2760
aatttcctaa aaaccaatcc tataaaatat atggtaatat accttataac ataagtacgg   2820
atataatacg caaaattgtt tttgatagta tagctaatga gatttattta atcgtggaat   2880
acgggtttgc taaaagatta ttaaatacaa aacgctcatt ggcattactt ttaatggcag   2940
aagttgatat ttctatatta agtatggttc caagagaata ttttcatcct aaacctaaag   3000
tgaatagctc acttatcaga ttaagtagaa aaaaatcaag aatatcacac aaagataaac   3060
aaaagtataa ttatttcgtt atgaaatggg ttaacaaaga atacaagaaa atatttacaa   3120
aaaatcaatt taacaattcc ttaaaacatg caggaattga cgatttaaac aatattagct   3180
ttgaacaatt cttatctctt ttcaatagct ataaattatt taataagtaa gttaagggat   3240
gcataaactg catcccttaa cttgtttttc gtgtgcctat tttttgtggc gcgcccttta   3300
caaaatcaaa cccgatcgcc tctctatttt gataaatcta tgtctactcc ctctgttacc   3360
cctgtagaat ctagcaccct aatcaaaacc cctgaactgc tggctccggc gggaaattgg   3420
gactgtgcga tcaccgccgt ggagaatggg gctgatgcga tttattttgg gctggataaa   3480
tttaatgccc ggatgcgatc acaaaacttt gtcgagtcag atttgccgga gttgatggca   3540
```

-continued

```
tacttacatc ggcgcggcgt gaagggctat gtgacgttaa atacgctgat tttcacctcg   3600
gaattggcgg cagtcgaaca atatttgcgg tcgattattg cggcgggagt cgatgcggcg   3660
atcgtccagg atgtggggct gtgccaatta atttggcaat tgtcgcccga ttttccgatc   3720
catggttcga cgcaaatgac cgtcaccagc gccgcagggg tcgagttcgc gcaaaacttg   3780
ggttgtgatt tggtggtatt ggcgcgggaa tgttcgatca aggaaatcaa taaaatccag   3840
caggaattgg gtcaacaaaa gatctcaatg ccgctagaag tgtttgtcca cggggcgttg   3900
tgcgtcgcct attctgggca atgtttaacc agtgaatccc tcggcggacg gtcggccaat   3960
cgcggagaat gcgcccaagc ctgccggatg ccctacgaaa tgattgtcga tggtaggcca   4020
tttgatctga gcgacagacg ttaccggccg gccaaaatga agtgaagttc ctatacttaa   4080
gcttaaaatg aagtgaagtt cctatacttt ctagagaata ggaacttcta tagtgagtcg   4140
aataagggcg acacaaaatt tattctaaat gcataataaa tactgataac atcttatagt   4200
ttgtattata ttttgtatta tcgttgacat gtataatttt gatatcaaaa actgattttc   4260
cctttattat tttcgagatt tattttctta attctcttta acaaactaga aatattgtat   4320
atacaaaaaa tcataaataa tagatgaata gtttaattat aggtgttcat caatcgaaaa   4380
agcaacgtat cttatttaaa gtgcgttgct tttttctcat ttataaggtt aaataattct   4440
catatatcaa gcaaagtgac aggcgccctt aaatattctg acaaatgctc tttccctaaa   4500
ctccccccat aaaaaaaccc gccgaagcgg gtttttacgt tatttgcgga ttaacgatta   4560
ctcgttatca gaaccgccca gggggcccga gcttaagact ggccgtcgtt ttacaacaca   4620
gaaagagttt gtagaaacgc aaaaaggcca tccgtcaggg gccttctgct tagtttgatg   4680
cctggcagtt ccctactctc gccttccgct tcctcgctca ctgactcgct gcgctcggtc   4740
gttcggctgc ggcgagcggt atcagctcac tcaaaggcgg taatacggtt atccacagaa   4800
tcaggggata acgcaggaaa gaacatgtga gcaaaaggcc agcaaaaggc caggaaccgt   4860
aaaaaggccg cgttgctggc gtttttccat aggctccgcc cccctgacga gcatcacaaa   4920
aatcgacgct caagtcagag gtggcgaaac ccgacaggac tataaagata ccaggcgttt   4980
ccccctggaa gctccctcgt gcgctctcct gttccgaccc tgccgcttac cggatacctg   5040
tccgcctttc tcccttcggg aagcgtggcg ctttctcata gctcacgctg taggtatctc   5100
agttcggtgt aggtcgttcg ctccaagctg ggctgtgtgc acgaaccccc cgttcagccc   5160
gaccgctgcg ccttatccgg taactatcgt cttgagtcca acccggtaag acacgactta   5220
tcgccactgg cagcagccac tggtaacagg attagcagag cgaggtatgt aggcggtgct   5280
acagagttct tgaagtggtg gcctaactac ggctacacta gaagaacagt atttggtatc   5340
tgcgctctgc tgaagccagt taccttcgga aaaagagttg gtagctcttg atccggcaaa   5400
caaaccaccg ctggtagcgg tggttttttt gtttgcaagc agcagattac gcgcagaaaa   5460
aaaggatctc aagaagatcc tttgatcttt tctacggggt ctgacgctca gtggaacgac   5520
gcgcgcgtaa ctcacgttaa gggattttgg tcatgagctt gcgccgtccc gtcaagtcag   5580
cgtaatgctc tgcttttaga aaaactcatc gagcatcaaa tgaaactgca atttattcat   5640
atcaggatta tcaataccat atttttgaaa aagccgtttc tgtaatgaag gagaaaactc   5700
accgaggcag ttccatagga tggcaagatc ctggtatcgg tctgcgattc cgactcgtcc   5760
aacatcaata caacctatta atttcccctc gtcaaaaata aggttatcaa gtgagaaatc   5820
accatgagtg acgactgaat ccggtgagaa tggcaaaagt ttatgcattt ctttccagac   5880
ttgttcaaca ggccagccat tacgctcgtc atcaaaatca ctcgcatcaa ccaaaccgtt   5940
```

```
attcattcgt gattgcgcct gagcgaggcg aaatacgcga tcgctgttaa aaggacaatt   6000

acaaacagga atcgagtgca accggcgcag gaacactgcc agcgcatcaa caatattttc   6060

acctgaatca ggatattctt ctaatacctg gaacgctgtt tttccgggga tcgcagtggt   6120

gagtaaccat gcatcatcag gagtacggat aaaatgcttg atggtcggaa gtggcataaa   6180

ttccgtcagc cagtttagtc tgaccatctc atctgtaaca tcattggcaa cgctaccttt   6240

gccatgtttc agaaacaact ctggcgcatc gggcttccca tacaagcgat agattgtcgc   6300

acctgattgc ccgacattat cgcgagccca tttataccca tataaatcag catccatgtt   6360

ggaatttaat cgcggcctcg acgtttcccg ttgaatatgg ctcatattct tcctttttca   6420

atattattga agcatttatc agggttattg tctcatgagc ggatacatat ttgaatgtat   6480

ttagaaaaat aaacaaatag gggtcagtgt tacaaccaat taaccaattc tgaacattat   6540

cgcgagccca tttatacctg aatatggctc ataacacccc ttgtttgcct ggcggcagta   6600

gcgcggtggt cccacctgac cccatgccga actcagaagt gaaacgccgt agcgccgatg   6660

gtagtgtggg gactccccat gcgagagtag ggaactgcca ggcatcaaat aaaacgaaag   6720

gctcagtcga aagactgggc ctttcgcccg ggctaattag gggtgtcgc ccttattcga   6780

ctctatagtg aagttcctat tctctagaaa gtataggaac ttctgaagtg gggaagctta   6840

agtataggaa cttctgaagt ggggcctgca gg                                 6872
```

<210> SEQ ID NO 41
<211> LENGTH: 7210
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
gaaaggctct tgaggctatc atgacagaag catcgcagcc tataaaatac gctggaaaag     60

aatataaata tgctgtttcg tatcatgtcc taaatgctgc tgattttggt gttccgcaat    120

ttagagaaag agtattcatc gtaggtaatc gtttgggcaa aacattccaa tttcctgaac    180

caactcatgg gcctagcaac caagcgagac agatagatct tttggcaagg cagctaaaac    240

cttacaaaac tgttcaagat gcaattagca ctctcccccc tgcaacccct ccttcagcga    300

tggcactaag agtttcgcag accataaaag ataggataaa gaatcatgga tattaaaaac    360

gttcatatca aaaatcacga acaaacagct catgcacctt ccactctaga aaaaattcgt    420

aaagtcaaac aagggggtaa actctcagaa cagacaaaga catttggttc aacctaccgc    480

aggttagatc cgaaccagcc atctcctaca gtgacccgta gtggttatcg agattttatt    540

catccttttg aagatcgaat gctcacagtt cgtgaactgg cttgtttgca aacctttccc    600

cttgattggg agtttaccgg aactcgactt gattcttata gtagtaaacg taaagtgacg    660

atgactcagt ttggacaagt gggtaatgca gtaccgccgt tacttgctga agctgttgct    720

aaagcggtta gcgaacagct tctggatgtc gcggccgcgt cgacttcgtt ataaaataaa    780

cttaacaaat ctatacccac ctgtagagaa gagtccctga atatcaaaat ggtgggataa    840

aaagctcaaa aaggaaagta ggctgtggtt ccctaggcaa cagtcttccc taccccactg    900

gaaactaaaa aaacgagaaa agttcgcacc gaacatcaat tgcataattt tagccctaaa    960

acataagctg aacgaaactg gttgtcttcc cttcccaatc caggacaatc tgagaatccc   1020

ctgcaacatt acttaacaaa aaagcaggaa taaaattaac aagatgtaac agacataagt   1080
```

-continued

```
cccatcaccg ttgtataaag ttaactgtgg gattgcaaaa gcattcaagc ctaggcgctg   1140
agctgtttga gcatcccggt ggcccttgtc gctgcctccg tgtttctccc tggatttatt   1200
taggtaatat ctctcataaa tccccgggta gttaacgaaa gttaatggag atcagtaaca   1260
ataactctag ggtcattact ttggactccc tcagtttatc cgggggaatt gtgtttaaga   1320
aaatcccaac tcataaagtc aagtaggaga ttaatcatat ggcgaccgtc ctctgcgtgc   1380
tgtaccccga ccccgtcgac ggctatccgc cgcgctacgt gcgcgacacg attcccgtca   1440
tcacgcacta cgcggacggc cagctcgcgc cgacgccgtc cgggccgccc ggttttcggc   1500
cgggcgaact cgtcggctcg gtatcgggcg cgctcgggtt gcgcgactat ctggcggcgc   1560
acggtcatac gctgatcgtg acgagcgaca aggacggccc cgactccgaa ttcgagcgcc   1620
ggctgccgga agcggacgtc gtgatttcgc agccgttctg gcccgcgtat ctgaccgccg   1680
aggggatcgc gcgcgcgccg aagctgcggc tcgcgctgac tgcgggcatc ggctccgatc   1740
acgtcgatct cgcggcggcc gcgcgcgcgg gcatcaccgt cgcggaagtc accggatcga   1800
acagcgtcag cgtcgccgag catgtcgtga tgacgacgct tgcgctcgtg cgcaactatc   1860
tgccgtcgca cgcgatcgcg cagcaaggcg gctggaacat cgccgactgc gtatcgcgca   1920
gctacgacat cgagggcatg catttcggca cggtcggcgc cggccgcatc gggctcgcgg   1980
tgctgcggcg gctgaagccg ttcgggctgg cgctgcacta tacgcagcgg catcggctcg   2040
atccggcgat cgaacacgaa ctcgcgctga cctatcacgc ggacgtcgcg tcgctcgcga   2100
gcgcggtcga catcgtgaat ctgcagattc cgctctatcc gtcgaccgag catctgttcg   2160
atgccgcaat gatcgcgcgc atgaagcgcg gcgcgtatct gatcaacacc gcgcgcgcga   2220
aactcgtcga tcgcgacgcg gtcgtgcgtg cggtcgcctc gggccatctg gccggctacg   2280
gcggcgacgt gtggtttccc gagcccgcac cggccgatca tccgtggcgc gcgatgccgt   2340
tcaacgggat gacgccgcat atctcgggca cgtcgctgtc cgcgcaggcg cgctacgcgg   2400
ccggtacgct cgaaattctg cagtgctggt tcgagcgccg gccgattcgc gaggcctacc   2460
tgatcgtcga cggcggcacg ctcgcgggca ccggcgagca gtcgtaccgg ctcacgtgac   2520
tcgaggcgag ctcagactgt tgtacagcat gctagctaca cagacgcgtc catggtaggt   2580
acctgttaac gttagaccgg tcaggatctg cagatgacac cgcggtgcag ctgaaggcca   2640
cgtgggccgt agggaattca ctagttttta attaacgtgc tataattata ctaattttat   2700
aaggaggaaa aaatatgggc atttttagta tttttgtaat cagcacagtt cattatcaac   2760
caaacaaaaa ataagtggtt ataatgaatc gttaataagc aaaattcata taaccaaatt   2820
aaagagggtt ataatgaacg agaaaaatat aaaacacagt caaaacttta ttacttcaaa   2880
acataaatata gataaaataa tgacaaatat aagattaaat gaacatgata atatctttga   2940
aatcggctca ggaaaaggcc attttaccct tgaattagta aagaggtgta atttcgtaac   3000
tgccattgaa atagaccata aattatgcaa aactacagaa aataaacttg ttgatcacga   3060
taatttccaa gttttaaaca aggatatatt gcagtttaaa tttcctaaaa accaatccta   3120
taaaatatat ggtaatatac cttataacat aagtacggat ataatacgca aaattgtttt   3180
tgatagtata gctaatgaga tttatttaat cgtggaatac gggtttgcta aaagattatt   3240
aaatacaaaa cgctcattgg cattactttt aatggcagaa gttgatattt ctatattaag   3300
tatggttcca agagaatatt ttcatcctaa acctaaagtg aatagctcac ttatcagatt   3360
aagtagaaaa aaatcaagaa tatcacacaa agataaacaa aagtataatt atttcgttat   3420
```

-continued gaaatgggtt aacaaagaat acaagaaaat atttacaaaa aatcaattta acaattcctt 3480
aaaacatgca ggaattgacg atttaaacaa tattagcttt gaacaattct tatctctttt 3540
caatagctat aaattattta ataagtaagt taagggatgc ataaactgca tcccttaact 3600
tgtttttcgt gtgcctattt tttgtggcgc gccctttaca aaatcaaacc cgatcgcctc 3660
tctattttga taaatctatg tctactccct ctgttacccc tgtagaatct agcaccctaa 3720
tcaaaacccc tgaactgctg gctccggcgg gaaattggga ctgtgcgatc accgccgtgg 3780
agaatggggc tgatgcgatt tattttgggc tggataaatt taatgcccgg atgcgatcac 3840
aaaactttgt cgagtcagat ttgccggagt tgatggcata cttacatcgg cgcggcgtga 3900
agggctatgt gacgttaaat acgctgattt tcacctcgga attggcggca gtcgaacaat 3960
atttgcggtc gattattgcg gcgggagtcg atgcggcgat cgtccaggat gtggggctgt 4020
gccaattaat ttggcaattg tcgcccgatt ttccgatcca tggttcgacg caaatgaccg 4080
tcaccagcgc cgcaggggtc gagttcgcgc aaaacttggg ttgtgatttg gtggtattgg 4140
cgcgggaatg ttcgatcaag gaaatcaata aaatccagca ggaattgggt caacaaaaga 4200
tctcaatgcc gctagaagtg tttgtccacg gggcgttgtg cgtcgcctat tctgggcaat 4260
gtttaaccag tgaatccctc ggcggacggt cggccaatcg cggagaatgc gcccaagcct 4320
gccggatgcc ctacgaaatg attgtcgatg gtaggccatt tgatctgagc gacagacgtt 4380
accggccggc caaaatgaag tgaagttcct atacttaagc ttaaaatgaa gtgaagttcc 4440
tatactttct agagaatagg aacttctata gtgagtcgaa taagggcgac acaaaattta 4500
ttctaaatgc ataataaata ctgataacat cttatagttt gtattatatt ttgtattatc 4560
gttgacatgt ataattttga tatcaaaaac tgattttccc tttattattt tcgagattta 4620
ttttcttaat tctctttaac aaactagaaa tattgtatat acaaaaaatc ataaataata 4680
gatgaatagt ttaattatag gtgttcatca atcgaaaaag caacgtatct tatttaaagt 4740
gcgttgcttt ttttcatttt ataaggttaa ataattctca tatatcaagc aaagtgacag 4800
gcgcccttaa atattctgac aaatgctctt tccctaaact ccccccataa aaaaacccgc 4860
cgaagcgggt ttttacgtta tttgcggatt aacgattact cgttatcaga accgcccagg 4920
gggcccgagc ttaagactgg ccgtcgtttt acaacacaga aagagtttgt agaaacgcaa 4980
aaaggccatc cgtcaggggc cttctgctta gtttgatgcc tggcagttcc ctactctcgc 5040
cttccgcttc ctcgctcact gactcgctgc gctcggtcgt tcggctgcgg cgagcggtat 5100
cagctcactc aaaggcggta atacggttat ccacagaatc aggggataac gcaggaaaga 5160
acatgtgagc aaaaggccag caaaaggcca ggaaccgtaa aaaggccgcg ttgctggcgt 5220
ttttccatag gctccgcccc cctgacgagc atcacaaaaa tcgacgctca agtcagaggt 5280
ggcgaaaccc gacaggacta taaagatacc aggcgtttcc ccctggaagc tccctcgtgc 5340
gctctcctgt tccgaccctg ccgcttaccg gatacctgtc cgcctttctc ccttcgggaa 5400
gcgtggcgct ttctcatagc tcacgctgta ggtatctcag ttcggtgtag gtcgttcgct 5460
ccaagctggg ctgtgtgcac gaaccccccg ttcagcccga ccgctgcgcc ttatccggta 5520
actatcgtct tgagtccaac ccggtaagac acgacttatc gccactggca gcagccactg 5580
gtaacaggat tagcagagcg aggtatgtag gcggtgctac agagttcttg aagtggtggg 5640
ctaactacgg ctacactaga agaacagtat ttggtatctg cgctctgctg aagccagtta 5700
ccttcggaaa aagagttggt agctcttgat ccggcaaaca aaccaccgct ggtagcggtg 5760
gtttttttgt ttgcaagcag cagattacgc gcagaaaaaa aggatctcaa gaagatcctt 5820
tgatcttttc tacggggtct gacgctcagt ggaacgacgc gcgcgtaact cacgttaagg 5880
gattttggtc atgagcttgc gccgtcccgt caagtcagcg taatgctctg cttttagaaa 5940
aactcatcga gcatcaaatg aaactgcaat ttattcatat caggattatc aataccatat 6000
ttttgaaaaa gccgtttctg taatgaagga gaaaactcac cgaggcagtt ccataggatg 6060
gcaagatcct ggtatcggtc tgcgattccg actcgtccaa catcaataca acctattaat 6120
ttcccctcgt caaaaataag gttatcaagt gagaaatcac catgagtgac gactgaatcc 6180
ggtgagaatg gcaaaagttt atgcatttct ttccagactt gttcaacagg ccagccatta 6240
cgctcgtcat caaaatcact cgcatcaacc aaaccgttat tcattcgtga ttgcgcctga 6300
gcgaggcgaa atacgcgatc gctgttaaaa ggacaattac aaacaggaat cgagtgcaac 6360
cggcgcagga acactgccag cgcatcaaca atattttcac ctgaatcagg atattcttct 6420
aatacctgga acgctgtttt tccggggatc gcagtggtga gtaaccatgc atcatcagga 6480
gtacggataa aatgcttgat ggtcggaagt ggcataaatt ccgtcagcca gtttagtctg 6540
accatctcat ctgtaacatc attggcaacg ctacctttgc catgtttcag aaacaactct 6600
ggcgcatcgg gcttcccata caagcgatag attgtcgcac ctgattgccc gacattatcg 6660
cgagcccatt tatacccata taaatcagca tccatgttgg aatttaatcg cggcctcgac 6720
gtttcccgtt gaatatggct catattcttc ctttttcaat attattgaag catttatcag 6780
ggttattgtc tcatgagcgg atacatattt gaatgtattt agaaaaataa acaaataggg 6840
gtcagtgtta caaccaatta accaattctg aacattatcg cgagcccatt tatacctgaa 6900
tatggctcat aacacccctt gtttgcctgg cggcagtagc gcggtggtcc cacctgaccc 6960
catgccgaac tcagaagtga aacgccgtag cgccgatggt agtgtgggga ctccccatgc 7020
gagagtaggg aactgccagg catcaaataa aacgaaaggc tcagtcgaaa gactgggcct 7080
ttcgcccggg ctaattaggg ggtgtcgccc ttattcgact ctatagtgaa gttcctattc 7140
tctagaaagt ataggaactt ctgaagtggg gaagcttaag tataggaact tctgaagtgg 7200
ggcctgcagg 7210

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
ctatcatatg gcgaccgtcc tctgcgtg 28

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ctatctcgag tcacgtgagc cggtacgact gct 33

<210> SEQ ID NO 44
<211> LENGTH: 386
<212> TYPE: PRT

<213> ORGANISM: Burkholdia multivorans

<400> SEQUENCE: 44

Met Ala Thr Val Leu Cys Val Leu Tyr Pro Asp Pro Val Asp Gly Tyr
1 5 10 15

Pro Pro Arg Tyr Val Arg Asp Thr Ile Pro Val Ile Thr His Tyr Ala
20 25 30

Asp Gly Gln Leu Ala Pro Thr Pro Ser Gly Pro Pro Gly Phe Arg Pro
35 40 45

Gly Glu Leu Val Gly Ser Val Ser Gly Ala Leu Gly Leu Arg Asp Tyr
50 55 60

Leu Ala Ala His Gly His Thr Leu Ile Val Thr Ser Asp Lys Asp Gly
65 70 75 80

Pro Asp Ser Glu Phe Glu Arg Arg Leu Pro Glu Ala Asp Val Val Ile
85 90 95

Ser Gln Pro Phe Trp Pro Ala Tyr Leu Thr Ala Glu Gly Ile Ala Arg
100 105 110

Ala Pro Lys Leu Arg Leu Ala Leu Thr Ala Gly Ile Gly Ser Asp His
115 120 125

Val Asp Leu Ala Ala Ala Ala Arg Ala Gly Ile Thr Val Ala Glu Val
130 135 140

Thr Gly Ser Asn Ser Val Ser Val Ala Glu His Val Val Met Thr Thr
145 150 155 160

Leu Ala Leu Val Arg Asn Tyr Leu Pro Ser His Ala Ile Ala Gln Gln
165 170 175

Gly Gly Trp Asn Ile Ala Asp Cys Val Ser Arg Ser Tyr Asp Ile Glu
180 185 190

Gly Met His Phe Gly Thr Val Gly Ala Gly Arg Ile Gly Leu Ala Val
195 200 205

Leu Arg Arg Leu Lys Pro Phe Gly Leu Ala Leu His Tyr Thr Gln Arg
210 215 220

His Arg Leu Asp Pro Ala Ile Glu His Glu Leu Ala Leu Thr Tyr His
225 230 235 240

Ala Asp Val Ala Ser Leu Ala Ser Ala Val Asp Ile Val Asn Leu Gln
245 250 255

Ile Pro Leu Tyr Pro Ser Thr Glu His Leu Phe Asp Ala Ala Met Ile
260 265 270

Ala Arg Met Lys Arg Gly Ala Tyr Leu Ile Asn Thr Ala Arg Ala Lys
275 280 285

Leu Val Asp Arg Asp Ala Val Val Arg Ala Val Ala Ser Gly His Leu
290 295 300

Ala Gly Tyr Gly Gly Asp Val Trp Phe Pro Glu Pro Ala Pro Ala Asp
305 310 315 320

His Pro Trp Arg Ala Met Pro Phe Asn Gly Met Thr Pro His Ile Ser
325 330 335

Gly Thr Ser Leu Ser Ala Gln Ala Arg Tyr Ala Ala Gly Thr Leu Glu
340 345 350

Ile Leu Gln Cys Trp Phe Glu Arg Arg Pro Ile Arg Glu Ala Tyr Leu
355 360 365

Ile Val Asp Gly Gly Thr Leu Ala Gly Thr Gly Glu Gln Ser Tyr Arg
370 375 380

Leu Thr
385

<210> SEQ ID NO 45
<211> LENGTH: 341
<212> TYPE: PRT
<213> ORGANISM: Synechococcus elongates

<400> SEQUENCE: 45

Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340

<210> SEQ ID NO 46
<211> LENGTH: 341
<212> TYPE: PRT
<213> ORGANISM: Synechococcus elongates

<400> SEQUENCE: 46

```
Met Phe Gly Leu Ile Gly His Leu Thr Ser Leu Glu Gln Ala Arg Asp
1               5                   10                  15

Val Ser Arg Arg Met Gly Tyr Asp Glu Tyr Ala Asp Gln Gly Leu Glu
            20                  25                  30

Phe Trp Ser Ser Ala Pro Pro Gln Ile Val Asp Glu Ile Thr Val Thr
        35                  40                  45

Ser Ala Thr Gly Lys Val Ile His Gly Arg Tyr Ile Glu Ser Cys Phe
    50                  55                  60

Leu Pro Glu Met Leu Ala Ala Arg Arg Phe Lys Thr Ala Thr Arg Lys
65                  70                  75                  80

Val Leu Asn Ala Met Ser His Ala Gln Lys His Gly Ile Asp Ile Ser
                85                  90                  95

Ala Leu Gly Gly Phe Thr Ser Ile Ile Phe Glu Asn Phe Asp Leu Ala
            100                 105                 110

Ser Leu Arg Gln Val Arg Asp Thr Thr Leu Glu Phe Glu Arg Phe Thr
        115                 120                 125

Thr Gly Asn Thr His Thr Ala Tyr Val Ile Cys Arg Gln Val Glu Ala
    130                 135                 140

Ala Ala Lys Thr Leu Gly Ile Asp Ile Thr Gln Ala Thr Val Ala Val
145                 150                 155                 160

Val Gly Ala Thr Gly Asp Ile Gly Ser Ala Val Cys Arg Trp Leu Asp
                165                 170                 175

Leu Lys Leu Gly Val Gly Asp Leu Ile Leu Thr Ala Arg Asn Gln Glu
            180                 185                 190

Arg Leu Asp Asn Leu Gln Ala Glu Leu Gly Arg Gly Lys Ile Leu Pro
        195                 200                 205

Leu Glu Ala Ala Leu Pro Glu Ala Asp Phe Ile Val Trp Val Ala Ser
    210                 215                 220

Met Pro Gln Gly Val Val Ile Asp Pro Ala Thr Leu Lys Gln Pro Cys
225                 230                 235                 240

Val Leu Ile Asp Gly Gly Tyr Pro Lys Asn Leu Gly Ser Lys Val Gln
                245                 250                 255

Gly Glu Gly Ile Tyr Val Leu Asn Gly Gly Val Val Glu His Cys Phe
            260                 265                 270

Asp Ile Asp Trp Gln Ile Met Ser Ala Ala Glu Met Ala Arg Pro Glu
        275                 280                 285

Arg Gln Met Phe Ala Cys Phe Ala Glu Ala Met Leu Leu Glu Phe Glu
    290                 295                 300

Gly Trp His Thr Asn Phe Ser Trp Gly Arg Asn Gln Ile Thr Ile Glu
305                 310                 315                 320

Lys Met Glu Ala Ile Gly Glu Ala Ser Val Arg His Gly Phe Gln Pro
                325                 330                 335

Leu Ala Leu Ala Ile
            340
```

<210> SEQ ID NO 47
<211> LENGTH: 339
<212> TYPE: PRT
<213> ORGANISM: Anabaena variabilis

<400> SEQUENCE: 47

```
Met Phe Gly Leu Ile Gly His Leu Thr Ser Leu Glu His Ala Gln Ala
1               5                   10                  15
```

```
Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Lys Val Thr
        35                  40                  45

Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190

Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
225                 230                 235                 240

Leu Leu Ile Asp Gly Gly Tyr Pro Lys Asn Leu Gly Thr Lys Val Gln
                245                 250                 255

Tyr Pro Gly Val Tyr Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
    290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val


<210> SEQ ID NO 48
<211> LENGTH: 339
<212> TYPE: PRT
<213> ORGANISM: Nostoc sp.

<400> SEQUENCE: 48

Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Lys Val Thr
        35                  40                  45
```

```
Ser Ile Thr Gly Glu Ile Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Val Leu Asn Ala Met Ala His Ala Gln Lys Asn Gly Ile Asp Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ser Gln Gln Leu Gly Ile Glu Leu Ser Gln Ala Thr Val Ala Ile
145                 150                 155                 160

Cys Gly Ala Thr Gly Asp Ile Gly Ser Ala Val Thr Arg Trp Leu Asp
                165                 170                 175

Ala Lys Thr Asp Val Lys Glu Leu Leu Leu Ile Ala Arg Asn Gln Glu
            180                 185                 190

Arg Leu Gln Glu Leu Gln Ser Glu Leu Gly Arg Gly Lys Ile Met Ser
        195                 200                 205

Leu Asp Glu Ala Leu Pro Gln Ala Asp Ile Val Val Trp Val Ala Ser
    210                 215                 220

Met Pro Lys Gly Val Glu Ile Asn Pro Gln Val Leu Lys Gln Pro Cys
225                 230                 235                 240

Leu Leu Ile Asp Gly Gly Tyr Pro Lys Asn Leu Gly Thr Lys Val Gln
                245                 250                 255

Tyr Pro Gly Val Tyr Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
    290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Val Lys His Gly Phe Arg Pro
                325                 330                 335

Leu Leu Val


<210> SEQ ID NO 49
<211> LENGTH: 339
<212> TYPE: PRT
<213> ORGANISM: Nostoc azollae

<400> SEQUENCE: 49

Met Phe Gly Leu Ile Gly His Leu Thr Ser Leu Glu His Ala Gln Ser
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp His Ile Thr Val Thr
        35                  40                  45

Ser Ile Thr Gly Gln Lys Ile Glu Gly Arg Tyr Val Glu Ser Cys Phe
    50                  55                  60

Leu Pro Glu Met Leu Ala Asn Arg Arg Ile Lys Ala Ala Thr Arg Lys
65                  70                  75                  80
```

```
Ile Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Asn Leu Glu
            100                 105                 110

Gln Phe Ser Gln Val Arg Asn Val Thr Leu Glu Phe Glu Arg Phe Thr
        115                 120                 125

Thr Gly Asn Thr His Thr Ala Tyr Ile Ile Cys Arg Gln Val Glu Glu
    130                 135                 140

Ala Ser Lys Gln Leu Gly Ile Glu Leu Ser Lys Ala Thr Val Ala Val
145                 150                 155                 160

Cys Gly Ala Thr Gly Asp Ile Gly Ser Ala Val Thr Arg Trp Leu Asp
                165                 170                 175

Lys Lys Thr Asp Val Gln Glu Leu Leu Leu Ile Ala Arg Asn Gln Glu
            180                 185                 190

Arg Leu Gln Glu Leu Gln Ala Glu Leu Gly Arg Gly Lys Ile Thr Asp
        195                 200                 205

Leu His Glu Ala Leu Pro Gln Ser Asp Ile Val Val Trp Val Ala Ser
    210                 215                 220

Met Pro Lys Gly Val Glu Ile Asp Pro Ile Val Leu Lys Gln Pro Cys
225                 230                 235                 240

Leu Leu Ile Asp Gly Gly Tyr Pro Lys Asn Leu Gly Thr Lys Ile Gln
                245                 250                 255

His Pro Gly Val Tyr Val Leu Asn Gly Gly Ile Val Glu His Ser Leu
            260                 265                 270

Asp Ile Asp Trp Lys Ile Met Lys Ile Val Ser Met Glu Val Pro Gly
        275                 280                 285

Arg Gln Leu Phe Ala Cys Phe Ala Glu Ser Met Leu Leu Glu Phe Glu
    290                 295                 300

Lys Leu Tyr Thr Asn Phe Ser Trp Gly Arg Asn Gln Ile Thr Val Asp
305                 310                 315                 320

Lys Met Asp His Ile Gly Gln Val Ser Val Lys His Gly Phe Lys Pro
                325                 330                 335

Leu Leu Val


<210> SEQ ID NO 50
<211> LENGTH: 340
<212> TYPE: PRT
<213> ORGANISM: Cyanothece sp.

<400> SEQUENCE: 50

Met Phe Gly Leu Ile Gly His Leu Thr Ser Leu Glu His Ala Gln Ser
1               5                   10                  15

Val Ala Glu Ala Leu Gly Tyr Pro Glu Tyr Ala Asn Gln Gly Leu Glu
            20                  25                  30

Phe Trp Cys Met Ala Pro Pro Gln Ile Val Asp Ser Ile Thr Val Thr
        35                  40                  45

Ser Ile Thr Gly Gln Lys Ile Tyr Gly Lys Tyr Val Glu Ser Cys Phe
    50                  55                  60

Leu Pro Glu Met Leu Ala Thr Gln Arg Ile Lys Ala Ala Thr Arg Lys
65                  70                  75                  80

Ile Leu Asn Ala Met Ala His Ala Gln Lys His Gly Ile Asp Ile Thr
                85                  90                  95

Ala Leu Gly Gly Phe Ser Ser Ile Ile Phe Glu Asn Phe Asn Leu His
            100                 105                 110
```

```
Thr Ile Thr Gln Ile His Asn Ile Lys Leu Glu Leu Gln Arg Phe Thr
        115                 120                 125

Thr Gly Asn Thr His Thr Ala Tyr Ile Ile Cys Arg Gln Val Glu Gln
    130                 135                 140

Ala Ser Ala Gln Ile Gly Ile Asp Leu Ser Lys Ala Thr Val Ala Val
145                 150                 155                 160

Cys Gly Ala Thr Gly Asp Ile Gly Ser Ala Val Cys Arg Trp Leu Asn
                165                 170                 175

Ser Arg Leu Asp Val Ala Glu Leu Leu Leu Val Ala Arg Asn Gln Glu
            180                 185                 190

Arg Leu Gln Glu Leu Gln Glu Glu Leu Gly Arg Gly Lys Ile Leu Ser
        195                 200                 205

Leu Glu Ala Ala Leu Pro Leu Ala Asp Ile Val Val Trp Val Ala Ser
    210                 215                 220

Met Pro Arg Gly Val Glu Ile Asp Pro Thr Ser Leu Arg Thr Pro Cys
225                 230                 235                 240

Leu Met Ile Asp Gly Gly Tyr Pro Lys Asn Leu Ala Thr Gln Ile Gln
                245                 250                 255

His Pro Gly Val His Val Leu Asn Gly Gly Ile Val Glu His Ser Leu
            260                 265                 270

Asp Ile Asp Trp Arg Ile Met Glu Ile Val Asn Met Ser Ile Pro Ser
        275                 280                 285

Arg Gln Leu Phe Ala Cys Phe Ala Glu Ser Met Leu Leu Glu Phe Glu
    290                 295                 300

Gln Trp Tyr Thr Asn Phe Ser Trp Gly Arg Asn Gln Ile Ser Val Glu
305                 310                 315                 320

Lys Met Glu Lys Ile Gly Gln Ile Ser Val Lys His Gly Phe Gln Pro
                325                 330                 335

Leu Leu Phe Gln
            340
```

<210> SEQ ID NO 51
<211> LENGTH: 346
<212> TYPE: PRT
<213> ORGANISM: Nodularia spumigena

<400> SEQUENCE: 51

```
Met Phe Gly Leu Ile Gly His Leu Thr Ser Leu Glu His Ala Gln Ser
1               5                   10                  15

Val Ala Lys Glu Leu Gly Tyr Pro Glu Tyr Ala Asp Gln Gly Leu Asp
            20                  25                  30

Phe Trp Cys Ser Ala Pro Pro Gln Ile Val Asp Glu Ile Thr Val Thr
        35                  40                  45

Ser Val Thr Gly Gln Thr Ile Glu Gly Arg Tyr Val Glu Ser Cys Phe
    50                  55                  60

Leu Pro Glu Met Leu Ala Asn Arg Arg Ile Lys Ala Ala Thr Arg Lys
65                  70                  75                  80

Ile Leu Asn Ala Met Ala His Ala Gln Lys His Gly Ile Asn Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Ile Lys Leu Glu Phe Glu Arg Phe Thr
        115                 120                 125

Thr Gly Asn Thr His Thr Ala Tyr Ile Ile Cys Arg Gln Val Glu Gln
```

```
    130                 135                 140

Ala Ser Lys Gln Ile Gly Ile Asp Leu Ser Lys Ala Thr Val Ala Ile
145                 150                 155                 160

Cys Gly Ala Thr Gly Asp Ile Gly Ser Ala Val Thr Arg Trp Leu Asp
                165                 170                 175

Ala Arg Thr Asp Val Lys Glu Leu Leu Leu Ile Ala Arg Asn His Glu
            180                 185                 190

Arg Leu Lys Asp Leu Gln Asp Glu Leu Gly Arg Gly Lys Ile Met Ala
        195                 200                 205

Leu Asn Glu Ala Leu Pro Glu Ala Asp Ile Val Val Trp Val Ala Ser
    210                 215                 220

Met Pro Lys Ser Met Glu Ile Asp Phe Gln Val Leu Lys Arg Pro Cys
225                 230                 235                 240

Leu Leu Ile Asp Gly Gly Tyr Pro Lys Asn Leu Ala Thr Lys Ile Gln
                245                 250                 255

Tyr Pro Gly Val His Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
    290                 295                 300

Lys Leu Tyr Thr Asn Phe Ser Trp Gly Arg Asn Gln Ile Thr Val Asp
305                 310                 315                 320

Lys Met Glu Gln Ile Gly Gln Ala Ser Ile Lys His Gly Phe Arg Pro
                325                 330                 335

Leu Leu Val Glu Ser Leu Val Val Asn Ser
            340                 345


<210> SEQ ID NO 52
<211> LENGTH: 341
<212> TYPE: PRT
<213> ORGANISM: Lyngbya sp.

<400> SEQUENCE: 52

Met Phe Gly Leu Ile Gly His Leu Thr Ser Leu Glu His Ala Gln Leu
1               5                   10                  15

Val Ala Lys Asp Leu Gly Tyr Pro Glu Tyr Ala Asp Gln Gly Leu Asp
            20                  25                  30

Phe Trp Cys Ser Ala Pro Pro Gln Ile Val Asp Glu Ile Lys Val Thr
        35                  40                  45

Ser Val Thr Gly Gln Val Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Ile Ile Asn Ala Met Ala His Ala Gln Lys His Gly Ile Asn Ile Thr
                85                  90                  95

Ala Leu Gly Gly Phe Ser Ser Ile Ile Phe Glu Asn Phe Asn Leu Glu
            100                 105                 110

Lys Ile Lys Gln Val Arg Asn Ile Lys Leu Glu Phe Glu Arg Phe Thr
        115                 120                 125

Thr Gly Asn Thr His Thr Ala Tyr Ile Ile Cys Ser Gln Val Glu Gln
    130                 135                 140

Met Ala Pro Lys Leu Gly Ile Asp Leu Ser Asn Ala Thr Val Ala Val
145                 150                 155                 160
```

```
Cys Gly Ala Thr Gly Asp Ile Gly Ser Ala Val Cys Arg Trp Leu Asn
                165                 170                 175

Gln Arg Thr Gln Val Gly Glu Leu Leu Leu Ile Ala Arg Asp Arg Glu
            180                 185                 190

Arg Leu Gln Asn Leu Gln Gly Glu Leu Gly Arg Gly Lys Ile Leu Gly
        195                 200                 205

Leu Glu Glu Ala Leu Pro Gln Ala Asn Val Val Val Trp Val Ala Ser
    210                 215                 220

Met Ala Lys Gly Val Asp Ile Asp Pro Ser Arg Leu Gln Gln Pro Cys
225                 230                 235                 240

Leu Leu Ile Asp Gly Gly Tyr Pro Lys Asn Met Ala Thr Lys Leu Gln
                245                 250                 255

His Pro Gly Val His Ile Leu Glu Gly Gly Ile Val Glu His Ser Leu
            260                 265                 270

Asp Ile Asp Trp Lys Ile Met Lys Ile Val Asn Met Gln Phe Pro Ala
        275                 280                 285

Arg Gln Leu Phe Ala Cys Phe Ala Glu Ala Met Leu Leu Glu Phe Glu
    290                 295                 300

Lys Ile Tyr Thr Asn Phe Ser Trp Gly Arg Asn Gln Ile Thr Val Asp
305                 310                 315                 320

Lys Met Asp Met Ile Gly Arg Val Ser Ile Lys His Gly Phe Lys Pro
                325                 330                 335

Leu Leu Leu Ser Leu
            340


<210> SEQ ID NO 53
<211> LENGTH: 339
<212> TYPE: PRT
<213> ORGANISM: Nostoc punctiforme

<400> SEQUENCE: 53

Met Phe Gly Leu Ile Gly His Leu Thr Ser Leu Glu His Ala Gln Ala
1               5                   10                  15

Val Ala Gln Glu Leu Gly Tyr Pro Glu Tyr Ala Asp Gln Gly Leu Asp
            20                  25                  30

Phe Trp Cys Ser Ala Pro Pro Gln Ile Val Asp Ser Ile Ile Val Thr
        35                  40                  45

Ser Val Thr Gly Gln Gln Ile Glu Gly Arg Tyr Val Glu Ser Cys Phe
    50                  55                  60

Leu Pro Glu Met Leu Ala Ser Arg Arg Ile Lys Ala Ala Thr Arg Lys
65                  70                  75                  80

Ile Leu Asn Ala Met Ala His Ala Gln Lys His Gly Ile Asn Ile Thr
                85                  90                  95

Ala Leu Gly Gly Phe Ser Ser Ile Ile Phe Glu Asn Phe Lys Leu Glu
            100                 105                 110

Gln Phe Ser Gln Val Arg Asn Ile Lys Leu Glu Phe Glu Arg Phe Thr
        115                 120                 125

Thr Gly Asn Thr His Thr Ala Tyr Ile Ile Cys Lys Gln Val Glu Glu
    130                 135                 140

Ala Ser Lys Gln Leu Gly Ile Asn Leu Ser Asn Ala Thr Val Ala Val
145                 150                 155                 160

Cys Gly Ala Thr Gly Asp Ile Gly Ser Ala Val Thr Arg Trp Leu Asp
                165                 170                 175

Ala Arg Thr Asp Val Gln Glu Leu Leu Leu Ile Ala Arg Asp Gln Glu
            180                 185                 190
```

```
Arg Leu Lys Glu Leu Gln Gly Glu Leu Gly Arg Gly Lys Ile Met Gly
        195                 200                 205

Leu Thr Glu Ala Leu Pro Gln Ala Asp Val Val Val Trp Val Ala Ser
    210                 215                 220

Met Pro Arg Gly Val Glu Ile Asp Pro Thr Thr Leu Lys Gln Pro Cys
225                 230                 235                 240

Leu Leu Ile Asp Gly Gly Tyr Pro Lys Asn Leu Ala Thr Lys Ile Gln
                245                 250                 255

Tyr Pro Gly Val His Val Leu Asn Gly Gly Ile Val Glu His Ser Leu
            260                 265                 270

Asp Ile Asp Trp Lys Ile Met Lys Ile Val Asn Met Asp Val Pro Ala
        275                 280                 285

Arg Gln Leu Phe Ala Cys Phe Ala Glu Ser Met Leu Leu Glu Phe Glu
    290                 295                 300

Lys Leu Tyr Thr Asn Phe Ser Trp Gly Arg Asn Gln Ile Thr Val Asp
305                 310                 315                 320

Lys Met Glu Gln Ile Gly Arg Val Ser Val Lys His Gly Phe Arg Pro
                325                 330                 335

Leu Leu Val


<210> SEQ ID NO 54
<211> LENGTH: 339
<212> TYPE: PRT
<213> ORGANISM: Trichodesmium erythraeum

<400> SEQUENCE: 54

Met Phe Gly Leu Ile Gly His Leu Thr Asn Leu Glu His Ala Gln Ser
1               5                   10                  15

Val Ala Arg Asp Leu Gly Tyr Pro Glu Tyr Ala Asp Gln Gly Leu Asp
            20                  25                  30

Phe Trp Cys Ser Ala Pro Pro Gln Ile Val Asp Thr Ile Lys Val Thr
        35                  40                  45

Ser Ile Thr Gly Gln Lys Ile Glu Gly Lys Tyr Val Glu Ser Cys Phe
    50                  55                  60

Leu Pro Glu Met Leu Ala Ser Ser Arg Ile Lys Ala Ala Thr Arg Lys
65                  70                  75                  80

Ile Met Asn Ala Met Ala His Ala Gln Lys His Gly Ile Asp Ile Thr
                85                  90                  95

Ala Leu Gly Gly Phe Ser Ser Ile Val Phe Glu Asn Phe Asn Leu Gln
            100                 105                 110

Lys Phe Lys Gln Ile Arg Asn Ile Thr Leu Glu Phe Lys Arg Phe Thr
        115                 120                 125

Thr Gly Asn Thr His Thr Ala Tyr Ile Val Cys Gln Gln Val Glu Gln
    130                 135                 140

Gly Ala Gln Lys Leu Gly Ile Asp Leu Ser Lys Ala Thr Val Ala Val
145                 150                 155                 160

Cys Gly Ala Thr Gly Asp Ile Gly Ser Ala Val Cys Arg Trp Leu Asn
                165                 170                 175

Thr Lys Thr Glu Val Glu Glu Leu Leu Leu Ile Ala Arg Lys Gln Glu
            180                 185                 190

Arg Leu Asn Ala Leu Gln Lys Glu Leu Lys Arg Gly Lys Ile Leu Glu
        195                 200                 205

Leu Asn Ser Ala Leu Pro Met Ala Asp Ile Ile Val Trp Val Ala Ser
    210                 215                 220
```

Ile Pro Glu Ala Leu Glu Ile Asn Pro Asn Val Leu Lys Lys Pro Cys
225 230 235 240

Leu Leu Ile Asp Gly Gly Tyr Pro Lys Asn Met Ala Thr Lys Val Gln
245 250 255

Gln Glu Gly Ile Tyr Val Leu Asn Gly Gly Ile Val Glu His Ser Leu
260 265 270

Asp Ile Asp Trp Lys Ile Met Lys Ile Val Asn Met Glu Val Pro Gly
275 280 285

Arg Gln Leu Phe Ala Cys Phe Ala Glu Ser Met Leu Leu Glu Phe Glu
290 295 300

Lys Leu Tyr Thr Asn Phe Ser Trp Gly Arg Asn Leu Ile Thr Val Glu
305 310 315 320

Lys Met Glu Leu Ile Gly Lys Leu Ser Val Lys His Gly Phe Lys Pro
325 330 335

Leu Met Leu

<210> SEQ ID NO 55
<211> LENGTH: 341
<212> TYPE: PRT
<213> ORGANISM: Acaryochloris marina

<400> SEQUENCE: 55

Met Phe Gly Leu Ile Gly His Leu Thr Ser Leu Gln His Ala Gln Ser
1 5 10 15

Val Ala Arg Glu Leu Gly Tyr Pro Glu Tyr Ala Asp Gln Gly Leu Asp
20 25 30

Phe Trp Cys Met Ala Pro Pro Gln Ile Val Asp Asp Ile Thr Val Thr
35 40 45

Ser Ile Thr Gly Gln Thr Ile Tyr Gly Lys Tyr Val Glu Ser Cys Phe
50 55 60

Leu Pro Glu Met Leu Ala Ser Gln Arg Ile Lys Ala Ala Thr Arg Lys
65 70 75 80

Ile Val Asn Ala Met Ala His Ala Gln Lys Asn Gly Ile Asn Ile Thr
85 90 95

Ala Leu Gly Gly Phe Ser Ser Ile Ile Phe Glu Asn Phe Asn Leu Gln
100 105 110

Arg Ile Thr Arg Ile Arg Asn Ile Gln Leu Asp Leu Gln Arg Phe Thr
115 120 125

Thr Gly Asn Thr His Thr Ala Tyr Ile Ile Cys Arg Gln Val Glu Gln
130 135 140

Gly Ala Gln Lys Leu Gly Ile Asp Leu Asn Lys Ala Thr Val Ala Val
145 150 155 160

Cys Gly Ala Thr Gly Asp Ile Gly Ser Ala Val Cys Arg Trp Leu Asp
165 170 175

Ala Arg Thr Asp Thr Ala Glu Leu Leu Leu Val Ala Arg His Gln Gly
180 185 190

Arg Leu Glu Thr Leu Gln Ser Glu Leu Gly Arg Gly Lys Ile Met Ser
195 200 205

Ile Glu Glu Ala Leu Pro Gln Ala Asp Ile Val Val Trp Val Ala Ser
210 215 220

Met Pro Lys Gly Ile Glu Ile Asp Ala Glu Asn Leu Lys His Pro Cys
225 230 235 240

Leu Met Ile Asp Gly Gly Tyr Pro Lys Asn Leu Gly Thr Lys Ile Gln
245 250 255

His Pro Asp Val His Ile Leu Asn Gly Gly Ile Val Glu His Ser Leu
260 265 270

Asp Ile Asp Trp Lys Ile Met His Ile Val Asn Met Asn Ile Pro Asn
275 280 285

Arg Gln Leu Phe Ala Cys Phe Ala Glu Ser Met Leu Leu Glu Phe Glu
290 295 300

Gln Leu His Thr Asn Phe Ser Trp Gly Arg Asn Glu Ile Thr Val Ala
305 310 315 320

Lys Met Glu Lys Ile Gly Glu Ile Ser Leu Lys His Gly Phe Lys Pro
325 330 335

Leu Ala Leu Ala Val
340

<210> SEQ ID NO 56
<211> LENGTH: 340
<212> TYPE: PRT
<213> ORGANISM: Cyanothece sp.

<400> SEQUENCE: 56

Met Phe Gly Leu Ile Gly His Leu Thr Ser Leu Glu His Ala Gln Gln
1 5 10 15

Val Ala Glu Ala Leu Gly Tyr Pro Glu Tyr Ala Asn Gln Gly Leu Asp
20 25 30

Phe Trp Cys Ala Ala Pro Pro Gln Ile Val Asp His Phe His Val Thr
35 40 45

Ser Val Thr Gly Gln Ile Ile Glu Gly Lys Tyr Val Glu Ser Cys Phe
50 55 60

Leu Pro Glu Met Leu Val Asn Arg Arg Ile Lys Ala Ala Ile Arg Lys
65 70 75 80

Ile Leu Asn Ala Met Ala Leu Ala Gln Lys Ala Asp Leu Asn Ile Thr
85 90 95

Ala Leu Gly Gly Phe Ser Ser Ile Ile Phe Glu Glu Phe Asn Leu Lys
100 105 110

Glu Asn Lys Gln Val Arg Asn Val Glu Leu Glu Phe Glu Arg Phe Thr
115 120 125

Thr Gly Asn Thr His Thr Ala Tyr Ile Ile Cys Arg Gln Leu Glu Gln
130 135 140

Val Ser Ala Gln Leu Gly Leu Asp Leu Ser Gln Ala Thr Val Ala Val
145 150 155 160

Cys Gly Ala Thr Gly Asp Ile Gly Ser Ala Val Cys Arg Trp Leu Asp
165 170 175

Gln Lys Thr Asp Val Ala Glu Leu Leu Leu Ile Ala Arg Asn Gln Glu
180 185 190

Arg Leu Gln Gly Leu Gln Ala Glu Leu Gly Arg Gly Lys Ile Met Glu
195 200 205

Leu Glu Glu Ala Leu Pro Gln Ala Asp Ile Ile Val Trp Val Ala Ser
210 215 220

Met Pro Lys Gly Val Glu Ile Asn Pro Glu Thr Leu Lys Lys Pro Cys
225 230 235 240

Leu Ile Ile Asp Gly Gly Tyr Pro Lys Asn Leu Gly Thr Gln Val Gln
245 250 255

His Pro Asp Val Tyr Val Leu Lys Gly Gly Ile Val Glu His Ser Leu
260 265 270

Asp Ile Asp Trp Lys Ile Met Glu Ile Val Ser Met Asp Ile Pro Ser

```
        275                 280                 285

Arg Gln Met Phe Ala Cys Phe Ala Glu Gly Ile Leu Leu Glu Phe Glu
    290                 295                 300

Gly Trp His Thr Asn Phe Ser Trp Gly Arg Asn Gln Ile Ser Val Pro
305                 310                 315                 320

Lys Met Glu Gln Ile Gly Glu Ala Ser Leu Lys His Gly Phe Arg Pro
                325                 330                 335

Leu Leu Ser Trp
            340


<210> SEQ ID NO 57
<211> LENGTH: 340
<212> TYPE: PRT
<213> ORGANISM: Cyanothece sp.

<400> SEQUENCE: 57

Met Phe Gly Leu Ile Gly His Leu Thr Ser Leu Glu His Ala Gln Gln
1               5                   10                  15

Val Ala Glu Ala Leu Gly Tyr Pro Glu Tyr Ala Asn Gln Gly Leu Asp
            20                  25                  30

Phe Trp Cys Ala Ala Pro Pro Gln Ile Val Asp His Phe His Val Thr
        35                  40                  45

Ser Val Thr Gly Gln Ile Ile Glu Gly Lys Tyr Val Glu Ser Cys Phe
    50                  55                  60

Leu Pro Glu Met Leu Val Asn Arg Arg Ile Lys Ala Ala Ile Arg Lys
65                  70                  75                  80

Ile Leu Asn Ala Met Ala Leu Ala Gln Lys Ala Asp Leu Asn Ile Thr
                85                  90                  95

Ala Leu Gly Gly Phe Ser Ser Ile Ile Phe Glu Glu Phe Asn Leu Lys
            100                 105                 110

Glu Asn Lys Gln Val Arg Asn Val Glu Leu Glu Phe Glu Arg Phe Thr
        115                 120                 125

Thr Gly Asn Thr His Thr Ala Tyr Ile Ile Cys Arg Gln Leu Glu Gln
    130                 135                 140

Val Ser Ala Gln Leu Gly Leu Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Gln Lys Thr Asp Val Ala Glu Leu Leu Leu Ile Ala Arg Asn Gln Glu
            180                 185                 190

Arg Leu Gln Gly Leu Gln Ala Glu Leu Gly Arg Gly Lys Ile Met Glu
        195                 200                 205

Leu Glu Glu Ala Leu Pro Gln Ala Asp Ile Ile Val Trp Val Ala Ser
    210                 215                 220

Met Pro Lys Gly Val Glu Ile Asn Pro Glu Thr Leu Lys Lys Pro Cys
225                 230                 235                 240

Leu Ile Ile Asp Gly Gly Tyr Pro Lys Asn Leu Gly Thr Gln Val Gln
                245                 250                 255

His Pro Asp Val Tyr Val Leu Lys Gly Gly Ile Val Glu His Ser Leu
            260                 265                 270

Asp Ile Asp Trp Lys Ile Met Glu Ile Val Ser Met Asp Ile Pro Ser
        275                 280                 285

Arg Gln Met Phe Ala Cys Phe Ala Glu Gly Ile Leu Leu Glu Phe Glu
    290                 295                 300
```

Gly Trp His Thr Asn Phe Ser Trp Gly Arg Asn Gln Ile Ser Val Pro
305 310 315 320

Lys Met Glu Gln Ile Gly Glu Ala Ser Leu Lys His Gly Phe Arg Pro
325 330 335

Leu Leu Ser Trp
340

<210> SEQ ID NO 58
<211> LENGTH: 340
<212> TYPE: PRT
<213> ORGANISM: Microcoleus chthonoplastes

<400> SEQUENCE: 58

Met Phe Gly Leu Ile Gly His Leu Thr Ser Leu Gln His Ala Gln Ala
1 5 10 15

Val Ala Arg Asp Leu Gly Tyr Pro Glu Tyr Ala Asp Gln Gly Leu Asp
20 25 30

Phe Trp Cys Ser Ala Pro Pro Gln Ile Val Asp Thr Ile Lys Val Thr
35 40 45

Ser Leu Thr Gly Glu Thr Ile Glu Gly Arg Tyr Val Glu Ser Cys Phe
50 55 60

Leu Pro Glu Met Leu Ala Thr Arg Arg Ile Lys Ala Ala Ile Arg Lys
65 70 75 80

Val Leu Asn Ala Met Ala His Ala Gln Lys Asn Gly Ile Glu Ile Thr
85 90 95

Ala Leu Gly Gly Phe Ser Ser Ile Ile Phe Glu Glu Phe His Leu Tyr
100 105 110

Glu Lys Ser Gln Val Arg Asn Ile Lys Leu Glu Phe Glu Arg Phe Thr
115 120 125

Thr Gly Asn Thr His Thr Ala Tyr Ile Ile Ser Ala Gln Val Glu Gln
130 135 140

Gly Ala Gln Lys Leu Gly Ile Asp Leu Ser Lys Ala Thr Val Ala Val
145 150 155 160

Cys Gly Ala Thr Gly Asp Ile Gly Ser Ala Val Cys Arg Trp Leu Asn
165 170 175

Thr Arg Thr Asp Val Ala Glu Ile Leu Leu Thr Ala Arg Asn Gln Glu
180 185 190

Arg Leu Gln Ala Leu Gln Asp Gln Leu Gly Arg Gly Lys Ile Met Gly
195 200 205

Leu Glu Glu Ala Leu Pro Gln Ala Asp Ile Ile Val Trp Val Ala Ser
210 215 220

Met Ser Lys Gly Ile Asp Ile Asp Ala Ser Leu Leu Lys Lys Pro Cys
225 230 235 240

Leu Leu Ile Asp Gly Gly Tyr Pro Lys Asn Leu Ala Thr Lys Leu Gln
245 250 255

His Pro Asp Ile Tyr Val Leu Asn Gly Gly Ile Val Glu His Ser Leu
260 265 270

Asp Ile Asp Trp Lys Ile Met Gln Ile Val Glu Met Lys Asp Pro Gly
275 280 285

Arg Gln Leu Phe Ala Cys Phe Ala Glu Ser Met Leu Leu Glu Phe Glu
290 295 300

Lys Trp Tyr Thr Asn Phe Ser Trp Gly Arg Asn Gln Ile Thr Val Glu
305 310 315 320

Lys Met Asp Lys Ile Gly Gln Val Ser Ile Lys His Gly Phe Arg Pro
325 330 335

```
Leu Leu Asn Val
            340


<210> SEQ ID NO 59
<211> LENGTH: 339
<212> TYPE: PRT
<213> ORGANISM: Arthrospira maxima

<400> SEQUENCE: 59

Met Phe Gly Leu Ile Gly His Leu Thr Ser Leu Glu His Ala Gln Val
1               5                   10                  15

Val Ala Arg Asp Leu Gly Tyr Ala Glu Tyr Ala Asp Gln Gly Leu Asp
            20                  25                  30

Phe Trp Cys Ser Ala Pro Pro Val Ile Val Glu Asp Leu Lys Val Thr
        35                  40                  45

Ser Ile Thr Gly Gln Val Ile Glu Gly Arg Tyr Val Glu Ser Cys Phe
    50                  55                  60

Leu Pro Glu Met Leu Ala Thr Asn Arg Met Lys Ala Ala Thr Arg Lys
65                  70                  75                  80

Ile Ile Asn Ala Met Ala His Ala Gln Lys Asn Gly Ile Asn Ile Thr
                85                  90                  95

Ala Leu Gly Gly Phe Ser Ser Ile Ile Leu Glu Arg Phe Asn Leu Asp
            100                 105                 110

Gln Leu Gly Arg Ile Arg Asn Ile Lys Leu Glu Phe Glu Arg Phe Thr
        115                 120                 125

Thr Gly Asn Thr His Thr Ala Tyr Ile Ile Cys Arg Gln Val Glu Gln
    130                 135                 140

Ala Ala Pro Lys Leu Gly Ile Asp Leu Ser Lys Ala Thr Val Ala Val
145                 150                 155                 160

Cys Gly Ala Thr Gly Asp Ile Gly Ser Ala Val Cys Arg Trp Leu Asn
                165                 170                 175

Gly Arg Leu Asp Val Ala Glu Ile Leu Leu Ile Ala Arg Asp Arg Gln
            180                 185                 190

Arg Leu Gln Asn Leu Gln Ala Glu Leu Gly Arg Gly Lys Ile Met Ala
        195                 200                 205

Leu Asp Glu Ala Leu Pro Gln Ala Asp Ile Val Val Trp Val Ala Ser
    210                 215                 220

Met Pro Gln Gly Val Glu Ile Asp Pro Glu Val Leu Lys Lys Pro Cys
225                 230                 235                 240

Leu Leu Ile Asp Gly Gly Tyr Pro Lys Asn Met Ala Thr Lys Phe Gln
                245                 250                 255

Ser Pro Gly Val His Val Leu Ser Gly Gly Ile Val Glu His Ala Leu
            260                 265                 270

Asp Ile Asp Trp Lys Ile Met Lys Ile Val Asn Met Asn Val Pro Gly
        275                 280                 285

Arg Gln Leu Phe Ala Cys Phe Ala Glu Ser Met Leu Leu Glu Phe Glu
    290                 295                 300

Ser Ile Tyr Thr Asn Phe Ser Trp Gly Arg Asn Gln Ile Thr Leu Asp
305                 310                 315                 320

Lys Met Asp Met Ile Gly Arg Met Ser Ile Lys His Gly Phe Lys Pro
                325                 330                 335

Leu Met Leu


<210> SEQ ID NO 60
```

<211> LENGTH: 340
<212> TYPE: PRT
<213> ORGANISM: Synechocystis sp.

<400> SEQUENCE: 60

Met Phe Gly Leu Ile Gly His Leu Thr Ser Leu Glu His Ala Gln Ala
1               5                   10                  15

Val Ala Glu Asp Leu Gly Tyr Pro Glu Tyr Ala Asn Gln Gly Leu Asp
            20                  25                  30

Phe Trp Cys Ser Ala Pro Pro Gln Val Val Asp Asn Phe Gln Val Lys
        35                  40                  45

Ser Val Thr Gly Gln Val Ile Glu Gly Lys Tyr Val Glu Ser Cys Phe
    50                  55                  60

Leu Pro Glu Met Leu Thr Gln Arg Arg Ile Lys Ala Ala Ile Arg Lys
65                  70                  75                  80

Ile Leu Asn Ala Met Ala Leu Ala Gln Lys Val Gly Leu Asp Ile Thr
                85                  90                  95

Ala Leu Gly Gly Phe Ser Ser Ile Val Phe Glu Glu Phe Asn Leu Lys
            100                 105                 110

Gln Asn Asn Gln Val Arg Asn Val Glu Leu Asp Phe Gln Arg Phe Thr
        115                 120                 125

Thr Gly Asn Thr His Thr Ala Tyr Val Ile Cys Arg Gln Val Glu Ser
    130                 135                 140

Gly Ala Lys Gln Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Ser Lys His Gln Val Lys Glu Leu Leu Leu Ile Ala Arg Asn Arg Gln
            180                 185                 190

Arg Leu Glu Asn Leu Gln Glu Glu Leu Gly Arg Gly Lys Ile Met Asp
        195                 200                 205

Leu Glu Thr Ala Leu Pro Gln Ala Asp Ile Ile Val Trp Val Ala Ser
    210                 215                 220

Met Pro Lys Gly Val Glu Ile Ala Gly Glu Met Leu Lys Lys Pro Cys
225                 230                 235                 240

Leu Ile Val Asp Gly Gly Tyr Pro Lys Asn Leu Asp Thr Arg Val Lys
                245                 250                 255

Ala Asp Gly Val His Ile Leu Lys Gly Gly Ile Val Glu His Ser Leu
            260                 265                 270

Asp Ile Thr Trp Glu Ile Met Lys Ile Val Glu Met Asp Ile Pro Ser
        275                 280                 285

Arg Gln Met Phe Ala Cys Phe Ala Glu Ala Ile Leu Leu Glu Phe Glu
    290                 295                 300

Gly Trp Arg Thr Asn Phe Ser Trp Gly Arg Asn Gln Ile Ser Val Asn
305                 310                 315                 320

Lys Met Glu Ala Ile Gly Glu Ala Ser Val Lys His Gly Phe Cys Pro
                325                 330                 335

Leu Val Ala Leu
            340

<210> SEQ ID NO 61
<211> LENGTH: 340
<212> TYPE: PRT
<213> ORGANISM: Cyanothece sp.

<400> SEQUENCE: 61

```
Met Phe Gly Leu Ile Gly His Leu Thr Ser Leu Glu His Ala Gln Ser
1               5                   10                  15

Val Ala Asp Ala Leu Gly Tyr Pro Glu Tyr Ala Asn Gln Gly Leu Asp
            20                  25                  30

Phe Trp Cys Ser Ala Pro Pro Gln Ile Val Asp His Phe His Val Thr
        35                  40                  45

Ser Val Thr Gly Gln Thr Ile Glu Gly Lys Tyr Val Glu Ser Cys Phe
    50                  55                  60

Leu Pro Glu Met Leu Met Asn Arg Arg Ile Lys Ala Ala Ile Arg Lys
65                  70                  75                  80

Ile Leu Asn Ala Met Ala Leu Ala Gln Lys Asn Ser Ile Asn Ile Thr
                85                  90                  95

Ala Leu Gly Gly Phe Ser Ser Ile Ile Phe Glu Glu Phe Asn Leu Lys
            100                 105                 110

Asp Asn Lys Gln Val Arg Asn Val Ser Leu Glu Phe Asp Arg Phe Thr
        115                 120                 125

Thr Gly Asn Thr His Thr Ala Tyr Val Ile Cys Arg Gln Val Glu Gln
    130                 135                 140

Gly Ser Ala Lys Leu Gly Ile Asp Leu Ser Lys Ala Thr Ile Ala Val
145                 150                 155                 160

Cys Gly Ala Thr Gly Asp Ile Gly Ser Gly Val Cys Arg Trp Leu Asp
                165                 170                 175

Arg Asn Thr Asn Thr Gln Glu Leu Leu Leu Ile Ala Arg Asn Gln Glu
            180                 185                 190

Arg Leu Lys Arg Leu Gln Asp Glu Leu Gly Arg Gly Lys Ile Met Gly
        195                 200                 205

Leu Glu Glu Ala Leu Pro Glu Ala Asp Val Ile Val Trp Val Ala Ser
    210                 215                 220

Met Pro Lys Gly Val Glu Ile Asn Pro Glu Thr Leu Lys Lys Pro Cys
225                 230                 235                 240

Leu Ile Ile Asp Gly Gly Tyr Pro Lys Asn Leu Asp Thr Lys Ile Lys
                245                 250                 255

His Ser Asp Val His Ile Leu Lys Gly Gly Ile Val Glu His Ser Leu
            260                 265                 270

Asp Ile Asp Trp Lys Ile Met Glu Ile Val Ser Met Asp Ile Pro Ser
        275                 280                 285

Arg Gln Met Phe Ala Cys Phe Ala Glu Ala Ile Leu Leu Glu Phe Glu
    290                 295                 300

Gln Trp His Thr Asn Phe Ser Trp Gly Arg Asn Gln Ile Thr Val Thr
305                 310                 315                 320

Lys Met Glu Gln Ile Gly Thr Ala Ser Val Lys His Gly Phe Gln Pro
                325                 330                 335

Leu Leu Asn Trp
            340
```

<210> SEQ ID NO 62
<211> LENGTH: 339
<212> TYPE: PRT
<213> ORGANISM: Synechococcus sp.

<400> SEQUENCE: 62

```
Met Phe Gly Leu Ile Gly His Leu Thr Ser Leu Glu His Ala Lys Ser
1               5                   10                  15

Val Ala His Lys Leu Gly Tyr Pro Glu Tyr Ala Glu Gln Gly Leu Asp
```

```
            20                  25                  30

Phe Trp Cys Ser Ala Pro Pro Gln Val Val Asp His Phe Lys Val Val
        35                  40                  45

Ser Ala Thr Gly Gln Thr Ile Glu Gly Lys Tyr Val Glu Ser Cys Phe
    50                  55                  60

Leu Pro Glu Met Leu Ala Asn Arg Arg Ile Lys Ala Ala Thr Arg Lys
65                  70                  75                  80

Ile Leu Asn Ala Met Ala His Ala Gln Lys Glu Gly Ile Asn Ile Thr
                85                  90                  95

Ala Leu Gly Gly Phe Ser Ser Ile Ile Phe Glu Asn Phe Lys Leu Glu
            100                 105                 110

Gln Ile Lys Arg Val Arg Asn Leu Asp Leu Asp Phe Ser Lys Phe Thr
        115                 120                 125

Thr Gly Asn Thr His Thr Ala Tyr Val Ile Cys Lys Gln Val Glu Glu
    130                 135                 140

Ala Ala Pro Ser Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Thr
                165                 170                 175

Ala Arg Thr Gly Val Lys Asn Leu Leu Leu Val Ala Arg Asn Gln Glu
            180                 185                 190

Arg Leu Glu Asn Leu Gln Ala Asp Leu Lys Phe Gly Gln Val Gln Thr
        195                 200                 205

Leu Asp Glu Ala Leu Pro Gln Ala Asp Val Val Val Trp Val Ala Ser
    210                 215                 220

Met Pro Lys Gly Val Glu Val Asp Leu Glu Thr Leu Lys Gln Pro Cys
225                 230                 235                 240

Leu Met Val Asp Gly Gly Tyr Pro Lys Asn Met Asp Val Thr Phe Ser
                245                 250                 255

His Pro Gly Ile Thr Val Leu Lys Gly Gly Ile Val Glu His Met Leu
            260                 265                 270

Asp Ile Asp Trp His Ile Met Asn Ile Val Asn Met Asp Val Pro Gly
        275                 280                 285

Arg Gln Leu Phe Ala Cys Phe Ala Glu Ser Met Leu Leu Glu Phe Glu
    290                 295                 300

Lys Leu His Thr Asn Phe Ser Trp Gly Arg Asn Gln Ile Thr Leu Glu
305                 310                 315                 320

Lys Met Asp Leu Ile Gly Glu Ala Ser Arg Arg His Gly Phe Lys Pro
                325                 330                 335

Leu Leu Thr
```

<210> SEQ ID NO 63
<211> LENGTH: 340
<212> TYPE: PRT
<213> ORGANISM: Cyanothece sp.

<400> SEQUENCE: 63

```
Met Phe Gly Leu Ile Gly His Leu Thr Ser Leu Glu His Ala His Ser
1               5                   10                  15

Val Ala Asp Ala Phe Gly Tyr Gly Pro Tyr Ala Thr Gln Gly Leu Asp
            20                  25                  30

Leu Trp Cys Ser Ala Pro Pro Gln Phe Val Glu His Phe His Val Thr
        35                  40                  45

Ser Ile Thr Gly Gln Thr Ile Glu Gly Lys Tyr Ile Glu Ser Ala Phe
```

-continued

```
    50                  55                  60

Leu Pro Glu Met Leu Ile Lys Arg Arg Ile Lys Ala Ala Ile Arg Lys
65                  70                  75                  80

Ile Leu Asn Ala Met Ala Phe Ala Gln Lys Asn Asn Leu Asn Ile Thr
                85                  90                  95

Ala Leu Gly Gly Phe Ser Ser Ile Ile Phe Glu Glu Phe Asn Leu Lys
            100                 105                 110

Glu Asn Arg Gln Val Arg Asn Val Ser Leu Glu Phe Asp Arg Phe Thr
        115                 120                 125

Thr Gly Asn Thr His Thr Ala Tyr Ile Ile Cys Arg Gln Val Glu Gln
    130                 135                 140

Ala Ser Ala Lys Leu Gly Ile Asp Leu Ser Gln Ala Thr Val Ala Ile
145                 150                 155                 160

Cys Gly Ala Thr Gly Asp Ile Gly Ser Ala Val Cys Arg Trp Leu Asp
                165                 170                 175

Arg Lys Thr Asp Thr Gln Glu Leu Phe Leu Ile Ala Arg Asn Lys Glu
            180                 185                 190

Arg Leu Gln Arg Leu Gln Asp Glu Leu Gly Arg Gly Lys Ile Met Gly
        195                 200                 205

Leu Glu Glu Ala Leu Pro Glu Ala Asp Ile Ile Val Trp Val Ala Ser
    210                 215                 220

Met Pro Lys Gly Val Glu Ile Asn Ala Glu Thr Leu Lys Lys Pro Cys
225                 230                 235                 240

Leu Ile Ile Asp Gly Gly Tyr Pro Lys Asn Leu Asp Thr Lys Ile Lys
                245                 250                 255

His Pro Asp Val His Ile Leu Lys Gly Gly Ile Val Glu His Ser Leu
            260                 265                 270

Asp Ile Asp Trp Lys Ile Met Glu Thr Val Asn Met Asp Val Pro Ser
        275                 280                 285

Arg Gln Met Phe Ala Cys Phe Ala Glu Ala Ile Leu Leu Glu Phe Glu
    290                 295                 300

Gln Trp His Thr Asn Phe Ser Trp Gly Arg Asn Gln Ile Thr Val Thr
305                 310                 315                 320

Lys Met Glu Gln Ile Gly Glu Ala Ser Val Lys His Gly Leu Gln Pro
                325                 330                 335

Leu Leu Ser Trp
            340


<210> SEQ ID NO 64
<211> LENGTH: 350
<212> TYPE: PRT
<213> ORGANISM: Gloeobacter violaceus

<400> SEQUENCE: 64

Met Phe Gly Leu Ile Gly His Leu Thr Asn Leu Ser His Ala Gln Arg
1               5                   10                  15

Val Ala Arg Asp Leu Gly Tyr Asp Glu Tyr Ala Ser His Asp Leu Glu
            20                  25                  30

Phe Trp Cys Met Ala Pro Pro Gln Ala Val Asp Glu Ile Thr Ile Thr
        35                  40                  45

Ser Val Thr Gly Gln Val Ile His Gly Gln Tyr Val Glu Ser Cys Phe
    50                  55                  60

Leu Pro Glu Met Leu Ala Gln Gly Arg Phe Lys Thr Ala Met Arg Lys
65                  70                  75                  80
```

```
Ile Leu Asn Ala Met Ala Leu Val Gln Lys Arg Gly Ile Asp Ile Thr
                85                  90                  95

Ala Leu Gly Gly Phe Ser Ser Ile Ile Phe Glu Asn Phe Ser Leu Asp
            100                 105                 110

Lys Leu Leu Asn Val Arg Asp Ile Thr Leu Asp Ile Gln Arg Phe Thr
        115                 120                 125

Thr Gly Asn Thr His Thr Ala Tyr Ile Leu Cys Gln Gln Val Glu Gln
    130                 135                 140

Gly Ala Val Arg Tyr Gly Ile Asp Pro Ala Lys Ala Thr Val Ala Val
145                 150                 155                 160

Val Gly Ala Thr Gly Asp Ile Gly Ser Ala Val Cys Arg Trp Leu Thr
                165                 170                 175

Asp Arg Ala Gly Ile His Glu Leu Leu Leu Val Ala Arg Asp Ala Glu
            180                 185                 190

Arg Leu Asp Arg Leu Gln Gln Glu Leu Gly Thr Gly Arg Ile Leu Pro
        195                 200                 205

Val Glu Glu Ala Leu Pro Lys Ala Asp Ile Val Val Trp Val Ala Ser
    210                 215                 220

Met Asn Gln Gly Met Ala Ile Asp Pro Ala Gly Leu Arg Thr Pro Cys
225                 230                 235                 240

Leu Leu Ile Asp Gly Gly Tyr Pro Lys Asn Met Ala Gly Thr Leu Gln
                245                 250                 255

Arg Pro Gly Ile His Ile Leu Asp Gly Gly Met Val Glu His Ser Leu
            260                 265                 270

Asp Ile Asp Trp Gln Ile Met Ser Phe Leu Asn Val Pro Asn Pro Ala
        275                 280                 285

Arg Gln Phe Phe Ala Cys Phe Ala Glu Ser Met Leu Leu Glu Phe Glu
    290                 295                 300

Gly Leu His Phe Asn Phe Ser Trp Gly Arg Asn His Ile Thr Val Glu
305                 310                 315                 320

Lys Met Ala Gln Ile Gly Ser Leu Ser Lys Lys His Gly Phe Arg Pro
                325                 330                 335

Leu Leu Glu Pro Ser Gln Arg Ser Gly Glu Leu Val His Gly
            340                 345                 350


<210> SEQ ID NO 65
<211> LENGTH: 339
<212> TYPE: PRT
<213> ORGANISM: Microcystis aeruginosa

<400> SEQUENCE: 65

Met Phe Gly Leu Ile Gly His Leu Thr Ser Leu Glu His Ala Gln Ser
1               5                   10                  15

Val Ala Asp Asp Leu Gly Tyr Pro Glu Tyr Ala Asn Gln Gly Leu Asp
            20                  25                  30

Phe Trp Cys Ala Ala Pro Pro Gln Ile Val Asp Asp Phe His Val Thr
        35                  40                  45

Ser Ile Thr Gly Gln Thr Ile Arg Gly Lys Tyr Ile Glu Ser Cys Phe
    50                  55                  60

Leu Pro Glu Met Leu Ser Asn Arg Trp Val Lys Ser Ala Ile Arg Lys
65                  70                  75                  80

Val Leu Asn Ala Met Ala Leu Ala Gln Lys Ser Asp Ile Asn Ile Thr
                85                  90                  95

Ala Leu Gly Gly Phe Ser Ser Ile Ile Phe Glu Glu Phe Asn Leu Lys
            100                 105                 110
```

```
Asp Asn Arg Gln Val Arg Asn Ile Glu Leu Asp Phe Gly Arg Phe Thr
        115                 120                 125

Thr Gly Asn Thr His Thr Ala Tyr Val Ile Cys Thr Gln Val Glu Thr
    130                 135                 140

Leu Ala Glu Lys Met Gly Ile Asp Leu Ala Gln Ser Thr Val Val Val
145                 150                 155                 160

Cys Gly Ala Thr Gly Asp Ile Gly Ser Ala Val Cys Arg Trp Leu Asn
                165                 170                 175

Glu Lys Thr Asp Thr Lys Glu Leu Ile Cys Val Ala Arg Asn Gln Glu
            180                 185                 190

Arg Leu Gln Ser Leu Gln Glu Glu Leu Gly Arg Gly Lys Ile Leu Pro
        195                 200                 205

Leu Glu Glu Ala Leu Pro Leu Ala Asp Ile Ile Val Trp Val Ala Ser
    210                 215                 220

Leu Pro Lys Gly Val Glu Ile Asp Pro Asp Lys Leu Lys Arg Pro Cys
225                 230                 235                 240

Ile Ile Ile Asp Gly Gly Tyr Pro Lys Asn Leu Gly Thr Val Leu Asn
                245                 250                 255

Ala Pro Asp Ile Ser Val Ile Lys Gly Gly Ile Val Glu His Ser Leu
            260                 265                 270

Asp Ile Asp Trp Lys Ile Met Lys Ile Val Asn Met Asp Ile Pro Ser
        275                 280                 285

Arg Gln Met Phe Ala Cys Phe Ala Glu Ala Ile Leu Leu Glu Leu Glu
    290                 295                 300

Gly Trp Gln Thr Asn Phe Ser Trp Gly Arg Asn Gln Ile Thr Val Pro
305                 310                 315                 320

Lys Met Glu Gln Ile Gly Ala Ala Ser Arg Lys His Gly Phe Gln Pro
                325                 330                 335

Leu Leu Phe


<210> SEQ ID NO 66
<211> LENGTH: 340
<212> TYPE: PRT
<213> ORGANISM: Crocosphaera watsonii

<400> SEQUENCE: 66

Met Phe Gly Leu Ile Gly His Leu Thr Ser Leu Glu His Ala His Ser
1               5                   10                  15

Val Ala Asp Ala Phe Gly Tyr Gly Pro Tyr Ala Thr Gln Gly Leu Asp
            20                  25                  30

Leu Trp Cys Ser Ala Pro Pro Gln Phe Val Glu Gln Phe His Val Thr
        35                  40                  45

Ser Ile Thr Gly Gln Thr Ile Glu Gly Lys Tyr Ile Glu Ser Ala Phe
    50                  55                  60

Leu Pro Glu Met Leu Met Lys Arg Arg Ile Lys Ala Ala Ile Arg Lys
65                  70                  75                  80

Ile Leu Asn Ala Met Ala Phe Ala Gln Lys Asn Asp Leu Asn Ile Thr
                85                  90                  95

Ala Leu Gly Gly Phe Ser Ser Ile Ile Phe Glu Glu Phe Asn Leu Lys
            100                 105                 110

Gly Asn Arg Gln Val Arg Asn Val Ser Leu Glu Phe Asp Arg Phe Thr
        115                 120                 125

Thr Gly Asn Thr His Thr Ala Tyr Ile Ile Ala Arg Gln Val Glu Gln
    130                 135                 140
```

Ala Ser Ala Lys Leu Gly Ile Asp Leu Ser Arg Ala Thr Val Ala Val
145 150 155 160

Cys Gly Ala Thr Gly Asp Ile Gly Ser Ala Val Cys Arg Trp Leu Asp
165 170 175

Arg Lys Thr Asp Thr Gln Glu Leu Leu Leu Ile Ala Arg Asn Gln Glu
180 185 190

Arg Leu Gln Arg Leu Gln Asp Glu Leu Gly Arg Gly Lys Ile Met Gly
195 200 205

Leu Glu Glu Ala Leu Pro Glu Ala Asp Val Ile Val Trp Val Ala Ser
210 215 220

Met Pro Lys Gly Val Glu Ile Asn Pro Glu Thr Leu Lys Lys Pro Cys
225 230 235 240

Leu Ile Val Asp Gly Gly Tyr Pro Lys Asn Leu Asp Thr Lys Ile Lys
245 250 255

His Pro Asp Val His Ile Leu Lys Gly Gly Val Val Glu His Ser Leu
260 265 270

Asp Ile Asp Trp Lys Ile Met Glu Thr Val Asn Met Asp Val Pro Ser
275 280 285

Arg Gln Met Phe Ala Cys Phe Ala Glu Ala Ile Leu Leu Glu Phe Glu
290 295 300

Gln Trp His Thr Asn Phe Ser Trp Gly Arg Asn Gln Ile Thr Val Thr
305 310 315 320

Lys Met Glu Gln Ile Gly Gly Ala Ser Val Lys His Gly Leu Gln Pro
325 330 335

Leu Leu Ser Trp
340

<210> SEQ ID NO 67
<211> LENGTH: 339
<212> TYPE: PRT
<213> ORGANISM: Microcystis aeruginosa

<400> SEQUENCE: 67

Met Phe Gly Leu Ile Gly His Leu Thr Ser Leu Glu His Ala Gln Ser
1 5 10 15

Val Ala Asp Asp Leu Gly Tyr Pro Glu Tyr Ala Asn Gln Gly Leu Asp
20 25 30

Phe Trp Cys Ala Ala Pro Pro Gln Ile Val Asp Asp Phe His Val Thr
35 40 45

Ser Ile Thr Gly Gln Thr Ile Thr Gly Lys Tyr Ile Glu Ser Cys Phe
50 55 60

Leu Pro Glu Met Leu Ser Asn Arg Trp Val Lys Ser Ala Ile Arg Lys
65 70 75 80

Val Leu Asn Ala Met Ala Leu Ala Gln Lys Ser Asp Ile Asn Ile Thr
85 90 95

Ala Leu Gly Gly Phe Ser Ser Ile Ile Phe Glu Glu Phe Asn Leu Lys
100 105 110

Asp Asn Arg Gln Val Arg Asn Ile Glu Leu Asp Phe Gly Arg Phe Thr
115 120 125

Thr Gly Asn Thr His Thr Ala Tyr Val Ile Cys Thr Gln Val Gln Thr
130 135 140

Leu Ala Asp Lys Met Gly Ile Asp Leu Ala Gln Ser Thr Val Val Val
145 150 155 160

Cys Gly Ala Thr Gly Asp Ile Gly Ser Ala Val Cys Arg Trp Leu Asn 165 170 175

Glu Lys Thr Asp Thr Lys Glu Leu Ile Cys Val Ala Arg Asn Gln Glu
180 185 190

Arg Leu Gln Ser Leu Gln Glu Glu Leu Gly Arg Gly Lys Ile Leu Pro
195 200 205

Leu Glu Glu Ala Leu Pro Leu Ala Asp Ile Ile Val Trp Val Ala Ser
210 215 220

Met Pro Lys Gly Val Glu Ile Asp Pro Asp Lys Leu Lys Arg Pro Cys
225 230 235 240

Leu Ile Ile Asp Gly Gly Tyr Pro Lys Asn Leu Gly Thr Val Leu Asn
245 250 255

Ala Pro Asp Val Ser Val Ile Lys Gly Gly Ile Val Glu His Ser Leu
260 265 270

Asp Ile Asp Trp Lys Ile Met Lys Ile Val Asn Met Asp Ile Pro Ser
275 280 285

Arg Gln Met Phe Ala Cys Phe Ala Glu Ala Ile Leu Leu Glu Leu Glu
290 295 300

Gly Trp Gln Thr Asn Phe Ser Trp Gly Arg Asn Gln Ile Ser Val Ser
305 310 315 320

Lys Met Glu Gln Ile Gly Ala Ala Ser Arg Lys His Gly Phe Gln Pro
325 330 335

Leu Leu Phe

<210> SEQ ID NO 68
<211> LENGTH: 348
<212> TYPE: PRT
<213> ORGANISM: Synechococcus sp.

<400> SEQUENCE: 68

Met Phe Gly Leu Ile Gly His Ser Thr Ser Leu Glu Gln Ala Arg Ser
1 5 10 15

Lys Ala Leu Glu Leu Gly Phe Pro Glu Tyr Ala Asp Gly Asp Leu Asp
20 25 30

Leu Trp Cys Val Ala Pro Pro Gln Leu Val Glu Asn Val Ser Ile Thr
35 40 45

Ser Pro Thr Gly Lys Thr Ile Glu Gly Ala Tyr Ile Asp Ser Val Phe
50 55 60

Val Pro Glu Met Leu Ser Arg Phe Lys Thr Ala Arg Arg Lys Val Leu
65 70 75 80

Asn Ala Met Glu Leu Ala Gln Lys Ser Gly Ile Asp Ile Thr Ala Leu
85 90 95

Gly Gly Phe Thr Ser Ile Ile Phe Glu Asn Phe Asn Leu Leu Lys Asn
100 105 110

Gln Gln Ile Arg Ser Thr Ala Leu Glu Trp Glu Arg Phe Thr Thr Gly
115 120 125

Asn Thr His Thr Ala Trp Val Ile Ala Gln Gln Val Glu Thr Asn Ala
130 135 140

Pro Ala Leu Gly Ile Asp Leu Ser Arg Ala Lys Val Ala Val Val Gly
145 150 155 160

Ala Thr Gly Asp Ile Gly Ser Ala Val Cys Arg Trp Leu Ser Gln Asn
165 170 175

Thr Gly Val Gly Glu Leu Leu Leu Val Ala Arg Gln Pro Gln Pro Leu
180 185 190

Leu Asp Leu Gln Ala Glu Leu Gly Ser Gly Arg Ile Leu Ser Leu Glu

```
        195                 200                 205

Glu Ala Leu Pro Glu Ala Asp Val Val Val Trp Val Ala Ser Leu Pro
    210                 215                 220

Gln Gly Leu Ser Ile Asp Pro Ala Ser Leu Lys Ser Pro Cys Leu Met
225                 230                 235                 240

Ile Asp Gly Gly Tyr Pro Lys Asn Leu Asp Ser Lys Val Thr Gly Ala
                245                 250                 255

Gly Val His Val Ile Lys Gly Gly Ile Val Glu Phe Trp Gln Asp Ile
            260                 265                 270

Gly Trp Gln Met Met Gln Val Ala Glu Met Glu Asn Pro Arg Arg Gln
        275                 280                 285

Leu Phe Ala Cys Phe Ala Glu Ala Met Leu Leu Glu Phe Glu Gly Leu
    290                 295                 300

His Thr Asn Phe Ser Trp Gly Arg Asn Asn Ile Thr Leu Ala Asn Met
305                 310                 315                 320

Glu Leu Ile Gly Ala Ala Ser Leu Arg His Gly Phe Arg Ser Ile Gly
                325                 330                 335

Leu Asn Gln Val Pro Arg Pro Gln Leu Ala Ala Val
            340                 345


<210> SEQ ID NO 69
<211> LENGTH: 349
<212> TYPE: PRT
<213> ORGANISM: Synechococcus sp.

<400> SEQUENCE: 69

Met Phe Gly Leu Ile Gly His Ser Ser Ser Phe Arg Asp Ala Arg Asn
1               5                   10                  15

Thr Ala Arg Asp Leu Gly Phe Glu Asp Leu Ala Asp Gly Glu Leu Asp
            20                  25                  30

Leu Trp Cys Ser Ala Pro Pro Gln Leu Val Glu Ser Phe Glu Val Thr
        35                  40                  45

Ser Ser Thr Gly Lys Thr Ile Glu Gly Thr Tyr Ile Asp Ser Cys Phe
    50                  55                  60

Val Pro Glu Met Leu Ser Arg Phe Lys Thr Ala Thr Arg Lys Val Gln
65                  70                  75                  80

Asn Ala Met Glu Leu Ala Gln Lys Arg Gly Ile Asn Ile Thr Ala Leu
                85                  90                  95

Gly Gly Phe Thr Ser Ile Ile Phe Glu Asn Phe Asn Leu Ala Lys Phe
            100                 105                 110

Gln Gln Ile Arg Ser Thr Leu Leu Gln Trp Asp Arg Phe Thr Thr Gly
        115                 120                 125

Asn Thr His Thr Ala Trp Val Ile Cys Arg Gln Val Glu Gln Asn Ala
    130                 135                 140

Pro Arg Leu Gly Ile Asp Leu Lys Ala Ala Lys Val Ala Val Val Gly
145                 150                 155                 160

Ala Thr Gly Asp Ile Gly Ser Ala Val Cys Arg Trp Met Ala Asn Lys
                165                 170                 175

Thr Gly Val Ala Glu Leu Leu Leu Val Ala Arg Gln Gln Gln Arg Leu
            180                 185                 190

Glu Asp Leu Arg Glu Glu Leu Gly Gly Gly Arg Ile Leu Thr Leu Glu
        195                 200                 205

Gln Ala Leu Pro Glu Ala Asp Val Val Val Trp Val Ala Ser Leu Pro
    210                 215                 220
```

```
Gln Thr Leu Glu Ile Asp Ser Asn Ser Leu Arg Lys Pro Cys Leu Met
225                 230                 235                 240

Ile Asp Gly Gly Tyr Pro Lys Asn Leu Asp Ser Lys Val Met Ser Glu
                245                 250                 255

His Val Thr Val Leu Lys Gly Gly Ile Val Glu Phe Ala Arg Asp Ile
            260                 265                 270

Gly Trp Gln Met Met Thr Val Ala Asp Met Ala Asn Pro Arg Arg Gln
        275                 280                 285

Leu Phe Ala Cys Phe Ala Glu Ala Met Leu Leu Glu Phe Glu Gly Ile
    290                 295                 300

His Thr Asn Phe Ser Trp Gly Arg Asn Asn Ile Thr Leu Glu Ala Met
305                 310                 315                 320

Glu Gln Ile Gly Met Ala Ser Ile Arg His Gly Phe Ser Ala Leu Gly
                325                 330                 335

Ile Asp Pro Asn Thr Leu Asn Pro Gln Pro Leu Ala Ala
            340                 345


<210> SEQ ID NO 70
<211> LENGTH: 346
<212> TYPE: PRT
<213> ORGANISM: Unknown
<220> FEATURE:
<223> OTHER INFORMATION: Description of Unknown: Uncultured
      marine type-A Synechococcus GOM 306
      polypeptide

<400> SEQUENCE: 70

Met Phe Gly Leu Ile Gly His Ser Thr Ser Phe Asp Ala Ala Arg Arg
1               5                   10                  15

Lys Ala Met Glu Leu Gly Phe Asp His Ile Ala Asp Gly Asp Leu Asp
            20                  25                  30

Val Trp Cys Ser Ala Pro Pro Gln Leu Val Glu His Val Glu Ile Ser
        35                  40                  45

Ser Pro Thr Gly Thr Thr Ile Lys Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
    130                 135                 140

Pro Thr Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Val Asp Leu Gln Ala Gln Ile Gly Gly Gly Arg Ile Leu Thr Leu Asp
        195                 200                 205

Glu Ala Leu Pro Glu Ala Asp Val Val Val Trp Val Ala Ser Met Pro
    210                 215                 220

Arg Thr Leu Glu Ile Asp Gln Ala Ser Leu Arg Lys Pro Cys Leu Met
```

```
225                 230                 235                 240

Ile Asp Gly Gly Tyr Pro Lys Asn Leu Asp Thr Lys Val Ala Gly Gly
                245                 250                 255

Gly Ile His Val Leu Lys Gly Gly Ile Val Glu Phe Cys Lys Asp Ile
            260                 265                 270

Gly Trp Thr Met Met Gln Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Asn Pro Ser Ala Gln Ala Ala Ala Ala
            340                 345


<210> SEQ ID NO 71
<211> LENGTH: 346
<212> TYPE: PRT
<213> ORGANISM: Synechococcus sp.

<400> SEQUENCE: 71

Met Phe Gly Leu Ile Gly His Ser Thr Ser Phe Asp Ala Ala Arg Arg
1               5                   10                  15

Lys Ala Met Glu Leu Gly Phe Asp His Ile Ala Asp Gly Asp Leu Asp
            20                  25                  30

Val Trp Cys Ser Ala Pro Pro Gln Leu Val Glu His Val Glu Ile Ser
        35                  40                  45

Ser Pro Thr Gly Thr Thr Ile Lys Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
    130                 135                 140

Pro Thr Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Leu Asp Leu Gln Ala Gln Ile Gly Gly Gly Arg Ile Leu Thr Leu Asp
        195                 200                 205

Glu Ala Leu Pro Glu Ala Asp Val Val Val Trp Val Ala Ser Met Pro
    210                 215                 220

Arg Thr Leu Glu Ile Asp Gln Ala Ser Leu Arg Lys Pro Cys Leu Met
225                 230                 235                 240

Ile Asp Gly Gly Tyr Pro Lys Asn Leu Asp Thr Lys Val Ala Gly Gly
                245                 250                 255
```

```
Gly Ile His Val Leu Lys Gly Gly Ile Val Glu Phe Cys Lys Asp Ile
            260                 265                 270

Gly Trp Thr Met Met Gln Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Asn Pro Ser Ala Gln Ala Ala Ala Ala
            340                 345


<210> SEQ ID NO 72
<211> LENGTH: 346
<212> TYPE: PRT
<213> ORGANISM: Synechococcus sp.

<400> SEQUENCE: 72

Met Phe Gly Leu Ile Gly His Ser Thr Ser Phe Glu Ala Ala Arg Arg
1               5                   10                  15

Lys Ala Ser Glu Leu Gly Phe Asp His Ile Ala Glu Gly Asp Leu Asp
            20                  25                  30

Val Trp Cys Ser Ala Pro Pro Gln Leu Val Glu His Val Glu Val Thr
        35                  40                  45

Ser Ala Thr Gly Arg Thr Ile Gln Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asp Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Ala Trp Glu Arg Phe Thr Thr Gly
        115                 120                 125

Asn Thr His Thr Ala Trp Val Ile Cys Arg Gln Val Glu Asn Asn Ala
    130                 135                 140

Pro Ala Leu Gly Ile Asp Leu Lys Lys Ala Ser Val Ala Val Val Gly
145                 150                 155                 160

Ala Thr Gly Asp Ile Gly Ser Ala Val Cys Arg Trp Leu Ser Ser Arg
                165                 170                 175

Thr Gly Val Ala Glu Leu Leu Leu Val Ala Arg Gln Gln Lys Pro Leu
            180                 185                 190

Glu Glu Leu Arg Glu Glu Leu Gly Gly Gly Arg Ile Leu Ser Leu Glu
        195                 200                 205

Asp Ala Leu Pro Glu Ala Asp Val Val Val Trp Val Ala Ser Met Pro
    210                 215                 220

Arg Thr Leu Glu Ile Asp Thr Ser Arg Leu Lys Thr Pro Cys Leu Met
225                 230                 235                 240

Ile Asp Gly Gly Tyr Pro Lys Asn Leu Asp Ala Arg Val Ala Ala Lys
                245                 250                 255

Gly Ile His Val Leu Lys Gly Gly Ile Val Glu Phe Phe Thr Asp Ile
            260                 265                 270

Gly Trp Ser Met Met Glu Ile Ala Glu Met Glu Lys Pro Gln Arg Gln
        275                 280                 285
```

```
Met Phe Ala Cys Phe Ala Glu Ala Met Leu Leu Glu Phe Glu Ser His
    290                 295                 300

His Thr Asn Phe Ser Trp Gly Arg Asn Asn Ile Thr Leu Glu Lys Met
305                 310                 315                 320

Asp Phe Ile Gly Gly Ala Ser Val Arg His Gly Phe Thr Thr Leu Asn
                325                 330                 335

Leu Gln Gly Leu Pro Gln Ala Ala Val Ala
            340                 345


<210> SEQ ID NO 73
<211> LENGTH: 346
<212> TYPE: PRT
<213> ORGANISM: Unknown
<220> FEATURE:
<223> OTHER INFORMATION: Description of Unknown: Uncultured
      marine type-A Synechococcus GOM 5D20
      polypeptide

<400> SEQUENCE: 73

Met Phe Gly Leu Ile Gly His Ser Thr Ser Phe Asp Ala Ala Arg Arg
1               5                   10                  15

Lys Ala Met Glu Leu Gly Phe Asp His Ile Ala Asp Gly Asp Leu Asp
            20                  25                  30

Val Trp Cys Ser Ala Pro Pro Gln Leu Val Glu His Val Glu Ile Ser
        35                  40                  45

Ser Pro Thr Gly Thr Thr Ile Lys Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Leu Asp Leu Gln Ala Gln Ile Gly Gly Gly Arg Ile Leu Thr Leu Asp
        195                 200                 205

Glu Ala Leu Pro Glu Ala Asp Val Val Val Trp Val Ala Ser Met Pro
    210                 215                 220

Arg Thr Leu Glu Ile Asp Gln Ser Ser Leu Pro Lys Pro Cys Leu Met
225                 230                 235                 240

Ile Asp Gly Gly Tyr Pro Lys Asn Leu Asp Ser Lys Val Ala Gly Gly
                245                 250                 255

Gly Ile His Val Leu Lys Gly Gly Ile Val Glu Phe Cys Lys Asp Ile
            260                 265                 270

Gly Trp Thr Met Met Gln Ile Ala Glu Met Asp Asn Pro Gln Arg Gln
        275                 280                 285
```

```
Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Asn Pro Ser Val Gln Ala Ala Ala Ala
            340                 345


<210> SEQ ID NO 74
<211> LENGTH: 346
<212> TYPE: PRT
<213> ORGANISM: Synechococcus sp.

<400> SEQUENCE: 74

Met Phe Gly Leu Ile Gly His Ser Thr Ser Phe Glu Ala Ala Arg Arg
1               5                   10                  15

Lys Ala Ser Asp Leu Gly Phe Asp His Ile Ala Glu Gly Asp Leu Asp
            20                  25                  30

Val Trp Cys Ser Ala Pro Pro Gln Leu Val Glu His Val Glu Val Thr
        35                  40                  45

Ser Pro Thr Gly Lys Ser Ile Gln Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asp Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Ala Trp Glu Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Lys Lys Ala Ser Val Ala Val Val Gly
145                 150                 155                 160

Ala Thr Gly Asp Ile Gly Ser Ala Val Cys Arg Trp Leu Ser Ser Arg
                165                 170                 175

Thr Gly Val Ala Glu Leu Leu Leu Val Ala Arg Gln Gln Lys Pro Leu
            180                 185                 190

Glu Asp Leu Arg Asp Glu Leu Gly Gly Gly Arg Ile Leu Ser Leu Glu
        195                 200                 205

Asp Ala Leu Pro Glu Ala Asp Val Val Val Trp Val Ala Ser Met Pro
    210                 215                 220

Arg Thr Leu Glu Ile Asp Ala Ser Arg Leu Lys Thr Pro Cys Leu Met
225                 230                 235                 240

Ile Asp Gly Gly Tyr Pro Lys Asn Leu Asp Ala Arg Val Ala Ala Lys
                245                 250                 255

Gly Ile His Val Leu Lys Gly Gly Ile Val Glu Phe Phe Thr Asp Ile
            260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Glu Phe Glu Ser His
    290                 295                 300

His Thr Asn Phe Ser Trp Gly Arg Asn Asn Ile Thr Leu Glu Lys Met
305                 310                 315                 320
```

```
Asp Phe Ile Gly Gly Ala Ser Val Arg His Gly Phe Ser Thr Leu Asn
                325                 330                 335

Leu Gln Gly Leu Pro Gln Ala Ala Ala Ala
            340                 345


<210> SEQ ID NO 75
<211> LENGTH: 346
<212> TYPE: PRT
<213> ORGANISM: Unknown
<220> FEATURE:
<223> OTHER INFORMATION: Description of Unknown: Uncultured
      marine type-A Synechococcus 5B2
      polypeptide

<400> SEQUENCE: 75

Met Phe Gly Leu Ile Gly His Ser Thr Ser Phe Asp Ala Ala Arg Arg
1               5                   10                  15

Lys Ala Leu Glu Leu Gly Phe Asp His Ile Ala Asp Gly Asp Leu Asp
            20                  25                  30

Val Trp Cys Ser Ala Pro Pro Gln Leu Val Glu His Val Glu Ile Thr
        35                  40                  45

Ser Pro Val Gly Thr Thr Ile Lys Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Ile Arg Ser Thr Thr Leu Glu Trp Gln Arg Phe Thr Thr Gly
        115                 120                 125

Asn Thr His Thr Ala Trp Val Ile Cys Arg Gln Val Glu Asn Asn Ala
    130                 135                 140

Pro Ala Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Thr Ala Arg
                165                 170                 175

Thr Gly Val Gly Glu Leu Leu Leu Val Ala Arg Gln Gln Gln Pro Leu
            180                 185                 190

Leu Asp Leu Gln Gly Glu Leu Gly Gly Gly Arg Ile Leu Ser Leu Asp
        195                 200                 205

Glu Ala Met Pro Glu Ala Asp Val Val Val Trp Val Ala Ser Met Pro
    210                 215                 220

Arg Thr Leu Gln Ile Asp Gln Glu Ser Leu Arg Lys Pro Cys Leu Met
225                 230                 235                 240

Ile Asp Gly Gly Tyr Pro Lys Asn Leu Asp Ala Lys Val Ala Gly Gly
                245                 250                 255

Gly Ile His Val Leu Lys Gly Gly Ile Val Glu Phe Cys Lys Asp Ile
            260                 265                 270

Gly Trp Thr Met Met Gln Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320
```

```
Asp Phe Ile Gly Gln Ala Ser Val Arg His Gly Phe Ser Thr Leu Asn
                325                 330                 335

Leu Asn Pro Ser Leu Gln Val Ala Ala Ala
            340                 345


<210> SEQ ID NO 76
<211> LENGTH: 346
<212> TYPE: PRT
<213> ORGANISM: Synechococcus sp.

<400> SEQUENCE: 76

Met Phe Gly Leu Ile Gly His Ser Thr Ser Phe Glu Ala Ala Arg Gln
1               5                   10                  15

Lys Ala Phe Glu Leu Gly Phe Asp His Ile Ala Asp Gly Asp Leu Asp
            20                  25                  30

Val Trp Cys Ser Ala Pro Pro Gln Leu Val Glu Thr Phe Asp Val Thr
        35                  40                  45

Ser Pro Thr Gly Arg Thr Ile Thr Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Glu Trp Glu Arg Phe Thr Thr Gly
        115                 120                 125

Asn Thr His Thr Ala Trp Val Ile Ser Arg Gln Val Glu Ile Asn Ala
    130                 135                 140

Pro Arg Leu Gly Ile Asp Leu Ser Lys Ala Arg Val Ala Val Val Gly
145                 150                 155                 160

Ala Thr Gly Asp Ile Gly Ser Ala Val Cys Arg Trp Leu Ser Gln Arg
                165                 170                 175

Thr Gly Val Ala Glu Leu Leu Leu Val Ala Arg Gln Gln Gln Pro Leu
            180                 185                 190

Leu Asp Leu Gln Lys Glu Leu Gly Gly Gly Arg Ile Leu Ser Leu Asp
        195                 200                 205

Glu Ala Val Pro Glu Ala Asp Val Val Val Trp Val Ala Ser Met Pro
    210                 215                 220

Arg Thr Leu Glu Ile Asp Ala Ala Ser Leu Arg Gln Pro Cys Leu Met
225                 230                 235                 240

Ile Asp Gly Gly Tyr Pro Lys Asn Leu Asn Ala Arg Ile Ala Gly Ser
                245                 250                 255

Gly Val His Val Leu Lys Gly Gly Ile Val Glu Phe Gly Ser Asp Ile
            260                 265                 270

Gly Trp Asn Met Met Glu Leu Ala Glu Met Glu Lys Pro Gln Arg Gln
        275                 280                 285

Met Phe Ala Cys Phe Ala Glu Ala Met Leu Leu Glu Phe Glu Ser Cys
    290                 295                 300

His Thr Asn Phe Ser Trp Gly Arg Asn Asn Ile Thr Leu Glu Lys Met
305                 310                 315                 320

Asp Phe Ile Gly Glu Ala Ser Arg Arg His Gly Phe Ser Thr Leu Asn
                325                 330                 335

Leu Ser Ala Pro Val Gln Val Ala Ala Ala
            340                 345
```

<210> SEQ ID NO 77
<211> LENGTH: 346
<212> TYPE: PRT
<213> ORGANISM: Synechococcus sp.

<400> SEQUENCE: 77

```
Met Phe Gly Leu Ile Gly His Ser Thr Ser Phe Glu Ala Ala Arg Arg
1               5                   10                  15

Lys Ala Leu Glu Leu Gly Phe Asp His Ile Ala Asp Gly Asp Leu Asp
            20                  25                  30

Val Trp Cys Ser Ala Pro Pro Gln Leu Val Glu His Val Glu Val Thr
        35                  40                  45

Ser Pro Ala Gly Ile Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Asp Trp Gln Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Thr Ala Arg
                165                 170                 175

Thr Asn Val Gly Glu Leu Leu Leu Val Ala Arg Gln Pro Gln Pro Leu
            180                 185                 190

Ala Asp Leu Gln Ala Glu Leu Gly Gly Gly Arg Ile Leu Ala Leu Ser
        195                 200                 205

Asp Ala Leu Ser Glu Ala Asp Val Val Val Trp Val Ala Ser Met Pro
    210                 215                 220

Arg Thr Leu Glu Ile Asp Asn Asn Ser Leu Lys Lys Pro Cys Leu Met
225                 230                 235                 240

Ile Asp Gly Gly Tyr Pro Lys Asn Leu Asp Ser Lys Val Ala Gly Gly
                245                 250                 255

Gly Ile His Val Leu Lys Gly Gly Ile Val Glu Phe Cys Arg Asp Ile
            260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Lys Thr Asn Leu Gln Ala Ala Val Ala
            340                 345
```

<210> SEQ ID NO 78
<211> LENGTH: 347
<212> TYPE: PRT

<213> ORGANISM: Prochlorococcus marinus

<400> SEQUENCE: 78

Met Phe Gly Leu Ile Gly His Ser Thr Ser Phe Lys Asp Ala Arg Gln
1 5 10 15

Lys Ala Met Asp Leu Gly Tyr Asp His Ile Ala Glu Gly Asp Leu Asp
20 25 30

Val Trp Cys Ser Ala Pro Pro Gln Leu Val Glu His Val Lys Val Val
35 40 45

Ser Ala Ile Gly Lys Thr Ile Glu Gly Ala Tyr Ile Asp Ser Cys Phe
50 55 60

Val Pro Glu Met Leu Ser Arg Phe Lys Thr Ala Arg Arg Lys Val Leu
65 70 75 80

Asn Ala Met Glu Leu Ala Gln Lys Lys Gly Ile Asn Ile Thr Ala Leu
85 90 95

Gly Gly Phe Thr Ser Ile Ile Phe Glu Asn Phe Asn Leu Leu Glu Asn
100 105 110

Lys Gln Val Arg Asn Thr Thr Leu Asp Trp Glu Arg Phe Thr Thr Gly
115 120 125

Asn Thr His Thr Ala Trp Val Ile Cys Arg Gln Leu Glu Ile Asn Ala
130 135 140

Pro Leu Leu Gly Ile Asp Leu Gln Lys Ala Arg Val Ala Val Val Gly
145 150 155 160

Ala Thr Gly Asp Ile Gly Ser Ala Val Cys Arg Trp Leu Ser Gln Arg
165 170 175

Thr Gly Val Ser Glu Leu Leu Leu Val Ala Arg Gln Gln Gln Pro Leu
180 185 190

Lys Asp Leu Gln Lys Asp Leu Gly Gly Gly Arg Val Leu Arg Leu Glu
195 200 205

Glu Ala Leu Pro Glu Ala Asp Ala Val Ile Trp Val Ala Ser Leu Pro
210 215 220

Lys Asn Leu Gln Ile Asp Lys Ser Lys Leu Arg Lys Pro Cys Leu Met
225 230 235 240

Ile Asp Gly Gly Tyr Pro Lys Asn Leu Asp Glu Lys Phe Ser Gly Ser
245 250 255

Gly Ile His Val Leu Lys Gly Gly Ile Val Glu Phe Phe Glu Asp Ile
260 265 270

Gly Trp Asn Met Met Glu Ile Ala Glu Met Asp Val Pro Gln Arg Gln
275 280 285

Met Phe Ala Cys Phe Ala Glu Ala Met Leu Leu Glu Phe Glu Asn Cys
290 295 300

His Thr Asn Phe Ser Trp Gly Arg Asn Asn Ile Thr Leu Glu Lys Met
305 310 315 320

Asp Phe Ile Gly Glu Ala Ser Leu Arg His Gly Phe Ser Val Leu Arg
325 330 335

Leu Gln Pro Asn Asn Leu Gln Ala Ala Phe Ala
340 345

<210> SEQ ID NO 79
<211> LENGTH: 345
<212> TYPE: PRT
<213> ORGANISM: Prochlorococcus marinus

<400> SEQUENCE: 79

Met Phe Gly Leu Ile Gly His Ser Thr Ser Phe Glu Asp Ala Arg Lys 1 5 10 15

Thr Ala Leu Gln Ile Gly Tyr Asp His Leu Asp Gly Asp Leu Asp Val
20 25 30

Trp Cys Ser Ala Pro Pro Gln Phe Leu Glu Gln Ile Glu Val Glu Ser
35 40 45

Leu Thr Gly Lys Lys Ile Glu Gly Ala Tyr Ile Asp Ser Cys Phe Val
50 55 60

Pro Glu Met Leu Ser Arg Phe Lys Thr Ala Arg Arg Lys Val Leu Asn
65 70 75 80

Ala Met Glu Met Ala Gln Lys Arg Gly Ile Gln Ile Ser Ala Leu Gly
85 90 95

Gly Phe Thr Ser Ile Ile Phe Glu Asn Phe Asn Leu Leu Lys His Gln
100 105 110

His Val Arg Asn Thr Thr Leu Glu Trp Glu Arg Phe Thr Thr Gly Asn
115 120 125

Thr His Thr Ala Trp Val Ile Cys Arg Gln Leu Glu Asn Asn Ala Pro
130 135 140

Leu Leu Gly Ile Asp Leu Ser Lys Ala Arg Val Ala Val Val Gly Ala
145 150 155 160

Thr Gly Asp Ile Gly Ser Ala Val Cys Arg Trp Leu Ser Ala Arg Thr
165 170 175

Gly Val Ala Glu Leu Leu Leu Val Ala Arg Gln Gln Gln Pro Leu Ile
180 185 190

Asp Leu Gln Thr Glu Leu Ala Gly Gly Arg Ile Leu Ser Leu Glu Glu
195 200 205

Ala Leu Pro Glu Ala Asp Val Val Val Trp Val Ala Ser Met Pro Arg
210 215 220

Thr Leu Glu Ile Asp Met Glu Ser Leu Arg Lys Pro Cys Leu Met Ile
225 230 235 240

Asp Gly Gly Tyr Pro Lys Asn Leu Asp Ala Lys Phe Ala Gly Ser Gly
245 250 255

Val His Val Leu Lys Gly Gly Ile Val Glu Phe Cys Asn Asp Ile Ser
260 265 270

Trp Asp Val Gly Trp Ile Ala Glu Met Asp Lys Pro Ala Arg Gln Met
275 280 285

Phe Ala Cys Phe Ala Glu Ala Met Leu Leu Glu Phe Glu Asn Cys His
290 295 300

Thr Asn Phe Ser Trp Gly Arg Asn Gln Ile Thr Leu Glu Lys Met Asp
305 310 315 320

Phe Ile Gly Met Ala Ser Leu Arg His Gly Phe Ser Ser Leu Asn Leu
325 330 335

Asn His Gln Leu Gln Ala Ala Ala Ala
340 345

<210> SEQ ID NO 80
<211> LENGTH: 346
<212> TYPE: PRT
<213> ORGANISM: Unknown
<220> FEATURE:
<223> OTHER INFORMATION: Description of Unknown: Uncultured marine type-A Synechococcus GOM 3M9 polypeptide

<400> SEQUENCE: 80

Met Phe Gly Leu Ile Gly His Ser Thr Ser Phe Asp Ala Ala Arg Arg
1 5 10 15

```
Lys Ala Met Glu Leu Gly Phe Asp His Ile Ala Glu Gly Asp Leu Asp
            20                  25                  30

Val Trp Cys Ser Ala Pro Pro Gln Leu Val Glu His Val Gln Val Thr
        35                  40                  45

Ser Pro Val Gly Thr Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Asp Ile Ala Ile Thr Ala Leu
                85                  90                  95

Gly Gly Phe Thr Ser Ile Ile Phe Glu Asn Phe Asn Leu Leu Gln Asn
            100                 105                 110

Gln Thr Val Arg Ser Thr Thr Leu Asp Trp Arg Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Ser Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Met Asp Leu Gln Lys Glu Leu Gly Gly Gly Arg Ile Leu Thr Leu Glu
        195                 200                 205

Glu Ala Leu Pro Glu Ala Asp Val Val Val Trp Val Ala Ser Met Pro
    210                 215                 220

Arg Thr Leu Gln Ile Asp Gln Asp Ser Leu Arg Ser Pro Cys Leu Met
225                 230                 235                 240

Ile Asp Gly Gly Tyr Pro Lys Asn Leu Asp Ala Lys Val Ala Gly Gly
                245                 250                 255

Gly Ile His Val Leu Lys Gly Gly Ile Val Glu Phe Cys Arg Asp Ile
            260                 265                 270

Gly Trp Thr Met Met Glu Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Gln Ser Arg Leu Gln Ala Ala Ala Ala
            340                 345


<210> SEQ ID NO 81
<211> LENGTH: 346
<212> TYPE: PRT
<213> ORGANISM: Unknown
<220> FEATURE:
<223> OTHER INFORMATION: Description of Unknown: Uncultured
      marine type-A Synechococcus GOM 4P21
      polypeptide

<400> SEQUENCE: 81

Met Phe Gly Leu Ile Gly His Ser Thr Ser Phe Asp Ala Ala Arg Arg
1               5                   10                  15
```

-continued

```
Lys Ala Met Glu Leu Gly Phe Asp His Ile Ala Glu Gly Asp Leu Asp
            20                  25                  30

Val Trp Cys Ser Ala Pro Pro Gln Leu Val Glu His Val Gln Val Thr
        35                  40                  45

Ser Pro Val Gly Thr Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Asp Ile Ala Ile Thr Ala Leu
                85                  90                  95

Gly Gly Phe Thr Ser Ile Ile Phe Glu Asn Phe Asn Leu Leu Gln Asn
            100                 105                 110

Gln Thr Val Arg Ser Thr Thr Leu Asp Trp Arg Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Ser Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Gly Val Gly Glu Leu Leu Leu Val Ala Arg Gln Gln Gln Pro Leu
            180                 185                 190

Met Asp Leu Gln Lys Glu Leu Gly Gly Gly Arg Ile Leu Thr Leu Glu
        195                 200                 205

Glu Ala Leu Pro Glu Ala Asp Val Val Val Trp Val Ala Ser Met Pro
    210                 215                 220

Arg Thr Leu Gln Ile Asp Gln Asp Ser Leu Arg Ser Pro Cys Leu Met
225                 230                 235                 240

Ile Asp Gly Gly Tyr Pro Lys Asn Leu Asp Ala Lys Val Ala Gly Gly
                245                 250                 255

Gly Ile His Val Leu Lys Gly Gly Ile Val Glu Phe Cys Arg Asp Ile
            260                 265                 270

Gly Trp Thr Met Met Glu Ile Ala Glu Met Glu Lys Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Gln Ser Arg Leu Gln Ala Ala Ala Ala
            340                 345
```

<210> SEQ ID NO 82
<211> LENGTH: 346
<212> TYPE: PRT
<213> ORGANISM: Synechococcus sp.

<400> SEQUENCE: 82

```
Met Phe Gly Leu Ile Gly His Ser Thr Ser Phe Glu Ala Ala Arg Arg
1               5                   10                  15

Lys Ala Leu Glu Leu Gly Phe Asp His Ile Ala Asp Gly Asp Leu Asp
            20                  25                  30

Val Trp Cys Ser Ala Pro Pro Gln Leu Val Glu His Val Glu Val Thr
        35                  40                  45
```

```
Ser Pro Ala Gly Ile Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Ile Arg Ser Thr Thr Leu Asp Trp Gln Arg Phe Thr Thr Gly
        115                 120                 125

Asn Thr His Thr Ala Trp Val Ile Cys Arg Gln Val Glu Asn Asn Ala
    130                 135                 140

Pro Ser Leu Gly Ile Asp Leu Lys Thr Ala Lys Val Ala Val Val Gly
145                 150                 155                 160

Ala Thr Gly Asp Ile Gly Ser Ala Val Cys Arg Trp Leu Ser Ala Arg
                165                 170                 175

Thr Asn Val Gly Glu Leu Leu Leu Val Ala Arg Gln Pro Gln Pro Leu
            180                 185                 190

Ala Asp Leu Gln Ser Glu Leu Gly Gly Gly Arg Ile Leu Ala Leu Ser
        195                 200                 205

Asp Ala Leu Ser Glu Ala Asp Val Val Val Trp Val Ala Ser Met Pro
    210                 215                 220

Arg Thr Leu Glu Ile Asp Asn Asn Ser Leu Lys Lys Pro Cys Leu Met
225                 230                 235                 240

Ile Asp Gly Gly Tyr Pro Lys Asn Leu Asp Ser Lys Val Ala Gly Gly
                245                 250                 255

Gly Ile His Val Leu Lys Gly Gly Ile Val Glu Phe Cys Arg Asp Ile
            260                 265                 270

Gly Trp Ser Met Met Glu Ile Ala Glu Met Glu Asn Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu Lys Thr Asn Leu Gln Ala Ala Ala Ala
            340                 345


<210> SEQ ID NO 83
<211> LENGTH: 349
<212> TYPE: PRT
<213> ORGANISM: Cyanobium sp.

<400> SEQUENCE: 83

Met Phe Gly Leu Ile Gly His Ser Thr Ser Phe Glu Glu Ala Arg Ala
1               5                   10                  15

Lys Ala Arg Ser Leu Gly Phe Asp Glu Tyr Ala Asp Gly Asp Leu Asp
            20                  25                  30

Met Trp Cys Ala Ala Pro Pro Gln Leu Val Glu Lys Val Thr Val Thr
        35                  40                  45

Ser Arg Thr Gly Lys Thr Ile Glu Gly Ala Tyr Ile Asp Ser Val Phe
    50                  55                  60

Val Pro Glu Met Leu Arg Arg Phe Lys Thr Ala Lys Arg Lys Val Leu
```

65 70 75 80

Lys Ala Met Glu Leu Ala Gln Arg Ser Gly Ile Asp Ile Thr Ala Leu
85 90 95

Gly Gly Phe Thr Ser Ile Ile Phe Glu Asp Met Asn Leu Leu Arg Glu
100 105 110

Glu Arg Val Ser Ala Val Gln Leu Asn Trp Glu Arg Phe Thr Thr Gly
115 120 125

Asn Thr His Thr Ala Trp Val Ile Cys Gln Gln Val Glu Arg Asn Ala
130 135 140

Ser Ser Leu Gly Ile Asp Leu Ala Ser Ala Lys Val Ala Val Val Gly
145 150 155 160

Ala Ser Gly Asp Ile Gly Ser Ala Val Cys Arg Trp Leu Gln Arg Arg
165 170 175

Gly Val Gly Glu Leu Leu Leu Val Ala Arg Arg Pro Gln Pro Leu Val
180 185 190

Asp Leu Gln Glu Ser Leu Gly Glu Gly Arg Ile Leu Asp Leu Glu Ala
195 200 205

Ala Leu Pro Glu Ala Asp Val Val Val Trp Val Ala Ser Leu Pro Gln
210 215 220

Ser Leu Gln Ile Asp Thr Ala Ser Leu Lys Arg Pro Cys Leu Met Ile
225 230 235 240

Asp Gly Gly Tyr Pro Lys Asn Leu Asp Ala Lys Ala Ala Ala Glu Gly
245 250 255

Val His Val Leu Lys Gly Gly Ile Val Glu Phe Trp Gln Asp Ile Gly
260 265 270

Trp Gln Met Met Glu Val Ala Glu Met Ala Val Pro Gln Arg Gln Met
275 280 285

Phe Ala Cys Phe Ala Glu Ala Met Leu Leu Asp Phe Glu Asp Leu His
290 295 300

Thr Asn Phe Ser Trp Gly Arg Asn Asn Ile Thr Leu Ala Ala Met Asp
305 310 315 320

Arg Ile Gly Glu Ala Ser Leu Arg His Gly Phe Glu Ala Leu Gly Leu
325 330 335

Gln His Ala Gly Ala Val Ser Pro Ala Leu Ala Ala Ala
340 345

<210> SEQ ID NO 84
<211> LENGTH: 346
<212> TYPE: PRT
<213> ORGANISM: Prochlorococcus marinus

<400> SEQUENCE: 84

Met Phe Gly Leu Ile Gly His Ser Thr Ser Phe Glu Asp Ala Lys Arg
1 5 10 15

Lys Ala Leu Gly Leu Gly Tyr Asp His Ile Ala Glu Gly Asp Leu Asp
20 25 30

Val Trp Cys Thr Ala Pro Pro Gln Leu Val Glu Asn Val Lys Val Val
35 40 45

Ser Ala Ile Gly Lys Thr Ile Glu Gly Ala Tyr Ile Asp Ser Cys Phe
50 55 60

Val Pro Glu Met Leu Ser Arg Phe Lys Thr Ala Arg Arg Lys Val Leu
65 70 75 80

Asn Ala Met Glu Leu Ala Gln Lys Lys Gly Ile Ser Ile Thr Ala Leu
85 90 95

Gly Gly Phe Thr Ser Ile Ile Phe Glu Asn Phe Asn Leu Leu Gln Asn
100 105 110

Gln Gln Val Arg Asn Thr Thr Leu Asp Trp Gln Arg Phe Thr Thr Gly
115 120 125

Asn Thr His Thr Ala Trp Val Ile Cys Arg Gln Leu Glu Gln Asn Ala
130 135 140

Pro Arg Ile Gly Ile Asp Leu Ser Lys Ser Lys Val Ala Val Val Gly
145 150 155 160

Ala Thr Gly Asp Ile Gly Ser Ala Val Cys Arg Trp Leu Ser Asn Arg
165 170 175

Thr Gly Val Ser Glu Leu Leu Leu Val Ala Arg Gln Gln Lys Pro Leu
180 185 190

Leu Glu Leu Gln Ser Gln Leu Gly Gly Gly Arg Ile Leu Ser Leu Asp
195 200 205

Asp Ala Leu Pro Glu Ala Asp Ile Val Ile Trp Val Ala Ser Met Pro
210 215 220

Lys Thr Leu Glu Ile Asp Pro Ser Lys Ile Lys Arg Pro Cys Leu Met
225 230 235 240

Ile Asp Gly Gly Tyr Pro Lys Asn Leu Gly Glu Lys Phe Ser Gly Pro
245 250 255

Gly Ile His Val Leu Lys Gly Gly Ile Val Gln Phe Phe Lys Asp Ile
260 265 270

Gly Trp Ser Met Met Glu Leu Ala Glu Met Glu Asn Pro Lys Arg Glu
275 280 285

Met Phe Ala Cys Phe Ala Glu Ala Met Leu Leu Glu Phe Glu Asn Cys
290 295 300

His Thr Asn Phe Ser Trp Gly Arg Asn Asn Ile Thr Leu Glu Lys Met
305 310 315 320

Asp Phe Ile Gly Lys Ala Ser Glu Arg His Gly Phe Ser Ala Val Gly
325 330 335

Leu Lys Ser Asn Ile Gln Thr Leu Thr Val
340 345

<210> SEQ ID NO 85
<211> LENGTH: 346
<212> TYPE: PRT
<213> ORGANISM: Prochlorococcus marinus

<400> SEQUENCE: 85

Met Phe Gly Leu Ile Gly His Ser Thr Ser Phe Glu Asp Ala Lys Arg
1 5 10 15

Lys Ala Ser Leu Leu Gly Phe Asp His Ile Ala Asp Gly Asp Leu Asp
20 25 30

Val Trp Cys Thr Ala Pro Pro Gln Leu Val Glu Asn Val Glu Val Lys
35 40 45

Ser Ala Thr Gly Ile Ser Ile Glu Gly Ser Tyr Ile Asp Ser Cys Phe
50 55 60

Val Pro Glu Met Leu Ser Arg Phe Lys Thr Ala Arg Arg Lys Val Leu
65 70 75 80

Asn Ala Met Glu Leu Ala Gln Lys Lys Gly Ile Asn Ile Thr Ala Leu
85 90 95

Gly Gly Phe Thr Ser Ile Ile Phe Glu Asn Phe Asn Leu Leu Gln His
100 105 110

Lys Gln Ile Arg Asn Thr Ser Leu Glu Trp Glu Arg Phe Thr Thr Gly
115 120 125

```
Asn Thr His Thr Ala Trp Val Ile Cys Arg Gln Leu Glu Ile Asn Ala
    130                 135                 140

Pro Lys Val Gly Ile Glu Leu Lys Lys Ala Thr Val Ala Val Val Gly
145                 150                 155                 160

Ala Thr Gly Asp Ile Gly Ser Ala Val Cys Arg Trp Leu Ile Asn Lys
                165                 170                 175

Thr Gly Ile Gly Glu Leu Leu Leu Val Ala Arg Gln Lys Glu Pro Leu
            180                 185                 190

Asp Asn Leu Gln Lys Glu Leu Asp Gly Gly Thr Ile Lys Ser Leu Asp
        195                 200                 205

Glu Ala Leu Pro Glu Ala Asp Ile Val Val Trp Val Ala Ser Met Pro
    210                 215                 220

Lys Thr Met Glu Ile Asn Thr Asn Asn Leu Lys Gln Pro Cys Leu Met
225                 230                 235                 240

Ile Asp Gly Gly Tyr Pro Lys Asn Leu Asp Glu Lys Phe Gln Gly Asn
                245                 250                 255

Asn Ile His Val Val Lys Gly Gly Ile Val Lys Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Val Lys His Gly Phe Ser Ala Ile Gly
                325                 330                 335

Leu Asp Lys His Pro Lys Val Leu Ala Val
            340                 345


<210> SEQ ID NO 86
<211> LENGTH: 346
<212> TYPE: PRT
<213> ORGANISM: Synechococcus sp.

<400> SEQUENCE: 86

Met Phe Gly Leu Ile Gly His Ser Thr Ser Phe Glu Ala Ala Arg Arg
1               5                   10                  15

Lys Ala Met Glu Leu Gly Phe Asp His Ile Ala Asp Gly Asp Leu Asp
            20                  25                  30

Val Trp Cys Ser Ala Pro Pro Gln Leu Val Glu His Val Glu Val Thr
        35                  40                  45

Ser Pro Val Gly Thr Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln Thr Val Arg Ser Thr Thr Leu Asp Trp Gln Arg Phe Thr Thr Gly
        115                 120                 125

Asn Thr His Thr Ala Trp Val Ile Cys Arg Gln Val Glu Asn Asn Ala
    130                 135                 140

Pro Thr Leu Gly Ile Asp Leu Ser Lys Ala Lys Val Ala Val Val Gly
```

```
145                 150                 155                 160

Ala Thr Gly Asp Ile Gly Ser Ala Val Cys Arg Trp Leu Gln Ala Arg
                165                 170                 175

Thr Arg Val Gly Glu Leu Leu Leu Val Ala Arg Gln Gln Gln Pro Leu
            180                 185                 190

Leu Asp Leu Gln Gln Glu Leu Gly Gly Gly Arg Ile Leu Ser Leu Asp
        195                 200                 205

Glu Ala Leu Pro Glu Ala Asp Val Val Val Trp Val Ala Ser Met Pro
    210                 215                 220

Arg Thr Leu Glu Ile Asp Gln Asp Ser Leu Lys Lys Pro Cys Leu Met
225                 230                 235                 240

Ile Asp Gly Gly Tyr Pro Lys Asn Leu Asp Thr Lys Val Ala Gly Gly
                245                 250                 255

Gly Ile His Val Leu Lys Gly Gly Ile Val Glu Phe Cys Arg Asp Ile
            260                 265                 270

Gly Trp Ser Met Met Ala Ile Ala Glu Met Glu Arg Pro Gln Arg Gln
        275                 280                 285

Met Phe Ala Cys Phe Ala Glu Ala Met Leu Leu Glu Phe Glu Arg Cys
    290                 295                 300

His Thr Asn Phe Ser Trp Gly Arg Asn Asn Ile Thr Leu Glu Lys Met
305                 310                 315                 320

Asp Phe Ile Gly Ala Ala Ser Val Arg His Gly Phe Ser Thr Leu Asn
                325                 330                 335

Leu His Pro Asn Leu Gln Ala Thr Ala Ala
            340                 345


<210> SEQ ID NO 87
<211> LENGTH: 346
<212> TYPE: PRT
<213> ORGANISM: Prochlorococcus marinus

<400> SEQUENCE: 87

Met Phe Gly Leu Ile Gly His Ser Thr Ser Phe Asp Asp Ala Lys Lys
1               5                   10                  15

Lys Ala Met Asp Leu Gly Tyr Asp His Ile Ala Gln Gly Asp Leu Asp
            20                  25                  30

Val Trp Cys Ser Ala Pro Pro Gln Leu Val Glu His Val Asn Ile Val
        35                  40                  45

Ser Ala Ile Gly Lys Asn Ile Glu Gly Ala Tyr Ile Asp Ser Cys Phe
    50                  55                  60

Val Pro Glu Met Leu Gly Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln Asn
            100                 105                 110

Lys Gln Val Arg Asn Thr Thr Leu Glu Trp Glu Arg Phe Thr Thr Gly
        115                 120                 125

Asn Thr His Thr Ala Trp Val Ile Cys Arg Gln Leu Glu Leu Asn Ala
    130                 135                 140

Pro Leu Leu Gly Ile Asp Leu Lys Lys Ala Arg Val Ala Val Val Gly
145                 150                 155                 160

Ala Thr Gly Asp Ile Gly Ser Ala Val Cys Arg Trp Leu Ser Glu Arg
                165                 170                 175
```

```
Thr Gly Val Gln Glu Leu Leu Leu Val Ala Arg Gln Gln Gln Pro Leu
            180                 185                 190

Ile Glu Leu Gln Lys Ser Leu Gly Gly Gly Lys Ile Leu Gly Leu Glu
        195                 200                 205

Asp Ala Leu Pro Glu Ala Asp Val Val Ile Trp Val Ala Ser Leu Pro
    210                 215                 220

Lys Thr Leu Glu Ile Asp Lys Ala Lys Leu Arg Lys Pro Cys Leu Met
225                 230                 235                 240

Ile Asp Gly Gly Tyr Pro Lys Asn Leu Asp Glu Lys Phe Asn Gly Ser
                245                 250                 255

Gly Val His Val Leu Lys Gly Gly Ile Val Glu Phe Phe Thr Asp Ile
            260                 265                 270

Gly Trp Ser Met Met Glu Leu Ala Ala Met Glu Lys Pro Arg Arg Glu
        275                 280                 285

Met Phe Ala Cys Phe Ala Glu Ala Met Leu Leu Glu Phe Glu Gly Cys
    290                 295                 300

His Thr Asn Phe Ser Trp Gly Arg Asn Asn Ile Thr Leu Glu Lys Met
305                 310                 315                 320

Asp Phe Ile Gly Gln Ala Ser Glu Lys His Gly Phe Ser Val Ile Gly
                325                 330                 335

Leu Asn Pro Lys Leu Gln Ala Ala Ile Ala
            340                 345
```

<210> SEQ ID NO 88
<211> LENGTH: 346
<212> TYPE: PRT
<213> ORGANISM: Prochlorococcus marinus

<400> SEQUENCE: 88

```
Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Ile Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Met Asn Ala
    130                 135                 140

Pro Lys Ile Gly Ile Asp Leu Lys Ser Ala Thr Val Ala Val Val Gly
145                 150                 155                 160

Ala Thr Gly Asp Ile Gly Ser Ala Val Cys Arg Trp Leu Ile Asn Lys
                165                 170                 175

Thr Gly Ile Gly Glu Leu Leu Leu Val Ala Arg Gln Lys Glu Pro Leu
            180                 185                 190

Asp Ser Leu Gln Lys Glu Leu Asp Gly Gly Thr Ile Lys Asn Leu Asp
        195                 200                 205
```

```
Glu Ala Leu Pro Glu Ala Asp Ile Val Val Trp Val Ala Ser Met Pro
    210                 215                 220

Lys Thr Met Glu Ile Asp Ala Asn Asn Leu Lys Gln Pro Cys Leu Met
225                 230                 235                 240

Ile Asp Gly Gly Tyr Pro Lys Asn Leu Asp Glu Lys Phe Gln Gly Asn
                245                 250                 255

Asn Ile His Val Val Lys Gly Gly Ile Val Arg Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Val Lys His Gly Phe Ser Ala Ile Gly
                325                 330                 335

Leu Asp Lys His Pro Lys Val Leu Ala Val
            340                 345


<210> SEQ ID NO 89
<211> LENGTH: 346
<212> TYPE: PRT
<213> ORGANISM: Prochlorococcus marinus

<400> SEQUENCE: 89

Met Phe Gly Leu Ile Gly His Ser Thr Ser Phe Glu Asp Ala Lys Arg
1               5                   10                  15

Lys Ala Ser Met Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Lys Gln Leu Glu Ile Asn Ala
    130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Ile Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Ser Leu Asp
        195                 200                 205

Glu Ala Leu Pro Gln Ala Asp Ile Val Val Trp Val Ala Ser Met Pro
    210                 215                 220

Lys Thr Ile Glu Ile Asp Thr Asp Asn Leu Lys Lys Pro Cys Leu Met
```

```
225                 230                 235                 240

Ile Asp Gly Gly Tyr Pro Lys Asn Leu Asp Glu Lys Phe Gln Gly Glu
                245                 250                 255

Asn Ile Tyr Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345


<210> SEQ ID NO 90
<211> LENGTH: 346
<212> TYPE: PRT
<213> ORGANISM: Synechococcus sp.

<400> SEQUENCE: 90

Met Phe Gly Leu Ile Gly His Ser Thr Ser Phe Glu Ala Ala Arg Arg
1               5                   10                  15

Lys Ala Ser Glu Leu Gly Phe Asp His Ile Ala Glu Gly Asp Leu Asp
            20                  25                  30

Val Trp Cys Ser Ala Pro Pro Gln Leu Val Glu His Val Glu Val Thr
        35                  40                  45

Ser Ala Thr Gly Lys Thr Ile Thr Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Gln His Val Arg Ser Thr Thr Leu Glu Trp Glu Arg Phe Thr Thr Gly
        115                 120                 125

Asn Thr His Thr Ala Trp Val Ile Ser Arg Gln Val Glu Asn Asn Ala
    130                 135                 140

Pro Leu Leu Gly Ile Asp Leu Ser Ser Ala Lys Val Ala Val Val Gly
145                 150                 155                 160

Ala Thr Gly Asp Ile Gly Ser Ala Val Cys Arg Trp Leu Ser Gln Arg
                165                 170                 175

Thr Gly Val Gly Glu Leu Leu Leu Val Ala Arg Gln Gln Gln Pro Leu
            180                 185                 190

Leu Asp Leu Gln Gln Glu Leu Gly Gly Gly Arg Ile Leu Ser Leu Asp
        195                 200                 205

Glu Ala Leu Pro Glu Ala Asp Val Val Val Trp Val Ala Ser Met Pro
    210                 215                 220

Arg Thr Leu Glu Ile Asp Ala Ala Ser Leu Arg Lys Pro Cys Leu Met
225                 230                 235                 240

Ile Asp Gly Gly Tyr Pro Lys Asn Leu Asp Ala Lys Val Ala Ser Ala
                245                 250                 255
```

```
Gly Val His Val Leu Lys Gly Gly Ile Val Glu Phe Gly Ser Asp Ile
            260                 265                 270

Gly Trp Ser Met Met Glu Ile Ala Glu Met Glu Lys Pro Gln Arg Gln
        275                 280                 285

Met Phe Ala Cys Phe Ala Glu Ala Met Leu Leu Asp Phe Glu Glu Cys
    290                 295                 300

His Thr Asn Phe Ser Trp Gly Arg Asn Asn Ile Thr Leu Glu Lys Met
305                 310                 315                 320

Asp Phe Ile Gly Glu Ala Ser Val Arg His Gly Phe Ser Thr Leu Asn
                325                 330                 335

Leu Asn Pro Gln Pro Gln Ala Ala Val Ala
            340                 345


<210> SEQ ID NO 91
<211> LENGTH: 346
<212> TYPE: PRT
<213> ORGANISM: Prochlorococcus marinus

<400> SEQUENCE: 91

Met Phe Gly Leu Ile Gly His Ser Thr Ser Phe Glu Asp Ala Lys Arg
1               5                   10                  15

Lys Ala Leu Gly Leu Gly Tyr Asp His Ile Ala Gln Gly Asp Leu Asp
            20                  25                  30

Val Trp Cys Thr Ala Pro Pro Gln Leu Val Glu Asn Val Lys Val Val
        35                  40                  45

Ser Ala Ile Gly Lys Thr Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Glu Ile Ser Ile Thr Ala Leu
                85                  90                  95

Gly Gly Phe Thr Ser Ile Ile Phe Glu Asn Phe Asn Leu Leu Gln Asn
            100                 105                 110

Gln Gln Val Arg Asn Thr Thr Leu Asp Trp Gln Arg Phe Thr Thr Gly
        115                 120                 125

Asn Thr His Thr Ala Trp Val Ile Cys Arg Gln Leu Glu Gln Asn Ala
    130                 135                 140

Pro Arg Ile Gly Ile Asp Leu Ser Lys Ser Lys Val Ala Val Val Gly
145                 150                 155                 160

Ala Thr Gly Asp Ile Gly Ser Ala Val Cys Arg Trp Leu Ser Asn Arg
                165                 170                 175

Thr Gly Val Ser Glu Leu Leu Leu Val Ala Arg Gln Gln Lys Pro Leu
            180                 185                 190

Leu Glu Leu Gln Ser Gln Leu Gly Gly Gly Arg Ile Leu Ser Leu Asp
        195                 200                 205

Asp Ala Leu Pro Glu Ala Asp Ile Val Ile Trp Val Ala Ser Met Pro
    210                 215                 220

Lys Thr Leu Glu Ile Asp Pro Ser Lys Ile Lys Arg Pro Cys Leu Met
225                 230                 235                 240

Ile Asp Gly Gly Tyr Pro Lys Asn Leu Gly Glu Lys Phe Ser Gly Pro
                245                 250                 255

Gly Ile His Val Leu Lys Gly Gly Ile Val Gln Phe Phe Lys Asp Ile
            260                 265                 270

Gly Trp Ser Met Met Glu Leu Ala Glu Met Glu Asn Pro Lys Arg Glu
        275                 280                 285
```

```
Met Phe Ala Cys Phe Ala Glu Ala Met Leu Leu Glu Phe Glu Asn Cys
    290                 295                 300

His Thr Asn Phe Ser Trp Gly Arg Asn Asn Ile Thr Leu Glu Lys Met
305                 310                 315                 320

Asp Phe Ile Gly Lys Ala Ser Glu Arg His Gly Phe Ser Ala Val Gly
                325                 330                 335

Leu Lys Ser Asn Ile Gln Thr Leu Thr Val
            340                 345


<210> SEQ ID NO 92
<211> LENGTH: 346
<212> TYPE: PRT
<213> ORGANISM: Prochlorococcus marinus

<400> SEQUENCE: 92

Met Phe Gly Leu Ile Gly His Ser Thr Ser Phe Glu Asp Ala Lys Arg
1               5                   10                  15

Lys Ala Ser Met Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Ile Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Thr Leu Asp
        195                 200                 205

Lys Ala Leu Pro Gln Ala Asp Ile Val Val Trp Val Ala Ser Met Pro
    210                 215                 220

Lys Thr Ile Glu Ile Asp Thr Asp Asn Leu Lys Lys Pro Cys Leu Met
225                 230                 235                 240

Ile Asp Gly Gly Tyr Pro Lys Asn Leu Asp Glu Lys Phe Gln Gly Glu
                245                 250                 255

Asn Ile His Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
```

```
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345


<210> SEQ ID NO 93
<211> LENGTH: 348
<212> TYPE: PRT
<213> ORGANISM: Synechococcus sp.

<400> SEQUENCE: 93

Met Phe Gly Leu Ile Gly His Ser Thr Ser Phe Glu Ala Ala Arg Arg
1               5                   10                  15

Lys Ala Leu Glu Leu Gly Phe Asp His Ile Ala Glu Gly Asp Leu Asp
            20                  25                  30

Val Trp Cys Ser Ala Pro Pro Gln Leu Val Glu His Leu Glu Val Thr
        35                  40                  45

Ser Leu Thr Gly Lys Lys Ile Glu Gly Ala Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Lys His
            100                 105                 110

Gln Thr Ile Arg Ser Thr Thr Leu Glu Trp Glu Arg Phe Thr Thr Gly
        115                 120                 125

Asn Thr His Thr Ala Trp Val Ile Ser Arg Gln Val Glu Ile Asn Ala
    130                 135                 140

Pro Leu Leu Gly Ile Asp Leu Ser Lys Ala Arg Val Ala Val Val Gly
145                 150                 155                 160

Ala Thr Gly Asp Ile Gly Ser Ala Val Cys Arg Trp Leu Thr Gln Arg
                165                 170                 175

Thr Gly Ile Lys Glu Leu Leu Met Val Ala Arg Gln Gln Gln Pro Leu
            180                 185                 190

Lys Asp Leu Gln Gln Glu Leu Glu Gly Gly Arg Ile Leu Ser Leu Asp
        195                 200                 205

Glu Ala Leu Pro Glu Ala Asp Val Val Val Trp Val Ala Ser Met Pro
    210                 215                 220

Arg Thr Leu Glu Ile Asp Ser Asp Arg Leu Gln Lys Pro Cys Leu Met
225                 230                 235                 240

Ile Asp Gly Gly Tyr Pro Lys Asn Leu Asp Ser Arg Val Ala Gly Gln
                245                 250                 255

Gly Val His Val Leu Lys Gly Gly Ile Val Glu Phe Val Ser Asp Ile
            260                 265                 270

Gly Trp Thr Met Met Glu Asn Ala Glu Trp Gln Met Glu Lys Pro Gln
        275                 280                 285

Arg Gln Met Phe Ala Cys Phe Ala Glu Ala Ile Leu Leu Glu Phe Glu
    290                 295                 300

Ala Cys His Thr Asn Phe Ser Trp Gly Arg Asn Asn Ile Thr Leu Glu
305                 310                 315                 320

Lys Met Asp Phe Ile Gly Ala Ala Ser Val Arg His Gly Phe Ser Thr
                325                 330                 335
```

```
Leu Asn Leu Gln Gly Gln Leu Gln Ala Ala Ala Ala
            340                 345


<210> SEQ ID NO 94
<211> LENGTH: 346
<212> TYPE: PRT
<213> ORGANISM: Prochlorococcus marinus

<400> SEQUENCE: 94

Met Phe Gly Leu Ile Gly His Ser Thr Ser Phe Glu Asp Ala Lys Arg
1               5                   10                  15

Lys Ala Ser Met Leu Gly Phe Asp His Ile Ala Asp Gly Asp Leu Asp
            20                  25                  30

Val Trp Cys Thr Ala Pro Pro Gln Leu Val Glu Asn Val Glu Val Arg
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Thr Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Thr Leu Asp
        195                 200                 205

Lys Ala Leu Pro Gln Ala Asp Ile Val Val Trp Val Ala Ser Met Pro
    210                 215                 220

Lys Thr Ile Glu Ile Asp Thr Asp Asn Leu Lys Lys Pro Cys Leu Met
225                 230                 235                 240

Ile Asp Gly Gly Tyr Pro Lys Asn Leu Asp Glu Lys Phe Gln Gly Glu
                245                 250                 255

Asn Ile His Val Leu Lys Gly Gly Ile Val Lys Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345


<210> SEQ ID NO 95
```

<211> LENGTH: 346
<212> TYPE: PRT
<213> ORGANISM: Prochlorococcus marinus

<400> SEQUENCE: 95

```
Met Phe Gly Leu Ile Gly His Ser Thr Ser Phe Glu Asp Ala Lys Arg
1               5                   10                  15

Lys Ala Ser Met Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45

Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Lys Gln Leu Glu Ile Asn Ala
    130                 135                 140

Pro Arg Ile Gly Ile Asp Leu Lys Lys Ala Thr Val Ala Val Ile Gly
145                 150                 155                 160

Ala Thr Gly Asp Ile Gly Ser Ala Val Cys Arg Trp Leu Ile Asn Lys
                165                 170                 175

Thr Gly Ile Ser Glu Leu Leu Met Val Ala Arg Gln Gln Glu Pro Leu
            180                 185                 190

Ala Leu Leu Gln Lys Glu Leu Asp Gly Gly Thr Ile Thr Ser Leu Asp
        195                 200                 205

Glu Ala Leu Pro Gln Ala Asp Ile Val Val Trp Val Ala Ser Met Pro
    210                 215                 220

Lys Thr Ile Glu Ile Asn Thr Asp Asn Leu Gln Lys Pro Cys Leu Met
225                 230                 235                 240

Ile Asp Gly Gly Tyr Pro Lys Asn Leu Asp Glu Lys Phe Gln Gly Glu
                245                 250                 255

Asn Ile Tyr Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345
```

<210> SEQ ID NO 96
<211> LENGTH: 341
<212> TYPE: PRT
<213> ORGANISM: Synechococcus sp.

<400> SEQUENCE: 96

```
Met Phe Gly Leu Ile Gly His Leu Thr Ser Leu Ala His Ala Lys Arg
1               5                   10                  15

Val Ala Asp Lys Leu Gly Tyr Ser Glu Tyr Ala Glu Ser Asp Leu Glu
            20                  25                  30

Phe Trp Cys Met Ala Pro Pro Gln Val Val Asp Glu Ile Val Val Thr
        35                  40                  45

Ser Ile Thr Gly Gln Lys Ile Tyr Gly Gln Tyr Val Glu Ser Cys Phe
    50                  55                  60

Leu Pro Glu Met Leu Ala Gly Gly Arg Val Lys Ala Ala Cys Arg Lys
65                  70                  75                  80

Ile Leu Asn Ala Met Ala Leu Ala Gln Arg Arg Gly Leu Asn Ile Thr
                85                  90                  95

Thr Leu Gly Gly Phe Ser Ser Ile Ile Phe Glu Asn Phe Arg Leu Asp
            100                 105                 110

Thr Leu Arg Arg Val Arg Asn Ile Asp Leu Glu Ile Arg Arg Phe Thr
        115                 120                 125

Thr Gly Asn Thr His Thr Ala Tyr Ile Ile Cys Gln Gln Leu Gln Ala
    130                 135                 140

Ala Ala Gln Arg Tyr Ala Met Asp Leu Ala Ala Ala Thr Val Ala Val
145                 150                 155                 160

Val Gly Ala Thr Gly Asp Ile Gly Ser Ala Ile Cys Gln Trp Leu Val
                165                 170                 175

Ala His Thr Ser Pro Ala Lys Leu Leu Leu Ile Ala Arg Glu Arg Arg
            180                 185                 190

Arg Leu Glu Glu Leu Gln Ala Lys Leu Lys Lys Gly Glu Val Cys Ser
        195                 200                 205

Leu Glu Glu Ala Leu Pro Arg Ala Asp Phe Ile Val Trp Val Ala Ser
    210                 215                 220

Met Ser Gln Gly Val Thr Leu Asp Pro Gln Val Leu Pro Asp Pro Cys
225                 230                 235                 240

Val Ile Ile Asp Gly Gly Tyr Pro Lys Asn Ile Ala Ser Lys Leu Gln
                245                 250                 255

Arg Lys Gly Leu Tyr Val Ile Asp Gly Gly Met Val Glu His Ser Leu
            260                 265                 270

Asp Ile Glu Trp Asn Ile Met Gln Phe Leu Asn Val Ala Asn Pro Ala
        275                 280                 285

Arg Gln Leu Phe Ala Cys Phe Ala Glu Ala Met Leu Leu Glu Phe Glu
    290                 295                 300

Gly Leu Tyr Thr Asn Phe Ser Trp Gly Arg Asn Leu Ile Thr Leu Glu
305                 310                 315                 320

Lys Leu Asp Leu Ile Gly Gln Leu Ser Arg Lys His Gly Phe Arg Pro
                325                 330                 335

Leu Met Pro Glu Ala
            340
```

<210> SEQ ID NO 97
<211> LENGTH: 341
<212> TYPE: PRT
<213> ORGANISM: Synechococcus sp.

<400> SEQUENCE: 97

```
Met Phe Gly Leu Ile Gly His Leu Thr Ser Leu Ala His Ala Lys Arg
1               5                   10                  15

Val Ala Asp Lys Leu Gly Tyr Ser Glu Tyr Ala Glu Ser Asp Leu Glu
```

```
            20                  25                  30

Phe Trp Cys Met Ala Pro Pro Gln Val Val Asp Glu Ile Thr Val Thr
        35                  40                  45

Ser Ile Thr Gly Gln Lys Ile Tyr Gly Gln Tyr Val Glu Ser Cys Phe
    50                  55                  60

Leu Pro Glu Met Leu Ala Gly Gly Arg Val Lys Ala Ala Cys Arg Lys
65                  70                  75                  80

Val Leu Asn Ala Met Ala Leu Ala Gln Arg Arg Gly Leu Asn Ile Thr
                85                  90                  95

Ala Leu Gly Gly Phe Ser Ser Ile Ile Phe Glu Thr Phe Arg Leu Asp
            100                 105                 110

Ser Leu Arg Arg Val Arg Asn Ile Asp Leu Glu Ile Gln Arg Phe Thr
        115                 120                 125

Thr Gly Asn Thr His Thr Ala Tyr Ile Ile Cys Gln Gln Leu Gln Leu
    130                 135                 140

Ala Ala Gln Arg Tyr Ala Met Asp Leu Ala Ala Ala Thr Val Ala Val
145                 150                 155                 160

Val Gly Ala Thr Gly Asp Ile Gly Ser Ala Ile Cys Gln Trp Leu Val
                165                 170                 175

Ala His Thr His Leu Gly Lys Leu Leu Leu Ile Ala Arg Glu Arg Arg
            180                 185                 190

Arg Leu Glu Glu Leu Gln Ala Lys Leu Lys Gln Gly Glu Ile Ser Ser
        195                 200                 205

Leu Glu Glu Ala Leu Pro Arg Ala Asp Phe Ile Val Trp Val Ala Ser
    210                 215                 220

Met Ser Gln Gly Met Ala Leu Asp Pro Gln Val Leu Pro Asp Pro Cys
225                 230                 235                 240

Val Ile Ile Asp Gly Gly Tyr Pro Lys Asn Ile Ala Ser Ser Leu Gln
                245                 250                 255

Arg Lys Gly Leu Tyr Val Ile Asp Gly Gly Met Val Glu His Ser Leu
            260                 265                 270

Asp Ile Glu Trp Asn Ile Met Gln Phe Leu Asn Val Ala Asn Pro Ala
        275                 280                 285

Arg Gln Leu Phe Ala Cys Phe Ala Glu Ser Met Leu Leu Glu Phe Glu
    290                 295                 300

Gly Leu Tyr Thr Asn Phe Ser Trp Gly Arg Asn Leu Ile Thr Leu Glu
305                 310                 315                 320

Lys Leu Asp Leu Ile Gly Gln Leu Ser Arg Lys His Gly Phe Arg Pro
                325                 330                 335

Leu Met Pro Glu Ala
            340


<210> SEQ ID NO 98
<211> LENGTH: 346
<212> TYPE: PRT
<213> ORGANISM: Prochlorococcus marinus

<400> SEQUENCE: 98

Met Phe Gly Leu Ile Gly His Ser Thr Ser Phe Glu Asp Ala Lys Arg
1               5                   10                  15

Lys Ala Ser Leu Leu Gly Phe Asp His Ile Ala Asp Gly Asp Leu Asp
            20                  25                  30

Val Trp Cys Thr Ala Pro Pro Gln Leu Val Glu Asn Val Glu Val Lys
        35                  40                  45
```

```
Ser Ala Thr Gly Ile Ser Ile Glu Gly Ser Tyr Ile Asp Ser Cys Phe
    50                  55                  60

Val Pro Glu Met Leu Ser Arg Phe Lys Thr Ala Arg Arg Lys Val Leu
65                  70                  75                  80

Asn Ala Met Glu Leu Ala Gln Lys Lys Gly Ile Asn Ile Thr Ala Leu
                85                  90                  95

Gly Gly Phe Thr Ser Ile Ile Phe Glu Asn Phe Asn Leu Leu Gln His
            100                 105                 110

Lys Gln Ile Arg Asn Thr Ser Leu Glu Trp Glu Arg Phe Thr Thr Gly
        115                 120                 125

Asn Thr His Thr Ala Trp Val Ile Cys Arg Gln Leu Glu Ile Asn Ala
    130                 135                 140

Pro Arg Ile Gly Ile Asp Leu Lys Thr Ala Thr Val Ala Val Ile Gly
145                 150                 155                 160

Ala Thr Gly Asp Ile Gly Ser Ala Val Cys Arg Trp Leu Val Asn Lys
                165                 170                 175

Thr Gly Ile Ser Glu Leu Leu Met Val Ala Arg Gln Gln Gln Pro Leu
            180                 185                 190

Thr Leu Leu Gln Lys Glu Leu Asp Gly Gly Thr Ile Lys Ser Leu Asp
        195                 200                 205

Glu Ala Leu Pro Gln Ala Asp Ile Val Val Trp Val Ala Ser Met Pro
    210                 215                 220

Lys Thr Ile Glu Ile Glu Ile Glu Asn Leu Lys Lys Pro Cys Leu Met
225                 230                 235                 240

Ile Asp Gly Gly Tyr Pro Lys Asn Leu Asp Glu Lys Phe Lys Gly Lys
                245                 250                 255

Asn Ile His Val Leu Lys Gly Gly Ile Val Glu Phe Phe Asn Asp Ile
            260                 265                 270

Gly Trp Asn Met Met Glu Leu Ala Glu Met Gln Asn Pro Gln Arg Glu
        275                 280                 285

Met Phe Ala Cys Phe Ala Glu Ala Met Ile Leu Glu Phe Glu Lys Cys
    290                 295                 300

His Thr Asn Phe Ser Trp Gly Arg Asn Asn Ile Ser Leu Glu Lys Met
305                 310                 315                 320

Glu Phe Ile Gly Ala Ala Ser Leu Lys His Gly Phe Ser Ala Ile Gly
                325                 330                 335

Leu Asp Lys Gln Pro Lys Val Leu Thr Val
            340                 345


<210> SEQ ID NO 99
<211> LENGTH: 231
<212> TYPE: PRT
<213> ORGANISM: Synechococcus elongates

<400> SEQUENCE: 99

Met Pro Gln Leu Glu Ala Ser Leu Glu Leu Asp Phe Gln Ser Glu Ser
1               5                   10                  15

Tyr Lys Asp Ala Tyr Ser Arg Ile Asn Ala Ile Val Ile Glu Gly Glu
            20                  25                  30

Gln Glu Ala Phe Asp Asn Tyr Asn Arg Leu Ala Glu Met Leu Pro Asp
        35                  40                  45

Gln Arg Asp Glu Leu His Lys Leu Ala Lys Met Glu Gln Arg His Met
    50                  55                  60

Lys Gly Phe Met Ala Cys Gly Lys Asn Leu Ser Val Thr Pro Asp Met
65                  70                  75                  80
```

```
Gly Phe Ala Gln Lys Phe Phe Glu Arg Leu His Glu Asn Phe Lys Ala
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Ala Phe Ala Arg Lys Ile Thr Glu Gly Val Val Arg Asp Glu
    130                 135                 140

Tyr Leu His Arg Asn Phe Gly Glu Glu Trp Leu Lys Ala Asn Phe Asp
145                 150                 155                 160

Ala Ser Lys Ala Glu Leu Glu Glu Ala Asn Arg Gln Asn Leu Pro Leu
                165                 170                 175

Val Trp Leu Met Leu Asn Glu Val Ala Asp Asp Ala Arg Glu Leu Gly
            180                 185                 190

Met Glu Arg Glu Ser Leu Val Glu Asp Phe Met Ile Ala Tyr Gly Glu
        195                 200                 205

Ala Leu Glu Asn Ile Gly Phe Thr Thr Arg Glu Ile Met Arg Met Ser
    210                 215                 220

Ala Tyr Gly Leu Ala Ala Val
225                 230
```

```
<210> SEQ ID NO 100
<211> LENGTH: 254
<212> TYPE: PRT
<213> ORGANISM: Synechococcus elongates

<400> SEQUENCE: 100

Met Arg Thr Pro Trp Asp Pro Pro Asn Pro Thr Phe Ser Leu Ser Ser
1               5                   10                  15

Val Ser Gly Asp Arg Arg Leu Met Pro Gln Leu Glu Ala Ser Leu Glu
            20                  25                  30

Leu Asp Phe Gln Ser Glu Ser Tyr Lys Asp Ala Tyr Ser Arg Ile Asn
        35                  40                  45

Ala Ile Val Ile Glu Gly Glu Gln Glu Ala Phe Asp Asn Tyr Asn Arg
    50                  55                  60

Leu Ala Glu Met Leu Pro Asp Gln Arg Asp Glu Leu His Lys Leu Ala
65                  70                  75                  80

Lys Met Glu Gln Arg His Met Lys Gly Phe Met Ala Cys Gly Lys Asn
                85                  90                  95

Leu Ser Val Thr Pro Asp Met Gly Phe Ala Gln Lys Phe Phe Glu Arg
            100                 105                 110

Leu His Glu Asn Phe Lys Ala Ala Ala Ala Glu Gly Lys Val Val Thr
        115                 120                 125

Cys Leu Leu Ile Gln Ser Leu Ile Ile Glu Cys Phe Ala Ile Ala Ala
    130                 135                 140

Tyr Asn Ile Tyr Ile Pro Val Ala Asp Ala Phe Ala Arg Lys Ile Thr
145                 150                 155                 160

Glu Gly Val Val Arg Asp Glu Tyr Leu His Arg Asn Phe Gly Glu Glu
                165                 170                 175

Trp Leu Lys Ala Asn Phe Asp Ala Ser Lys Ala Glu Leu Glu Glu Ala
            180                 185                 190

Asn Arg Gln Asn Leu Pro Leu Val Trp Leu Met Leu Asn Glu Val Ala
        195                 200                 205

Asp Asp Ala Arg Glu Leu Gly Met Glu Arg Glu Ser Leu Val Glu Asp
```

```
    210                 215                 220

Phe Met Ile Ala Tyr Gly Glu Ala Leu Glu Asn Ile Gly Phe Thr Thr
225                 230                 235                 240

Arg Glu Ile Met Arg Met Ser Ala Tyr Gly Leu Ala Ala Val
                245                 250


<210> SEQ ID NO 101
<211> LENGTH: 231
<212> TYPE: PRT
<213> ORGANISM: Arthrospira maxima

<400> SEQUENCE: 101

Met Pro Gln Leu Glu Thr Ile Thr Glu Leu Asp Phe Gln Asn Glu Thr
1               5                   10                  15

Tyr Lys Asp Ala Tyr Ser Arg Ile Asn Ala Ile Val Ile Glu Gly Glu
            20                  25                  30

Gln Glu Ala Ser Asp Asn Tyr Ile Lys Leu Gly Glu Met Leu Pro Glu
        35                  40                  45

Glu Arg Glu Glu Leu Ile Arg Leu Ser Lys Met Glu Lys Arg His Lys
    50                  55                  60

Lys Gly Phe Gln Ala Cys Gly Arg Asn Leu Glu Val Thr Pro Asp Met
65                  70                  75                  80

Asp Phe Gly Arg Glu Phe Phe Ala Lys Leu His Gly Asn Phe Gln Lys
                85                  90                  95

Ala Ala Ala Glu Gly Lys Leu Val Thr Cys Leu Leu Ile Gln Ser Leu
            100                 105                 110

Ile Ile Glu Ser Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Glu His Leu Asn Phe Gly Glu Glu Trp Leu Lys Ala His Phe Glu
145                 150                 155                 160

Glu Ser Lys Ala Glu Leu Glu Glu Ala Asn Arg Gln Asn Leu Pro Leu
                165                 170                 175

Val Trp Lys Met Leu Asn Gln Val Glu Lys Asp Ala Ser Ile Leu Gly
            180                 185                 190

Met Glu Lys Glu Ala Leu Ile Glu Asp Phe Met Ile Ala Tyr Gly Glu
        195                 200                 205

Ala Leu Ser Asn Ile Gly Phe Thr Thr Arg Asp Ile Met Arg Met Ser
    210                 215                 220

Ala Tyr Gly Leu Ala Gly Val
225                 230


<210> SEQ ID NO 102
<211> LENGTH: 239
<212> TYPE: PRT
<213> ORGANISM: Microcoleus chthonoplastes

<400> SEQUENCE: 102

Met Gln Thr Gly Glu Asn Leu Leu Met Gln Gln Leu Thr Val Ser Gln
1               5                   10                  15

Glu Leu Asp Phe Asn Ser Glu Thr Tyr Lys Asp Ala Tyr Ser Arg Ile
            20                  25                  30

Asn Ala Ile Val Ile Glu Gly Glu Gln Glu Ala His Gln Asn Tyr Ile
        35                  40                  45

Gln Leu Ala Glu Leu Leu Pro Asp Gln Lys Asp Glu Leu Thr Ser Leu
```

```
    50                  55                  60

Ala Lys Met Glu Asn Arg His Lys Lys Gly Phe Gln Ala Cys Gly Arg
65                  70                  75                  80

Asn Leu Ser Val Thr Ala Asp Met Glu Phe Ala Lys Glu Tyr Phe Ser
                85                  90                  95

Asp Leu His Gln Asn Phe Gln Thr Ala Ala Ala Ser Gly Asn Ile Val
            100                 105                 110

Thr Cys Leu Leu Ile Gln Ser Leu Ile Ile Glu Cys Phe Ala Ile Ala
        115                 120                 125

Ala Tyr Asn Ile Tyr Ile Pro Val Ala Asp Pro Phe Ala Arg Lys Ile
    130                 135                 140

Thr Glu Gly Val Val Lys Asp Glu Tyr Met His Leu Asn Phe Gly Glu
145                 150                 155                 160

Glu Trp Leu Lys Glu Asn Phe Glu Ala Ser Lys Thr Glu Leu Glu Gln
                165                 170                 175

Ala Asn Lys Gln Asn Leu Pro Leu Val Trp Arg Met Leu Asn Gln Val
            180                 185                 190

Glu Lys Asp Ala His Ile Leu Gly Met Glu Lys Asp Ala Leu Val Glu
        195                 200                 205

Asp Phe Met Ile Ala Tyr Gly Glu Ala Leu Ser Asn Ile Gly Phe Thr
    210                 215                 220

Thr Arg Asp Ile Met Arg Met Ser Ala Tyr Gly Leu Thr Ala Ala
225                 230                 235


<210> SEQ ID NO 103
<211> LENGTH: 231
<212> TYPE: PRT
<213> ORGANISM: Lyngbya sp.

<400> SEQUENCE: 103

Met Pro Gln Leu Glu Ala Ile Ala Glu Ile Asp Phe Asn Thr Asn Thr
1               5                   10                  15

Tyr Lys Asp Ala Tyr Ser Arg Ile Asn Ala Ile Val Ile Glu Gly Glu
            20                  25                  30

Gln Val Ala His Asp Asn Tyr Ile Lys Leu Gly Glu Met Leu Pro Asp
        35                  40                  45

Gln Lys Asp Glu Leu Val Arg Leu Ser Lys Met Glu Lys Arg His Met
    50                  55                  60

Lys Gly Phe Gln Ala Cys Gly Arg Asn Leu Glu Val Thr Ala Asp Met
65                  70                  75                  80

Asp Tyr Ala His Gln Phe Phe Ser Gln Leu His Gln Asn Phe Lys Asp
                85                  90                  95

Ala Ala Ala Gln Gly Lys Val Val Thr Cys Leu Leu Ile Gln Ser Leu
            100                 105                 110

Ile Ile Glu Ser Phe Ala Ile Ala Ala Tyr Asn Ile Tyr Ile Pro Val
        115                 120                 125

Ala Asp Pro Phe Ala Arg Lys Ile Thr Glu Gly Val Val Asp Asp Glu
    130                 135                 140

Tyr Met His Leu Asn Phe Gly Glu Glu Trp Leu Lys Ala His Phe Glu
145                 150                 155                 160

Glu Ser Lys Ala Glu Leu Gln Glu Ala Asn Ser Gln Asn Leu Pro Leu
                165                 170                 175

Val Trp Lys Met Leu Asn Glu Val Glu Asn Asp Ala His Ile Leu Gly
            180                 185                 190
```

```
Met Glu Lys Asp Ala Leu Val Glu Asp Phe Met Ile Ala Tyr Gly Glu
        195                 200                 205

Ala Leu Asn Asn Ile Gly Phe Thr Thr Arg Glu Ile Met Arg Met Ser
    210                 215                 220

Ala His Gly Leu Thr Thr Ala
225                 230


<210> SEQ ID NO 104
<211> LENGTH: 231
<212> TYPE: PRT
<213> ORGANISM: Nodularia spumigena

<400> SEQUENCE: 104

Met Gln Gln Leu Ala Ala Glu Leu Lys Ile Asp Phe Gln Ser Glu Lys
1               5                   10                  15

Tyr Lys Asp Ala Tyr Ser Arg Ile Asn Ala Ile Val Ile Glu Gly Glu
            20                  25                  30

Gln Glu Ala His Asp Asn Tyr Ile Thr Leu Gly Glu Met Leu Pro Glu
        35                  40                  45

Leu Lys Asp Glu Leu Ile Arg Leu Ser Lys Met Glu Ser Arg His Lys
    50                  55                  60

Lys Gly Phe Glu Ala Cys Gly Arg Asn Leu Ser Val Lys Pro Asp Met
65                  70                  75                  80

Pro Phe Ala Gln Lys Phe Phe Ser Gly Leu His Glu Asn Phe Gln Lys
                85                  90                  95

Ala Ala Ala Glu Gly Gln Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Ser His Leu Asn Phe Gly Glu Val Trp Leu Lys Glu Asn Phe Ala
145                 150                 155                 160

Gln Ser Lys Ala Glu Leu Glu Ala Ala Asn Arg Gln Asn Leu Pro Ile
                165                 170                 175

Val Trp Lys Met Leu Asn Glu Val Glu Asn Asp Ala His Val Leu Ala
            180                 185                 190

Met Glu Lys Glu Ala Leu Val Glu Asp Phe Met Ile Gln Tyr Gly Glu
        195                 200                 205

Thr Leu Ser Asn Ile Gly Phe Thr Thr Arg Asp Ile Met Lys Met Ser
    210                 215                 220

Ala Tyr Gly Leu Thr Ala Ala
225                 230


<210> SEQ ID NO 105
<211> LENGTH: 231
<212> TYPE: PRT
<213> ORGANISM: Microcystis aeruginosa

<400> SEQUENCE: 105

Met Pro Glu Leu Ala Val Pro Leu Glu Leu Asp Phe Thr Ser Glu Thr
1               5                   10                  15

Tyr Lys Ser Ala Tyr Ser Arg Ile Asn Ala Ile Val Ile Glu Gly Glu
            20                  25                  30

Tyr Glu Ala Asn Ser Asn Tyr Ile Gln Leu Ala Asp Ile Leu Thr Asp
        35                  40                  45
```

```
Asn Lys Glu Glu Leu His Arg Leu Ala Lys Met Glu Asn Arg His Met
    50                  55                  60

Lys Gly Phe Gln Ala Cys Gly Gln Asn Leu Lys Ile Thr Pro Asp Met
65                  70                  75                  80

Asp Tyr Ala Arg Glu Phe Phe Ser Ser Leu His Asn Asn Phe Gln Ile
                85                  90                  95

Ala Tyr Ala Glu Gly Lys Val Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Leu His Leu Asn Phe Gly Glu Glu Trp Leu Lys Ala Asn Phe Glu
145                 150                 155                 160

Thr Ala Lys Glu Glu Leu Glu Ala Ala Asn Arg Ala Asn Leu Pro Ile
                165                 170                 175

Val Trp Arg Met Leu Asn Gln Val Glu Asn Asp Ala Arg Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Asp Ile Met Arg Met Ser
    210                 215                 220

Ala Tyr Gly Leu Thr Ala Val
225                 230


<210> SEQ ID NO 106
<211> LENGTH: 231
<212> TYPE: PRT
<213> ORGANISM: Microcystis aeruginosa

<400> SEQUENCE: 106

Met Pro Glu Leu Ala Val Pro Leu Glu Leu Asp Phe Thr Ser Glu Thr
1               5                   10                  15

Tyr Lys Ser Ala Tyr Ser Arg Ile Asn Ala Ile Val Ile Glu Gly Glu
            20                  25                  30

Tyr Glu Ala Asn Ser Asn Tyr Ile Gln Leu Ala Asp Ile Leu Thr Asp
        35                  40                  45

Asn Lys Glu Glu Leu His Arg Leu Ala Lys Met Glu Asn Arg His Met
    50                  55                  60

Lys Gly Phe Gln Ala Cys Gly Gln Asn Leu Gln Ile Thr Pro Asp Met
65                  70                  75                  80

Glu Tyr Ala Lys Glu Phe Phe Ser Ser Leu His Asn Asn Phe Gln Ile
                85                  90                  95

Ala Tyr Ala Glu Gly Lys Val Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Ser Val Val Lys Asp Glu
    130                 135                 140

Tyr Leu His Leu Asn Phe Gly Glu Glu Trp Leu Lys Ala Asn Phe Glu
145                 150                 155                 160

Thr Ala Lys Glu Glu Leu Glu Ala Ala Asn Arg Ala Asn Leu Pro Ile
                165                 170                 175

Val Trp Arg Met Leu Asn Gln Val Glu Asp Asp Ala Arg Val Leu Ala
            180                 185                 190
```

```
Met Glu Lys Glu Ala Leu Val Glu Asp Phe Met Ile Ser Tyr Gly Glu
        195                 200                 205

Ala Leu Asn Asn Ile Gly Phe Ser Thr Arg Asp Ile Met Arg Met Ser
    210                 215                 220

Ala Tyr Gly Leu Thr Ala Val
225                 230


<210> SEQ ID NO 107
<211> LENGTH: 231
<212> TYPE: PRT
<213> ORGANISM: Nostoc sp.

<400> SEQUENCE: 107

Met Gln Gln Val Ala Ala Asp Leu Glu Ile Asp Phe Lys Ser Glu Lys
1               5                   10                  15

Tyr Lys Asp Ala Tyr Ser Arg Ile Asn Ala Ile Val Ile Glu Gly Glu
            20                  25                  30

Gln Glu Ala Tyr Glu Asn Tyr Ile Gln Leu Ser Gln Leu Leu Pro Asp
        35                  40                  45

Asp Lys Glu Asp Leu Ile Arg Leu Ser Lys Met Glu Ser Arg His Lys
    50                  55                  60

Lys Gly Phe Glu Ala Cys Gly Arg Asn Leu Gln Val Ser Pro Asp Met
65                  70                  75                  80

Glu Phe Ala Lys Glu Phe Phe Ala Gly Leu His Gly Asn Phe Gln Lys
                85                  90                  95

Ala Ala Ala Glu Gly Lys Ile Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Ser His Leu Asn Phe Gly Glu Val Trp Leu Gln Lys Asn Phe Ala
145                 150                 155                 160

Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Ala Val Leu Ala
            180                 185                 190

Met Glu Lys Glu Ala Leu Val Glu Asp Phe Met Ile Gln Tyr Gly Glu
        195                 200                 205

Ala Leu Ser Asn Ile Gly Phe Thr Thr Arg Asp Ile Met Arg Met Ser
    210                 215                 220

Ala Tyr Gly Leu Thr Ala Ala
225                 230


<210> SEQ ID NO 108
<211> LENGTH: 231
<212> TYPE: PRT
<213> ORGANISM: Anabaena variabilis

<400> SEQUENCE: 108

Met Gln Gln Val Ala Ala Asp Leu Glu Ile Asp Phe Lys Ser Glu Lys
1               5                   10                  15

Tyr Lys Asp Ala Tyr Ser Arg Ile Asn Ala Ile Val Ile Glu Gly Glu
            20                  25                  30

Gln Glu Ala Tyr Glu Asn Tyr Ile Gln Leu Ser Gln Leu Leu Pro Asp
        35                  40                  45
```

Asp Lys Glu Asp Leu Ile Arg Leu Ser Lys Met Glu Ser Arg His Lys
    50                  55                  60

Lys Gly Phe Glu Ala Cys Gly Arg Asn Leu Gln Val Ser Pro Asp Ile
65                  70                  75                  80

Glu Phe Ala Lys Glu Phe Phe Ala Gly Leu His Gly Asn Phe Gln Lys
                85                  90                  95

Ala Ala Ala Glu Gly Lys Val Val Thr Cys Leu Leu Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Ser His Leu Asn Phe Gly Glu Val Trp Leu Gln Lys Asn Phe Ala
145                 150                 155                 160

Gln Ser Lys Ala Glu Leu Glu Glu Ala Asn Arg His Asn Leu Pro Ile
                165                 170                 175

Val Trp Lys Met Leu Asn Gln Val Ala Asp Asp Ala Ala Val Leu Ala
            180                 185                 190

Met Glu Lys Glu Ala Leu Val Glu Asp Phe Met Ile Gln Tyr Gly Glu
        195                 200                 205

Ala Leu Ser Asn Ile Gly Phe Thr Thr Arg Asp Ile Met Arg Met Ser
    210                 215                 220

Ala Tyr Gly Leu Thr Ala Ala
225                 230

<210> SEQ ID NO 109
<211> LENGTH: 231
<212> TYPE: PRT
<213> ORGANISM: Crocosphaera watsonii

<400> SEQUENCE: 109

Met Gln Glu Leu Ala Val Arg Ser Glu Leu Asp Phe Asn Ser Glu Thr
1               5                   10                  15

Tyr Lys Asp Ala Tyr Ser Arg Ile Asn Ala Ile Val Ile Glu Gly Glu
            20                  25                  30

Gln Glu Ala Tyr Glu Asn Tyr Ile Asp Met Gly Glu Leu Leu Pro Gly
        35                  40                  45

Asp Lys Asp Glu Leu Ile Arg Leu Ser Lys Met Glu Asn Arg His Lys
    50                  55                  60

Lys Gly Phe Gln Ala Cys Gly Lys Asn Leu Lys Val Thr Pro Asp Met
65                  70                  75                  80

Asp Tyr Ala Glu Arg Phe Phe Ser Gln Leu His Gly Asn Phe Gln Thr
                85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Asn Val Val Lys Asp Glu
    130                 135                 140

Tyr Ser His Leu Asn Phe Gly Glu Val Trp Leu Lys Glu Asn Phe Glu
145                 150                 155                 160

Ala Ser Lys Ala Glu Leu Glu Gln Ala Asn Lys Glu Asn Leu Pro Ile
                165                 170                 175

Val Trp Gln Met Leu Asn Glu Val Glu Asp Asp Ala Glu Ile Leu Gly

```
            180                 185                 190

Met Glu Lys Glu Ala Leu Val Glu Asp Phe Met Ile Ser Tyr Gly Glu
        195                 200                 205

Ala Leu Gly Asn Ile Gly Phe Ser Thr Arg Glu Ile Met Lys Met Ser
    210                 215                 220

Ala His Gly Leu Ala Ala Val
225                 230


<210> SEQ ID NO 110
<211> LENGTH: 251
<212> TYPE: PRT
<213> ORGANISM: Trichodesmium erythraeum

<400> SEQUENCE: 110

Met Pro Lys Leu Glu Ile Ile Pro Thr Met Asp Ser Gln Ser Glu Thr
1               5                   10                  15

Lys Leu Glu Lys Val Lys Ser Gln Ser Glu Gly Asp Gln Ile Asn Phe
            20                  25                  30

Glu Thr Glu Thr Tyr Lys Asp Ala Tyr Ser Arg Ile Asn Ala Ile Val
        35                  40                  45

Ile Glu Gly Glu Gln Glu Ala Tyr Lys Asn Tyr Ile Lys Leu Ala Glu
    50                  55                  60

Met Leu Pro Asp Glu Lys Asp Glu Leu Ile Lys Leu Ser Lys Met Glu
65                  70                  75                  80

Asn Arg His Lys Lys Gly Phe Glu Ala Cys Gly Arg Asn Leu His Val
                85                  90                  95

Thr Pro Asp Met Glu Phe Ala Lys Lys Phe Phe Glu Pro Leu His Glu
            100                 105                 110

Asn Phe Gln Thr Ala Ala Ala Thr Gly Asn Val Val Thr Cys Leu Leu
        115                 120                 125

Ile Gln Ser Leu Ile Ile Glu Cys Phe Ala Ile Ala Ala Tyr Asn Ile
    130                 135                 140

Tyr Ile Pro Val Ala Asp Pro Phe Ala Arg Lys Ile Thr Glu Ser Val
145                 150                 155                 160

Val Lys Asp Glu Tyr Ser His Leu Asn Phe Gly Glu Val Trp Leu Lys
                165                 170                 175

Glu Tyr Phe Glu Asp Ser Lys Gln Glu Leu Gln Lys Ala Asn Arg Gln
            180                 185                 190

Asn Leu Pro Leu Val Trp Lys Met Leu Asn Gln Val Glu Lys Asp Ala
        195                 200                 205

Lys Thr Leu Glu Met Glu Lys Glu Ala Leu Ile Glu Asp Phe Met Ile
    210                 215                 220

Ala Tyr Gly Glu Ala Leu Asn Asn Ile Gly Phe Thr Thr Gly Glu Ile
225                 230                 235                 240

Met Arg Met Ser Ala Tyr Gly Leu Ile Ala Ala
                245                 250


<210> SEQ ID NO 111
<211> LENGTH: 231
<212> TYPE: PRT
<213> ORGANISM: Synechococcus sp.

<400> SEQUENCE: 111

Met Gln Thr Leu Glu Val Ser Pro Ala Met Asp Phe Gln Ser Glu Thr
1               5                   10                  15

Tyr Lys Asp Ala Tyr Ser Arg Ile Asn Ala Ile Val Ile Glu Gly Glu
```

```
            20                  25                  30

Leu Glu Ala Asn Asn Asn Tyr Lys Gln Leu Ser Glu His Leu Gly Asp
        35                  40                  45

Phe Lys Asp Asp Leu Leu Lys Leu Ala Arg Met Glu Asn Arg His Met
    50                  55                  60

Lys Gly Phe Gln Ala Cys Gly Lys Asn Leu Ser Val Asn Pro Asp Met
65                  70                  75                  80

Pro Phe Ala Lys Glu Phe Phe Ala Gln Leu His Asp Asn Phe Gln Thr
                85                  90                  95

Ala Leu Ala Glu Gly Lys Ile Val Thr Cys Leu Leu Ile Gln Ser Leu
            100                 105                 110

Ile Ile Glu Thr Phe Ala Ile Ser Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Met His Leu Asn Phe Gly Glu Glu Trp Leu Lys Ala Asn Phe Glu
145                 150                 155                 160

Ala Ser Lys Ala Glu Leu Glu Thr Ala Asn Arg Ala Asn Leu Pro Leu
                165                 170                 175

Ile Trp Lys Met Leu Asn Gln Val Glu Glu Asp Ala Ala Val Leu Gly
            180                 185                 190

Met Glu Lys Asp Ala Leu Ile Glu Asp Phe Met Ile Thr Tyr Gly Glu
        195                 200                 205

Ala Leu Ala Asn Ile Gly Phe Ser Ala Arg Asp Val Met Arg Leu Ser
    210                 215                 220

Ala Gln Gly Leu Ala Ala Val
225                 230


<210> SEQ ID NO 112
<211> LENGTH: 232
<212> TYPE: PRT
<213> ORGANISM: Nostoc azollae

<400> SEQUENCE: 112

Met Gln Gln Leu Val Glu Glu Ile Glu Lys Ile Asp Phe Gln Ser Glu
1               5                   10                  15

Lys Tyr Lys Asp Ala Tyr Ser Arg Ile Asn Ala Ile Val Ile Glu Gly
            20                  25                  30

Glu Gln Glu Ala His Glu Asn Tyr Ile Thr Leu Ala Lys Leu Leu Pro
        35                  40                  45

Glu Ser Lys Glu Glu Leu Met Arg Leu Ser Lys Met Glu Ser Arg His
    50                  55                  60

Lys Lys Gly Phe Glu Ala Cys Gly Arg Asn Leu Gln Val Thr Pro Asp
65                  70                  75                  80

Met Gln Phe Ala Lys Glu Phe Phe Ser Gly Leu His Gln Asn Phe Gln
                85                  90                  95

Thr Ala Ala Ala Ala Gly Asn Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160
```

```
Ala Glu Ser Lys Ala Glu Leu Asp Asp Ala Asn Arg Gln Asn Leu Pro
                165                 170                 175

Ile Val Trp Gln Met Leu Asn Gln Val Ala Asp Asp Ala Arg Val Leu
            180                 185                 190

Ala Met Glu Lys Glu Ala Leu Val Glu Asp Phe Met Ile Gln Tyr Gly
        195                 200                 205

Glu Ala Leu Ser Asn Ile Gly Phe Thr Thr Arg Asp Ile Ile Arg Leu
    210                 215                 220

Ser Ala Tyr Gly Leu Ala Thr Val
225                 230
```

<210> SEQ ID NO 113
<211> LENGTH: 231
<212> TYPE: PRT
<213> ORGANISM: Synechocystis sp.

<400> SEQUENCE: 113

```
Met Pro Glu Leu Ala Val Arg Thr Glu Phe Asp Tyr Ser Ser Glu Ile
1               5                   10                  15

Tyr Lys Asp Ala Tyr Ser Arg Ile Asn Ala Ile Val Ile Glu Gly Glu
            20                  25                  30

Gln Glu Ala Tyr Ser Asn Tyr Leu Gln Met Ala Glu Leu Leu Pro Glu
        35                  40                  45

Asp Lys Glu Glu Leu Thr Arg Leu Ala Lys Met Glu Asn Arg His Lys
    50                  55                  60

Lys Gly Phe Gln Ala Cys Gly Asn Asn Leu Gln Val Asn Pro Asp Met
65                  70                  75                  80

Pro Tyr Ala Gln Glu Phe Phe Ala Gly Leu His Gly Asn Phe Gln His
                85                  90                  95

Ala Phe Ser Glu Gly Lys Val Val Thr Cys Leu Leu Ile Gln Ala Leu
            100                 105                 110

Ile Ile Glu Ala Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Thr His Leu Asn Tyr Gly Glu Glu Trp Leu Lys Ala Asn Phe Ala
145                 150                 155                 160

Thr Ala Lys Glu Glu Leu Glu Gln Ala Asn Lys Glu Asn Leu Pro Leu
                165                 170                 175

Val Trp Lys Met Leu Asn Gln Val Gln Gly Asp Ala Lys Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Arg Met Ser
    210                 215                 220

Ser Tyr Gly Leu Ala Gly Val
225                 230
```

<210> SEQ ID NO 114
<211> LENGTH: 231
<212> TYPE: PRT
<213> ORGANISM: Cyanothece sp.

<400> SEQUENCE: 114

```
Met Gln Glu Leu Ala Leu Arg Ser Glu Leu Asp Phe Asn Ser Glu Thr
1               5                   10                  15
```

Tyr Lys Asp Ala Tyr Ser Arg Ile Asn Ala Ile Val Ile Glu Gly Glu
20 25 30

Gln Glu Ala Tyr Gln Asn Tyr Leu Asp Met Ala Gln Leu Leu Pro Glu
35 40 45

Asp Glu Ala Glu Leu Ile Arg Leu Ser Lys Met Glu Asn Arg His Lys
50 55 60

Lys Gly Phe Gln Ala Cys Gly Lys Asn Leu Asn Val Thr Pro Asp Met
65 70 75 80

Asp Tyr Ala Gln Gln Phe Phe Ala Glu Leu His Gly Asn Phe Gln Lys
85 90 95

Ala Lys Ala Glu Gly Lys Ile Val Thr Cys Leu Leu Ile Gln Ser Leu
100 105 110

Ile Ile Glu Ala Phe Ala Ile Ala Ala Tyr Asn Ile Tyr Ile Pro Val
115 120 125

Ala Asp Pro Phe Ala Arg Lys Ile Thr Glu Gly Val Val Lys Asp Glu
130 135 140

Tyr Thr His Leu Asn Phe Gly Glu Val Trp Leu Lys Glu His Phe Glu
145 150 155 160

Ala Ser Lys Ala Glu Leu Glu Asp Ala Asn Lys Glu Asn Leu Pro Leu
165 170 175

Val Trp Gln Met Leu Asn Gln Val Glu Lys Asp Ala Glu Val Leu Gly
180 185 190

Met Glu Lys Glu Ala Leu Val Glu Asp Phe Met Ile Ser Tyr Gly Glu
195 200 205

Ala Leu Ser Asn Ile Gly Phe Ser Thr Arg Glu Ile Met Lys Met Ser
210 215 220

Ala Tyr Gly Leu Arg Ala Ala
225 230

<210> SEQ ID NO 115
<211> LENGTH: 231
<212> TYPE: PRT
<213> ORGANISM: Cyanothece sp.

<400> SEQUENCE: 115

Met Gln Glu Leu Ala Leu Arg Ser Glu Leu Asp Phe Asn Ser Glu Thr
1 5 10 15

Tyr Lys Asp Ala Tyr Ser Arg Ile Asn Ala Ile Val Ile Glu Gly Glu
20 25 30

Gln Glu Ala His Gln Asn Tyr Ile Asp Met Ala Gln Leu Leu Pro Glu
35 40 45

Asp Glu Ala Glu Leu Ile Arg Leu Ser Lys Met Glu Asn Arg His Lys
50 55 60

Lys Gly Phe Gln Ala Cys Gly Lys Asn Leu Asp Val Thr Pro Asp Met
65 70 75 80

Asp Tyr Ala Gln Gln Phe Phe Ser Gln Leu His Asn Asn Phe Gln Thr
85 90 95

Ala Lys Ala Glu Gly Lys Ile Val Thr Cys Leu Leu Ile Gln Ser Leu
100 105 110

Ile Ile Glu Ala Phe Ala Ile Ala Ala Tyr Asn Ile Tyr Ile Pro Val
115 120 125

Ala Asp Pro Phe Ala Arg Lys Ile Thr Glu Gly Val Val Lys Asp Glu
130 135 140

Tyr Thr His Leu Asn Phe Gly Glu Ile Trp Leu Lys Glu His Phe Glu
145 150 155 160

```
Ala Ser Lys Ala Glu Leu Glu Glu Ala Asn Lys Lys Asn Leu Pro Ile
                165                 170                 175

Val Trp Gln Met Leu Asn Gln Val Glu Lys Asp Ala Glu Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Lys Met Ser
    210                 215                 220

Ser His Gly Leu Ser Ala Ala
225                 230


<210> SEQ ID NO 116
<211> LENGTH: 231
<212> TYPE: PRT
<213> ORGANISM: Cyanothece sp.

<400> SEQUENCE: 116

Met Pro Gln Val Gln Ser Pro Ser Ala Ile Asp Phe Tyr Ser Glu Thr
1               5                   10                  15

Tyr Gln Asp Ala Tyr Ser Arg Ile Asp Ala Ile Val Ile Glu Gly Glu
            20                  25                  30

Gln Glu Ala His Asp Asn Tyr Leu Lys Leu Thr Glu Leu Leu Pro Asp
        35                  40                  45

Cys Gln Glu Asp Leu Val Arg Leu Ala Lys Met Glu Ala Arg His Lys
    50                  55                  60

Lys Gly Phe Glu Ala Cys Gly Arg Asn Leu Lys Val Thr Pro Asp Met
65                  70                  75                  80

Glu Phe Ala Gln Gln Phe Phe Ala Asp Leu His Asn Asn Phe Gln Lys
                85                  90                  95

Ala Ala Ala Ala Asn Lys Ile Ala Thr Cys Leu Val Ile Gln Ala Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Asn Val Val Lys Asp Glu
    130                 135                 140

Tyr Thr His Leu Asn Phe Gly Glu Glu Trp Leu Lys Ala Asn Phe Asp
145                 150                 155                 160

Ser Gln Arg Glu Glu Val Glu Ala Ala Asn Arg Glu Asn Leu Pro Ile
                165                 170                 175

Val Trp Arg Met Leu Asn Gln Val Glu Thr Asp Ala His Val Leu Gly
            180                 185                 190

Met Glu Lys Glu Ala Leu Val Glu Ser Phe Met Ile Gln Tyr Gly Glu
        195                 200                 205

Ala Leu Glu Asn Ile Gly Phe Ser Thr Arg Glu Ile Met Arg Met Ser
    210                 215                 220

Val Tyr Gly Leu Ser Ala Ala
225                 230


<210> SEQ ID NO 117
<211> LENGTH: 232
<212> TYPE: PRT
<213> ORGANISM: Nostoc punctiforme

<400> SEQUENCE: 117

Met Gln Gln Leu Thr Asp Gln Ser Lys Glu Leu Asp Phe Lys Ser Glu
1               5                   10                  15
```

```
Thr Tyr Lys Asp Ala Tyr Ser Arg Ile Asn Ala Ile Val Ile Glu Gly
            20                  25                  30

Glu Gln Glu Ala His Glu Asn Tyr Ile Thr Leu Ala Gln Leu Leu Pro
        35                  40                  45

Glu Ser His Asp Glu Leu Ile Arg Leu Ser Lys Met Glu Ser Arg His
    50                  55                  60

Lys Lys Gly Phe Glu Ala Cys Gly Arg Asn Leu Ala Val Thr Pro Asp
65                  70                  75                  80

Leu Gln Phe Ala Lys Glu Phe Phe Ser Gly Leu His Gln Asn Phe Gln
                85                  90                  95

Thr Ala Ala Ala Glu Gly Lys Val Val Thr Cys Leu Leu Ile Gln Ser
            100                 105                 110

Leu Ile Ile Glu Cys Phe Ala Ile Ala Ala Tyr Asn Ile Tyr Ile Pro
        115                 120                 125

Val Ala Asp Asp Phe Ala Arg Lys Ile Thr Glu Gly Val Val Lys Glu
    130                 135                 140

Glu Tyr Ser His Leu Asn Phe Gly Glu Val Trp Leu Lys Glu His Phe
145                 150                 155                 160

Ala Glu Ser Lys Ala Glu Leu Glu Leu Ala Asn Arg Gln Asn Leu Pro
                165                 170                 175

Ile Val Trp Lys Met Leu Asn Gln Val Glu Gly Asp Ala His Thr Met
            180                 185                 190

Ala Met Glu Lys Asp Ala Leu Val Glu Asp Phe Met Ile Gln Tyr Gly
        195                 200                 205

Glu Ala Leu Ser Asn Ile Gly Phe Ser Thr Arg Asp Ile Met Arg Leu
    210                 215                 220

Ser Ala Tyr Gly Leu Ile Gly Ala
225                 230


<210> SEQ ID NO 118
<211> LENGTH: 231
<212> TYPE: PRT
<213> ORGANISM: Acaryochloris marina

<400> SEQUENCE: 118

Met Pro Gln Thr Gln Ala Ile Ser Glu Ile Asp Phe Tyr Ser Asp Thr
1               5                   10                  15

Tyr Lys Asp Ala Tyr Ser Arg Ile Asp Gly Ile Val Ile Glu Gly Glu
            20                  25                  30

Gln Glu Ala His Glu Asn Tyr Ile Arg Leu Gly Glu Met Leu Pro Glu
        35                  40                  45

His Gln Asp Asp Phe Ile Arg Leu Ser Lys Met Glu Ala Arg His Lys
    50                  55                  60

Lys Gly Phe Glu Ala Cys Gly Arg Asn Leu Lys Val Thr Cys Asp Leu
65                  70                  75                  80

Asp Phe Ala Arg Arg Phe Phe Ser Asp Leu His Lys Asn Phe Gln Asp
                85                  90                  95

Ala Ala Ala Glu Asp Lys Val Pro Thr Cys Leu Val Ile Gln Ser Leu
            100                 105                 110

Ile Ile Glu Cys Phe Ala Ile Ala Ala Tyr Asn Ile Tyr Ile Pro Val
        115                 120                 125

Ala Asp Asp Phe Ala Arg Lys Ile Thr Glu Ser Val Val Lys Asp Glu
    130                 135                 140

Tyr Gln His Leu Asn Tyr Gly Glu Glu Trp Leu Lys Ala His Phe Asp
```

145 150 155 160

Asp Val Lys Ala Glu Ile Gln Glu Ala Asn Arg Lys Asn Leu Pro Ile
165 170 175

Val Trp Arg Met Leu Asn Glu Val Asp Lys Asp Ala Ala Val Leu Gly
180 185 190

Met Glu Lys Glu Ala Leu Val Glu Asp Phe Met Ile Gln Tyr Gly Glu
195 200 205

Ala Leu Ser Asn Ile Gly Phe Ser Thr Gly Glu Ile Met Arg Met Ser
210 215 220

Ala Tyr Gly Leu Val Ala Ala
225 230

<210> SEQ ID NO 119
<211> LENGTH: 231
<212> TYPE: PRT
<213> ORGANISM: Cyanothece sp.

<400> SEQUENCE: 119

Met Gln Glu Leu Val Gln Arg Ser Glu Leu Asp Phe Thr Asn Pro Thr
1 5 10 15

Tyr Lys Asp Ala Tyr Ser Arg Ile Asn Ala Ile Val Ile Glu Gly Glu
20 25 30

Gln Glu Ala His Gln Asn Tyr Ile Asp Met Ala Gln Leu Leu Pro Glu
35 40 45

His Gln Glu Glu Leu Ile Arg Leu Ser Lys Met Glu Asn Arg His Lys
50 55 60

Lys Gly Phe Glu Ala Cys Gly Asn Asn Leu Ser Val Thr Pro Asp Met
65 70 75 80

Gln Tyr Ala Gln Glu Phe Phe Ser Ser Leu His Gly Asn Phe Gln Lys
85 90 95

Ala Lys Ala Glu Gly Lys Ile Val Thr Cys Leu Leu Ile Gln Ser Leu
100 105 110

Ile Ile Glu Ala Phe Ala Ile Ala Ala Tyr Asn Ile Tyr Ile Pro Val
115 120 125

Ala Asp Pro Phe Ala Arg Lys Ile Thr Glu Gly Val Val Lys Asp Glu
130 135 140

Tyr Thr His Leu Asn Phe Gly Glu Val Trp Leu Gln Glu His Phe Glu
145 150 155 160

Glu Ser Lys Ala Glu Leu Glu Glu Ala Asn Lys Ala Asn Leu Pro Ile
165 170 175

Val Trp Glu Met Leu Asn Gln Val Glu Gly Asp Ala Lys Val Leu Gly
180 185 190

Met Glu Lys Glu Ala Leu Val Glu Asp Phe Met Ile Ser Tyr Gly Glu
195 200 205

Ala Leu Ser Asn Ile Gly Phe Ser Thr Arg Asp Ile Met Arg Met Ser
210 215 220

Ser His Gly Leu Val Ala Ala
225 230

<210> SEQ ID NO 120
<211> LENGTH: 231
<212> TYPE: PRT
<213> ORGANISM: Cyanothece sp.

<400> SEQUENCE: 120

Met Gln Glu Leu Val Gln Arg Ser Glu Leu Asp Phe Thr Asn Pro Thr

```
1               5                   10                  15

Tyr Lys Asp Ala Tyr Ser Arg Ile Asn Ala Ile Val Ile Glu Gly Glu
            20                  25                  30

Gln Glu Ala His Gln Asn Tyr Ile Asp Met Ala Gln Leu Leu Pro Glu
        35                  40                  45

His Gln Glu Glu Leu Ile Arg Leu Ser Lys Met Glu Asn Arg His Lys
    50                  55                  60

Lys Gly Phe Glu Ala Cys Gly Asn Asn Leu Ser Val Thr Pro Asp Met
65                  70                  75                  80

Gln Tyr Ala Gln Glu Phe Phe Ser Ser Leu His Gly Asn Phe Gln Lys
                85                  90                  95

Ala Lys Ala Glu Gly Lys Ile Val Thr Cys Leu Leu Ile Gln Ser Leu
            100                 105                 110

Ile Ile Glu Ala Phe Ala Ile Ala Ala Tyr Asn Ile Tyr Ile Pro Val
        115                 120                 125

Ala Asp Pro Phe Ala Arg Lys Ile Thr Glu Gly Val Val Lys Asp Glu
    130                 135                 140

Tyr Thr His Leu Asn Phe Gly Glu Val Trp Leu Gln Glu His Phe Glu
145                 150                 155                 160

Glu Ser Lys Ala Glu Leu Glu Glu Ala Asn Lys Ala Asn Leu Pro Ile
                165                 170                 175

Val Trp Glu Met Leu Asn Gln Val Glu Gly Asp Ala Lys Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Asp Ile Met Arg Met Ser
    210                 215                 220

Ser His Gly Leu Val Ala Ala
225                 230


<210> SEQ ID NO 121
<211> LENGTH: 240
<212> TYPE: PRT
<213> ORGANISM: Synechococcus sp.

<400> SEQUENCE: 121

Met Asn Val Leu Pro Asn Thr Pro Gln Pro Leu Ala Asp Glu Gly Gly
1               5                   10                  15

Thr Thr Leu Asp Tyr Gly Ser Ala Val Tyr Arg Gln Ala Tyr Ser Arg
            20                  25                  30

Ile Asn Gly Ile Val Ile Glu Gly Glu Gln Glu Ala His Asp Asn Tyr
        35                  40                  45

Leu Lys Leu Ala Glu Met Leu Pro Glu Gly Ala Glu Glu Leu His Lys
    50                  55                  60

Leu Ala Lys Met Glu Leu Arg His Met Lys Gly Phe Gln Ser Cys Gly
65                  70                  75                  80

Lys Asn Leu Gln Val Glu Pro Asp Arg Glu Phe Ala Arg Thr Phe Phe
                85                  90                  95

Ala Pro Leu Arg Asn Asn Phe Gln Lys Ala Ala Ala Ala Gly Asp Leu
            100                 105                 110

Val Thr Cys Leu Val Ile Gln Ser Leu Ile Ile Glu Cys Phe Ala Ile
        115                 120                 125

Ala Ala Tyr Asn Ile Tyr Ile Pro Val Ala Asp Glu Phe Ala Arg Lys
    130                 135                 140
```

```
Ile Thr Glu Gly Val Val Lys Asp Glu Tyr Leu His Leu Asn Phe Gly
145                 150                 155                 160

Glu Arg Trp Leu Gly Glu His Phe Gly Glu Val Lys Gly Gln Ile Glu
                165                 170                 175

Ala Ala Asn Ala Gln Asn Leu Pro Leu Val Trp Gln Met Leu Gln Gln
            180                 185                 190

Val Asp Gln Asp Val Glu Ala Ile Tyr Met Asp Arg Glu Ala Ile Val
        195                 200                 205

Glu Asp Phe Met Ile Ala Tyr Gly Glu Ala Leu Ala Asn Ile Gly Phe
    210                 215                 220

Ser Thr Arg Glu Val Met Arg Leu Ser Ala Gln Gly Leu Arg Ala Ala
225                 230                 235                 240


<210> SEQ ID NO 122
<211> LENGTH: 241
<212> TYPE: PRT
<213> ORGANISM: Synechococcus sp.

<400> SEQUENCE: 122

Met Ala Ser Ser Leu Leu Asp Pro Ala Val Asp Gly Thr Pro Val Leu
1               5                   10                  15

Asp Val Glu Leu Pro Asp Phe Thr Thr Glu Ala Tyr Lys Ser Ala Tyr
            20                  25                  30

Ser Arg Ile Asn Ala Ile Val Ile Glu Gly Glu Gln Glu Ala His Asp
        35                  40                  45

Asn Tyr Ile Ser Leu Gly Thr Leu Ile Pro Asp Gln Ala Asp Glu Leu
    50                  55                  60

Ala Gln Leu Ala Arg Met Glu Met Lys His Met Lys Gly Phe Gln Ala
65                  70                  75                  80

Cys Gly Lys Asn Leu Ser Val Glu Pro Asp Met Val Phe Ala Lys Glu
                85                  90                  95

Phe Phe Ser Asp Leu His Gly Asn Phe Arg Ser Ala Leu Glu Glu Asn
            100                 105                 110

Lys Val Val Thr Cys Leu Val Ile Gln Ala Leu Met Ile Glu Ala Phe
        115                 120                 125

Ala Ile Ala Ala Tyr His Ile Tyr Ile Pro Val Ala Asp Pro Phe Ala
    130                 135                 140

Arg Lys Ile Thr Glu Gly Val Val Lys Asp Glu Tyr Thr His Leu Asn
145                 150                 155                 160

Tyr Gly Gln Glu Trp Leu Lys Ala Asn Phe Asp Ser Ser Arg Asp Glu
                165                 170                 175

Ile Ile Glu Ala Asn Lys Ala Asn Leu Pro Ile Ile Arg Arg Met Leu
            180                 185                 190

Glu Glu Val Ala Asp Asp Ala Ala Glu Leu Lys Met Glu Lys Glu Ser
        195                 200                 205

Leu Ile Glu Asp Phe Leu Ile Ala Tyr Gln Glu Ala Leu Met Asp Ile
    210                 215                 220

Gly Phe Asn Ser Arg Asp Leu Ala Arg Met Ser Ala Ala Ala Leu Val
225                 230                 235                 240

Ala


<210> SEQ ID NO 123
<211> LENGTH: 243
<212> TYPE: PRT
<213> ORGANISM: Synechococcus sp.
```

<400> SEQUENCE: 123

```
Met Pro Thr Pro Val Thr Ser Glu Val Ala Val Leu Asp Gly Gln Ala
1               5                   10                  15

Gly Ser Ala Gln Ala Leu Pro Asp Phe Ser Ser Glu Ala Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ser Leu Gly Thr Leu Ile Pro Glu Gln Ala Asp
    50                  55                  60

Glu Leu Ala Arg Leu Ala Arg Met Glu Met Lys His Met Lys Gly Phe
65                  70                  75                  80

Met Ser Cys Gly Arg Asn Leu Gly Val Glu Ala Asp Met Pro Phe Ala
                85                  90                  95

Lys Glu Phe Phe Gly Pro Leu His Gly Asn Phe Gln Thr Ala Leu Lys
            100                 105                 110

Glu Gly Lys Val Val Thr Cys Leu Leu Ile Gln Ala Leu Leu Ile Glu
        115                 120                 125

Ala Phe Ala Ile Ser Ala Tyr His Ile Tyr Ile Pro Val Ala Asp Pro
    130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Glu Ala Ser Arg
                165                 170                 175

Glu Glu Leu Met Glu Ala Asn Lys Val Asn Leu Pro Leu Ile Arg Ser
            180                 185                 190

Met Leu Glu Gln Val Ala Lys Asp Ala Ala Val Leu Lys Met Glu Lys
        195                 200                 205

Glu Asp Leu Ile Glu Asp Phe Leu Ile Ala Tyr Gln Glu Ala Leu Glu
    210                 215                 220

Glu Ile Gly Phe Thr Ser Arg Asp Ile Ala Arg Met Ala Ala Ala Ala
225                 230                 235                 240

Leu Ser Ile
```

<210> SEQ ID NO 124
<211> LENGTH: 239
<212> TYPE: PRT
<213> ORGANISM: Synechococcus sp.

<400> SEQUENCE: 124

```
Met Thr Thr Leu Asn Ala Pro Glu Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Gly Ser Leu Ile Pro Asp Gln Lys Asp Glu Leu Ala Lys
    50                  55                  60

Leu Ala Arg Met Glu Met Lys His Met Lys Gly Phe Thr Ser Cys Gly
65                  70                  75                  80

Arg Asn Leu Gly Val Glu Ala Asp Met Val Phe Ala Lys Lys Phe Phe
                85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
```

```
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Glu Glu
            180                 185                 190

Val Ala Ser Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
    210                 215                 220

Thr Ser Arg Asp Ile Ala Arg Met Ala Ala Ala Ala Leu Ala Val
225                 230                 235


<210> SEQ ID NO 125
<211> LENGTH: 243
<212> TYPE: PRT
<213> ORGANISM: Synechococcus sp.

<400> SEQUENCE: 125

Met Pro Thr Pro Val Thr Ser Glu Val Ala Val Leu Asp Glu Gln Ala
1               5                   10                  15

Gly Ser Ala Ser Leu Leu Pro Asp Phe Ser Ser Glu Ala Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ser Leu Gly Thr Leu Ile Pro Asp Gln Ala Asp
    50                  55                  60

Glu Leu Ala Arg Leu Ala Arg Met Glu Met Lys His Met Lys Gly Phe
65                  70                  75                  80

Thr Ser Cys Gly Arg Asn Leu Gly Val Asp Ala Asp Met Pro Phe Ala
                85                  90                  95

Lys Thr Phe Phe Ala Pro Leu His Gly Asn Phe Gln Thr Ala Leu Lys
            100                 105                 110

Asp Gly Lys Val Val Thr Cys Leu Leu Ile Gln Ala Leu Leu Ile Glu
        115                 120                 125

Ala Phe Ala Ile Ser Ala Tyr His Ile Tyr Ile Pro Val Ala Asp Pro
    130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Asp Ala Ser Arg
                165                 170                 175

Glu Glu Leu Met Glu Ala Asn Lys Val Asn Leu Pro Leu Ile Arg Ser
            180                 185                 190

Met Leu Glu Gln Val Ala Glu Asp Ala Ala Val Leu Lys Met Glu Lys
        195                 200                 205

Glu Asp Leu Ile Glu Asp Phe Leu Ile Ala Tyr Gln Glu Ala Leu Glu
    210                 215                 220

Gln Ile Gly Phe Thr Ser Arg Asp Ile Ala Arg Met Ala Ala Ala Ala
225                 230                 235                 240

Leu Ala Val
```

<210> SEQ ID NO 126
<211> LENGTH: 239
<212> TYPE: PRT
<213> ORGANISM: Unknown
<220> FEATURE:
<223> OTHER INFORMATION: Description of Unknown: Uncultured
      marine type-A Synechococcus GOM 3O12
      polypeptide

<400> SEQUENCE: 126

```
Met Thr Thr Leu Asn Ala Pro Glu Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Gly Thr Leu Ile Pro Asp Gln Lys Asp Glu Leu Ala Lys
    50                  55                  60

Leu Ala Arg Met Glu Met Lys His Met Lys Gly Phe Thr Ser Cys Gly
65                  70                  75                  80

Arg Asn Leu Gly Val Glu Ala Asp Leu Ala Phe Ala Lys Lys Phe Phe
                85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Glu Asp
            180                 185                 190

Val Ala Ser Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
    210                 215                 220

Thr Ser Arg Asp Ile Ala Arg Met Ala Ala Ala Ala Leu Ala Val
225                 230                 235
```

<210> SEQ ID NO 127
<211> LENGTH: 243
<212> TYPE: PRT
<213> ORGANISM: Synechococcus sp.

<400> SEQUENCE: 127

```
Met Ala Pro Ala Asn Val Leu Pro Asn Thr Pro Pro Ser Pro Thr Asp
1               5                   10                  15

Gly Gly Gly Thr Ala Leu Asp Tyr Ser Ser Pro Arg Tyr Arg Gln Ala
            20                  25                  30

Tyr Ser Arg Ile Asn Gly Ile Val Ile Glu Gly Glu Gln Glu Ala His
        35                  40                  45

Asp Asn Tyr Leu Lys Leu Ala Glu Met Leu Pro Glu Ala Ala Glu Glu
    50                  55                  60

Leu Arg Lys Leu Ala Lys Met Glu Leu Arg His Met Lys Gly Phe Gln
65                  70                  75                  80
```

```
Ala Cys Gly Lys Asn Leu Gln Val Glu Pro Asp Val Glu Phe Ala Arg
                85                  90                  95

Ala Phe Phe Ala Pro Leu Arg Asp Asn Phe Gln Ser Ala Ala Ala Ala
            100                 105                 110

Gly Asp Leu Val Ser Cys Phe Val Ile Gln Ser Leu Ile Ile Glu Cys
        115                 120                 125

Phe Ala Ile Ala Ala Tyr Asn Ile Tyr Ile Pro Val Ala Asp Asp Phe
    130                 135                 140

Ala Arg Lys Ile Thr Glu Gly Val Val Lys Asp Glu Tyr Leu His Leu
145                 150                 155                 160

Asn Phe Gly Glu Arg Trp Leu Gly Glu His Phe Ala Glu Val Lys Ala
                165                 170                 175

Gln Ile Glu Ala Ala Asn Ala Gln Asn Leu Pro Leu Val Arg Gln Met
            180                 185                 190

Leu Gln Gln Val Glu Ala Asp Val Glu Ala Ile Tyr Met Asp Arg Glu
        195                 200                 205

Ala Ile Val Glu Asp Phe Met Ile Ala Tyr Gly Glu Ala Leu Ala Ser
    210                 215                 220

Ile Gly Phe Asn Thr Arg Glu Val Met Arg Leu Ser Ala Gln Gly Leu
225                 230                 235                 240

Arg Ala Ala


<210> SEQ ID NO 128
<211> LENGTH: 239
<212> TYPE: PRT
<213> ORGANISM: Unknown
<220> FEATURE:
<223> OTHER INFORMATION: Description of Unknown: Uncultured
      marine type-A Synechococcus GOM 306
      polypeptide

<400> SEQUENCE: 128

Met Thr Thr Leu Asn Ala Pro Glu Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Gly Ser Leu Ile Pro Asp Gln Lys Asp Glu Leu Ala Lys
    50                  55                  60

Leu Ala Arg Met Glu Met Lys His Met Lys Gly Phe Thr Ser Cys Gly
65                  70                  75                  80

Arg Asn Leu Gly Val Glu Ala Asp Met Val Phe Ala Lys Thr Phe Phe
                85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Glu Glu
            180                 185                 190
```

```
Val Ala Ser Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
    210                 215                 220

Thr Ser Arg Asp Ile Ala Arg Met Ala Ala Ala Ala Leu Ala Val
225                 230                 235


<210> SEQ ID NO 129
<211> LENGTH: 239
<212> TYPE: PRT
<213> ORGANISM: Unknown
<220> FEATURE:
<223> OTHER INFORMATION: Description of Unknown: Uncultured
      marine type-A Synechococcus GOM 3M9
      polypeptide

<400> SEQUENCE: 129

Met Thr Thr Leu Asn Ala Pro Glu Ala Ser Val Met Glu Gly Gln Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Gly Thr Leu Ile Pro Asp Gln Ala Glu Glu Leu Ala Arg
    50                  55                  60

Leu Ala Arg Met Glu Met Lys His Met Lys Gly Phe Thr Ser Cys Gly
65                  70                  75                  80

Arg Asn Leu Gly Val Gln Ala Asp Met Ala Phe Ala Arg Lys Phe Phe
                85                  90                  95

Glu Pro Leu His Gly Asn Phe Gln Ser Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Glu Glu Leu Phe
                165                 170                 175

Glu Ala Asn Lys Ala Asn Leu Pro Leu Ile Arg Ser Met Leu Glu Asp
            180                 185                 190

Val Ala Ala Asp Ala Ala Val Leu His Met Glu Lys Glu Asp Leu Ile
        195                 200                 205

Glu Asp Phe Leu Ile Ala Tyr Asn Glu Ala Leu Ser Glu Ile Gly Phe
    210                 215                 220

Ser Ser Arg Asp Ile Ala Arg Met Ala Ala Ala Ala Leu Ala Leu
225                 230                 235


<210> SEQ ID NO 130
<211> LENGTH: 242
<212> TYPE: PRT
<213> ORGANISM: Synechococcus sp.

<400> SEQUENCE: 130

Met Pro Thr Leu Asp Ser Thr Leu Val Ala Val Leu Asp Asp Gln Gln
1               5                   10                  15

Gly Leu Ala Glu Leu Pro Asp Phe Thr Thr Asp Ala Tyr Lys Asp Ala
```

```
            20                  25                  30

Tyr Ser Arg Ile Asn Ala Ile Val Ile Glu Gly Glu Lys Glu Ala His
        35                  40                  45

Asp Asn Tyr Leu Ser Leu Gly Thr Leu Ile Pro Glu Gln Ala Glu Glu
    50                  55                  60

Leu Ala Lys Leu Ala Lys Met Glu Met Lys His Met Lys Gly Phe Thr
65                  70                  75                  80

Ala Cys Ala Lys Asn Leu Asp Val Val Ala Asp Met Pro Phe Ala Gln
                85                  90                  95

Glu Phe Phe Ala Pro Leu His Gly Asn Phe Gln Ser Ala Leu Lys Glu
            100                 105                 110

Gly Lys Val Val Thr Cys Leu Leu Ile Gln Ala Leu Leu Ile Glu Ala
        115                 120                 125

Phe Ala Ile Ser Ala Tyr His Ile Tyr Ile Pro Val Ala Asp Pro Phe
    130                 135                 140

Ala Arg Lys Ile Thr Glu Gly Val Val Lys Asp Glu Tyr Thr His Leu
145                 150                 155                 160

Asn Tyr Gly Gln Glu Trp Leu Lys Ala Asn Phe Glu Ala Ser Arg Asp
                165                 170                 175

Glu Leu Met Glu Ala Asn Lys Val Asn Leu Pro Leu Ile Arg Ser Met
            180                 185                 190

Leu Glu Gln Val Ala Ala Asp Ala Ser Val Leu His Met Glu Lys Glu
        195                 200                 205

Asp Leu Ile Glu Asp Phe Leu Ile Ala Tyr Gln Glu Ala Leu Asn Glu
    210                 215                 220

Ile Gly Phe Ser Ser Arg Asp Ile Ala Arg Met Ala Ala Ala Ala Leu
225                 230                 235                 240

Ser Ile


<210> SEQ ID NO 131
<211> LENGTH: 239
<212> TYPE: PRT
<213> ORGANISM: Unknown
<220> FEATURE:
<223> OTHER INFORMATION: Description of Unknown: Uncultured
      marine type-A Synechococcus 5B2
      polypeptide

<400> SEQUENCE: 131

Met Thr Thr Leu Asn Ala Pro Asp Ala Ala Val Val Glu Gly Leu Asp
1               5                   10                  15

Ala Leu Pro Asp Phe Thr Thr Glu Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ala Leu Gly Thr Leu Ile Pro Asp Gln Lys Asp Glu Leu Ala Arg
    50                  55                  60

Leu Ala Arg Met Glu Met Lys His Met Lys Gly Phe Thr Ser Cys Gly
65                  70                  75                  80

Arg Asn Leu Gly Val Lys Ala Asp Met Val Phe Ala Lys Thr Phe Phe
                85                  90                  95

Glu Pro Leu His Arg Asn Phe Gln Ser Ala Leu Gln Glu Gly Lys Val
            100                 105                 110

Val Thr Cys Leu Leu Ile Gln Ala Leu Leu Ile Glu Ala Phe Ala Ile
        115                 120                 125
```

```
Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Leu Phe
                165                 170                 175

Glu Ala Asn Lys Ala Asn Leu Pro Leu Ile Arg Ser Met Leu Asp Asp
            180                 185                 190

Val Ala Gly Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
    210                 215                 220

Thr Ser Arg Asp Ile Ala Arg Met Ala Ala Ala Ala Leu Ala Val
225                 230                 235


<210> SEQ ID NO 132
<211> LENGTH: 253
<212> TYPE: PRT
<213> ORGANISM: Synechococcus sp.

<400> SEQUENCE: 132

Met Pro Ser Leu Glu Thr Thr Ile Ala Ala Ser Glu Thr Ala Ser Ala
1               5                   10                  15

Ser Ala Ser Met Ala Val Gly Gly Ser Val Glu Gln Asp Leu Gly Leu
            20                  25                  30

Pro Asp Phe Ser Ser Ser Thr Tyr Lys Asp Ala Tyr Ser Arg Ile Asn
        35                  40                  45

Ala Ile Val Ile Glu Gly Glu Gln Glu Ala His Asp Asn Tyr Ile Ser
    50                  55                  60

Leu Gly His Leu Ile Pro Asp Gln Ala Glu Glu Leu Glu Arg Leu Ala
65                  70                  75                  80

Arg Met Glu Leu Lys His Lys Lys Gly Phe Thr Ala Cys Ala Lys Asn
                85                  90                  95

Leu Ser Val Ile Ala Asp Met Asp Phe Ala Lys Glu Phe Phe Ser Pro
            100                 105                 110

Leu His Gly Asn Phe Gln Ala Ala Leu Ala Glu Gly Lys Val Val Thr
        115                 120                 125

Cys Leu Leu Ile Gln Ala Ile Leu Ile Glu Ala Phe Ala Ile Ser Ala
    130                 135                 140

Tyr His Ile Tyr Ile Pro Val Ala Asp Pro Phe Ala Arg Lys Ile Thr
145                 150                 155                 160

Glu Gly Val Val Lys Asp Glu Tyr Thr His Leu Asn Tyr Gly Gln Glu
                165                 170                 175

Trp Leu Lys Ala Asn Leu Glu Ser Ser Arg Gly Glu Leu Glu Gln Ala
            180                 185                 190

Asn Arg Val Asn Leu Pro Leu Val Arg Lys Met Leu Glu Gln Val Ala
        195                 200                 205

Gly Asp Ala Ala Val Leu His Met Asp Gln Glu Asp Leu Met Ala Asp
    210                 215                 220

Phe Met Thr Ser Tyr Gln Glu Ala Leu Thr Asp Ile Gly Phe Thr Thr
225                 230                 235                 240

Arg Glu Ile Ala Lys Met Ala Thr Ala Ala Leu Leu Gly
                245                 250


<210> SEQ ID NO 133
```

<211> LENGTH: 235
<212> TYPE: PRT
<213> ORGANISM: Gloeobacter violaceus

<400> SEQUENCE: 133

Met Asn Arg Thr Ala Pro Ser Ser Ala Ala Leu Asp Tyr Arg Ser Asp
1 5 10 15

Thr Tyr Arg Asp Ala Tyr Ser Arg Ile Asn Ala Ile Val Leu Glu Gly
20 25 30

Glu Arg Glu Ala His Ala Asn Tyr Leu Thr Leu Ala Glu Met Leu Pro
35 40 45

Asp His Ala Glu Ala Leu Lys Lys Leu Ala Ala Met Glu Asn Arg His
50 55 60

Phe Lys Gly Phe Gln Ser Cys Ala Arg Asn Leu Glu Val Thr Pro Asp
65 70 75 80

Asp Pro Phe Ala Arg Ala Tyr Phe Glu Gln Leu Asp Gly Asn Phe Gln
85 90 95

Gln Ala Ala Ala Glu Gly Asp Leu Thr Thr Cys Met Val Ile Gln Ala
100 105 110

Leu Ile Ile Glu Cys Phe Ala Ile Ala Ala Tyr Asn Val Tyr Ile Pro
115 120 125

Val Ala Asp Ala Phe Ala Arg Lys Val Thr Glu Gly Val Val Lys Asp
130 135 140

Glu Tyr Thr His Leu Asn Phe Gly Gln Gln Trp Leu Lys Glu Arg Phe
145 150 155 160

Val Thr Val Arg Glu Gly Ile Glu Arg Ala Asn Ala Gln Asn Leu Pro
165 170 175

Ile Val Trp Arg Met Leu Asn Ala Val Glu Ala Asp Thr Glu Val Leu
180 185 190

Gln Met Asp Lys Glu Ala Ile Val Glu Asp Phe Met Ile Ala Tyr Gly
195 200 205

Glu Ala Leu Gly Asp Ile Gly Phe Ser Met Arg Asp Val Met Lys Met
210 215 220

Ser Ala Arg Gly Leu Ala Ser Ala Pro Arg Gln
225 230 235

<210> SEQ ID NO 134
<211> LENGTH: 243
<212> TYPE: PRT
<213> ORGANISM: Synechococcus sp.

<400> SEQUENCE: 134

Met Pro Thr Leu Asn Ser Pro Glu Val Ala Ala Ile Ser Asp Gln Asp
1 5 10 15

Gly Ser Ala Ser Gln Leu Pro Asp Phe Ser Ser Ala Ala Tyr Lys Asp
20 25 30

Ala Tyr Ser Arg Ile Asn Ala Ile Val Ile Glu Gly Glu Gln Glu Ala
35 40 45

His Asp Asn Tyr Ile Ser Leu Gly Thr Leu Ile Pro Asp Gln Ala Asp
50 55 60

Glu Leu Lys Gly Leu Ala Arg Met Glu Met Lys His Met Lys Gly Phe
65 70 75 80

Thr Ala Cys Gly Asn Asn Leu Gly Val Thr Ala Asp Met Asp Phe Ala
85 90 95

Arg Thr Phe Phe Ala Pro Leu His Gly Asn Phe Gln Lys Ala Met Lys
100 105 110

```
Glu Gly Lys Val Val Thr Cys Leu Leu Ile Gln Ala Leu Leu Ile Glu
        115                 120                 125

Ala Phe Ala Ile Ser Ala Tyr His Ile Tyr Ile Pro Val Ala Asp Pro
    130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Glu Ala Ser Lys
                165                 170                 175

Asp Glu Leu Met Glu Ala Asn Lys Val Asn Leu Pro Leu Ile Arg Ser
            180                 185                 190

Met Leu Glu Glu Val Ala Lys Asp Ala Ala Val Leu His Met Glu Lys
        195                 200                 205

Glu Asp Leu Ile Glu Asp Phe Leu Ile Ala Tyr Gln Glu Ala Leu Asn
    210                 215                 220

Glu Ile Gly Phe Ser Ser Arg Asp Ile Ala Arg Met Ala Ala Ala Ala
225                 230                 235                 240

Leu Ala Val


<210> SEQ ID NO 135
<211> LENGTH: 243
<212> TYPE: PRT
<213> ORGANISM: Synechococcus sp.

<400> SEQUENCE: 135

Met Pro Thr Leu Glu Thr Ser Glu Val Ala Val Leu Glu Asp Ser Met
1               5                   10                  15

Ala Ser Gly Ser Arg Leu Pro Asp Phe Thr Ser Glu Ala Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ala Leu Gly Thr Leu Ile Pro Glu Gln Lys Asp
    50                  55                  60

Glu Leu Ala Arg Leu Ala Arg Met Glu Met Lys His Met Lys Gly Phe
65                  70                  75                  80

Thr Ser Cys Gly Arg Asn Leu Gly Val Glu Ala Asp Leu Pro Phe Ala
                85                  90                  95

Lys Glu Phe Phe Ala Pro Leu His Gly Asn Phe Gln Ala Ala Leu Gln
            100                 105                 110

Glu Gly Lys Val Val Thr Cys Leu Leu Ile Gln Ala Leu Leu Ile Glu
        115                 120                 125

Ala Phe Ala Ile Ser Ala Tyr His Ile Tyr Ile Pro Val Ala Asp Pro
    130                 135                 140

Phe Ala Arg Lys Ile Thr Glu Gly Val Val Lys Asp Glu Tyr Thr His
145                 150                 155                 160

Leu Asn Tyr Gly Gln Glu Trp Leu Lys Ala Asn Phe Glu Ala Ser Lys
                165                 170                 175

Asp Glu Leu Met Glu Ala Asn Lys Ala Asn Leu Pro Leu Ile Arg Ser
            180                 185                 190

Met Leu Glu Gln Val Ala Ala Asp Ala Ala Val Leu Gln Met Glu Lys
        195                 200                 205

Glu Asp Leu Ile Glu Asp Phe Leu Ile Ala Tyr Gln Glu Ala Leu Cys
    210                 215                 220

Glu Ile Gly Phe Ser Ser Arg Asp Ile Ala Arg Met Ala Ala Ala Ala
225                 230                 235                 240
```

Leu Ala Val

<210> SEQ ID NO 136
<211> LENGTH: 239
<212> TYPE: PRT
<213> ORGANISM: Synechococcus sp.

<400> SEQUENCE: 136

```
Met Thr Thr Leu Asn Ala Pro Glu Ala Pro Val Leu Glu Gly Gln Asp
1               5                   10                  15

Ala Leu Pro Asp Phe Thr Thr Ala Ala Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Gly Thr Leu Ile Pro Glu Gln Ala Glu Glu Leu Lys Arg
    50                  55                  60

Leu Ala Arg Met Glu Met Lys His Met Lys Gly Phe Thr Ser Cys Gly
65                  70                  75                  80

Arg Asn Leu Gly Val Glu Ala Asp Leu Pro Phe Ala Lys Lys Phe Phe
                85                  90                  95

Glu Pro Leu His Gly Asn Phe Gln Ala Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asn Glu Leu Phe
                165                 170                 175

Glu Ala Asn Lys Ala Asn Leu Pro Leu Ile Arg Ser Met Leu Glu Asp
            180                 185                 190

Val Ala Ala Asp Ala Ala Val Leu His Met Glu Lys Glu Asp Leu Ile
        195                 200                 205

Glu Asp Phe Leu Ile Ala Tyr Gln Glu Ala Leu Gly Glu Ile Gly Phe
    210                 215                 220

Thr Ser Arg Asp Ile Ala Arg Met Ala Ala Ala Ala Leu Ala Val
225                 230                 235
```

<210> SEQ ID NO 137
<211> LENGTH: 243
<212> TYPE: PRT
<213> ORGANISM: Prochlorococcus marinus

<400> SEQUENCE: 137

```
Met Pro Thr Leu Glu Met Pro Glu Ala Ala Val Leu Asp Ser Thr Val
1               5                   10                  15

Gly Ser Ser Glu Ala Leu Pro Asp Phe Thr Ser Asp Ala Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ala Ile Gly Thr Leu Leu Pro Asp His Val Glu
    50                  55                  60

Glu Leu Lys Arg Leu Ala Lys Met Glu Met Arg His Lys Lys Gly Phe
65                  70                  75                  80
```

```
Thr Ala Cys Gly Lys Asn Leu Gly Val Thr Ala Asp Met Asp Phe Ala
                85                  90                  95

Arg Glu Phe Phe Ala Pro Leu Arg Asp Asn Phe Gln Thr Ala Leu Glu
            100                 105                 110

Gln Gly Lys Thr Pro Thr Cys Leu Leu Ile Gln Ala Leu Leu Ile Glu
        115                 120                 125

Ala Phe Ala Ile Ser Ala Tyr His Thr Tyr Ile Pro Val Ser Asp Pro
    130                 135                 140

Phe Ala Arg Lys Ile Thr Glu Gly Val Val Lys Asp Glu Tyr Thr His
145                 150                 155                 160

Leu Asn Tyr Gly Glu Ala Trp Leu Lys Ala Asn Leu Glu Ser Cys Arg
                165                 170                 175

Glu Glu Leu Leu Glu Ala Asn Arg Glu Asn Leu Pro Leu Ile Arg Arg
            180                 185                 190

Met Leu Asp Gln Val Ala Gly Asp Ala Ala Val Leu Gln Met Asp Lys
        195                 200                 205

Glu Asp Leu Ile Glu Asp Phe Leu Ile Ala Tyr Gln Glu Ser Leu Thr
    210                 215                 220

Glu Ile Gly Phe Asn Thr Arg Glu Ile Thr Arg Met Ala Ala Ala Ala
225                 230                 235                 240

Leu Val Ser


<210> SEQ ID NO 138
<211> LENGTH: 249
<212> TYPE: PRT
<213> ORGANISM: Cyanobium sp.

<400> SEQUENCE: 138

Met Ala Ser Val Ala His Pro Ala Val Ala Val Gln Pro Ala Thr Lys
1               5                   10                  15

Pro Ala Asp Thr Ala Ala Glu Arg Gly Asp Gly Leu Pro Asp Phe Ser
            20                  25                  30

Ser Asp Thr Tyr Lys Asp Ala Tyr Ser Arg Ile Asn Ala Ile Val Ile
        35                  40                  45

Glu Gly Glu Gln Glu Ala His Asp Asn Tyr Ile Ala Leu Gly Thr Leu
    50                  55                  60

Ile Pro Asp Gln Ala Asp Glu Leu Ala Lys Leu Ala Arg Met Glu Leu
65                  70                  75                  80

Lys His Met Lys Gly Phe Thr Ala Cys Ala Asn Asn Leu Gly Val Thr
                85                  90                  95

Ala Asp Met Pro Phe Ala Lys Glu Phe Phe Ala Pro Leu His Gly Asn
            100                 105                 110

Phe Gln Arg Ala Leu Ala Glu Gly Lys Val Thr Thr Cys Leu Leu Ile
        115                 120                 125

Gln Ala Ile Leu Ile Glu Ala Phe Ala Ile Ser Ala Tyr His Ile Tyr
    130                 135                 140

Ile Pro Val Ala Asp Pro Phe Ala Arg Arg Ile Thr Glu Gly Val Val
145                 150                 155                 160

Lys Asp Glu Tyr Thr His Leu Asn Tyr Gly Gln Glu Trp Leu Lys Ala
                165                 170                 175

Asn Leu Ala Asp Val Arg Glu Glu Leu Glu Gln Ala Asn Arg Glu Asn
            180                 185                 190

Leu Pro Leu Val Arg Lys Met Leu Glu Gln Val Ala Gly Asp Ala Ala
        195                 200                 205
```

```
Val Leu Gln Met Asp Lys Glu Asp Leu Met Ala Asp Phe Leu Ser Ser
    210                 215                 220

Tyr Gln Glu Ala Leu Met Asp Ile Gly Phe Thr Gly Arg Glu Ile Ala
225                 230                 235                 240

Lys Leu Ala Ala Ala Ala Leu Val Gly
                245


<210> SEQ ID NO 139
<211> LENGTH: 243
<212> TYPE: PRT
<213> ORGANISM: Prochlorococcus marinus

<400> SEQUENCE: 139

Met Pro Thr Leu Glu Met Pro Val Ala Ala Val Leu Asp Ser Thr Val
1               5                   10                  15

Gly Ser Ser Glu Ala Leu Pro Asp Phe Thr Ser Asp Arg Tyr Lys Asp
            20                  25                  30

Ala Tyr Ser Arg Ile Asn Ala Ile Val Ile Glu Gly Glu Gln Glu Ala
        35                  40                  45

His Asp Asn Tyr Ile Ala Ile Gly Thr Leu Leu Pro Asp His Val Glu
    50                  55                  60

Glu Leu Lys Arg Leu Ala Lys Met Glu Met Arg His Lys Lys Gly Phe
65                  70                  75                  80

Thr Ala Cys Gly Lys Asn Leu Gly Val Glu Ala Asp Met Asp Phe Ala
                85                  90                  95

Arg Glu Phe Phe Ala Pro Leu Arg Asp Asn Phe Gln Thr Ala Leu Gly
            100                 105                 110

Gln Gly Lys Thr Pro Thr Cys Leu Leu Ile Gln Ala Leu Leu Ile Glu
        115                 120                 125

Ala Phe Ala Ile Ser Ala Tyr His Thr Tyr Ile Pro Val Ser Asp Pro
    130                 135                 140

Phe Ala Arg Lys Ile Thr Glu Gly Val Val Lys Asp Glu Tyr Thr His
145                 150                 155                 160

Leu Asn Tyr Gly Glu Ala Trp Leu Lys Ala Asn Leu Glu Ser Cys Arg
                165                 170                 175

Glu Glu Leu Leu Glu Ala Asn Arg Glu Asn Leu Pro Leu Ile Arg Arg
            180                 185                 190

Met Leu Asp Gln Val Ala Gly Asp Ala Ala Val Leu Gln Met Asp Lys
        195                 200                 205

Glu Asp Leu Ile Glu Asp Phe Leu Ile Ala Tyr Gln Glu Ser Leu Thr
    210                 215                 220

Glu Ile Gly Phe Asn Thr Arg Glu Ile Thr Arg Met Ala Ala Ala Ala
225                 230                 235                 240

Leu Val Ser


<210> SEQ ID NO 140
<211> LENGTH: 239
<212> TYPE: PRT
<213> ORGANISM: Synechococcus sp.

<400> SEQUENCE: 140

Met Pro Thr Leu Asn Ala Pro Glu Val Ser Val Leu Glu Gly Gln Asp
1               5                   10                  15

Ala Leu Pro Asp Phe Thr Thr Ala Glu Tyr Lys Asp Ala Tyr Ser Arg
            20                  25                  30

Ile Asn Ala Ile Val Ile Glu Gly Glu Gln Glu Ala His Asp Asn Tyr
```

```
        35                  40                  45

Ile Ser Leu Gly Thr Leu Ile Pro Glu Gln Ala Asp Glu Leu Ser Arg
    50                  55                  60

Leu Ala Arg Met Glu Met Lys His Met Lys Gly Phe Thr Ala Cys Ala
65                  70                  75                  80

Arg Asn Leu Gly Val Glu Ala Asp Met Pro Phe Ala Lys Asp Phe Phe
                85                  90                  95

Gly Pro Leu His Gly Asn Phe Gln Val Ala Leu Lys Glu Gly Lys Val
            100                 105                 110

Val Thr Cys Leu Leu Ile Gln Ala Leu Leu Ile Glu Ala Phe Ala Ile
        115                 120                 125

Ser Ala Tyr His Ile Tyr Ile Pro Val Ala Asp Pro Phe Ala Arg Lys
    130                 135                 140

Ile Thr Glu Gly Val Val Lys Asp Glu Tyr Thr His Leu Asn Tyr Gly
145                 150                 155                 160

Gln Glu Trp Leu Lys Ala Asn Phe Glu Ala Ser Lys Asp Glu Met Phe
                165                 170                 175

Ala Ala Asn Lys Ala Asn Leu Pro Leu Ile Arg Ser Met Leu Glu Gly
            180                 185                 190

Val Ala Ala Asp Ala Ala Val Leu His Met Glu Lys Glu Asp Leu Ile
        195                 200                 205

Glu Asp Phe Leu Ile Ala Tyr Gln Glu Ala Leu Asn Glu Ile Gly Phe
    210                 215                 220

Ser Ser Arg Asp Ile Ala Lys Met Ala Ala Ala Ala Leu Ala Ile
225                 230                 235


<210> SEQ ID NO 141
<211> LENGTH: 251
<212> TYPE: PRT
<213> ORGANISM: Prochlorococcus marinus

<400> SEQUENCE: 141

Met His Asn Glu Leu Lys Ile Thr Asp Met Gln Thr Leu Glu Ser Asn
1               5                   10                  15

Lys Lys Thr Ile Glu Glu Ser Thr Asn Ser Ile Ser Leu Asp Leu Pro
            20                  25                  30

Asp Phe Thr Thr Asp Ser Tyr Lys Asp Ala Tyr Ser Arg Ile Asn Ala
        35                  40                  45

Ile Val Ile Glu Gly Glu Gln Glu Ala His Asp Asn Tyr Ile Ser Ile
    50                  55                  60

Ala Thr Leu Ile Pro Asn Glu Leu Glu Glu Leu Thr Lys Leu Ala Arg
65                  70                  75                  80

Met Glu Met Lys His Lys Lys Gly Phe Thr Ala Cys Gly Arg Asn Leu
                85                  90                  95

Asp Val Val Ala Asp Met Glu Phe Ala Lys Lys Phe Phe Ser Lys Leu
            100                 105                 110

His Gly Asn Phe Gln Val Ala Leu Lys Lys Gly Asn Val Thr Thr Cys
        115                 120                 125

Leu Leu Ile Gln Ala Ile Leu Ile Glu Ala Phe Ala Ile Ser Ala Tyr
    130                 135                 140

Asn Val Tyr Ile Arg Val Ala Asp Pro Phe Ala Lys Lys Ile Thr Glu
145                 150                 155                 160

Gly Val Val Lys Asp Glu Tyr Leu His Leu Asn Tyr Gly Gln Gln Trp
                165                 170                 175
```

```
Leu Lys Glu Asn Leu Ser Thr Cys Lys Asp Glu Leu Met Glu Ala Asn
            180                 185                 190

Lys Val Asn Leu Pro Leu Ile Lys Lys Met Leu Asp Glu Val Ala Asp
        195                 200                 205

Asp Ala Ser Val Leu Ala Met Asp Arg Glu Glu Leu Met Glu Glu Phe
    210                 215                 220

Met Ile Ala Tyr Gln Asp Thr Leu Met Glu Ile Gly Leu Asp Asn Arg
225                 230                 235                 240

Glu Ile Ala Arg Met Ala Met Ala Ala Ile Val
                245                 250


<210> SEQ ID NO 142
<211> LENGTH: 229
<212> TYPE: PRT
<213> ORGANISM: Synechococcus sp.

<400> SEQUENCE: 142

Met Leu Glu Gly Gln Asp Ala Leu Pro Asp Phe Thr Thr Ala Glu Tyr
1               5                   10                  15

Lys Asp Ala Tyr Ser Arg Ile Asn Ala Ile Val Ile Glu Gly Glu Gln
            20                  25                  30

Glu Ala His Asp Asn Tyr Ile Ser Leu Gly Thr Leu Ile Pro Glu Gln
        35                  40                  45

Ala Glu Glu Leu Ser Arg Leu Ala Arg Met Glu Met Lys His Met Lys
    50                  55                  60

Gly Phe Thr Ala Cys Ala Arg Asn Leu Gly Val Glu Ala Asp Met Pro
65                  70                  75                  80

Phe Ala Lys Glu Phe Phe Gly Pro Leu His Gly Asn Phe Gln Val Ala
                85                  90                  95

Leu Lys Glu Gly Lys Val Val Thr Cys Leu Leu Ile Gln Ala Leu Leu
            100                 105                 110

Ile Glu Ala Phe Ala Ile Ser Ala Tyr His Ile Tyr Ile Pro Val Ala
        115                 120                 125

Asp Pro Phe Ala Arg Lys Ile Thr Glu Gly Val Val Lys Asp Glu Tyr
    130                 135                 140

Thr His Leu Asn Tyr Gly Gln Glu Trp Leu Lys Ala Asn Phe Glu Ala
145                 150                 155                 160

Ser Lys Asp Glu Met Phe Ala Ala Asn Lys Ala Asn Leu Pro Leu Ile
                165                 170                 175

Arg Ser Met Leu Glu Gly Val Ala Ala Asp Ala Ala Val Leu His Met
            180                 185                 190

Glu Lys Glu Asp Leu Ile Glu Asp Phe Leu Ile Ala Tyr Gln Glu Ala
        195                 200                 205

Leu Asn Glu Ile Gly Phe Ser Ser Arg Asp Ile Ala Lys Met Ala Ala
    210                 215                 220

Ala Ala Leu Ala Ile
225


<210> SEQ ID NO 143
<211> LENGTH: 251
<212> TYPE: PRT
<213> ORGANISM: Prochlorococcus marinus

<400> SEQUENCE: 143

Met His Asn Glu Leu Lys Ile Thr Asp Met Gln Thr Leu Glu Ser Asn
1               5                   10                  15
```

```
Lys Lys Thr Ile Glu Glu Ser Ile Asn Pro Ile Ser Leu Asp Leu Pro
            20                  25                  30

Asp Phe Thr Thr Asp Ser Tyr Lys Asp Ala Tyr Ser Arg Ile Asn Ala
        35                  40                  45

Ile Val Ile Glu Gly Glu Gln Glu Ala His Asp Asn Tyr Ile Ser Ile
    50                  55                  60

Ala Thr Leu Ile Pro Asn Glu Val Glu Glu Leu Thr Lys Leu Ala Arg
65                  70                  75                  80

Met Glu Met Lys His Lys Lys Gly Phe Thr Ala Cys Gly Arg Asn Leu
                85                  90                  95

Gly Val Val Ala Asp Met Asp Phe Ala Lys Lys Phe Phe Ser Lys Leu
            100                 105                 110

His Gly Asn Phe Gln Val Ala Leu Glu Lys Gly Asn Leu Thr Thr Cys
        115                 120                 125

Leu Leu Ile Gln Ala Ile Leu Ile Glu Ala Phe Ala Ile Ser Ala Tyr
    130                 135                 140

Asn Val Tyr Ile Arg Val Ala Asp Pro Phe Ala Lys Lys Ile Thr Glu
145                 150                 155                 160

Gly Val Val Lys Asp Glu Tyr Leu His Leu Asn Tyr Gly Gln Glu Trp
                165                 170                 175

Leu Lys Glu Asn Leu Ser Thr Cys Lys Glu Glu Leu Met Glu Ala Asn
            180                 185                 190

Lys Val Asn Leu Pro Leu Ile Lys Lys Met Leu Asp Glu Val Ala Asp
        195                 200                 205

Asp Ala Ser Val Leu Ala Met Asp Lys Glu Glu Leu Met Glu Glu Phe
    210                 215                 220

Met Ile Ala Tyr Gln Asp Thr Leu Met Glu Ile Gly Leu Asp Asn Arg
225                 230                 235                 240

Glu Ile Ala Arg Met Ala Met Ala Ala Ile Val
                245                 250


<210> SEQ ID NO 144
<211> LENGTH: 238
<212> TYPE: PRT
<213> ORGANISM: Prochlorococcus marinus

<400> SEQUENCE: 144

Met Gln Thr Leu Glu Ser Asn Lys Lys Thr Asn Leu Glu Asn Ser Ile
1               5                   10                  15

Asp Leu Pro Asp Phe Thr Thr Asp Ser Tyr Lys Asp Ala Tyr Ser Arg
            20                  25                  30

Ile Asn Ala Ile Val Ile Glu Gly Glu Gln Glu Ala His Asp Asn Tyr
        35                  40                  45

Ile Ser Leu Ala Thr Leu Ile Pro Asn Glu Leu Glu Glu Leu Thr Lys
    50                  55                  60

Leu Ala Lys Met Glu Leu Lys His Lys Arg Gly Phe Thr Ala Cys Gly
65                  70                  75                  80

Arg Asn Leu Gly Val Gln Ala Asp Met Ile Phe Ala Lys Glu Phe Phe
                85                  90                  95

Ser Lys Leu His Gly Asn Phe Gln Val Ala Leu Ser Asn Gly Lys Thr
            100                 105                 110

Thr Thr Cys Leu Leu Ile Gln Ala Ile Leu Ile Glu Ala Phe Ala Ile
        115                 120                 125

Ser Ala Tyr His Val Tyr Ile Arg Val Ala Asp Pro Phe Ala Lys Lys
    130                 135                 140
```

```
Ile Thr Gln Gly Val Val Lys Asp Glu Tyr Leu His Leu Asn Tyr Gly
145                 150                 155                 160

Gln Glu Trp Leu Lys Glu Asn Leu Ala Thr Cys Lys Asp Glu Leu Met
                165                 170                 175

Glu Ala Asn Lys Val Asn Leu Pro Leu Ile Lys Lys Met Leu Asp Gln
            180                 185                 190

Val Ser Glu Asp Ala Ser Val Leu Ala Met Asp Arg Glu Glu Leu Met
        195                 200                 205

Glu Glu Phe Met Ile Ala Tyr Gln Asp Thr Leu Leu Glu Ile Gly Leu
    210                 215                 220

Asp Asn Arg Glu Ile Ala Arg Met Ala Met Ala Ala Ile Val
225                 230                 235
```

<210> SEQ ID NO 145
<211> LENGTH: 242
<212> TYPE: PRT
<213> ORGANISM: Prochlorococcus marinus

<400> SEQUENCE: 145

```
Met Pro Thr Leu Glu Ser Ser Glu Val Ala Val Ile Ser Asp Leu Glu
1               5                   10                  15

Gly Arg Asp Gly Ser Leu Pro Asp Phe Thr Thr Glu Gln Tyr Lys Asp
            20                  25                  30

Ala Tyr Ser Arg Ile Asn Ala Ile Val Ile Glu Gly Glu Lys Glu Ala
        35                  40                  45

His Asp Asn Tyr Val Ala Ile Gly Thr Val Ile Pro Glu Lys Ala Asp
    50                  55                  60

Glu Leu Lys Lys Leu Ala Ile Met Glu Leu Arg His Met Lys Gly Phe
65                  70                  75                  80

Thr Ala Cys Gly Lys Asn Leu Gly Val Val Ala Asp Met Glu Phe Ala
                85                  90                  95

Gln Arg Phe Phe Ala Pro Leu His Gly Asn Phe Gln Lys Ala Leu Glu
            100                 105                 110

Asn Gly Lys Ile Thr Thr Cys Phe Leu Ile Gln Ala Ile Leu Ile Glu
        115                 120                 125

Ala Phe Ala Ile Ser Ala Tyr His Val Tyr Ile Arg Val Ala Asp Pro
    130                 135                 140

Phe Ala Lys Lys Ile Thr Glu Gly Val Val Lys Asp Glu Tyr Leu His
145                 150                 155                 160

Leu Asn Tyr Gly Gln Glu Trp Leu Lys Ala Asn Leu Ala Thr Cys Lys
                165                 170                 175

Asp Glu Leu Ile Ala Ala Asn Lys Glu Asn Leu Pro Leu Ile Asn Ser
            180                 185                 190

Met Leu Asp Gln Val Ala Asn Asp Ala Gln Val Leu Tyr Met Glu Lys
        195                 200                 205

Glu Glu Leu Met Glu Glu Phe Met Ile Ala Tyr Gln Asp Ser Leu Met
    210                 215                 220

Glu Ile Gly Leu Asp Ala Arg Glu Ile Ala Arg Met Ala Leu Ala Ala
225                 230                 235                 240

Ile Ala
```

<210> SEQ ID NO 146
<211> LENGTH: 241
<212> TYPE: PRT
<213> ORGANISM: Prochlorococcus marinus

<400> SEQUENCE: 146

Met Gln Ala Phe Ala Ser Asn Asn Leu Thr Val Glu Lys Glu Glu Leu
1 5 10 15

Ser Ser Asn Ser Leu Pro Asp Phe Thr Ser Glu Ser Tyr Lys Asp Ala
20 25 30

Tyr Ser Arg Ile Asn Ala Val Val Ile Glu Gly Glu Gln Glu Ala Tyr
35 40 45

Ser Asn Phe Leu Asp Leu Ala Lys Leu Ile Pro Glu His Ala Asp Glu
50 55 60

Leu Val Arg Leu Gly Lys Met Glu Lys Lys His Met Asn Gly Phe Cys
65 70 75 80

Ala Cys Gly Arg Asn Leu Ala Val Lys Pro Asp Met Pro Phe Ala Lys
85 90 95

Thr Phe Phe Ser Lys Leu His Asn Asn Phe Leu Glu Ala Phe Lys Val
100 105 110

Gly Asp Thr Thr Thr Cys Leu Leu Ile Gln Cys Ile Leu Ile Glu Ser
115 120 125

Phe Ala Ile Ser Ala Tyr His Val Tyr Ile Arg Val Ala Asp Pro Phe
130 135 140

Ala Lys Arg Ile Thr Glu Gly Val Val Gln Asp Glu Tyr Leu His Leu
145 150 155 160

Asn Tyr Gly Gln Glu Trp Leu Lys Ala Asn Leu Glu Thr Val Lys Lys
165 170 175

Asp Leu Met Arg Ala Asn Lys Glu Asn Leu Pro Leu Ile Lys Ser Met
180 185 190

Leu Asp Glu Val Ser Asn Asp Ala Glu Val Leu His Met Asp Lys Glu
195 200 205

Glu Leu Met Glu Glu Phe Met Ile Ala Tyr Gln Asp Ser Leu Leu Glu
210 215 220

Ile Gly Leu Asp Asn Arg Glu Ile Ala Arg Met Ala Leu Ala Ala Val
225 230 235 240

Ile

<210> SEQ ID NO 147
<211> LENGTH: 241
<212> TYPE: PRT
<213> ORGANISM: Prochlorococcus marinus

<400> SEQUENCE: 147

Met Gln Ala Phe Ala Ser Asn Asn Leu Thr Val Glu Lys Glu Glu Leu
1 5 10 15

Ser Ser Asp Ser Leu Pro Asp Phe Thr Ser Glu Ser Tyr Lys Asp Ala
20 25 30

Tyr Ser Arg Ile Asn Ala Val Val Ile Glu Gly Glu Gln Glu Ala Tyr
35 40 45

Ser Asn Phe Leu Asp Leu Ala Lys Leu Ile Pro Glu His Ala Asp Glu
50 55 60

Leu Val Arg Leu Gly Lys Met Glu Lys Lys His Met Asn Gly Phe Cys
65 70 75 80

Ala Cys Gly Arg Asn Leu Ala Val Lys Pro Asp Met Pro Phe Ala Lys
85 90 95

Thr Phe Phe Ser Lys Leu His Asn Asn Phe Leu Glu Ala Phe Lys Val
100 105 110

```
Gly Asp Thr Thr Thr Cys Leu Leu Ile Gln Cys Ile Leu Ile Glu Ser
        115                 120                 125

Phe Ala Ile Ser Ala Tyr His Val Tyr Ile Arg Val Ala Asp Pro Phe
    130                 135                 140

Ala Lys Arg Ile Thr Glu Gly Val Val Gln Asp Glu Tyr Leu His Leu
145                 150                 155                 160

Asn Tyr Gly Gln Glu Trp Leu Lys Ala Asn Leu Glu Thr Val Lys Lys
                165                 170                 175

Asp Leu Met Arg Ala Asn Lys Glu Asn Leu Pro Leu Ile Lys Ser Met
            180                 185                 190

Leu Asp Glu Val Ser Asn Asp Ala Glu Val Leu His Met Asp Lys Glu
        195                 200                 205

Glu Leu Met Glu Glu Phe Met Ile Ala Tyr Gln Asp Ser Leu Leu Glu
    210                 215                 220

Ile Gly Leu Asp Asn Arg Glu Ile Ala Arg Met Ala Leu Ala Ala Val
225                 230                 235                 240

Ile


<210> SEQ ID NO 148
<211> LENGTH: 237
<212> TYPE: PRT
<213> ORGANISM: Prochlorococcus marinus

<400> SEQUENCE: 148

Met Gln Thr Leu Thr Asn Gln Val Ala Ser Ala Asp Glu Leu Asp Asn
1               5                   10                  15

Leu Pro Asp Phe Ser Ser Ser Gln Tyr Lys Asp Ala Tyr Ser Arg Ile
            20                  25                  30

Asn Ala Ile Val Ile Glu Gly Glu Lys Glu Ala His Asp Asn Tyr Met
        35                  40                  45

Ser Ile Gly Thr Leu Ile Pro Asp Lys Ala Asp Glu Leu Lys Lys Leu
    50                  55                  60

Ala Val Met Glu Leu Lys His Met Arg Gly Phe Thr Ala Cys Gly Lys
65                  70                  75                  80

Asn Leu Gly Val Lys Ala Asp Ile Pro Phe Ala Glu Lys Phe Phe Ser
                85                  90                  95

Pro Leu His Gly Asn Phe Gln Lys Ala Phe Lys Glu Glu Asn Leu Thr
            100                 105                 110

Thr Cys Phe Leu Ile Gln Ala Ile Leu Ile Glu Ala Phe Ala Ile Ser
        115                 120                 125

Ala Tyr His Val Tyr Ile Arg Val Ala Asp Pro Phe Ala Lys Lys Ile
    130                 135                 140

Thr Glu Asn Val Val Lys Asp Glu Tyr Leu His Leu Asn Tyr Gly Gln
145                 150                 155                 160

Gln Trp Leu Lys Ala Asn Leu Asp Thr Cys Lys Glu Glu Leu Met Lys
                165                 170                 175

Ala Asn Lys Glu Asn Leu Pro Leu Ile Lys Ser Met Leu Asp Gln Val
            180                 185                 190

Ala Asp Asp Ala Cys Ser Leu Ser Met Asp Lys Glu Glu Leu Met Glu
        195                 200                 205

Glu Phe Met Ile Ala Tyr Gln Asp Ser Leu Leu Glu Ile Gly Leu Asp
    210                 215                 220

Ser Arg Glu Ile Ala Arg Met Ala Leu Ala Ala Leu Val
225                 230                 235
```

<210> SEQ ID NO 149
<211> LENGTH: 243
<212> TYPE: PRT
<213> ORGANISM: Prochlorococcus marinus

<400> SEQUENCE: 149

Met Gln Thr Leu Glu Ser Asn Lys Asn Ile Gln Ile Gly Ser Ser Pro
1               5                   10                  15

Glu Ser Asp Ser Ala Asn Leu Pro Asp Phe Thr Thr Asp Ala Tyr Lys
            20                  25                  30

Asp Ala Tyr Ser Arg Ile Asn Ala Ile Val Ile Glu Gly Glu Gln Glu
        35                  40                  45

Ala Tyr Asp Asn Tyr Ile Ser Ile Ala Thr Leu Leu Pro Asn Asp Ser
    50                  55                  60

Glu Glu Leu Thr Lys Leu Ala Lys Met Glu Leu Lys His Lys Arg Gly
65                  70                  75                  80

Phe Thr Ala Cys Gly Lys Asn Leu Gly Val Glu Ala Asp Met Ser Phe
                85                  90                  95

Ala Lys Glu Phe Phe Ser Lys Leu His Gly Asn Phe Gln Ala Ala Leu
            100                 105                 110

Lys Asn Glu Ser Leu Thr Thr Cys Leu Leu Ile Gln Ala Ile Leu Ile
        115                 120                 125

Glu Ala Phe Ala Ile Ser Ala Tyr His Val Tyr Ile Arg Val Ala Asp
    130                 135                 140

Pro Phe Ala Lys Lys Ile Thr Gln Gly Val Val Asn Asp Glu Tyr Leu
145                 150                 155                 160

His Leu Asn Tyr Gly Glu Lys Trp Leu Lys Glu Asn Leu Ser Thr Cys
                165                 170                 175

Lys Asp Glu Leu Ile Ala Ala Asn Lys Val Asn Leu Pro Ile Ile Lys
            180                 185                 190

Lys Met Leu Asp Gln Val Ala Asp Asp Ala Ala Thr Leu Ala Met Asp
        195                 200                 205

Lys Glu Glu Leu Met Glu Glu Phe Met Ile Ala Tyr Gln Asp Ala Leu
    210                 215                 220

Leu Glu Met Gly Leu Asp Asn Arg Glu Ile Ala Arg Met Ala Met Ala
225                 230                 235                 240

Ala Ile Val

<210> SEQ ID NO 150
<211> LENGTH: 250
<212> TYPE: PRT
<213> ORGANISM: Prochlorococcus marinus

<400> SEQUENCE: 150

Met Asn Lys Ser Leu Thr Asp Met Gln Thr Leu Glu Ser Lys Lys Asp
1               5                   10                  15

Ile Gln Leu Glu Gly Ser Thr Asp Asn Asp Ser Ala Asn Leu Pro Asp
            20                  25                  30

Phe Thr Thr Asp Ala Tyr Lys Asp Ala Tyr Ser Arg Ile Asn Ala Ile
        35                  40                  45

Val Ile Glu Gly Glu Gln Glu Ala Tyr Asp Asn Tyr Ile Ser Ile Ala
    50                  55                  60

Thr Leu Leu Pro Asn Asp Ser Glu Glu Leu Thr Lys Leu Ala Lys Met
65                  70                  75                  80

Glu Leu Lys His Lys Arg Gly Phe Thr Ala Cys Gly Lys Asn Leu Gly

-continued

```
                85                  90                  95

Val Glu Ala Asp Met Pro Phe Ala Lys Glu Phe Phe Ser Lys Leu His
            100                 105                 110

Gly Asn Phe Gln Ile Ala Leu Lys Asp Gly Asn Leu Thr Thr Cys Leu
        115                 120                 125

Leu Ile Gln Ala Ile Leu Ile Glu Ala Phe Ala Ile Ser Ala Tyr His
    130                 135                 140

Val Tyr Ile Arg Val Ala Asp Pro Phe Ala Lys Lys Ile Thr Gln Gly
145                 150                 155                 160

Val Val Asn Asp Glu Tyr Leu His Leu Asn Tyr Gly Glu Lys Trp Leu
                165                 170                 175

Lys Glu Asn Leu His Thr Cys Lys Asp Glu Leu Ile Ala Ala Asn Lys
            180                 185                 190

Val Asn Leu Pro Leu Ile Lys Lys Met Leu Asp Gln Val Ala Glu Asp
        195                 200                 205

Ala Ala Thr Leu Ser Met Asp Lys Glu Glu Leu Met Glu Glu Phe Met
    210                 215                 220

Ile Ala Tyr Gln Asp Ala Leu Leu Glu Met Gly Leu Asp Asn Arg Glu
225                 230                 235                 240

Ile Ala Arg Met Ala Met Ala Ala Ile Val
                245                 250
```